US012643931B2

(12) United States Patent
Hanson et al.

(10) Patent No.: US 12,643,931 B2
(45) Date of Patent: Jun. 2, 2026

(54) CALR AND JAK2 T-CELL RECEPTORS

(71) Applicant: Janssen Biotech, Inc., Horsham, PA (US)

(72) Inventors: Rebecca Hanson, Harleysville, PA (US); Vinod Krishna, Philadelphia, PA (US); Manuel Alejandro Sepulveda, West Windsor, NJ (US); Patrick Wilkinson, Collegeville, PA (US)

(73) Assignee: Janssen Biotech, Inc., Horsham, PA (US)

( * ) Notice: Subject to any disclaimer, the term of this patent is extended or adjusted under 35 U.S.C. 154(b) by 917 days.

(21) Appl. No.: 17/712,661

(22) Filed: Apr. 4, 2022

(65) Prior Publication Data

US 2023/0079750 A1 Mar. 16, 2023

Related U.S. Application Data

(60) Provisional application No. 63/170,711, filed on Apr. 5, 2021.

(51) Int. Cl.
*C07K 14/725* (2006.01)
*C07K 14/705* (2006.01)
*C12N 15/86* (2006.01)

(52) U.S. Cl.
CPC .......... *C07K 14/7051* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 4,690,915 | A | 9/1987 | Rosenberg |
| 4,844,893 | A | 7/1989 | Honsik et al. |
| 5,033,252 | A | 7/1991 | Carter |
| 5,052,558 | A | 10/1991 | Carter |
| 5,126,132 | A | 6/1992 | Rosenberg |
| 5,323,907 | A | 6/1994 | Kalvelage |
| 5,443,983 | A | 8/1995 | Ochoa et al. |
| 5,747,323 | A | 5/1998 | Darlix et al. |
| 5,766,920 | A | 6/1998 | Babbitt et al. |
| 5,846,827 | A | 12/1998 | Celis et al. |
| 6,040,177 | A | 3/2000 | Riddell et al. |
| 6,194,207 | B1 | 2/2001 | Bell et al. |
| 6,204,058 | B1 | 3/2001 | Bolton |
| 6,210,662 | B1 | 4/2001 | Laus et al. |
| 6,210,963 | B1 | 4/2001 | Haddada et al. |
| 6,225,044 | B1 | 5/2001 | Klein et al. |
| 6,227,368 | B1 | 5/2001 | Truc |
| 6,251,385 | B1 | 6/2001 | Terman |
| 6,255,073 | B1 | 7/2001 | Cai et al. |
| 6,312,948 | B1 | 11/2001 | Cohen-Haguenauer |
| 7,270,811 | B2 | 9/2007 | Bout et al. |
| 7,329,731 | B2 | 2/2008 | Jakobsen et al. |
| 7,569,664 | B2 | 8/2009 | Jakobsen et al. |
| 9,133,264 | B2 | 9/2015 | Blankenstein et al. |
| 9,624,292 | B2 | 4/2017 | Voss et al. |
| 9,884,075 | B2 | 2/2018 | Bethune et al. |
| 2004/0147021 | A1 | 7/2004 | Schuler et al. |
| 2004/0173778 | A1 | 9/2004 | Roncarolo et al. |
| 2016/0130319 | A1 | 5/2016 | Li |
| 2018/0104359 | A1 | 4/2018 | Kamrud |
| 2018/0171340 | A1 | 6/2018 | Kamrud et al. |
| 2019/0225692 | A1 * | 7/2019 | Sissons .................. A61K 39/12 |
| 2020/0123220 | A1 | 4/2020 | Raffaele |

FOREIGN PATENT DOCUMENTS

| | | | | |
|---|---|---|---|---|
| WO | WO 95/01447 | A1 | 1/1995 | |
| WO | WO 97/35996 | A1 | 10/1997 | |
| WO | WO 00/70071 | A1 | 11/2000 | |
| WO | 2005/071093 | A2 | 8/2005 | |
| WO | WO 2007/104792 | A2 | 9/2007 | |
| WO | WO 2010/086189 | A2 | 8/2010 | |
| WO | WO-2016095783 | A1 * | 6/2016 | ............. A61K 38/17 |
| WO | 2017/211371 | A2 | 12/2017 | |
| WO | WO 2018/075235 | A1 | 4/2018 | |
| WO | WO 2018/106615 | A2 | 6/2018 | |
| WO | WO-2018197492 | A1 * | 11/2018 | ............. A61K 35/17 |
| WO | WO-2019036688 | A1 * | 2/2019 | ......... A61K 39/0011 |
| WO | WO 2020/037239 | A1 | 2/2020 | |
| WO | WO 2020/227091 | A1 | 11/2020 | |
| WO | 2021/099906 | A1 | 5/2021 | |

OTHER PUBLICATIONS

English translation of WO2016095783A1 (Year: 2016).*
Altschul, S.F., et al., "Basic Local Alignment Search Tool", (1990), J. Mol. Biol., vol. 215, pp. 403-410.
Danos, O., et al., "Safe and efficient generation of recombinant retroviruses with amphotropic and ecotropic host ranges", (1988), Proc. Natl. Acad. Sci. USA, vol. 85, pp. 6460-6464.
Gilboa, E., "Retroviral Gene Transfer: Application to Human Therapy", (1988), Adv. Exp. Med. Biol, vol. 241, pp. 29-33.
Gorchakov, R., et al., "A New Role for ns Polyprotein Cleavage in Sindbis Virus Replication", (2008), Journal of Virology, vol. 82, No. 13, pp. 6218-6231.
Kim, D.Y., et al., "Enhancement of protein expression by alphavirus replicons by designing self-replicating subgenomic RNAs", (2014), PNAS, vol. 111, No. 29, pp. 10708-10713.
Markowitz, D., et al., "Construction and Use of a Safe and Efficient Amphotropic Packaging Cell Line", (1988), Virology, vol. 167, pp. 400-406.
Toribio, R., et al., "An RNA trapping mechanism in Alphavirus mRNA promotes ribosome stalling and translation initiation", (2016), Nucleic Acids Research, vol. 44, No. 9, pp. 4368-4380.

(Continued)

*Primary Examiner* — Christopher M Babic
*Assistant Examiner* — Marisol Ann O'Neill
(74) *Attorney, Agent, or Firm* — BakerHostetler

(57) ABSTRACT

Described herein are T-cell receptors (TCRs) that bind to CALR or JAK2 antigens. Also described are T-cell receptors (TCRs), polynucleotides, vectors that encode the TCRs, and cells comprising the TCRs, and methods of treatment.

20 Claims, No Drawings

Specification includes a Sequence Listing.

(56) References Cited

OTHER PUBLICATIONS

Ventoso, I., "Adaptive Changes in Alphavirus mRNA Translation Allowed Colonization of Vertebrate Hosts", (2012), vol. 86, No. 17, pp. 9484-9494.
International Search Report from PCT/US2022/023238 mailed Sep. 9, 2022.
Altschul et al., "Basic Local Alignment Search Tool", J. Mol. Biol., 1993, 215, 403-410.
Danos and Mulligan, "Safe and Efficient generation of recombinant retrovirus with amphotropic and ecotropic host ranges", Proc. Natl. Acad. Sci. USA, 1988, 85, 6460-6464.
Gilboa et al., "Retroviral Gene Transfer: Applications to Human Therapy", Adv. Exp. Med. Biol., 1988, 241, 29.
Gorchakov et al., "A New Role for ns Polyprotein Cleavage in Sindbis Virus Replication", J. Virol., Jul. 2008, 82(13), 6218-6231.
Hoganson et al., "Development of a Stable Adenoviral Vector Formulation", Bioprocessing Journal, Mar. 2002, 43-48.
Kim et al., "Enhancement of protein expression by alphavirus replicons by designing self-replicating subgenomic RNAs", PNAS, 2014, 111, 10708-10713.
Markowitz et al., "Construction and use of a safe and efficient amphotropic packaging cell line", Virol., 1988, 167, 400-406.
Miller et al., "Improved Retroviral Vectors for gene transfer and expression", BioTechniques, Oct. 1989, 7, 980-990.
Toribio et al., "An RNA trapping mechanism in Alphavirus mRNA promotes ribosome stalling and translation initiation", Nucleic Acids res., May 19, 2016, 44(9), 4368-4380.
Ventoso, "Adaptive Changes in Alphavirus mRNA Translation Allowed Colonization of Vertebrate Hosts", J. Virol., Sep. 2012, vol. 86, 9484-9494.
Holmstrom et al., "Spontaneous T-cell responses against the immune check point programmed-death-ligand 1 (PD-L1) in patients with chronic myeloproliferative neoplasms correlate with disease stage and clinical response", Oncoimmunology, Jan. 22, 2018, vol. 7, No. 6, e1433521, 6 Pages.
Holmstrom et al., "The JAK2V617F and CALR exon 9 mutations are shared immunogenic neoantigens in hematological malignancy", Oncoimmunology, 2017, vol. 6, No. 11, e1358334, 3 pages.
Holmstrom et al., "Therapeutic cancer vaccination against mutant calreticulin in myeloproliferative neoplasms induces expansion of specific T cells in the periphery but specific T cells fail to enrich in the bone marrow", Front Immunol., vol. 14, 1240678, Aug. 17, 2023, pp. 1-14.
Kang et al., "Coexistence of JAK2 and CALR mutations and their clinical implications in patients with essential thrombocythemia", Oncotarget, vol. 7, No. 35, Jul. 30, 2016, pp. 57036-57049.
Masarova et al., "The Rationale for Immunotherapy in Myeloproliferative Neoplasms", Current Hematologic Malignancy Reports, vol. 14, No. 4, Jun. 21, 2019, pp. 310-327.
Nasillo et al., "Inflammatory Microenvironment and Specific T Cells in Myeloproliferative Neoplasms: Immunopathogenesis and Novel Immunotherapies", Int J Mol Sci., Feb. 14, 2021, vol. 22.

* cited by examiner

CALR AND JAK2 T-CELL RECEPTORS

CLAIM OF PRIORITY

This application claims priority to U.S. Provisional Application No. 63/170,711 filed on Apr. 5, 2021 titled "CALR AND JAK2 T-CELL RECEPTORS" which is incorporated herein by reference in its entirety.

SEQUENCE LISTING

The instant application contains a sequence listing which has been submitted electronically in ASCII format and is hereby incorporated by reference in its entirety. Said ASCII copy, created on Feb. 24, 2022, is named 103693_002708_SL.txt and is 511,902 bytes in size.

TECHNICAL FIELD

Provided are T-cell receptors (TCRs) that bind to CALR or JAK2 antigens. Also provided are TCRs, polynucleotides and vectors that encode the TCRs, cells comprising the TCRs, and methods of treatment.

BACKGROUND

Janus Kinase 2 (JAK2) is a cytoplasmic protein involved in a signaling pathway known to regulate cell growth and proliferation, mainly through cytokine receptors on the cell surface. This pathway is important for generation and differentiation of blood cells from hemopoietic stem cells in the bone marrow. Lack of JAK2 is embryonic lethal due to lack of erythropoiesis (red blood cell production). JAK2 mutations have been corelated with myeloproliferative neoplasms (MPNs), such as polycythemia vera (PV), essential thromocythemia (ET), and primary myelofibrosis (PM). The most clinically relevant mutation is V617F, where the valine at amino acid position 617 is replaced by the amino acid phenylalanine. This mutation is an activating mutation making cells more sensitive to growth factors, leading to increased blood cell proliferation in these diseases. The prevalence of this mutation in MPN is high. Almost 100% of PV, 50% of PM, and 60% of ET patients harbor this mutation. The current standard of care treatment for MPN is Ruxolitinib, a JAK inhibitor, but this treatment is not curative. An unmet medical need still remains for treatment of these diseases.

SUMMARY

Described herein are T-cell receptors (TCRs) comprising an alpha chain and a beta chain, wherein the alpha chain comprises a complementarity determining region 3 (CDR3) comprising an amino acid sequence provided in Table 4, and the beta chain comprises a CDR3 comprising a corresponding amino acid sequence provided in Table 5 (i.e. the beta chain CDR3 provided in Table 5 is in the same row number (row 1, for example) as the alpha chain CDR3 provided in Table 4 (row 1, for example)).

Also described herein are TCRs comprising an alpha chain and a beta chain, wherein the alpha chain comprises a complementarity determining region 1 (CDR1) comprising an amino acid sequence provided in Table 4, a complementarity determining region 2 (CDR2) comprising an amino acid sequence provided in Table 4, and a CDR3 comprising an amino acid sequence provided in Table 4, and the corresponding beta chain comprises a CDR1 comprising an amino acid sequence provided in Table 5, a CDR2 comprising an amino acid sequence provided in Table 5, and a CDR3 comprising an amino acid sequence provided in Table 5 (i.e. the beta chain CDRs provided in Table 5 are in the same row number (row 1, for example) as the alpha chain CDRs provided in Table 4 (row 1, for example)).

In certain embodiments, the alpha chain comprises a variable and joining (VJ) region comprising an amino acid sequence that is at least 90%, 95%, 96%, 97%, 98%, 99% or 100% identical to an amino acid sequence provided in Table 4, and the corresponding beta chain comprises a variable, diversity and joining (VDJ) region comprising an amino acid sequence that is at least 90%, 95%, 96%, 97%, 98%, 99% or 100% identical to an amino acid sequence provided in Table 5. An alpha chain VJ region corresponds to a beta chain VDJ region if they appear in the same row in Table 4 and Table 5 (i.e. the beta chain VDJ region provided in Table 5 is in the same row number (row 1, for example) as the alpha chain VJ region provided in Table 4 (row 1, for example)).

In certain embodiments, the alpha chain comprises an amino acid sequence that is at least 90%, 95%, 96%, 97%, 98%, 99% or 100% identical to an amino acid sequence provided in Table 4, and the corresponding beta chain comprises an amino acid sequence that is at least 90%, 95%, 96%, 97%, 98%, 99% or 100% identical to an amino acid sequence provided in Table 5 (i.e. the beta chain provided in Table 5 is in the same row number (row 1, for example) as the alpha chain provided in Table 4 (row 1, for example)).

Also described herein are nucleic acid molecules encoding the disclosed TCRs.

Also described herein are vectors comprising a disclosed nucleic acid molecule.

Further described provided are cells transformed to express any of the nucleic acid molecules described herein.

Still further described are cells comprising any of the disclosed vectors. In certain embodiments, the cell is a CD8+ T cell.

Also provided are pharmaceutical compositions comprising any of the disclosed TCRs, any of the disclosed nucleic acid molecules, any of the disclosed vectors, or any of the disclosed cells.

DETAILED DESCRIPTION OF ILLUSTRATIVE EMBODIMENTS

The disclosed T-cell receptors (TCRs), polynucleotides, vectors, compositions, kits, and cells may be understood more readily by reference to the following detailed description, which forms a part of this disclosure. It is to be understood that the disclosed TCRs, polynucleotides, vectors, compositions, kits, and cells are not limited to those specifically described and/or shown herein, and that the terminology used herein is for the purpose of describing particular embodiments by way of example only and is not intended to be limiting of the claimed TCRs, polynucleotides, vectors, compositions, kits, and cells.

Unless specifically stated otherwise, any description as to a possible mechanism or mode of action or reason for improvement is meant to be illustrative only, and the disclosed TCRs, polynucleotides, vectors, compositions, kits, and cells are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value unless the context clearly dictates otherwise.

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of"; similarly, the term "consisting essentially of" is intended to include examples encompassed by the term "consisting of".

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about". In other cases, the gradations used in a series of values may be used to determine the intended range available to the term "about" for each value.

If not otherwise specified, the term "about" signifies a variance of 10% of the associated value. Thus, the term "about" is used to encompass variations of ±10% or less, variations of ±5% or less, variations of ±1% or less, variations of ±0.5% or less, or variations of ±0.10% or less from the specified value.

When a list is presented, unless stated otherwise, it is to be understood that each individual element of that list, and every combination of that list, is a separate embodiment. For example, a list of embodiments presented as "A, B, or C" is to be interpreted as including the embodiments, "A", "B", "C", "A or B", "A or C", "B or C", or "A, B, or C".

As used herein, the singular forms "a", "an", and "the" include the plural.

As used herein, the term "at least one" means "one or more."

The terms "kit" and "article of manufacture" are used as synonyms.

"9-mer" or "9mer" refers to a polypeptide that is nine amino acids in length.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

T-Cell Receptors

Disclosed herein are TCRs that bind to CALR and JAK2 epitopes. In some embodiments, the TCRs bind to a JAK2 epitope comprising the amino acid sequence of VLNYGVCFC (SEQ ID NO: 681). In some embodiments, the TCRs bind to a JAK2 epitope comprising the amino acid sequence of FCGDENILV (SEQ ID NO: 682). In some embodiments, the TCRs bind to a CALR epitope contained within the amino acid sequence (SEQ ID NO: 683)
MKDKQDEEQRTRRMMRTKMRMRRMRRTRRKMRRKMSPARPRTSCREACLQ

GWTEAAYEEAEDNCRRMMRTKAAY*VLNYGVCFC*AAY*FCGDENILV*, wherein the mutant CALR type 1 sequence is underlined, the mutant CALR type II sequence is underlined and bold, and the mutant JAK2 sequences are underlined an italics. In some embodiments, the TCRs bind to a mutJAK2 and mutCALR antigen construct comprising an amino acid sequence of SEQ ID NO: 702.

The disclosed TCRs may be identified based on T-cell binding to the CALR and JAK2 epitopes, followed by sequencing of the TCR. The TCRs may be obtained from as T cells. The TCRs may be further engineered to improve their affinity, stability, solubility, or the like. For example, TCRs may be cysteine stabilized, expressed as soluble TCRs, as single chain TCRs, as a fusion with N-terminal or C-terminal epitope tags, engineered to improve stability with mutations in hydrophobic core, such as positions 11, 13, 19, 21, 53, 76, 89, 91 or 94 of the a chain, or domain swapped with a and p chain variable and/or constant domains swapped as described in U.S. Pat. Nos. 7,329,731, 7,569,664, 9,133,264, 9,624,292, US2016/0130319 and U.S. Pat. No. 9,884,075.

Described herein are TCRs comprising an alpha chain and a beta chain, wherein the alpha chain comprises a CDR3 comprising an amino acid sequence provided in Table 4, and the beta chain comprises a CDR3 comprising a corresponding amino acid sequence provided in Table 5. (i.e. the beta chain CDR3 provided in Table 5 is in the same row number (row 1, for example) as the alpha chain CDR3 provided in Table 4 (row 1, for example)).

Also described herein are TCRs comprising an alpha chain and a beta chain, wherein the alpha chain comprises a CDR1 comprising an amino acid sequence provided in Table 4, a CDR2 comprising an amino acid sequence provided in Table 4, and a CDR3 comprising an amino acid sequence provided in Table 4, and the corresponding beta chain comprises a CDR1 comprising an amino acid sequence provided in Table 5, a CDR2 comprising an amino acid sequence provided in Table 5, and a CDR3 comprising an amino acid sequence provided in Table 5 (i.e. the beta chain CDRs provided in Table 5 are in the same row number (row 1, for example) as the alpha chain CDRs provided in Table 4 (row 1, for example)).

In certain embodiments, the alpha chain comprises a variable and joining (VJ) region comprising an amino acid sequence that is at least 90%, 95%, 96%, 97%, 98%, 99% or 100% identical to an amino acid sequence provided in Table 4, and the corresponding beta chain comprises a variable, diversity and joining (VDJ) region comprising an amino acid sequence that is at least 90%, 95%, 96%, 97%, 98%, 99% or 100% identical to an amino acid sequence provided in Table 5 (i.e. the beta chain VDJ region provided in Table 5 is in the same row number (row 1, for example) as the alpha chain VJ region provided in Table 4 (row 1, for example)).

In certain embodiments, the alpha chain comprises an amino acid sequence that is at least 90%, 95%, 96%, 97%, 98%, 99% or 100% identical to an amino acid sequence provided in Table 4, and the corresponding beta chain comprises an amino acid sequence that is at least 90%, 95%, 96%, 97%, 98%, 99% or 100% identical to an amino acid sequence provided in Table 5 (i.e. the beta chain provided in Table 5 is in the same row number (row 1, for example) as the alpha chain provided in Table 4 (row 1, for example)).

Described herein is a TCR comprising an alpha chain and a beta chain, wherein the alpha chain comprises a CDR3 comprising the amino acid sequence of SEQ ID NO: 7, and the beta chain comprises a CDR3 comprising the amino acid sequence of SEQ ID NO: 245. Also described herein is a TCR comprising an alpha chain and a beta chain, wherein the alpha chain comprises a CDR1 comprising the amino acid sequence of SEQ ID NO: 3, a CDR2 comprising the amino acid sequence of SEQ ID NO: 5, and a CDR3 comprising the amino acid sequence of SEQ ID NO: 7, and the beta chain comprises a CDR1 comprising the amino acid sequence of SEQ ID NO: 241, a CDR2 comprising the amino acid sequence of SEQ ID NO: 243, and a CDR3 comprising the amino acid sequence of SEQ ID NO: 245. In certain embodiments, the alpha chain comprises a VJ region comprising an amino acid sequence that is at least 90%, 95%, 96%, 97%, 98%, 99% or 100% identical to the amino acid sequence of SEQ ID NO: 479, and the beta chain comprises a VDJ region comprising an amino acid sequence that is at least 90%, 95%, 96%, 97%, 98%, 99% or 100% identical to the amino acid sequence of SEQ ID NO: 581. In certain embodiments, the alpha chain comprises an amino acid sequence that is at least 90%, 95%, 96%, 97%, 98%, 99% or 100% identical to the amino acid sequence of SEQ ID NO: 477, and the beta chain comprises an amino acid sequence that is at least 90%, 95%, 96%, 97%, 98%, 99% or 100% identical to the amino acid sequence of SEQ ID NO: 579.

Described herein is a TCR comprising an alpha chain and a beta chain, wherein the alpha chain comprises a CDR3 comprising the amino acid sequence of SEQ ID NO: 14, and the beta chain comprises a CDR3 comprising the amino acid sequence of SEQ ID NO: 252. Also described herein is a TCR comprising an alpha chain and a beta chain, wherein the alpha chain comprises a CDR1 comprising the amino acid sequence of SEQ ID NO: 10, a CDR2 comprising the amino acid sequence of SEQ ID NO: 12, and a CDR3 comprising the amino acid sequence of SEQ ID NO: 14, and the beta chain comprises a CDR1 comprising the amino acid sequence of SEQ ID NO: 248, a CDR2 comprising the amino acid sequence of SEQ ID NO: 250, and a CDR3 comprising the amino acid sequence of SEQ ID NO: 252. In certain embodiments, the alpha chain comprises a VJ region comprising an amino acid sequence that is at least 90%, 95%, 96%, 97%, 98%, 99% or 100% identical to the amino acid sequence of SEQ ID NO: 482, and the beta chain comprises a VJD region comprising an amino acid sequence that is at least 90%, 95%, 96%, 97%, 98%, 99% or 100% identical to the amino acid sequence of SEQ ID NO: 584. In certain embodiments, the alpha chain comprises an amino acid sequence that is at least 90%, 95%, 96%, 97%, 98%, 99% or 100% identical to the amino acid sequence of SEQ ID NO: 480, and the beta chain comprises an amino acid sequence that is at least 90%, 95%, 96%, 97%, 98%, 99% or 100% identical to the amino acid sequence of SEQ ID NO: 582.

Described herein is a TCR comprising an alpha chain and a beta chain, wherein the alpha chain comprises a CDR3 comprising the amino acid sequence of SEQ ID NO: 21, and the beta chain comprises a CDR3 comprising the amino acid sequence of SEQ ID NO: 259. Also described herein is a TCR comprising an alpha chain and a beta chain, wherein the alpha chain comprises a CDR1 comprising the amino acid sequence of SEQ ID NO: 17, a CDR2 comprising the amino acid sequence of SEQ ID NO: 19, and a CDR3 comprising the amino acid sequence of SEQ ID NO: 21, and the beta chain comprises a CDR1 comprising the amino acid sequence of SEQ ID NO: 255, a CDR2 comprising the amino acid sequence of SEQ ID NO: 257, and a CDR3 comprising the amino acid sequence of SEQ ID NO: 259. In certain embodiments, the alpha chain comprises a VJ region comprising an amino acid sequence that is at least 90%, 95%, 96%, 97%, 98%, 99% or 100% identical to the amino acid sequence of SEQ ID NO: 485, and the beta chain comprises a VJD region comprising an amino acid sequence that is at least 90%, 95%, 96%, 97%, 98%, 99% or 100% identical to the amino acid sequence of SEQ ID NO: 587. In certain embodiments, the alpha chain comprises an amino acid sequence that is at least 90%, 95%, 96%, 97%, 98%, 99% or 100% identical to the amino acid sequence of SEQ ID NO: 483, and the beta chain comprises an amino acid sequence that is at least 90%, 95%, 96%, 97%, 98%, 99% or 100% identical to the amino acid sequence of SEQ ID NO: 585.

Described herein is a TCR comprising an alpha chain and a beta chain, wherein the alpha chain comprises a CDR3 comprising the amino acid sequence of SEQ ID NO: 28, and the beta chain comprises a CDR3 comprising the amino acid sequence of SEQ ID NO: 266. Also described herein is a TCR comprising an alpha chain and a beta chain, wherein the alpha chain comprises a CDR1 comprising the amino acid sequence of SEQ ID NO: 24, a CDR2 comprising the amino acid sequence of SEQ ID NO: 26, and a CDR3 comprising the amino acid sequence of SEQ ID NO: 28, and the beta chain comprises a CDR1 comprising the amino acid sequence of SEQ ID NO: 262, a CDR2 comprising the amino acid sequence of SEQ ID NO: 264, and a CDR3 comprising the amino acid sequence of SEQ ID NO: 266. In certain embodiments, the alpha chain comprises a VJ region comprising an amino acid sequence that is at least 90%, 95%, 96%, 97%, 98%, 99% or 100% identical to the amino acid sequence of SEQ ID NO: 488, and the beta chain comprises a VJD region comprising an amino acid sequence that is at least 90%, 95%, 96%, 97%, 98%, 99% or 100% identical to the amino acid sequence of SEQ ID NO: 590. In certain embodiments, the alpha chain comprises an amino acid sequence that is at least 90%, 95%, 96%, 97%, 98%, 99% or 100% identical to the amino acid sequence of SEQ ID NO: 486, and the beta chain comprises an amino acid sequence that is at least 90%, 95%, 96%, 97%, 98%, 99% or 100% identical to the amino acid sequence of SEQ ID NO: 588.

Described herein is a TCR comprising an alpha chain and a beta chain, wherein the alpha chain comprises a CDR3 comprising the amino acid sequence of SEQ ID NO: 35, and the beta chain comprises a CDR3 comprising the amino acid sequence of SEQ ID NO: 273. Also described herein is a TCR comprising an alpha chain and a beta chain, wherein the alpha chain comprises a CDR1 comprising the amino acid sequence of SEQ ID NO: 31, a CDR2 comprising the amino acid sequence of SEQ ID NO: 33, and a CDR3 comprising the amino acid sequence of SEQ ID NO: 35, and the beta chain comprises a CDR1 comprising the amino acid sequence of SEQ ID NO: 269, a CDR2 comprising the amino acid sequence of SEQ ID NO: 271, and a CDR3 comprising the amino acid sequence of SEQ ID NO: 273. In certain embodiments, the alpha chain comprises a VJ region comprising an amino acid sequence that is at least 90%, 95%, 96%, 97%, 98%, 99% or 100% identical to the amino acid sequence of SEQ ID NO: 491, and the beta chain comprises a VJD region comprising an amino acid sequence that is at least 90%, 95%, 96%, 97%, 98%, 99% or 100% identical to the amino acid sequence of SEQ ID NO: 593. In certain embodiments, the alpha chain comprises an amino acid sequence that is at least 90%, 95%, 96%, 97%, 98%, 99% or 100% identical to the amino acid sequence of SEQ ID NO: 489, and the beta chain comprises an amino acid sequence that is at least 90%, 95%, 96%, 97%, 98%, 99% or 100% identical to the amino acid sequence of SEQ ID NO: 591.

Described herein is a TCR comprising an alpha chain and a beta chain, wherein the alpha chain comprises a CDR3 comprising the amino acid sequence of SEQ ID NO: 42, and the beta chain comprises a CDR3 comprising the amino acid sequence of SEQ ID NO: 280. Also described herein is a TCR comprising an alpha chain and a beta chain, wherein the alpha chain comprises a CDR1 comprising the amino acid sequence of SEQ ID NO: 38, a CDR2 comprising the amino acid sequence of SEQ ID NO: 40, and a CDR3 comprising the amino acid sequence of SEQ ID NO: 42, and the beta chain comprises a CDR1 comprising the amino acid sequence of SEQ ID NO: 276, a CDR2 comprising the amino acid sequence of SEQ ID NO: 278, and a CDR3 comprising the amino acid sequence of SEQ ID NO: 280. In certain embodiments, the alpha chain comprises a VJ region comprising an amino acid sequence that is at least 90%, 95%, 96%, 97%, 98%, 99% or 100% identical to the amino acid sequence of SEQ ID NO: 494, and the beta chain comprises a VJD region comprising an amino acid sequence that is at least 90%, 95%, 96%, 97%, 98%, 99% or 100% identical to the amino acid sequence of SEQ ID NO: 596. In certain embodiments, the alpha chain comprises an amino acid sequence that is at least 90%, 95%, 96%, 97%, 98%, 99% or 100% identical to the amino acid sequence of SEQ ID NO: 492, and the beta chain comprises an amino acid sequence that is at least 90%, 95%, 96%, 97%, 98%, 99% or 100% identical to the amino acid sequence of SEQ ID NO: 594.

Described herein is a TCR comprising an alpha chain and a beta chain, wherein the alpha chain comprises a CDR3 comprising the amino acid sequence of SEQ ID NO: 49, and the beta chain comprises a CDR3 comprising the amino acid sequence of SEQ ID NO: 287. Also described herein is a TCR comprising an alpha chain and a beta chain, wherein the alpha chain comprises a CDR1 comprising the amino acid sequence of SEQ ID NO: 45, a CDR2 comprising the amino acid sequence of SEQ ID NO: 47, and a CDR3 comprising the amino acid sequence of SEQ ID NO: 49, and the beta chain comprises a CDR1 comprising the amino acid sequence of SEQ ID NO: 283, a CDR2 comprising the amino acid sequence of SEQ ID NO: 285, and a CDR3 comprising the amino acid sequence of SEQ ID NO: 287. In certain embodiments, the alpha chain comprises a VJ region comprising an amino acid sequence that is at least 90%, 95%, 96%, 97%, 98%, 99% or 100% identical to the amino acid sequence of SEQ ID NO: 497, and the beta chain comprises a VJD region comprising an amino acid sequence that is at least 90%, 95%, 96%, 97%, 98%, 99% or 100% identical to the amino acid sequence of SEQ ID NO: 599. In certain embodiments, the alpha chain comprises an amino acid sequence that is at least 90%, 95%, 96%, 97%, 98%, 99% or 100% identical to the amino acid sequence of SEQ ID NO: 495, and the beta chain comprises an amino acid sequence that is at least 90%, 95%, 96%, 97%, 98%, 99% or 100% identical to the amino acid sequence of SEQ ID NO: 597.

Described herein is a TCR comprising an alpha chain and a beta chain, wherein the alpha chain comprises a CDR3 comprising the amino acid sequence of SEQ ID NO: 56, and the beta chain comprises a CDR3 comprising the amino acid sequence of SEQ ID NO: 294. Also described herein is a TCR comprising an alpha chain and a beta chain, wherein the alpha chain comprises a CDR1 comprising the amino acid sequence of SEQ ID NO: 52, a CDR2 comprising the amino acid sequence of SEQ ID NO: 54, and a CDR3 comprising the amino acid sequence of SEQ ID NO: 56, and the beta chain comprises a CDR1 comprising the amino acid sequence of SEQ ID NO: 290, a CDR2 comprising the amino acid sequence of SEQ ID NO: 292, and a CDR3 comprising the amino acid sequence of SEQ ID NO: 294. In certain embodiments, the alpha chain comprises a VJ region comprising an amino acid sequence that is at least 90%, 95%, 96%, 97%, 98%, 99% or 100% identical to the amino acid sequence of SEQ ID NO: 500, and the beta chain comprises a VJD region comprising an amino acid sequence that is at least 90%, 95%, 96%, 97%, 98%, 99% or 100% identical to the amino acid sequence of SEQ ID NO: 602. In certain embodiments, the alpha chain comprises an amino acid sequence that is at least 90%, 95%, 96%, 97%, 98%, 99% or 100% identical to the amino acid sequence of SEQ ID NO: 498, and the beta chain comprises an amino acid sequence that is at least 90%, 95%, 96%, 97%, 98%, 99% or 100% identical to the amino acid sequence of SEQ ID NO: 600.

Described herein is a TCR comprising an alpha chain and a beta chain, wherein the alpha chain comprises a CDR3 comprising the amino acid sequence of SEQ ID NO: 63, and the beta chain comprises a CDR3 comprising the amino acid sequence of SEQ ID NO: 301. Also described herein is a TCR comprising an alpha chain and a beta chain, wherein the alpha chain comprises a CDR1 comprising the amino acid sequence of SEQ ID NO: 59, a CDR2 comprising the amino acid sequence of SEQ ID NO: 61, and a CDR3 comprising the amino acid sequence of SEQ ID NO: 63, and the beta chain comprises a CDR1 comprising the amino acid sequence of SEQ ID NO: 297, a CDR2 comprising the amino acid sequence of SEQ ID NO: 299, and a CDR3 comprising the amino acid sequence of SEQ ID NO: 301. In certain embodiments, the alpha chain comprises a VJ region comprising an amino acid sequence that is at least 90%, 95%, 96%, 97%, 98%, 99% or 100% identical to the amino acid sequence of SEQ ID NO: 503, and the beta chain comprises a VJD region comprising an amino acid sequence that is at least 90%, 95%, 96%, 97%, 98%, 99% or 100% identical to the amino acid sequence of SEQ ID NO: 605. In certain embodiments, the alpha chain comprises an amino acid sequence that is at least 90%, 95%, 96%, 97%, 98%, 99% or 100% identical to the amino acid sequence of SEQ ID NO: 501, and the beta chain comprises an amino acid sequence that is at least 90%, 95%, 96%, 97%, 98%, 99% or 100% identical to the amino acid sequence of SEQ ID NO: 603.

Described herein is a TCR comprising an alpha chain and a beta chain, wherein the alpha chain comprises a CDR3 comprising the amino acid sequence of SEQ ID NO: 70, and the beta chain comprises a CDR3 comprising the amino acid sequence of SEQ ID NO: 308. Also described herein is a TCR comprising an alpha chain and a beta chain, wherein the alpha chain comprises a CDR1 comprising the amino acid sequence of SEQ ID NO: 66, a CDR2 comprising the amino acid sequence of SEQ ID NO: 68, and a CDR3 comprising the amino acid sequence of SEQ ID NO: 70, and the beta chain comprises a CDR1 comprising the amino acid sequence of SEQ ID NO: 304, a CDR2 comprising the amino acid sequence of SEQ ID NO: 306, and a CDR3 comprising the amino acid sequence of SEQ ID NO: 308. In certain embodiments, the alpha chain comprises a VJ region comprising an amino acid sequence that is at least 90%, 95%, 96%, 97%, 98%, 99% or 100% identical to the amino acid sequence of SEQ ID NO: 506, and the beta chain comprises a VJD region comprising an amino acid sequence that is at least 90%, 95%, 96%, 97%, 98%, 99% or 100% identical to the amino acid sequence of SEQ ID NO: 608. In certain embodiments, the alpha chain comprises an amino acid sequence that is at least 90%, 95%, 96%, 97%, 98%, 99% or 100% identical to the amino acid sequence of SEQ ID NO: 504, and the beta chain comprises an amino acid sequence that is at least 90%, 95%, 96%, 97%, 98%, 99% or 100% identical to the amino acid sequence of SEQ ID NO: 606.

Described herein is a TCR comprising an alpha chain and a beta chain, wherein the alpha chain comprises a CDR3 comprising the amino acid sequence of SEQ ID NO: 77, and the beta chain comprises a CDR3 comprising the amino acid sequence of SEQ ID NO: 315. Also described herein is a TCR comprising an alpha chain and a beta chain, wherein the alpha chain comprises a CDR1 comprising the amino acid sequence of SEQ ID NO: 73, a CDR2 comprising the amino acid sequence of SEQ ID NO: 75, and a CDR3 comprising the amino acid sequence of SEQ ID NO: 77, and the beta chain comprises a CDR1 comprising the amino acid sequence of SEQ ID NO: 311, a CDR2 comprising the amino acid sequence of SEQ ID NO: 313, and a CDR3 comprising the amino acid sequence of SEQ ID NO: 315. In certain embodiments, the alpha chain comprises a VJ region comprising an amino acid sequence that is at least 90%, 95%, 96%, 97%, 98%, 99% or 100% identical to the amino acid sequence of SEQ ID NO: 509, and the beta chain comprises a VJD region comprising an amino acid sequence that is at least 90%, 95%, 96%, 97%, 98%, 99% or 100% identical to the amino acid sequence of SEQ ID NO: 611. In certain embodiments, the alpha chain comprises an amino acid sequence that is at least 90%, 95%, 96%, 97%, 98%, 99% or 100% identical to the amino acid sequence of SEQ ID NO: 507, and the beta chain comprises an amino acid sequence that is at least 90%, 95%, 96%, 97%, 98%, 99% or 100% identical to the amino acid sequence of SEQ ID NO: 609.

Described herein is a TCR comprising an alpha chain and a beta chain, wherein the alpha chain comprises a CDR3 comprising the amino acid sequence of SEQ ID NO: 84, and the beta chain comprises a CDR3 comprising the amino acid sequence of SEQ ID NO: 322. Also described herein is a TCR comprising an alpha chain and a beta chain, wherein the alpha chain comprises a CDR1 comprising the amino acid sequence of SEQ ID NO: 80, a CDR2 comprising the amino acid sequence of SEQ ID NO: 82, and a CDR3 comprising the amino acid sequence of SEQ ID NO: 84, and the beta chain comprises a CDR1 comprising the amino acid sequence of SEQ ID NO: 318, a CDR2 comprising the amino acid sequence of SEQ ID NO: 320, and a CDR3 comprising the amino acid sequence of SEQ ID NO: 322. In certain embodiments, the alpha chain comprises a VJ region comprising an amino acid sequence that is at least 90%, 95%, 96%, 97%, 98%, 99% or 100% identical to the amino acid sequence of SEQ ID NO: 512, and the beta chain comprises a VJD region comprising an amino acid sequence that is at least 90%, 95%, 96%, 97%, 98%, 99% or 100% identical to the amino acid sequence of SEQ ID NO: 614. In certain embodiments, the alpha chain comprises an amino acid sequence that is at least 90%, 95%, 96%, 97%, 98%, 99% or 100% identical to the amino acid sequence of SEQ ID NO: 510, and the beta chain comprises an amino acid sequence that is at least 90%, 95%, 96%, 97%, 98%, 99% or 100% identical to the amino acid sequence of SEQ ID NO: 612.

Described herein is a TCR comprising an alpha chain and a beta chain, wherein the alpha chain comprises a CDR3 comprising the amino acid sequence of SEQ ID NO: 91, and the beta chain comprises a CDR3 comprising the amino acid sequence of SEQ ID NO: 329. Also described herein is a TCR comprising an alpha chain and a beta chain, wherein the alpha chain comprises a CDR1 comprising the amino acid sequence of SEQ ID NO: 87, a CDR2 comprising the amino acid sequence of SEQ ID NO: 89, and a CDR3 comprising the amino acid sequence of SEQ ID NO: 91, and the beta chain comprises a CDR1 comprising the amino acid sequence of SEQ ID NO: 325, a CDR2 comprising the amino acid sequence of SEQ ID NO: 327, and a CDR3 comprising the amino acid sequence of SEQ ID NO: 329. In certain embodiments, the alpha chain comprises a VJ region comprising an amino acid sequence that is at least 90%, 95%, 96%, 97%, 98%, 99% or 100% identical to the amino acid sequence of SEQ ID NO: 515, and the beta chain comprises a VJD region comprising an amino acid sequence that is at least 90%, 95%, 96%, 97%, 98%, 99% or 100% identical to the amino acid sequence of SEQ ID NO: 617. In certain embodiments, the alpha chain comprises an amino acid sequence that is at least 90%, 95%, 96%, 97%, 98%, 99% or 100% identical to the amino acid sequence of SEQ ID NO: 513, and the beta chain comprises an amino acid sequence that is at least 90%, 95%, 96%, 97%, 98%, 99% or 100% identical to the amino acid sequence of SEQ ID NO: 615.

Described herein is a TCR comprising an alpha chain and a beta chain, wherein the alpha chain comprises a CDR3 comprising the amino acid sequence of SEQ ID NO: 98, and the beta chain comprises a CDR3 comprising the amino acid sequence of SEQ ID NO: 336. Also described herein is a TCR comprising an alpha chain and a beta chain, wherein the alpha chain comprises a CDR1 comprising the amino acid sequence of SEQ ID NO: 94, a CDR2 comprising the amino acid sequence of SEQ ID NO: 96, and a CDR3 comprising the amino acid sequence of SEQ ID NO: 98, and the beta chain comprises a CDR1 comprising the amino acid sequence of SEQ ID NO: 332, a CDR2 comprising the amino acid sequence of SEQ ID NO: 334, and a CDR3 comprising the amino acid sequence of SEQ ID NO: 336. In certain embodiments, the alpha chain comprises a VJ region comprising an amino acid sequence that is at least 90%, 95%, 96%, 97%, 98%, 99% or 100% identical to the amino acid sequence of SEQ ID NO: 518, and the beta chain comprises a VJD region comprising an amino acid sequence that is at least 90%, 95%, 96%, 97%, 98%, 99% or 100% identical to the amino acid sequence of SEQ ID NO: 620. In certain embodiments, the alpha chain comprises an amino acid sequence that is at least 90%, 95%, 96%, 97%, 98%, 99% or 100% identical to the amino acid sequence of SEQ ID NO: 516, and the beta chain comprises an amino acid sequence that is at least 90%, 95%, 96%, 97%, 98%, 99% or 100% identical to the amino acid sequence of SEQ ID NO: 618.

Described herein is a TCR comprising an alpha chain and a beta chain, wherein the alpha chain comprises a CDR3 comprising the amino acid sequence of SEQ ID NO: 105, and the beta chain comprises a CDR3 comprising the amino acid sequence of SEQ ID NO: 343. Also described herein is a TCR comprising an alpha chain and a beta chain, wherein the alpha chain comprises a CDR1 comprising the amino acid sequence of SEQ ID NO: 101, a CDR2 comprising the amino acid sequence of SEQ ID NO: 103, and a CDR3 comprising the amino acid sequence of SEQ ID NO: 105, and the beta chain comprises a CDR1 comprising the amino acid sequence of SEQ ID NO: 339, a CDR2 comprising the amino acid sequence of SEQ ID NO: 341, and a CDR3 comprising the amino acid sequence of SEQ ID NO: 343. In certain embodiments, the alpha chain comprises a VJ region comprising an amino acid sequence that is at least 90%, 95%, 96%, 97%, 98%, 99% or 100% identical to the amino acid sequence of SEQ ID NO: 521, and the beta chain comprises a VJD region comprising an amino acid sequence that is at least 90%, 95%, 96%, 97%, 98%, 99% or 100% identical to the amino acid sequence of SEQ ID NO: 623. In certain embodiments, the alpha chain comprises an amino acid sequence that is at least 90%, 95%, 96%, 97%, 98%, 99% or 100% identical to the amino acid sequence of SEQ ID NO: 519, and the beta chain comprises an amino acid sequence that is at least 90%, 95%, 96%, 97%, 98%, 99% or 100% identical to the amino acid sequence of SEQ ID NO: 621.

Described herein is a TCR comprising an alpha chain and a beta chain, wherein the alpha chain comprises a CDR3 comprising the amino acid sequence of SEQ ID NO: 112, and the beta chain comprises a CDR3 comprising the amino acid sequence of SEQ ID NO: 350. Also described herein is a TCR comprising an alpha chain and a beta chain, wherein the alpha chain comprises a CDR1 comprising the amino acid sequence of SEQ ID NO: 108, a CDR2 comprising the amino acid sequence of SEQ ID NO: 110, and a CDR3 comprising the amino acid sequence of SEQ ID NO: 112, and the beta chain comprises a CDR1 comprising the amino acid sequence of SEQ ID NO: 346, a CDR2 comprising the amino acid sequence of SEQ ID NO: 348, and a CDR3 comprising the amino acid sequence of SEQ ID NO: 350. In certain embodiments, the alpha chain comprises a VJ region comprising an amino acid sequence that is at least 90%, 95%, 96%, 97%, 98%, 99% or 100% identical to the amino acid sequence of SEQ ID NO: 524, and the beta chain comprises a VJD region comprising an amino acid sequence that is at least 90%, 95%, 96%, 97%, 98%, 99% or 100% identical to the amino acid sequence of SEQ ID NO: 626. In certain embodiments, the alpha chain comprises an amino acid sequence that is at least 90%, 95%, 96%, 97%, 98%, 99% or 100% identical to the amino acid sequence of SEQ ID NO: 522, and the beta chain comprises an amino acid sequence that is at least 90%, 95%, 96%, 97%, 98%, 99% or 100% identical to the amino acid sequence of SEQ ID NO: 624.

Described herein is a TCR comprising an alpha chain and a beta chain, wherein the alpha chain comprises a CDR3 comprising the amino acid sequence of SEQ ID NO: 119, and the beta chain comprises a CDR3 comprising the amino acid sequence of SEQ ID NO: 357. Also described herein is a TCR comprising an alpha chain and a beta chain, wherein the alpha chain comprises a CDR1 comprising the amino acid sequence of SEQ ID NO: 115, a CDR2 comprising the amino acid sequence of SEQ ID NO: 117, and a CDR3 comprising the amino acid sequence of SEQ ID NO: 119, and the beta chain comprises a CDR1 comprising the amino acid sequence of SEQ ID NO: 353, a CDR2 comprising the amino acid sequence of SEQ ID NO: 355, and a CDR3 comprising the amino acid sequence of SEQ ID NO: 357. In certain embodiments, the alpha chain comprises a VJ region comprising an amino acid sequence that is at least 90%, 95%, 96%, 97%, 98%, 99% or 100% identical to the amino acid sequence of SEQ ID NO: 527, and the beta chain comprises a VJD region comprising an amino acid sequence that is at least 90%, 95%, 96%, 97%, 98%, 99% or 100% identical to the amino acid sequence of SEQ ID NO: 629. In certain embodiments, the alpha chain comprises an amino acid sequence that is at least 90%, 95%, 96%, 97%, 98%, 99% or 100% identical to the amino acid sequence of SEQ ID NO: 525, and the beta chain comprises an amino acid sequence that is at least 90%, 95%, 96%, 97%, 98%, 99% or 100% identical to the amino acid sequence of SEQ ID NO: 627.

Described herein is a TCR comprising an alpha chain and a beta chain, wherein the alpha chain comprises a CDR3 comprising the amino acid sequence of SEQ ID NO: 126, and the beta chain comprises a CDR3 comprising the amino acid sequence of SEQ ID NO: 364. Also described herein is a TCR comprising an alpha chain and a beta chain, wherein the alpha chain comprises a CDR1 comprising the amino acid sequence of SEQ ID NO: 122, a CDR2 comprising the amino acid sequence of SEQ ID NO: 124, and a CDR3 comprising the amino acid sequence of SEQ ID NO: 126, and the beta chain comprises a CDR1 comprising the amino acid sequence of SEQ ID NO: 360, a CDR2 comprising the amino acid sequence of SEQ ID NO: 362, and a CDR3 comprising the amino acid sequence of SEQ ID NO: 364. In certain embodiments, the alpha chain comprises a VJ region comprising an amino acid sequence that is at least 90%, 95%, 96%, 97%, 98%, 99% or 100% identical to the amino acid sequence of SEQ ID NO: 530, and the beta chain comprises a VJD region comprising an amino acid sequence that is at least 90%, 95%, 96%, 97%, 98%, 99% or 100% identical to the amino acid sequence of SEQ ID NO: 632. In certain embodiments, the alpha chain comprises an amino acid sequence that is at least 90%, 95%, 96%, 97%, 98%, 99% or 100% identical to the amino acid sequence of SEQ ID NO: 528, and the beta chain comprises an amino acid sequence that is at least 90%, 95%, 96%, 97%, 98%, 99% or 100% identical to the amino acid sequence of SEQ ID NO: 630.

Described herein is a TCR comprising an alpha chain and a beta chain, wherein the alpha chain comprises a CDR3 comprising the amino acid sequence of SEQ ID NO: 133, and the beta chain comprises a CDR3 comprising the amino acid sequence of SEQ ID NO: 371. Also described herein is a TCR comprising an alpha chain and a beta chain, wherein the alpha chain comprises a CDR1 comprising the amino acid sequence of SEQ ID NO: 129, a CDR2 comprising the amino acid sequence of SEQ ID NO: 131, and a CDR3 comprising the amino acid sequence of SEQ ID NO: 133, and the beta chain comprises a CDR1 comprising the amino acid sequence of SEQ ID NO: 367, a CDR2 comprising the amino acid sequence of SEQ ID NO: 369, and a CDR3 comprising the amino acid sequence of SEQ ID NO: 371. In certain embodiments, the alpha chain comprises a VJ region comprising an amino acid sequence that is at least 90%, 95%, 96%, 97%, 98%, 99% or 100% identical to the amino acid sequence of SEQ ID NO: 533, and the beta chain comprises a VJD region comprising an amino acid sequence that is at least 90%, 95%, 96%, 97%, 98%, 99% or 100% identical to the amino acid sequence of SEQ ID NO: 635. In certain embodiments, the alpha chain comprises an amino acid sequence that is at least 90%, 95%, 96%, 97%, 98%, 99% or 100% identical to the amino acid sequence of SEQ ID NO: 531, and the beta chain comprises an amino acid sequence that is at least 90%, 95%, 96%, 97%, 98%, 99% or 100% identical to the amino acid sequence of SEQ ID NO: 633.

Described herein is a TCR comprising an alpha chain and a beta chain, wherein the alpha chain comprises a CDR3 comprising the amino acid sequence of SEQ ID NO: 140, and the beta chain comprises a CDR3 comprising the amino acid sequence of SEQ ID NO: 378. Also described herein is a TCR comprising an alpha chain and a beta chain, wherein the alpha chain comprises a CDR1 comprising the amino acid sequence of SEQ ID NO: 136, a CDR2 comprising the amino acid sequence of SEQ ID NO: 138, and a CDR3 comprising the amino acid sequence of SEQ ID NO: 140, and the beta chain comprises a CDR1 comprising the amino acid sequence of SEQ ID NO: 374, a CDR2 comprising the amino acid sequence of SEQ ID NO: 376, and a CDR3 comprising the amino acid sequence of SEQ ID NO: 378. In certain embodiments, the alpha chain comprises a VJ region comprising an amino acid sequence that is at least 90%, 95%, 96%, 97%, 98%, 99% or 100% identical to the amino acid sequence of SEQ ID NO: 536, and the beta chain comprises a VJD region comprising an amino acid sequence that is at least 90%, 95%, 96%, 97%, 98%, 99% or 100% identical to the amino acid sequence of SEQ ID NO: 638. In certain embodiments, the alpha chain comprises an amino acid sequence that is at least 90%, 95%, 96%, 97%, 98%, 99% or 100% identical to the amino acid sequence of SEQ ID NO: 534, and the beta chain comprises an amino acid sequence that is at least 90%, 95%, 96%, 97%, 98%, 99% or 100% identical to the amino acid sequence of SEQ ID NO: 636.

Described herein is a TCR comprising an alpha chain and a beta chain, wherein the alpha chain comprises a CDR3 comprising the amino acid sequence of SEQ ID NO: 147, and the beta chain comprises a CDR3 comprising the amino acid sequence of SEQ ID NO: 385. Also described herein is a TCR comprising an alpha chain and a beta chain, wherein the alpha chain comprises a CDR1 comprising the amino acid sequence of SEQ ID NO: 143, a CDR2 comprising the amino acid sequence of SEQ ID NO: 145, and a CDR3 comprising the amino acid sequence of SEQ ID NO: 147, and the beta chain comprises a CDR1 comprising the amino acid sequence of SEQ ID NO: 381, a CDR2 comprising the amino acid sequence of SEQ ID NO: 383, and a CDR3 comprising the amino acid sequence of SEQ ID NO: 385. In certain embodiments, the alpha chain comprises a VJ region comprising an amino acid sequence that is at least 90%, 95%, 96%, 97%, 98%, 99% or 100% identical to the amino acid sequence of SEQ ID NO: 539, and the beta chain comprises a VJD region comprising an amino acid sequence that is at least 90%, 95%, 96%, 97%, 98%, 99% or 100% identical to the amino acid sequence of SEQ ID NO: 641. In certain embodiments, the alpha chain comprises an amino acid sequence that is at least 90%, 95%, 96%, 97%, 98%, 99% or 100% identical to the amino acid sequence of SEQ ID NO: 537, and the beta chain comprises an amino acid sequence that is at least 90%, 95%, 96%, 97%, 98%, 99% or 100% identical to the amino acid sequence of SEQ ID NO: 639.

Described herein is a TCR comprising an alpha chain and a beta chain, wherein the alpha chain comprises a CDR3 comprising the amino acid sequence of SEQ ID NO: 154, and the beta chain comprises a CDR3 comprising the amino acid sequence of SEQ ID NO: 392. Also described herein is a TCR comprising an alpha chain and a beta chain, wherein the alpha chain comprises a CDR1 comprising the amino acid sequence of SEQ ID NO: 150, a CDR2 comprising the amino acid sequence of SEQ ID NO: 152, and a CDR3 comprising the amino acid sequence of SEQ ID NO: 154, and the beta chain comprises a CDR1 comprising the amino acid sequence of SEQ ID NO: 388, a CDR2 comprising the amino acid sequence of SEQ ID NO: 390, and a CDR3 comprising the amino acid sequence of SEQ ID NO: 392. In certain embodiments, the alpha chain comprises a VJ region comprising an amino acid sequence that is at least 90%, 95%, 96%, 97%, 98%, 99% or 100% identical to the amino acid sequence of SEQ ID NO: 542, and the beta chain comprises a VJD region comprising an amino acid sequence that is at least 90%, 95%, 96%, 97%, 98%, 99% or 100% identical to the amino acid sequence of SEQ ID NO: 644. In certain embodiments, the alpha chain comprises an amino acid sequence that is at least 90%, 95%, 96%, 97%, 98%, 99% or 100% identical to the amino acid sequence of SEQ ID NO: 540, and the beta chain comprises an amino acid sequence that is at least 90%, 95%, 96%, 97%, 98%, 99% or 100% identical to the amino acid sequence of SEQ ID NO: 642.

Described herein is a TCR comprising an alpha chain and a beta chain, wherein the alpha chain comprises a CDR3 comprising the amino acid sequence of SEQ ID NO: 161, and the beta chain comprises a CDR3 comprising the amino acid sequence of SEQ ID NO: 399. Also described herein is a TCR comprising an alpha chain and a beta chain, wherein the alpha chain comprises a CDR1 comprising the amino acid sequence of SEQ ID NO: 157, a CDR2 comprising the amino acid sequence of SEQ ID NO: 159, and a CDR3 comprising the amino acid sequence of SEQ ID NO: 161, and the beta chain comprises a CDR1 comprising the amino acid sequence of SEQ ID NO: 395, a CDR2 comprising the amino acid sequence of SEQ ID NO: 397, and a CDR3 comprising the amino acid sequence of SEQ ID NO: 399. In certain embodiments, the alpha chain comprises a VJ region comprising an amino acid sequence that is at least 90%, 95%, 96%, 97%, 98%, 99% or 100% identical to the amino acid sequence of SEQ ID NO: 545, and the beta chain comprises a VJD region comprising an amino acid sequence that is at least 90%, 95%, 96%, 97%, 98%, 99% or 100% identical to the amino acid sequence of SEQ ID NO: 647. In certain embodiments, the alpha chain comprises an amino acid sequence that is at least 90%, 95%, 96%, 97%, 98%, 99% or 100% identical to the amino acid sequence of SEQ ID NO: 543, and the beta chain comprises an amino acid sequence that is at least 90%, 95%, 96%, 97%, 98%, 99% or 100% identical to the amino acid sequence of SEQ ID NO: 645.

Described herein is a TCR comprising an alpha chain and a beta chain, wherein the alpha chain comprises a CDR3 comprising the amino acid sequence of SEQ ID NO: 168, and the beta chain comprises a CDR3 comprising the amino acid sequence of SEQ ID NO: 406. Also described herein is a TCR comprising an alpha chain and a beta chain, wherein the alpha chain comprises a CDR1 comprising the amino acid sequence of SEQ ID NO: 164, a CDR2 comprising the amino acid sequence of SEQ ID NO: 166, and a CDR3 comprising the amino acid sequence of SEQ ID NO: 168, and the beta chain comprises a CDR1 comprising the amino acid sequence of SEQ ID NO: 402, a CDR2 comprising the amino acid sequence of SEQ ID NO: 404, and a CDR3 comprising the amino acid sequence of SEQ ID NO: 406. In certain embodiments, the alpha chain comprises a VJ region comprising an amino acid sequence that is at least 90%, 95%, 96%, 97%, 98%, 99% or 100% identical to the amino acid sequence of SEQ ID NO: 548, and the beta chain comprises a VJD region comprising an amino acid sequence that is at least 90%, 95%, 96%, 97%, 98%, 99% or 100% identical to the amino acid sequence of SEQ ID NO: 650. In certain embodiments, the alpha chain comprises an amino acid sequence that is at least 90%, 95%, 96%, 97%, 98%, 99% or 100% identical to the amino acid sequence of SEQ ID NO: 546, and the beta chain comprises an amino acid sequence that is at least 90%, 95%, 96%, 97%, 98%, 99% or 100% identical to the amino acid sequence of SEQ ID NO: 648.

Described herein is a TCR comprising an alpha chain and a beta chain, wherein the alpha chain comprises a CDR3 comprising the amino acid sequence of SEQ ID NO: 175, and the beta chain comprises a CDR3 comprising the amino acid sequence of SEQ ID NO: 413. Also described herein is a TCR comprising an alpha chain and a beta chain, wherein the alpha chain comprises a CDR1 comprising the amino acid sequence of SEQ ID NO: 171, a CDR2 comprising the amino acid sequence of SEQ ID NO: 173, and a CDR3 comprising the amino acid sequence of SEQ ID NO: 175, and the beta chain comprises a CDR1 comprising the amino acid sequence of SEQ ID NO: 409, a CDR2 comprising the amino acid sequence of SEQ ID NO: 411, and a CDR3 comprising the amino acid sequence of SEQ ID NO: 413. In certain embodiments, the alpha chain comprises a VJ region comprising an amino acid sequence that is at least 90%, 95%, 96%, 97%, 98%, 99% or 100% identical to the amino acid sequence of SEQ ID NO: 551, and the beta chain comprises a VJD region comprising an amino acid sequence that is at least 90%, 95%, 96%, 97%, 98%, 99% or 100% identical to the amino acid sequence of SEQ ID NO: 653. In certain embodiments, the alpha chain comprises an amino acid sequence that is at least 90%, 95%, 96%, 97%, 98%, 99% or 100% identical to the amino acid sequence of SEQ ID NO: 549, and the beta chain comprises an amino acid sequence that is at least 90%, 95%, 96%, 97%, 98%, 99% or 100% identical to the amino acid sequence of SEQ ID NO: 651.

Described herein is a TCR comprising an alpha chain and a beta chain, wherein, the alpha chain comprises a CDR3 comprising the amino acid sequence of SEQ ID NO: 182, and the beta chain comprises a CDR3 comprising the amino acid sequence of SEQ ID NO: 420. Also described herein is a TCR comprising an alpha chain and a beta chain, wherein the alpha chain comprises a CDR1 comprising the amino acid sequence of SEQ ID NO: 178, a CDR2 comprising the amino acid sequence of SEQ ID NO: 180, and a CDR3 comprising the amino acid sequence of SEQ ID NO: 182, and the beta chain comprises a CDR1 comprising the amino acid sequence of SEQ ID NO: 416, a CDR2 comprising the amino acid sequence of SEQ ID NO: 418, and a CDR3 comprising the amino acid sequence of SEQ ID NO: 420. In certain embodiments, the alpha chain comprises a VJ region comprising an amino acid sequence that is at least 90%, 95%, 96%, 97%, 98%, 99% or 100% identical to the amino acid sequence of SEQ ID NO: 554, and the beta chain comprises a VJD region comprising an amino acid sequence that is at least 90%, 95%, 96%, 97%, 98%, 99% or 100% identical to the amino acid sequence of SEQ ID NO: 656. In certain embodiments, the alpha chain comprises an amino acid sequence that is at least 90%, 95%, 96%, 97%, 98%, 99% or 100% identical to the amino acid sequence of SEQ ID NO: 552, and the beta chain comprises an amino acid sequence that is at least 90%, 95%, 96%, 97%, 98%, 99% or 100% identical to the amino acid sequence of SEQ ID NO: 654.

Described herein is a TCR comprising an alpha chain and a beta chain, wherein the alpha chain comprises a CDR3 comprising the amino acid sequence of SEQ ID NO: 189, and the beta chain comprises a CDR3 comprising the amino acid sequence of SEQ ID NO: 427. Also described herein is a TCR comprising an alpha chain and a beta chain, wherein the alpha chain comprises a CDR1 comprising the amino acid sequence of SEQ ID NO: 185, a CDR2 comprising the amino acid sequence of SEQ ID NO: 187, and a CDR3 comprising the amino acid sequence of SEQ ID NO: 189, and the beta chain comprises a CDR1 comprising the amino acid sequence of SEQ ID NO: 423, a CDR2 comprising the amino acid sequence of SEQ ID NO: 425, and a CDR3 comprising the amino acid sequence of SEQ ID NO: 427. In certain embodiments, the alpha chain comprises a VJ region comprising an amino acid sequence that is at least 90%, 95%, 96%, 97%, 98%, 99% or 100% identical to the amino acid sequence of SEQ ID NO: 557, and the beta chain comprises a VJD region comprising an amino acid sequence that is at least 90%, 95%, 96%, 97%, 98%, 99% or 100% identical to the amino acid sequence of SEQ ID NO: 659. In certain embodiments, the alpha chain comprises an amino acid sequence that is at least 90%, 95%, 96%, 97%, 98%, 99% or 100% identical to the amino acid sequence of SEQ ID NO: 555, and the beta chain comprises an amino acid sequence that is at least 90%, 95%, 96%, 97%, 98%, 99% or 100% identical to the amino acid sequence of SEQ ID NO: 657.

Described herein is a TCR comprising an alpha chain and a beta chain, wherein, the alpha chain comprises a CDR3 comprising the amino acid sequence of SEQ ID NO: 196, and the beta chain comprises a CDR3 comprising the amino acid sequence of SEQ ID NO: 434. Also described herein is a TCR comprising an alpha chain and a beta chain, wherein the alpha chain comprises a CDR1 comprising the amino acid sequence of SEQ ID NO: 192, a CDR2 comprising the amino acid sequence of SEQ ID NO: 194, and a CDR3 comprising the amino acid sequence of SEQ ID NO: 196, and the beta chain comprises a CDR1 comprising the amino acid sequence of SEQ ID NO: 430, a CDR2 comprising the amino acid sequence of SEQ ID NO: 432, and a CDR3 comprising the amino acid sequence of SEQ ID NO: 434. In certain embodiments, the alpha chain comprises a VJ region comprising an amino acid sequence that is at least 90%, 95%, 96%, 97%, 98%, 99% or 100% identical to the amino acid sequence of SEQ ID NO: 560, and the beta chain comprises a VJD region comprising an amino acid sequence that is at least 90%, 95%, 96%, 97%, 98%, 99% or 100% identical to the amino acid sequence of SEQ ID NO: 662. In certain embodiments, the alpha chain comprises an amino acid sequence that is at least 90%, 95%, 96%, 97%, 98%, 99% or 100% identical to the amino acid sequence of SEQ ID NO: 558, and the beta chain comprises an amino acid sequence that is at least 90%, 95%, 96%, 97%, 98%, 99% or 100% identical to the amino acid sequence of SEQ ID NO: 660.

Described herein is a TCR comprising an alpha chain and a beta chain, wherein the alpha chain comprises a CDR3 comprising the amino acid sequence of SEQ ID NO: 203, and the beta chain comprises a CDR3 comprising the amino acid sequence of SEQ ID NO: 441. Also described herein is a TCR comprising an alpha chain and a beta chain, wherein the alpha chain comprises a CDR1 comprising the amino acid sequence of SEQ ID NO: 199, a CDR2 comprising the amino acid sequence of SEQ ID NO: 201, and a CDR3 comprising the amino acid sequence of SEQ ID NO: 203, and the beta chain comprises a CDR1 comprising the amino acid sequence of SEQ ID NO: 437, a CDR2 comprising the amino acid sequence of SEQ ID NO: 439, and a CDR3 comprising the amino acid sequence of SEQ ID NO: 441. In certain embodiments, the alpha chain comprises a VJ region comprising an amino acid sequence that is at least 90%, 95%, 96%, 97%, 98%, 99% or 100% identical to the amino acid sequence of SEQ ID NO: 563, and the beta chain comprises a VJD region comprising an amino acid sequence that is at least 90%, 95%, 96%, 97%, 98%, 99% or 100% identical to the amino acid sequence of SEQ ID NO: 665. In certain embodiments, the alpha chain comprises an amino acid sequence that is at least 90%, 95%, 96%, 97%, 98%, 99% or 100% identical to the amino acid sequence of SEQ ID NO: 561, and the beta chain of comprises an amino acid sequence that is at least 90%, 95%, 96%, 97%, 98%, 99% or 100% identical to the amino acid sequence of SEQ ID NO: 663.

Described herein is a TCR comprising an alpha chain and a beta chain, wherein the alpha chain comprises a CDR3 comprising the amino acid sequence of SEQ ID NO: 210, and the beta chain comprises a CDR3 comprising the amino acid sequence of SEQ ID NO: 448. Also described herein is a TCR comprising an alpha chain and a beta chain, wherein the alpha chain comprises a CDR1 comprising the amino acid sequence of SEQ ID NO: 206, a CDR2 comprising the amino acid sequence of SEQ ID NO: 208, and a CDR3 comprising the amino acid sequence of SEQ ID NO: 210, and the beta chain comprises a CDR1 comprising the amino acid sequence of SEQ ID NO: 444, a CDR2 comprising the amino acid sequence of SEQ ID NO: 446, and a CDR3 comprising the amino acid sequence of SEQ ID NO: 448. In certain embodiments, the alpha chain comprises a VJ region comprising an amino acid sequence that is at least 90%, 95%, 96%, 97%, 98%, 99% or 100% identical to the amino acid sequence of SEQ ID NO: 566, and the beta chain comprises a VJD region comprising an amino acid sequence that is at least 90%, 95%, 96%, 97%, 98%, 99% or 100% identical to the amino acid sequence of SEQ ID NO: 668. In certain embodiments, the alpha chain comprises an amino acid sequence that is at least 90%, 95%, 96%, 97%, 98%, 99% or 100% identical to the amino acid sequence of SEQ ID NO: 564, and the beta chain comprises an amino acid sequence that is at least 90%, 95%, 96%, 97%, 98%, 99% or 100% identical to the amino acid sequence of SEQ ID NO: 666.

Described herein is a TCR comprising an alpha chain and a beta chain, wherein the alpha chain comprises a CDR3 comprising the amino acid sequence of SEQ ID NO: 217, and the beta chain comprises a CDR3 comprising the amino acid sequence of SEQ ID NO: 455. Also described herein is a TCR comprising an alpha chain and a beta chain, wherein the alpha chain comprises a CDR1 comprising the amino acid sequence of SEQ ID NO: 213, a CDR2 comprising the amino acid sequence of SEQ ID NO: 215, and a CDR3 comprising the amino acid sequence of SEQ ID NO: 217, and the beta chain comprises a CDR1 comprising the amino acid sequence of SEQ ID NO: 451, a CDR2 comprising the amino acid sequence of SEQ ID NO: 453, and a CDR3 comprising the amino acid sequence of SEQ ID NO: 455. In certain embodiments, the alpha chain comprises a VJ region comprising an amino acid sequence that is at least 90%, 95%, 96%, 97%, 98%, 99% or 100% identical to the amino acid sequence of SEQ ID NO: 569, and the beta chain comprises a VJD region comprising an amino acid sequence that is at least 90%, 95%, 96%, 97%, 98%, 99% or 100% identical to the amino acid sequence of SEQ ID NO: 671. In certain embodiments, the alpha chain comprises an amino acid sequence that is at least 90%, 95%, 96%, 97%, 98%, 99% or 100% identical to the amino acid sequence of SEQ ID NO: 567, and the beta chain comprises an amino acid sequence that is at least 90%, 95%, 96%, 97%, 98%, 99% or 100% identical to the amino acid sequence of SEQ ID NO: 669.

Described herein is a TCR comprising an alpha chain and a beta chain, wherein the alpha chain comprises a CDR3 comprising the amino acid sequence of SEQ ID NO: 224, and the beta chain comprises a CDR3 comprising the amino acid sequence of SEQ ID NO: 462. Also described herein is a TCR comprising an alpha chain and a beta chain, wherein the alpha chain comprises a CDR1 comprising the amino acid sequence of SEQ ID NO: 220, a CDR2 comprising the amino acid sequence of SEQ ID NO: 222, and a CDR3 comprising the amino acid sequence of SEQ ID NO: 224, and the beta chain comprises a CDR1 comprising the amino acid sequence of SEQ ID NO: 458, a CDR2 comprising the amino acid sequence of SEQ ID NO: 460, and a CDR3 comprising the amino acid sequence of SEQ ID NO: 462. In certain embodiments, the alpha chain comprises a VJ region comprising an amino acid sequence that is at least 90%, 95%, 96%, 97%, 98%, 99% or 100% identical to the amino acid sequence of SEQ ID NO: 572, and the beta chain comprises a VJD region comprising an amino acid sequence that is at least 90%, 95%, 96%, 97%, 98%, 99% or 100% identical to the amino acid sequence of SEQ ID NO: 674. In certain embodiments, the alpha chain comprises an amino acid sequence that is at least 90%, 95%, 96%, 97%, 98%, 99% or 100% identical to the amino acid sequence of SEQ ID NO: 570, and the beta chain comprises an amino acid sequence that is at least 90%, 95%, 96%, 97%, 98%, 99% or 100% identical to the amino acid sequence of SEQ ID NO: 672.

Described herein is a TCR comprising an alpha chain and a beta chain, wherein the alpha chain comprises a CDR3 comprising the amino acid sequence of SEQ ID NO: 231, and the beta chain comprises a CDR3 comprising the amino acid sequence of SEQ ID NO: 469. Also described herein is a TCR comprising an alpha chain and a beta chain, wherein the alpha chain comprises a CDR1 comprising the amino acid sequence of SEQ ID NO: 227, a CDR2 comprising the amino acid sequence of SEQ ID NO: 229, and a CDR3 comprising the amino acid sequence of SEQ ID NO: 231, and the beta chain comprises a CDR1 comprising the amino acid sequence of SEQ ID NO: 465, a CDR2 comprising the amino acid sequence of SEQ ID NO: 467, and a CDR3 comprising the amino acid sequence of SEQ ID NO: 469. In certain embodiments, the alpha chain comprises a VJ region comprising an amino acid sequence that is at least 90%, 95%, 96%, 97%, 98%, 99% or 100% identical to the amino acid sequence of SEQ ID NO: 575, and the beta chain comprises a VJD region comprising an amino acid sequence that is at least 90%, 95%, 96%, 97%, 98%, 99% or 100% identical to the amino acid sequence of SEQ ID NO: 677. In certain embodiments, the alpha chain comprises an amino acid sequence that is at least 90%, 95%, 96%, 97%, 98%, 99% or 100% identical to the amino acid sequence of SEQ ID NO: 573, and the beta chain comprises an amino acid sequence that is at least 90%, 95%, 96%, 97%, 98%, 99% or 100% identical to the amino acid sequence of SEQ ID NO: 675.

Described herein is a TCR comprising an alpha chain and a beta chain, wherein, the alpha chain comprises a CDR3 comprising the amino acid sequence of SEQ ID NO: 238, and the beta chain comprises a CDR3 comprising the amino acid sequence of SEQ ID NO: 476. Also described herein is a TCR comprising an alpha chain and a beta chain, wherein the alpha chain comprises a CDR1 comprising the amino acid sequence of SEQ ID NO: 234, a CDR2 comprising the amino acid sequence of SEQ ID NO: 236, and a CDR3 comprising the amino acid sequence of SEQ ID NO: 238, and the beta chain comprises a CDR1 comprising the amino acid sequence of SEQ ID NO: 472, a CDR2 comprising the amino acid sequence of SEQ ID NO: 474, and a CDR3 comprising the amino acid sequence of SEQ ID NO: 476. In certain embodiments, the alpha chain comprises a VJ region comprising an amino acid sequence that is at least 90%, 95%, 96%, 97%, 98%, 99% or 100% identical to the amino acid sequence of SEQ ID NO: 578, and the beta chain comprises a VJD region comprising an amino acid sequence that is at least 90%, 95%, 96%, 97%, 98%, 99% or 100% identical to the amino acid sequence of SEQ ID NO: 680. In certain embodiments, the alpha chain comprises an amino acid sequence that is at least 90%, 95%, 96%, 97%, 98%, 99% or 100% identical to the amino acid sequence of SEQ ID NO: 576, and the beta chain comprises an amino acid sequence that is at least 90%, 95%, 96%, 97%, 98%, 99% or 100% identical to the amino acid sequence of SEQ ID NO: 678.

Polynucleotides

The disclosure also provides polynucleotides that encode any of the disclosed TCRs.

Described herein are polynucleotides that encode a TCR comprising an alpha chain and a beta chain, wherein the alpha chain comprises a CDR3 comprising an amino acid sequence provided in Table 4, and the corresponding beta chain comprises a CDR3 comprising a corresponding amino acid sequence provided in Table 5. Described herein are polynucleotides that encode a TCR comprising an alpha chain and a beta chain, wherein the alpha chain comprises a CDR3 that is encoded by a nucleic acid sequence provided in Table 4, and the corresponding beta chain comprises a CDR3 that is encoded by a corresponding nucleic acid sequence provided in Table 5 (i.e. the beta chain CDR3 provided in Table 5 is in the same row number (row 1, for example) as the alpha chain CDR3 provided in Table 4 (row 1, for example)).

Also described herein are polynucleotides that encode a TCR comprising an alpha chain and a beta chain, wherein the alpha chain comprises a CDR1 comprising the amino acid sequence provided in Table 4, a CDR2 comprising an amino acid sequence provided in Table 4, and a CDR3 comprising an amino acid sequence provided in Table 4, and the corresponding beta chain comprises a CDR1 comprising an amino acid sequence provided in Table 5, a CDR2 comprising an amino acid sequence provided in Table 5, and a CDR3 comprising an amino acid sequence provided in Table 5. Also described herein are polynucleotides that encode a TCR comprising an alpha chain and a beta chain, wherein the alpha chain comprises a CDR1 that is encoded by a nucleic acid sequence provided in Table 4, a CDR2 that is encoded by a nucleic acid sequence provided in Table 4, and a CDR3 that is encoded by a nucleic acid sequence provided in Table 4, and the corresponding beta chain comprises a CDR1 that is encoded by a nucleic acid sequence provided in Table 5, a CDR2 that is encoded by a nucleic acid sequence provided in Table 5, and a CDR3 that is encoded by a nucleic acid sequence provided in Table 5 (i.e. the beta chain CDRs provided in Table 5 are in the same row number (row 1, for example) as the alpha chain CDRs provided in Table 4 (row 1, for example)).

Also described herein are polynucleotides that encode a TCR comprising an alpha chain and a beta chain, wherein the alpha chain comprises a VJ region comprising an amino acid sequence that is at least 90%, 95%, 96%, 97%, 98%, 99% or 100% identical to an amino acid sequence provided in Table 4, and the corresponding beta chain comprises a VDJ region comprising an amino acid sequence that is at least 90%, 95%, 96%, 97%, 98%, 99% or 100% identical to an amino acid sequence provided in Table 5. Also described herein are polynucleotides that encode a TCR comprising an alpha chain and a beta chain, wherein the alpha chain comprises a VJ region that is encoded by a nucleic acid sequence that is at least 90%, 95%, 96%, 97%, 98%, 99% or 100% identical to a nucleic acid sequence provided in Table 4, and the corresponding beta chain comprises a VDJ region that is encoded by a nucleic acid sequence that is at least 90%, 95%, 96%, 97%, 98%, 99% or 100% identical to a nucleic acid sequence provided in Table 5 (i.e. the beta chain VDJ region provided in Table 5 is in the same row number (row 1, for example) as the alpha chain VJ region provided in Table 4 (row 1, for example)).

Also described herein are polynucleotides that encode a TCR comprising an alpha chain and a beta chain, wherein the alpha chain comprises an amino acid sequence that is at least 90%, 95%, 96%, 97%, 98%, 99% or 100% identical to an amino acid sequence provided in Table 4, and the corresponding beta chain comprises an amino acid sequence that is at least 90%, 95%, 96%, 97%, 98%, 99% or 100% identical to an amino acid sequence provided in Table 5. Also described herein are polynucleotides that encode a TCR comprising an alpha chain and a beta chain, wherein the alpha chain is encoded by a nucleic acid sequence that is at least 90%, 95%, 96%, 97%, 98%, 99% or 100% identical to a nucleic acid sequence provided in Table 4, and the corresponding beta chain is encoded by a nucleic acid sequence that is at least 90%, 95%, 96%, 97%, 98%, 99% or 100% identical to a nucleic acid sequence provided in Table 5 (i.e. the beta chain provided in Table 5 is in the same row number (row 1, for example) as the alpha chain provided in Table 4 (row 1, for example)).

Described herein are polynucleotides that encode a TCR comprising an alpha chain and a beta chain, wherein the alpha chain comprises a CDR3 that is encoded by the nucleic acid sequence of SEQ ID NO: 6, and the beta chain comprises a CDR3 that is encoded by the nucleic acid sequence of SEQ ID NO: 244. Also described herein are polynucleotides that encode a TCR comprising an alpha chain and a beta chain, wherein the alpha chain comprises a CDR1 that is encoded by the nucleic acid sequence of SEQ ID NO: 2, a CDR2 that is encoded by the nucleic acid sequence of SEQ ID NO: 4, and a CDR3 that is encoded by the nucleic acid sequence of SEQ ID NO: 6, and the beta chain comprises a CDR1 that is encoded by the nucleic acid sequence of SEQ ID NO: 240, a CDR2 that is encoded by the nucleic acid sequence of SEQ ID NO: 242, and a CDR3 that is encoded by the nucleic acid sequence of SEQ ID NO: 244. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 478, and the beta chain comprises a variable, diversity and joining (VDJ) region that is encoded by a nucleic acid sequence that is at least 90%, 95%, 96%, 97%, 98%, 99% or 100% identical to the nucleic acid sequence of SEQ ID NO: 580. In certain embodiments, the alpha chain is encoded by a nucleic acid sequence that is at least 90%, 95%, 96%, 97%, 98%, 99% or 100% identical to the nucleic acid sequence of SEQ ID NO: 1, and the beta chain is encoded by a nucleic acid sequence that is at least 90%, 95%, 96%, 97%, 98%, 99% or 100% identical to the nucleic acid sequence of SEQ ID NO: 239.

Described herein are polynucleotides that encode a TCR comprising an alpha chain and a beta chain, wherein the alpha chain comprises a CDR3 that is encoded by the nucleic acid sequence of SEQ ID NO: 13, and the beta chain comprises a CDR3 that is encoded by the nucleic acid sequence of SEQ ID NO: 251. Also described herein are polynucleotides that encode a TCR comprising an alpha chain and a beta chain, wherein the alpha chain comprises a CDR1 that is encoded by the nucleic acid sequence of SEQ ID NO: 9, a CDR2 that is encoded by the nucleic acid sequence of SEQ ID NO: 11, and a CDR3 that is encoded by the nucleic acid sequence of SEQ ID NO: 13, and the beta chain comprises a CDR1 that is encoded by the nucleic acid sequence of SEQ ID NO: 247, a CDR2 that is encoded by the nucleic acid sequence of SEQ ID NO: 249, and a CDR3 that is encoded by the nucleic acid sequence of SEQ ID NO: 251. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 481, and the beta chain comprises a VJD region that is encoded by a nucleic acid sequence that is at least 90%, 95%, 96%, 97%, 98%, 99% or 100% identical to the nucleic acid sequence of SEQ ID NO: 583. In certain embodiments, the alpha chain of is encoded by a nucleic acid sequence that is at least 90%, 95%, 96%, 97%, 98%, 99% or 100% identical to the nucleic acid sequence of SEQ ID NO: 8, and the beta chain is encoded by a nucleic acid sequence that is at least 90%, 95%, 96%, 97%, 98%, 99% or 100% identical to the nucleic acid sequence of SEQ ID NO: 246.

Described herein are polynucleotides that encode a TCR comprising an alpha chain and a beta chain, wherein the alpha chain comprises a CDR3 that is encoded by the nucleic acid sequence of SEQ ID NO: 20, and the beta chain comprises a CDR3 that is encoded by the nucleic acid sequence of SEQ ID NO: 258. Also described herein are polynucleotides that encode a TCR comprising an alpha chain and a beta chain, wherein the alpha chain comprises a CDR1 that is encoded by the nucleic acid sequence of SEQ ID NO: 16, a CDR2 that is encoded by the nucleic acid sequence of SEQ ID NO: 18, and a CDR3 that is encoded by the nucleic acid sequence of SEQ ID NO: 20, and the beta chain comprises a CDR1 that is encoded by the nucleic acid sequence of SEQ ID NO: 254, a CDR2 that is encoded by the nucleic acid sequence of SEQ ID NO: 256, and a CDR3 that is encoded by the nucleic acid sequence of SEQ ID NO: 258. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 484, and the beta chain comprises a VJD region that is encoded by a nucleic acid sequence that is at least 90%, 95%, 96%, 97%, 98%, 99% or 100% identical to the nucleic acid sequence of SEQ ID NO: 586. In certain embodiments, the alpha chain is encoded by a nucleic acid sequence that is at least 90%, 95%, 96%, 97%, 98%, 99% or 100% identical to the nucleic acid sequence of SEQ ID NO: 15, and the beta chain is encoded by a nucleic acid sequence that is at least 90%, 95%, 96%, 97%, 98%, 99% or 100% identical to the nucleic acid sequence of SEQ ID NO: 253.

Described herein are polynucleotides that encode a TCR comprising an alpha chain and a beta chain, wherein the alpha chain comprises a CDR3 that is encoded by the nucleic acid sequence of SEQ ID NO: 27, and the beta chain comprises a CDR3 that is encoded by the nucleic acid sequence of SEQ ID NO: 265. Also described herein are polynucleotides that encode a TCR comprising an alpha chain and a beta chain, wherein the alpha chain comprises a CDR1 that is encoded by the nucleic acid sequence of SEQ ID NO: 23, a CDR2 that is encoded by the nucleic acid sequence of SEQ ID NO: 25, and a CDR3 that is encoded by the nucleic acid sequence of SEQ ID NO: 27, and the beta chain comprises a CDR1 that is encoded by the nucleic acid sequence of SEQ ID NO: 261, a CDR2 that is encoded by the nucleic acid sequence of SEQ ID NO: 263, and a CDR3 that is encoded by the nucleic acid sequence of SEQ ID NO: 265. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 487, and the beta chain comprises a VJD region that is encoded by a nucleic acid sequence that is at least 90%, 95%, 96%, 97%, 98%, 99% or 100% identical to the nucleic acid sequence of SEQ ID NO: 589. In certain embodiments, the alpha chain is encoded by a nucleic acid sequence that is at least 90%, 95%, 96%, 97%, 98%, 99% or 100% identical to the nucleic acid sequence of SEQ ID NO: 22, and the beta chain is encoded by a nucleic acid sequence that is at least 90%, 95%, 96%, 97%, 98%, 99% or 100% identical to the nucleic acid sequence of SEQ ID NO: 260.

Described herein are polynucleotides that encode a TCR comprising an alpha chain and a beta chain, wherein the alpha chain comprises a CDR3 that is encoded by the nucleic acid sequence of SEQ ID NO: 34, and the beta chain comprises a CDR3 that is encoded by the nucleic acid sequence of SEQ ID NO: 272. Also described herein are polynucleotides that encode a TCR comprising an alpha chain and a beta chain, wherein the alpha chain comprises a CDR1 that is encoded by the nucleic acid sequence of SEQ ID NO: 30, a CDR2 that is encoded by the nucleic acid sequence of SEQ ID NO: 32, and a CDR3 that is encoded by the nucleic acid sequence of SEQ ID NO: 34, and the beta chain comprises a CDR1 that is encoded by the nucleic acid sequence of SEQ ID NO: 268, a CDR2 that is encoded by the nucleic acid sequence of SEQ ID NO: 270, and a CDR3 that is encoded by the nucleic acid sequence of SEQ ID NO: 272. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 490, and the beta chain comprises a VJD region that is encoded by a nucleic acid sequence that is at least 90%, 95%, 96%, 97%, 98%, 99% or 100% identical to the nucleic acid sequence of SEQ ID NO: 592. In certain embodiments, the alpha chain is encoded by a nucleic acid sequence that is at least 90%, 95%, 96%, 97%, 98%, 99% or 100% identical to the nucleic acid sequence of SEQ ID NO: 29, and the beta chain is encoded by a nucleic acid sequence that is at least 90%, 95%, 96%, 97%, 98%, 99% or 100% identical to the nucleic acid sequence of SEQ ID NO: 267.

Described herein are polynucleotides that encode a TCR comprising an alpha chain and a beta chain, wherein the alpha chain comprises a CDR3 that is encoded by the nucleic acid sequence of SEQ ID NO: 41, and the beta chain comprises a CDR3 that is encoded by the nucleic acid sequence of SEQ ID NO: 279. Also described herein are polynucleotides that encode a TCR comprising an alpha chain and a beta chain, wherein the alpha chain comprises a CDR1 that is encoded by the nucleic acid sequence of SEQ ID NO: 37, a CDR2 that is encoded by the nucleic acid sequence of SEQ ID NO: 39, and a CDR3 that is encoded by the nucleic acid sequence of SEQ ID NO: 41, and the beta chain comprises a CDR1 that is encoded by the nucleic acid sequence of SEQ ID NO: 275, a CDR2 that is encoded by the nucleic acid sequence of SEQ ID NO: 277, and a CDR3 that is encoded by the nucleic acid sequence of SEQ ID NO: 279. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 493, and the beta chain comprises a VJD region that is encoded by a nucleic acid sequence that is at least 90%, 95%, 96%, 97%, 98%, 99% or 100% identical to the nucleic acid sequence of SEQ ID NO: 595. In certain embodiments, the alpha chain is encoded by a nucleic acid sequence that is at least 90%, 95%, 96%, 97%, 98%, 99% or 100% identical to the nucleic acid sequence of SEQ ID NO: 36, and the beta chain is encoded by a nucleic acid sequence that is at least 90%, 95%, 96%, 97%, 98%, 99% or 100% identical to the nucleic acid sequence of SEQ ID NO: 274.

Described herein are polynucleotides that encode a TCR comprising an alpha chain and a beta chain, wherein the alpha chain comprises a CDR3 that is encoded by the nucleic acid sequence of SEQ ID NO: 48, and the beta chain comprises a CDR3 that is encoded by the nucleic acid sequence of SEQ ID NO: 286. Also described herein are polynucleotides that encode a TCR comprising an alpha chain and a beta chain, wherein the alpha chain comprises a CDR1 that is encoded by the nucleic acid sequence of SEQ ID NO: 44, a CDR2 that is encoded by the nucleic acid sequence of SEQ ID NO: 46, and a CDR3 that is encoded by the nucleic acid sequence of SEQ ID NO: 48, and the beta chain comprises a CDR1 that is encoded by the nucleic acid sequence of SEQ ID NO: 282, a CDR2 that is encoded by the nucleic acid sequence of SEQ ID NO: 284, and a CDR3 that is encoded by the nucleic acid sequence of SEQ ID NO: 286. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 496, and the beta chain comprises a VJD region that is encoded by a nucleic acid sequence that is at least 90%, 95%, 96%, 97%, 98%, 99% or 100% identical to the nucleic acid sequence of SEQ ID NO: 598. In certain embodiments, the alpha chain is encoded by a nucleic acid sequence that is at least 90%, 95%, 96%, 97%, 98%, 99% or 100% identical to the nucleic acid sequence of SEQ ID NO: 43, and the beta chain is encoded by a nucleic acid sequence that is at least 90%, 95%, 96%, 97%, 98%, 99% or 100% identical to the nucleic acid sequence of SEQ ID NO: 281.

Described herein are polynucleotides that encode a TCR comprising an alpha chain and a beta chain, wherein the alpha chain comprises a CDR3 that is encoded by the nucleic acid sequence of SEQ ID NO: 55, and the beta chain comprises a CDR3 that is encoded by the nucleic acid sequence of SEQ ID NO: 293. Also described herein are polynucleotides that encode a TCR comprising an alpha chain and a beta chain, wherein the alpha chain comprises a CDR1 that is encoded by the nucleic acid sequence of SEQ ID NO: 51, a CDR2 that is encoded by the nucleic acid sequence of SEQ ID NO: 53, and a CDR3 that is encoded by the nucleic acid sequence of SEQ ID NO: 55, and the beta chain comprises a CDR1 that is encoded by the nucleic acid sequence of SEQ ID NO: 289, a CDR2 that is encoded by the nucleic acid sequence of SEQ ID NO: 291, and a CDR3 that is encoded by the nucleic acid sequence of SEQ ID NO: 293. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 499, and the beta chain comprises a VJD region that is encoded by a nucleic acid sequence that is at least 90%, 95%, 96%, 97%, 98%, 99% or 100% identical to the nucleic acid sequence of SEQ ID NO: 601. In certain embodiments, the alpha chain is encoded by a nucleic acid sequence that is at least 90%, 95%, 96%, 97%, 98%, 99% or 100% identical to the nucleic acid sequence of SEQ ID NO: 50, and the beta chain is encoded by a nucleic acid sequence that is at least 90%, 95%, 96%, 97%, 98%, 99% or 100% identical to the nucleic acid sequence of SEQ ID NO: 288.

Described herein are polynucleotides that encode a TCR comprising an alpha chain and a beta chain, wherein the alpha chain comprises a CDR3 that is encoded by the nucleic acid sequence of SEQ ID NO: 62, and the beta chain comprises a CDR3 that is encoded by the nucleic acid sequence of SEQ ID NO: 300. Also described herein are polynucleotides that encode a TCR comprising an alpha chain and a beta chain, wherein the alpha chain comprises a CDR1 that is encoded by the nucleic acid sequence of SEQ ID NO: 58, a CDR2 that is encoded by the nucleic acid sequence of SEQ ID NO: 60, and a CDR3 that is encoded by the nucleic acid sequence of SEQ ID NO: 62, and the beta chain comprises a CDR1 that is encoded by the nucleic acid sequence of SEQ ID NO: 296, a CDR2 that is encoded by the nucleic acid sequence of SEQ ID NO: 298, and a CDR3 that is encoded by the nucleic acid sequence of SEQ ID NO: 300. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 502, and the beta chain comprises a VJD region that is encoded by a nucleic acid sequence that is at least 90%, 95%, 96%, 97%, 98%, 99% or 100% identical to the nucleic acid sequence of SEQ ID NO: 604. In certain embodiments, the alpha chain is encoded by a nucleic acid sequence that is at least 90%, 95%, 96%, 97%, 98%, 99% or 100% identical to the nucleic acid sequence of SEQ ID NO: 57, and the beta chain is encoded by a nucleic acid sequence that is at least 90%, 95%, 96%, 97%, 98%, 99% or 100% identical to the nucleic acid sequence of SEQ ID NO: 295.

Described herein are polynucleotides that encode a TCR comprising an alpha chain and a beta chain, wherein the alpha chain comprises a CDR3 that is encoded by the nucleic acid sequence of SEQ ID NO: 69, and the beta chain comprises a CDR3 that is encoded by the nucleic acid sequence of SEQ ID NO: 307. Also described herein are polynucleotides that encode a TCR comprising an alpha chain and a beta chain, wherein the alpha chain comprises a CDR1 that is encoded by the nucleic acid sequence of SEQ ID NO: 65, a CDR2 that is encoded by the nucleic acid sequence of SEQ ID NO: 67, and a CDR3 that is encoded by the nucleic acid sequence of SEQ ID NO: 69, and the beta chain comprises a CDR1 that is encoded by the nucleic acid sequence of SEQ ID NO: 303, a CDR2 that is encoded by the nucleic acid sequence of SEQ ID NO: 305, and a CDR3 that is encoded by the nucleic acid sequence of SEQ ID NO: 307. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 505, and the beta chain comprises a VJD region that is encoded by a nucleic acid sequence that is at least 90%, 95%, 96%, 97%, 98%, 99% or 100% identical to the nucleic acid sequence of SEQ ID NO: 607. In certain embodiments, the alpha chain is encoded by a nucleic acid sequence that is at least 90%, 95%, 96%, 97%, 98%, 99% or 100% identical to the nucleic acid sequence of SEQ ID NO: 64, and the beta chain is encoded by a nucleic acid sequence that is at least 90%, 95%, 96%, 97%, 98%, 99% or 100% identical to the nucleic acid sequence of SEQ ID NO: 302.

Described herein are polynucleotides that encode a TCR comprising an alpha chain and a beta chain, wherein the alpha chain comprises a CDR3 that is encoded by the nucleic acid sequence of SEQ ID NO: 76, and the beta chain comprises a CDR3 that is encoded by the nucleic acid sequence of SEQ ID NO: 314. Also described herein are polynucleotides that encode a TCR comprising an alpha chain and a beta chain, wherein the alpha chain comprises a CDR1 that is encoded by the nucleic acid sequence of SEQ ID NO: 72, a CDR2 that is encoded by the nucleic acid sequence of SEQ ID NO: 74, and a CDR3 that is encoded by the nucleic acid sequence of SEQ ID NO: 76, and the beta chain comprises a CDR1 that is encoded by the nucleic acid sequence of SEQ ID NO: 310, a CDR2 that is encoded by the nucleic acid sequence of SEQ ID NO: 312, and a CDR3 that is encoded by the nucleic acid sequence of SEQ ID NO: 314. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 508, and the beta chain comprises a VJD region that is encoded by a nucleic acid sequence that is at least 90%, 95%, 96%, 97%, 98%, 99% or 100% identical to the nucleic acid sequence of SEQ ID NO: 610. In certain embodiments, the alpha chain is encoded by a nucleic acid sequence that is at least 90%, 95%, 96%, 97%, 98%, 99% or 100% identical to the nucleic acid sequence of SEQ ID NO: 71, and the beta chain is encoded by a nucleic acid sequence that is at least 90%, 95%, 96%, 97%, 98%, 99% or 100% identical to the nucleic acid sequence of SEQ ID NO: 309.

Described herein are polynucleotides that encode a TCR comprising an alpha chain and a beta chain, wherein the alpha chain comprises a CDR3 that is encoded by the nucleic acid sequence of SEQ ID NO: 83, and the beta chain comprises a CDR3 that is encoded by the nucleic acid sequence of SEQ ID NO: 321. Also described herein are polynucleotides that encode a TCR comprising an alpha chain and a beta chain, wherein the alpha chain comprises a CDR1 that is encoded by the nucleic acid sequence of SEQ ID NO: 79, a CDR2 that is encoded by the nucleic acid sequence of SEQ ID NO: 81, and a CDR3 that is encoded by the nucleic acid sequence of SEQ ID NO: 83, and the beta chain comprises a CDR1 that is encoded by the nucleic acid sequence of SEQ ID NO: 317, a CDR2 that is encoded by the nucleic acid sequence of SEQ ID NO: 319, and a CDR3 that is encoded by the nucleic acid sequence of SEQ ID NO: 321. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 511, and the beta chain comprises a VJD region that is encoded by a nucleic acid sequence that is at least 90%, 95%, 96%, 97%, 98%, 99% or 100% identical to the nucleic acid sequence of SEQ ID NO: 613. In certain embodiments, the alpha chain is encoded by a nucleic acid sequence that is at least 90%, 95%, 96%, 97%, 98%, 99% or 100% identical to the nucleic acid sequence of SEQ ID NO: 78, and the beta chain is encoded by a nucleic acid sequence that is at least 90%, 95%, 96%, 97%, 98%, 99% or 100% identical to the nucleic acid sequence of SEQ ID NO: 316.

Described herein are polynucleotides that encode a TCR comprising an alpha chain and a beta chain, wherein the alpha chain comprises a CDR3 that is encoded by the nucleic acid sequence of SEQ ID NO: 90, and the beta chain comprises a CDR3 that is encoded by the nucleic acid sequence of SEQ ID NO: 328. Also described herein are polynucleotides that encode a TCR comprising an alpha chain and a beta chain, wherein the alpha chain comprises a CDR1 that is encoded by the nucleic acid sequence of SEQ ID NO: 86, a CDR2 that is encoded by the nucleic acid sequence of SEQ ID NO: 88, and a CDR3 that is encoded by the nucleic acid sequence of SEQ ID NO: 90, and the beta chain comprises a CDR1 that is encoded by the nucleic acid sequence of SEQ ID NO: 324, a CDR2 that is encoded by the nucleic acid sequence of SEQ ID NO: 326, and a CDR3 that is encoded by the nucleic acid sequence of SEQ ID NO: 328. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 514, and the beta chain comprises a VJD region that is encoded by a nucleic acid sequence that is at least 90%, 95%, 96%, 97%, 98%, 99% or 100% identical to the nucleic acid sequence of SEQ ID NO: 616. In certain embodiments, the alpha chain is encoded by a nucleic acid sequence that is at least 90%, 95%, 96%, 97%, 98%, 99% or 100% identical to the nucleic acid sequence of SEQ ID NO: 85, and the beta chain is encoded by a nucleic acid sequence that is at least 90%, 95%, 96%, 97%, 98%, 99% or 100% identical to the nucleic acid sequence of SEQ ID NO: 323.

Described herein are polynucleotides that encode a TCR comprising an alpha chain and a beta chain, wherein the alpha chain comprises a CDR3 that is encoded by the nucleic acid sequence of SEQ ID NO: 97, and the beta chain comprises a CDR3 that is encoded by the nucleic acid sequence of SEQ ID NO: 335. Also described herein are polynucleotides that encode a TCR comprising an alpha chain and a beta chain, wherein the alpha chain comprises a CDR1 that is encoded by the nucleic acid sequence of SEQ ID NO: 93, a CDR2 that is encoded by the nucleic acid sequence of SEQ ID NO: 95, and a CDR3 that is encoded by the nucleic acid sequence of SEQ ID NO: 97, and the beta chain comprises a CDR1 that is encoded by the nucleic acid sequence of SEQ ID NO: 331, a CDR2 that is encoded by the nucleic acid sequence of SEQ ID NO: 333, and a CDR3 that is encoded by the nucleic acid sequence of SEQ ID NO: 335. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 517, and the beta chain comprises a VJD region that is encoded by a nucleic acid sequence that is at least 90%, 95%, 96%, 97%, 98%, 99% or 100% identical to the nucleic acid sequence of SEQ ID NO: 619. In certain embodiments, the alpha chain is encoded by a nucleic acid sequence that is at least 90%, 95%, 96%, 97%, 98%, 99% or 100% identical to the nucleic acid sequence of SEQ ID NO: 92, and the beta chain is encoded by a nucleic acid sequence that is at least 90%, 95%, 96%, 97%, 98%, 99% or 100% identical to the nucleic acid sequence of SEQ ID NO: 330.

Described herein are polynucleotides that encode a TCR comprising an alpha chain and a beta chain, wherein the alpha chain comprises a CDR3 that is encoded by the nucleic acid sequence of SEQ ID NO: 104, and the beta chain comprises a CDR3 that is encoded by the nucleic acid sequence of SEQ ID NO: 342. Also described herein are polynucleotides that encode a TCR comprising an alpha chain and a beta chain, wherein the alpha chain comprises a CDR1 that is encoded by the nucleic acid sequence of SEQ ID NO: 100, a CDR2 that is encoded by the nucleic acid sequence of SEQ ID NO: 102, and a CDR3 that is encoded by the nucleic acid sequence of SEQ ID NO: 104, and the beta chain comprises a CDR1 that is encoded by the nucleic acid sequence of SEQ ID NO: 338, a CDR2 that is encoded by the nucleic acid sequence of SEQ ID NO: 340, and a CDR3 that is encoded by the nucleic acid sequence of SEQ ID NO: 342. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 520, and the beta chain comprises a VJD region that is encoded by a nucleic acid sequence that is at least 90%, 95%, 96%, 97%, 98%, 99% or 100% identical to the nucleic acid sequence of SEQ ID NO: 622. In certain embodiments, the alpha chain is encoded by a nucleic acid sequence that is at least 90%, 95%, 96%, 97%, 98%, 99% or 100% identical to the nucleic acid sequence of SEQ ID NO: 99, and the beta chain is encoded by a nucleic acid sequence that is at least 90%, 95%, 96%, 97%, 98%, 99% or 100% identical to the nucleic acid sequence of SEQ ID NO: 337.

Described herein are polynucleotides that encode a TCR comprising an alpha chain and a beta chain, wherein the alpha chain comprises a CDR3 that is encoded by the nucleic acid sequence of SEQ ID NO: 111, and the beta chain comprises a CDR3 that is encoded by the nucleic acid sequence of SEQ ID NO: 349. Also described herein are polynucleotides that encode a TCR comprising an alpha chain and a beta chain, wherein the alpha chain comprises a CDR1 that is encoded by the nucleic acid sequence of SEQ ID NO: 107, a CDR2 that is encoded by the nucleic acid sequence of SEQ ID NO: 109, and a CDR3 that is encoded by the nucleic acid sequence of SEQ ID NO: 111, and the beta chain comprises a CDR1 that is encoded by the nucleic acid sequence of SEQ ID NO: 345, a CDR2 that is encoded by the nucleic acid sequence of SEQ ID NO: 347, and a CDR3 that is encoded by the nucleic acid sequence of SEQ ID NO: 349. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 523, and the beta chain comprises a VJD region that is encoded by a nucleic acid sequence that is at least 90%, 95%, 96%, 97%, 98%, 99% or 100% identical to the nucleic acid sequence of SEQ ID NO: 625. In certain embodiments, the alpha chain is encoded by a nucleic acid sequence that is at least 90%, 95%, 96%, 97%, 98%, 99% or 100% identical to the nucleic acid sequence of SEQ ID NO: 106, and the beta chain is encoded by a nucleic acid sequence that is at least 90%, 95%, 96%, 97%, 98%, 99% or 100% identical to the nucleic acid sequence of SEQ ID NO: 344.

Described herein are polynucleotides that encode a TCR comprising an alpha chain and a beta chain, wherein the alpha chain comprises a CDR3 that is encoded by the nucleic acid sequence of SEQ ID NO: 118, and the beta chain comprises a CDR3 that is encoded by the nucleic acid sequence of SEQ ID NO: 356. Also described herein are polynucleotides that encode a TCR comprising an alpha chain and a beta chain, wherein the alpha chain comprises a CDR1 that is encoded by the nucleic acid sequence of SEQ ID NO: 114, a CDR2 that is encoded by the nucleic acid sequence of SEQ ID NO: 116, and a CDR3 that is encoded by the nucleic acid sequence of SEQ ID NO: 118, and the beta chain comprises a CDR1 that is encoded by the nucleic acid sequence of SEQ ID NO: 352, a CDR2 that is encoded by the nucleic acid sequence of SEQ ID NO: 354, and a CDR3 that is encoded by the nucleic acid sequence of SEQ ID NO: 356. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 526, and the beta chain comprises a VJD region that is encoded by a nucleic acid sequence that is at least 90%, 95%, 96%, 97%, 98%, 99% or 100% identical to the nucleic acid sequence of SEQ ID NO: 628. In certain embodiments, the alpha chain is encoded by a nucleic acid sequence that is at least 90%, 95%, 96%, 97%, 98%, 99% or 100% identical to the nucleic acid sequence of SEQ ID NO: 113, and the beta chain is encoded by a nucleic acid sequence that is at least 90%, 95%, 96%, 97%, 98%, 99% or 100% identical to the nucleic acid sequence of SEQ ID NO: 351.

Described herein are polynucleotides that encode a TCR comprising an alpha chain and a beta chain, wherein the alpha chain comprises a CDR3 that is encoded by the nucleic acid sequence of SEQ ID NO: 125, and the beta chain comprises a CDR3 that is encoded by the nucleic acid sequence of SEQ ID NO: 363. Also described herein are polynucleotides that encode a TCR comprising an alpha chain and a beta chain, wherein the alpha chain comprises a CDR1 that is encoded by the nucleic acid sequence of SEQ ID NO: 121, a CDR2 that is encoded by the nucleic acid sequence of SEQ ID NO: 123, and a CDR3 that is encoded by the nucleic acid sequence of SEQ ID NO: 125, and the beta chain comprises a CDR1 that is encoded by the nucleic acid sequence of SEQ ID NO: 359, a CDR2 that is encoded by the nucleic acid sequence of SEQ ID NO: 361, and a CDR3 that is encoded by the nucleic acid sequence of SEQ ID NO: 363. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 529, and the beta chain comprises a VJD region that is encoded by a nucleic acid sequence that is at least 90%, 95%, 96%, 97%, 98%, 99% or 100% identical to the nucleic acid sequence of SEQ ID NO: 631. In certain embodiments, the alpha chain is encoded by a nucleic acid sequence that is at least 90%, 95%, 96%, 97%, 98%, 99% or 100% identical to the nucleic acid sequence of SEQ ID NO: 120, and the beta chain is encoded by a nucleic acid sequence that is at least 90%, 95%, 96%, 97%, 98%, 99% or 100% identical to the nucleic acid sequence of SEQ ID NO: 358.

Described herein are polynucleotides that encode a TCR comprising an alpha chain and a beta chain, wherein the alpha chain comprises a CDR3 that is encoded by the nucleic acid sequence of SEQ ID NO: 132, and the beta chain comprises a CDR3 that is encoded by the nucleic acid sequence of SEQ ID NO: 370. Also described herein are polynucleotides that encode a TCR comprising an alpha chain and a beta chain, wherein the alpha chain comprises a CDR1 that is encoded by the nucleic acid sequence of SEQ ID NO: 128, a CDR2 that is encoded by the nucleic acid sequence of SEQ ID NO: 130, and a CDR3 that is encoded by the nucleic acid sequence of SEQ ID NO: 132, and the beta chain comprises a CDR1 that is encoded by the nucleic acid sequence of SEQ ID NO: 366, a CDR2 that is encoded by the nucleic acid sequence of SEQ ID NO: 368, and a CDR3 that is encoded by the nucleic acid sequence of SEQ ID NO: 370. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 532, and the beta chain comprises a VJD region that is encoded by a nucleic acid sequence that is at least 90%, 95%, 96%, 97%, 98%, 99% or 100% identical to the nucleic acid sequence of SEQ ID NO: 634. In certain embodiments, the alpha chain is encoded by a nucleic acid sequence that is at least 90%, 95%, 96%, 97%, 98%, 99% or 100% identical to the nucleic acid sequence of SEQ ID NO: 127, and the beta chain is encoded by a nucleic acid sequence that is at least 90%, 95%, 96%, 97%, 98%, 99% or 100% identical to the nucleic acid sequence of SEQ ID NO: 365.

Described herein are polynucleotides that encode a TCR comprising an alpha chain and a beta chain, wherein the alpha chain comprises a CDR3 that is encoded by the nucleic acid sequence of SEQ ID NO: 139, and the beta chain comprises a CDR3 that is encoded by the nucleic acid sequence of SEQ ID NO: 377. Also described herein are polynucleotides that encode a TCR comprising an alpha chain and a beta chain, wherein the alpha chain comprises a CDR1 that is encoded by the nucleic acid sequence of SEQ ID NO: 135, a CDR2 that is encoded by the nucleic acid sequence of SEQ ID NO: 137, and a CDR3 that is encoded by the nucleic acid sequence of SEQ ID NO: 139, and the beta chain comprises a CDR1 that is encoded by the nucleic acid sequence of SEQ ID NO: 373, a CDR2 that is encoded by the nucleic acid sequence of SEQ ID NO: 375, and a CDR3 that is encoded by the nucleic acid sequence of SEQ ID NO: 377. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 535, and the beta chain comprises a VJD region that is encoded by a nucleic acid sequence that is at least 90%, 95%, 96%, 97%, 98%, 99% or 100% identical to the nucleic acid sequence of SEQ ID NO: 637. In certain embodiments, the alpha chain is encoded by a nucleic acid sequence that is at least 90%, 95%, 96%, 97%, 98%, 99% or 100% identical to the nucleic acid sequence of SEQ ID NO: 134, and the beta chain is encoded by a nucleic acid sequence that is at least 90%, 95%, 96%, 97%, 98%, 99% or 100% identical to the nucleic acid sequence of SEQ ID NO: 372.

Described herein are polynucleotides that encode a TCR comprising an alpha chain and a beta chain, wherein the alpha chain comprises a CDR3 that is encoded by the nucleic acid sequence of SEQ ID NO: 146, and the beta chain comprises a CDR3 that is encoded by the nucleic acid sequence of SEQ ID NO: 384. Also described herein are polynucleotides that encode a TCR comprising an alpha chain and a beta chain, wherein the alpha chain comprises a CDR1 that is encoded by the nucleic acid sequence of SEQ ID NO: 142, a CDR2 that is encoded by the nucleic acid sequence of SEQ ID NO: 144, and a CDR3 that is encoded by the nucleic acid sequence of SEQ ID NO: 146, and the beta chain comprises a CDR1 that is encoded by the nucleic acid sequence of SEQ ID NO: 380, a CDR2 that is encoded by the nucleic acid sequence of SEQ ID NO: 382, and a CDR3 that is encoded by the nucleic acid sequence of SEQ ID NO: 384. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 538, and the beta chain comprises a VJD region that is encoded by a nucleic acid sequence that is at least 90%, 95%, 96%, 97%, 98%, 99% or 100% identical to the nucleic acid sequence of SEQ ID NO: 640. In certain embodiments, the alpha chain is encoded by a nucleic acid sequence that is at least 90%, 95%, 96%, 97%, 98%, 99% or 100% identical to the nucleic acid sequence of SEQ ID NO: 141, and the beta chain is encoded by a nucleic acid sequence that is at least 90%, 95%, 96%, 97%, 98%, 99% or 100% identical to the nucleic acid sequence of SEQ ID NO: 379.

Described herein are polynucleotides that encode a TCR comprising an alpha chain and a beta chain, wherein the alpha chain comprises a CDR3 that is encoded by the nucleic acid sequence of SEQ ID NO: 153, and the beta chain comprises a CDR3 that is encoded by the nucleic acid sequence of SEQ ID NO: 391. Also described herein are polynucleotides that encode a TCR comprising an alpha chain and a beta chain, wherein the alpha chain comprises a CDR1 that is encoded by the nucleic acid sequence of SEQ ID NO: 149, a CDR2 that is encoded by the nucleic acid sequence of SEQ ID NO: 151, and a CDR3 that is encoded by the nucleic acid sequence of SEQ ID NO: 153, and the beta chain comprises a CDR1 that is encoded by the nucleic acid sequence of SEQ ID NO: 387, a CDR2 that is encoded by the nucleic acid sequence of SEQ ID NO: 389, and a CDR3 that is encoded by the nucleic acid sequence of SEQ ID NO: 391. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 541, and the beta chain comprises a VJD region that is encoded by a nucleic acid sequence that is at least 90%, 95%, 96%, 97%, 98%, 99% or 100% identical to the nucleic acid sequence of SEQ ID NO: 643. In certain embodiments, the alpha chain is encoded by a nucleic acid sequence that is at least 90%, 95%, 96%, 97%, 98%, 99% or 100% identical to the nucleic acid sequence of SEQ ID NO: 148, and the beta chain is encoded by a nucleic acid sequence that is at least 90%, 95%, 96%, 97%, 98%, 99% or 100% identical to the nucleic acid sequence of SEQ ID NO: 386.

Described herein are polynucleotides that encode a TCR comprising an alpha chain and a beta chain, wherein the alpha chain comprises a CDR3 that is encoded by the nucleic acid sequence of SEQ ID NO: 160, and the beta chain comprises a CDR3 that is encoded by the nucleic acid sequence of SEQ ID NO: 398. Also described herein are polynucleotides that encode a TCR comprising an alpha chain and a beta chain, wherein the alpha chain comprises a CDR1 that is encoded by the nucleic acid sequence of SEQ ID NO: 156, a CDR2 that is encoded by the nucleic acid sequence of SEQ ID NO: 158, and a CDR3 that is encoded by the nucleic acid sequence of SEQ ID NO: 160, and the beta chain comprises a CDR1 that is encoded by the nucleic acid sequence of SEQ ID NO: 394, a CDR2 that is encoded by the nucleic acid sequence of SEQ ID NO: 396, and a CDR3 that is encoded by the nucleic acid sequence of SEQ ID NO: 398. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 544, and the beta chain comprises a VJD region that is encoded by a nucleic acid sequence that is at least 90%, 95%, 96%, 97%, 98%, 99% or 100% identical to the nucleic acid sequence of SEQ ID NO: 646. In certain embodiments, the alpha chain is encoded by a nucleic acid sequence that is at least 90%, 95%, 96%, 97%, 98%, 99% or 100% identical to the nucleic acid sequence of SEQ ID NO: 155, and the beta chain is encoded by a nucleic acid sequence that is at least 90%, 95%, 96%, 97%, 98%, 99% or 100% identical to the nucleic acid sequence of SEQ ID NO: 393.

Described herein are polynucleotides that encode a TCR comprising an alpha chain and a beta chain, wherein the alpha chain comprises a CDR3 that is encoded by the nucleic acid sequence of SEQ ID NO: 167, and the beta chain comprises a CDR3 that is encoded by the nucleic acid sequence of SEQ ID NO: 405. Also described herein are polynucleotides that encode a TCR comprising an alpha chain and a beta chain, wherein the alpha chain comprises a CDR1 that is encoded by the nucleic acid sequence of SEQ ID NO: 163, a CDR2 that is encoded by the nucleic acid sequence of SEQ ID NO: 165, and a CDR3 that is encoded by the nucleic acid sequence of SEQ ID NO: 167, and the beta chain comprises a CDR1 that is encoded by the nucleic acid sequence of SEQ ID NO: 401, a CDR2 that is encoded by the nucleic acid sequence of SEQ ID NO: 403, and a CDR3 that is encoded by the nucleic acid sequence of SEQ ID NO: 405. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 547, and the beta chain comprises a VJD region that is encoded by a nucleic acid sequence that is at least 90%, 95%, 96%, 97%, 98%, 99% or 100% identical to the nucleic acid sequence of SEQ ID NO: 649. In certain embodiments, the alpha chain is encoded by a nucleic acid sequence that is at least 90%, 95%, 96%, 97%, 98%, 99% or 100% identical to the nucleic acid sequence of SEQ ID NO: 162, and the beta chain is encoded by a nucleic acid sequence that is at least 90%, 95%, 96%, 97%, 98%, 99% or 100% identical to the nucleic acid sequence of SEQ ID NO: 400.

Described herein are polynucleotides that encode a TCR comprising an alpha chain and a beta chain, wherein the alpha chain comprises a CDR3 that is encoded by the nucleic acid sequence of SEQ ID NO: 174, and the beta chain comprises a CDR3 that is encoded by the nucleic acid sequence of SEQ ID NO: 412. Also described herein are polynucleotides that encode a TCR comprising an alpha chain and a beta chain, wherein the alpha chain comprises a CDR1 that is encoded by the nucleic acid sequence of SEQ ID NO: 170, a CDR2 that is encoded by the nucleic acid sequence of SEQ ID NO: 172, and a CDR3 that is encoded by the nucleic acid sequence of SEQ ID NO: 174, and the beta chain comprises a CDR1 that is encoded by the nucleic acid sequence of SEQ ID NO: 408, a CDR2 that is encoded by the nucleic acid sequence of SEQ ID NO: 410, and a CDR3 that is encoded by the nucleic acid sequence of SEQ ID NO: 412. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 550, and the beta chain comprises a VJD region that is encoded by a nucleic acid sequence that is at least 90%, 95%, 96%, 97%, 98%, 99% or 100% identical to the nucleic acid sequence of SEQ ID NO: 652. In certain embodiments, the alpha chain is encoded by a nucleic acid sequence that is at least 90%, 95%, 96%, 97%, 98%, 99% or 100% identical to the nucleic acid sequence of SEQ ID NO: 169, and the beta chain is encoded by a nucleic acid sequence that is at least 90%, 95%, 96%, 97%, 98%, 99% or 100% identical to the nucleic acid sequence of SEQ ID NO: 407.

Described herein are polynucleotides that encode a TCR comprising an alpha chain and a beta chain, wherein, the alpha chain comprises a CDR3 that is encoded by the nucleic acid sequence of SEQ ID NO: 181, and the beta chain comprises a CDR3 that is encoded by the nucleic acid sequence of SEQ ID NO: 419. Also described herein are polynucleotides that encode a TCR comprising an alpha chain and a beta chain, wherein the alpha chain comprises a CDR1 that is encoded by the nucleic acid sequence of SEQ ID NO: 177, a CDR2 that is encoded by the nucleic acid sequence of SEQ ID NO: 179, and a CDR3 that is encoded by the nucleic acid sequence of SEQ ID NO: 181, and the beta chain comprises a CDR1 that is encoded by the nucleic acid sequence of SEQ ID NO: 415, a CDR2 that is encoded by the nucleic acid sequence of SEQ ID NO: 417, and a CDR3 that is encoded by the nucleic acid sequence of SEQ ID NO: 419. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 553, and the beta chain comprises a VJD region that is encoded by a nucleic acid sequence that is at least 90%, 95%, 96%, 97%, 98%, 99% or 100% identical to the nucleic acid sequence of SEQ ID NO: 655. In certain embodiments, the alpha chain is encoded by a nucleic acid sequence that is at least 90%, 95%, 96%, 97%, 98%, 99% or 100% identical to the nucleic acid sequence of SEQ ID NO: 176, and the beta chain is encoded by a nucleic acid sequence that is at least 90%, 95%, 96%, 97%, 98%, 99% or 100% identical to the nucleic acid sequence of SEQ ID NO: 414.

Described herein are polynucleotides that encode a TCR comprising an alpha chain and a beta chain, wherein the alpha chain comprises a CDR3 that is encoded by the nucleic acid sequence of SEQ ID NO: 188, and the beta chain comprises a CDR3 that is encoded by the nucleic acid sequence of SEQ ID NO: 426. Also described herein are polynucleotides that encode a TCR comprising an alpha chain and a beta chain, wherein the alpha chain comprises a CDR1 that is encoded by the nucleic acid sequence of SEQ ID NO: 184, a CDR2 that is encoded by the nucleic acid sequence of SEQ ID NO: 186, and a CDR3 that is encoded by the nucleic acid sequence of SEQ ID NO: 188, and the beta chain comprises a CDR1 that is encoded by the nucleic acid sequence of SEQ ID NO: 422, a CDR2 that is encoded by the nucleic acid sequence of SEQ ID NO: 424, and a CDR3 that is encoded by the nucleic acid sequence of SEQ ID NO: 426. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 556, and the beta chain comprises a VJD region that is encoded by a nucleic acid sequence that is at least 90%, 95%, 96%, 97%, 98%, 99% or 100% identical to the nucleic acid sequence of SEQ ID NO: 658. In certain embodiments, the alpha chain is encoded by a nucleic acid sequence that is at least 90%, 95%, 96%, 97%, 98%, 99% or 100% identical to the nucleic acid sequence of SEQ ID NO: 183, and the beta chain is encoded by a nucleic acid sequence that is at least 90%, 95%, 96%, 97%, 98%, 99% or 100% identical to the nucleic acid sequence of SEQ ID NO: 421.

Described herein are polynucleotides that encode a TCR comprising an alpha chain and a beta chain, wherein the alpha chain comprises a CDR3 that is encoded by the nucleic acid sequence of SEQ ID NO: 195, and the beta chain comprises a CDR3 that is encoded by the nucleic acid sequence of SEQ ID NO: 433. Also described herein are polynucleotides that encode a TCR comprising an alpha chain and a beta chain, wherein the alpha chain comprises a CDR1 that is encoded by the nucleic acid sequence of SEQ ID NO: 191, a CDR2 that is encoded by the nucleic acid sequence of SEQ ID NO: 193, and a CDR3 that is encoded by the nucleic acid sequence of SEQ ID NO: 195, and the beta chain comprises a CDR1 that is encoded by the nucleic acid sequence of SEQ ID NO: 429, a CDR2 that is encoded by the nucleic acid sequence of SEQ ID NO: 431, and a CDR3 that is encoded by the nucleic acid sequence of SEQ ID NO: 433. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 559, and the beta chain comprises a VJD region that is encoded by a nucleic acid sequence that is at least 90%, 95%, 96%, 97%, 98%, 99% or 100% identical to the nucleic acid sequence of SEQ ID NO: 661. In certain embodiments, the alpha chain is encoded by a nucleic acid sequence that is at least 90%, 95%, 96%, 97%, 98%, 99% or 100% identical to the nucleic acid sequence of SEQ ID NO: 190, and the beta chain is encoded by a nucleic acid sequence that is at least 90%, 95%, 96%, 97%, 98%, 99% or 100% identical to the nucleic acid sequence of SEQ ID NO: 428.

Described herein are polynucleotides that encode a TCR comprising an alpha chain and a beta chain, wherein the alpha chain comprises a CDR3 that is encoded by the nucleic acid sequence of SEQ ID NO: 202, and the beta chain comprises a CDR3 that is encoded by the nucleic acid sequence of SEQ ID NO: 440. Also described herein are polynucleotides that encode a TCR comprising an alpha chain and a beta chain, wherein the alpha chain comprises a CDR1 that is encoded by the nucleic acid sequence of SEQ ID NO: 198, a CDR2 that is encoded by the nucleic acid sequence of SEQ ID NO: 200, and a CDR3 that is encoded by the nucleic acid sequence of SEQ ID NO: 202, and the beta chain comprises a CDR1 that is encoded by the nucleic acid sequence of SEQ ID NO: 436, a CDR2 that is encoded by the nucleic acid sequence of SEQ ID NO: 438, and a CDR3 that is encoded by the nucleic acid sequence of SEQ ID NO: 440. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 562, and the beta chain comprises a VJD region that is encoded by a nucleic acid sequence that is at least 90%, 95%, 96%, 97%, 98%, 99% or 100% identical to the nucleic acid sequence of SEQ ID NO: 664. In certain embodiments, the alpha chain is encoded by a nucleic acid sequence that is at least 90%, 95%, 96%, 97%, 98%, 99% or 100% identical to the nucleic acid sequence of SEQ ID NO: 197, and the beta chain is encoded by a nucleic acid sequence that is at least 90%, 95%, 96%, 97%, 98%, 99% or 100% identical to the nucleic acid sequence of SEQ ID NO: 435.

Described herein are polynucleotides that encode a TCR comprising an alpha chain and a beta chain, wherein the alpha chain comprises a CDR3 that is encoded by the nucleic acid sequence of SEQ ID NO: 209, and the beta chain comprises a CDR3 that is encoded by the nucleic acid sequence of SEQ ID NO: 447. Also described herein are polynucleotides that encode a TCR comprising an alpha chain and a beta chain, wherein the alpha chain comprises a CDR1 that is encoded by the nucleic acid sequence of SEQ ID NO: 205, a CDR2 that is encoded by the nucleic acid sequence of SEQ ID NO: 207, and a CDR3 that is encoded by the nucleic acid sequence of SEQ ID NO: 209, and the beta chain comprises a CDR1 that is encoded by the nucleic acid sequence of SEQ ID NO: 443, a CDR2 that is encoded by the nucleic acid sequence of SEQ ID NO: 445, and a CDR3 that is encoded by the nucleic acid sequence of SEQ ID NO: 447. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 565, and the beta chain comprises a VJD region that is encoded by a nucleic acid sequence that is at least 90%, 95%, 96%, 97%, 98%, 99% or 100% identical to the nucleic acid sequence of SEQ ID NO: 667. In certain embodiments, the alpha chain is encoded by a nucleic acid sequence that is at least 90%, 95%, 96%, 97%, 98%, 99% or 100% identical to the nucleic acid sequence of SEQ ID NO: 204, and the beta chain is encoded by a nucleic acid sequence that is at least 90%, 95%, 96%, 97%, 98%, 99% or 100% identical to the nucleic acid sequence of SEQ ID NO: 442.

Described herein are polynucleotides that encode a TCR comprising an alpha chain and a beta chain, wherein the alpha chain comprises a CDR3 that is encoded by the nucleic acid sequence of SEQ ID NO: 216, and the beta chain comprises a CDR3 that is encoded by the nucleic acid sequence of SEQ ID NO: 454. Also described herein are polynucleotides that encode a TCR comprising an alpha chain and a beta chain, wherein the alpha chain comprises a CDR1 that is encoded by the nucleic acid sequence of SEQ ID NO: 212, a CDR2 that is encoded by the nucleic acid sequence of SEQ ID NO: 214, and a CDR3 that is encoded by the nucleic acid sequence of SEQ ID NO: 216, and the beta chain comprises a CDR1 that is encoded by the nucleic acid sequence of SEQ ID NO: 450, a CDR2 that is encoded by the nucleic acid sequence of SEQ ID NO: 452, and a CDR3 that is encoded by the nucleic acid sequence of SEQ ID NO: 454. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 568, and the beta chain comprises a VJD region that is encoded by a nucleic acid sequence that is at least 90%, 95%, 96%, 97%, 98%, 99% or 100% identical to the nucleic acid sequence of SEQ ID NO: 670. In certain embodiments, the alpha chain is encoded by a nucleic acid sequence that is at least 90%, 95%, 96%, 97%, 98%, 99% or 100% identical to the nucleic acid sequence of SEQ ID NO: 211, and the beta chain is encoded by a nucleic acid sequence that is at least 90%, 95%, 96%, 97%, 98%, 99% or 100% identical to the nucleic acid sequence of SEQ ID NO: 449.

Described herein are polynucleotides that encode a TCR comprising an alpha chain and a beta chain, wherein the alpha chain comprises a CDR3 that is encoded by the nucleic acid sequence of SEQ ID NO: 223, and the beta chain comprises a CDR3 that is encoded by the nucleic acid sequence of SEQ ID NO: 461. Also described herein are polynucleotides that encode a TCR comprising an alpha chain and a beta chain, wherein the alpha chain comprises a CDR1 that is encoded by the nucleic acid sequence of SEQ ID NO: 219, a CDR2 that is encoded by the nucleic acid sequence of SEQ ID NO: 221, and a CDR3 that is encoded by the nucleic acid sequence of SEQ ID NO: 223, and the beta chain comprises a CDR1 that is encoded by the nucleic acid sequence of SEQ ID NO: 457, a CDR2 that is encoded by the nucleic acid sequence of SEQ ID NO: 459, and a CDR3 that is encoded by the nucleic acid sequence of SEQ ID NO: 461. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 571, and the beta chain comprises a VJD region that is encoded by a nucleic acid sequence that is at least 90%, 95%, 96%, 97%, 98%, 99% or 100% identical to the nucleic acid sequence of SEQ ID NO: 673. In certain embodiments, the alpha chain is encoded by a nucleic acid sequence that is at least 90%, 95%, 96%, 97%, 98%, 99% or 100% identical to the nucleic acid sequence of SEQ ID NO: 218, and the beta chain is encoded by a nucleic acid sequence that is at least 90%, 95%, 96%, 97%, 98%, 99% or 100% identical to the nucleic acid sequence of SEQ ID NO: 456.

Described herein are polynucleotides that encode a TCR comprising an alpha chain and a beta chain, wherein the alpha chain comprises a CDR3 that is encoded by the nucleic acid sequence of SEQ ID NO: 230, and the beta chain comprises a CDR3 that is encoded by the nucleic acid sequence of SEQ ID NO: 468. Also described herein are polynucleotides that encode a TCR comprising an alpha chain and a beta chain, wherein the alpha chain comprises a CDR1 that is encoded by the nucleic acid sequence of SEQ ID NO: 226, a CDR2 that is encoded by the nucleic acid sequence of SEQ ID NO: 228, and a CDR3 that is encoded by the nucleic acid sequence of SEQ ID NO: 230, and the beta chain comprises a CDR1 that is encoded by the nucleic acid sequence of SEQ ID NO: 464, a CDR2 that is encoded by the nucleic acid sequence of SEQ ID NO: 466, and a CDR3 that is encoded by the nucleic acid sequence of SEQ ID NO: 468. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 574, and the beta chain comprises a VJD region that is encoded by a nucleic acid sequence that is at least 90%, 95%, 96%, 97%, 98%, 99% or 100% identical to the nucleic acid sequence of SEQ ID NO: 676. In certain embodiments, the alpha chain is encoded by a nucleic acid sequence that is at least 90%, 95%, 96%, 97%, 98%, 99% or 100% identical to the nucleic acid sequence of SEQ ID NO: 225, and the beta chain is encoded by a nucleic acid sequence that is at least 90%, 95%, 96%, 97%, 98%, 99% or 100% identical to the nucleic acid sequence of SEQ ID NO: 463.

Described herein are polynucleotides that encode a TCR comprising an alpha chain and a beta chain, wherein the alpha chain comprises a CDR3 that is encoded by the nucleic acid sequence of SEQ ID NO: 237, and the beta chain comprises a CDR3 that is encoded by the nucleic acid sequence of SEQ ID NO: 475. Also described herein are polynucleotides that encode a TCR comprising an alpha chain and a beta chain, wherein the alpha chain comprises a CDR1 that is encoded by the nucleic acid sequence of SEQ ID NO: 233, a CDR2 that is encoded by the nucleic acid sequence of SEQ ID NO: 235, and a CDR3 that is encoded by the nucleic acid sequence of SEQ ID NO: 237, and the beta chain comprises a CDR1 that is encoded by the nucleic acid sequence of SEQ ID NO: 471, a CDR2 that is encoded by the nucleic acid sequence of SEQ ID NO: 473, and a CDR3 that is encoded by the nucleic acid sequence of SEQ ID NO: 475. In certain embodiments, the alpha chain comprises a VJ region that is encoded by a nucleic acid sequence that is at least 90%, 95%, 96%, 97%, 98%, 99% or 100% identical to the nucleic acid sequence of SEQ ID NO: 577, and the beta chain comprises a VJD region that is encoded by a nucleic acid sequence that is at least 90%, 95%, 96%, 97%, 98%, 99% or 100% identical to the nucleic acid sequence of SEQ ID NO: 679. In certain embodiments, the alpha chain is encoded by a nucleic acid sequence that is at least 90%, 95%, 96%, 97%, 98%, 99% or 100% identical to the nucleic acid sequence of SEQ ID NO: 232, and the beta chain is encoded by a nucleic acid sequence that is at least 90%, 95%, 96%, 97%, 98%, 99% or 100% identical to the nucleic acid sequence of SEQ ID NO: 470.

In some embodiments, the polynucleotide comprises DNA.

In some embodiments, the polynucleotide comprises RNA.

In some embodiments, the RNA is mRNA.

In some embodiments, the polynucleotide comprises a promoter, an enhancer, a polyadenylation site, a Kozak sequence, a stop codon, or any combination thereof.

Methods of generating polynucleotides of the disclosure are known in the art and include chemical synthesis, enzymatic synthesis (e.g. in vitro transcription), enzymatic or chemical cleavage of a longer precursor, chemical synthesis of smaller fragments of the polynucleotides followed by ligation of the fragments or known PCR methods. The polynucleotide sequence to be synthesized may be designed with the appropriate codons for the desired amino acid sequence. In general, preferred codons may be selected for the intended host in which the sequence will be used for expression.

Vectors

The disclosure also provides vectors comprising any of the polynucleotides disclosed herein. The disclosure also provides vectors comprising a polynucleotide encoding for any of the polypeptides disclosed herein.

Described herein are vectors comprising polynucleotides that encode a TCR comprising an alpha chain and a beta chain, wherein the alpha chain comprises a CDR3 comprising an amino acid sequence provided in Table 4, and the corresponding beta chain comprises a CDR3 comprising a corresponding amino acid sequence provided in Table 5. Described herein are vectors comprising polynucleotides that encode a TCR comprising an alpha chain and a beta chain, wherein the alpha chain comprises a CDR3 that is encoded by a nucleic acid sequence provided in Table 4, and the corresponding beta chain comprises a CDR3 that is encoded by a corresponding nucleic acid sequence provided in Table 5.

Also described herein are vectors comprising polynucleotides that encode a TCR comprising an alpha chain and a beta chain, wherein the alpha chain comprises a CDR1 comprising the amino acid sequence provided in Table 4, a CDR2 comprising an amino acid sequence provided in Table 4, and a CDR3 comprising an amino acid sequence provided in Table 4, and the corresponding beta chain comprises a CDR1 comprising an amino acid sequence provided in Table 5, a CDR2 comprising an amino acid sequence provided in Table 5, and a CDR3 comprising an amino acid sequence provided in Table 5.

Also described herein are vectors comprising polynucleotides that encode a TCR comprising an alpha chain and a beta chain, wherein the alpha chain comprises a CDR1 that is encoded by a nucleic acid sequence provided in Table 4, a CDR2 that is encoded by a nucleic acid sequence provided in Table 4, and a CDR3 that is encoded by a nucleic acid sequence provided in Table 4, and the corresponding beta chain comprises a CDR1 that is encoded by a nucleic acid sequence provided in Table 5, a CDR2 that is encoded by a nucleic acid sequence provided in Table 5, and a CDR3 that is encoded by a nucleic acid sequence provided in Table 5.

Also described herein are vectors comprising polynucleotides that encode a TCR comprising an alpha chain and a beta chain, wherein the alpha chain comprises a VJ region comprising an amino acid sequence that is at least 90%, 95%, 96%, 97%, 98%, 99% or 100% identical to an amino acid sequence provided in Table 4, and the corresponding beta chain comprises a VDJ region comprising an amino acid sequence that is at least 90%, 95%, 96%, 97%, 98%, 99% or 100% identical to an amino acid sequence provided in Table 5.

Also described herein are vectors comprising polynucleotides that encode a TCR comprising an alpha chain and a beta chain, wherein the alpha chain comprises a VJ region that is encoded by a nucleic acid sequence that is at least 90%, 95%, 96%, 97%, 98%, 99% or 100% identical to a nucleic acid sequence provided in Table 4, and the corresponding beta chain comprises a VDJ region that is encoded by a nucleic acid sequence that is at least 90%, 95%, 96%, 97%, 98%, 99% or 100% identical to a nucleic acid sequence provided in Table 5.

Also described herein are vectors comprising polynucleotides that encode a TCR comprising an alpha chain and a beta chain, wherein the alpha chain comprises an amino acid sequence that is at least 90%, 95%, 96%, 97%, 98%, 99% or 100% identical to an amino acid sequence provided in Table 4, and the corresponding beta chain comprises an amino acid sequence that is at least 90%, 95%, 96%, 97%, 98%, 99% or 100% identical to an amino acid sequence provided in Table 5.

Also described herein are vectors comprising polynucleotides that encode a TCR polypeptide comprising an alpha chain and a beta chain, wherein the alpha chain is encoded by a nucleic acid sequence that is at least 90%, 95%, 96%, 97%, 98%, 99% or 100% identical to a nucleic acid sequence provided in Table 4, and the corresponding beta chain is encoded by a nucleic acid sequence that is at least 90%, 95%, 96%, 97%, 98%, 99% or 100% identical to a nucleic acid sequence provided in Table 5.

The vector may be a vector intended for expression of the polynucleotide of the disclosure in any host, such as bacteria, yeast, or a mammal. Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed or transduced with the desired DNA sequences. Exemplary vectors are plasmids, cosmids, phages, viral vectors, or artificial chromosomes.

Suitable vectors that may be used include, but are not limited to—Bacterial: pBs, phagescript, PsiX174, pBluescript SK, pBs KS, pNH8a, pNH16a, pNH18a, pNH46a (Stratagene, La Jolla, Calif., USA), pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene), pSVK3, pBPV, pMSG and pSVL (Pharmacia).

The disclosure provides an expression vector comprising the polynucleotide of the disclosure. The disclosure also provides an expression vector comprising the polynucleotide encoding for the polypeptide of the disclosure.

Other Viral Vectors and Recombinant Viruses

The disclosure also provides a viral vector comprising any of the polynucleotides of the disclosure.

The disclosure also provides a viral vector comprising a polynucleotide encoding any of the TCR polypeptides of the disclosure.

Viral vectors are derived from naturally occurring virus genomes, which typically are modified to be replication incompetent, e.g. non-replicating. Non-replicating viruses require the provision of proteins in trans for replication. Typically, those proteins are stably or transiently expressed in a viral producer cell line, thereby allowing replication of the virus. The viral vectors are, thus, typically infectious, and non-replicating. Viral vectors may be adenovirus vectors, adeno-associated virus (AAV) vectors (e.g., AAV type 5 and type 2), Great ape adenovirus vectors (GAd), alphavirus vectors (e.g., Venezuelan equine encephalitis virus (VEEV), Sindbis virus (SIN), Semliki forest virus (SFV), and VEE-SIN chimeras), herpes virus vectors (e.g. vectors derived from cytomegaloviruses, like rhesus cytomegalovirus (RhCMV)), arena virus vectors (e.g. lymphocytic choriomeningitis virus (LCMV) vectors), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus vectors, lentivirus vectors, viral like particles, LNP encapsulated self-replicating RNA derived from alpha virus, and bacterial spores.

In some embodiments, the viral vector is derived from adenovirus, poxvirus, alphavirus, adeno-associated virus, retrovirus, or a self-replicating RNA molecule.

In some embodiments, the viral vector is derived from an adenovirus.

Suitable adenovirus vectors include, for example, hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAdl7, ChAd19, ChAd20, ChAd22, ChAd24, ChAd26, ChAd30, ChAd3l, ChAd37, ChAd38, ChAd44, ChAd55, ChAd63, ChAd73, ChAd82, ChAd83, ChAd146, ChAd147, PanAd1, PanAd2, and PanAd3.

Adenovirus vectors may be derived from human adenovirus (Ad) but also from adenoviruses that infect other species, such as bovine adenovirus (e.g. bovine adenovirus 3, BAdV3), a canine adenovirus (e.g. CAdV2), a porcine adenovirus (e.g. PAdV3 or 5), or great apes, such as Chimpanzee (Pan), Gorilla (Gorilla), Orangutan (Pongo), Bonobo (Pan paniscus) and common chimpanzee (Pan troglodytes). Typically, naturally occurring great ape adenoviruses are isolated from stool samples of the respective great ape.

Human adenovirus vectors may be derived from various adenovirus serotypes, for example from human adenovirus serotypes hAd5, hAd7, hAd11, hAd26, hAd34, hAd35, hAd48, hAd49 or hAd50 (the serotypes are also referred to as Ad5, Ad7, Ad11, Ad26, Ad34, Ad35, Ad48, Ad49 or Ad50).

Great ape adenovirus (GAd) vectors may be derived from various adenovirus serotypes, for example from great ape adenovirus serotypes GAd20, GAd19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAdl7, ChAd19, ChAd20, ChAd22, ChAd24, ChAd26, ChAd30, ChAd3l, ChAd37, ChAd38, ChAd44, ChAd55, ChAd63, ChAd73, ChAd82, ChAd83, ChAd146, ChAd147, PanAd1, PanAd2, or PanAd3.

Adenovirus vectors are known in the art. The sequences of most of the human and non-human adenoviruses are known, and for others can be obtained using routine procedures. An exemplary genome sequence of Ad26 is found in GenBank Accession number EF153474 and in Int. Pat. Publ. No. WO2007/104792. An exemplary genome sequence of Ad35 is found in Int. Pat. Publ. No. W02000/70071. Vectors based on Ad26 are described for example, in Int. Pat. Publ. No. WO2007/104792. Vectors based on Ad35 are described for example in U.S. Pat. No. 7,270,811 and Int. Pat. Publ. No. W02000/70071. Vectors based on ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in WO2005/071093. Vectors based on PanAd1, PanAd2, PanAd3, ChAd55, ChAd73, ChAd83, ChAd146, and ChAd147 are described in Int. Pat. Publ. No. WO2010/086189.

In some embodiments, the viral vector is a poxvirus. In some embodiments, the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Poxvirus (Poxviridae) vectors may be derived from smallpox virus (variola), vaccinia virus, cowpox virus or monkeypox virus. Exemplary vaccinia viruses are the Copenhagen vaccinia virus (W), New York Attenuated Vaccinia Virus (NYVAC), ALVAC, TROVAC or Modified Vaccinia Ankara (MVA).

MVA originates from the dermal vaccinia strain Ankara (Chorioallantois vaccinia Ankara (CVA) virus) that was maintained in the Vaccination Institute, Ankara, Turkey for many years and used as the basis for vaccination of humans.

In some embodiments, the viral vector is an adeno-associated virus. The viral vector comprising the polynucleotides of the disclosure may be derived from human adeno-associated viruses, such as AAV-2 (adeno-associated virus type 2). An attractive feature of AAV vectors is that they do not express any viral genes. The only viral DNA sequences included in the AAV vectors are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ particles or copies of DNA in contrast to naked DNA doses of 50 g or about $10^{15}$ copies. AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay).

The viral vector comprising the polynucleotide of the disclosure also include Retroviral vectors. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (Int. Pat. Publ. No. WO1995/01447). Generally, a retroviral vector contains deletions of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by a retrotransposon such as VL30 (see, e.g., U.S. Pat. No. 5,747,323).

The polynucleotides encoding the polypeptide of the disclosure may be inserted downstream of the encapsidation sequence, such as in opposite direction relative to the retroviral genome. Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in Miller and Rosman, 1989, BioTechniques 7: 980; Danos and Mulligan, 1988, Proc. Natl. Acad. Sci. USA 85: 6460; Markowitz, et al., 1988, Virol. 167: 400. The product of the env gene is responsible for the binding of the viral particle to the viral receptors present on the surface of the target cell and, therefore determines the host range of the retroviral particle. Packaging cell line, such as the PA317 cells (ATCC CRL 9078) or 293EI6 (WO97/35996) containing an amphotropic envelope protein may therefore be used to allow infection of human and other species' target cells. The retroviral particles are recovered from the culture supernatant and may optionally be further purified according to standard techniques (e.g. chromatography, ultracentrifugation).

The disclosure also provides a host cell comprising any of the above vectors.

Suitable host cells include prokaryotic or eukaryotic host cells. In some embodiments, the host cell is PER.C6, PER.C6 TetO, a chicken embryo fibroblast (CEF), CHO, HEK293, HT-1080, HKB-11, CAP, HuH-7, or Age1 cell line.

Self-Replicating RNA Molecules

Provided herein is a viral vector comprising any of the polynucleotides of the disclosure, wherein the vector is a self-replicating RNA molecule.

Self-replicating RNA may be derived from alphavirus. Alphaviruses may belong to the VEEV/EEEV group, or the SF group, or the SIN group. Non-limiting examples of SF group alphaviruses include Semliki Forest virus, O'Nyong-Nyong virus, Ross River virus, Middelburg virus, Chikungunya virus, Barmah Forest virus, Getah virus, Mayaro virus, Sagiyama virus, Bebaru virus, and Una virus. Non-limiting examples of SIN group alphaviruses include Sindbis virus, Girdwood S. A. virus, South African Arbovirus No. 86, Ockelbo virus, Aura virus, Babanki virus, Whataroa virus, and Kyzylagach virus. Non-limiting examples of VEEV/EEEV group alphaviruses include Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), and Una virus (UNAV).

The self-replicating RNA molecules can be derived from alphavirus genomes, meaning that they have some of the structural characteristics of alphavirus genomes, or similar to them. The self-replicating RNA molecules can be derived from modified alphavirus genomes.

Self-replicating RNA molecules may be derived from Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. Virulent and avirulent alphavirus strains are both suitable. In some embodiments, the alphavirus RNA replicon is of a Sindbis virus (SIN), a Semliki Forest virus (SFV), a Ross River virus (RRV), a Venezuelan equine encephalitis virus (VEEV), or an Eastern equine encephalitis virus (EEEV).

In some embodiments, the alphavirus-derived self-replicating RNA molecule is a Venezuelan equine encephalitis virus (VEEV).

The self-replicating RNA molecules can contain RNA sequences from (or amino acid sequences encoded by) a wild-type New World or Old World alphavirus genome. Any of the self-replicating RNA molecules disclosed herein can contain RNA sequences "derived from" or "based on" wild type alphavirus genome sequences, meaning that they have at least 60% or at least 65% or at least 68% or at least 70% or at least 80% or at least 85% or at least 90% or at least 95% or at least 97% or at least 98% or at least 99% or 100% or 80-99% or 90-100% or 95-99% or 95-100% or 97-99% or 98-99% sequence identity with an RNA sequence (which can be a corresponding RNA sequence) from a wild type RNA alphavirus genome, which can be a New World or Old World alphavirus genome.

Self-replicating RNA molecules contain all of the genetic information required for directing their own amplification or self-replication within a permissive cell. To direct their own replication, self-replicating RNA molecules encode polymerase, replicase, or other proteins which may interact with viral or host cell-derived proteins, nucleic acids or ribonucleoproteins to catalyze the RNA amplification process; and contain cis-acting RNA sequences required for replication and transcription of the replicon-encoded RNA. Thus, RNA replication leads to the production of multiple daughter RNAs. These daughter RNAs, as well as collinear subgenomic transcripts, can be translated to provide in situ expression of a gene of interest, or can be transcribed to provide further transcripts with the same sense as the delivered RNA which are translated to provide in situ expression of the gene of interest. The overall results of this sequence of transcriptions is a huge amplification in the number of the introduced replicon RNAs and so the encoded gene of interest becomes a major polypeptide product of the cells.

There are two open reading frames (ORF's) in the genome of alphaviruses, non-structural (ns) and structural genes. The ns ORF encodes proteins (nsP1-nsP4) necessary for transcription and replication of viral RNA and are produced as a polyprotein and are the virus replication machinery. The structural ORF encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion. The four ns protein genes are encoded by genes in the 5' two-thirds of the genome, while the three structural proteins are translated from a subgenomic mRNA colinear with the 3' one-third of the genome.

Self-replicating RNA molecules can be used as basis of introducing foreign sequences to host cells by replacing viral sequences encoding structural genes or inserting the foreign sequences 5' or 3' of the sequences encoding the structural genes. They can be engineered to replace the viral structural genes downstream of the replicase, which are under control of a subgenomic promoter, by genes of interest (GOI), e.g. the polynucleotide encoding for the polypeptide of the disclosure. Upon transfection, the replicase which is translated immediately, interacts with the 5' and 3' termini of the genomic RNA, and synthesizes complementary genomic RNA copies. Those act as templates for the synthesis of novel positive-stranded, capped, and poly-adenylated genomic copies, and subgenomic transcripts. Amplification eventually leads to very high RNA copy numbers of up to $2\times10^5$ copies per cell. The result is a uniform and/or enhanced expression of a GOI (e.g. the polynucleotide encoding for the polypeptide of the disclosure) that can affect efficacy or therapeutic impact of a treatment.

The disclosure provides a self-replicating RNA molecule containing all of the genetic information required for directing its own amplification or self-replication within a permissive cell.

The disclosure also provides a self-replicating RNA molecule that can be used as the basis of introducing foreign sequences to host cells (e.g. the polynucleotides encoding the polypeptides of the disclosure) by replacing viral sequences encoding structural genes.

Provided herein is a viral vector comprising any of the polynucleotides of the disclosure, wherein the vector is a self-replicating RNA molecule.

Any of the above self-replicating RNA molecules can further comprise one or more of the following:

one or more nonstructural genes nsP1, nsP2, nsP3 and nsP4;

at least one of a DLP motif, a 5' UTR, a 3'UTR and a Poly A; and a subgenomic promoter.

In some embodiments, for example, the self-replicating RNA molecule can comprise one or more of the following:

one or more nonstructural genes nsP1, nsP2, nsP3 and nsP4;

at least one of a DLP motif, a 5' UTR, a 3'UTR and a Poly A; and a subgenomic promoter; and an RNA encoding for amino acids of SEQ ID NOs: 8 or 10, and operably linked to the subgenomic promoter.

In some embodiments, the self-replicating RNA molecule comprises an RNA sequence encoding a protein or peptide; 5' and 3' alphavirus untranslated regions; RNA sequences encoding amino acid sequences derived from New World alphavirus VEEV nonstructural proteins nsP1, nsP2, nsP3 and nsP4; a sub-genomic promoter that is operably linked to and regulates translation of the RNA sequence encoding the protein; a 5' cap and a 3' poly-A tail; positive sense, single-stranded RNA; a DLP from Sindbis virus upstream of the non-structural protein 1(nsP1); a 2A ribosome skipping element; and a nsp1 nucleotide repeat downstream of the 5'-UTR and upstream of the DLP.

In some embodiments, the self-replicating RNA molecules may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size.

Any of the above-disclosed self-replicating RNA molecules can further include a coding sequence for an autoprotease peptide (e.g., autocatalytic self-cleaving peptide), where the coding sequence for the autoprotease is optionally operably linked upstream to the nucleic acid sequence encoding the GOI.

Generally, any proteolytic cleavage site known in the art can be incorporated into the nucleic acid molecules of the disclosure and can be, for example, proteolytic cleavage sequences that are cleaved post-production by a protease. Further suitable proteolytic cleavage sites also include proteolytic cleavage sequences that can be cleaved following addition of an external protease. As used herein the term "autoprotease" refers to a "self-cleaving" peptide that possesses autoproteolytic activity and is capable of cleaving itself from a larger polypeptide moiety. First identified in the foot-and-mouth disease virus (FMDV), a member of the picornavirus group, several autoproteases have been subsequently identified such as, for example, "2A like" peptides from equine rhinitis A virus (E2A), porcine teschovirus-1 (P2A) and Thosea asigna virus (T2A), and their activities in proteolytic cleavage have been shown in various ex vitro and in vivo eukaryotic systems. As such, the concept of autoproteases is available to one of skill in the art as many naturally occurring autoprotease systems have been identified. Well studied autoprotease systems are e.g. viral proteases, developmental proteins (e.g. HetR, Hedgehog proteins), RumA autoprotease domain, UmuD, etc.). Non-limiting examples of autoprotease peptides suitable for the compositions and methods of the present disclosure include the peptide sequences from porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

In some embodiments, the coding sequence for the autoprotease peptide is operably linked downstream of the DLP motif and upstream to the GOI.

In some embodiments, the autoprotease peptide comprises, or consists of, a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the autoprotease peptide includes a peptide sequence of porcine teschovirus-1 2A (P2A).

In some embodiments, the autoprotease peptide is selected from the group consisting of porcine teschovirus-1 2A (P2A), foot-and-mouth disease virus (FMDV) 2A (F2A), Equine Rhinitis A Virus (ERAV) 2A (E2A), Thosea asigna virus 2A (T2A), cytoplasmic polyhedrosis virus 2A (BmCPV2A), Flacherie Virus 2A (BmIFV2A), and a combination thereof.

In some embodiments, the autoprotease peptide is porcine teschovirus-1 2A (P2A).

The incorporation of the P2A peptide in the modified viral RNA replicons allows release of protein encoded by GOI (e.g. the polynucleotides encoding the TCR polypeptides of the disclosure) from the capsid-GOI fusion.

In some embodiments disclosed herein, the porcine teschovirus-1 2A (P2A) peptide sequence is engineered in-frame immediately after the DLP sequence and in-frame immediately upstream of all GOI.

Any of the above-disclosed self-replicating RNA molecules can further include a coding sequence downstream Loop (DLP) motif.

Some viruses have sequences capable of forming one or more stem-loop structures which regulate, for example increase, capsid gene expression. Viral capsid enhancer as used herein refers to a regulatory element comprising sequences capable of forming such stem-loop structures. In some examples, the stem-loop structures are formed by sequences within the coding sequence of a capsid protein and named Downstream Loop (DLP) sequence. As disclosed herein, these stem-loop structures or variants thereof can be used to regulate, for example increase, expression level of genes of interest. For example, these stem-loop structures or variants thereof can be used in a recombinant vector (e.g., in a heterologous viral genome) for enhancing transcription and/or translation of coding sequence operably linked downstream thereto.

Alphavirus replication in host cells is known to induce the double-stranded RNA-dependent protein kinase (PKR). PKR phosphorylates the eukaryotic translation initiation factor 2α (eIF2α). Phosphorylation of eIF2α blocks translation initiation of mRNA and in doing so keeps viruses from a completing a productive replication cycle. Infection of cells with Sindbis virus induces PKR that results in phosphorylation of eIF2α, yet the viral subgenomic mRNA is efficiently translated while translation of all other cellular mRNAs is restricted. The efficient translation of the viral subgenomic mRNA in Sindbis virus is made possible by the presence of a stable RNA hairpin loop (or DLP motif) located downstream of the wild type AUG initiator codon for the virus capsid protein (e.g., capsid enhancer). It has been reported that the DLP structure can stall a ribosome on the wild type AUG and this supports translation of the subgenomic mRNA without the requirement for functional eIF2α. Thus, subgenomic mRNAs of Sindbis virus (SINV) as well as of other alphaviruses are efficiently translated even in cells that have highly active PKR resulting in complete phosphorylation of eIF2α.

The DLP structure was first characterized in Sindbis virus (SINV) 26S mRNA and also detected in Semliki Forest virus (SFV). Similar DLP structures have been reported to be present in at least 14 other members of the Alphavirus genus including New World (for example, MAYV, UNAV, EEEV (NA), EEEV (SA), AURAV) and Old World (SV, SFV, BEBV, RRV, SAG, GETV, MIDV, CHIKV, and ONNV) members. The predicted structures of these Alphavirus 26S mRNAs were constructed based on SHAPE (selective 2'-hydroxyl acylation and primer extension) data (Toribio et al., Nucleic Acids Res. May 19; 44(9):4368-80, 2016), the content of which is hereby incorporated by reference). Stable stem-loop structures were detected in all cases except for CHIKV and ONNV, whereas MAYV and EEEV showed DLPs of lower stability (Toribio et al., 2016 supra). The highest DLP activities were reported for those Alphaviruses that contained the most stable DLP structures.

As an example, members of the Alphavirus genus can resist the activation of antiviral RNA-activated protein kinase (PKR) by means of the downstream loop (DLP) present within viral 26S transcripts, which allows an eIF2-independent translation initiation of these mRNAs. The downstream loop (DLP), is located downstream from the AUG in SINV 26S mRNA and in other members of the Alphavirus genus.

In some embodiments, the nucleic acid molecules of the disclosure can include a coding sequence for a GOI operably linked to DLP motif(s) and/or the coding sequence for the DLP motifs.

In some embodiments, the self-replicating RNA molecule of the disclosure comprises a downstream loop (DLP).

In some embodiments, the downstream loop (DLP) comprises at least one RNA-stem-loop.

In some instances, DLP activity depends on the distance between the DLP motif and the initiation codon AUG (AUGi). The AUG-DLP spacing in Alphavirus 26S mRNAs is tuned to the topology of the ES6S region of the ribosomal 18S rRNA in a way that allows the placement of the AUGi in the P site of the 40S subunit stalled by the DLP, allowing the incorporation of Met-tRNA without the participation of eIF2. In the case of Sindbis virus, the DLP motif is found in the first ~150 nt of the Sindbis subgenomic RNA. The hairpin is located downstream of the Sindbis capsid AUG initiation codon (AUG at nt 50 of the Sindbis subgenomic RNA) and results in stalling a ribosome such that the correct capsid gene AUG is used to initiate translation. Previous studies of sequence comparisons and structural RNA analysis revealed the evolutionary conservation of DLP in SINV and predicted the existence of equivalent DLP structures in many members of the Alphavirus genus (see e.g., Ventoso, J. Virol. 9484-9494, Vol. 86, September 2012).

Without being bound by any particular theory, it is believed that placing the DLP motif upstream of a coding sequence for any GOI typically results in a fusion-protein of N-terminal capsid amino acids that are encoded in the hairpin region to the GOI encoded protein because initiation occurs on the capsid AUG not the GOI AUG.

In some embodiments, the self-replicating RNA molecule comprises a downstream loop placed upstream of the non-structural protein 1 (nsP1).

In some embodiments, the downstream loop is placed upstream of the non-structural protein 1 (nsP1) and is joined to the nsP1 by a porcine teschovirus-1 2A (P2A) ribosome skipping element.

The DLP-containing self-replicating RNA of the disclosure can be useful in conferring a resistance to the innate immune system in a subject. Unmodified RNA replicons are sensitive to the initial innate immune system state of cells they are introduced into. If the cells/individuals are in a highly active innate immune system state, the RNA replicon performance (e.g., replication and expression of a GOI) can be negatively impacted. By engineering a DLP to control initiation of protein translation, particularly of non-structural proteins, the impact of the pre-existing activation state of the innate immune system to influence efficient RNA replicon replication is removed or lessened. The result is more uniform and/or enhanced expression of a GOI that can impact efficacy or therapeutic impact of a treatment.

The DLP motif of the self-replicating RNA can confer efficient mRNA translation in cellular environments where cellular mRNA translation is inhibited. When a DLP is linked with translation of a replicon vector's non-structural protein genes the replicase and transcriptase proteins are capable of initiating functional replication in PKR activated cellular environments. When a DLP is linked with translation of subgenomic mRNAs robust GOI expression is possible even when cellular mRNA is restricted due to innate immune activation. Accordingly, engineering self-replicating RNA that contain DLP structures to help drive translation of both non-structural protein genes and subgenomic mRNAs provides a powerful way to overcome innate immune activation.

Examples of a self-replicating RNA vector comprising a DLP motif are described in US Patent Application Publication US2018/0171340 and the International Patent Application Publication WO2018106615, the content of which is incorporated herein by reference in its entirety.

Any of the above-disclosed self-replicating RNA molecules can further comprise nonstructural genes nsP1, nsP2, nsP3 and/or nsP4. In some embodiments, the self-replicating RNA molecule does not encode a functional viral structural protein.

Alphavirus genomes encode non-structural proteins nsP1, nsP2, nsP3, and nsP4, which are produced as a single polyprotein precursor, sometimes designated P1234 (or nsP1-4 or nsP1234), and which is cleaved into the mature proteins through proteolytic processing. nsP1 can be about 60 kDa in size and may have methyltransferase activity and be involved in the viral capping reaction. nsP2 has a size of about 90 kDa and may have helicase and protease activity while nsP3 is about 60 kDa and contains three domains: a macrodomain, a central (or alphavirus unique) domain, and a hypervariable domain (HVD). nsP4 is about 70 kDa in size and contains the core RNA-dependent RNA polymerase (RdRp) catalytic domain. After infection the alphavirus genomic RNA is translated to yield a P1234 polyprotein, which is cleaved into the individual proteins.

Alphavirus genomes also encode three structural proteins: the core nucleocapsid protein C, and the envelope proteins P62 and E1 that associate as a heterodimer. Structural proteins are under the control of a subgenomic promoter and can be replaced by the GIO.

In some embodiments, the self-replicating RNA can lack (or not contain) the sequence(s) of at least one (or all) of the structural viral proteins (e.g. nucleocapsid protein C, and envelope proteins P62, 6K, and E1). In these embodiments, the sequences encoding one or more structural genes can be substituted with one or more sequences such as, for example, a coding sequence for at least one protein or peptide (or other gene of interest (GOI)) e.g. the TCR polypeptides of the disclosure.

In some embodiments, the self-replicating RNA lack sequences encoding alphavirus structural proteins; or do not encode alphavirus (or, optionally, any other) structural proteins. In some embodiments, the self-replicating RNA molecules are further devoid of a part or the entire coding region for one or more viral structural proteins. For example, the alphavirus expression system may be devoid of a portion of or the entire coding sequence for one or more of the viral capsid protein C, E1 glycoprotein, E2 glycoprotein, E3 protein and 6K protein.

In some embodiments, the self-replicating RNA molecule does not contain coding sequences for at least one of the structural viral proteins. In these instances, the sequences encoding structural genes can be substituted with one or more sequences such as, for example, a coding sequence for a GOI (e.g., the TCR polypeptides).

The disclosure also provides a self-replicating RNA molecule comprising nonstructural genes nsP1, nsP2, nsP3 and nsP4, and wherein the self-replicating RNA molecule does not encode a functional viral structural protein.

In some embodiments, the disclosure provides a self-replicating RNA molecule comprising the coding sequence for at least one, at least two, at least three, or at least four nonstructural viral proteins (e.g. nsP1, nsP2, nsP3, nsP4).

The nsP1, nsP2, nsP3, and nsP4 proteins encoded by the replicon are functional or biologically active proteins.

In some embodiments, the self-replicating RNA molecule includes the coding sequence for a portion of the at least one nonstructural viral protein. For example, the self-replicating RNA molecules can include about 10%, 20%, 30%, 40%, 50%, 60%, 70%, 80%, 90%, 95%, 100%, or a range between any two of these values, of the encoding sequence for the at least one nonstructural viral protein. In some embodiments, the self-replicating RNA molecule can include the coding sequence for a substantial portion of the at least one nonstructural viral protein. As used herein, a "substantial portion" of a nucleic acid sequence encoding a nonstructural viral protein comprises enough of the nucleic acid sequence encoding the nonstructural viral protein to afford putative identification of that protein, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993).

In some embodiments, the self-replicating RNA molecule can include the entire coding sequence for the at least one nonstructural protein. In some embodiments, the self-replicating RNA molecule comprises substantially all the coding sequence for the native viral nonstructural proteins. In certain embodiments, the one or more nonstructural viral proteins are derived from the same virus.

In some embodiments, the downstream loop DLP of the self-replicating RNA molecule placed upstream of the non-structural protein 1(nsP1) is derived from Sindbis virus.

In some embodiments, the self-replicating RNA molecule comprises nsP1, nsP2, nsP3, and nsP4 sequences derived from the Venezuelan equine encephalitis virus (VEEV) and a DLP motif derived from the Sindbis virus (SIN).

In some embodiments, the self-replicating RNA molecules also have an RNA sub-sequence encoding an amino acid sequence derived from an alphavirus nsP3 macro domain, and an RNA sub-sequence encoding an amino acid sequence derived from an alphavirus nsP3 central domain. The self-replicating RNA molecules can also have an RNA sub-sequence encoding an amino acid sequence derived entirely from an Old World alphavirus nsP3 hypervariable domain, or can have an amino acid sequence having a portion derived from a New World alphavirus nsP3 hypervariable domain and a portion derived from an Old World alphavirus nsP3 hypervariable domain. i.e. the hyper variable domain (HVD) can be a hybrid or chimeric New World/Old World sequence.

In some embodiments, the self-replicating RNA molecules can have an RNA sequence encoding amino acid sequences derived from wild type New World alphavirus nsP1, nsP2, nsP3, and nsP4 protein sequences. In other embodiments, the one or more nonstructural proteins are derived from different viruses.

In some embodiments, the self-replicating RNA molecule may have an RNA sequence encoding an nsP3 macro domain derived from a wild type alphavirus nsP3, and an nsP3 central domain derived from a wild type alphavirus nsP3. In various embodiments, the macro and central domain(s) can both be derived from a New World wild type alphavirus nsP3 or can both be derived from an Old World wild type alphavirus nsP3 protein. In other embodiments, the macro domain can be derived from a New World wild type alphavirus macro domain and the central domain can be derived from an Old World wild type alphavirus central domain, or vice versa. The various domains can be of any sequence described herein.

In some embodiments, the self-replicating RNA molecule contains non VEEV nonstructural proteins nsP1, nsP2, nsP3 and nsP4.

The accumulated experimental evidence has demonstrated that replication/amplification of VEEV and other alphavirus genomes and their defective interfering (DI) RNAs is determined by three promoter elements: (i) the conserved 3'-terminal sequence element (3' CSE) and the following poly(A) tail; (ii) the 5' UTR, which functions as a key promoter element for both negative- and positive-strand RNA synthesis; and (iii) the 51-nt conserved sequence element (51-nt CSE), which is located in the nsP1-coding sequence and functions as an enhancer of alphavirus genome replication (Kim et al., PNAS, 2014, 111: 10708-10713, and references therein).

Any of the above-disclosed self-replicating RNA molecules can further include an unmodified 5' untranslated region (5'UTR).

Previous studies have demonstrated that during VEEV and Sindbis virus infections only a small portion of viral nonstructural proteins (nsPs) is colocalized with dsRNA replication intermediates. Thus, it appears that a large fraction of nsPs are not involved in RNA replication (Gorchakov R, et al. (2008) A new role for ns polyprotein cleavage in Sindbis virus replication. J Virol 82(13):6218-6231). This has provided an opportunity to exploit the under used ns proteins for amplification of the subgenomic RNAs encoding proteins of interest, which is normally transcribed from the subgenomic promoter and is not further amplified.

In some embodiments, a fragment of the nsP1 of the self-replicating RNA molecule of the disclosure is duplicated downstream of the 5'-UTR and upstream of the DLP.

In some embodiments, the first 193 nucleotides of nsP1 are duplicated downstream of the 5' UTR and upstream of the DLP.

In some embodiments, the self-replicating RNA molecule comprises a modified 5' untranslated region (5'-UTR). For example, the modified 5'-UTR can comprise one or more nucleotide substitutions at position 1, 2, 4, or a combination thereof. Preferably, the modified 5'-UTR comprises a nucleotide substitution at position 2, more preferably the modified 5'-UTR has a U->G substitution at position 2. Examples of such self-replicating RNA molecules are described in US Patent Application Publication US2018/0104359 and International Patent Application Publication WO2018075235, the content of which is incorporated herein by reference in its entirety.

In some embodiments, the UTRs can be wild type New World or Old World alphavirus UTR sequences, or a sequence derived from any of them. The 5' UTR can be of any suitable length, such as about 60 nt or 50-70 nt or 40-80 nt. In some embodiments the 5' UTR can also have conserved primary or secondary structures (e.g. one or more stem-loop(s)) and can participate in the replication of alphavirus or of replicon RNA. The 3' UTR can be up to several hundred nucleotides, for example it can be 50-900 or 100-900 or 50-800 or 100-700 or 200 nt-700 nt. The '3 UTR also can have secondary structures, e.g. a step loop, and can be followed by a polyadenylate tract or poly-A tail.

The 5' and 3' untranslated regions can be operably linked to any of the other sequences encoded by the replicon. The UTRs can be operably linked to a promoter and/or sequence encoding a protein or peptide by providing sequences and spacing necessary for recognition and transcription of the other encoded sequences.

The GOI (e.g. the polynucleotides encoding the TCR polypeptides of the disclosure) can be expressed under the control of a subgenomic promoter. In certain embodiments, instead of the native subgenomic promoter, the subgenomic RNA can be placed under control of internal ribosome entry site (IRES) derived from encephalomyocarditis viruses (EMCV), Bovine Viral Diarrhea Viruses (BVDV), polioviruses, Foot-and-mouth disease viruses (FMD), enterovirus 71, or hepatitis C viruses. Subgenomic promoters range from 24 nucleotides (Sindbis virus) to over 100 nucleotides (Beet necrotic yellow vein virus) and are usually found upstream of the transcription start.

The self-replicating RNA molecules can have a 3' poly-A tail. It can also include a poly-A polymerase recognition sequence (e.g. AAUAAA) near its 3' end.

In those instances where the self-replicating RNA molecule is to be packaged into a recombinant alphavirus particle, it can contain one or more sequences, so-called packaging signals, which serve to initiate interactions with alphavirus structural proteins that lead to particle formation. In some embodiments, the alphavirus particles comprise RNA derived from one or more alphaviruses, and structural proteins wherein at least one of said structural proteins is derived from two or more alphaviruses.

In some embodiments, the self-replicating RNA molecule comprises a VEEV derived vector wherein the structural viral proteins (e.g. nucleocapsid protein C, and envelope proteins P62, 6K, and E1) are removed and replaced by the coding sequence of the polypeptides of the disclosure.

Engineered Cells Expressing the TCRs of the Disclosure

Engineered cells expressing the TCRs that specifically bind the CALR and JAK2 epitopes of the disclosure are within the scope of the disclosure. The present disclosure provides engineered cells (e.g., T cells) comprising any one of an alpha TCR chain and any one of a beta TCR chain, as disclosed in Tables 4 and 5. These engineered cells can be used to treat various disorders or disease, such as cancer, myeloproliferative disease and cardiovascular disease.

Suitable engineered cells include those obtained from, for example, animals and humans.

In some embodiments, the cell comprising the TCR of the disclosure is a T cell, a natural killer (NK) cell, a cytotoxic T lymphocyte (CTL), a regulatory T cell (Treg), a human embryonic stem cell, a lymphoid progenitor cell, a T cell-precursor cell, a pluripotent stem cell or induced pluripotent stem cell (iPSC) from which lymphoid cells may be differentiated. In some embodiments, the isolated cell comprising the TCR of the disclosure is a T cell. The T cell may be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from any source, including bone marrow, blood, lymph node, thymus, or other tissues or fluids. T cells may also be enriched for or purified. The T cell may be a human T cell. The T cell may be a T cell isolated from a human. The T cell can be any type of T cell and may be of any developmental stage, including, CD4+ CD8+ double positive T cells, CD8+ T cells (e.g., cytotoxic T cells), CD4+ helper T cells, e.g., Th1 and Th2 cells, peripheral blood mononuclear cells (PBMCs), peripheral blood leukocytes (PBLs), tumor infiltrating cells, memory T cells, naïve T cells, and the like. The T cell may be a CD8+ T cell or a CD4+ T cell. The T cell may be an αβ T cell or a γδ T cell.

In some embodiments, the isolated cell comprising the TCR of the disclosure is a NK cell.

In some embodiments, the isolated cell comprising the TCR of the disclosure is a αβ T cell.

In some embodiments, the isolated cell comprising the TCR of the disclosure is a γδ T cell.

In some embodiments, the isolated cell comprising the TCR of the disclosure is a CD8+ cytotoxic T lymphocyte In some embodiments, the isolated cell comprising the TCR of the disclosure is a human embryonic stem cell.

In some embodiments, the isolated cell comprising the TCR of the disclosure is a lymphoid progenitor cell.

In some embodiments, the isolated cell comprising the TCR of the disclosure is a pluripotent stem cell.

In some embodiments, the isolated cell comprising the TCR of the disclosure is an induced pluripotent stem cell (iPSC).

In some embodiments, the isolated cell comprising the TCR of the disclosure is a CD4+T lymphocyte. In certain embodiments, the CD4+T lymphocyte is a $Th_1$ cell. In certain embodiments, the CD4+T lymphocyte is a $Th_2$ cell. In certain embodiments, the CD4+T lymphocyte is a $Th_{17}$ cell. In certain embodiments, the CD4+T lymphocyte is a $T_{reg}$ cell. In certain embodiments, the CD4+T lymphocyte is a $T_{FH}$ cell Methods of Generating Engineered Cells Expressing the TCRs of the Disclosure Described herein are methods for generating engineered cells comprising any one of an alpha TCR chain and any one of a beta TCR chain, as disclosed in Tables 4 and 5.

In some embodiments, to produce an engineered cell for use as a cell therapy product, cells, preferably autologous T cells, are obtained from a pheresis sample withdrawn from a subject and are modified with a vector of the disclosure that encodes the desired TCR alpha and beta sequences. When encountered by the engineered cells, targeted cells may be killed by the engineered cells by virtue of the ability of the engineered cells, such as engineered T cells, to exhibit specific target cell cytotoxicity (i.e., specific cell killing).

The pheresis sample may be collected from the subject by any of a number of suitable lymphocytapheresis, lymphapheresis, and leukaphoresis procedures now known or that become available in the art, which provide for the collection of peripheral blood leukocytes (PBLs) from collected peripheral blood, and from which leukocytes may be separated from other plasma components of the sample. Exemplary procedures are illustrated in, e.g., U.S. Patent Application Publication Numbers US 2004/0173778 and US 200/40147021, and U.S. Pat. Nos. 4,690,915, 5,126,132, 6,255,073, 5,846,827, 6,251,385, 6,225,044, 6,210,963, 6,194,207, 5,443,983, 6,040,177, 5,766,920, 6,210,662, 6,204,058, and 6,227,368.

Selected naive cells, preferably naïve T cells, may be substantially separated from non-selected pheresis sample components. In certain embodiments, naive T cells, which may be naive CD4+ T cells, naive CD8+ T cells, or naive CD4+ T cells and naive CD8+ T cells, are substantially separated from other PBLs, e.g., non-T cells. Methods for selection of PBLs include procedures employing Ficoll gradients, technique employing immunopurification (e.g., monoclonal antibodies directed against cell surface markers, such as CD molecules, and beads, such as Sepharose-, Protein A-, and Protein G-conjugated beads to which the antibodies may be adsorbed, and magnetic beads to which antibodies may be adsorbed), flow cytometry, and fluorescence-activated cell sorter (FACS) analysis.

In certain embodiments, selected naive T cells are substantially purified by magnetic bead purification systems such as those available in the art, e.g., Miltenyi beads (Myltenyi Biotec) and Dynabead systems (Dynal Biotech) combined with cell sorting procedures, such as FACS-based methods, or other appropriate cell sorting devices and methodologies.

A subject from whom a pheresis product comprising naive cells may be obtained is preferably a mammal in need of treatment, such as a dog, a cat, a horse, a rat, rabbit, mouse, a non-human primate, or a human. More preferably, the subject is a human patient in need of treatment for a cancer, a myeloproliferative disease, or a cardiovascular disease. Alternatively, in appropriate circumstances immune cells, such as naive T cells, that are not derived from a subject to be treated, but which are derived from another compatible source such as an immune cell donor, or even an immortalized or transformed immune cell line, may be employed to prepare cell therapy products in accordance with the invention.

The thus-selected naive cells, preferably naïve T cells, are then modified introducing a viral vector comprising any of the disclosed polynucleotides into the cells using known methods. The cells are able to replicate in vivo, resulting in long-term persistence that can lead to sustained tumor control.

In some embodiments, the naive cells, preferably naïve T cells, are transduced with any of the disclosed TCRs, resulting in constitutive expression of the TCR on the surface of the cell. The cells expressing the TCR may further be engineered to express one or more co-stimulatory molecules. Exemplary co-stimulatory molecules are CD28, ICOS, LIGHT, GITR, 4-1BB and OX40. The cells expressing the TCR may further be engineered to produce one or more cytokines or chemokines or proinflammatory mediators, such as TNFα, IFNγ, IL-2, IL-3, IL-6, IL-7, IL-11, IL-12, IL-15, IL-17 or IL-21. The cells may have their endogenous TCR locus and/or HLA locus inactivated using known gene editing technologies.

The engineered cells may optionally be expanded to produce therapeutic compositions and cell therapy products comprising engineered cells of a desired phenotype and number. An exemplary T cell expansion procedure includes incubating activated T cells with irradiated non-CD8+ cells in the presence of selected cytokines and an anti-CD3 antibody preparation to promote non-specific activated T cell expansion. Selection of the expansion protocols to be employed are within the purview of the artisan and may be facilitated by guidance in the art.

Compositions

The disclosure also provides compositions comprising any of the polynucleotides, any of the polypeptides, or any of the vectors disclosed herein. In some embodiments, the compositions may comprise a vector comprising any of the nucleotides disclosed herein.

The compositions may comprise or may be formulated into a pharmaceutical composition comprising the composition and a pharmaceutically acceptable excipient. "Pharmaceutically acceptable" refers to the excipient that at the dosages and concentrations employed, will not cause unwanted or harmful effects in the subjects to which they are administered and include carrier, buffers, stabilizers, or other materials well known to those skilled in the art. The precise nature of the carrier or other material may depend on the route of administration, e.g., intramuscular, subcutaneous, oral, intravenous, cutaneous, intramucosal (e.g., gut), intranasal or intraperitoneal routes. Liquid carriers such as water, petroleum, animal or vegetable oils, mineral oil or synthetic oil may be included. Physiological saline solution, dextrose or other saccharide solution or glycols such as ethylene glycol, propylene glycol or polyethylene glycol may be included. Exemplary formulation are the Adenovirus World Standard (Hoganson et al, 2002): 20 mM Tris pH 8, 25 mM NaCl, 2.5% glycerol; or 20 mM Tris, 2 mM MgCl2, 25 mM NaCl, sucrose 10% w/v, polysorbate-80 0.02% w/v; or 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Many other buffers can be used, and examples of suitable formulations for the storage and for pharmaceutical administration of purified pharmaceutical preparations are known.

Kits/Articles of Manufacture

Kits and articles of manufacture are also described. Such kits include a package or container that is compartmentalized to receive one or more dosages of the pharmaceutical compositions disclosed herein. Suitable containers include, for example, bottles. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert.

In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions provided herein are also prepared, placed in an appropriate container, and labeled for treatment of an indicated condition.

Method of Treatment or Use

Provided herein are methods for treating a subject with any of the disclosed compositions or engineered cells. The compositions and engineered cells of the disclosure may be used to treat, prevent, or reduce the risk of a clinical condition.

In some embodiments, the clinical condition is a cancer, a myeloproliferative disease, or a cardiovascular disease.

In some embodiments, the myeloproliferative disease is selected from primary myelofibrosis (MPN), polycythemia vera (PV), essential thrombocythemia (ET), primary myelofibrosis (PFM), secondary myelofibrosis, acute myeloid leukemia (AML), secondary AML, chronic myelogenous leukemia (CML), clonal hematopoiesis of indeterminate potential (CHIP), and chronic myelomonocytic leukemia (CMML).

In some embodiments, the cancer is selected from lung cancer, lymphoid cancer, acute lymphoid leukemia, acute myeloid leukemia, chronic myelogenous leukemia, Burkitt's lymphoma, Hodgkin's lymphoma, plasma cell myeloma, biliary tract cancer, bladder cancer, liver cancer, pancreatic cancer, prostate cancer, skin cancer, thyroid cancer, stomach cancer, large intestine cancer, colon cancer, urinary tract cancer, central nervous system cancer, neuroblastoma, kidney cancer, breast cancer, cervical cancer, testicular cancer, and soft tissue cancer.

In some embodiments, the cardiovascular disease is selected from an acute coronary syndrome, an ischemic cerebrovascular disease, an ischemic heart disease, a thrombosis, a venous thromboembolism, a deep vein thrombosis, a pulmonary embolism, a catastrophic intra-abdominal thromboses, a peripheral arterial disease, a hypertension, a heart failure, an atrial fibrillation, a coronary heart disease, an atherosclerosis, and a clonal hematopoiesis.

In some embodiments, the methods comprise administering to the subject in need thereof a composition comprising any of the polynucleotides, any of the polypeptides, or any of the vectors disclosed herein. In some embodiments, the compositions may comprise a vector comprising any of the nucleotides disclosed herein.

In some embodiments, the methods comprise administering to the subject in need thereof a composition comprising any of the polynucleotides disclosed herein, wherein the polynucleotides encode a TCR comprising an alpha chain and a beta chain, wherein the alpha chain comprises a CDR3 comprising an amino acid sequence provided in Table 4, and the corresponding beta chain comprises a CDR3 comprising a corresponding amino acid sequence provided in Table 5. In some embodiments, the methods disclosed herein comprise administering to the subject in need thereof a composition comprising polynucleotides that encode a TCR comprising an alpha chain and a beta chain, wherein the alpha chain comprises a CDR3 that is encoded by a nucleic acid sequence provided in Table 4, and the corresponding beta chain comprises a CDR3 that is encoded by a corresponding nucleic acid sequence provided in Table 5 (i.e. the beta chain CDR3 provided in Table 5 is in the same row number (row 1, for example) as the alpha chain CDR3 provided in Table 4 (row 1, for example)). For the sake of brevity, each possible alternative is not parsed out, but each constitute as separate embodiments as if fully described.

In some embodiments, the methods comprise administering to the subject in need thereof a composition comprising polynucleotides that encode a TCR comprising an alpha chain and a beta chain, wherein the alpha chain comprises a CDR1 comprising the amino acid sequence provided in Table 4, a CDR2 comprising an amino acid sequence provided in Table 4, and a CDR3 comprising an amino acid sequence provided in Table 4, and the corresponding beta chain comprises a CDR1 comprising an amino acid sequence provided in Table 5, a CDR2 comprising an amino acid sequence provided in Table 5, and a CDR3 comprising an amino acid sequence provided in Table 5. In some embodiments, the methods comprise administering to the subject in need thereof a composition comprising polynucleotides that encode a TCR comprising an alpha chain and a beta chain, wherein the alpha chain comprises a CDR1 that is encoded by a nucleic acid sequence provided in Table 4, a CDR2 that is encoded by a nucleic acid sequence provided in Table 4, and a CDR3 that is encoded by a nucleic acid sequence provided in Table 4, and the corresponding beta chain comprises a CDR1 that is encoded by a nucleic acid sequence provided in Table 5, a CDR2 that is encoded by a nucleic acid sequence provided in Table 5, and a CDR3 that is encoded by a nucleic acid sequence provided in Table 5 (i.e. the beta chain CDRs provided in Table 5 are in the same row number (row 1, for example) as the alpha chain CDRs provided in Table 4 (row 1, for example)). For the sake of brevity, each possible alternative is not parsed out, but each constitute separate embodiments as if fully described.

In some embodiments, the methods comprise administering to the subject in need thereof a composition comprising polynucleotides that encode a TCR comprising an alpha chain and a beta chain, wherein the alpha chain comprises a VJ region comprising an amino acid sequence that is at least 90%, 95%, 96%, 97%, 98%, 99% or 100% identical to an amino acid sequence provided in Table 4, and the corresponding beta chain comprises a VDJ region comprising an amino acid sequence that is at least 90%, 95%, 96%, 97%, 98%, 99% or 100% identical to an amino acid sequence provided in Table 5. In some embodiments, the methods comprise administering to the subject in need thereof a composition comprising polynucleotides that encode a TCR comprising an alpha chain and a beta chain, wherein the alpha chain comprises a VJ region that is encoded by a nucleic acid sequence that is at least 90%, 95%, 96%, 97%, 98%, 99% or 100% identical to a nucleic acid sequence provided in Table 4, and the corresponding beta chain comprises a VDJ region that is encoded by a nucleic acid sequence that is at least 90%, 95%, 96%, 97%, 98%, 99% or 100% identical to a nucleic acid sequence provided in Table 5 (i.e. the beta chain VDJ region provided in Table 5 is in the same row number (row 1, for example) as the alpha chain VJ region provided in Table 4 (row 1, for example)). For the sake of brevity, each possible alternative is not parsed out, but each constitute separate embodiments as if fully described.

In some embodiments, the methods comprise administering to the subject in need thereof a composition comprising polynucleotides that encode a TCR comprising an alpha chain and a beta chain, wherein the alpha chain comprises an amino acid sequence that is at least 90%, 95%, 96%, 97%, 98%, 99% or 100% identical to an amino acid sequence provided in Table 4, and the corresponding beta chain comprises an amino acid sequence that is at least 90%, 95%, 96%, 97%, 98%, 99% or 100% identical to an amino acid sequence provided in Table 5. Also described herein are polynucleotides that encode a TCR comprising an alpha chain and a beta chain, wherein the alpha chain is encoded by a nucleic acid sequence that is at least 90%, 95%, 96%, 97%, 98%, 99% or 100% identical to a nucleic acid sequence provided in Table 4, and the corresponding beta chain is encoded by a nucleic acid sequence that is at least 90%, 95%, 96%, 97%, 98%, 99% or 100% identical to a nucleic acid sequence provided in Table 5 (i.e. the beta chain provided in Table 5 is in the same row number (row 1, for example) as the alpha chain provided in Table 4 (row 1, for example)). For the sake of brevity, each possible alternative is not parsed out, but each constitute separate embodiments as if fully described.

In some embodiments, the methods comprise administering to the subject in need thereof a composition comprising a viral vector comprising a polynucleotide encoding any of the TCR polypeptides of the disclosure. In any of the methods disclosed herein, the composition that is administered to a subject may comprise a vector selected from an adenovirus vector, an alphaviral vector, a poxvirus vector, an adeno-associated virus vector, a retrovirus vector, a self-replicating RNA molecule, and a combination thereof. In some embodiments, the vector is selected from Ad26 vector, MVA vector, GAd20 vector, a self-replicating RNA molecule, and combinations thereof.

In some embodiments, the methods comprise administering to the subject in need thereof a composition comprising any of the polypeptides disclosed herein, wherein the polypeptides are TCRs. In some embodiments, the methods comprise administering to the subject in need thereof a composition comprising a TCR comprising an alpha chain and a beta chain, wherein the alpha chain comprises a CDR3 comprising an amino acid sequence provided in Table 4, and the beta chain comprises a CDR3 comprising a corresponding amino acid sequence provided in Table 5. (i.e. the beta chain CDR3 provided in Table 5 is in the same row number (row 1, for example) as the alpha chain CDR3 provided in Table 4 (row 1, for example)). For the sake of brevity, each possible alternative is not parsed out, but each constitute separate embodiments as if fully described.

In some embodiments, the methods comprise administering to the subject in need thereof a composition comprising a TCR comprising an alpha chain and a beta chain, wherein the alpha chain comprises a CDR1 comprising an amino acid sequence provided in Table 4, a CDR2 comprising an amino acid sequence provided in Table 4, and a CDR3 comprising an amino acid sequence provided in Table 4, and the corresponding beta chain comprises a CDR1 comprising an amino acid sequence provided in Table 5, a CDR2 comprising an amino acid sequence provided in Table 5, and a CDR3 comprising an amino acid sequence provided in Table 5 (i.e. the beta chain CDRs provided in Table 5 are in the same row number (row 1, for example) as the alpha chain CDRs provided in Table 4 (row 1, for example)). For the sake of brevity, each possible alternative is not parsed out, but each constitute separate embodiments as if fully described.

In some embodiments, the methods comprise administering to the subject in need thereof a composition comprising a TCR comprising an alpha chain and a beta chain, wherein the alpha chain comprises a variable and joining (VJ) region comprising an amino acid sequence that is at least 90%, 95%, 96%, 97%, 98%, 99% or 100% identical to an amino acid sequence provided in Table 4, and the corresponding beta chain comprises a variable, diversity and joining (VDJ) region comprising an amino acid sequence that is at least 90%, 95%, 96%, 97%, 98%, 99% or 100% identical to an amino acid sequence provided in Table 5 (i.e. the beta chain VDJ region provided in Table 5 is in the same row number (row 1, for example) as the alpha chain VJ region provided in Table 4 (row 1, for example)). For the sake of brevity, each possible alternative is not parsed out, but each constitute separate embodiments as if fully described.

In some embodiments, the methods comprise administering to the subject in need thereof a composition comprising a TCR comprising an alpha chain and a beta chain, wherein the alpha chain comprises an amino acid sequence that is at least 90%, 95%, 96%, 97%, 98%, 99% or 100% identical to an amino acid sequence provided in Table 4, and the corresponding beta chain comprises an amino acid sequence that is at least 90%, 95%, 96%, 97%, 98%, 99% or 100% identical to an amino acid sequence provided in Table 5 (i.e. the beta chain provided in Table 5 is in the same row number (row 1, for example) as the alpha chain provided in Table 4 (row 1, for example)). For the sake of brevity, each possible alternative is not parsed out, but each constitute separate embodiments as if fully described.

In some embodiments, the methods comprise administering to the subject in need thereof any of the engineered cells disclosed herein. In certain embodiments, the engineered cells comprise any one of an alpha TCR chain and any one of a beta TCR chain, as disclosed in Tables 4 and 5. For the sake of brevity, each possible alternative is not parsed out, but each constitute separate embodiments as if fully described.

In some embodiments, the methods comprise administering to the subject in need thereof an engineered cell comprising any of the polypeptides disclosed herein, wherein the polypeptides are TCRs. In some embodiments, the methods comprise administering to the subject in need thereof an engineered cell comprising a TCR comprising an alpha chain and a beta chain, wherein the alpha chain comprises a CDR3 comprising an amino acid sequence provided in Table 4, and the beta chain comprises a CDR3 comprising a corresponding amino acid sequence provided in Table 5. (i.e. the beta chain CDR3 provided in Table 5 is in the same row number (row 1, for example) as the alpha chain CDR3 provided in Table 4 (row 1, for example)). For the sake of brevity, each possible alternative is not parsed out, but each constitute separate embodiments as if fully described.

In some embodiments, the methods comprise administering to the subject in need thereof an engineered cell comprising a TCR comprising an alpha chain and a beta chain, wherein the alpha chain comprises a CDR1 comprising an amino acid sequence provided in Table 4, a CDR2 comprising an amino acid sequence provided in Table 4, and a CDR3 comprising an amino acid sequence provided in Table 4, and the corresponding beta chain comprises a CDR1 comprising an amino acid sequence provided in Table 5, a CDR2 comprising an amino acid sequence provided in Table 5, and a CDR3 comprising an amino acid sequence provided in Table 5 (i.e. the beta chain CDRs provided in Table 5 are in the same row number (row 1, for example) as the alpha chain CDRs provided in Table 4 (row 1, for example)). For the sake of brevity, each possible alternative is not parsed out, but each constitute separate embodiments as if fully described.

In some embodiments, the methods comprise administering to the subject in need thereof an engineered cell comprising a TCR comprising an alpha chain and a beta chain, wherein the alpha chain comprises a variable and joining (VJ) region comprising an amino acid sequence that is at least 90%, 95%, 96%, 97%, 98%, 99% or 100% identical to an amino acid sequence provided in Table 4, and the corresponding beta chain comprises a variable, diversity and joining (VDJ) region comprising an amino acid sequence that is at least 90%, 95%, 96%, 97%, 98%, 99% or 100% identical to an amino acid sequence provided in Table 5 (i.e. the beta chain VDJ region provided in Table 5 is in the same row number (row 1, for example) as the alpha chain VJ region provided in Table 4 (row 1, for example)). For the sake of brevity, each possible alternative is not parsed out, but each constitute separate embodiments as if fully described.

In some embodiments, the methods comprise administering to the subject in need thereof an engineered cell comprising a TCR comprising an alpha chain and a beta chain, wherein the alpha chain comprises an amino acid sequence that is at least 90%, 95%, 96%, 97%, 98%, 99% or 100% identical to an amino acid sequence provided in Table 4, and the corresponding beta chain comprises an amino acid sequence that is at least 90%, 95%, 96%, 97%, 98%, 99% or 100% identical to an amino acid sequence provided in Table 5 (i.e. the beta chain provided in Table 5 is in the same row number (row 1, for example) as the alpha chain provided in Table 4 (row 1, for example)). For the sake of brevity, each possible alternative is not parsed out, but each constitute separate embodiments as if fully described.

In some embodiments, the engineered cell comprising the TCR is a T cell, a natural killer (NK) cell, a cytotoxic T lymphocyte (CTL), a regulatory T cell (Treg), a human embryonic stem cell, a lymphoid progenitor cell, a T cell-precursor cell, a pluripotent stem cell or induced pluripotent stem cell (iPSC) from which lymphoid cells may be differentiated.

In certain embodiments, the engineered cell is derived from naïve cells that are obtained from a subject in need of treatment. In certain embodiments, the engineered cell is not derived from a subject in need of treatment, but is instead derived from another compatible source such as an immune cell donor, or an immortalized or transformed immune cell line.

In some embodiments, desired amounts of engineered cells are employed to prepare a cell therapy product for therapeutic administration. In certain embodiments, the cell therapy product is reinfused or transfused back into the subject from whom the pheresis sample used to derive the cell therapy product was obtained. Reinfusion procedures that may be employed include those procedures disclosed in, for example, U.S. Pat. Nos. 4,844,893 and 4,690,915. In certain embodiments, the cell therapy product is reinfused or transfused back into a different subject from whom the pheresis sample used to derive the cell therapy product was obtained.

In some embodiments, prior to administration one or more quality assurance tests are performed on the activated T lymphocytes or cell therapy product. In some embodiments, the quality assurance testing comprises performing one or more tests to confirm: HLA match between patient and T lymphocytes; flow cytometry analysis (CD8+, TCR+); sterility (no bacterial or fungal growth); gram-stain negative for bacteria; mycoplasma negative for PCR/ELISA; no residual *Drosophila* DNA; absence of insect virus cDNA; viability (>72% viable); and cytolytic activity by CTL assay.

Dose and Route of Administration

In some embodiments, desired amounts of viral vectors are employed to prepare a composition for therapeutic administration.

In some embodiments, the compositions comprising viral vectors is administered at a dose from about $1\times10^4$ IFU (Infectious Unit) to about $1\times10^{11}$ IFU per dose.

In certain embodiments, the viral vector is an adenovirus vector, an Ad26 vector, a GAd20 vector, a poxvirus vector or an MVA vector.

In some embodiments, the compositions comprising self-replicating RNA molecule is administered at a dose from about 1 microgram to about 100 micrograms.

In some embodiments, the compositions disclosed herein may be administered to a subject by a variety of routes such as subcutaneous, topical, oral and intramuscular. Administration of the compositions may be accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present disclosure also has the objective of providing suitable topical, oral, systemic and parenteral formulations for use in the methods of prophylaxis and treatment.

In some embodiments, intramuscular administration of the composition can be achieved by using a needle. An alternative is the use of a needleless injection device to administer the composition (using, e.g., Biojector™) or a freeze-dried powder containing the composition. For intravenous, cutaneous or subcutaneous injection, or injection at the site of affliction, the composition may be the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation may also be employed.

The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners.

In some embodiments, desired amounts of engineered cells are employed to prepare a cell therapy product for therapeutic administration.

To treat a subject, an effective amount of a cell therapy product is administered to a subject suffering from or diagnosed as having a disease, disorder, or condition. The subject can be a human patient in need of treatment for a cancer, a myeloproliferative disease, or a cardiovascular disease.

Effective amounts or doses of the cell therapy products may be ascertained by routine methods such as modeling, dose escalation studies or clinical trials, and by taking into consideration routine factors, e.g., the mode or route of administration or product delivery, the pharmacokinetics of the cell therapy product, the severity and course of the disease, disorder, or condition, the subject's previous or ongoing therapy, the subject's health status and response to drugs, and the judgment of a treating physician. As exemplary dosage amounts, cell populations may comprise from about $1\times10^6$ to about $1\times10^{12}$ activated T cells, such as $1\times10^8$ to $1\times10^{11}$ or $1\times10^9$ to $1\times10^{10}$ activated T cells for an adult human.

The cell therapy product can be prepared as a therapeutic composition comprising engineered cells, preferably engineered T cells, and a vehicle suitable for the maintenance of the engineered cells until they are infused into the subject, such as a pharmaceutically acceptable diluent or solvent.

Any suitable technique for administering compositions comprising cellular components into a subject may be employed. For example, administration of the engineered T cell via intravenous infusion may be employed. Multiple infusions may be required or indicated, and these infusions may occur over a period of several weeks or longer. Exemplary techniques are described in, for example, U.S. Pat. Nos. 4,844,893 and 4,690,915.

EXAMPLES

These examples are provided for illustrative purposes only and not to limit the scope of the claims provided herein.

Example 1. TCR Sequence Analysis

12 Day Assay—Transduction, Endogenous, Exogenous—10× Endpoint

Single cell TCR α/β and RNA sequencing was performed on CD8+ T cell samples isolated from a leukopak from four healthy human donors. Dendritic cells from each donor were treated with the following: a) DMSO treatment or exogenously loaded single 9-mer peptide corresponding to one of two mutJAK2 epitopes ("exogenous treatment"), b) transfection with a tandem minigene construct composed of the combined mutJAK2 and mutCALR epitopes (mutCALR type I and mutCALR type II) ("endogenous treatment"), or c) transduction with an Ad5 virus containing the mutJAK2 and mutCALR antigen construct ("Ad5 treatment").

The 9-mer peptides corresponding to two mutJAK2 epitopes have the following amino acid sequences: VLNYGVCFC (SEQ ID NO: 681) and FCGDENILV (SEQ ID NO: 682). The tandem minigene construct composed of the combined mutJAK2 and mutCALR epitopes has the amino acid sequence:

(SEQ ID NO: 683)
MKDKQDEEQRTRRMMRTKMRMRRMRRTRRKMRRKMSPARPRTSCREACLQ

GWTEAAYEEAEDNCRRMMRTKAAY*VLNYGVCFC*AAY*FCGDENILV*.

In SEQ ID NO: 683, the mutCALR type 1 sequence is underlined, the mutCALR type II sequence is underlined and bold, and the two mutJAK2 sequences are underlined an italics.

The mutJAK2 and mutCALR antigen construct (also known as LS_CALR_JAK2-2×9mer (HEME002)) that is contained within the Ad5 virus has the following amino acid sequence:

(SEQ ID NO: 702)
MACPGFLWALVISTCLEFSMAMKDKQDEEQRTRRMMRTKMRMR

RMRRTRRKMRRKMSPARPRTSCREACLQGWTEAAYEEAEDNCR

RMMRTKAAYVLNYGVCFCAAYFCGDENILV.

Subsequently, autologous pan-T cells were added to the co-culture to initiate TCR stimulation.

In all cases, the TCRs were stimulated for 11 days, followed by overnight re-stimulation treatment with individual peptides. Cells were harvested and CD8+ T cells were isolated using negative selection magnetic bead capture techniques. These isolated CD8+ T cells were analyzed using the 10× genomics single cell sequencing platform.

Procedure

Day −2 (for Ad5 treatment) or Day −1 (for exogenous and endogenous treatment): Donor dendritic cells (DC) from the four healthy human donors described, above, were thawed in IMDM5, (IMDM5 Media: Gibco™, 12440 supplemented with 5% human antibody serum Sigma, H3667) with 1× anti-aggregate (C.T.L., CTL-AA-001). The cells were washed by centrifuging at 1300 rpm for five minutes and resuspended in IMDM5 containing 50 ng/mL GM-CSF and IL-4. The cells were plated into 6 well plates at ~1-1.5e6 cells/well in 2 mL IMDM5 and incubated overnight at 37° C./5% CO2.

Day −1 (for Ad5 treatment): DCs were removed from plates, and wells of same donors were combined. Cells were washed in IMDM5 and counted and resuspended at a density of 6e5 cells/mL. 50 μL of cells were seeded (for a density of 3e4 cells/well) to appropriate wells of clear, round bottom 96 well plates according to plate layout. At least one row/column was left empty around outside edges of plates and filled with 100 μL DPBS. In a BSL2+ environment, Ad5 constructs were diluted in IMDM5 media with 2× (final concentration: 5 μg/mL) Polybrene (Millipore™, Cat #: TR-1003-G) to concentrations of 5,000 Multiplicity of Infection (MOI) per 50 μL. 50 μL of each construct was added to the appropriate wells of DCs according to plate layout. Plates were returned to incubator at 37° C./5% CO2 overnight.

Day 0 (for endogenous treatment): DCs were removed from the plates, and wells of same donors were combined. Cells were washed in IMDM5 and counted and resuspended at a density of 5e5 cells/mL. 500 μL of cells were seeded (for a density of 2.5e5 cells/well) to appropriate wells of 24 well plates according to plate layout. Following NanoJuice™ Kit Protocol, (Millipore Sigma™, 71902), Opti-MEM™ was combined with core transfection reagent and transfection booster and incubated at room temperature (RT) for five minutes. DNA was added to the appropriate tubes and mixed by gentle pipetting. Tubes were incubated at RT for 15 minutes. 20 μL of each preparation was added dropwise to the appropriate wells as indicated in plate layout. Plates were rocked gently to mix and incubated at 37° C./5% CO2 for six hours. Wells were transferred from endogenous transfection pates to microcentrifuge tubes. Tubes were centrifuged at 1500×g for five minutes. Cells were resuspended in 500 μL DPBS. Washes were repeated for a total of two washes. After the final wash, cells were resuspended in 500 μL IMDM5. Cells were pipetted to mix and 65 μL was transferred to appropriate wells indicated in the plate layout. The corresponding donor PanT cells (i.e. the PanT cells from the same donor as the dendritic cells) were thawed in IMDM5 with 1× anti-aggregate and washed by centrifuging at 1300 rpm for five minutes. Cells were resuspended in IMDM5 at 3e6 cells/mL. 100 μL of prepared PanT donor cells was added to corresponding donor DC wells according to plate layout (for a density of 3e5 PanT cells/well. Final ratio 1:10 DC:PanT). 200 μL of DPBS was added to outer wells of the plate(s). Plates were returned to incubator at 37° C./5% CO2.

Day 0 (for exogenous treatment): DCs were removed from plates, and wells of same donors were combined. Cells were washed in IMDM5 and counted and resuspended at a density of 3e5 cells/mL. 100 μL of cells were seeded (for a density of 3e4 cells/well) to appropriate wells in clear 96 well round bottom plate(s) as indicated in the plate layout. Peptides were diluted to 20× final concentrations in IMDM5 and 5 μL of the diluted peptides were added to appropriate exogenous wells according to the plate layout. 200 μL DPBS was added to outside wells and incubated at 37° C./5% CO2 for one and a half to two hours. After incubation, plates were placed in a room temperature irradiator for a calculated time to achieve the desired dose of 50 grays of radiation. Corresponding donor PanT cells were thawed in IMDM5 with 1× anti-aggregate and washed by centrifuging at 1300 rpm for five minutes. Cells were resuspended in IMDM5 at 3e6 cells/mL. 100 μL of prepared PanT donor cells were added to corresponding donor DC wells according to plate layout (for a density of 3e5 PanT cells/well. Final ratio 1:10 DC:PanT). The plates were returned to the incubator at 37° C./5% CO2.

Day 0 (for Ad5 treatment): After the plates were incubated with Ad5 for ~20 hours they were removed from the incubator. The plates were washed by centrifuging at 300×g for five minutes and pellets were resuspended in DPBS (Gibco™, 14140). Washes were repeated for a total of three washes. After the final wash, cells were resuspended in 100 μL IMDM5. Corresponding donor PanT cells were thawed in IMDM5 with 1× anti-aggregate. Cells were washed by centrifuging at 1300 rpm for five minutes and then were resuspended in IMDM5 at 3e6 cells/mL. 100 μL of prepared PanT donor cells were added to corresponding donor DC wells according to the plate layout (for a density of 3e5 PanT cells/well. Final ratio 1:10 DC:PanT). 200 μL of DPBS was added to outer wells of plates. Plates were returned to the incubator at 37° C./5% CO2.

Day 3 and following Day 3 (for all treatments): IMDM5 media was prepared with IL-2, IL-7, and IL-15 at 2× final concentrations. (Final concentrations: IL-2: 50 IU/mL, IL-7: 25 ng/mL, and IL-15: 25 ng/mL). 100 μL media was removed from each well and replaced with prepared IMDM5 cytokine media. Plates were gently rocked to mix and returned to the incubator at 37° C./5% CO2. This protocol was repeated every 2-3 days after, up to day 12, with the exception that IL-2 concentration was increased to 100 IU/mL.

Day 11: (If restim fell on a day when media needs to be refreshed, refresh was performed first). Peptides were prepared corresponding to exogenous, endogenous, or Ad5 constructs in IMDM5 for the restim of the PanT cells. For single peptide restim a final concentration of 5 μg/mL was used. For the CALR peptide pool, each peptide was used at a final concentration of 1 μg/mL (peptides were pooled at 500× final concentration prior to adding to plates). DMSO control was prepared in IMDM5 to match the highest concentration of peptide used (5 μg/mL). 5 μL of each preparation were added to appropriate wells. The plates were gently rocked to mix. The plates were returned to the incubator and incubated overnight (~18 hours) at 37° C./5% CO2.

The sequences for the CALR peptide pool are provided in Table 1:

TABLE 1

| peptide name | peptide sequences | Sequence Identifier |
|---|---|---|
| 1.2 | RPRTSCREA | SEQ ID NO: 684 |
| 1.3 | SPARPRTSC | SEQ ID NO: 685 |
| 1.4 | RKMSPARPR | SEQ ID NO: 686 |
| 1.5 | MRRKMSPAR | SEQ ID NO: 687 |
| 1.6 | KMRRKMSPA | SEQ ID NO: 688 |
| 1.7 | TRRKMRRKM | SEQ ID NO: 689 |
| 1.8 | RTRRKMRRK | SEQ ID NO: 690 |
| 1.9 | RRTRRKMRR | SEQ ID NO: 691 |
| 1.1 | RMRRTRRKM | SEQ ID NO: 692 |
| 1.11 | RRMRRTRRK | SEQ ID NO: 693 |
| 1.12 | MRRMRRTRR | SEQ ID NO: 694 |
| 1.14 | MRMRRMRRT | SEQ ID NO: 695 |
| 1.15 | KMRMRRMRR | SEQ ID NO: 696 |
| 1.17 | MRTKMRMRR | SEQ ID NO: 697 |
| 1.18 | MMRTKMRMR | SEQ ID NO: 698 |
| 1.19 | RMMRTKMRM | SEQ ID NO: 699 |

TABLE 1-continued

| peptide name | peptide sequences | Sequence Identifier |
|---|---|---|
| 1.23 | RRMMRTKMR | SEQ ID NO: 700 |
| 1.25 | RTRRMMRTK | SEQ ID NO: 701 |

Day 12 (for all treatments): A vial of PanT cells were thawed from each donor (to be used as baselines) in IMDM5 with 1× anti-aggregate and washed by centrifuging at 1300 rpm for five minutes and resuspend in IMDM5. Replicates of each sample were combined into tubes on ice and centrifuged at 1500 rpm for five minutes at 4° C. Supernatant was removed and 300 μL running buffer was added to wash. The tubes were centrifuged again, and supernatant was removed. The antibody cocktail provided in the CD8 T cells negative selection bead kit was prepared, scaled accordingly (40 μL buffer and 10 μL antibody per sample). The antibody cocktail included: biotin-conjugated monoclonal anti-human antibodies against CD4, CD15, CD16, CD19, CD34, CD36, CD56, CD123, TCR γ/δ, and CD235a (Glycophorin A), MicroBeads conjugated to monoclonal anti-CD14 antibody (isotype: mouse IgG2a), anti-CD61 antibody (isotype: mouse IgG1), and anti-biotin antibody (isotype: mouse IgG1).

50 μL prepared antibody cocktail was added to each sample and incubated for five minutes on ice. Bead cocktail was prepared and scaled accordingly (30 μL buffer and 20 μL beads per sample). 50 μL was added to each sample and incubate for ten minutes on ice. 400 μL buffer was added to bring sample volumes to 500 μL. 400 μL buffer was added to baseline samples to bring volumes to 500 μL. The Manual CD8+ Separation protocol (MACS Miltenyi Biotec™, 130-096-495) was followed. Columns and tubes (15 mL) were set up and rinsed with 3 mL buffer to pre-wet. 500 μL of cells was added and flow through was collected. Cells were washed with 3 mL buffer and collected. Cells were counted and washed by centrifuging at 1500 rpm for five minutes. The cells were resuspended in PBS at 1e4 cells/mL.

Single Cell V(D)J 10× Genomics Protocols

The Single Cell V(D)J (variable, diverse, and joining) 10× genomics protocols (Chromium™ Single Cell V(D)J Reagent Kits User Guide—CG000086) was used for measuring immune repertoire information and gene expression from the same cell. Cells obtained from the 12 Day Assay were washed and resuspended in 1× phosphate-buffered saline (PBS) containing 0.04% bovine serum albumin (BSA) to achieve target cell concentration (~20,000 cells/sample). Gel Bead-in-Emulsions (GEMs) were generated by combining barcoded single cell VDJ 5' Gel beads, a Master Mix with cells, and partitioning oil on a 10× Chromium™ Controller Single Cell A Chip. Following GEM generation, the Gel Bead dissolved, and any co-partitioned cell was lysed. Oligonucleotides containing sequencing primers, 10× cell barcode, 10× unique molecular identifier (UMI) barcode, and template switch oligo (TSO) were released and mixed with the cell lysate and Master Mix containing reverse transcription (RT) reagents. Incubation of GEM-RT produced barcoded full-length cDNA from mRNA. 10× barcoded full-length cDNA from GEM-RT was purified and amplified via polymerase chain reaction (PCR) (14 cycles) with primers against the 5' and 3' ends added during GEM-RT. Full Length VDJ segments were enriched from amplified cDNA with primers specific to TCR region. Enzymatic fragmentation and size selection were used to optimize the cDNA amplicon size prior to 5' gene expression (GEX) library construction. P5 (AATGATACGGCGACCACCGA) (SEQ ID NO: 703), P7 (CAAGCAGAAGACGGCAT-ACGAGAT) (SEQ ID NO: 704), a sample index (NNNNNNNN) (SEQ ID NO: 705), and Illumina™ R2 (AGATCGGAAGAGCACACGTCTGAACTCCAGTCAC) (SEQ ID NO: 706) sequence were added via End Repair, A tailing, Adaptor Ligation and Sample Index PCR. The final libraries contained the P5 and P7 priming sites used in Illumina™ Sequencing. Pooled/normalized libraries were sequenced at the recommended depth/run parameters. Libraries sequenced on NovaSeqe produced high quality data with expected Q30 (sequencing Analysis Viewer) scores. Multiplexed sequences were de-multiplexed and analyzed using The Chromium™ Single Cell Immune Profiling Software Suite.

Example 2. Identification of TCRs Enriched Upon Stimulation

Identifying Expanded TCRs

To identify TCRs enriched due to antigen stimulation, T-cell receptor alpha/beta (TCR $\alpha/\beta$) sequences from T-cell populations treated with either endogenous minigene or by Ad5 transduction were compared against corresponding sequences from T-cell populations obtained by stimulation against an empty minigene (i.e. no antigen) or an Ad5 null construct (i.e. Ad5 transfection without an antigen cassette). For TCR$\alpha/\beta$ sequences obtained from stimulation by exogenously loaded dendritic cells (DC's), the corresponding DMSO treated controls (i.e. DMSO+no antigen stimulation) were used. TCR $\alpha/\beta$ sequences present in cell populations enriched at a false discovery rate (FDR) of <0.0003 and a minimum of 2 fold increase in TCR proportions compared to controls were selected for further analysis. TCR c/p sequences that were highly abundant (~1.0% or higher) both in the controls and treatment conditions and that were significantly enriched were also chosen for further examination.

Identifying Expanded TCR Sequences from Activated T Cells

To further triage the number of TCRs for experimental validation, single cell RNA (scRNA) sequencing data was obtained from the same cells. The T-cell activation markers considered for mRNA based gating of T cells were TNF, GZMB, CD69 and PRF1 (Perforin). These markers and their cutoffs are listed in Table 2, below. TCRs which were both clonally expanded and present in cells with higher than the cutoff mRNA expression in all 4 genes were given the highest priority. In addition, TCRs that shared sequence identity with known self-antigens or viral antigens were eliminated from further consideration. The IEDB (www.iedb.org) public repository database was used to identify the self/viral antigen responsive TCR sequences.

TABLE 2

T cell marker genes and cutoffs

| T cell Activation Marker Genes | mRNA normalized expression cutoff (log units) |
|---|---|
| TNF, CD69, PRF1 | 0.5 |
| GZMB | 1.0 |

scRNA Analysis

The Seurat R package was used to perform the scRNA sequencing analysis. The samples were first quality controlled using high mitochondrial content (>5%), excessively low (<300) counts, and library size criteria. Cells that failed to pass quality control (QC) thresholds were removed. After QC filtering, the SCTransform algorithm was used to normalize and transform raw RNA read counts. Samples pre- and post-12 day expansion were combined using the sample Integration method implemented in Seurat. A principal component analysis (PCA), followed by uniform manifold approximation and projection (UMAP) clustering on the first 30 principal components was performed. The normalized mRNA data was then utilized, and the expression profiles of various T cell activation markers were examined to establish the cutoff criteria. The activation profiles showed a generally bimodal distribution, and the cutoff was chosen at the point of the trough between the two neighboring peaks of the bimodal distribution. See table 1 for cut-off values.

Table 3 provides donor number, treatment condition, the V(D)J genes, and the constant genes for thirty-four sequenced T-cell receptors.

TABLE 3

| | | | | Alpha Chain | | | | Beta Chain | | | |
|---|---|---|---|---|---|---|---|---|---|---|---|
| ID | Donor | Treatment Condition | Antigen | V Genes | D Genes | J Genes | Constant Genes | V Genes | D Genes | J Genes | Constant Genes |
| 1 | 274 | Ad5 | CALR | TRAV39 | — | TRAJ34 | TRAC | TRBV12-5 | TRBD1 | TRBJ2-7 | TRBC2 |
| 2 | 274 | Ad5 | CALR | TRAV3 | — | TRAJ22 | TRAC | TRBV2 | TRBD1 | TRBJ2-1 | TRBC2 |
| 3 | 118 | Ad5 | CALR | TRAV4 | — | TRAJ22 | TRAC | TRBV6-1 | TRBD1 | TRBJ1-1 | TRBC1 |
| 4 | 118 | Ad5 | JAK2ep2 | TRAV41 | — | TRAJ45 | TRAC | TRBV6-5 | TRBD2 | TRBJ2-7 | TRBC2 |
| 5 | 118 | Ad5 | JAK2ep2 | TRAV12-2 | — | TRAJ41 | TRAC | TRBV5-1 | TRBD1 | TRBJ1-1 | TRBC1 |
| 6 | 118 | Ad5 | JAK2ep2 | TRAV38-2DV8 | — | TRAJ49 | TRAC | TRBV2 | TRBD1 | TRBJ2-7 | TRBC2 |
| 7 | 118 | Ad5 | JAK2ep2 | TRAV39 | — | TRAJ33 | TRAC | TRBV10-2 | TRBD1 | TRBJ2-7 | TRBC2 |
| 8 | 118 | Ad5 | CALR | TRAV12-2 | — | TRAJ13 | TRAC | TRBV6-5 | TRBD2 | TRBJ2-7 | TRBC2 |
| 9 | 274 | Ad5 | JAK2ep2 | TRAV1-1 | — | TRAJ4 | TRAC | TRBV7-6 | — | TRBJ2-7 | TRBC2 |
| 10 | 118 | Ad5 | JAK2ep1 | TRAV26-2 | — | TRAJ45 | TRAC | TRBV19 | — | TRBJ1-5 | TRBC1 |
| 11 | 644 | Ad5 | JAK2ep2 | TRAV1-2 | — | TRAJ29 | TRAC | TRBV7-9 | — | TRBJ2-2 | TRBC2 |
| 12 | 118 | Ad5 | JAK2ep1 | TRAV38-2DV8 | — | TRAJ34 | TRAC | TRBV27 | TRBD2 | TRBJ2-7 | TRBC2 |
| 13 | 118 | Ad5 | CALR | TRAV12-3 | — | TRAJ45 | TRAC | TRBV7-3 | TRBD2 | TRBJ2-1 | TRBC2 |
| 14 | 118 | Ad5 | CALR | TRAV35 | — | TRAJ47 | TRAC | TRBV5-8 | — | TRBJ2-7 | TRBC2 |
| 15 | 118 | Exogenous | JAK2ep2 | TRAV2 | — | TRAJ43 | TRAC | TRBV27 | TRBD1 | TRBJ2-3 | TRBC2 |
| 16 | LP263 | Exogenous | JAK2ep1 | TRAV1-1 | — | TRAJ31 | TRAC | TRBV7-9 | TRBD2 | TRBJ2-1 | TRBC2 |
| 17 | LP263 | Exogenous | JAK2ep2 | TRAV1-2 | — | TRAJ43 | TRAC | TRBV7-9 | TRBD2 | TRBJ1-1 | TRBC1 |
| 18 | 644 | Ad5 | JAK2ep1 | TRAV38-1 | — | TRAJ58 | TRAC | TRBV7-9 | — | TRBJ2-7 | TRBC2 |

TABLE 3-continued

| | | | | Alpha Chain | | | | Beta Chain | | | |
|---|---|---|---|---|---|---|---|---|---|---|---|
| ID | Donor | Treatment Condition | Antigen | V Genes | D Genes | J Genes | Constant Genes | V Genes | D Genes | J Genes | Constant Genes |
| 19 | 118 | Ad5 | JAK2ep2 | TRAV4 | — | TRAJ33 | TRAC | TRBV14 | — | TRBJ2-1 | TRBC2 |
| 20 | 644 | Ad5 | JAK2ep2 | TRAV13-1 | — | TRAJ43 | TRAC | TRBV11-2 | TRBD2 | TRBJ2-6 | TRBC2 |
| 21 | 118 | Ad5 | JAK2ep2 | TRAV19 | — | TRAJ17 | TRAC | TRBV5-6 | TRBD1 | TRBJ2-6 | TRBC2 |
| 22 | 118 | Endogenous | CALR | TRAV4 | — | TRAJ42 | TRAC | TRBV27 | TRBD1 | TRBJ2-2 | TRBC2 |
| 23 | LP263 | Exogenous | JAK2ep2 | TRAV14D V4 | — | TRAJ12 | TRAC | TRBV7-9 | TRBD1 | TRBJ1-6 | TRBC1 |
| 24 | 118 | Ad5 | JAK2ep2 | TRAV29D V5 | — | TRAJ42 | TRAC | TRBV2 | TRBD1 | TRBJ1-1 | TRBC1 |
| 25 | 274 | Ad5 | CALR | TRAV14D V4 | — | TRAJ22 | TRAC | TRBV2 | TRBD1 | TRBJ1-2 | TRBC1 |
| 26 | 118 | Ad5 | JAK2ep1 | TRAV29D V5 | — | TRAJ52 | TRAC | TRBV7-8 | — | TRBJ2-1 | TRBC2 |
| 27 | 118 | Ad5 | CALR | TRAV8-4 | — | TRAJ4 | TRAC | TRBV27 | TRBD1 | TRBJ1-5 | TRBC1 |
| 28 | 274 | Ad5 | CALR | TRAV19 | — | TRAJ30 | TRAC | TRBV20-1 | TRBD2 | TRBJ2-1 | TRBC2 |
| 29 | 118 | Ad5 | JAK2ep2 | TRAV29D V5 | — | TRAJ23 | TRAC | TRBV20-1 | TRBD1 | TRBJ2-1 | TRBC2 |
| 30 | 118 | Ad5 | CALR | TRAV9-2 | — | TRAJ20 | TRAC | TRBV20-1 | TRBD2 | TRBJ1-1 | TRBC1 |
| 31 | 274 | Ad5 | CALR | TRAV12-2 | — | TRAJ4 | TRAC | TRBV3-1 | TRBD2 | TRBJ2-7 | TRBC2 |
| 32 | 644 | Ad5 | JAK2ep2 | TRAV4 | — | TRAJ37 | TRAC | TRBV3-1 | TRBD2 | TRBJ2-7 | TRBC2 |
| 33 | 644 | Ad5 | JAK2ep2 | TRAV38-2DV8 | — | TRAJ43 | TRAC | TRBV6-5 | TRBD1 | TRBJ2-7 | TRBC2 |
| 34 | 644 | Ad5 | JAK2ep2 | TRAV12-1 | — | TRAJ6 | TRAC | TRBV20-1 | — | TRBJ1-3 | TRBC1 |

Table 4 provides the full length alpha chain sequences as well as the nucleotide (NT) and amino acid (AA) sequences of the alpha chain CDR1, CDR2 and CDR3, defined by IMGT, for each of the thirty-four T-cell receptors described in Table 3. Table 5 provides the full length beta chain sequences as well as the nucleotide and amino acid sequences of the beta chain CDR1, CDR2 and CDR3, defined by IMGT, for each of the thirty-four T-cell receptors described in Table 3. For both Table 4 and Table 5, the TCR alpha or beta (full length) amino acid sequence that was derived from the scRNA analysis had an incomplete constant gene sequence. In order to complete this, alignments of the incomplete constant region sequence were performed against the canonical TCRB1 and TCRB2 sequences, and the additional missing portion appended. In two instances, the alignments had incomplete query coverage, in these cases the overhanging portion in the incomplete gene was deleted and the correct TCRB sequence appended. For the TCR alpha gene, the missing portion of the TCR alpha gene sequence was appended. The full constant gene is identified by name in Table 3. The VJ/VDJ portion of the TCR alpha or beta (full length) amino acid sequence is underlined, the constant region is in underlined and bold, and the unmarked sequence is the leader sequence. For the corresponding nucleotide sequences in Tables 4 and 5, the leader sequence is underlined, the constant region is underlined and bolded, and the VJ/VDJ portion of the full length TCR nucleotide sequence is unmarked.

TABLE 4

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| 1 | GGGGCAGGATGTGATTCTAA<br>TTGGTTGGAACATCTTTTGA<br>AATCGTGTTTCTGTAGAGAA<br>AGAAAAACTACCATATTTGG<br>ATAGCCCTGGCCAACTTTCA<br>AGGCTCCTAAATCTGAGTTT<br>TCAGTGAACTGGACAGAAAA<br>AAAAAATGAAGAAGCTACTA<br>GCAATGATTCTGTGGCTTCA<br>ACTAGACCGGTTAAGTGGAG<br>AGCTGAAAGTGGAACAAAA<br>CCCTCTGTTCCTGAGCATGC<br>AGGAGGGAAAAAACTATAC<br>CATCTACTGCAATTATTCAA<br>CCACTTCAGACAGACTGTAT<br>TGGTACAGGCAGGATCCTGG<br>GAAAAGTCTGGAATCTCTGT<br>TTGTGTTGCTATCAAATGGA<br>GCAGTGAAGCAGGAGGGAC<br>GATTAATGGCCTCACTTGAT<br>ACCAAAGCCCGTCTCAGCAC<br>CCTCCACATCACAGCTGCCG<br>TGCATGACCTCTCTGCCACCT<br>ACTTCTGTGCCGCCCGATCTT<br>ATAACACCGACAAGCTCATC<br>TTTGGGACTGGGACCAGATT<br>ACAAGTCTTTCCAAAT**ATCC**<br>**AGAACCCTGACCCTGCCGT**<br>**GTACCAGCTGAGAGACTCT**<br>**AAATCCAGTGACAAGTCTG**<br>**TCTGCCTATTCACCGATTT**<br>**TGATTCTCAAACAAATGTG**<br>**TCACAAAGTAAGGATTCTG**<br>**ATGTGTATATCACAGACAA**<br>**AACTGTGCTAGACATGAGG**<br>**TCTATGGACTTCAAGAGCA**<br>**ACAGTGCTGTGGCCTGGAG**<br>**CAACAAATCTGACTTTGCA**<br>**TGTGCAAACGCCTTCAACA**<br>**ACAGCATTATTCCAGAAGA**<br>**CACCTTCTTCCCCAGCCCA**<br>**GAAAGTTCCTGTGATGTCA**<br>**AGCTGGTCGAGAAAAGCTT**<br>**TGAAACAGATACGAACCTA**<br>**AACTTTCAAAACCTGTCAG**<br>**TGATTGGGTTCCGAATCCT**<br>**CCTCCTGAAAGTGGCCGGG** | MKKLLAMILW<br>LQLDRLSGELK<br>VEQNPLFLSMQ<br>EGKNYTIYCNY<br>STTSDRLYWYR<br>QDPGKSLESLF<br>VLLSNGAVKQE<br>GRLMASLDTKA<br>RLSTLHITAAV<br>HDLSATYFCAA<br>RSYNTDKLIFGT<br>GTRLQVFP**NIQ**<br>**NPDPAVYQLR**<br>**DSKSSDKSVCL**<br>**FTDFDSQTNVS**<br>**QSKDSDVYITD**<br>**KTVLDMRSMD**<br>**FKSNSAVAWS**<br>**NKSDFACANA**<br>**FNNSIIPEDTFF**<br>**PSPESSCDVKL**<br>**VEKSFETDTNL**<br>**NFQNLSVIGFR**<br>**ILLLKVAGFNL**<br>**LMTLRLWSS**<br>(SEQ ID NO: 477) | GAGCTGAAAG<br>TGGAACAAAA<br>CCCTCTGTTCC<br>TGAGCATGCA<br>GGAGGGAAAA<br>AACTATACCAT<br>CTACTGCAATT<br>ATTCAACCACT<br>TCAGACAGACT<br>GTATTGGTACA<br>GGCAGGATCCT<br>GGGAAAAGTC<br>TGGAATCTCTG<br>TTTGTGTTGCT<br>ATCAAATGGA<br>GCAGTGAAGC<br>AGGAGGGACG<br>ATTAATGGCCT<br>CACTTGATACC<br>AAAGCCCGTCT<br>CAGCACCCTCC<br>ACATCACAGCT<br>GCCGTGCATGA<br>CCTCTCTGCCA<br>CCTACTTCTGT<br>GCCGCCCGATC<br>TTATAACACCG<br>ACAAGCTCATC<br>TTTGGGACTGG<br>GACCAGATTAC<br>AAGTCTTTCCA<br>A<br>(SEQ ID NO: 478) | ELKVEQNPLFL<br>SMQEGKNYTIY<br>CNYSTTSDRLY<br>WYRQDPGKSLE<br>SLFVLLSNGAV<br>KQEGRLMASLD<br>TKARLSTLHITA<br>AVHDLSATYFC<br>AARSYNTDKLI<br>FGTGTRLQVFP<br>(SEQ ID NO: 479) | ACCA<br>CTTC<br>AGAC<br>AGA<br>(SEQ ID NO: 2) | TTSDR<br>(SEQ ID NO: 3) | ACCA<br>CTTC<br>AGAC<br>AGA<br>(SEQ ID NO: 4) | LLSNG<br>AV<br>(SEQ ID NO: 5) | GCCG<br>CCCG<br>ATCTT<br>ATAA<br>CACC<br>GACA<br>AGCT<br>CATC<br>(SEQ ID NO: 6) | CAAR<br>SYNT<br>DKLIF<br>(SEQ ID NO: 7) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | TTTAATCTGCTCATGACGCTGCGGCTGTGGTCCAGC (SEQ ID NO: 1) | | | | | | | | | |
| 2 | TGGGGAGTCTTGCTCCTCACAGAGCTTTGAGGAGCTGGATCAAAATTGTGCTCCACAGAGAGAAGATACCGGTGTCGGGAAGCACCAGTGCCCTGAGGAAGGGCCATTTCCAAAAGCCCTGTGCTGACACAGGGTTGCTGGTTCCTCTTCAAGAGCCCACTCTCTGGGGTGGGGCCATATCTCCAGCAGAGGTGGGCTGGAAAGGACCCCCCCAATCCCGCCCGCCGTGAGCTTAGCTGGAGCCATGGCCTCTGCACCCATCTCGATGCTTGCGATGCTCTTCACATTGAGTGGGCTGAGAGCTCAGTCAGTGGCTCAGCCGGAAGATCAGGTCAACGTTGCTGAAGGGAATCCTCTGACTGTGAAATGCACCTATTCAGTCTCTGGAAACCCTTATCTTTTTTGGTATGTTCAATACCCCAACCGAGGCCTCCAGTTCCTTCTGAAATACATCACAGGGGATAACCTGGTTAAAGGCAGCTATGGCTTTGAAGCTGAATTTAACAAGAGCCAAACCTCCTTCCACCTGAAGAAACCATCTGCCCTTGTGAGCGACTCCGCTTTGTACTTCTGTGCTGTGAGAGACATGGGGGGTTCTGCAAGGCAACTGACCTTTGGATCTGGGACACAATTGACTGTTTTACCTGA**TATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTA** | MASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDMGGSARQLTFGSGTQLTVL**PDIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS** (SEQ ID NO: 480) | GCTCAGTCAGTGGCTCAGCCGGAAGATCAGGTCAACGTTGCTGAAGGGAATCCTCTGACTGTGAAATGCACCTATTCAGTCTCTGGAAACCCTTATCTTTTTTGGTATGTTCAATACCCCAACCGAGGCCTCCAGTTCCTTCTGAAATACATCACAGGGGATAACCTGGTTAAAGGCAGCTATGGCTTTGAAGCTGAATTTAACAAGAGCCAAACCTCCTTCCACCTGAAGAAACCATCTGCCCTTGTGAGCGACTCCGCTTTGTACTTCTGTGCTGTGAGAGACATGGGGGGTTCTGCAAGGCAACTGACCTTTGGATCTGGGACACAATTGACTGTTTTACCTG (SEQ ID NO: 481) | AQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDMGGSARQLTFGSGTQLTVLP (SEQ ID NO: 482) | GTCTCTGGAAACCCTTAT (SEQ ID NO: 9) | VSGNPY (SEQ ID NO: 10) | TACATCACAGGGGATAACCTGGTT (SEQ ID NO: 11) | YITGDNLV (SEQ ID NO: 12) | GCTGTGAGAGACATGGGGGGTTCTGCAAGGCAACTGACC (SEQ ID NO: 13) | CAVRDMGGSARQLTF (SEQ ID NO: 14) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | TTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 8) | | | | | | | | | |
| 3 | GAGCCTGAGTGACAGCTGCTGGTGTGGGCCCTGGCAGTTGCTGCTGGGCTCATTGCAGCTCAGACACAGCAAAAGAGCCTAGAACCTGGGTCCTAGTTTGCACCTAGAATATGAGGCAAGTGGCGAGAGTGATCGTGTTCCTGACCCTGAGTACTTTGAGCCTTGCTAAGACCACCCAGCCCATCTCCATGGACTCATATGAAGGACAAGAAGTGAACATAACCTGTAGCCACAACAACATTGCTACAAATGATTATATCACGTGGTACCAACAGTTTCCCAGCCAAGGACCACGATTTATTATTCAAGGATACAAGACAAAAGTTACAAACGAAGTGGCCTCCCTGTTTATCCCTGCCGACAGAAAGTCCAGCACTCTGAGCCTGCCCCGGGTTTCCCTGAGCGACACTGCTGTGTACTACTGCCTCGTGGGGACGTTTTCTGGTTCTGCAAGGCAACTGACCTTTGGATCTGGGACACAATTGACTGTTTTACCTGATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCA | NMRQVARVIVFLTLSTLSLAKTTQPISMDSYEGQEVNITCSHNNIATNDYITWYQQFPSQGPRFIIQGYKTKVTNEVASLFIPADRKSSTLSLPRVSLSDTAVYYCLVGTFSGSARQLTFGSGTQLTVLPDIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS (SEQ ID NO: 483) | CTTGCTAAGACCACCCAGCCCATCTCCATGGACTCATATGAAGGACAAGAAGTGAACATAACCTGTAGCCACAACAACATTGCTACAAATGATTATATCACGTGGTACCAACAGTTTCCCAGCCAAGGACCACGATTTATTATTCAAGGATACAAGACAAAAGTTACAAACGAAGTGGCCTCCCTGTTTATCCCTGCCGACAGAAAGTCCAGCACTCTGAGCCTGCCCCGGGTTTCCCTGAGCGACACTGCTGTGTACTACTGCCTCGTGGGGACGTTTTCTGGTTCTGCAAGGCAACTGACCTTTGGATCTGGGACACAATTGACTGTTTTACCTG (SEQ ID NO: 484) | LAKTTQPISMDSYEGQEVNITCSHNNIATNDYITWYQQFPSQGPRFIIQGYKTKVTNEVASLFIPADRKSSTLSLPRVSLSDTAVYYCLVGTFSGSARQLTFGSGTQLTVLP (SEQ ID NO: 485) | AACATTGCTACAAATGATTAT (SEQ ID NO: 16) | NIATNDY (SEQ ID NO: 17) | GGATACAAGACAAAA (SEQ ID NO: 18) | GYKTK (SEQ ID NO: 19) | CTCGTGGGGACGTTTTCTGGTTCTGCAAGGCAACTGACC (SEQ ID NO: 20) | CLVGTFSGSARQLTF (SEQ ID NO: 21) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | ACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 15) | | | | | | | | | |
| 4 | GGCATAATAAATGTCTACGCCTCATGCCACTAGGTGGCAATGTGGGTGTTATACTGAAAAGATCACAGATGGTTCACTTTGCAAGTAAAACTGTAAATGTTCTTAAGTGTGCATTTCTGCTGCTTCTGATGGGCTGAAAATCCCCTTTGATTTCTAAAGTAAATGTAGAGACGTTTTAAAAATAAAGGACTCCTTTGTCCAAGATATATTCCGAAATCCTCCAACAGAGACCTGTGTGAGCTTCTGCTGCAGTAATAATGGTGAAGATCCGGCAATTTTTGTTGGCTATTTTGTGGCTTCAGCTAAGCTGTGTAAGTGCCGCCAAAAATGAAGTGGAGCAGAGTCCTCAGAACCTGACTGCCCAGGAAGGAGAATTTATCACAATCAACTGCAGTTACTCGGTAGGAATAAGTGCCTTACACTGGCTGCAACAGCATCCAGGAGGAGGCATTGTTTCCTTGTTTATGCTGAGCTCAGGGAAGAAGAAGCATGGAAGATTAATTGCCACAATAAACATACAGGAAAGCACAGCTCCCTGCACATCACAGCCTCCCATCCCAGAGACTCTGCCGTCTACATCTGTGCTGTCAGCACCTCTATGTATTCAGGAGGAGGTGCTGACGGACTCACCTTTGGCAAAGGGACTCATCTAATCATCCAGCCCTATATCCAGAACCCTGACCCTGCCGTGTACCAGCTGAGAGACTCTAAATCCAGTGACAAGTCTGTCTGCCTATTC | MVKIRQFLLAILWLQLSCVSAAKNEVEQSPQNLTAQEGEFITINCSYSVGISALHWLQQHPGGGIVSLFMLSSGKKKHGRLIATINIQEKHSSLHITASHPRDSAVYICAVSTSMYSGGGADGLTFGKGTHLIIQPYIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS (SEQ ID NO: 486) | AAAAATGAAGTGGAGCAGAGTCCTCAGAACCTGACTGCCCAGGAAGGAGAATTTATCACAATCAACTGCAGTTACTCGGTAGGAATAAGTGCCTTACACTGGCTGCAACAGCATCCAGGAGGAGGCATTGTTTCCTTGTTTATGCTGAGCTCAGGGAAGAAGAAGCATGGAAGATTAATTGCCACAATAAACATACAGGAAAAGCACAGCTCCCTGCACATCACAGCCTCCCATCCCAGAGACTCTGCCGTCTACATCTGTGCTGTCAGCACCTCTATGTATTCAGGAGGAGGTGCTGACGGACTCACCTTTGGCAAAGGGACTCATCTAATCATCCAGCCCT (SEQ ID NO: 487) | KNEVEQSPQNLTAQEGEFITINCSYSVGISALHWLQQHPGGGIVSLFMLSSGKKKHGRLIATINIQEKHSSLHITASHPRDSAVYICAVSTSMYSGGGADGLTFGKGTHLIIQP (SEQ ID NO: 488) | GTAGGAATAAGTGCC (SEQ ID NO: 23) | VGISA (SEQ ID NO: 24) | CTGAGCTCAGGGAAG (SEQ ID NO: 25) | LSSGK (SEQ ID NO: 26) | GCTGTCAGCACCTCTATGTATTCAGGAGGAGGTGCTGACGGACTCACC (SEQ ID NO: 27) | CAVSTSMYSGGGADGLTF (SEQ ID NO: 28) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | ACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 22) | | | | | | | | | |
| 5 | GGCTTAGTGGTGAATTAGGGGTGTTAAAAAGAGCATCATTTTTTTGAACTGGTAAAGCAGATTCTTTTTATGATTTTTAAAGTAGAAATATCCATTCCAGGTGCATTTTTTTAAGGGTTTAAAATTTGAATCCTCAGTGAACCAGGGCAGAGAAGAATGATGAAATCCTTGAGAGTTTTACTAGTGATCCTGTGGCTTCAGTTGAGCTGGGTTTGGAGCCAACAGAAGGAGGTGGAGCAGAATTCTGGACCCCTCAGTGTTCCAGAGGGAGCCATTGCCTCTCTCAACTGCACTTACAGTGACCGAGGTTCCCAGTCCTTCTTCTGGTACAGACAATATTCTGGGAAAAGCCCTGAGTTGATAATGTCCATATACTCCAATGGTGACAAAGAAGATGGAAGGTTTACAGCACAGCTCAATAAAGCCAGCCAGTATGTTTCTCTGCTCATCAGAGACTCCCAGCCCAGTGATTCAGCCACCTACCTCTGTGCCGTGAAGGGAGGGTATGCACTCAACTTCGGCAAAGGCACCTCGCTGTTGGTCACACCCCATATCCAGAACC | MMKSLRVLLVILWLQLSWVWSQQKEVEQNSGPLSVPEGAIASLNCTYSDRGSQSFFWYRQYSGKSPELIMSIYSNGDKEDGRFTAQLNKASQYVSLLIRDSQPSDSATYLCAVKGGYALNFGKGTSLLVTPHIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS (SEQ ID NO: 489) | CAGAAGGAGGTGGAGCAGAATTCTGGACCCCTCAGTGTTCCAGAGGGAGCCATTGCCTCTCTCAACTGCACTTACAGTGACCGAGGTTCCCAGTCCTTCTTCTGGTACAGACAATATTCTGGGAAAAGCCCTGAGTTGATAATGTCCATATACTCCAATGGTGACAAAGAAGATGGAAGGTTTACAGCACAGCTCAATAAAGCCAGCCAGTATGTTTCTCTGCTCATCAGAGACTCCCAGCCCAGTGATTCAGCCACCTACCTCTGTGCCGTGAAGGGAGGGTATGCACTCAACTTC | QKEVEQNSGPLSVPEGAIASLNCTYSDRGSQSFFWYRQYSGKSPELIMSIYSNGDKEDGRFTAQLNKASQYVSLLIRDSQPSDSATYLCAVKGGYALNFGKGTSLLVTP (SEQ ID NO: 491) | GACCGAGGTTCCCAGTCC (SEQ ID NO: 30) | DRGSQS (SEQ ID NO: 31) | ATATACTCCAATGGTGAC (SEQ ID NO: 32) | IYSNGD (SEQ ID NO: 33) | GCCGTGAAGGGAGGGTATGCACTCAACTTC (SEQ ID NO: 34) | CAVKGGYALNF (SEQ ID NO: 35) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | **CTGACCCTGCCGTGTACCA**<br>**GCTGAGAGACTCTAAATCC**<br>**AGTGACAAGTCTGTCTGCC**<br>**TATTCACCGATTTTGATTCT**<br>**CAAACAAATGTGTCACAAA**<br>**GTAAGGATTCTGATGTGTA**<br>**TATCACAGACAAAACTGTG**<br>**CTAGACATGAGGTCTATGG**<br>**ACTTCAAGAGCAACAGTGC**<br>**TGTGGCCTGGAGCAACAAA**<br>**TCTGACTTTGCATGTGCAA**<br>**ACGCCTTCAACAACAGCAT**<br>**TATTCCAGAAGACACCTTC**<br>**TTCCCCAGCCCAGAAAGTT**<br>**CCTGTGATGTCAAGCTGGT**<br>**CGAGAAAAGCTTTGAAACA**<br>**GATACGAACCTAAACTTTC**<br>**AAAACCTGTCAGTGATTGG**<br>**GTTCCGAATCCTCCTCCTG**<br>**AAAGTGGCCGGGTTTAATC**<br>**TGCTCATGACGCTGCGGCT**<br>**GTGGTCCAGC**<br>(SEQ ID NO: 29) | | GGCAAAGGCA<br>CCTCGCTGTTG<br>GTCACACCCC<br>(SEQ ID NO:<br>490) | | | | | | | |
| 6 | GGCCCATTTCCTGTTCTGAA<br>GCAGCTACGGCACCAGTGCA<br>GCTGATACTCAAGGTTCAGA<br>TCAGAAGAGGAGGCTTCTCA<br>CCCTGCAGCAGGGACCTGTG<br>AGCATGGCATGCCCTGGCTT<br>CCTGTGGGCACTTGTGATCT<br>CCACCTGTCTTGAATTTAGC<br>ATGGCTCAGACAGTCACTCA<br>GTCTCAACCAGAGATGTCTG<br>TGCAGGAGGCAGAGACCGTG<br>ACCCTGAGCTGCACATATGA<br>CACCAGTGAGAGTGATTATT<br>ATTTATTCTGGTACAAGCAG<br>CCTCCCAGCAGGCAGATGAT<br>TCTCGTTATTCGCCAAGAAG<br>CTTATAAGCAACAGAATGCA<br>ACAGAGAATCGTTTCTCTGT<br>GAACTTCCAGAAAGCAGCCA<br>AATCCTTCAGTCTCAAGATC<br>TCAGACTCACAGCTGGGGGA<br>TGCCGCGATGTATTTCTGTGC<br>TTATAGTCCCCCCCTCCCCGG<br>TAACCAGTTCTATTTTGGGA<br>CAGGGACAAGTTTGACGGTC | MACPGFLWAL<br>VISTCLEFSMAQ<br>TVTQSQPEMSV<br>QEAETVTLSCT<br>YDTSESDYYLF<br>WYKQPPSRQMI<br>LVIRQEAYKQQ<br>NATENRFSVNF<br>QKAAKSFSLKIS<br>DSQLGDAAMY<br>FCAYSPPLPGN<br>QFYFGTGTSLT<br>VIP**NIQNPDPA**<br>**VYQLRDSKSSD**<br>**KSVCLFTDFDS**<br>**QTNVSQSKDSD**<br>**VYITDKTVLD**<br>**MRSMDFKSNS**<br>**AVAWSNKSDF**<br>**ACANAFNNSII**<br>**PEDTFFPSPESS**<br>**CDVKLVEKSF**<br>**ETDTNLNFQN**<br>**LSVIGFRILLL**<br>**KVAGFNLLMT** | GCTCAGACAGT<br>CACTCAGTCTC<br>AACCAGAGAT<br>GTCTGTGCAGG<br>AGGCAGAGAC<br>CGTGACCCTGA<br>GCTGCACATAT<br>GACACCAGTG<br>AGAGTGATTAT<br>TATTTATTCTG<br>GTACAAGCAG<br>CCTCCCAGCAG<br>GCAGATGATTC<br>TCGTTATTCGC<br>CAAGAAGCTT<br>ATAAGCAACA<br>GAATGCAACA<br>GAGAATCGTTT<br>CTCTGTGAACT<br>TCCAGAAAGC<br>AGCCAAATCCT<br>TCAGTCTCAAG<br>ATCTCAGACTC<br>ACAGCTGGGG<br>GATGCCGCGAT | AQTVTQSQPEM<br>SVQEAETVTLS<br>CTYDTSESDYY<br>LFWYKQPPSRQ<br>MILVIRQEAYK<br>QQNATENRFSV<br>NFQKAAKSFSL<br>KISDSQLGDAA<br>MYFCAYSPPLP<br>GNQFYFGTGTS<br>LTVIP<br>(SEQ ID NO:<br>494) | ACCA<br>GTGA<br>GAGT<br>GATT<br>ATTA<br>T<br>(SEQ<br>ID NO:<br>37) | TSESD<br>YY<br>(SEQ<br>ID NO:<br>38) | CAAG<br>AAGC<br>TTAT<br>AAGC<br>AACA<br>GAAT<br>(SEQ<br>ID NO:<br>39) | QEAY<br>KQQN<br>(SEQ<br>ID NQ<br>40) | GCTT<br>ATAG<br>TCCC<br>CCCC<br>TCCC<br>CGGT<br>AACC<br>AGTT<br>CTAT<br>(SEQ<br>ID NO:<br>41) | CAYSP<br>PLPGN<br>QFYF<br>(SEQ<br>ID NO:<br>42) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | ATTCCAAATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 36) | LRLWSS (SEQ ID NO: 492) | GTATTTCTGTGCTTATAGTCCCCCCCTCCCCGGTAACCAGTTCTATTTTGGGACAGGGACAAGTTTGACGGTCATTCCAA (SEQ ID NO: 493) | | | | | | | |
| 7 | GCTTTTTTGAAATCGTGTTTCTGTAGAGAAAGAAAAACTACCATATTTGGATAGCCCTGGCCAACTTTCAAGGCTCCTAAATCTGAGTTTTCAGTGAACTGGACAGAAAAAAAAAATGAAGAAGCTACTAGCAATGATTCTGTGGCTTCAACTAGACCGGTTAAGTGGAGAGCTGAAAGTGGAACAAAACCCTCTGTTCCTGAGCATGCAGGAGGGAAAAAACTATACCATCTACTGCAATTATTCAACCACTTCAGACAGACTGTATTGGTACAGGCAGGATCCTGGGAAAAGTCTGGAATCTCTGTTTGTGTTGCTATCAAATGGAGCAGTGAAGCAGGAGGGACGATTAATGGCCTCACTTGATACCAAAGCCCGTCTCAGCACCCTCCACATCACAGCTGCCGTGCATGACCTCTCTGCCACCTACTTCTGTGCCGGTGAACCTGATAGCAACTATCAGTTAATCTGGGGCGCTGG | MKKLLAMILWLQLDRLSGELKVEQNPLFLSMQEGKNYTIYCNYSTTSDRLYWYRQDPGKSLESLFVLLSNGAVKQEGRLMASLDTKARLSTLHITAAVHDLSATYFCAGEPDSNYQLIWGAGTKLIIKPDIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNL | GAGCTGAAAGTGGAACAAAACCCTCTGTTCCTGAGCATGCAGGAGGGAAAAAACTATACCATCTACTGCAATTATTCAACCACTCAGACAGACTGTATTGGTACAGGCAGGATCCTGGGAAAAGTCTGGAATCTCTGTTTGTGTTGCTATCAAATGGAGCAGTGAAGCAGGAGGGACGATTAATGGCCTCACTTGATACCAAAGCCCGTCTCAGCACCCTCCACATCACAGCTGCCGTGCATGACCTCTCTGCCA | ELKVEQNPLFLSMQEGKNYTIYCNYSTTSDRLYWYRQDPGKSLESLFVLLSNGAVKQEGRLMASLDTKARLSTLHITAAVHDLSATYFCAGEPDSNYQLIWGAGTKLIIKP (SEQ ID NO: 497) | ACCACTTCAGACAGA (SEQ ID NO: 44) | TTSDR (SEQ ID NO: 45) | TTGCTATCAAATGGAGCAGTG (SEQ ID NO: 46) | LLSNGAV (SEQ ID NO: 47) | GCCGGTGAACCTGATAGCAACTATCAGTTAATC (SEQ ID NO: 48) | CAGEPDSNYQLIW (SEQ ID NO: 49) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | GACCAAGCTAATTATAAAGC<br>CAGATATCCAGAACCCTGA<br>CCCTGCCGTGTACCAGCTG<br>AGAGACTCTAAATCCAGTG<br>ACAAGTCTGTCTGCCTATT<br>CACCGATTTTGATTCTCAA<br>ACAAATGTGTCACAAAGTA<br>AGGATTCTGATGTGTATAT<br>CACAGACAAAACTGTGCTA<br>GACATGAGGTCTATGGACT<br>TCAAGAGCAACAGTGCTGT<br>GGCCTGGAGCAACAAATCT<br>GACTTTGCATGTGCAAACG<br>CCTTCAACAACAGCATTAT<br>TCCAGAAGACACCTTCTTC<br>CCCAGCCCAGAAAGTTCCT<br>GTGATGTCAAGCTGGTCGA<br>GAAAAGCTTTGAAACAGAT<br>ACGAACCTAAACTTTCAAA<br>ACCTGTCAGTGATTGGGTT<br>CCGAATCCTCCTCCTGAAA<br>GTGGCCGGGTTTAATCTGC<br>TCATGACGCTGCGGCTGTG<br>GTCCAGC (SEQ ID NO: 43) | LMTLRLWSS<br>(SEQ ID NO: 495) | CCTACTTCTGT<br>GCCGGTGAAC<br>CTGATAGCAAC<br>TATCAGTTAAT<br>CTGGGGCGCTG<br>GGACCAAGCT<br>AATTATAAAGC<br>CAG<br>(SEQ ID NO: 496) | | | | | | | |
| 8 | AGAGAGAGAGAGAGAGAGA<br>GGAGGAGGAGGAGGAGGAG<br>GAAGGATGAGGGGAGGGGC<br>TTAGTGGTGAATTAGGGGTG<br>TTAAAAAGAGCATCATTTTT<br>TTGAACTGGTAAAGCAGATT<br>CTTTTTATGATTTTTAAAGTA<br>GAAATATCCATTCCAGGTGC<br>ATTTTTTAAGGGTTTAAAATT<br>TGAATCCTCAGTGAACCAGG<br>GCAGAGAAGAATGATGAAA<br>TCCTTGAGAGTTTTACTAGTG<br>ATCCTGTGGCTTCAGTTGAG<br>CTGGGTTTGGAGCCAACAGA<br>AGGAGGTGGAGCAGAATTCT<br>GGACCCCTCAGTGTTCCAGA<br>GGGAGCCATTGCCTCTCTCA<br>ACTGCACTTACAGTGACCGA<br>GGTTCCCAGTCCTTCTTCTGG<br>TACAGACAATATTCTGGGAA<br>AAGCCCTGAGTTGATAATGT<br>CCATATACTCCAATGGTGAC<br>AAAGAAGATGGAAGGTTTAC<br>AGCACAGCTCAATAAAGCCA | MMKSLRVLLVI<br>LWLQLSWVWS<br>QQKEVEQNSGP<br>LSVPEGAIASLN<br>CTYSDRGSQSF<br>FWYRQYSGKSP<br>ELIMSIYSNGDK<br>EDGRFTAQLNK<br>ASQYVSLLIRDS<br>QPSDSATYLCA<br>VGGAGGYQKV<br>TFGTGTKLQVIP<br>NIQNPDPAVYQ<br>LRDSKSSDKSV<br>CLFTDFDSQTN<br>VSQSKDSDVYI<br>TDKTVLDMRS<br>MDFKSNSAVA<br>WSNKSDFACA<br>NAFNNSIIPEDT<br>FFPSPESSCDV<br>KLVEKSFETDT<br>NLNFQNLSVIG<br>FRILLLKVAGF | CAGAAGGAGG<br>TGGAGCAGAA<br>TTCTGGACCCC<br>TCAGTGTTCCA<br>GAGGGAGCCA<br>TTGCCTCTCTC<br>AACTGCACTTA<br>CAGTGACCGA<br>GGTTCCCAGTC<br>CTTCTTCTGGT<br>ACAGACAATA<br>TTCTGGGAAAA<br>GCCCTGAGTTG<br>ATAATGTCCAT<br>ATACTCCAATG<br>GTGACAAAGA<br>AGATGGAAGG<br>TTTACAGCACA<br>GCTCAATAAA<br>GCCAGCCAGT<br>ATGTTTCTCTG<br>CTCATCAGAGA<br>CTCCCAGCCCA<br>GTGATTCAGCC | QKEVEQNSGPL<br>SVPEGAIASLNC<br>TYSDRGSQSFF<br>WYRQYSGKSPE<br>LIMSIYSNGDKE<br>DGRFTAQLNKA<br>SQYVSLLIRDSQ<br>PSDSATYLCAV<br>GGAGGYQKVT<br>FGTGTKLQVIP<br>(SEQ ID NO: 500) | GACC<br>GAGG<br>TTCCC<br>AGTC<br>C<br>(SEQ ID NO: 51) | DRGS<br>QS<br>(SEQ ID NO: 52) | ATAT<br>ACTC<br>CAAT<br>GGTG<br>AC<br>(SEQ ID NO: 53) | IYSNG<br>D<br>(SEQ ID NO: 54) | GCCG<br>TGGG<br>GGGG<br>GCCG<br>GGGG<br>TTAC<br>CAGA<br>AAGT<br>TACC<br>(SEQ ID NO: 55) | CAVG<br>GAGG<br>YQKV<br>TF<br>(SEQ ID NO: 56) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | GCCAGTATGTTTCTCTGCTCATCAGAGACTCCCAGCCCAGTGATTCAGCCACCTACCTCTGTGCCGTGGGGGGGGCCGGGGGTTACCAGAAAGTTACCTTTGGAACTGGAACAAAGCTCCAAGTCATCCCAAATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 50) | NLLMTLRLWSS (SEQ ID NO: 498) | ACCTACCTCTGTGCCGTGGGGGGGGCCGGGGGTTACCAGAAAGTTACCTTTGGAACTGGAACAAAGCTCCAAGTCATCCCAA (SEQ ID NO: 499) | | | | | | | |
| 9 | GTCCTCCCTTTGTATTTCTACTGGGTTTTGCATCCGGACTGATCTTCCTTCCCTCACCCACATGAAGTGTCTACCTTCTGCAGACTACAGTGGCTCAGGAACCGGGGATGCAGTGCCAGGCTCATGGTATCCTGCAGCAGATGTGGGGAGCTTTCCTTCTCTATGTTTCCATGAAGATGGGAGGCACTGCAGGACAAAGCCTTGAGCAGCCCTCTGAAGTGACAGCTGTGGAAGGAGCCATTGTCCAGATAAACTGCACGTACCAGACATCTGGGTTTTATGGGCTGTCCTGGTACCAGCAACATGATGGCGGAGCACCCACATTTCTTTCTTACAATGCTCTGGATGGTTTGGAGGAGACAGG | MQCQAHGILQQMWGAFLLYVSMKMGGTAGQSLEQPSEVTAVEGAIVQINCTYQTSGFYGLSWYQQHDGGAPTFLSYNALDGLEETGRFSSFLSRSDSYGYLLLQELQMKDSASYFCAVRDPLSGGYNKLIFGAGTRLAVHPYIQNPDPAVYQLRDSKSSDKSVCLFTDFDSQTNVSQSKDSDVYITDKTVLDMRSM | GGACAAAGCCTTGAGCAGCCCTCTGAAGTGACAGCTGTGGAAGGAGCCATTGTCCAGATAAACTGCACGTACCAGACATCTGGGTTTTATGGGCTGTCCTGGTACCAGCAACATGATGGCGGAGCACCCACATTTCTTTCTTACAATGCTCTGGATGGTTTGGAGGAGACAGGTCGTTTTTCTTCATTCCTT | GQSLEQPSEVTAVEGAIVQINCTYQTSGFYGLSWYQQHDGGAPTFLSYNALDGLEETGRFSSFLSRSDSYGYLLLQELQMKDSASYFCAVRDPLSGGYNKLIFGAGTRLAVHP (SEQ ID NO: 503) | ACATCTGGGTTTTATGGG (SEQ ID NO: 58) | TSGFYG (SEQ ID NO: 59) | AATGCTCTGGATGGTTTG (SEQ ID NO: 60) | NALDGL (SEQ ID NO: 61) | GCTGTGAGAGATCCTCTTCTGGTGGCTACAATAAGCTGATT (SEQ ID NO: 62) | CAVRDPLSGGYNKLIF (SEQ ID NO: 63) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | TCGTTTTTCTTCATTCCTTAG<br>TCGCTCTGATAGTTATGGTTA<br>CCTCCTTCTACAGGAGCTCC<br>AGATGAAAGACTCTGCCTCT<br>TACTTCTGCGCTGTGAGAGA<br>TCCTCTTTCTGGTGGCTACAA<br>TAAGCTGATTTTTGGAGCAG<br>GGACCAGGCTGGCTGTACAC<br>CCATAT**ATCCAGAACCCTG**<br>**ACCCTGCCGTGTACCAGCT**<br>**GAGAGACTCTAAATCCAGT**<br>**GACAAGTCTGTCTGCCTAT**<br>**TCACCGATTTTGATTCTCA**<br>**AACAAATGTGTCACAAAGT**<br>**AAGGATTCTGATGTGTATA**<br>**TCACAGACAAAACTGTGCT**<br>**AGACATGAGGTCTATGGAC**<br>**TTCAAGAGCAACAGTGCTG**<br>**TGGCCTGGAGCAACAAATC**<br>**TGACTTTGCATGTGCAAAC**<br>**GCCTTCAACAACAGCATTA**<br>**TTCCAGAAGACACCTTCTT**<br>**CCCCAGCCCAGAAAGTTCC**<br>**TGTGATGTCAAGCTGGTCG**<br>**AGAAAAGCTTTGAAACAGA**<br>**TACGAACCTAAACTTTCAA**<br>**AACCTGTCAGTGATTGGGT**<br>**TCCGAATCCTCCTCCTGAA**<br>**AGTGGCCGGGTTTAATCTG**<br>**CTCATGACGCTGCGGCTGT**<br>**GGTCCAGC** (SEQ ID NO: 57) | **DFKSNSAVAW**<br>**SNKSDFACANA**<br>**FNNSIIPEDTFF**<br>**PSPESSCDVKL**<br>**VEKSFETDTNL**<br>**NFQNLSVIGFR**<br>**ILLLKVAGFNL**<br>**LMTLRLWSS**<br>(SEQ ID NO: 501) | AGTCGCTCTGA<br>TAGTTATGGTT<br>ACCTCCTTCTA<br>CAGGAGCTCC<br>AGATGAAAGA<br>CTCTGCCTCTT<br>ACTTCTGCGCT<br>GTGAGAGATC<br>CTCTTTCTGGT<br>GGCTACAATA<br>AGCTGATTTTT<br>GGAGCAGGGA<br>CCAGGCTGGCT<br>GTACACCCAT<br>(SEQ ID NO: 502) | | | | | | | |
| 10 | GAGCACTCAAATTGAAACCT<br>GCCTGATGTGGGATGTGCTG<br>TGGCTGCTGCTTTGTTGCTTG<br>GGACCTCCTCTGACCTAGGA<br>TCAGACACAGAGTCTGAGTT<br>CTGGGGCCTGGAACCTCAAT<br>GTGCACTTGAACAATGAAGT<br>TGGTGACAAGCATTACTGTA<br>CTCCTATCTTTGGGTATTATG<br>GGTGATGCTAAGACCACACA<br>GCCAAATTCAATGGAGAGTA<br>ACGAAGAAGAGCCTGTTCAC<br>TTGCCTTGTAACCACTCCAC<br>AATCAGTGGAACTGATTACA<br>TACATTGGTATCGACAGCTT<br>CCCTCCCAGGGTCCAGAGTA<br>CGTGATTCATGGTCTTACAA | MKLVTSITVLLS<br>LGIMGDAKTTQ<br>PNSMESNEEEP<br>VHLPCNHSTISG<br>TDYIHWYRQLP<br>SQGPEYVIHGL<br>TSNVNNRMASL<br>AIAEDRKSSTLI<br>LHRATLRDAAV<br>YYCILYSGGGA<br>DGLTFGKGTHL<br>IIQP**YIQNPDPA**<br>**VYQLRDSKSSD**<br>**KSVCLFTDFDS**<br>**QTNVSQSKDSD**<br>**VYITDKTVLD**<br>**MRSMDFKSNS** | GATGCTAAGA<br>CCACACAGCC<br>AAATTCAATGG<br>AGAGTAACGA<br>AGAAGAGCCT<br>GTTCACTTGCC<br>TTGTAACCACT<br>CCACAATCAGT<br>GGAACTGATTA<br>CATACATTGGT<br>ATCGACAGCTT<br>CCCTCCCAGGG<br>TCCAGAGTACG<br>TGATTCATGGT<br>CTTACAAGCAA<br>TGTGAACAAC<br>AGAATGGCCTC | DAKTTQPNSME<br>SNEEEPVHLPC<br>NHSTISGTDYIH<br>WYRQLPSQGPE<br>YVIHGLTSNVN<br>NRMASLAIAED<br>RKSSTLILHRAT<br>LRDAAVYYCIL<br>YSGGGADGLTF<br>GKGTHLIIQP<br>(SEQ ID NO: 506) | ACAA<br>TCAG<br>TGGA<br>ACTG<br>ATTA<br>C<br>(SEQ ID NO: 65) | TISGT<br>DY<br>(SEQ ID NO: 66) | GGTC<br>TTAC<br>AAGC<br>AAT<br>(SEQ ID NO: 67) | GLTSN<br>(SEQ ID NO: 68) | ATCC<br>TGTA<br>TTCA<br>GGAG<br>GAGG<br>TGCT<br>GACG<br>GACT<br>CACC<br>(SEQ ID NO: 69) | CILYS<br>GGGA<br>DGLTF<br>(SEQ ID NO: 70) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | GCAATGTGAACAACAGAATGGCCTCTCTGGCAATCGCTGAAGACAGAAAGTCCAGTACCTTGATCCTGCACCGTGCTACCTTGAGAGATGCTGCTGTGTACTACTGCATCCTGTATTCAGGAGGAGGTGCTGACGGACTCACCTTTGGCAAAGGGACTCATCTAATCATCCAGCCCTATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 64) | AVAWSNKSDFACANAFNNSIIPEDTFFPSPESSCDVKLVEKSFETDTNLNFQNLSVIGFRILLLKVAGFNLLMTLRLWSS (SEQ ID NO: 504) | TCTGGCAATCGCTGAAGACAGAAAGTCCAGTACCTTGATCCTGCACCGTGCTACCTTGAGAGATGCTGCTGTGTACTACTGCATCCTGTATTCAGGAGGAGGTGCTGACGGACTCACCTTTGGCAAAGGGACTCATCTAATCATCCAGCCCT (SEQ ID NO: 505) | | | | | | | |
| 11 | TTCCTGTCTTGAGAAGAGAAACACTTATGGGGAAATTGAATACTTTGTCTTTTTTTTTTTTTTTTTTGAGACGGAGTCTCACTTTGTCGCCCAGGCTGGAGTGCAGTGGCGCGATCTCTGCTCACTGCAAACTCCGCCTCCCGGGTTCCCGCCATTCTCCTGCCTCAGCCTCTCGAGTAGCTGGGACTACAGGCGCCCGCCACAGCGCCCAGCTAATTTTTTTGTATTTTTTGGTAGAGACGGGGTTTCACCGTGTTAGCCAGGATGGTCTCGATCTCCTGACCTCGTGATCCGCCCACCTCGGCCTCCCAAAGCGCTGGGATTA | MAQELGMQCQARGILQQMWGVFLLYVSMKMGGTTGQNIDQPTEMTATEGAIVQINCTYQTSGFNGLFWYQQHAGEAPTFLSYNVLDGLEEKGRFSSFLSRSKGYSYLLLKELQMKDSASYLCAGLFGNTPLVFGKGTRLSVIANIQNPDPAVYQLRDSKSSDKSVCLFTDFDS | GGACAAAACATTGACCAGCCCACTGAGATGACAGCTACGGAAGGTGCCATTGTCCAGATCAACTGCACGTACCAGACATCTGGGTTCAACGGGCTGTTCTGGTACCAGCAACATGCTGGCGAAGCACCCACATTTCTGTCTTACAATGTTCTGGATGGTTTGGAGGAGAAA | GQNIDQPTEMTATEGAIVQINCTYQTSGFNGLFWYQQHAGEAPTFLSYNVLDGLEEKGRFSSFLSRSKGYSYLLLKELQMKDSASYLCAGLFGNTPLVFGKGTRLSVIA (SEQ ID NO: 509) | ACATCTGGGTTCAACGG (SEQ ID NO: 72) | TSGFNG (SEQ ID NO: 73) | AATGTTCTGGATGGTTTG (SEQ ID NO: 74) | NVLDGL (SEQ ID NO: 75) | GCTGGCCTCTTCGGAAACACACCTCTTGTC (SEQ ID NO: 76) | CAGLFGNTPLVF (SEQ ID NO: 77) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | AAGGCGTGAGCCACCGCGCC<br>CGGCCTACTTTGTCTTATGTT<br>ATTCCCATTTGCCGTCTCTGT<br>TCCTTATACATTATGCTTTTT<br>CAACTTTACCAGAATCACTT<br>GGATTAAAACCCGTGGATTT<br>CTCAGTAGGAAATGTTCATG<br>TGAAGACACTTCTGTAGTAA<br>CAGAACCTACAGCTGCTCCT<br>GTAGAAGGAAGTTGAAAGTC<br>ATCCCTTCAAGAAAGGGGCT<br>CCTCCCCTTGTAATTCTACTG<br>GGTTTTGCATCCAGACTGAG<br>TTTCCTTCCCTCACCCACATG<br>AAGTGTCTACCTTCTGCAGA<br>CTCCAATGGCTCAGGAACTG<br>GGAATGCAGTGCCAGGCTCG<br>TGGTATCCTGCAGCAGATGT<br>GGGGAGTTTTCCTTCTTTATG<br>TTTCCATGAAGATGGGAGGC<br>ACTACAGGACAAAACATTGA<br>CCAGCCCACTGAGATGACAG<br>CTACGGAAGGTGCCATTGTC<br>CAGATCAACTGCACGTACCA<br>GACATCTGGGTTCAACGGGC<br>TGTTCTGGTACCAGCAACAT<br>GCTGGCGAAGCACCCACATT<br>TCTGTCTTACAATGTTCTGGA<br>TGGTTTGGAGGAGAAAGGTC<br>GTTTTTCTTCATTCCTTAGTC<br>GGTCTAAAGGGTACAGTTAC<br>CTCCTTTTGAAGGAGCTCCA<br>GATGAAAGACTCTGCCTCTT<br>ACCTCTGTGCTGGCCTCTTCG<br>GAAACACACCTCTTGTCTTT<br>GGAAAGGGCACAAGACTTTC<br>TGTGATTGCAAATATCCAGA<br>ACCCTGACCCTGCCGTGTA<br>CCAGCTGAGAGACTCTAAA<br>TCCAGTGACAAGTCTGTCT<br>GCCTATTCACCGATTTTGA<br>TTCTCAAACAAATGTGTCA<br>CAAAGTAAGGATTCTGATG<br>TGTATATCACAGACAAAAC<br>TGTGCTAGACATGAGGTCT<br>ATGGACTTCAAGAGCAACA<br>GTGCTGTGGCCTGGAGCAA<br>CAAATCTGACTTTGCATGT<br>GCAAACGCCTTCAACAACA | QTNVSQSKDSD<br>VYITDKTVLD<br>MRSMDFKSNS<br>AVAWSNKSDF<br>ACANAFNNSII<br>PEDTFFPSPESS<br>CDVKLVEKSF<br>ETDTNLNFQN<br>LSVIGFRILLL<br>KVAGFNLLMT<br>LRLWSS<br>(SEQ ID NO: 507) | GGTCGTTTTTC<br>TTCATTCCTTA<br>GTCGGTCTAAA<br>GGGTACAGTTA<br>CCTCCTTTTGA<br>AGGAGCTCCA<br>GATGAAAGAC<br>TCTGCCTCTTA<br>CCTCTGTGCTG<br>GCCTCTTCGGA<br>AACACACCTCT<br>TGTCTTTGGAA<br>AGGGCACAAG<br>ACTTTCTGTGA<br>TTGCAA<br>(SEQ ID NO: 508) | | | | | | | |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | GCATTATTCCAGAAGACAC<br>CTTCTTCCCCAGCCCAGAA<br>AGTTCCTGTGATGTCAAGC<br>TGGTCGAGAAAAGCTTTGA<br>AACAGATACGAACCTAAAC<br>TTTCAAAACCTGTCAGTGA<br>TTGGGTTCCGAATCCTCCT<br>CCTGAAAGTGGCCGGGTTT<br>AATCTGCTCATGACGCTGC<br>GGCTGTGGTCCAGC (SEQ<br>ID NO: 71) | | | | | | | | | |
| 12 | TGGGGCTGTTCTGAAGCAGC<br>TACGGCACCAGTGCAGCTGA<br>TACTCAAGGTTCAGATCAGA<br>AGAGGAGGCTTCTCACCCTG<br>CAGCAGGGACCTGTGAGCAT<br>GGCATGCCCTGGCTTCCTGT<br>GGGCACTTGTGATCTCCACC<br>TGTCTTGAATTTAGCATGGCT<br>CAGACAGTCACTCAGTCTCA<br>ACCAGAGATGTCTGTGCAGG<br>AGGCAGAGACCGTGACCCTG<br>AGCTGCACATATGACACCAG<br>TGAGAGTGATTATTATTTATT<br>CTGGTACAAGCAGCCTCCCA<br>GCAGGCAGATGATTCTCGTT<br>ATTCGCCAAGAAGCTTATAA<br>GCAACAGAATGCAACAGAG<br>AATCGTTTCTCTGTGAACTTC<br>CAGAAAGCAGCCAAATCCTT<br>CAGTCTCAAGATCTCAGACT<br>CACAGCTGGGGGATGCCGCG<br>ATGTATTTCTGTGCTTATTTT<br>AACACCGACAAGCTCATCTT<br>TGGGACTGGGACCAGATTAC<br>AAGTCTTTCCAAATATCCAG<br>AACCCTGACCCTGCCGTGT<br>ACCAGCTGAGAGACTCTAA<br>ATCCAGTGACAAGTCTGTC<br>TGCCTATTCACCGATTTTG<br>ATTCTCAAACAAATGTGTC<br>ACAAAGTAAGGATTCTGAT<br>GTGTATATCACAGACAAAA<br>CTGTGCTAGACATGAGGTC<br>TATGGACTTCAAGAGCAAC<br>AGTGCTGTGGCCTGGAGCA<br>ACAAATCTGACTTTGCATG<br>TGCAAACGCCTTCAACAAC | MACPGFLWAL<br>VISTCLEFSMAQ<br>TVTQSQPEMSV<br>QEAETVTLSCT<br>YDTSESDYYLF<br>WYKQPPSRQMI<br>LVIRQEAYKQQ<br>NATENRFSVNF<br>QKAAKSFSLKIS<br>DSQLGDAAMY<br>FCAYFNTDKLIF<br>GTGTRLQVFPN<br>IQNPDPAVYQL<br>RDSKSSDKSVC<br>LFTDFDSQTNV<br>SQSKDSDVYIT<br>DKTVLDMRSM<br>DFKSNSAVAW<br>SNKSDFACANA<br>FNNSIIPEDTFF<br>PSPESSCDVKL<br>VEKSFETDTNL<br>NFQNLSVIGFR<br>ILLLKVAGFNL<br>LMTLRLWSS<br>(SEQ ID NO:<br>510) | GCTCAGACAGT<br>CACTCAGTCTC<br>AACCAGAGAT<br>GTCTGTGCAGG<br>AGGCAGAGAC<br>CGTGACCCTGA<br>GCTGCACATAT<br>GACACCAGTG<br>AGAGTGATTAT<br>TATTTATTCTG<br>GTACAAGCAG<br>CCTCCCAGCAG<br>GCAGATGATTC<br>TCGTTATTCGC<br>CAAGAAGCTT<br>ATAAGCAACA<br>GAATGCAACA<br>GAGAATCGTTT<br>CTCTGTGAACT<br>TCCAGAAAGC<br>AGCCAAATCCT<br>TCAGTCTCAAG<br>ATCTCAGACTC<br>ACAGCTGGGG<br>GATGCCGCGAT<br>GTATTTCTGTG<br>CTTATTTTAAC<br>ACCGACAAGC<br>TCATCTTTGGG<br>ACTGGGACCA<br>GATTACAAGTC<br>TTTCCAA<br>(SEQ ID NO:<br>511) | AQTVTQSQPEM<br>SVQEAETVTLS<br>CTYDTSESDYY<br>LFWYKQPPSRQ<br>MILVIRQEAYK<br>QQNATENRFSV<br>NFQKAAKSFSL<br>KISDSQLGDAA<br>MYFCAYFNTD<br>KLIFGTGTRLQ<br>VFP<br>(SEQ ID NO:<br>512) | ACCA<br>GTGA<br>GAGT<br>GATT<br>ATTA<br>T<br>(SEQ<br>ID NO:<br>79) | TSESD<br>YY<br>(SEQ<br>ID NO:<br>80) | CAAG<br>AAGC<br>TTAT<br>AAGC<br>AACA<br>GAAT<br>(SEQ<br>ID NO:<br>81) | QEAY<br>KQQN<br>(SEQ<br>ID NO:<br>82) | GCTT<br>ATTTT<br>AACA<br>CCGA<br>CAAG<br>CTCA<br>TC<br>(SEQ<br>ID NO:<br>83) | CAYF<br>NTDK<br>LIF<br>(SEQ<br>ID NO:<br>84) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | AGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 78) | | | | | | | | | |
| 13 | GGCACACACACACATGAATAAGAGCAAGACAGAGGGAGAGATGAGGGAGGAGCTTAATGATGGAGCAGAGGTGTTAAAAAGAACATCCTTTTTCTAATTGGTAGGACAGATTTCTTTTATGATTCCTACAGCAGAAAAATGAGAAACGTTTGTTATTATTTTTTTTTCGTGTTTAAGGTTTGAATCCTCAGTGAACCAGGGCAGAAAAGAATGATGAAATCCTTGAGAGTTTTACTGGTGATCCTGTGGCTTCAGTTAAGCTGGGTTTGGAGCCAACAGAAGGAGGTGGAGCAGGATCCTGGACCACTCAGTGTTCCAGAGGGAGCCATTGTTTCTCTCAACTGCACTTACAGCAACAGTGCTTTTCAATACTTCATGTGGTACAGACAGTATTCCAGAAAAGGCCCTGAGTTGCTGATGTACACATACTCCAGTGGTAACAAAGAAGATGGAAGGTTTACAGCACAGGTCGATAAATCCAGCAAGTATATCTCCTTGTTCATCAGAGACTCACAGCCCAGTGATTCAGCCACCTACCTCTGTGCAATGGGGGGCCAAGGAGGTGCTGACGGACTCACCTTTGGCAAAGGGACTCATCTAATCATCCAGCCCTATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTG | MMKSLRVLLVILWLQLSWVWSQQKEVEQDPGPLSVPEGAIVSLNCTYSNSAFQYFMWYRQYSRKGPELLMYTYSSGNKEDGRFTAQVDKSSKYISLFIRDSQPSDSATYLCAMGGQGGADGLTFGKGTHLIIQPYIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS (SEQ ID NO: 513) | CAGAAGGAGGTGGAGCAGGATCCTGGACCACTCAGTGTTCCAGAGGGAGCCATTGTTTCTCTCAACTGCACTTACAGCAACAGTGCTTTTCAATACTTCATGTGGTACAGACAGTATTCCAGAAAAGGCCCTGAGTTGCTGATGTACACATACTCCAGTGGTAACAAAGAAGATGGAAGGTTTACAGCACAGGTCGATAAATCCAGCAAGTATATCTCCTTGTTCATCAGAGACTCACAGCCCAGTGATTCAGCCACCTACCTCTGTGCAATGGGGGGCCAAGGAGGTGCTGACGGACTCACCTTTGGCAAAGGGACTCATCTAATCATCCAGCCCT (SEQ ID NO: 514) | QKEVEQDPGPLSVPEGAIVSLNCTYSNSAFQYFMWYRQYSRKGPELLMYTYSSGNKEDGRFTAQVDKSSKYISLFIRDSQPSDSATYLCAMGGQGGADGLTFGKGTHLIIQP (SEQ ID NO: 515) | AACAGTGCTTTTCAATAC (SEQ ID NO: 86) | NSAFQY (SEQ ID NO: 87) | ACATACTCCAGTGGTAAC (SEQ ID NO: 88) | TYSSGN (SEQ ID NO: 89) | GCAATGGGGGGCCAAGGAGGTGCTGACGGACTCACC (SEQ ID NO: 90) | CAMGGQGGADGLTF (SEQ ID NO: 91) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | TATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 85) | | | | | | | | | |
| 14 | GGGAGTGTCACTCTAAGCCCAAGAGAGTTTCTTGAAGCAAAAAAAAAAAAAAACCCATTCAGGAAATAATTCTTTGCTGATAAGGATGCTCCTTGAACATTTATTAATAATCTTGTGGATGCAGCTGACATGGGTCAGTGGTCAACAGCTGAATCAGAGTCCTCAATCTATGTTTATCCAGGAAGGAGAAGATGTCTCCATGAACTGCACTTCTTCAAGCATATTTAACACCTGGCTATGGTACAAGCAGGACCCTGGGGAAGGTCCTGTCCTCTTGATAGCCTTATATAAGGCTGGTGAATTGACCTCAAATGGAAGACTGACTGCTCAGTTTGGTATAACCAGAAAGGACAGCTTCCTGAATATCTCAGCATCCATACCTAGTGATGTAGGCATCTACTTCTGTGCTGGCCCCAAGAGGGAATATGGAAACAAGCTGGTCTTTGGCGCAGGAACCATTCTGAGAGTCAAGTCCTATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACA | MLLEHLLIILWMQLTWVSGQQLNQSPQSMFIQEGEDVSMNCTSSSIFNTWLWYKQDPGEGPVLLIALYKAGELTSNGRLTAQFGITRKDSFLNISASIPSDVGIYFCAGPKREYGNKLVFGAGTILRVKSYIQNPDPAVYQLRDSKSSDKSVCLFTDFDSQTNVSQSKDSDVYITDKTVLDMRSMDFKSNSAVAWSNKSDFACANAFNNSIIPEDTFFPSESSCDVKLVEKSFETDTNLNFQNLSVIGFRILLLKVAGFNLLMTLRLWSS (SEQ ID NO: 516) | GGTCAACAGCTGAATCAGAGTCCTCAATCTATGTTTATCCAGGAAGGAGAAGATGTCTCCATGAACTGCACTTCTTCAAGCATATTTAACACCTGGCTATGGTACAAGCAGGACCCTGGGGAAGGTCCTGTCCTCTTGATAGCCTTATATAAGGCTGGTGAATTGACCTCAAATGGAAGACTGACTGCTCAGTTTGGTATAACCAGAAAGGACAGCTTCCTGAATATCTCAGCATCCATACCTAGTGATGTAGGCATCTACTTCTGTGCTGGCCCCAAGAGGGAATATGGAAACAAGCTGGTCTTTGGCGCAGGAACCATTCTGAGAGTCA | GQQLNQSPQSMFIQEGEDVSMNCTSSSIFNTWLWYKQDPGEGPVLLIALYKAGELTSNGRLTAQFGITRKDSFLNISASIPSDVGIYFCAGPKREYGNKLVFGAGTILRVKS (SEQ ID NO: 518) | AGCATATTTAACACC (SEQ ID NO: 93) | SIFNT (SEQ ID NO: 94) | TTATATAAGGCTGGTGAATTG (SEQ ID NO: 95) | LYKAGEL (SEQ ID NO: 96) | GCTGGCCCCAAGAGGGAATATGGAAACAAGCTGGTC (SEQ ID NO: 97) | CAGPKREYGNKLVF (SEQ ID NO: 98) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | AAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 92) | | AGTCCT (SEQ ID NO: 517) | | | | | | | |
| 15 | GGGGACAACTGTAGCAACCCTTCTAAAGGTTGTAGATTCTGGCTGATGATGTCACTGACACAAAGGAAAAAATGCAAAACAGGTAGTCTTAAATAAGCATTCTGGTGAGACCAACTGCATTTTGGCCATGGCTTTGCAGAGCACTCTGGGGGCGGTGTGGCTAGGGCTTCTCCTCAACTCTCTCTGGAAGGTTGCAGAAAGCAAGGACCAAGTGTTTCAGCCTTCCACAGTGGCATCTTCAGAGGGAGCTGTGGTGGAAATCTTCTGTAATCACTCTGTGTCCAATGCTTACAACTTCTTCTGGTACCTTCACTTCCCGGGATGTGCACCAAGACTCCTTGTTAAAGGCTCAAAGCCTTCTCAGCAGGGACGATACAACATGACCTATGAACGGTTCTCTTCATCGCTGCTCATCCTCCAGGTGCGGGAGGCAGATGCTGCTGTTTACTACTGTGCTGTGGAGGATAACAATAACAATGACATGCGCTTTGGAGCAGGGACCAGACTGACAGTAAAACCAAATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGA | MALQSTLGAVWLGLLLNSLWKVAESKDQVFQPSTVASSEGAVVEIFCNHSVSNAYNFFWYLHFPGCAPRLLVKGSKPSQQGRYNMTYERFSSSLLILQVREADAAVYYCAVEDNNNNDMRFGAGTRLTVKPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS (SEQ ID NO: 519) | AAGGACCAAGTGTTTCAGCCTTCCACAGTGGCATCTTCAGAGGGAGCTGTGGTGGAAATCTTCTGTAATCACTCTGTGTCCAATGCTTACAACTTCTTCTGGTACCTTCACTTCCCGGGATGTGCACCAAGACTCCTTGTTAAAGGCTCAAAGCCTTCTCAGCAGGGACGATACAACATGACCTATGAACGGTTCTCTTCATCGCTGCTCATCCTCCAGGTGCGGGAGGCAGATGCTGCTGTTTACTACTGTGCTGTGGAGGATAACAATAACAATGACATGCGCTTTGGAGCAGGGACCAGACTGACAGTAAAACCAA (SEQ ID NO: 520) | KDQVFQPSTVASSEGAVVEIFCNHSVSNAYNFFWYLHFPGCAPRLLVKGSKPSQQGRYNMTYERFSSSLLILQVREADAAVYYCAVEDNNNNDMRFGAGTRLTVKP (SEQ ID NO: 521) | GTGTCCAATGCTTACAAC (SEQ ID NO: 100) | VSNAYN (SEQ ID NO: 101) | GGCTCAAAGCCT (SEQ ID NQ 102) | GSKP (SEQ ID NO: 103) | GCTGTGGAGGATAACAATAACAATGACATGCGC (SEQ ID NO: 104) | CAVEDNNNNDMRF (SEQ ID NO: 105) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | **TTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC** (SEQ ID NO: 99) | | | | | | | | | |
| 16 | TCAAATTGACTAGTTTTGACTTTGCCTTATGTTCCCATTTGTTTTCTCTGTTCTTTACATGTTCGATGTTCACCATAATCACTTGGATTAAAATGTGTGGATTAGTTTTTGGAGATAGGGACCTCACCATGTTGCTTAGGCTGGTCTCCAGTTCCTGGCCTCAAGGGATTCTTCTACCTCAGCGTCTTGAGTAGCTGGGATTACAGGCATAAGCCACTGTGCCCAGCTTAAAACCTGTGGATTTATCAGTAGAAAATGTTCATGTAAAGATACTCCTGTAAGAGAAACCATAGCTGCTCCAGTGGAAGGAAGCTTAAACTCATCCCTTCAAGAAAGAAGCTCCTCCCTTTGTATTTCTACTGGGTTTTGCATCCGGACTGATCTTCCTTCCCTCACCCACATGAAGTGTCTACCTTCTGCAGACTACAGTGGCTCAGGAACCGGGGATGCAGTGCCAGGCTCATGGTATCCTGCAGCAGATGTGGGGAGCTTTCCTTCTCTATGTTTCCATGAAGATGGGAGGCACTGCAGGACAAAGCCTTGAGCAGCCCTCTGAAGTGACAGCTGTGGAAGGAGCCATTGTCCAGATAAACTGCACGTACCAGACATCTGGGTTTTATGGGCTGT | MQCQAHGILQQMWGAFLLYVSMKMGGTAGQSLEQPSEVTAVEGAIVQINCTYQTSGFYGLSWYQQHDGGAPTFLSYNALDGLEETGRFSSFLSRSDSYGYLLLQELQMKDSASYFCAVNNNARLMFGDGTQLVVKP**NIQNPDPAVYQLRDSKSSDKSVCLFTDFDSQTNVSQSKDSDVYITDKTVLDMRSMDFKSNSAVAWSNKSDFACANAFNNSIIPEDTFFPSESSCDVKLVEKSFETDTNLNFQNLSVIGFRILLKVAGFNLLMTLRLWSS** (SEQ ID NO: 522) | GGACAAAGCCTTGAGCAGCCCTCTGAAGTGACAGCTGTGGAAGGAGCCATTGTCCAGATAAACTGCACGTACCAGACATCTGGGTTTTATGGGCTGTCCTGGTACCAGCAACATGATGGCGGAGCACCCACATTTCTTTCTTACAATGCTCTGGATGGTTTGGAGGAGACAGGTCGTTTTTCTTCATTCCTTAGTCGCTCTGATAGTTATGGTTACCTCCTTCTACAGGAGCTCCAGATGAAAGACTCTGCCTCTTACTTCTGCGCTGTGAATAACAATGCCAGACTCATGTTTGGAGATGGAACTCAGCTGGTGGTGAAGCCCA | GQSLEQPSEVTAVEGAIVQINCTYQTSGFYGLSWYQQHDGGAPTFLSYNALDGLEETGRFSSFLSRSDSYGYLLLQELQMKDSASYFCAVNNNARLMFGDGTQLVVKP (SEQ ID NO: 524) | ACATCTGGGTTTTATGGG (SEQ ID NO: 107) | TSGFYG (SEQ ID NO: 108) | AATGCTCTGGATGGTTTG (SEQ ID NO: 109) | NALDGL (SEQ ID NO: 110) | GCTGTGAATAACAATGCCAGACTCATG (SEQ ID NO: 111) | CAVNNARLMF (SEQ ID NO: 112) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | CCTGGTACCAGCAACATGATGGCGGAGCACCCACATTTCTTTCTTACAATGCTCTGGATGGTTTGGAGGAGACAGGTCGTTTTTCTTCATTCCTTAGTCGCTCTGATAGTTATGGTTACCTCCTTCTACAGGAGCTCCAGATGAAAGACTCTGCCTCTTACTTCTGCGCTGTGAATAACAATGCCAGACTCATGTTTGGAGATGGAACTCAGCTGGTGGTGAAGCCCAAT**ATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC** (SEQ ID NO: 106) | | (SEQ ID NO: 523) | | | | | | | |
| 17 | TGTCTTGAGAAGAGAAACACTTATGGGGAAATTGAATACTTTTTTTTTTTTTTTTTTTGAGACGGAGTCTCACTTTGTCGCCCAGGCTGGAGTGCAGTGGCGCGATCTCTGCTCACTGCAAACTCCGCCTCCCGGGTTCCCGCCATTCTCCTGCCTCAGCCTCTCGAGTAGCTGGGACTACAGGCGCCCGCCACAGCGCCCAGCTAATTTTTTTGTATTTTTTGGTAGAGACGGGGTTTCACCGTGTTAGCCAGGATGGTCTC | MAQELGMQCQARGILQQMWGVFLLYVSMKMGGTTGQNIDQPTEMTATEGAIVQINCTYQTSGFNGLFWYQQHAGEAPTFLSYNVLDGLEEKGRFSSFLSRSKGYSYLLLKELQMKDSASYLCAVRDPGNDMRFGAGTRLT | GGACAAAACATTGACCAGCCCACTGAGATGACAGCTACGGAAGGTGCCATTGTCCAGATCAACTGCACGTACCAGACATCTGGGTTCAACGGGCTGTTCTGGTACCAGCAACATGCTGGCGAAGCACCCACATTTCTGT | GQNIDQPTEMTATEGAIVQINCTYQTSGFNGLFWYQQHAGEAPTFLSYNVLDGLEEKGRFSSFLSRSKGYSYLLLKELQMKDSASYLCAVRDPGNDMRFGAGTRLTVKP (SEQ ID NO: 527) | ACATCTGGGTTCAACGG (SEQ ID NO: 114) | TSGFNG (SEQ ID NO: 115) | AATGTTCTGGATGGTTTG (SEQ ID NO: 116) | NVLDGL (SEQ ID NO: 117) | GCTGTGAGAGATCCGGGCAATGACATGCGC (SEQ ID NO: 118) | CAVRDPGNDMRF (SEQ ID NO: 119) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | GATCTCCTGACCTCGTGATC<br>CGCCCACCTCGGCCTCCCAA<br>AGCGCTGGGATTAAAGGCGT<br>GAGCCACCGCGCCCGGCCTA<br>CTTTGTCTTATGTTATTCCCA<br>TTTGCCGTCTCTGTTCCTTAT<br>ACATTATGCTTTTTCAACTTT<br>ACCAGAATCACTTGGATTAA<br>AACCCGTGGATTTCTCAGTA<br>GGAAATGTTCATGTGAAGAC<br>ACTTCTGTAGTAACAGAACC<br>TACAGCTGCTCCTGTAGAAG<br>GAAGTTGAAAGTCATCCCTT<br>CAAGAAAGGGGCTCCTCCCC<br>TTGTAATTCTACTGGGTTTTG<br>CATCCAGACTGAGTTTCCTTC<br>CCTCACCCACATGAAGTGTC<br>TACCTTCTGCAGACTCCAAT<br>GGCTCAGGAACTGGGAATGC<br>AGTGCCAGGCTCGTGGTATC<br>CTGCAGCAGATGTGGGGAGT<br>TTTCCTTCTTTATGTTTCCAT<br>GAAGATGGGAGGCACTACA<br>GGACAAAACATTGACCAGCC<br>CACTGAGATGACAGCTACGG<br>AAGGTGCCATTGTCCAGATC<br>AACTGCACGTACCAGACATC<br>TGGGTTCAACGGGCTGTTCT<br>GGTACCAGCAACATGCTGGC<br>GAAGCACCCACATTTCTGTC<br>TTACAATGTTCTGGATGGTTT<br>GGAGGAGAAAGGTCGTTTTT<br>CTTCATTCCTTAGTCGGTCTA<br>AAGGGTACAGTTACCTCCTT<br>TTGAAGGAGCTCCAGATGAA<br>AGACTCTGCCTCTTACCTCTG<br>TGCTGTGAGAGATCCGGGCA<br>ATGACATGCGCTTTGGAGCA<br>GGGACCAGACTGACAGTAAA<br>ACCAAAT**ATCCAGAACCCT**<br>**GACCCTGCCGTGTACCAGC**<br>**TGAGAGACTCTAAATCCAG**<br>**TGACAAGTCTGTCTGCCTA**<br>**TTCACCGATTTTGATTCTC**<br>**AAACAAATGTGTCACAAAG**<br>**TAAGGATTCTGATGTGTAT**<br>**ATCACAGACAAAACTGTGC**<br>**TAGACATGAGGTCTATGGA**<br>**CTTCAAGAGCAACAGTGCT** | VKP**NIQNPDPA**<br>**VYQLRDSKSSD**<br>**KSVCLFTDFDS**<br>**QTNVSQSKDSD**<br>**VYITDKTVLD**<br>**MRSMDFKSNS**<br>**AVAWSNKSDF**<br>**ACANAFNNSII**<br>**PEDTFFPSPESS**<br>**CDVKLVEKSF**<br>**ETDTNLNFQN**<br>**LSVIGFRILLL**<br>**KVAGFNLLMT**<br>**LRLWSS**<br>(SEQ ID NO: 525) | CTTACAATGTT<br>CTGGATGGTTT<br>GGAGGAGAAA<br>GGTCGTTTTTC<br>TTCATTCCTTA<br>GTCGGTCTAAA<br>GGGTACAGTTA<br>CCTCCTTTTGA<br>AGGAGCTCCA<br>GATGAAAGAC<br>TCTGCCTCTTA<br>CCTCTGTGCTG<br>TGAGAGATCC<br>GGGCAATGAC<br>ATGCGCTTTGG<br>AGCAGGGACC<br>AGACTGACAG<br>TAAAACCAA<br>(SEQ ID NO: 526) | | | | | | | |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | GTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 113) | | | | | | | | | |
| 18 | GGGACCCACCTATCATAGCATTTCCTGCCCTGAAGGAGAATTCTCACCAAGCACAGAGGAGAACCCATCAGAGCAGGAGACTTTTCACTCTGCAGGGGAGCGCTGTCAGCATGACACGAGTTAGCTTGCTGTGGGCAGTCGTGGTCTCCACCTGTCTTGAATCCGGCATGGCCCAGACAGTCACTCAGTCTCAACCAGAGATGTCTGTGCAGGAGGCAGAGACTGTGACCCTGAGTTGCACATATGACACCAGTGAGAATAATTATTATTTGTTCTGGTACAAGCAGCCTCCCAGCAGGCAGATGATTCTCGTTATTCGCCAAGAAGCTTATAAGCAACAGAATGCAACGGAGAATCGTTTCTCTGTGAACTTCCAGAAAGCAGCCAAATCCTTCAGTCTCAAGATCTCAGACTCACAGCTGGGGGACACTGCGATGTATTTCTGTGCTTTCGGGGGAGAAACCAGTGGCTCTAGGTTGACCTTTGGGGAAGGAACACAGCTCACAGTGAATCCTGATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGG | MTRVSLLWAVVVSTCLESGMAQTVTQSQPEMSVQEAETVTLSCTYDTSENNYYLFWYKQPPSRQMILVIRQEAYKQQNATENRFSVNFQKAAKSFSLKISDSQLGDTAMYFCAFGGETSGSRLTFGEGTQLTVNPDIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS (SEQ ID NO: 528) | GCCCAGACAGTCACTCAGTCTCAACCAGAGATGTCTGTGCAGGAGGCAGAGACTGTGACCCTGAGTTGCACATATGACACCAGTGAGAATAATTATTATTTGTTCTGGTACAAGCAGCCTCCCAGCAGGCAGATGATTCTCGTTATTCGCCAAGAAGCTTATAAGCAACAGAATGCAACGGAGAATCGTTTCTCTGTGAACTTCCAGAAAGCAGCCAAATCCTTCAGTCTCAAGATCTCAGACTCACAGCTGGGGGACACTGCGATGTATTTCTGTGCTTTCGGGGGAGAAACCAGTGGCTCTAGGTTGACCTTTGGGGAAGGAACACAGCTCACAGTGAATCCTG (SEQ ID NO: | AQTVTQSQPEMSVQEAETVTLSCTYDTSENNYYLFWYKQPPSRQMILVIRQEAYKQQNATENRFSVNFQKAAKSFSLKISDSQLGDTAMYFCAFGGETSGSRLTFGEGTQLTVNP (SEQ ID NO: 530) | ACCAGTGAGAATAATTATTAT (SEQ ID NO: 121) | TSENNYY (SEQ ID NO: 122) | CAAGAAGCTTATAAGCAACAGAAT (SEQ ID NO: 123) | QEAYKQQN (SEQ ID NO: 124) | GCTTTCGGGGGAGAAACCAGTGGCTCTAGGTTGACC (SEQ ID NO: 125) | CAFGGETSGSRLTF (SEQ ID NO: 126) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | TCTATGGACTTCAAGAGCA<br>ACAGTGCTGTGGCCTGGAG<br>CAACAAATCTGACTTTGCA<br>TGTGCAAACGCCTTCAACA<br>ACAGCATTATTCCAGAAGA<br>CACCTTCTTCCCCAGCCCA<br>GAAAGTTCCTGTGATGTCA<br>AGCTGGTCGAGAAAAGCTT<br>TGAAACAGATACGAACCTA<br>AACTTTCAAAACCTGTCAG<br>TGATTGGGTTCCGAATCCT<br>CCTCCTGAAAGTGGCCGGG<br>TTTAATCTGCTCATGACGC<br>TGCGGCTGTGGTCCAGC<br>(SEQ ID NO: 120) | | 529) | | | | | | | |
| 19 | AGGGATGTTTTTCTTATATGG<br>GGAGTTGCTGCTGGGCTCAT<br>TGCAGCTCAGACACAGCAAA<br>AGAGCCTAGAACCTGGGTCC<br>TAGTTTGCACCTAGAATATG<br>AGGCAAGTGGCGAGAGTGAT<br>CGTGTTCCTGACCCTGAGTA<br>CTTTGAGCCTTGCTAAGACC<br>ACCCAGCCCATCTCCATGGA<br>CTCATATGAAGGACAAGAAG<br>TGAACATAACCTGTAGCCAC<br>AACAACATTGCTACAAATGA<br>TTATATCACGTGGTACCAAC<br>AGTTTCCCAGCCAAGGACCA<br>CGATTTATTATTCAAGGATA<br>CAAGACAAAAGTTACAAACG<br>AAGTGGCCTCCCTGTTTATCC<br>CTGCCGACAGAAAGTCCAGC<br>ACTCTGAGCCTGCCCCGGGT<br>TTCCCTGAGCGACACTGCTG<br>TGTACTACTGCCTCGTGGGT<br>GACAAAGGAAGCAACTATCA<br>GTTAATCTGGGGCGCTGGGA<br>CCAAGCTAATTATAAAGCCA<br>GATATCCAGAACCCTGACC<br>CTGCCGTGTACCAGCTGAG<br>AGACTCTAAATCCAGTGAC<br>AAGTCTGTCTGCCTATTCA<br>CCGATTTTGATTCTCAAAC<br>AAATGTGTCACAAAGTAAG<br>GATTCTGATGTGTATATCA<br>CAGACAAAACTGTGCTAGA<br>CATGAGGTCTATGGACTTC | MRQVARVIVFL<br>TLSTLSLAKTTQ<br>PISMDSYEGQE<br>VNITCSHNNIAT<br>NDYITWYQQFP<br>SQGPRFIIQGYK<br>TKVTNEVASLFI<br>PADRKSSTLSLP<br>RVSLSDTAVYY<br>CLVGDKGSNY<br>QLIWGAGTKLII<br>KPDIQNPDPAV<br>YQLRDSKSSDK<br>SVCLFTDFDSQ<br>TNVSQSKDSDV<br>YITDKTVLDM<br>RSMDFKSNSA<br>VAWSNKSDFA<br>CANAFNNSIIPE<br>DTFFPSPESSC<br>DVKLVEKSFET<br>DTNLNFQNLSV<br>IGFRILLLKVA<br>GFNLLMTLRL<br>WSS<br>(SEQ ID NO: 531) | CTTGCTAAGAC<br>CACCCAGCCCA<br>TCTCCATGGAC<br>TCATATGAAGG<br>ACAAGAAGTG<br>AACATAACCTG<br>TAGCCACAAC<br>AACATTGCTAC<br>AAATGATTATA<br>TCACGTGGTAC<br>CAACAGTTTCC<br>CAGCCAAGGA<br>CCACGATTTAT<br>TATTCAAGGAT<br>ACAAGACAAA<br>AGTTACAAAC<br>GAAGTGGCCTC<br>CCTGTTTATCC<br>CTGCCGACAG<br>AAAGTCCAGC<br>ACTCTGAGCCT<br>GCCCCGGGTTT<br>CCCTGAGCGAC<br>ACTGCTGTGTA<br>CTACTGCCTCG<br>TGGGTGACAA<br>AGGAAGCAAC<br>TATCAGTTAAT<br>CTGGGGCGCTG<br>GGACCAAGCT<br>AATTATAAAGC<br>CAG<br>(SEQ ID NO: | LAKTTQPISMD<br>SYEGQEVNITCS<br>HNNIATNDYIT<br>WYQQFPSQGPR<br>FIIQGYKTKVTN<br>EVASLFIPADRK<br>SSTLSLPRVSLS<br>DTAVYYCLVG<br>DKGSNYQLIWG<br>AGTKLIIKP<br>(SEQ ID NO: 533) | AACA<br>TTGCT<br>ACAA<br>ATGA<br>TTAT<br>(SEQ ID NO: 128) | NIATN<br>DY<br>(SEQ ID NO: 129) | GGAT<br>ACAA<br>GACA<br>AAA<br>(SEQ ID NO: 130) | GYKT<br>K<br>(SEQ ID NO: 131) | CTCG<br>TGGG<br>TGAC<br>AAAG<br>GAAG<br>CAAC<br>TATC<br>AGTT<br>AATC<br>(SEQ ID NO: 132) | CLVG<br>DKGS<br>NYQLI<br>W<br>(SEQ ID NO: 133) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | AAGAGCAACAGTGCTGTGG<br>CCTGGAGCAACAAATCTGA<br>CTTTGCATGTGCAAACGCC<br>TTCAACAACAGCATTATTC<br>CAGAAGACACCTTCTTCCC<br>CAGCCCAGAAAGTTCCTGT<br>GATGTCAAGCTGGTCGAGA<br>AAAGCTTTGAAACAGATAC<br>GAACCTAAACTTTCAAAAC<br>CTGTCAGTGATTGGGTTCC<br>GAATCCTCCTCCTGAAAGT<br>GGCCGGGTTTAATCTGCTC<br>ATGACGCTGCGGCTGTGGT<br>CCAGC<br>(SEQ ID NO: 127) | | 532) | | | | | | | |
| 20 | GAAGTTCAGTAGTTAGGGAT<br>GTGGCCACAAGATGGCAGTG<br>CTCCTCTGCTGAGGCAGAAT<br>ACAGGGTTCACTTTAGTGTG<br>TCCTGAATGAATAGGTTTAT<br>GGTAGCAGCAGAGCCTTTTT<br>CTTATTGGTTGGCTACACAG<br>TGTGAGAAACCCCTATGGCT<br>GCCAGAGGAGAGAAGAGAC<br>AACCTGATGATAGAAGTAAC<br>TCTTATAACTGGAGGTTGCA<br>GGTCAATGACTGATCTTAAT<br>TGGGAAGAACAAGGATGAC<br>ATCCATTCGAGCTGTATTTAT<br>ATTCCTGTGGCTGCAGCTGG<br>ACTTGGTGAATGGAGAGAAT<br>GTGGAGCAGCATCCTTCAAC<br>CCTGAGTGTCCAGGAGGGAG<br>ACAGCGCTGTTATCAAGTGT<br>ACTTATTCAGACAGTGCCTC<br>AAACTACTTCCCTTGGTATA<br>AGCAAGAACTTGGAAAAAG<br>ACCTCAGCTTATTATAGACA<br>TTCGTTCAAATGTGGGCGAA<br>AAGAAAGACCAACGAATTGC<br>TGTTACATTGAACAAGACAG<br>CCAAACATTTCTCCCTGCAC<br>ATCACAGAGACCCAACCTGA<br>AGACTCGGCTGTCTACTTCT<br>GTGCAGCAAGTTATCTCCCT<br>GACATGCGCTTTGGAGCAGG<br>GACCAGACTGACAGTAAAAC<br>CAAATATCCAGAACCCTGA | MTSIRAVFIFLW<br>LQLDLVNGENV<br>EQHPSTLSVQE<br>GDSAVIKCTYS<br>DSASNYFPWYK<br>QELGKRPQLIID<br>IRSNVGEKKDQ<br>RIAVTLNKTAK<br>HFSLHITETQPE<br>DSAVYFCAASY<br>LPDMRFGAGTR<br>LTVKPNIQNPD<br>PAVYQLRDSKS<br>SDKSVCLFTDF<br>DSQTNVSQSKD<br>SDVYITDKTVL<br>DMRSMDFKSN<br>SAVAWSNKSD<br>FACANAFNNSI<br>IPEDTFFPSPES<br>SCDVKLVEKSF<br>ETDTNLNFQN<br>LSVIGFRILLL<br>KVAGFNLLMT<br>LRLWSS<br>(SEQ ID NO:<br>534) | GGAGAGAATG<br>TGGAGCAGCA<br>TCCTTCAACCC<br>TGAGTGTCCAG<br>GAGGGAGACA<br>GCGCTGTTATC<br>AAGTGTACTTA<br>TTCAGACAGTG<br>CCTCAAACTAC<br>TTCCCTTGGTA<br>TAAGCAAGAA<br>CTTGGAAAAA<br>GACCTCAGCTT<br>ATTATAGACAT<br>TCGTTCAAATG<br>TGGGCGAAAA<br>GAAAGACCAA<br>CGAATTGCTGT<br>TACATTGAACA<br>AGACAGCCAA<br>ACATTTCTCCC<br>TGCACATCACA<br>GAGACCCAAC<br>CTGAAGACTCG<br>GCTGTCTACTT<br>CTGTGCAGCAA<br>GTTATCTCCCT<br>GACATGCGCTT<br>TGGAGCAGGG<br>ACCAGACTGA<br>CAGTAAAACC<br>AA<br>(SEQ ID NO: | GENVEQHPSTL<br>SVQEGDSAVIK<br>CTYSDSASNYF<br>PWYKQELGKRP<br>QLIIDIRSNVGE<br>KKDQRIAVTLN<br>KTAKHFSLHITE<br>TQPEDSAVYFC<br>AASYLPDMRFG<br>AGTRLTVKP<br>(SEQ ID NO:<br>536) | GACA<br>GTGC<br>CTCA<br>AACT<br>AC<br>(SEQ<br>ID NO:<br>135) | DSAS<br>NY<br>SEQ<br>ID NO:<br>136) | ATTC<br>GTTC<br>AAAT<br>GTGG<br>GCGA<br>A<br>(SEQ<br>ID NO:<br>137) | IRSNV<br>GE<br>(SEQ<br>ID NO:<br>138) | GCAG<br>CAAG<br>TTATC<br>TCCCT<br>GACA<br>TGCG<br>C<br>(SEQ<br>ID NO:<br>139) | CAAS<br>YLPD<br>MRF<br>(SEQ<br>ID NO:<br>140) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | CCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 134) | | 535) | | | | | | | |
| 21 | GTCTAGCATCTTCCATCTCTACAGGAAGTATGTGACATGACACAGTCAAACTCATCATATATCTGTTAACTATACTTCCTGTAAAAGGCAGAAGCCTCACACAGCCCAGTAACTTTGCTAGTACCTCTTGAGTGCAAGGTGGAGAATTAAGATCTGGATTTGAGACGGAGCACGGAACATTTCACTCAGGGGAAGAGCTATGAACATGCTGACTGCCAGCCTGTTGAGGGCAGTCATAGCCTCCATCTGTGTTGTATCCAGCATGGCTCAGAAGGTAACTCAAGCGCAGACTGAAATTTCTGTGGTGGAGAAGGAGGATGTGACCTTGGACTGTGTGTATGAAACCCGTGATACTACTTATTACTTATTCTGGTACAAGCAACCACCAAGTGGAGAATTGGTTTTCCTTATTCGTCGGAACTCTTTTGATGAGCAAAATGAAATAAGTGGTCGGTATTCTTGGAACTTCCAGAAATCCACCAGTTCCTTCAACTTCACCATCACAGCCTCACAAGTCGTGGACT | MNMLTASLLRAVIASICVVSSMAQKVTQAQTEISVVEKEDVTLDCVYETRDTTYYLFWYKQPPSGELVFLIRRNSFDEQNEISGRYSWNFQKSTSSFNFTITASQVVDSAVYFCALSELKAAGNKLTFGGGTRVLVKPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS | GCTCAGAAGGTAACTCAAGCGCAGACTGAAATTTCTGTGGTGGAGAAGGAGGATGTGACCTTGGACTGTGTGTATGAAACCCGTGATACTACTTATTACTTATTCTGGTACAAGCAACCACCAAGTGGAGAATTGGTTTCCTTATTCGTCGGAACTCTTTGATGAGCAAAATGAAATAAGTGGTCGGTATTCTTGGAACTTCCAGAAATCCACCAGTTCCTTCAACTTCACCATCACAGCCTCACAAGTCGTGGACTCAGCAGTATACTTCTGTGC | AQKVTQAQTEISVVEKEDVTLDCVYETRDTTYYLFWYKQPPSGELVFLIRRNSFDEQNEISGRYSWNFQKSTSSFNFTITASQVVDSAVYFCALSELKAAGNKLTFGGGTRVLVKP (SEQ ID NO: 539) | ACCCGTGATACTACTTATTAC (SEQ ID NO: 142) | TRDTTYY (SEQ ID NO: 143) | CGGAACTCTTTTGATGAGCAAAAT (SEQ ID NO: 144) | RNSFDEQN (SEQ ID NO: 145) | GCTCTGAGTGAGCTCAAAGCTGCAGGCAACAAGCTAACT (SEQ ID NO: 146) | CALSELKAAGNKLTF (SEQ ID NO: 147) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | CAGCAGTATACTTCTGTGCTCTGAGTGAGCTCAAAGCTGCAGGCAACAAGCTAACTTTTGGAGGAGGAACCAGGGTGCTAGTTAAACCAAAT**ATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC** (SEQ ID NO: 141) | (SEQ ID NO: 537) | TCTGAGTGAGCTCAAAGCTGCAGGCAACAAGCTAACTTTTGGAGGAGGAACCAGGGTGCTAGTTAAACCAA (SEQ ID NO: 538) | | | | | | | |
| 22 | GGCTGTACTGGGGCAGCCTGAGTGACAGCTGCTGGTGTGGGCCCTGGCAGTTGCTGCTGGGCTCATTGCAGCTCAGACACAGCAAAAGAGCCTAGAACCTGGGTCCTAGTTTGCACCTAGAATATGAGGCAAGTGGCGAGAGTGATCGTGTTCCTGACCCTGAGTACTTTGAGCCTTGCTAAGACCACCCAGCCCATCTCCATGGACTCATATGAAGGACAAGAAGTGAACATAACCTGTAGCCACAACAACATTGCTACAAATGATTATATCACGTGGTACCAACAGTTTCCCAGCCAAGGACCACGATTTATTATTCAAGGATACAAGACAAAAGTTACAAACGAAGTGGCCTCCCTGTTTATCCCTGCCGACAGAAAGTCCAGCACTCTGAGCCTGC | MRQVARVIVFLTLSTLSLAKTTQPISMDSYEGQEVNITCSHNNIATNDYITWYQQFPSQGPRFIIQGYKTKVTNEVASLFIPADRKSSTLSLPRVSLSDTAVYYCLVGDKVYGGSQGNLIFGKGTKLSVKP**NIQNPDPAVYQLRDSKSSDKSVCLFTDFDSQTNVSQSKDSDVYITDKTVLDMRSMDFKSNSAVAWSNKSDFACANAFNNSIIPEDTFFPSP** | CTTGCTAAGACCACCCAGCCCATCTCCATGGACTCATATGAAGGACAAGAAGTGAACATAACCTGTAGCCACAACAACATTGCTACAAATGATTATATCACGTGGTACCAACAGTTTCCCAGCCAAGGACCACGATTTATTATTCAAGGATACAAGACAAAAGTTACAAACGAAGTGGCCTCCCTGTTTATCCCTGCCGACAGAAAGTCCAGC | LAKTTQPISMDSYEGQEVNITCSHNNIATNDYITWYQQFPSQGPRFIIQGYKTKVTNEVASLFIPADRKSSTLSLPRVSLSDTAVYYCLVGDKVYGGSQGNLIFGKGTKLSVKP (SEQ ID NO: 542) | AACATTGCTACAAATGATTAT (SEQ ID NO: 149) | NIATNDY (SEQ ID NO: 150) | GGATACAAGACAAAA (SEQ ID NO: 151) | GYKTK (SEQ ID NO: 152) | CTCGTGGGTGACAAGGTTTATGGAGGAAGCCAAGGAAATCTCATC (SEQ ID NO: 153) | CLVGDKVYGGSQGNLIF (SEQ ID NO: 154) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | CCCGGGTTTCCCTGAGCGAC ACTGCTGTGTACTACTGCCTC GTGGGTGACAAGGTTTATGG AGGAAGCCAAGGAAATCTCA TCTTTGGAAAAGGCACTAAA CTCTCTGTTAAACCAAATAT CCAGAACCCTGACCCTGCC GTGTACCAGCTGAGAGACT CTAAATCCAGTGACAAGTC TGTCTGCCTATTCACCGAT TTTGATTCTCAAACAAATG TGTCACAAAGTAAGGATTC TGATGTGTATATCACAGAC AAAACTGTGCTAGACATGA GGTCTATGGACTTCAAGAG CAACAGTGCTGTGGCCTGG AGCAACAAATCTGACTTTG CATGTGCAAACGCCTTCAA CAACAGCATTATTCCAGAA GACACCTTCTTCCCCAGCC CAGAAAGTTCCTGTGATGT CAAGCTGGTCGAGAAAAGC TTTGAAACAGATACGAACC TAAACTTTCAAAACCTGTC AGTGATTGGGTTCCGAATC CTCCTCCTGAAAGTGGCCG GGTTTAATCTGCTCATGAC GCTGCGGCTGTGGTCCAGC (SEQ ID NO: 148) | ESSCDVKLVEK SFETDTNLNFQ NLSVIGFRILLL KVAGFNLLMT LRLWSS (SEQ ID NO: 540) | ACTCTGAGCCT GCCCCGGGTTT CCCTGAGCGAC ACTGCTGTGTA CTACTGCCTCG TGGGTGACAA GGTTTATGGAG GAAGCCAAGG AAATCTCATCT TTGGAAAAGG CACTAAACTCT CTGTTAAACCA A (SEQ ID NO: 541) | | | | | | | |
| 23 | GGGGAGTTGGTTGATCCAAA AGAAAGTCTGCATTGGGTGA GCTTCTCAGCCAGTACATAG AGAAGTGTGAGATGACACAC ACTAGTTTGCTATACCAGGA AACCTCTGTTTCCTGTTCTAG GGCAGCAGTAGCAGCAGCAC ATGGCCCAGTAATTCTTCTCT CACCATGCCAGGTTCACTTC ACAGTACAGAGTCCTGAAAA TAAAGAAGAAAATTTTTTTT TATCTAGAAAAAGAACCAAA CATGTCACTTTCTAGCCTGCT GAAGGTGGTCACAGCTTCAC TGTGGCTAGGACCTGGCATT GCCCAGAAGATAACTCAAAC CCAACCAGGAATGTTCGTGC AGGAAAAGGAGGCTGTGACT CTGGACTGCACATATGACAC | MSLSSLLKVVT ASLWLGPGIAQ KITQTQPGMFV QEKEAVTLDCT YDTSDPSYGLF WYKQPSSGEMI FLIYQGSYDQQ NATEGRYSLNF QKARKSANLVI SASQLGDSAMY FCAMREGQDSS YKLIFGSGTRLL VRPDIQNPDPA VYQLRDSKSSD KSVCLFTDFDS QTNVSQSKDSD VYITDKTVLD MRSMDFKSNS AVAWSNKSDF | GCCCAGAAGA TAACTCAAACC CAACCAGGAA TGTTCGTGCAG GAAAAGGAGG CTGTGACTCTG GACTGCACATA TGACACCAGTG ATCCAAGTTAT GGTCTATTCTG GTACAAGCAG CCCAGCAGTG GGGAAATGAT TTTTCTTATTT ATCAGGGGTCT TATGACCAGCA AAATGCAACA GAAGGTCGCT ACTCATTGAAT | AQKITQTQPGM FVQEKEAVTLD CTYDTSDPSYG LFWYKQPSSGE MIFLIYQGSYD QQNATEGRYSL NFQKARKSANL VISASQLGDSA MYFCAMREGQ DSSYKLIFGSGT RLLVRP (SEQ ID NO: 545) | ACCA GTGA TCCA AGTT ATGG T (SEQ ID NO: 156) | TSDPS YG (SEQ ID NO: 157) | CAGG GGTC TTAT GACC AGCA AAAT (SEQ ID NO: 158) | QGSY DQQN (SEQ ID NO: 159) | GCAA TGAG AGAG GGCC AGGA TAGC AGCT ATAA ATTG ATC (SEQ ID NO: 160) | CAMR EGQD SSYKL IF (SEQ ID NO: 161) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | CAGTGATCCAAGTTATGGTCTATTCTGGTACAAGCAGCCCAGCAGTGGGGAAATGATTTTTCTTATTTATCAGGGGTCTTATGACCAGCAAAATGCAACAGAAGGTCGCTACTCATTGAATTTCCAGAAGGCAAGAAAATCCGCCAACCTTGTCATCTCCGCTTCACAACTGGGGGACTCAGCAATGTATTTCTGTGCAATGAGAGAGGGCCAGGATAGCAGCTATAAATTGATCTTCGGGAGTGGGACCAGACTGCTGGTCAGGCCTGAT**ATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC** (SEQ ID NO: 155) | **ACANAFNNSIIPEDTFFPSPESSCDVKLVEKSFETDTNLNFQNLSVIGFRILLLKVAGFNLLMTLRLWSS** (SEQ ID NO: 543) | TTCCAGAAGGCAAGAAAATCCGCCAACCTTGTCATCTCCGCTTCACAACTGGGGGACTCAGCAATGTATTTCTGTGCAATGAGAGAGGGCCAGGATAGCAGCTATAAATTGATCTTCGGGAGTGGGACCAGACTGCTGGTCAGGCCTG (SEQ ID NO: 544) | | | | | | | |
| 24 | TCTGGGGTTCATATGTAAAATGAAGGGTCTGTGGAAGGACATGAATAAAGCACAGGAGGTTGAAGTCAGATTTGCAGCTTTCTAGGCAGGAGACAAGACAATCTGCATCTTCACAGGAGGGATGGCCATGCTCCTGGGGGCATCAGTGCTGATTCTGTGGCTTCAGCCAGACTGGGTAAACAGTCAACAGAAGAATGATGACCAGCAAGTTAAGCAAAAT | MAMLLGASVLILWLQPDWVNSQQKNDDQQVKQNSPSLSVQEGRISILNCDYTNSMFDYFLWYKKYPAEGPTFLISISSIKDKNEDGRFTVFLNKSAKHLSLHIVPSQPGDSAVYFCAARIYG | GACCAGCAAGTTAAGCAAAATTCACCATCCCTGAGCGTCCAGGAAGGAAGAATTTCTATTCTGAACTGTGACTATACTAACAGCATGTTTGATTATTTCCTATGGTACAAAAAATAC | DQQVKQNSPSLSVQEGRISILNCDYTNSMFDYFLWYKKYPAEGPTFLISISSIKDKNEDGRFTVFLNKSAKHLSLHIVPSQPGDSAVYFCAARIYGGSQGNLIFGKGTKLSVKP (SEQ ID NO: | AACAGCATGTTTGATTAT (SEQ ID NO: 163) | NSMFDY (SEQ ID NO: 164) | ATAAGTTCCATTAAGGATAAA (SEQ ID NO: 165) | ISSIKDK (SEQ ID NO: 166) | GCAGCAAGGATTTATGGAGGAAGCCAAGGAAATCTCATC (SEQ | CAARIYGGSQGNLIF (SEQ ID NO: 168) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | TCACCATCCCTGAGCGTCCAGGAAGGAAGAATTTCTATTCTGAACTGTGACTATACTAACAGCATGTTTGATTATTTCCTATGGTACAAAAAATACCCTGCTGAAGGTCCTACATTCCTGATATCTATAAGTTCCATTAAGGATAAAAATGAAGATGGAAGATTCACTGTCTTCTTAAACAAAAGTGCCAAGCACCTCTCTCTGCACATTGTGCCCTCCCAGCCTGGAGACTCTGCAGTGTACTTCTGTGCAGCAAGGATTTATGGAGGAAGCCAAGGAAATCTCATCTTTGGAAAAGGCACTAAACTCTCTGTTAAACCAAATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 162) | GSQGNLIFGKGTKLSVKPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS (SEQ ID NO: 546) | CCTGCTGAAGGTCCTACATTCCTGATATCTATAAGTTCCATTAAGGATAAAAATGAAGATGGAAGATTCACTGTCTTCTTAAACAAAAGTGCCAAGCACCTCTCTCTGCACATTGTGCCCTCCCAGCCTGGAGACTCTGCAGTGTACTTCTGTGCAGCAAGGATTTATGGAGGAAGCCAAGGAAATCTCATCTTTGGAAAAGGCACTAAACTCTCTGTTAAACCA (SEQ ID NO: 547) | 548) | | | | | ID NO: 167) | |
| 25 | GAAAGTCTGCATTGGGTGAGCTTCTCAGCCAGTACATAGAGAAGTGTGAGATGACACACACTAGTTTGCTATACCAGGAAACCTCTGTTTCCTGTTCTAGGGCAGCAGTAGCAGCAGCACATGGCCCAGTAATTCTTCTCTCACCATGCCAGGTTCACTTCA | MSLSSLLKVVTASLWLGPGIAQKITQTQPGMFVQEKEAVTLDCTYDTSDPSYGLFWYKQPSSGEMIFLIYQGSYDQQNATEGRYSLNF | GCCCAGAAGATAACTCAAACCCAACCAGGAATGTTCGTGCAGGAAAAGGAGGCTGTGACTCTGGACTGCACATATGACACCAGTG | AQKITQTQPGMFVQEKEAVTLDCTYDTSDPSYGLFWYKQPSSGEMIFLIYQGSYDQQNATEGRYSLNFQKARKSANLVISASQLGDSA | ACCAGTGATCCAAGTTATGGT (SEQ ID NO: | TSDPSYG (SEQ ID NO: 171) | CAGGGGTCTTATGACCAGCAAAAT (SEQ ID NO: | QGSYDQQN (SEQ ID NO: 173) | GCAATGAGAGAGGGCGAACCTTCTGGTTCTGCAA | CAMREGEPSGSARQLTF (SEQ ID NO: 175) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | CAGTACAGAGTCCTGAAAAT<br>AAAGAAGAAAATTTTTTTTT<br>ATCTAGAAAAAGAACCAAAC<br>ATGTCACTTTCTAGCCTGCTG<br>AAGGTGGTCACAGCTTCACT<br>GTGGCTAGGACCTGGCATTG<br>CCCAGAAGATAACTCAAACC<br>CAACCAGGAATGTTCGTGCA<br>GGAAAAGGAGGCTGTGACTC<br>TGGACTGCACATATGACACC<br>AGTGATCCAAGTTATGGTCT<br>ATTCTGGTACAAGCAGCCCA<br>GCAGTGGGGAAATGATTTTT<br>CTTATTTATCAGGGGTCTTAT<br>GACCAGCAAAATGCAACAG<br>AAGGTCGCTACTCATTGAAT<br>TTCCAGAAGGCAAGAAAATC<br>CGCCAACCTTGTCATCTCCG<br>CTTCACAACTGGGGGACTCA<br>GCAATGTACTTCTGTGCAAT<br>GAGAGAGGGCGAACCTTCTG<br>GTTCTGCAAGGCAACTGACC<br>TTTGGATCTGGGACACAATT<br>GACTGTTTTACCTGAT**ATCC**<br>**AGAACCCTGACCCTGCCGT**<br>**GTACCAGCTGAGAGACTCT**<br>**AAATCCAGTGACAAGTCTG**<br>**TCTGCCTATTCACCGATTT**<br>**TGATTCTCAAACAAATGTG**<br>**TCACAAAGTAAGGATTCTG**<br>**ATGTGTATATCACAGACAA**<br>**AACTGTGCTAGACATGAGG**<br>**TCTATGGACTTCAAGAGCA**<br>**ACAGTGCTGTGGCCTGGAG**<br>**CAACAAATCTGACTTTGCA**<br>**TGTGCAAACGCCTTCAACA**<br>**ACAGCATTATTCCAGAAGA**<br>**CACCTTCTTCCCCAGCCCA**<br>**GAAAGTTCCTGTGATGTCA**<br>**AGCTGGTCGAGAAAAGCTT**<br>**TGAAACAGATACGAACCTA**<br>**AACTTTCAAAACCTGTCAG**<br>**TGATTGGGTTCCGAATCCT**<br>**CCTCCTGAAAGTGGCCGGG**<br>**TTTAATCTGCTCATGACGC**<br>**TGCGGCTGTGGTCCAGC**<br>(SEQ ID NO: 169) | QKARKSANLVI<br>SASQLGDSAMY<br>FCAMREGEPSG<br>SARQLTFGSGT<br>QLTVLP**DIQNP**<br>**DPAVYQLRDS**<br>**KSSDKSVCLFT**<br>**DFDSQTNVSQS**<br>**KDSDVYITDKT**<br>**VLDMRSMDFK**<br>**SNSAVAWSNK**<br>**SDFACANAFNN**<br>**SIIPEDTFFPSP**<br>**ESSCDVKLVEK**<br>**SFETDTNLNFQ**<br>**NLSVIGFRILLL**<br>**KVAGFNLLMT**<br>**LRLWSS**<br>(SEQ ID NO: 549) | ATCCAAGTTAT<br>GGTCTATTCTG<br>GTACAAGCAG<br>CCCAGCAGTG<br>GGGAAATGAT<br>TTTTCTTATTT<br>ATCAGGGGTCT<br>TATGACCAGCA<br>AAATGCAACA<br>GAAGGTCGCT<br>ACTCATTGAAT<br>TTCCAGAAGGC<br>AAGAAAATCC<br>GCCAACCTTGT<br>CATCTCCGCTT<br>CACAACTGGG<br>GGACTCAGCA<br>ATGTACTTCTG<br>TGCAATGAGA<br>GAGGGCGAAC<br>CTTCTGGTTCT<br>GCAAGGCAAC<br>TGACCTTTGGA<br>TCTGGGACACA<br>ATTGACTGTTT<br>TACCTG<br>(SEQ ID NO: 550) | MYFCAMREGE<br>PSGSARQLTFGS<br>GTQLTVLP<br>(SEQ ID NO: 551) | 170) | | 172) | | GGCA<br>ACTG<br>ACC<br>(SEQ ID NO: 174) | |
| 26 | TGGGGTTCATATGTAAAATG | MAMLLGASVLI | GACCAGCAAG | DQQVKQNSPSL | AACA | NSMF | ATAA | ISSIKD | GCAG | CAVN |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | AAGGGTCTGTGGAAGGACAT<br>GAATAAAGCACAGGAGGTTG<br>AAGTCAGATTTGCAGCTTTC<br>TAGGCAGGAGACAAGACAA<br>TCTGCATCTTCACAGGAGGG<br>ATGGCCATGCTCCTGGGGGC<br>ATCAGTGCTGATTCTGTGGC<br>TTCAGCCAGACTGGGTAAAC<br>AGTCAACAGAAGAATGATGA<br>CCAGCAAGTTAAGCAAAATT<br>CACCATCCCTGAGCGTCCAG<br>GAAGGAAGAATTTCTATTCT<br>GAACTGTGACTATACTAACA<br>GCATGTTTGATTATTTCCTAT<br>GGTACAAAAAATACCCTGCT<br>GAAGGTCCTACATTCCTGAT<br>ATCTATAAGTTCCATTAAGG<br>ATAAAAATGAAGATGGAAG<br>ATTCACTGTCTTCTTAAACAA<br>AAGTGCCAAGCACCTCTCTC<br>TGCACATTGTGCCCTCCCAG<br>CCTGGAGACTCTGCAGTGTA<br>CTTCTGTGCAGTTAATGCTG<br>GTGGTACTAGCTATGGAAAG<br>CTGACATTTGGACAAGGGAC<br>CATCTTGACTGTCCATCCAA<br>ATATCCAGAACCCTGACCC<br>TGCCGTGTACCAGCTGAGA<br>GACTCTAAATCCAGTGACA<br>AGTCTGTCTGCCTATTCAC<br>CGATTTTGATTCTCAAACA<br>AATGTGTCACAAAGTAAGG<br>ATTCTGATGTGTATATCAC<br>AGACAAAACTGTGCTAGAC<br>ATGAGGTCTATGGACTTCA<br>AGAGCAACAGTGCTGTGGC<br>CTGGAGCAACAAATCTGAC<br>TTTGCATGTGCAAACGCCT<br>TCAACAACAGCATTATTCC<br>AGAAGACACCTTCTTCCCC<br>AGCCCAGAAAGTTCCTGTG<br>ATGTCAAGCTGGTCGAGAA<br>AAGCTTTGAAACAGATACG<br>AACCTAAACTTTCAAAACC<br>TGTCAGTGATTGGGTTCCG<br>AATCCTCCTCCTGAAAGTG<br>GCCGGGTTTAATCTGCTCA<br>TGACGCTGCGGCTGTGGTC<br>CAGC | LWLQPDWVNS<br>QQKNDDQQVK<br>QNSPSLSVQEG<br>RISILNCDYTNS<br>MFDYFLWYKK<br>YPAEGPTFLISIS<br>SIKDKNEDGRF<br>TVFLNKSAKHL<br>SLHIVPSQPGDS<br>AVYFCAVNAG<br>GTSYGKLTFGQ<br>GTILTVHPNIQN<br>PDPAVYQLRDS<br>KSSDKSVCLFT<br>DFDSQTNVSQS<br>KDSDVYITDKT<br>VLDMRSMDFK<br>SNSAVAWSNK<br>SDFACANAFNN<br>SIIPEDTFFPSP<br>ESSCDVKLVEK<br>SFETDTNLNFQ<br>NLSVIGFRILLL<br>KVAGFNLLMT<br>LRLWSS<br>(SEQ ID NO:<br>552) | TTAAGCAAAAT<br>TCACCATCCCT<br>GAGCGTCCAG<br>GAAGGAAGAA<br>TTTCTATTCTG<br>AACTGTGACTA<br>TACTAACAGCA<br>TGTTTGATTAT<br>TTCCTATGGTA<br>CAAAAAATAC<br>CCTGCTGAAGG<br>TCCTACATTCC<br>TGATATCTATA<br>AGTTCCATTAA<br>GGATAAAAAT<br>GAAGATGGAA<br>GATTCACTGTC<br>TTCTTAAACAA<br>AAGTGCCAAG<br>CACCTCTCTCT<br>GCACATTGTGC<br>CCTCCCAGCCT<br>GGAGACTCTGC<br>AGTGTACTTCT<br>GTGCAGTTAAT<br>GCTGGTGGTAC<br>TAGCTATGGAA<br>AGCTGACATTT<br>GGACAAGGGA<br>CCATCTTGACT<br>GTCCATCCAA<br>(SEQ ID NO:<br>553) | SVQEGRISILNC<br>DYTNSMFDYFL<br>WYKKYPAEGP<br>TFLISISSIKDKN<br>EDGRFTVFLNK<br>SAKHLSLHIVPS<br>QPGDSAVYFCA<br>VNAGGTSYGKL<br>TFGQGTILTVHP<br>(SEQ ID NO:<br>554) | GCAT<br>GTTT<br>GATT<br>AT<br>SEQ<br>ID NO:<br>177) | DY<br>(SEQ<br>ID NO:<br>178) | GTTC<br>CATT<br>AAGG<br>ATAA<br>A<br>(SEQ<br>ID NO:<br>179) | K<br>(SEQ<br>ID NO:<br>180) | TTAA<br>TGCT<br>GGTG<br>GTAC<br>TAGC<br>TATG<br>GAAA<br>GCTG<br>ACA<br>(SEQ<br>ID NO:<br>181) | AGGT<br>SYGK<br>LTF<br>(SEQ<br>ID NO:<br>182) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | (SEQ ID NO: 176) | | | | | | | | | |
| 27 | GACATTTCTCAAATGAGAAG<br>CAAACAGTTCACTTCCTTGG<br>ATCCGTGGTTTCGCCTGTGG<br>CCTTCAGGGGGCGACGTTGC<br>ACTAAGGAGGCATCTGTGTT<br>CATTGCCGACCATCCTCATC<br>CACTGAGCCTCCTCCCTGCA<br>GCTGGCTGATGTAGCTCACT<br>GGTGTCTGTGTAGATAGGGA<br>GCTGTGATGAGAACAAGAGG<br>TCAGAACACATCCAGGCTCC<br>TTAAGAGAAAGCCTTTCTTT<br>AACCATTTTTGAAACCCTTC<br>AAAGGCAGAGACTTGTCCAG<br>CCTAACCTGCCTGCTGCTCCT<br>AGCTCCTGAGGCTCAGGGCC<br>CTTGGCTTCTGTCCGCTCTGC<br>TCAGGGCCCTCCAGCGTGGC<br>CACTGCTCAGCCATGCTCCT<br>GCTGCTCGTCCCAGTGCTCG<br>AGGTGATTTTTACCCTGGGA<br>GGAACCAGAGCCCAGTCGGT<br>GACCCAGCTTGGCAGCCACG<br>TCTCTGTCTCTGAGGGAGCC<br>CTGGTTCTGCTGAGGTGCAA<br>CTACTCATCGTCTGTTCCACC<br>ATATCTCTTCTGGTATGTGCA<br>ATACCCCAACCAAGGACTCC<br>AGCTTCTCCTGAAGTACACA<br>ACAGGGGCCACCCTGGTTAA<br>AGGCATCAACGGTTTTGAGG<br>CTGAATTTAAGAAGAGTGAA<br>ACCTCCTTCCACCTGACGAA<br>ACCCTCAGCCCATATGAGCG<br>ACGCGGCTGAGTACTTCTGT<br>GCTGTGAGTGAGAAGTTTTC<br>TGGTGGCTACAATAAGCTGA<br>TTTTTGGAGCAGGGACCAGG<br>CTGGCTGTACACCCATATAT<br>CCAGAACCCTGACCCTGCC<br>GTGTACCAGCTGAGAGACT<br>CTAAATCCAGTGACAAGTC<br>TGTCTGCCTATTCACCGAT<br>TTTGATTCTCAAACAAATG<br>TGTCACAAAGTAAGGATTC<br>TGATGTGTATATCACAGAC<br>AAAACTGTGCTAGACATGA | MLLLLVPVLEV<br>IFTLGGTRAQSV<br>TQLGSHVSVSE<br>GALVLLRCNYS<br>SSVPPYLFWYV<br>QYPNQGLQLLL<br>KYTTGATLVKG<br>INGFEAEFKKSE<br>TSFHLTKPSAH<br>MSDAAEYFCA<br>VSEKFSGGYNK<br>LIFGAGTRLAV<br>HPYIQNPDPAV<br>YQLRDSKSSDK<br>SVCLFTDFDSQ<br>TNVSQSKDSDV<br>YITDKTVLDM<br>RSMDFKSNSA<br>VAWSNKSDFA<br>CANAFNNSIIPE<br>DTFFPSPESSC<br>DVKLVEKSFET<br>DTNLNFQNLSV<br>IGFRILLLKVA<br>GFNLLMTLRL<br>WSS<br>(SEQ ID NO:<br>555) | GCCCAGTCGGT<br>GACCCAGCTTG<br>GCAGCCACGTC<br>TCTGTCTCTGA<br>GGGAGCCCTG<br>GTTCTGCTGAG<br>GTGCAACTACT<br>CATCGTCTGTT<br>CCACCATATCT<br>CTTCTGGTATG<br>TGCAATACCCC<br>AACCAAGGAC<br>TCCAGCTTCTC<br>CTGAAGTACAC<br>AACAGGGGCC<br>ACCCTGGTTAA<br>AGGCATCAAC<br>GGTTTTGAGGC<br>TGAATTTAAGA<br>AGAGTGAAAC<br>CTCCTTCCACC<br>TGACGAAACC<br>CTCAGCCCATA<br>TGAGCGACGC<br>GGCTGAGTACT<br>TCTGTGCTGTG<br>AGTGAGAAGT<br>TTTCTGGTGGC<br>TACAATAAGCT<br>GATTTTTGGAG<br>CAGGGACCAG<br>GCTGGCTGTAC<br>ACCCAT<br>(SEQ ID NO:<br>556) | AQSVTQLGSHV<br>SVSEGALVLLR<br>CNYSSSVPPYLF<br>WYVQYPNQGL<br>QLLLKYTTGAT<br>LVKGINGFEAE<br>FKKSETSFHLTK<br>PSAHMSDAAEY<br>FCAVSEKFSGG<br>YNKLIFGAGTR<br>LAVHP<br>(SEQ ID NO:<br>557) | TCGT<br>CTGTT<br>CCAC<br>CATA<br>T<br>(SEQ<br>ID NO:<br>184) | SSVPP<br>Y<br>(SEQ<br>ID NO:<br>185) | TACA<br>CAAC<br>AGGG<br>GCCA<br>CCCT<br>GGTT<br>(SEQ<br>ID NO:<br>186) | YTTG<br>ATLV<br>(SEQ<br>ID NO:<br>187) | GCTG<br>TGAG<br>TGAG<br>AAGT<br>TTTCT<br>GGTG<br>GCTA<br>CAAT<br>AAGC<br>TGAT<br>T<br>(SEQ<br>ID NO:<br>188) | CAVS<br>EKFSG<br>GYNK<br>LIF<br>SEQ<br>ID NO:<br>189) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | **GGTCTATGGACTTCAAGAG**<br>**CAACAGTGCTGTGGCCTGG**<br>**AGCAACAAATCTGACTTTG**<br>**CATGTGCAAACGCCTTCAA**<br>**CAACAGCATTATTCCAGAA**<br>**GACACCTTCTTCCCCAGCC**<br>**CAGAAAGTTCCTGTGATGT**<br>**CAAGCTGGTCGAGAAAAGC**<br>**TTTGAAACAGATACGAACC**<br>**TAAACTTTCAAAACCTGTC**<br>**AGTGATTGGGTTCCGAATC**<br>**CTCCTCCTGAAAGTGGCCG**<br>**GGTTTAATCTGCTCATGAC**<br>**GCTGCGGCTGTGGTCCAGC**<br>(SEQ ID NO: 183) | | | | | | | | | |
| 28 | TGGGGGTTAACTATACTTCC<br>TGTAAAAGGCAGAAGCCTCA<br>CACAGCCCAGTAACTTTGCT<br>AGTACCTCTTGAGTGCAAGG<br>TGGAGAATTAAGATCTGGAT<br>TTGAGACGGAGCACGGAACA<br>TTTCACTCAGGGGAAGAGCT<br>ATGAACATGCTGACTGCCAG<br>CCTGTTGAGGGCAGTCATAG<br>CCTCCATCTGTGTTGTATCCA<br>GCATGGCTCAGAAGGTAACT<br>CAAGCGCAGACTGAAATTTC<br>TGTGGTGGAGAAGGAGGATG<br>TGACCTTGGACTGTGTGTAT<br>GAAACCCGTGATACTACTTA<br>TTACTTATTCTGGTACAAGC<br>AACCACCAAGTGGAGAATTG<br>GTTTTCCTTATTCGTCGGAAC<br>TCTTTTGATGAGCAAAATGA<br>AATAAGTGGTCGGTATTCTT<br>GGAACTTCCAGAAATCCACC<br>AGTTCCTTCAACTTCACCATC<br>ACAGCCTCACAAGTCGTGGA<br>CTCAGCAGTATACTTCTGTG<br>CTCTGAGTGAGGCAAAAGAT<br>GACAAGATCATCTTTGGAAA<br>AGGGACACGACTTCATATTC<br>TCCCCAAT**ATCCAGAACCCT**<br>**GACCCTGCCGTGTACCAGC**<br>**TGAGAGACTCTAAATCCAG**<br>**TGACAAGTCTGTCTGCCTA**<br>**TTCACCGATTTTGATTCTC**<br>**AAACAAATGTGTCACAAAG** | MNMLTASLLR<br>AVIASICVVSSM<br>AQKVTQAQTEI<br>SVVEKEDVTLD<br>CVYETRDTTYY<br>LFWYKQPPSGE<br>LVFLIRRNSFDE<br>QNEISGRYSWN<br>FQKSTSSFNFTI<br>TASQVVDSAVY<br>FCALSEAKDDK<br>IIFGKGTRLHILP<br>**NIQNPDPAVYQ**<br>**LRDSKSSDKSV**<br>**CLFTDFDSQTN**<br>**VSQSKDSDVYI**<br>**TDKTVLDMRS**<br>**MDFKSNSAVA**<br>**WSNKSDFACA**<br>**NAFNNSIIPEDT**<br>**FFPSPESSCDV**<br>**KLVEKSFETDT**<br>**NLNFQNLSVIG**<br>**FRILLLKVAGF**<br>**NLLMTLRLWS**<br>**S**<br>(SEQ ID NO: 558) | GCTCAGAAGG<br>TAACTCAAGCG<br>CAGACTGAAA<br>TTTCTGTGGTG<br>GAGAAGGAGG<br>ATGTGACCTTG<br>GACTGTGTGTA<br>TGAAACCCGTG<br>ATACTACTTAT<br>TACTTATTCTG<br>GTACAAGCAA<br>CCACCAAGTG<br>GAGAATTGGTT<br>TTCCTTATTCG<br>TCGGAACTCTT<br>TTGATGAGCAA<br>AATGAAATAA<br>GTGGTCGGTAT<br>TCTTGGAACTT<br>CCAGAAATCC<br>ACCAGTTCCTT<br>CAACTTCACCA<br>TCACAGCCTCA<br>CAAGTCGTGG<br>ACTCAGCAGTA<br>TACTTCTGTGC<br>TCTGAGTGAGG<br>CAAAAGATGA<br>CAAGATCATCT<br>TTGGAAAAGG<br>GACACGACTTC<br>ATATTCTCCCC<br>A | AQKVTQAQTEI<br>SVVEKEDVTLD<br>CVYETRDTTYY<br>LFWYKQPPSGE<br>LVFLIRRNSFDE<br>QNEISGRYSWN<br>FQKSTSSFNFTI<br>TASQVVDSAVY<br>FCALSEAKDDK<br>IIFGKGTRLHILP<br>(SEQ ID NO: 560) | ACCC<br>GTGA<br>TACT<br>ACTT<br>ATTA<br>C<br>(SEQ ID NO: 191) | TRDTT<br>YY<br>(SEQ ID NO: 192) | CGGA<br>ACTC<br>TTTTG<br>ATGA<br>GCAA<br>AAT<br>(SEQ ID NQ 193) | RNSFD<br>EQN<br>(SEQ ID NO: 194) | GCTC<br>TGAG<br>TGAG<br>GCAA<br>AAGA<br>TGAC<br>AAGA<br>TCAT<br>C<br>(SEQ ID NO: 195) | CALSE<br>AKDD<br>KIIF<br>(SEQ ID NO: 196) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | TAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 190) | | (SEQ ID NO: 559) | | | | | | | |
| 29 | CTCCTATATCGGTTTTTCTTATATGGGAGAATCTCCATGGCAGCGTTTTCTTATATGGGGTTCATATGTAAAATGAAGGGTCTGTGGAAGGACATGAATAAAGCACAGGAGGTTGAAGTCAGATTTGCAGCTTTCTAGGCAGGAGACAAGACAATCTGCATCTTCACAGGAGGGATGGCCATGCTCCTGGGGGCATCAGTGCTGATTCTGTGGCTTCAGCCAGACTGGGTAAACAGTCAACAGAAGAATGATGACCAGCAAGTTAAGCAAAATTCACCATCCCTGAGCGTCCAGGAAGGAAGAATTTCTATTCTGAACTGTGACTATACTAACAGCATGTTTGATTATTTCCTATGGTACAAAAAATACCCTGCTGAAGGTCCTACATTCCTGATATCTATAAGTTCCATTAAGGATAAAAATGAAGATGGAAGATTCACTGTCTTCTTAAACAAAAGTGCCAAGCACCTCTCTCTGCACATTGTGCCCTCCCAGCCTGGAGACTCTGCAGTGTACTTCTGTGCCATTTATAACCAGGGAGGAAAGCTTATCTTCGGACAGGGAACGGAGTTATCTGTGAAACCCAATATCCAGAACCCTGAC | MAMLLGASVLILWLQPDWVNSQQKNDDQQVKQNSPSLSVQEGRISILNCDYTNSMFDYFLWYKKYPAEGPTFLISISSIKDKNEDGRFTVFLNKSAKHLSLHIVPSQPGDSAVYFCAIYNQGGKLIFGQGTELSVKPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS (SEQ ID NO: 561) | GACCAGCAAGTTAAGCAAAATTCACCATCCCTGAGCGTCCAGGAAGGAAGAATTTCTATTCTGAACTGTGACTATACTAACAGCATGTTTGATTATTTCCTATGGTACAAAAAATACCCTGCTGAAGGTCCTACATTCCTGATATCTATAAGTTCCATTAAGGATAAAAATGAAGATGGAAGATTCACTGTCTTCTTAAACAAAAGTGCCAAGCACCTCTCTCTGCACATTGTGCCCTCCCAGCCTGGAGACTCTGCAGTGTACTTCTGTGCCATTTATAACCAGGGAGGAAAGCTTATCTTCGGACAGGGAACGGAGTT | DQQVKQNSPSLSVQEGRISILNCDYTNSMFDYFLWYKKYPAEGPTFLISISSIKDKNEDGRFTVFLNKSAKHLSLHIVPSQPGDSAVYFCAIYNQGGKLIFGQGTELSVKP (SEQ ID NO: 563) | AACAGCATGTTTGATTAT (SEQ ID NO: 198) | NSMFDY (SEQ ID NO: 199) | ATAAGTTCCATTAAGGATAAA (SEQ ID NO: 200) | ISSIKDK (SEQ ID NO: 201) | GCCATTTATAACCAGGGAGGAAAGCTTATC (SEQ ID NO: 202) | CAIYNQGGKLIF (SEQ ID NO: 203) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | CCTGCCGTGTACCAGCTGA<br>GAGACTCTAAATCCAGTGA<br>CAAGTCTGTCTGCCTATTC<br>ACCGATTTTGATTCTCAAA<br>CAAATGTGTCACAAAGTAA<br>GGATTCTGATGTGTATATC<br>ACAGACAAAACTGTGCTAG<br>ACATGAGGTCTATGGACTT<br>CAAGAGCAACAGTGCTGTG<br>GCCTGGAGCAACAAATCTG<br>ACTTTGCATGTGCAAACGC<br>CTTCAACAACAGCATTATT<br>CCAGAAGACACCTTCTTCC<br>CCAGCCCAGAAAGTTCCTG<br>TGATGTCAAGCTGGTCGAG<br>AAAAGCTTTGAAACAGATA<br>CGAACCTAAACTTTCAAAA<br>CCTGTCAGTGATTGGGTTC<br>CGAATCCTCCTCCTGAAAG<br>TGGCCGGGTTTAATCTGCT<br>CATGACGCTGCGGCTGTGG<br>TCCAGC<br>(SEQ ID NO: 197) | | ATCTGTGAAAC<br>CCA<br>(SEQ ID NO:<br>562) | | | | | | | |
| 30 | TACATTCTCAATTTCTTATAT<br>GGGGACTGTGATTTCTTCAT<br>GTTAAGGATCAAGACCATTA<br>TTTGGGTAACACACTAAAGA<br>TGAACTATTCTCCAGGCTTA<br>GTATCTCTGATACTCTTACTG<br>CTTGGAAGAACCCGTGGAAA<br>TTCAGTGACCCAGATGGAAG<br>GGCCAGTGACTCTCTCAGAA<br>GAGGCCTTCCTGACTATAAA<br>CTGCACGTACACAGCCACAG<br>GATACCCTTCCCTTTTCTGGT<br>ATGTCCAATATCCTGGAGAA<br>GGTCTACAGCTCCTCCTGAA<br>AGCCACGAAGGCTGATGACA<br>AGGGAAGCAACAAAGGTTTT<br>GAAGCCACATACCGTAAAGA<br>AACCACTTCTTTCCACTTGGA<br>GAAAGGCTCAGTTCAAGTGT<br>CAGACTCAGCGGTGTACTTC<br>TGTGCTCTGATGACCGACTA<br>CAAGCTCAGCTTTGGAGCCG<br>GAACCACAGTAACTGTAAGA<br>GCAAATATCCAGAACCCTG<br>ACCCTGCCGTGTACCAGCT | MNYSPGLVSLI<br>LLLLGRTRGNS<br>VTQMEGPVTLS<br>EEAFLTINCTYT<br>ATGYPSLFWYV<br>QYPGEGLQLLL<br>KATKADDKGS<br>NKGFEATYRKE<br>TTSFHLEKGSV<br>QVSDSAVYFCA<br>LMTDYKLSFGA<br>GTTVTVRANIQ<br>NPDPAVYQLR<br>DSKSSDKSVCL<br>FTDFDSQTNVS<br>QSKDSDVYITD<br>KTVLDMRSMD<br>FKSNSAVAWS<br>NKSDFACANA<br>FNNSIIPEDTFF<br>PSPESSCDVKL<br>VEKSFETDTNL<br>NFQNLSVIGFR<br>ILLLKVAGFNL<br>LMTLRLWSS | GGAAATTCAGT<br>GACCCAGATG<br>GAAGGGCCAG<br>TGACTCTCTCA<br>GAAGAGGCCT<br>TCCTGACTATA<br>AACTGCACGTA<br>CACAGCCACA<br>GGATACCCTTC<br>CCTTTTCTGGT<br>ATGTCCAATAT<br>CCTGGAGAAG<br>GTCTACAGCTC<br>CTCCTGAAAGC<br>CACGAAGGCT<br>GATGACAAGG<br>GAAGCAACAA<br>AGGTTTTGAAG<br>CCACATACCGT<br>AAAGAAACCA<br>CTTCTTTCCAC<br>TTGGAGAAAG<br>GCTCAGTTCAA<br>GTGTCAGACTC<br>AGCGGTGTACT | GNSVTQMEGPV<br>TLSEEAFLTINC<br>TYTATGYPSLF<br>WYVQYPGEGL<br>QLLLKATKADD<br>KGSNKGFEATY<br>RKETTSFHLEK<br>GSVQVSDSAVY<br>FCALMTDYKLS<br>FGAGTTVTVRA<br>(SEQ ID NO:<br>566) | GCCA<br>CAGG<br>ATAC<br>CCTTC<br>C<br>(SEQ<br>ID NO:<br>205) | ATGY<br>PS<br>(SEQ<br>ID NO:<br>206) | GCCA<br>CGAA<br>GGCT<br>GATG<br>ACAA<br>G<br>(SEQ<br>ID NO:<br>207) | ATKA<br>DDK<br>(SEQ<br>ID NO:<br>208) | GCTC<br>TGAT<br>GACC<br>GACT<br>ACAA<br>GCTC<br>AGC<br>(SEQ<br>ID NO:<br>209) | CALM<br>TDYK<br>LSF<br>(SEQ<br>ID NO:<br>210) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | GAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 204) | (SEQ ID NO: 564) | TCTGTGCTCTGATGACCGACTACAAGCTCAGCTTTGGAGCCGGAACCACAGTAACTGTAAGAGCAA (SEQ ID NO: 565) | | | | | | | |
| 31 | GGGAGTGGTGAATTAGGGGTGTTAAAAAGAGCATCATTTTTTTGAACTGGTAAAGCAGATTCTTTTTATGATTTTTAAAGTAGAAATATCCATTCCAGGTGCATTTTTTAAGGGTTTAAAATTTGAATCCTCAGTGAACCAGGGCAGAGAAGAATGATGAAATCCTTGAGAGTTTTACTAGTGATCCTGTGGCTTCAGTTGAGCTGGGTTTGGAGCCAACAGAAGGAGGTGGAGCAGAATTCTGGACCCCTCAGTGTTCCAGAGGGAGCCATTGCCTCTCTCAACTGCACTTACAGTGACCGAGGTTCCCAGTCCTTCTTCTGGTACAGACAATATTCTGGGAAAAGCCCTGAGTTGATAATGTCCATATACTCCAATGGTGACAAAGAAGATGGAAGGTTTACAGCACAGCTCAATAAAGCCAGCCAGTATGTTTCTCTGCTCATCAGAGACTCCCAGCCCAGTGATTCAGCCACCTACCTCTGTGCCGTGAGGAGTGTAGGGGTTTCTGGTGGCTACAATAA | MMKSLRVLLVILWLQLSWVWSQQKEVEQNSGPLSVPEGAIASLNCTYSDRGSQSFFWYRQYSGKSPELIMSIYSNGDKEDGRFTAQLNKASQYVSLLIRDSQPSDSATYLCAVRSVGVSGGYNKLIFGAGTRLAVHPYIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS | CAGAAGGAGGTGGAGCAGAATTCTGGACCCCTCAGTGTTCCAGAGGGAGCCATTGCCTCTCTCAACTGCACTTACAGTGACCGAGGTTCCCAGTCCTTCTTCTGGTACAGACAATATTCTGGGAAAAGCCCTGAGTTGATAATGTCCATATACTCCAATGGTGACAAAGAAGATGGAAGGTTTACAGCACAGCTCAATAAAGCCAGCCAGTATGTTTCTCTGCTCATCAGAGACTCCCAGCCCAGTGATTCAGCCACCTACCTCTGTGCCGTGAGG | QKEVEQNSGPLSVPEGAIASLNCTYSDRGSQSFFWYRQYSGKSPELIMSIYSNGDKEDGRFTAQLNKASQYVSLLIRDSQPSDSATYLCAVRSVGVSGGYNKLIFGAGTRLAVHP (SEQ ID NO: 569) | GACCGAGGTTCCCAGTCC (SEQ ID NO: 212) | DRGSQS (SEQ ID NO: 213) | ATATACTCCAATGGTGAC (SEQ ID NO: 214) | IYSNGD (SEQ ID NO: 215) | GCCGTGAGGAGTGTAGGGGTTTCTGGTGGCTACAATAAGCTGATT (SEQ ID NO: 216) | CAVRSVGVSGGYNKLIF (SEQ ID NO: 217) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | GCTGATTTTTGGAGCAGGGA<br>CCAGGCTGGCTGTACACCCA<br>TATATCCAGAACCCTGACC<br>CTGCCGTGTACCAGCTGAG<br>AGACTCTAAATCCAGTGAC<br>AAGTCTGTCTGCCTATTCA<br>CCGATTTTGATTCTCAAAC<br>AAATGTGTCACAAAGTAAG<br>GATTCTGATGTGTATATCA<br>CAGACAAAACTGTGCTAGA<br>CATGAGGTCTATGGACTTC<br>AAGAGCAACAGTGCTGTGG<br>CCTGGAGCAACAAATCTGA<br>CTTTGCATGTGCAAACGCC<br>TTCAACAACAGCATTATTC<br>CAGAAGACACCTTCTTCCC<br>CAGCCCAGAAAGTTCCTGT<br>GATGTCAAGCTGGTCGAGA<br>AAAGCTTTGAAACAGATAC<br>GAACCTAAACTTTCAAAAC<br>CTGTCAGTGATTGGGTTCC<br>GAATCCTCCTCCTGAAAGT<br>GGCCGGGTTTAATCTGCTC<br>ATGACGCTGCGGCTGTGGT<br>CCAGC<br>(SEQ ID NO: 211) | (SEQ ID NO:<br>567) | AGTGTAGGGG<br>TTTCTGGTGGC<br>TACAATAAGCT<br>GATTTTTGGAG<br>CAGGGACCAG<br>GCTGGCTGTAC<br>ACCCAT<br>(SEQ ID NO:<br>568) | | | | | | | |
| 32 | GGGTGACAGCTGCTGGTGTG<br>GGCCCTGGCAGTTGCTGCTG<br>GGCTCATTGCAGCTCAGACA<br>CAGCAAAAGAGCCTAGAACC<br>TGGGTCCTAGTTTGCACCTA<br>GAATATGAGGCAAGTGGCGA<br>GAGTGATCGTGTTCCTGACC<br>CTGAGTACTTTGAGCCTTGCT<br>AAGACCACCCAGCCCATCTC<br>CATGGACTCATATGAAGGAC<br>AAGAAGTGAACATAACCTGT<br>AGCCACAACAACATTGCTAC<br>AAATGATTATATCACGTGGT<br>ACCAACAGTTTCCCAGCCAA<br>GGACCACGATTTATTATTCA<br>AGGATACAAGACAAAAGTTA<br>CAAACGAAGTGGCCTCCCTG<br>TTTATCCCTGCCGACAGAAA<br>GTCCAGCACTCTGAGCCTGC<br>CCCGGGTTTCCCTGAGCGAC<br>ACTGCTGTGTACTACTGCCTC<br>GTTCTACTCTCTAGCAACAC | MRQVARVIVFL<br>TLSTLSLAKTTQ<br>PISMDSYEGQE<br>VNITCSHNNIAT<br>NDYITWYQQFP<br>SQGPRFIIQGYK<br>TKVTNEVASLFI<br>PADRKSSTLSLP<br>RVSLSDTAVYY<br>CLVLLSSNTGK<br>LIFGQGTTLQV<br>KPDIQNPDPAV<br>YQLRDSKSSDK<br>SVCLFTDFDSQ<br>TNVSQSKDSDV<br>YITDKTVLDM<br>RSMDFKSNSA<br>VAWSNKSDFA<br>CANAFNNSIIPE<br>DTFFPSPESSC<br>DVKLVEKSFET<br>DTNLNFQNLSV | CTTGCTAAGAC<br>CACCCAGCCCA<br>TCTCCATGGAC<br>TCATATGAAGG<br>ACAAGAAGTG<br>AACATAACCTG<br>TAGCCACAAC<br>AACATTGCTAC<br>AAATGATTATA<br>TCACGTGGTAC<br>CAACAGTTTCC<br>CAGCCAAGGA<br>CCACGATTTAT<br>TATTCAAGGAT<br>ACAAGACAAA<br>AGTTACAAAC<br>GAAGTGGCCTC<br>CCTGTTTATCC<br>CTGCCGACAG<br>AAAGTCCAGC<br>ACTCTGAGCCT<br>GCCCCGGGTTT | LAKTTQPISMD<br>SYEGQEVNITCS<br>HNNIATNDYIT<br>WYQQFPSQGPR<br>FIIQGYKTKVTN<br>EVASLFIPADRK<br>SSTLSLPRVSLS<br>DTAVYYCLVLL<br>SSNTGKLIFGQG<br>TTLQVKP<br>(SEQ ID NO:<br>572) | AACA<br>TTGCT<br>ACAA<br>ATGA<br>TTAT<br>(SEQ<br>ID NO:<br>219) | NIATN<br>DY<br>(SEQ<br>ID NO:<br>220) | GGAT<br>ACAA<br>GACA<br>AAA<br>(SEQ<br>ID NO:<br>221) | GYKT<br>K<br>(SEQ<br>ID NO:<br>222) | CTCG<br>TTCTA<br>CTCTC<br>TAGC<br>AACA<br>CAGG<br>CAAA<br>CTAA<br>TC<br>(SEQ<br>ID NO:<br>223) | CLVLL<br>SSNTG<br>KLIF<br>(SEQ<br>ID NO:<br>224) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | AGGCAAACTAATCTTTGGGCAAGGGACAACTTTACAAGTAAAACCAGATATCCAGAACCCTGACCCTGCCGTGTACCAGCTGAGAGACTCTAAATCCAGTGACAAGTCTGTCTGCCTATTCACCGATTTTGATTCTCAAACAAATGTGTCACAAAGTAAGGATTCTGATGTGTATATCACAGACAAAACTGTGCTAGACATGAGGTCTATGGACTTCAAGAGCAACAGTGCTGTGGCCTGGAGCAACAAATCTGACTTTGCATGTGCAAACGCCTTCAACAACAGCATTATTCCAGAAGACACCTTCTTCCCCAGCCCAGAAAGTTCCTGTGATGTCAAGCTGGTCGAGAAAAGCTTTGAAACAGATACGAACCTAAACTTTCAAAACCTGTCAGTGATTGGGTTCCGAATCCTCCTCCTGAAAGTGGCCGGGTTTAATCTGCTCATGACGCTGCGGCTGTGGTCCAGC (SEQ ID NO: 218) | IGFRILLLKVAGFNLLMTLRLWSS (SEQ ID NO: 570) | CCCTGAGCGACACTGCTGTGTACTACTGCCTCGTTCTACTCTCTAGCAACACAGGCAAACTAATCTTTGGGCAAGGGACAACTTTACAAGTAAAACCAG (SEQ ID NO: 571) | | | | | | | |
| 33 | TGGGGCTGTTCTGAAGCAGCTACGGCACCAGTGCAGCTGATACTCAAGGTTCAGATCAGAAGAGGAGGCTTCTCACCCTGCAGCAGGGACCTGTGAGCATGGCATGCCCTGGCTTCCTGTGGGCACTTGTGATCTCCACCTGTCTTGAATTTAGCATGGCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGG | MACPGFLWALVISTCLEFSMAQTVTQSQPEMSVQEAETVTLSCTYDTSESDYYLFWYKQPPSRQMILVIRQEAYKQQNATENRFSVNFQKAAKSFSLKISDSQLGDAAMYFCAYRSANNNDMRFGAGTRLTVKPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFET | GCTCAGACAGTCACTCAGTCTAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAG | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSANNNDMRFGAGTRLTVKP (SEQ ID NO: 575) | ACCAGTGAGAGTGATTATTAT (SEQ ID NO: 226) | TSESDYY (SEQ ID NO: 227) | CAAGAAGCTTATAAGCAACAGAAT (SEQ ID NO: 228) | QEAYKQQN (SEQ ID NQ 229) | GCTTATAGGAGCGCGAATAACAATGACATGCGC (SEQ ID NO: 230) | CAYRSANNNDMRF (SEQ ID NO: 231) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | AGCGCGAATAACAATGACAT<br>GCGCTTTGGAGCAGGGACCA<br>GACTGACAGTAAAACCAAAT<br>**ATCCAGAACCCTGACCCTG**<br>**CCGTGTACCAGCTGAGAGA**<br>**CTCTAAATCCAGTGACAAG**<br>**TCTGTCTGCCTATTCACCG**<br>**ATTTTGATTCTCAAACAAA**<br>**TGTGTCACAAAGTAAGGAT**<br>**TCTGATGTGTATATCACAG**<br>**ACAAAACTGTGCTAGACAT**<br>**GAGGTCTATGGACTTCAAG**<br>**AGCAACAGTGCTGTGGCCT**<br>**GGAGCAACAAATCTGACTT**<br>**TGCATGTGCAAACGCCTTC**<br>**AACAACAGCATTATTCCAG**<br>**AAGACACCTTCTTCCCCAG**<br>**CCCAGAAAGTTCCTGTGAT**<br>**GTCAAGCTGGTCGAGAAAA**<br>**GCTTTGAAACAGATACGAA**<br>**CCTAAACTTTCAAAACCTG**<br>**TCAGTGATTGGGTTCCGAA**<br>**TCCTCCTCCTGAAAGTGGC**<br>**CGGGTTTAATCTGCTCATG**<br>**ACGCTGCGGCTGTGGTCCA**<br>**GC**<br>(SEQ ID NO: 225) | **DTNLNFQNLSV**<br>**IGFRILLLKVA**<br>**GFNLLMTLRL**<br>**WSS**<br>(SEQ ID NO: 573) | ATCTCAGACTC<br>ACAGCTGGGG<br>GATGCCGCGAT<br>GTATTTCTGTG<br>CTTATAGGAGC<br>GCGAATAACA<br>ATGACATGCGC<br>TTTGGAGCAGG<br>GACCAGACTG<br>ACAGTAAAAC<br>CAA<br>(SEQ ID NO: 574) | | | | | | | |
| 34 | GGGGGTGTGTGTGTGTGCTT<br>GAGAGAGAGAGAAGGAGAG<br>AAAGAGAGAGAATGGGAAG<br>GGCGATAAGAGGAGGGGTT<br>AGTGATATACCAGGGGTTGT<br>GAAAATAACCTCTTTTTTCTA<br>ATTGGTAGGACAGATTCTTT<br>TTATGATTCCTAAAGTGGAA<br>GAAATAAAGTATCTCTGCTA<br>TGTTCATTTCTTTTTGGATTG<br>AAAATTTTAATCCTCAGTGA<br>ACCAGGGCAGAAAAGAATG<br>ATGATATCCTTGAGAGTTTT<br>ACTGGTGATCCTGTGGCTTC<br>AGTTAAGCTGGGTTTGGAGC<br>CAACGGAAGGAGGTGGAGC<br>AGGATCCTGGACCCTTCAAT<br>GTTCCAGAGGGAGCCACTGT<br>CGCTTTCAACTGTACTTACA<br>GCAACAGTGCTTCTCAGTCT<br>TTCTTCTGGTACAGACAGGA | MMISLRVLLVIL<br>WLQLSWVWSQ<br>RKEVEQDPGPF<br>NVPEGATVAFN<br>CTYSNSASQSFF<br>WYRQDCRKEP<br>KLLMSVYSSGN<br>EDGRFTAQLNR<br>ASQYISLLIRDS<br>KLSDSATYLCV<br>VFPGGSYIPTFG<br>RGTSLIVHP**YIQ**<br>**KPDPAVYQLR**<br>**DSKSSDKSVCL**<br>**FTDFDSQTNVS**<br>**QSKDSDVYITD**<br>**KTVLDMRSMD**<br>**FKSNSAVAWS**<br>**NKSDFACANA**<br>**FNNSIIPEDTFF**<br>**PSPESSCDVKL** | CGGAAGGAGG<br>TGGAGCAGGA<br>TCCTGGACCCT<br>TCAATGTTCCA<br>GAGGGAGCCA<br>CTGTCGCTTTC<br>AACTGTACTTA<br>CAGCAACAGT<br>GCTTCTCAGTC<br>TTTCTTCTGGT<br>ACAGACAGGA<br>TTGCAGGAAA<br>GAACCTAAGTT<br>GCTGATGTCCG<br>TATACTCCAGT<br>GGTAATGAAG<br>ATGGAAGGTTT<br>ACAGCACAGC<br>TCAATAGAGCC<br>AGCCAGTATAT<br>TTCCCTGCTCA | RKEVEQDPGPF<br>NVPEGATVAFN<br>CTYSNSASQSFF<br>WYRQDCRKEP<br>KLLMSVYSSGN<br>EDGRFTAQLNR<br>ASQYISLLIRDS<br>KLSDSATYLCV<br>VFPGGSYIPTFG<br>RGTSLIVHP<br>(SEQ ID NO: 578) | AACA<br>GTGC<br>TTCTC<br>AGTC<br>T<br>(SEQ ID NO: 233) | NSAS<br>QS<br>(SEQ ID NO: 234) | GTAT<br>ACTC<br>CAGT<br>GGTA<br>AT<br>(SEQ ID NO: 235) | VYSS<br>GN<br>(SEQ ID NO: 236) | GTGG<br>TTTTC<br>CCAG<br>GAGG<br>AAGC<br>TACA<br>TACC<br>TACA<br>(SEQ ID NO: 237) | CVVFP<br>GGSYI<br>PTF<br>(SEQ ID NO: 238) |

TABLE 4-continued

| ID | TCR ALPHA (FULL LENGTH) (NT) | TCR ALPHA (FULL LENGTH) (AA) | TCR ALPHA (V-J REGION) (NT) | TCR ALPHA (V-J REGION) (AA) | CDR1 (NT) | CDR1 (AA) | CDR2 (NT) | CDR2 (AA) | CDR3 (NT) | CDR3 (AA) |
|---|---|---|---|---|---|---|---|---|---|---|
| | TTGCAGGAAAGAACCTAAGT TGCTGATGTCCGTATACTCC AGTGGTAATGAAGATGGAAG GTTTACAGCACAGCTCAATA GAGCCAGCCAGTATATTTCC CTGCTCATCAGAGACTCCAA GCTCAGTGATTCAGCCACCT ACCTCTGTGTGGTTTTCCCAG GAGGAAGCTACATACCTACA TTTGGAAGAGGAACCAGCCT TATTGTTCATCCGTAT**ATCC AGAAGCCTGACCCTGCCGT GTACCAGCTGAGAGACTCT AAATCCAGTGACAAGTCTG TCTGCCTATTCACCGATTT TGATTCTCAAACAAATGTG TCACAAAGTAAGGATTCTG ATGTGTATATCACAGACAA AACTGTGCTAGACATGAGG TCTATGGACTTCAAGAGCA ACAGTGCTGTGGCCTGGAG CAACAAATCTGACTTTGCA TGTGCAAACGCCTTCAACA ACAGCATTATTCCAGAAGA CACCTTCTTCCCCAGCCCA GAAAGTTCCTGTGATGTCA AGCTGGTCGAGAAAAGCTT TGAAACAGATACGAACCTA AACTTTCAAAACCTGTCAG TGATTGGGTTCCGAATCCT CCTCCTGAAAGTGGCCGGG TTTAATCTGCTCATGACGC TGCGGCTGTGGTCCAGC** (SEQ ID NO: 232) | **VEKSFETDTNL NFQNLSVIGFR ILLLKVAGFNL LMTLRLWSS** (SEQ ID NO: 576) | TCAGAGACTCC AAGCTCAGTG ATTCAGCCACC TACCTCTGTGT GGTTTTCCCAG GAGGAAGCTA CATACCTACAT TTGGAAGAGG AACCAGCCTTA TTGTTCATCCG T (SEQ ID NO: 577) | | | | | | | |

TABLE 5

| ID | TCR BETA (FULL LENGTH) (NT) | TCR BETA (FULL LENGTH) (AA) | TCR BETA (VDJ REGION) (NT) | TCR BETA (VDJ REGION) (AA) | CDR1 (NT) |
|---|---|---|---|---|---|
| 1 | AGAAAGCAGAATGGGTGATGTGATGTGCAATGCCACAGAAGCACTGCAGCCAGGAGAGGTGACAGCTAATGGGGATGTTTGGAGTCTTTGAGTGAACCAAACACATCCCAGAGTAATTGTAATTTATTTCAGTCAATCTTCTGTACAGACTTAGCATTCACCTTTGGAGGAAGGTCCTTTGAGCAGGGACAGAGATGGTGATGTCACTGACAGTCCCCCTTTTACTCTGGGTGAGAGGTCTAGAATCCTCAGCTCCTGTATTCGTGCCCACAAGGGCCTCATCTAGGTGAAGGCTCCACCTGCCCCACCCTGCCATGGCCACCAGGCTCCTCTGCTGTGTGGTTCTTTGTCTCCTGGGAGAAGAGCTTATAGATGCTAGAGTCACCCAGACACCAAGGCACAAGGTGACAGAGATGGGACAAGAAGTAACAATGAGATGTCAGCCAATTTAGGCCACAATACTGTTTTCTGGTACAGACAGACCATGATGCAAGGACTGGAGTTGCTGGCTTACTTCCGCAACCGGGCTCCTCTAGATGATTCGGGGATGCCGAAGGATCGATTCTCAGCAGAGATGCCTGATGCAACTTTAGCCACTCTGAAGATCCAGCCCTCAGAACCCAGGGACTCAGCTGTGTATTTTTGTGCTAGTGGTTTGGCCCTCACTGAGGGGGGCTGGTACGAGCAGTACTTCGGGCCGGGCACCAGGCTCACGGTCACAGAGGACCTGAAAAACGTGTTCCCACCCGAGGTCGCTGTGTTTGAGCCATCAGAAGCAGAGATCTCCCACACCCAAAAGGCCACACTGGTATGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCTGTCACCCAGATCGTCAGCGCCGAGGCCTGGGGTAGAGCAGACTGTGGCTTCACCTCCGAGTCTTACCAGCAAGGGGTCCTGTCTGCCACCATCCTCTATGAGATCTTGCTAGGGAAGGCCACCTTGTATGCCGTGCTGGTCAGTGCCCTCGTGCTGATGGCCATGGTCAAGAGAAAGGATTCCAGAGGCTAG (SEQ ID NO: 239) | MATRLLCCVVLCLLGEELIDARVTQTPRHKVTEMGQEVTMRCQPILGHNTVFWYRQTMMQGLELLAYFRNRAPLDDSGMPKDRFSAEMPDATLATLKIQPSEPRDSAVYFCASGLALTEGGWYEQYFGPGTRLTVTEDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG (SEQ ID NO: 579) | GATGCTAGAGTCACCCAGACACCAAGGCACAAGGTGACAGAGATGGGACAAGAAGTAACAATGAGATGTCAGCCAATTTTAGGCCACAATACTGTTTTCTGGTACAGACAGACCATGATGCAAGGACTGGAGTTGCTGGCTTACTTCCGCAACCGGGCTCCTCTAGATGATTCGGGGATGCCGAAGGATCGATTCTCAGCAGAGATGCCTGATGCAACTTTAGCCACTCTGAAGATCCAGCCCTCAGAACCCAGGGACTCAGCTGTGTATTTTTGTGCTAGTGGTTTGGCCCTCACTGAGGGGGGCTGGTACGAGCAGTACTTCGGGCCGGGCACCAGGCTCACGGTCACAG (SEQ ID NO: 580) | DARVTQTPRHKVTEMGQEVTMRCQPILGHNTVFWYRQTMMQGLELLAYFRNRAPLDDSGMPKDRFSAEMPDATLATLKIQPSEPRDSAVYFCASGLALTEGGWYEQYFGPGTRLTVT (SEQ ID NO: 581) | TTAGGCCACAATACT (SEQ ID NO: 240) |
| 2 | GGGCCAGAGACACCAGTAATTCTGCCAGACCTTGCCTGTGGGGCCATGGGAGCTCAAAATGCCCCTCCTTTCCTCCACAGGACCAGATGCCTGAGCTAGGAAAGGCCTCATTCCTGCTGTGATCCTGCCATGGATACCTGGCTCGTATGCTGGGCAATTTTTAGTCTCTTGAAAGCAGGACT | MDTWLVCWAIFSLLKAGLTEPEVTQTPSHQVTQMGQEVILRCVPISNHLYFYWYRQILGQKVEFLVSFYNNEISEKSEIFDDQFSVERPDGSNFTLKIRSTK | GAACCTGAAGTCACCCAGACTCCCAGCCATCAGGTCACACAGATGGGACAGGAAGTGATCTTGCGCTGTGTCCCCATCTCTAATCACTTATACTTC | EPEVTQTPSHQVTQMGQEVILRCVPISNHLYFYWYRQILGQKVEFLVSFYNNEISEKSEIFDDQFSVERPDGSNFTLKIRSTKLEDSAMYFCASLRWDGDN | TCTAATCACTTATAC (SEQ ID NO: 247) |

TABLE 5-continued

| | | | | | |
|---|---|---|---|---|---|
| | CACAGAACCTGAAGTCACCCAGACTCCCAGCCATCAGGTCACACAGATGGGACAGGAAGTGATCTTGCGCTGTGTCCCCATCTCTAATCACTTATACTTCTATTGGTACAGACAAATCTTGGGGCAGAAAGTCGAGTTTCTGGTTTCCTTTTATAATAATGAAATCTCAGAGAAGTCTGAAATATTCGATGATCAATTCTCAGTTGAAAGGCCTGATGGATCAAATTTCACTCTGAAGATCCGGTCCACAAAGCTGGAGGACTCAGCCATGTACTTCTGTGCCAGCCTCCGATGGGACGGGGACAATGAGCAGTTCTTCGGGCCAGGGACACGGCTCACCGTGCTAGAGGACCTGAAAAACGTGTTCCCACCCGAGGTCGCTGTGTTTGAGCCATCAGAAGCAGAGATCTCCCACACCCAAAAGGCCACACTGGTATGCCTGCCACAGGCTTCTACCCCGCCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCTGTCACCCAGATCGTCAGCGCCGAGGCCTGGGGTAGAGCAGACTGTGGCTTCACCTCCGAGTCTTACCAGCAAGGGGTCCTGTCTGCCACCATCCTCTATGAGATCTTGCTAGGGAAGGCCACCTTGTATGCCGTGCTGGTCAGTGCCCTCGTGCTGATGGCCATGGTCAAGAGAAAGGATTCCAGAGGCTAG (SEQ ID NO: 246) | LEDSAMYFCASLRWDGDNEQFFGPGTRLTVLEDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG (SEQ ID NO: 582) | TATTGGTACAGACAAATCTTGGGGCAGAAAGTCGAGTTTCTGGTTTCCTTTTATAATAATGAAATCTCAGAGAAGTCTGAAATATTCGATGATCAATTCTCAGTTGAAAGGCCTGATGGATCAAATTTCACTCTGAAGATCCGGTCCACAAAGCTGGAGGACTCAGCCATGTACTTCTGTGCCAGCCTCCGATGGGACGGGGACAATGAGCAGTTCTTCGGGCCAGGGACACGGCTCACCGTGCTAG (SEQ ID NO: 583) | EQFFGPGTRLTVL (SEQ ID NO: 584) | |
| 3 | GAATTTGACCATCTGGGGAAGGGGCGTGGCCTCTCCTGACAGGAAGGCTCTGGGGCCCAGGCAGGGAGAATGAAGTCTCAGAATGACCCCCTTGAGAGTACTGTTCCCCTATCACCGATGCACAGACCCAGAAGACCCCTCCATCCTGTAGCACCTGCCATGAGCATCGGGCTCCTGTGCTGTGTGGCCTTTTCTCTCCTGTGGGCAAGTCCAGTGAATGCTGGTGTCACTCAGACCCCAAAATTCCAGGTCCTGAAGACAGGACAGAGCATGACACTGCAGTGTGCCCAGGATATGAACCATAACTCCATGTACTGGTATCGACAAGACCCAGGCATGGGACTGAGGCTGATTTATTACTCAGCTTCTGAGGGTACCACTGACAAAGGAGAAGTCCCCAATGGCTACAATGTCTCCAGATTAAACAAACGGGAGTTCTCGCTCAGGCTGGAGTCGGCTGCTCCCTCCCAGACATCTGTGTACTTCTGTGCCAGCAGGGACAGGGCCCTGAACACTGAAGCTTTCTTTGGACAAGGCACCAGACTCACAGTTGTAGAGGACCTGAACAAGGTGTTCCCACCCGAGGTCGCTGTGTTTGAGCCATCAGAAGCAGAGATCTCCCACACCCAAAAGGCCA | MKSQNDPLESTVPLSPMHRPRRPLHPVAPAMSIGLLCCVAFSLLWASPVNAGVTQTPKFQVLKTGQSMTLQCAQDMNHNSMYWYRQDPGMGLRLIYYSASEGTTDKGEVPNGYNVSRLNKREFSLRLESAAPSQTSVYFCASRDRALNTEAFFGQGTRLTVVEDLNKVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVK | AATGCTGGTGTCACTCAGACCCCAAAATTCCAGGTCCTGAAGACAGGACAGAGCATGACACTGCAGTGTGCCCAGGATATGAACCATAACTCCATGTACTGGTATCGACAAGACCCAGGCATGGGACTGAGGCTGATTTATTACTCAGCTTCTGAGGGTACCACTGACAAAGGAGAAGTCCCCAATGGCTACAATGTCTCCAGATTAAACAAACGGGAGTTCTCGCTCAGGCTGGAGTCGGCTGCTCCCTCCCAGACATCTGTGTACTTCTGTGCCAGCAGGGACAGGGCCCTGAACACTGAAGCTTTCTTTGGACAAGGCACCAGACTCACAGTTGTAG | NAGVTQTPKFQVLKTGQSMTLQCAQDMNHNSMYWYRQDPGMGLRLIYYSASEGTTDKGEVPNGYNVSRLNKREFSLRLESAAPSQTSVYFCASRDRALNTEAFFGQGTRLTVV (SEQ ID NO: 587) | ATGAACCATAACTCC (SEQ ID NO: 254) |

TABLE 5-continued

| | | | | | |
|---|---|---|---|---|---|
| | CACTGGTGTGCCTGGCCAC<br>AGGCTTCTACCCCGACCAC<br>GTGGAGCTGAGCTGGTGG<br>GTGAATGGGAAGGAGGTG<br>CACAGTGGGGTCAGCACAG<br>ACCCGCAGCCCCTCAAGGA<br>GCAGCCCGCCCTCAATGAC<br>TCCAGATACTGCCTGAGCA<br>GCCGCCTGAGGGTCTCGGC<br>CACCTTCTGGCAGAACCCC<br>CGCAACCACTTCCGCTGTC<br>AAGTCCAGTTCTACGGGCT<br>CTCGGAGAATGACGAGTGG<br>ACCCAGGATAGGGCCAAAC<br>CCGTCCCCAGATCGTCAG<br>CGCCGAGGCCTGGGGTAG<br>AGCAGACTGTGGCTTTACC<br>TCGGTGTCCTACCAGCAAG<br>GGGTCCTGTCTGCCACCAT<br>CCTCTATGAGATCCTGCTA<br>GGGAAGGCCACCCTGTATG<br>CTGTGCTGGTCAGCGCCCT<br>TGTGTTGATGGCCATGGTC<br>AAGAGAAAGGATTTCTGA<br>(SEQ ID NO: 253) | RKDF<br>(SEQ ID NO: 585) | (SEQ ID NO: 586) | | |
| 4 | GAAGAAGTCTCATCTGTCAG<br>TGAGTTGACAAGAAACAGAG<br>CAAAACGACTCCTCCAATGT<br>TGACGAGCCTGCCCCTGGGA<br>TTTGGAAACTTCATAACAGA<br>AAAAACCAATATAGACAAA<br>GGATTTTAAACAGGATTAAG<br>CTGTTCACTGGTGCATTTATT<br>TTGGATTTGACCATCTGGGG<br>AATGGGTGTGGCCTCTCCTG<br>GCCTCTCCCTCCCTGGGGCC<br>CAGGCAGGGAGAATGTCTCA<br>GAATGACTTCCTTGAGAGTC<br>CTGCTCCCCTTTCATCAATGC<br>ACAGATACAGAAGACCCCTC<br>CGTCATGCAGCATCTGCCAT<br>GAGCATCGGCCTCCTGTGCT<br>GTGCAGCCTTGTCTCTCCTGT<br>GGGCAGGTCCAGTGAATGCT<br>GGTGTCACTCAGACCCCAAA<br>ATTCCAGGTCCTGAAGACAG<br>GACAGAGCATGACACTGCAG<br>TGTGCCCAGGATATGAACCA<br>TGAATACATGTCCTGGTATC<br>GACAAGACCCAGGCATGGG<br>GCTGAGGCTGATTCATTACT<br>CAGTTGGTGCTGGTATCACT<br>GACCAAGGAGAAGTCCCCAA<br>TGGCTACAATGTCTCCAGAT<br>CAACCACAGAGGATTTCCCG<br>CTCAGGCTGCTGTCGGCTGC<br>TCCCTCCCAGACATCTGTGT<br>ACTTCTGTGCCAGCAGAAAC<br>GGCGGGACACTAATCTACGA<br>GCAGTACTTCGGGCCGGGCA<br>CCAGGCTCACGGTCACAGAG<br>GACCTGAAAAACGTGTTCC<br>CACCCGAGGTCGCTGTGTT<br>TGAGCCATCAGAAGCAGAG<br>ATCTCCCACACCCAAAAGG<br>CCACACTGGTATGCCTGGC<br>CACAGGCTTCTACCCCGAC<br>CACGTGGAGCTGAGCTGGT<br>GGGTGAATGGGAAGGAGG<br>TGCACAGTGGGGTCAGCAC<br>AGACCGCAGCCCCTCAAG<br>GAGCAGCCCGCCCTCAATG<br>ACTCCAGATACTGCCTGAG<br>CAGCCGCCTGAGGGTCTCG<br>GCCACCTTCTGGCAGAACC<br>CCCGCAACCACTTCCGCTG<br>TCAAGTCCAGTTCTACGGG<br>CTCTCGGAGAATGACGAGT<br>GGACCCAGGATAGGGCCA | MGVASPGLSLP<br>GAQAGRMSQN<br>DFLESPAPLSSM<br>HRYRRPLRHAA<br>SAMSIGLLCCA<br>ALSLLWAGPVN<br>AGVTQTPKFQV<br>LKTGQSMTLQC<br>AQDMNHEYMS<br>WYRQDPGMGL<br>RLIHYSVGAGIT<br>DQGEVPNGYN<br>VSRSTTEDFPLR<br>LLSAAPSQTSV<br>YFCASRNGGTL<br>IYEQYFGPGTRL<br>TVTEDLKNVFP<br>PEVAVFEPSEA<br>EISHTQKATLV<br>CLATGFYPDH<br>VELSWWVNG<br>KEVHSGVSTDP<br>QPLKEQPALN<br>DSRYCLSSRLR<br>VSATFWQNPR<br>NHFRCQVQFY<br>GLSENDEWTQ<br>DRAKPVTQIVS<br>AEAWGRADCG<br>FTSESYQQGVL<br>SATILYEILLG<br>KATLYAVLVS<br>ALVLMAMVK<br>RKDSRG<br>(SEQ ID NO: 588) | AATGCTGGTGT<br>CACTCAGACCC<br>CAAAATTCCAG<br>GTCCTGAAGAC<br>AGGACAGAGC<br>ATGACACTGCA<br>GTGTGCCCAGG<br>ATATGAACCAT<br>GAATACATGTC<br>CTGGTATCGAC<br>AAGACCCAGG<br>CATGGGGCTG<br>AGGCTGATTCA<br>TTACTCAGTTG<br>GTGCTGGTATC<br>ACTGACCAAG<br>GAGAAGTCCC<br>CAATGGCTACA<br>ATGTCTCCAGA<br>TCAACCACAG<br>AGGATTTCCCG<br>CTCAGGCTGCT<br>GTCGGCTGCTC<br>CCTCCCAGACA<br>TCTGTGTACTT<br>CTGTGCCAGCA<br>GAAACGGCGG<br>GACACTAATCT<br>ACGAGCAGTA<br>CTTCGGGCCGG<br>GCACCAGGCTC<br>ACGGTCACAG<br>(SEQ ID NO: 589) | NAGVTQTPKFQ<br>VLKTGQSMTLQ<br>CAQDMNHEYM<br>SWYRQDPGMG<br>LRLIHYSVGAGI<br>TDQGEVPNGYN<br>VSRSTTEDFPLR<br>LLSAAPSQTSV<br>YFCASRNGGTL<br>IYEQYFGPGTRL<br>TVT<br>(SEQ ID NO: 590) | ATGA<br>ACCA<br>TGAA<br>TAC<br>(SEQ ID NO: 261) |

TABLE 5-continued

| | | | | | |
|---|---|---|---|---|---|
| | AACCTGTCACCCAGATCGT<br>CAGCGCCGAGGCCTGGGG<br>TAGAGCAGACTGTGGCTTC<br>ACCTCCGAGTCTTACCAGC<br>AAGGGGTCCTGTCTGCCAC<br>CATCCTCTATGAGATCTTG<br>CTAGGGAAGGCCACCTTGT<br>ATGCCGTGCTGGTCAGTGC<br>CCTCGTGCTGATGGCCATG<br>GTCAAGAGAAAGGATTCCA<br>GAGGCTAG<br>(SEQ ID NO: 260) | | | | |
| 5 | TGGGGGCAATGCCCAAAACC<br>CCAGCTCTCAGAGGACCAGT<br>ATCCCTCACAGGGTGACACC<br>TGACCAGCTCTGTCCCACCT<br>GGCCATGGGCTCCAGGTACC<br>TCTGATGGGAAGACCTTTGT<br>CTCTTGGGAACAAGTGAATC<br>CTTGGCACAGGCCCAGTGGA<br>TTCTGCTGTGCAGAACAGAG<br>AGCAGTGGACCTCAGGAGGC<br>CTGCAAGGGGAGGACATAG<br>GACAGTGACATCACAGTATG<br>CCCCTCCCACCAGGAAAAGC<br>AAGGCTGAGAATTTAGCTCT<br>TTCCCAGGAGGACCAAGCCC<br>TGAGCACAGACACAGTGCTG<br>CCTGCCCCTTTGTGCCATGG<br>GCTCCAGGCTGCTCTGTTGG<br>GTGCTGCTTTGTCTCCTGGGA<br>GCAGGCCCAGTAAAGGCTGG<br>AGTCACTCAAACTCCAAGAT<br>ATCTGATCAAAACGAGAGGA<br>CAGCAAGTGACACTGAGCTG<br>CTCCCCTATCTCTGGGCATA<br>GGAGTGTATCCTGGTACCAA<br>CAGACCCCAGGACAGGGCCT<br>TCAGTTCCTCTTTGAATACTT<br>CAGTGAGACACAGAGAAAC<br>AAAGGAAACTTCCCTGGTCG<br>ATTCTCAGGGCGCCAGTTCT<br>CTAACTCTCGCTCTGAGATG<br>AATGTGAGCACCTTGGAGCT<br>GGGGGACTCGGCCCTTTATC<br>TTTGCGCCAGCAGGCAGCGG<br>ACAGAACTTGAAGCTTTCTT<br>TGGACAAGGCACCAGACTCA<br>CAGTTGTAGAGGACCTGAA<br>CAAGGTGTTCCCACCCGAG<br>GTCGCTGTGTTTGAGCCAT<br>CAGAAGCAGAGATCTCCCA<br>CACCCAAAAGGCCACACTG<br>GTGTGCCTGGCCACAGGCT<br>TCTACCCCGACCACGTGGA<br>GCTGAGCTGGTGGGTGAAT<br>GGGAAGGAGGTGCACAGT<br>GGGGTCAGCACAGACCCG<br>CAGCCCCTCAAGGAGCAGC<br>CCGCCCTCAATGACTCCAG<br>ATACTGCCTGAGCAGCCGC<br>CTGAGGGTCTCGGCCACCT<br>TCTGGCAGAACCCCCGCAA<br>CCACTTCCGCTGTCAAGTC<br>CAGTTCTACGGGCTCTCGG<br>AGAATGACGAGTGGACCCA<br>GGATAGGGCCAAACCCGTC<br>ACCCAGATCGTCAGCGCCG<br>AGGCCTGGGGTAGAGCAG<br>ACTGTGGCTTTACCTCGGT<br>GTCCTACCAGCAAGGGGTC<br>CTGTCTGCCACCATCCTCT<br>ATGAGATCCTGCTAGGGAA<br>GGCCACCCTGTATGCTGTG<br>CTGGTCAGCGCCCTTGTGT<br>TGATGGCCATGGTCAAGAG<br>AAAGGATTTCTGA<br>(SEQ ID NO: 267) | MGSRLLCWVL<br>LCLLGAGPVKA<br>GVTQTPRYLIK<br>TRGQQVTLSCS<br>PISGHRSVSWY<br>QQTPGQGLQFL<br>FEYFSETQRNK<br>GNFPGRFSGRQ<br>FSNSRSEMNVS<br>TLELGDSALYL<br>CASRQRTELEA<br>FFGQGTRLTVV<br>EDLNKVFPPEV<br>AVFEPSEAEIS<br>HTQKATLVCL<br>ATGFYPDHVE<br>LSWWVNGKE<br>VHSGVSTDPQP<br>LKEQPALNDS<br>RYCLSSRLRVS<br>ATFWQNPRNH<br>FRCQVQFYGL<br>SENDEWTQDR<br>AKPVTQIVSAE<br>AWGRADCGFT<br>SVSYQQGVLSA<br>TILYEILLGKA<br>TLYAVLVSALV<br>LMAMVKRKD<br>F<br>(SEQ ID NO: 591) | AAGGCTGGAG<br>TCACTCAAACT<br>CCAAGATATCT<br>GATCAAAACG<br>AGAGGACAGC<br>AAGTGACACT<br>GAGCTGCTCCC<br>CTATCTCTGGG<br>CATAGGAGTGT<br>ATCCTGGTACC<br>AACAGACCCC<br>AGGACAGGGC<br>CTTCAGTTCCT<br>CTTTGAATACT<br>TCAGTGAGAC<br>ACAGAGAAAC<br>AAAGGAAACT<br>TCCCTGGTCGA<br>TTCTCAGGGCG<br>CCAGTTCTCTA<br>ACTCTCGCTCT<br>GAGATGAATG<br>TGAGCACCTTG<br>GAGCTGGGGG<br>ACTCGGCCCTT<br>TATCTTTGCGC<br>CAGCAGGCAG<br>CGGACAGAAC<br>TTGAAGCTTTC<br>TTTGGACAAGG<br>CACCAGACTCA<br>CAGTTGTAG<br>(SEQ ID NO: 592) | KAGVTQTPRYL<br>IKTRGQQVTLS<br>CSPISGHRSVSW<br>YQQTPGQGLQF<br>LFEYFSETQRN<br>KGNFPGRFSGR<br>QFSNSRSEMNV<br>STLELGDSALY<br>LCASRQRTELE<br>AFFGQGTRLTV<br>V<br>(SEQ ID NO: 593) | TCTG<br>GGCA<br>TAGG<br>AGT<br>(SEQ ID NO: 268) |

TABLE 5-continued

| | | | | | |
|---|---|---|---|---|---|
| 6 | GGCCAGAGACACCAGTAATT CTGCCAGACCTTGCCTGTGG GGCCATGGGAGCTCAAAATG CCCCTCCTTTCCTCCACAGGA CCAGATGCCTGAGCTAGGAA AGGCCTCATTCCTGCTGTGA TCCTGCCATGGATACCTGGC TCGTATGCTGGGCAATTTTTA GTCTCTTGAAAGCAGGACTC ACAGAACCTGAAGTCACCCA GACTCCCAGCCATCAGGTCA CACAGATGGGACAGGAAGT GATCTTGCGCTGTGTCCCCAT CTCTAATCACTTATACTTCTA TTGGTACAGACAAATCTTGG GGCAGAAAGTCGAGTTTCTG GTTTCCTTTTATAATAATGAA ATCTCAGAGAAGTCTGAAAT ATTCGATGATCAATTCTCAG TTGAAAGGCCTGATGGATCA AATTTCACTCTGAAGATCCG GTCCACAAAGCTGGAGGACT CAGCCATGTACTTCTGTGCC AGCAGTGAAGCCCCTGACAG GGGTACCTACGAGCAGTACT TCGGGCCGGGCACCAGGCTC ACGGTCACAGAGG**ACCTGA AAAACGTGTTCCCACCCGA GGTCGCTGTGTTTGAGCCA TCAGAAGCAGAGATCTCCC ACACCCAAAAGGCCACACT GGTGTGCCTGGCCACAGGC TTCTACCCCGACCACGTGG AGCTGAGCTGGTGGGTGAA TGGGAAGGAGGTGCACAG TGGGGTCAGCACAGACCCG CAGCCCCTCAAGGAGCAGC CCGCCCTCAATGACTCCAG ATACTGCCTGAGCAGCCGC CTGAGGGTCTCGGCCACCT TCTGGCAGAACCCCCGCAA CCACTTCCGCTGTCAAGTC CAGTTCTACGGGCTCTCGG AGAATGACGAGTGGACCCA GGATAGGGCCAAACCTGTC ACCCAGATCGTCAGCGCCG AGGCCTGGGGTAGAGCAG ACTGTGGCTTCACCTCCGA GTCTTACCAGCAAGGGGTC CTGTCTGCCACCATCCTCT ATGAGATCTTGCTAGGGAA GGCCACCTTGTATGCCGTG CTGGTCAGTGCCCTCGTGC TGATGGCCATGGTCAAGAG AAAGGATTCCAGAGGCTAG** (SEQ ID NO: 274) | MDTWLVCWAI FSLLKAGLTEPE VTQTPSHQVTQ MGQEVILRCVPI SNHLYFYWYR QILGQKVEFLV SFYNNEISEKSE IFDDQFSVERPD GSNFTLKIRSTK LEDSAMYFCAS SEAPDRGTYEQ YFGPGTRLTVT **EDLKNVFPPEV AVFEPSEAEIS HTQKATLVCL ATGFYPDHVE LSWWVNGKE VHSGVSTDPQP LKEQPALNDS RYCLSSRLRVS ATFWQNPRNH FRCQVQFYGL SENDEWTQDR AKPVTQIVSAE AWGRADCGFT SESYQQGVLSA TILYEILLGKA TLYAVLVSALV LMAMVKRKDS RG** (SEQ ID NO: 594) | GAACCTGAAG TCACCCAGACT CCCAGCCATCA GGTCACACAG ATGGGACAGG AAGTGATCTTG CGCTGTGTCCC CATCTCTAATC ACTTATACTTC TATTGGTACAG ACAAATCTTGG GGCAGAAAGT CGAGTTTCTGG TTTCCTTTTAT AATAATGAAA TCTCAGAGAA GTCTGAAATAT TCGATGATCAA TTCTCAGTTGA AAGGCCTGAT GGATCAAATTT CACTCTGAAGA TCCGGTCCACA AAGCTGGAGG ACTCAGCCATG TACTTCTGTGC CAGCAGTGAA GCCCCTGACAG GGGTACCTACG AGCAGTACTTC GGGCCGGGCA CCAGGCTCACG GTCACAG (SEQ ID NO: 595) | EPEVTQTPSHQ VTQMGQEVILR CVPISNHLYFY WYRQILGQKVE FLVSFYNNEISE KSEIFDDQFSVE RPDGSNFTLKIR STKLEDSAMYF CASSEAPDRGT YEQYFGPGTRL TVT (SEQ ID NO: 596) | TCTA ATCA CTTAT AC (SEQ ID NO: 275) |
| 7 | GGGGACTGAGAGCTCAACTT CAATTTGCCCACAGCAGGGC TGGGAGACACAAGATCCTGC CCTGGAGCTGAAATGGGCAC CAGGCTCTTCTTCTATGTGGC CCTTTGTCTGCTGTGGGCAG GACACAGGGATGCTGGAATC ACCCAGAGCCCAAGATACAA GATCACAGAGACAGGAAGG CAGGTGACCTTGATGTGTCA CCAGACTTGGAGCCACAGCT ATATGTTCTGGTATCGACAA GACCTGGGACATGGGCTGAG GCTGATCTATTACTCAGCAG CTGCTGATATTACAGATAAA GGAGAAGTCCCCGATGGCTA CGTTGTCTCCAGATCCAAGA CAGAGAATTTCCCCCTCACT CTGGAGTCAGCTACCCGCTC CCAGACATCTGTGTATTTCTG CGCCAGCAGTGAGTTGGGCA GGGGTTTCTACGAGCAGTAC TTCGGGCCGGGCACCAGGCT | MGTRLFFYVAL CLLWAGHRDA GITQSPRYKITE TGRQVTLMCH QTWSHSYMFW YRQDLGHGLRL IYYSAAADITD KGEVPDGYVVS RSKTENFPLTLE SATRSQTSVYF CASSELGRGFY EQYFGPGTRLT **VTEDLKNVFPP EVAVFEPSEAE ISHTQKATLVC LATGFYPDHV ELSWWVNGKE VHSGVSTDPQP LKEQPALNDS RYCLSSRLRVS ATFWQNPRNH FRCQVQFYGL SENDEWTQDR** | GATGCTGGAAT CACCCAGAGC CCAAGATACA AGATCACAGA GACAGGAAGG CAGGTGACCTT GATGTGTCACC AGACTTGGAG CCACAGCTATA TGTTCTGGTAT CGACAAGACC TGGGACATGG GCTGAGGCTG ATCTATTACTC AGCAGCTGCTG ATATTACAGAT AAAGGAGAAG TCCCCGATGGC TACGTTGTCTC CAGATCCAAG ACAGAGAATTT CCCCCTCACTC TGGAGTCAGCT | DAGITQSPRYKI TETGRQVTLMC HQTWSHSYMF WYRQDLGHGL RLIYYSAAADIT DKGEVPDGYV VSRSKTENFPLT LESATRSQTSV YFCASSELGRG FYEQYFGPGTR LTVT (SEQ ID NO: 599) | TGGA GCCA CAGC TAT (SEQ ID NO: 282) |

TABLE 5-continued

| | | | | | |
|---|---|---|---|---|---|
| | CACGGTCACAGAGGACCTG<br>AAAAACGTGTTCCCACCCG<br>AGGTCGCTGTGTTTGAGCC<br>ATCAGAAGCAGAGATCTCC<br>CACACCCAAAAGGCCACAC<br>TGGTGTGCCTGGCCACAGG<br>CTTCTACCCCGACCACGTG<br>GAGCTGAGCTGGTGGGTG<br>AATGGGAAGGAGGTGCAC<br>AGTGGGGTCAGCACAGACC<br>CGCAGCCCCTCAAGGAGCA<br>GCCCGCCCTCAATGACTCC<br>AGATACTGCCTGAGCAGCC<br>GCCTGAGGGTCTCGGCCAC<br>CTTCTGGCAGAACCCCCGC<br>AACCACTTCCGCTGTCAAG<br>TCCAGTTCTACGGGCTCTC<br>GGAGAATGACGAGTGGAC<br>CCAGGATAGGGCCAAACCT<br>GTCACCCAGATCGTCAGCG<br>CCGAGGCCTGGGGTAGAG<br>CAGACTGTGGCTTCACCTC<br>CGAGTCTTACCAGCAAGGG<br>GTCCTGTCTGCCACCATCC<br>TCTATGAGATCTTGCTAGG<br>GAAGGCCACCTTGTATGCC<br>GTGCTGGTCAGTGCCCTCG<br>TGCTGATGGCCATGGTCAA<br>GAGAAAGGATTCCAGAGGC<br>TAG<br>(SEQ ID NO: 281) | AKPVTQIVSAE<br>AWGRADCGFT<br>SESYQQGVLSA<br>TILYEILLGKA<br>TLYAVLVSALV<br>LMAMVKRKDS<br>RG<br>(SEQ ID NO:<br>597) | ACCCGCTCCCA<br>GACATCTGTGT<br>ATTTCTGCGCC<br>AGCAGTGAGTT<br>GGGCAGGGGT<br>TTCTACGAGCA<br>GTACTTCGGGC<br>CGGGCACCAG<br>GCTCACGGTCA<br>CAG<br>(SEQ ID NO:<br>598) | | |
| 8 | GATGGAAAGCAAGAGCCCTG<br>GGTGGAGCTGAAGGTGCTCA<br>GCTGGGTTTGTCAGAAGTCT<br>CATCTGTCACTGTTCACTGGT<br>GCATTTATTTGGATTTGACC<br>ATCTGGGGAATGGGTGTGGC<br>CTCTCCTGGCCTCTCCCTCCC<br>TGGGGCCCAGGCAGGGAGA<br>ATGTCTCAGAATGACTTCCTT<br>GAGAGTCCTGCTCCCCTTTC<br>ATCAATGCACAGATACAGAA<br>GACCCCTCCGTCATGCAGCA<br>TCTGCCATGAGCATCGGCCT<br>CCTGTGCTGTGCAGCCTTGTC<br>TCTCCTGTGGGCAGGTCCAG<br>TGAATGCTGGTGTCACTCAG<br>ACCCCAAAATTCCAGGTCCT<br>GAAGACAGGACAGAGCATG<br>ACACTGCAGTGTGCCCAGGA<br>TATGAACCATGAATACATGT<br>CCTGGTATCGACAAGACCCA<br>GGCATGGGGCTGAGGCTGAT<br>TCATTACTCAGTTGGTGCTG<br>GTATCACTGACCAAGGAGAA<br>GTCCCCAATGGCTACAATGT<br>CTCCAGATCAACCACAGAGG<br>ATTTCCCGCTCAGGCTGCTGT<br>CGGCTGCTCCCTCCCAGACA<br>TCTGTGTACTTCTGTGCCAGC<br>AGCCATCTGGGGGCGGGAGG<br>GCCGCACGAGCAGTACTTCG<br>GGCCGGGCACCAGGCTCACG<br>GTCACAGAGGACCTGAAAA<br>ACGTGTTCCCACCCGAGGT<br>CGCTGTGTTTGAGCCATCA<br>GAAGCAGAGATCTCCCACA<br>CCCAAAAGGCCACACTGGT<br>GTGCCTGGCCACAGGCTTC<br>TACCCCGACCACGTGGAGC<br>TGAGCTGGTGGGTGAATGG<br>GAAGGAGGTGCACAGTGG<br>GGTCAGCACAGACCCGCAG<br>CCCCTCAAGGAGCAGCCCG<br>CCCTCAATGACTCCAGATA<br>CTGCCTGAGCAGCCGCCTG<br>AGGGTCTCGGCCACCTTCT<br>GGCAGAACCCCCGCAACCA<br>CTTCCGCTGTCAAGTCCAG | MGVASPGLSLP<br>GAQAGRMSQN<br>DFLESPAPLSSM<br>HRYRRPLRHAA<br>SAMSIGLLCCA<br>ALSLLWAGPVN<br>AGVTQTPKFQV<br>LKTGQSMTLQC<br>AQDMNHEYMS<br>WYRQDPGMGL<br>RLIHYSVGAGIT<br>DQGEVPNGYN<br>VSRSTTEDFPLR<br>LLSAAPSQTSV<br>YFCASSHLGAG<br>GPHEQYFGPGT<br>RLTVTEDLKNV<br>FPPEVAVFEPS<br>EAEISHTQKAT<br>LVCLATGFYP<br>DHVELSWWVN<br>GKEVHSGVST<br>DPQPLKEQPA<br>LNDSRYCLSSR<br>LRVSATFWQN<br>PRNHFRCQVQ<br>FYGLSENDEW<br>TQDRAKPVTQI<br>VSAEAWGRAD<br>CGFTSESYQQ<br>GVLSATILYEI<br>LLGKATLYAV<br>LVSALVLMAM<br>VKRKDSRG<br>(SEQ ID NO:<br>600) | AATGCTGGTGT<br>CACTCAGACCC<br>CAAAATTCCAG<br>GTCCTGAAGAC<br>AGGACAGAGC<br>ATGACACTGCA<br>GTGTGCCCAGG<br>ATATGAACCAT<br>GAATACATGTC<br>CTGGTATCGAC<br>AAGACCCAGG<br>CATGGGGCTG<br>AGGCTGATTCA<br>TTACTCAGTTG<br>GTGCTGGTATC<br>ACTGACCAAG<br>GAGAAGTCCC<br>CAATGGCTACA<br>ATGTCTCCAGA<br>TCAACCACAG<br>AGGATTTCCCG<br>CTCAGGCTGCT<br>GTCGGCTGCTC<br>CCTCCCAGACA<br>TCTGTGTACTT<br>CTGTGCCAGCA<br>GCCATCTGGGG<br>GCGGGAGGGC<br>CGCACGAGCA<br>GTACTTCGGGC<br>CGGGCACCAG<br>GCTCACGGTCA<br>CAG<br>(SEQ ID NO:<br>601) | NAGVTQTPKFQ<br>VLKTGQSMTLQ<br>CAQDMNHEYM<br>SWYRQDPGMG<br>LRLIHYSVGAGI<br>TDQGEVPNGYN<br>VSRSTTEDFPLR<br>LLSAAPSQTSV<br>YFCASSHLGAG<br>GPHEQYFGPGT<br>RLTVT<br>(SEQ ID NO:<br>602) | ATGA<br>ACCA<br>TGAA<br>TAC<br>(SEQ<br>ID NO:<br>289) |

TABLE 5-continued

| | | | | | |
|---|---|---|---|---|---|
| | TTCTACGGGCTCTCGGAGA<br>ATGACGAGTGGACCCAGGA<br>TAGGGCCAAACCTGTCACC<br>CAGATCGTCAGCGCCGAGG<br>CCTGGGGTAGAGCAGACTG<br>TGGCTTCACCTCCGAGTCT<br>TACCAGCAAGGGGTCCTGT<br>CTGCCACCATCCTCTATGA<br>GATCTTGCTAGGGAAGGCC<br>ACCTTGTATGCCGTGCTGG<br>TCAGTGCCCTCGTGCTGAT<br>GGCCATGGTCAAGAGAAAG<br>GATTCCAGAGGCTAG<br>(SEQ ID NO: 288) | | | | |
| 9 | GGTGACTGGGGGAATGGAG<br>GAGGCTGGAGCATGAATGGG<br>GATGGCACTGGGGACCCTGA<br>CTTGCAGGAAATGCAATGAG<br>CTCACCACTTTGTGCCCTATG<br>TTAGGGGCGGTGTTGGTGCA<br>TCCTAGAGTAAATGTCCAGC<br>AGACAAAGGAGCAAGAAGC<br>GGCTGTGGGATGACAAGATA<br>AACTCAGAGATACAGCATGA<br>GACCTCCGGGTCCAGACAGC<br>TCTGGAGCCCAAGGCGATGA<br>GCCATGCATTGATGTTGTTA<br>AAAAGGAGCTGATAAATATT<br>TAAAGCAGCACCCAACTGTG<br>TTCTAATAGAAATGCTGTGA<br>TCCTGAGGTCCTGGGGATTG<br>AGAGAGGAAGTGATGTCACT<br>GTGGGAACTGCCCTGTGGAG<br>ACAAGGACATCCCTCATCCT<br>CTGCTGCTGCTCACAGTGAC<br>ACTGATCTGGTAAAGCCCTC<br>ATCCTGTCCTGACCCTGCCAT<br>GGGCACCAGTCTCCTATGCT<br>GGGTGGTCCTGGGTTTCCTA<br>GGGACAGATCACACAGGTGC<br>TGGAGTCTCCCAGTCTCCCA<br>GGTACAAAGTCACAAAGAG<br>GGGACAGGATGTAGCTCTCA<br>GGTGTGATCCAATTTCGGGT<br>CATGTATCCCTTTATTGGTAC<br>CGACAGGCCCTGGGGCAGGG<br>CCCAGAGTTTCTGACTTACTT<br>CAATTATGAAGCCCAACAAG<br>ACAAATCAGGGCTGCCCAAT<br>GATCGGTTCTCTGCAGAGAG<br>GCCTGAGGGATCCATCTCCA<br>CTCTGACGATCCAGCGCACA<br>GAGCAGCGGGACTCGGCCAT<br>GTATCGCTGTGCCAGCAGCC<br>ATACTGACGGCTCCTACGAG<br>CAGTACTTCGGGCCGGGCAC<br>CAGGCTCACGGTCACAGAGG<br>ACCTGAAAAACGTGTTCCC<br>ACCCGAGGTCGCTGTGTTT<br>GAGCCATCAGAAGCAGAGA<br>TCTCCCACACCCAAAAGGC<br>CACACTGGTATGCCTGGCC<br>ACAGGCTTCTACCCCGACC<br>ACGTGGAGCTGAGCTGGTG<br>GGTGAATGGGAAGGAGGT<br>GCACAGTGGGGTCAGCACA<br>GACCCGCAGCCCCTCAAGG<br>AGCAGCCCGCCCTCAATGA<br>CTCCAGATACTGCCTGAGC<br>AGCCGCCTGAGGGTCTCGG<br>CCACCTTCTGGCAGAACCC<br>CCGCAACCACTTCCGCTGT<br>CAAGTCCAGTTCTACGGGC<br>TCTCGGAGAATGACGAGTG<br>GACCCAGGATAGGGCCAAA<br>CCTGTCACCCAGATCGTCA<br>GCGCCGAGGCCTGGGGTA<br>GAGCAGACTGTGGCTTCAC<br>CTCCGAGTCTTACCAGCAA | MGTSLLCWVV<br>LGFLGTDHTGA<br>GVSQSPRYKVT<br>KRGQDVALRC<br>DPISGHVSLYW<br>YRQALGQGPEF<br>LTYFNYEAQQD<br>KSGLPNDRFSA<br>ERPEGSISTLTIQ<br>RTEQRDSAMYR<br>CASSHTDGSYE<br>QYFGPGTRLTV<br>TEDLKNVFPPE<br>VAVFEPSEAEI<br>SHTQKATLVC<br>LATGFYPDHV<br>ELSWWVNGKE<br>VHSGVSTDPQP<br>LKEQPALNDS<br>RYCLSSRLRVS<br>ATFWQNPRNH<br>FRCQVQFYGL<br>SENDEWTQDR<br>AKPVTQIVSAE<br>AWGRADCGFT<br>SESYQQGVLSA<br>TILYEILLGKA<br>TLYAVLVSALV<br>LMAMVKRKDS<br>RG<br>(SEQ ID NO: 603) | GGTGCTGGAGT<br>CTCCCAGTCTC<br>CCAGGTACAA<br>AGTCACAAAG<br>AGGGGACAGG<br>ATGTAGCTCTC<br>AGGTGTGATCC<br>AATTTCGGGTC<br>ATGTATCCCTT<br>TATTGGTACCG<br>ACAGGCCCTG<br>GGGCAGGGCC<br>CAGAGTTTCTG<br>ACTTACTTCAA<br>TTATGAAGCCC<br>AACAAGACAA<br>ATCAGGGCTGC<br>CCAATGATCGG<br>TTCTCTGCAGA<br>GAGGCCTGAG<br>GGATCCATCTC<br>CACTCTGACGA<br>TCCAGCGCACA<br>GAGCAGCGGG<br>ACTCGGCCATG<br>TATCGCTGTGC<br>CAGCAGCCAT<br>ACTGACGGCTC<br>CTACGAGCAGT<br>ACTTCGGGCCG<br>GGCACCAGGC<br>TCACGGTCACA<br>G<br>(SEQ ID NO: 604) | GAGVSQSPRYK<br>VTKRGQDVAL<br>RCDPISGHVSLY<br>WYRQALGQGP<br>EFLTYFNYEAQ<br>QDKSGLPNDRF<br>SAERPEGSISTL<br>TIQRTEQRDSA<br>MYRCASSHTDG<br>SYEQYFGPGTR<br>LTVT<br>(SEQ ID NO: 605) | TCGG<br>GTCA<br>TGTA<br>TCC<br>(SEQ ID NO: 296) |

TABLE 5-continued

| | | | | | |
|---|---|---|---|---|---|
| | **GGGGTCCTGTCTGCCACCATCCTCTATGAGATCTTGCTAGGGAAGGCCACCTTGTATGCCGTGCTGGTCAGTGCCCTCGTGCTGATGGCCATGGTCAAGAGAAAGGATTCCAGAGGCTAG** (SEQ ID NO: 295) | | | | |
| 10 | TGGGGACAGATGCAATGCAGAGTTATGGGAGGTGCGAATGACTCTGCTCTCTGTCCTGTCTCCTCATCTGCAAAATTAGGAAGCCTGTCTTGATTATCTCCAGGAACCTCCCACCTCTTCATTCCAGCCTCTGACAAACTCTGCACATTAGGCCAGGAGAAGCCCCCGAGCCAAGTCTCTTTTCTCATTCTCTTCCAACAAGTGCTTGGAGCTCCAAGAAGGCCCCCTTTGCACTATGAGCAACCAGGTGCTCTGCTGTGTGGTCCTTTGTCTCCTGGGAGCAAACACCGTGGATGGTGGAATCACTCAGTCCCCAAAGTACCTGTTCAGAAAGGAAGGACAGAATGTGACCCTGAGTTGTGAACAGAATTTGAACCACGATGCCATGTACTGGTACCGACAGGACCCAGGGCAAGGGCTGAGATTGATCTACTACTCACAGATAGTAAATGACTTTCAGAAAGGAGATATAGCTGAAGGGTACAGCGTCTCTCGGGAGAAGAAGGAATCCTTTCCTCTCACTGTGACATCGGCCCAAAAGAACCCGACAGCTTTCTATCTCTGTGCCAGTAGCATAGGGGCATTTGCTGGTCAGCCCCAGCATTTTGGTGATGGGACTCGACTCTCCATCCTAGAG**GACCTGAACAAGGTGTTCCCACCCGAGGTCGCTGTGTTTGAGCCATCAGAAGCAGAGATCTCCCACACCCAAAAGGCCACACTGGTGTGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCCGTCACCCAGATCGTCAGCGCCGAGGCCTGGGGTAGAGCAGACTGTGGCTTTACCTCGGTGTCCTACCAGCAAGGGGTCCTGTCTGCCACCATCCTCTATGAGATCCTGCTAGGGAAGGCCACCCTGTATGCTGTGCTGGTCAGCGCCCTTGTGTTGATGGCCATGGTCAAGAGAAAGGATTTCTGA** (SEQ ID NO: 302) | MSNQVLCCVVLCLLGANTVDGGITQSPKYLFRKEGQNVTLSCEQNLNHDAMYWYRQDPGQGLRLIYYSQIVNDFQKGDIAEGYSVSREKKESFPLTVTSAQKNPTAFYLCASSIGAFAGQPQHFGDGTRLSIL**EDLNKVFPPEVAVFEPSEAEISHTQKATLVCLATGFYPDHVELSWWVNGKEVHSGVSTDPQPLKEQPALNDSRYCL** (SEQ ID NO: 506) | GATGGTGGAATCACTCAGTCCCCAAAGTACCTGTTCAGAAAGGAAGGACAGAATGTGACCCTGAGTTGTGAACAGAATTTGAACCACGATGCCATGTACTGGTACCGACAGGACCCAGGGCAAGGGCTGAGATTGATCTACTACTCACAGATAGTAAATGACTTTCAGAAAGGAGATATAGCTGAAGGGTACAGCGTCTCTCGGGAGAAGAAGGAATCCTTTCCTCTCACTGTGACATCGGCCCAAAAGAACCCGACAGCTTTCTATCTCTGTGCCAGTAGCATAGGGGCATTTGCTGGTCAGCCCCAGCATTTTGGTGATGGGACTCGACTCTCCATCCTAG (SEQ ID NO: 607) | DGGITQSPKYLFRKEGQNVTLSCEQNLNHDAMYWYRQDPGQGLRLIYYSQIVNDFQKGDIAEGYSVSREKKESFPLTVTSAQKNPTAFYLCASSIGAFAGQPQHFGDGTRLSIL (SEQ ID NO: 608) | TTGAACCACGATGCC (SEQ ID NO: 303) |
| 11 | TGGGGGTCACTGTGGGAACTGCTCTGTGGCGACAAGGACGTCCCTCATCCTCTGCTCCTGCTCACAGTGACCCTGATCTGGTAAAGCTCCCATCCTGCCCTGACCCTGCCATGGGCACCAGCCTCCTCTGCTGGATGGCCCTGTGTCTCCTGGGGGCAGATCACGCAGATACTGGAGTCTCCCAGAACCCCAGACACAAGAT | MGTSLLCWMALCLLGADHADTGVSQNPRHKITKRGQNVTFRCDPISEHNRLYWYRQTLGQGPEFLTYFQNEAQLEKSRLLSDRFSAERPKGSFSTLEIQRTEQGDSAMYLC | GATACTGGAGTCTCCCAGAACCCCAGACACAAGATCACAAAGAGGGGACAGAATGTAACTTTCAGGTGTGATCCAATTTCTGAACACAACCGCCTTTATTGGTACCG | DTGVSQNPRHKITKRGQNVTFRCDPISEHNRLYWYRQTLGQGPEFLTYFQNEAQLEKSRLLSDRFSAERPKGSFSTLEIQRTEQGDSAMYLCASSLAPTPGPDTGELFFGE | TCTGAACACAACCGC (SEQ ID NO: 310) |

TABLE 5-continued

| | | | | | |
|---|---|---|---|---|---|
| | CACAAAGAGGGGACAGAAT GTAACTTTCAGGTGTGATCC AATTTCTGAACACAACCGCC TTTATTGGTACCGACAGACC CTGGGGCAGGGCCCAGAGTT TCTGACTTACTTCCAGAATG AAGCTCAACTAGAAAAATCA AGGCTGCTCAGTGATCGGTT CTCTGCAGAGAGGCCTAAGG GATCTTTCTCCACCTTGGAG ATCCAGCGCACAGAGCAGGG GGACTCGGCCATGTATCTCT GTGCCAGCAGCTTAGCGCCT ACCCCCGGGCCGGACACCGG GGAGCTGTTTTTGGAGAAG GCTCTAGGCTGACCGTACTG GAGGACCTGAAAAACGTGT TCCCACCCGAGGTCGCTGT GTTTGAGCCATCAGAAGCA GAGATCTCCCACACCCAAA AGGCCACACTGGTGTGCCT GGCCACAGGCTTCTACCCC GACCACGTGGAGCTGAGCT GGTGGGTGAATGGGAAGG AGGTGCACAGTGGGGTCA GCACAGACCCGCAGCCCCT CAAGGAGCAGCCCGCCCTC AATGACTCCAGATACTGCC TGAGCAGCCGCCTGAGGGT CTCGGCCACCTTCTGGCAG AACCCCCGCAACCACTTCC GCTGTCAAGTCCAGTTCTA CGGGCTCTCGGAGAATGAC GAGTGGACCCAGGATAGG GCCAAACCTGTCACCCAGA TCGTCAGCGCCGAGGCCTG GGGTAGAGCAGACTGTGG CTTCACCTCCGAGTCTTAC CAGCAAGGGGTCCTGTCTG CCACCATCCTCTATGAGAT CTTGCTAGGGAAGGCCACC TTGTATGCCGTGCTGGTCA GTGCCCTCGTGCTGATGGC CATGGTCAAGAGAAAGGAT TCCAGAGGCTAG (SEQ ID NO: 309) | ASSLAPTPGPDT GELFFGEGSRLT VLEDLKNVFPP EVAVFEPSEAE ISHTQKATLVC LATGFYPDHV ELSWWVNGKE VHSGVSTDPQP LKEQPALNDS RYCLSSRLRVS ATFWQNPRNH FRCQVQFYGL SENDEWTQDR AKPVTQIVSAE AWGRADCGFT SESYQQGVLSA TILYEILLGKA TLYAVLVSALV LMAMVKRKDS RG (SEQ ID NO: 609) | ACAGACCCTG GGGCAGGGCC CAGAGTTTCTG ACTTACTTCCA GAATGAAGCT CAACTAGAAA AATCAAGGCT GCTCAGTGATC GGTTCTCTGCA GAGAGGCCTA AGGGATCTTTC TCCACCTTGGA GATCCAGCGC ACAGAGCAGG GGGACTCGGC CATGTATCTCT GTGCCAGCAG CTTAGCGCCTA CCCCCGGGCCG GACACCGGGG AGCTGTTTTT GGAGAAGGCT CTAGGCTGACC GTACTGG (SEQ ID NO: 610) | GSRLTVL (SEQ ID NO: 611) | |
| 12 | GGCGTTTGTACACTTCAGCC CTCTGAGCTGAAGTGGGAGT GGTTTCTCTCCTGAAAATGTT TCTGAGGCCCAAATAGCTGA AGAGGTGGAGACGTTACAGA AACCACCTGGAGCCCCCAGA ACTGGCAGACACCTGCCTGA TGCTGCCATGGGCCCCCAGC TCCTTGGCTATGTGGTCCTTT GCCTTCTAGGAGCAGGCCCC CTGGAAGCCCAAGTGACCCA GAACCCAAGATACCTCATCA CAGTGACTGGAAAGAAGTTA ACAGTGACTTGTTCTCAGAA TATGAACCATGAGTATATGT CCTGGTATCGACAAGACCCA GGGCTGGGCTTAAGGCAGAT CTACTATTCAATGAATGTTG AGGTGACTGATAAGGGAGAT GTTCCTGAAGGGTACAAAGT CTCTCGAAAAGAGAAGAGG AATTTCCCCCTGATCCTGGA GTCGCCCAGCCCCAACCAGA CCTCTCTGTACTTCTGTGCCA GCAGTTTAGGGAATATCTAC GAGCAGTACTTCGGGCCGGG CACCAGGCTCACGGTCACAG AGGACCTGAAAAACGTGTT CCCACCCGAGGTCGCTGTG TTTGAGCCATCAGAAGCAG AGATCTCCCACACCCAAAA GGCCACACTGGTGTGCCTG GCCACAGGCTTCTACCCCG | MGPQLLGYVV LCLLGAGPLEA QVTQNPRYLIT VTGKKLTVTCS QNMNHEYMSW YRQDPGLGLRQ IYYSMNVEVTD KGDVPEGYKVS RKEKRNFPLILE SPSPNQTSLYFC ASSLGNIYEQYF GPGTRLTVTED LKNVFPPEVAV FEPSEAEISHT QKATLVCLAT GFYPDHVELS WWVNGKEVH SGVSTDPQPLK EQPALNDSRY CLSSRLRVSAT FWQNPRNHFR CQVQFYGLSE NDEWTQDRAK PVTQIVSAEAW GRADCGFTSES YQQGVLSATIL YEILLGKATLY AVLVSALVLM AMVKRKDSRG (SEQ ID NO: 612) | GAAGCCCAAG TGACCCAGAA CCCAAGATACC TCATCACAGTG ACTGGAAAGA AGTTAACAGTG ACTTGTTCTCA GAATATGAAC CATGAGTATAT GTCCTGGTATC GACAAGACCC AGGGCTGGGC TTAAGGCAGAT CTACTATTCAA TGAATGTTGAG GTGACTGATAA GGGAGATGTTC CTGAAGGGTA CAAAGTCTCTC GAAAAGAGAA GAGGAATTTCC CCCTGATCCTG GAGTCGCCCA GCCCCAACCA GACCTCTCTGT ACTTCTGTGCC AGCAGTTTAGG GAATATCTACG AGCAGTACTTC GGGCCGGGCA CCAGGCTCACG GTCACAG (SEQ ID NO: | EAQVTQNPRYL ITVTGKKLTVT CSQNMNHEYM SWYRQDPGLGL RQIYYSMNVEV TDKGDVPEGYK VSRKEKRNFPLI LESPSPNQTSLY FCASSLGNIYEQ YFGPGTRLTVT (SEQ ID NO: 614) | ATGA ACCA TGAG TAT (SEQ ID NO: 317) |

TABLE 5-continued

| | | | | | |
|---|---|---|---|---|---|
| | ACCACGTGGAGCTGAGCTG<br>GTGGGTGAATGGGAAGGA<br>GGTGCACAGTGGGGTCAG<br>CACAGACCCGCAGCCCCTC<br>AAGGAGCAGCCCGCCCTCA<br>ATGACTCCAGATACTGCCT<br>GAGCAGCCGCCTGAGGGT<br>CTCGGCCACCTTCTGGCAG<br>AACCCCCGCAACCACTTCC<br>GCTGTCAAGTCCAGTTCTA<br>CGGGCTCTCGGAGAATGAC<br>GAGTGGACCCAGGATAGG<br>GCCAAACCTGTCACCCAGA<br>TCGTCAGCGCCGAGGCCTG<br>GGGTAGAGCAGACTGTGG<br>CTTCACCTCCGAGTCTTAC<br>CAGCAAGGGGTCCTGTCTG<br>CCACCATCCTCTATGAGAT<br>CTTGCTAGGGAAGGCCACC<br>TTGTATGCCGTGCTGGTCA<br>GTGCCCTCGTGCTGATGGC<br>CATGGTCAAGAGAAAGGAT<br>TCCAGAGGCTAG (SEQ ID<br>NO: 316) | | 613) | | |
| 13 | GAGAGAGGAAGTGATGTCAC<br>TGTGGGTACTGTTCTGTGTCA<br>GGACAAGGACGTCCCTCCTC<br>CTCTGCTCCTGCTCACAGTG<br>ACCCTGATCTGGTAAAGCTC<br>CCATCCTGCCCTGACTCTGTC<br>ATGGGCACCAGGCTCCTCTG<br>CTGGGCAGCCCTGTGCCTCC<br>TGGGGGCAGATCACACAGGT<br>GCTGGAGTCTCCCAGACCCC<br>CAGTAACAAGGTCACAGAGA<br>AGGGAAAATATGTAGAGCTC<br>AGGTGTGATCCAATTTCAGG<br>TCATACTGCCCTTTACTGGTA<br>CCGACAAAGCCTGGGGCAGG<br>GCCCAGAGTTTCTAATTTACT<br>TCCAAGGCACGGGTGCGGCA<br>GATGACTCAGGGCTGCCCAA<br>CGATCGGTTCTTTGCAGTCA<br>GGCCTGAGGGATCCGTCTCT<br>ACTCTGAAGATCCAGCGCAC<br>AGAGCGGGGGGACTCAGCC<br>GTGTATCTCTGTGCCAGCAG<br>CTTAGGGAGCGGTGAGCAGT<br>TCTTCGGGCCAGGGACACGG<br>CTCACCGTGCTAGAGGACCT<br>GAAAAACGTGTTCCCACCC<br>GAGGTCGCTGTGTTTGAGC<br>CATCAGAAGCAGAGATCTC<br>CCACACCCAAAAGGCCACA<br>CTGGTGTGCCTGGCCACAG<br>GCTTCTACCCCGACCACGT<br>GGAGCTGAGCTGGTGGGT<br>GAATGGGAAGGAGGTGCA<br>CAGTGGGGTCAGCACAGAC<br>CCGCAGCCCCTCAAGGAGC<br>AGCCCGCCCTCAATGACTC<br>CAGATACTGCCTGAGCAGC<br>CGCCTGAGGGTCTCGGCCA<br>CCTTCTGGCAGAACCCCCG<br>CAACCACTTCCGCTGTCAA<br>GTCCAGTTCTACGGGCTCT<br>CGGAGAATGACGAGTGGA<br>CCCAGGATAGGGCCAAACC<br>TGTCACCCAGATCGTCAGC<br>GCCGAGGCCTGGGGTAGA<br>GCAGACTGTGGCTTCACCT<br>CCGAGTCTTACCAGCAAGG<br>GGTCCTGTCTGCCACCATC<br>CTCTATGAGATCTTGCTAG<br>GGAAGGCCACCTTGTATGC<br>CGTGCTGGTCAGTGCCCTC<br>GTGCTGATGGCCATGGTCA<br>AGAGAAAGGATTCCAGAGG<br>CTAG | MGTRLLCWAA<br>LCLLGADHTGA<br>GVSQTPSNKVT<br>EKGKYVELRCD<br>PISGHTALYWY<br>RQSLGQGPEFLI<br>YFQGTGAADDS<br>GLPNDRFFAVR<br>PEGSVSTLKIQR<br>TERGDSAVYLC<br>ASSLGSGEQFF<br>GPGTRLTVLED<br>LKNVFPPEVAV<br>FEPSEAEISHT<br>QKATLVCLAT<br>GFYPDHVELS<br>WWVNGKEVH<br>SGVSTDPQPLK<br>EQPALNDSRY<br>CLSSRLRVSAT<br>FWQNPRNHFR<br>CQVQFYGLSE<br>NDEWTQDRAK<br>PVTQIVSAEAW<br>GRADCGFTSES<br>YQQGVLSATIL<br>YEILLGKATLY<br>AVLVSALVLM<br>AMVKRKDSRG<br>(SEQ ID NO:<br>615) | GGTGCTGGAGT<br>CTCCCAGACCC<br>CCAGTAACAA<br>GGTCACAGAG<br>AAGGGAAAAT<br>ATGTAGAGCTC<br>AGGTGTGATCC<br>AATTTCAGGTC<br>ATACTGCCCTT<br>TACTGGTACCG<br>ACAAAGCCTG<br>GGGCAGGGCC<br>CAGAGTTTCTA<br>ATTTACTTCCA<br>AGGCACGGGT<br>GCGGCAGATG<br>ACTCAGGGCTG<br>CCCAACGATCG<br>GTTCTTTGCAG<br>TCAGGCCTGAG<br>GGATCCGTCTC<br>TACTCTGAAGA<br>TCCAGCGCACA<br>GAGCGGGGGG<br>ACTCAGCCGTG<br>TATCTCTGTGC<br>CAGCAGCTTAG<br>GGAGCGGTGA<br>GCAGTTCTTCG<br>GGCCAGGGAC<br>ACGGCTCACCG<br>TGCTAG<br>(SEQ ID NO:<br>616) | GAGVSQTPSNK<br>VTEKGKYVELR<br>CDPISGHTALY<br>WYRQSLGQGPE<br>FLIYFQGTGAA<br>DDSGLPNDRFF<br>AVRPEGSVSTL<br>KIQRTERGDSA<br>VYLCASSLGSG<br>EQFFGPGTRLT<br>VL<br>(SEQ ID NO:<br>617) | TCAG<br>GTCA<br>TACT<br>GCC<br>(SEQ<br>ID NO:<br>324) |

TABLE 5-continued

| | | | | | |
|---|---|---|---|---|---|
| | (SEQ ID NO: 323) | | | | |
| 14 | TGGGGGTCTTGGGTGCTTGCTTCCCCTTCCTTCTGCCTTGGATAACAGCAGGAGGCCCTCATCAGTTATGGACCCTTGATCTTGGACTTCCCAGTCTCCAGATCTACAACCCAGCTCTGCTTTGGATCTGATCAGATGGACTAAATCTTGGGGACTCTGCACCACTGGCCACTGAGGAAAGGGAAGAGAATGTTGCCTGGGACAGGAAAATATAGAAAATGAAGGCCCAGAACTCACTCGGCTCTTCCCCAGGAAGACCAAGCCCTGAATCAGGTGCAGTGCCGCCTGGCCCACTGTGCCATGGGACCCAGGCTCCTCTTCTGGGCACTGCTTTGTCTCCTCGGAACAGGCCCAGTGGAGGCTGGAGTCACACAAAGTCCCACACACCTGATCAAAACGAGAGGACAGCAAGCGACTCTGAGATGCTCTCCTATCTCTGGGCACACCAGTGTGTACTGGTACCAACAGGCCCTGGGTCTGGGCCTCCAGTTCCTCCTTTGGTATGACGAGGGTGAAGAGAGAAACAGAGGAAACTTCCCTCCTAGATTTTCAGGTCGCCAGTTCCCTAATTATAGCTCTGAGCTGAATGTGAACGCCTTGGAGCTGGAGGACTCGGCCCTGTATCTCTGTGCCAGCAGCTTACAGACATCCTACGAGCAGTACTTCGGGCCGGGCACCAGGCTCACGGTCACAGAGG**ACCTGAAAAACGTGTTCCCACCCGAGGTCGCTGTGTTTGAGCCATCAGAAGCAGAGATCTCCCACACCCAAAAGGCCACACTGGTATGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCTGTCACCCAGATCGTCAGCGCCGAGGCCTGGGGTAGAGCAGACTGTGGCTTCACCTCCGAGTCTTACCAGCAAGGGGTCCTGTCTGCCACCATCCTCTATGAGATCTTGCTAGGGAAGGCCACCTTGTATGCCGTGCTGGTCAGTGCCCTCGTGCTGATGGCCATGGTCAAGAGAAAGGATTCCAGAGGCTAG** (SEQ ID NO: 330) | MGPRLLFWALLCLLGTGPVEAGVTQSPTHLIKTRGQQATLRCSPISGHTSVYWYQQALGLGLQFLLWYDEGEERNRGNFPPRFSGRQFPNYSSELNVNALELEDSALYLCASSLQTSYEQYFGPGTRLTVT**EDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG** (SEQ ID NO: 618) | GAGGCTGGAGTCACACAAAGTCCCACACACCTGATCAAAACGAGAGGACAGCAAGCGACTCTGAGATGCTCTCCTATCTCTGGGCACACCAGTGTGTACTGGTACCAACAGGCCCTGGGTCTGGGCCTCCAGTTCCTCCTTTGGTATGACGAGGGTGAAGAGAGAAACAGAGGAAACTTCCCTCCTAGATTTTCAGGTCGCCAGTTCCCTAATTATAGCTCTGAGCTGAATGTGAACGCCTTGGAGCTGGAGGACTCGGCCCTGTATCTCTGTGCCAGCAGCTTACAGACATCCTACGAGCAGTACTTCGGGCCGGGCACCAGGCTCACGGTCACAG (SEQ ID NO: 619) | EAGVTQSPTHLIKTRGQQATLRCSPISGHTSVYWYQQALGLGLQFLLWYDEGEERNRGNFPPRFSGRQFPNYSSELNVNALELEDSALYLCASSLQTSYEQYFGPGTRLTVT (SEQ ID NO: 620) | TCTGGGCACACCAGT (SEQ ID NO: 331) |
| 15 | GGGCTCAGCCTGAGTTGGCTGTGTTGCGTTTGTACACTTCAGCCCTCTGAGCTGAAGTGGGAGTGGTTTCTCTCCTGAAAATGTTTCTGAGGCCCAAATAGCTGAAGAGGTGGAGACGTTACAGAAACCACCTGGAGCCCCCAGAACTGGCAGACACCTGCCTGATGCTGCCATGGGCCCCCAGCTCCTTGGCTATGTGGTCCTTTGCCTTCTAGGAGCAGGCCCCCTGGAAGCCCAAGTGACCCAGAACCCAAGATACCT | MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSLSWGTGKRADTQYFGPGTRLTVL**EDLKNVF** | GAAGCCCAAGTGACCCAGAACCCAAGATACCTCATCACAGTGACTGGAAAGAAGTTAACAGTGACTTGTTCTCAGAATATGAACCATGAGTATATGTCCTGGTATCGACAAGACCCAGGGCTGGGCTTAAGGCAGAT | EAQVTQNPRYLITVTGKKLTVTCSQNMNHEYMSWYRQDPGLGLRQIYYSMNVEVTDKGDVPEGYKVSRKEKRNFPLILESPSPNQTSLYFCASSLSWGTGKRADTQYFGPGTRLTVL (SEQ ID NO: 623) | ATGAACCATGAGTAT SEQ ID NO: 338) |

TABLE 5-continued

| | | | | | |
|---|---|---|---|---|---|
| | CATCACAGTGACTGGAAAGA<br>AGTTAACAGTGACTTGTTCT<br>CAGAATATGAACCATGAGTA<br>TATGTCCTGGTATCGACAAG<br>ACCCAGGGCTGGGCTTAAGG<br>CAGATCTACTATTCAATGAA<br>TGTTGAGGTGACTGATAAGG<br>GAGATGTTCCTGAAGGGTAC<br>AAAGTCTCTCGAAAAGAGAA<br>GAGGAATTTCCCCCTGATCC<br>TGGAGTCGCCCAGCCCCAAC<br>CAGACCTCTCTGTACTTCTGT<br>GCCAGCAGTTTATCGTGGGG<br>GACCGGCAAAAGAGCAGAT<br>ACGCAGTATTTTGGCCCAGG<br>CACCCGGCTGACAGTGCTCG<br>AG**GACCTGAAAAACGTGTT**<br>**CCCACCCGAGGTCGCTGTG**<br>**TTTGAGCCATCAGAAGCAG**<br>**AGATCTCCCACACCCAAAA**<br>**GGCCACACTGGTGTGCCTG**<br>**GCCACAGGCTTCTACCCCG**<br>**ACCACGTGGAGCTGAGCTG**<br>**GTGGGTGAATGGGAAGGA**<br>**GGTGCACAGTGGGGTCAG**<br>**CACAGACCCGCAGCCCCTC**<br>**AAGGAGCAGCCCGCCCTCA**<br>**ATGACTCCAGATACTGCCT**<br>**GAGCAGCCGCCTGAGGGT**<br>**CTCGGCCACCTTCTGGCAG**<br>**AACCCCCGCAACCACTTCC**<br>**GCTGTCAAGTCCAGTTCTA**<br>**CGGGCTCTCGGAGAATGAC**<br>**GAGTGGACCCAGGATAGG**<br>**GCCAAACCTGTCACCCAGA**<br>**TCGTCAGCGCCGAGGCCTG**<br>**GGGTAGAGCAGACTGTGG**<br>**CTTCACCTCCGAGTCTTAC**<br>**CAGCAAGGGGTCCTGTCTG**<br>**CCACCATCCTCTATGAGAT**<br>**CTTGCTAGGGAAGGCCACC**<br>**TTGTATGCCGTGCTGGTCA**<br>**GTGCCCTCGTGCTGATGGC**<br>**CATGGTCAAGAGAAAGGAT**<br>**TCCAGAGGCTAG** (SEQ ID NO: 337) | **PPEVAVFEPSE**<br>**AEISHTQKATL**<br>**VCLATGFYPD**<br>**HVELSWWVN**<br>**GKEVHSGVST**<br>**DPQPLKEQPA**<br>**LNDSRYCLSSR**<br>**LRVSATFWQN**<br>**PRNHFRCQVQ**<br>**FYGLSENDEW**<br>**TQDRAKPVTQI**<br>**VSAEAWGRAD**<br>**CGFTSESYQQ**<br>**GVLSATILYEI**<br>**LLGKATLYAV**<br>**LVSALVLMAM**<br>**VKRKDSRG**<br>(SEQ ID NO: 621) | CTACTATTCAA<br>TGAATGTTGAG<br>GTGACTGATAA<br>GGGAGATGTTC<br>CTGAAGGGTA<br>CAAAGTCTCTC<br>GAAAAGAGAA<br>GAGGAATTTCC<br>CCCTGATCCTG<br>GAGTCGCCCA<br>GCCCCAACCA<br>GACCTCTCTGT<br>ACTTCTGTGCC<br>AGCAGTTTATC<br>GTGGGGGACC<br>GGCAAAAGAG<br>CAGATACGCA<br>GTATTTTGGCC<br>CAGGCACCCG<br>GCTGACAGTGC<br>TCG<br>(SEQ ID NO: 622) | | |
| 16 | CGAAGGCGGAGGGTGGAAT<br>GCGGGCAGCAGCCCCCTGGA<br>GGGCTGAGTGGGGAAAACA<br>AAATGGACCTCACAGAAGCT<br>GTGTGTGTGGAAACCCACTT<br>CTGACTTATCACTTGTCATGA<br>ATTCTATGCTTCATGGTGTTA<br>CACCGTTTATTGTTTCTGATG<br>AGTGACAGTAATTATTTTCTT<br>TCTTGCTGGTACATAATAAA<br>GTGGTGCACATCAGAGTTGC<br>TGCCATCTTAGACTTAACTC<br>ATCAGTATCAGGTGATCCTG<br>AGGCTCAGTGATGTCACTGT<br>GGGAACTGCTCTGTGGCGAC<br>AAGGACGTCCCTCATCCTCT<br>GCTCCTGCTCACAGTGACCC<br>TGATCTGGTAAAGCTCCCAT<br>CCTGCCCTGACCCTGCCATG<br>GGCACCAGCCTCCTCTGCTG<br>GATGGCCCTGTGTCTCCTGG<br>GGGCAGATCACGCAGATACT<br>GGAGTCTCCCAGGACCCCAG<br>ACACAAGATCACAAAGAGG<br>GGACAGAATGTAACTTTCAG<br>GTGTGATCCAATTTCTGAAC<br>ACAACCGCCTTTATTGGTAC<br>CGACAGACCCTGGGGCAGGG<br>CCCAGAGTTTCTGACTTACTT<br>CCAGAATGAAGCTCAACTAG<br>AAAAATCAAGGCTGCTCAGT<br>GATCGGTTCTCTGCAGAGAG<br>GCCTAAGGGATCTTTCTCCA | MGTSLLCWMA<br>LCLLGADHADT<br>GVSQDPRHKIT<br>KRGQNVTFRCD<br>PISEHNRLYWY<br>RQTLGQGPEFL<br>TYFQNEAQLEK<br>SRLLSDRFSAER<br>PKGSFSTLEIQR<br>TEQGDSAMYLC<br>ASSLVGGGSNE<br>QFFGPGTRLTV<br>**LEDLKNVFPPE**<br>**VAVFEPSEAEI**<br>**SHTQKATLVC**<br>**LATGFYPDHV**<br>**ELSWWVNGKE**<br>**VHSGVSTDPQP**<br>**LKEQPALNDS**<br>**RYCLSSRLRVS**<br>**ATFWQNPRNH**<br>**FRCQVQFYGL**<br>**SENDEWTQDR**<br>**AKPVTQIVSAE**<br>**AWGRADCGFT**<br>**SESYQQGVLSA**<br>**TILYEILLGKA**<br>**TLYAVLVSALV**<br>**LMAMVKRKDS**<br>**RG**<br>(SEQ ID NO: 624) | GATACTGGAGT<br>CTCCCAGGACC<br>CCAGACACAA<br>GATCACAAAG<br>AGGGGACAGA<br>ATGTAACTTTC<br>AGGTGTGATCC<br>AATTTCTGAAC<br>ACAACCGCCTT<br>TATTGGTACCG<br>ACAGACCCTG<br>GGGCAGGGCC<br>CAGAGTTTCTG<br>ACTTACTTCCA<br>GAATGAAGCT<br>CAACTAGAAA<br>AATCAAGGCT<br>GCTCAGTGATC<br>GGTTCTCTGCA<br>GAGAGGCCTA<br>AGGGATCTTTC<br>TCCACCTTGGA<br>GATCCAGCGC<br>ACAGAGCAGG<br>GGGACTCGGC<br>CATGTATCTCT<br>GTGCCAGCAG<br>CTTAGTTGGCG<br>GCGGGAGCAA<br>TGAGCAGTTCT<br>TCGGGCCAGG<br>GACACGGCTC<br>ACCGTGCTAG | DTGVSQDPRHK<br>ITKRGQNVTFR<br>CDPISEHNRLY<br>WYRQTLGQGP<br>EFLTYFQNEAQ<br>LEKSRLLSDRFS<br>AERPKGSFSTLE<br>IQRTEQGDSAM<br>YLCASSLVGGG<br>SNEQFFGPGTR<br>LTVL<br>(SEQ ID NO: 626) | TCTG<br>AACA<br>CAAC<br>CGC<br>(SEQ ID NO: 345) |

TABLE 5-continued

| | | | | | |
|---|---|---|---|---|---|
| | CCTTGGAGATCCAGCGCACA<br>GAGCAGGGGGACTCGGCCAT<br>GTATCTCTGTGCCAGCAGCT<br>TAGTTGGCGGCGGGAGCAAT<br>GAGCAGTTCTTCGGGCCAGG<br>GACACGGCTCACCGTGCTAG<br>AGGACCTGAAAAACGTGTT<br>CCCACCCGAGGTCGCTGTG<br>TTTGAGCCATCAGAAGCAG<br>AGATCTCCCACACCCAAAA<br>GGCCACACTGGTGTGCCTG<br>GCCACAGGCTTCTACCCCG<br>ACCACGTGGAGCTGAGCTG<br>GTGGGTGAATGGGAAGGA<br>GGTGCACAGTGGGGTCAG<br>CACAGACCCGCAGCCCCTC<br>AAGGAGCAGCCCGCCCTCA<br>ATGACTCCAGATACTGCCT<br>GAGCAGCCGCCTGAGGGT<br>CTCGGCCACCTTCTGGCAG<br>AACCCCCGCAACCACTTCC<br>GCTGTCAAGTCCAGTTCTA<br>CGGGCTCTCGGAGAATGAC<br>GAGTGGACCCAGGATAGG<br>GCCAAACCTGTCACCCAGA<br>TCGTCAGCGCCGAGGCCTG<br>GGGTAGAGCAGACTGTGG<br>CTTCACCTCCGAGTCTTAC<br>CAGCAAGGGGTCCTGTCTG<br>CCACCATCCTCTATGAGAT<br>CTTGCTAGGGAAGGCCACC<br>TTGTATGCCGTGCTGGTCA<br>GTGCCCTCGTGCTGATGGC<br>CATGGTCAAGAGAAAGGAT<br>TCCAGAGGCTAG<br>(SEQ ID NO: 344) | | (SEQ ID NO:<br>625) | | |
| 17 | GACCTCCCACTCCTACCCAG<br>ACCGTGGATGGGCAGGAAAT<br>GCAGGAACAGAGCCAGAAA<br>CAGGAGATCTCCAAGGAAGG<br>TTGACAGTCAGCACTGGGAT<br>CGTCTGTGTAAAGTGCTGCT<br>GAAGCAGCCAGGTGGCATGT<br>CCAGCCGACAATGCGAAAGG<br>AAAAAGTGAGAAGACTTCCC<br>GAAGGCGGAGGGTGGAATG<br>CGGGCAGCAGCCCCCTGGAG<br>GGCTGAGTGGGGAAAACAA<br>AATGGACCTCACAGAAGCTG<br>TGTGTGTGGAAACCCACTTC<br>TGACTTATCACTTGTCATGA<br>ATTCTATGCTTCATGGTGTTA<br>CACCGTTTATTGTTTCTGATG<br>AGTGACAGTAATTATTTTCTT<br>TCTTGCTGGTACATAATAAA<br>GTGGTGCACATCAGAGTTGC<br>TGCCATCTTAGACTTAACTC<br>ATCAGTATCAGGTGATCCTG<br>AGGCTCAGTGATGTCACTGT<br>GGGAACTGCTCTGTGGCGAC<br>AAGGACGTCCCTCATCCTCT<br>GCTCCTGCTCACAGTGACCC<br>TGATCTGGTAAAGCTCCCAT<br>CCTGCCCTGACCCTGCCATG<br>GGCACCAGCCTCCTCTGCTG<br>GATGGCCCTGTGTCTCCTGG<br>GGGCAGATCACGCAGATACT<br>GGAGTCTCCCAGGACCCCAG<br>ACACAAGATCACAAAGAGG<br>GGACAGAATGTAACTTTCAG<br>GTGTGATCCAATTTCTGAAC<br>ACAACCGCCTTTATTGGTAC<br>CGACAGACCCTGGGGCAGGG<br>CCCAGAGTTTCTGACTTACTT<br>CCAGAATGAAGCTCAACTAG<br>AAAAATCAAGGCTGCTCAGT<br>GATCGGTTCTCTGCAGAGAG<br>GCCTAAGGGATCTTTCTCCA<br>CCTTGGAGATCCAGCGCACA | MGTSLLCWMA<br>LCLLGADHADT<br>GVSQDPRHKIT<br>KRGQNVTFRCD<br>PISEHNRLYWY<br>RQTLGQGPEFL<br>TYFQNEAQLEK<br>SRLLSDRFSAER<br>PKGSFSTLEIQR<br>TEQGDSAMYLC<br>ASSLVGGTEAF<br>FGQGTRLTVVE<br>DLNKVFPPEVA<br>VFEPSEAEISH<br>TQKATLVCLA<br>TGFYPDHVELS<br>WWVNGKEVH<br>SGVSTDPQPLK<br>EQPALNDSRY<br>CLSSRLRVSAT<br>FWQNPRNHFR<br>CQVQFYGLSE<br>NDEWTQDRAK<br>PVTQIVSAEAW<br>GRADCGFTSVS<br>YQQGVLSATIL<br>YEILLGKATLY<br>AVLVSALVLM<br>AMVKRKDF<br>(SEQ ID NO:<br>627) | GATACTGGAGT<br>CTCCCAGGACC<br>CCAGACACAA<br>GATCACAAAG<br>AGGGGACAGA<br>ATGTAACTTTC<br>AGGTGTGATCC<br>AATTTCTGAAC<br>ACAACCGCCTT<br>TATTGGTACCG<br>ACAGACCCTG<br>GGGCAGGGCC<br>CAGAGTTTCTG<br>ACTTACTTCCA<br>GAATGAAGCT<br>CAACTAGAAA<br>AATCAAGGCT<br>GCTCAGTGATC<br>GGTTCTCTGCA<br>GAGAGGCCTA<br>AGGGATCTTTC<br>TCCACCTTGGA<br>GATCCAGCGC<br>ACAGAGCAGG<br>GGGACTCGGC<br>CATGTATCTCT<br>GTGCCAGCAG<br>CTTAGTCGGAG<br>GCACTGAAGCT<br>TTCTTTGGACA<br>AGGCACCAGA<br>CTCACAGTTGT<br>AG<br>(SEQ ID NO:<br>628) | DTGVSQDPRHK<br>ITKRGQNVTFR<br>CDPISEHNRLY<br>WYRQTLGQGP<br>EFLTYFQNEAQ<br>LEKSRLLSDRFS<br>AERPKGSFSTLE<br>IQRTEQGDSAM<br>YLCASSLVGGT<br>EAFFGQGTRLT<br>VV<br>(SEQ ID NO:<br>629) | TCTG<br>AACA<br>CAAC<br>CGC<br>(SEQ<br>ID NO:<br>352) |

TABLE 5-continued

| | | | | | |
|---|---|---|---|---|---|
| | GAGCAGGGGGACTCGGCCAT<br>GTATCTCTGTGCCAGCAGCT<br>TAGTCGGAGGCACTGAAGCT<br>TTCTTTGGACAAGGCACCAG<br>ACTCACAGTTGTAGAG**GACC**<br>**TGAACAAGGTGTTCCCACC**<br>**CGAGGTCGCTGTGTTTGAG**<br>**CCATCAGAAGCAGAGATCT**<br>**CCCACACCCAAAAGGCCAC**<br>**ACTGGTGTGCCTGGCCACA**<br>**GGCTTCTACCCCGACCACG**<br>**TGGAGCTGAGCTGGTGGGT**<br>**GAATGGGAAGGAGGTGCA**<br>**CAGTGGGGTCAGCACAGAC**<br>**CCGCAGCCCCTCAAGGAGC**<br>**AGCCCGCCCTCAATGACTC**<br>**CAGATACTGCCTGAGCAGC**<br>**CGCCTGAGGGTCTCGGCCA**<br>**CCTTCTGGCAGAACCCCCG**<br>**CAACCACTTCCGCTGTCAA**<br>**GTCCAGTTCTACGGGCTCT**<br>**CGGAGAATGACGAGTGGA**<br>**CCCAGGATAGGGCCAAACC**<br>**CGTCACCCAGATCGTCAGC**<br>**GCCGAGGCCTGGGGTAGA**<br>**GCAGACTGTGGCTTTACCT**<br>**CGGTGTCCTACCAGCAAGG**<br>**GGTCCTGTCTGCCACCATC**<br>**CTCTATGAGATCCTGCTAG**<br>**GGAAGGCCACCCTGTATGC**<br>**TGTGCTGGTCAGCGCCCTT**<br>**GTGTTGATGGCCATGGTCA**<br>**AGAGAAAGGATTTCTGA**<br>(SEQ ID NO: 351) | | | | |
| 18 | GGGCCATCTTAGACTTAACT<br>CATCAGTATCAGGTGATCCT<br>GAGGCTCAGTGATGTCACTG<br>TGGGAACTGCTCTGTGGCGA<br>CAAGGACGTCCCTCATCCTC<br>TGCTCCTGCTCACAGTGACC<br>CTGATCTGGTAAAGCTCCCA<br>TCCTGCCCTGACCCTGCCAT<br>GGGCACCAGCCTCCTCTGCT<br>GGATGGCCCTGTGTCTCCTG<br>GGGGCAGATCACGCAGATAC<br>TGGAGTCTCCCAGGACCCCA<br>GACACAAGATCACAAAGAG<br>GGGACAGAATGTAACTTTCA<br>GGTGTGATCCAATTTCTGAA<br>CACAACCGCCTTTATTGGTA<br>CCGACAGACCCTGGGGCAGG<br>GCCCAGAGTTTCTGACTTAC<br>TTCCAGAATGAAGCTCAACT<br>AGAAAAATCAAGGCTGCTCA<br>GTGATCGGTTCTCTGCAGAG<br>AGGCCTAAGGGATCTTTCTC<br>CACCTTGGAGATCCAGCGCA<br>CAGAGCAGGGGGACTCGGCC<br>ATGTATCTCTGTGCCAGCAG<br>CCCCGATCGGAATCTCGGGC<br>AGTACTTCGGGCCGGGCACC<br>AGGCTCACGGTCACAGAG**GA**<br>**CCTGAAAAACGTGTTCCCA**<br>**CCCGAGGTCGCTGTGTTTG**<br>**AGCCATCAGAAGCAGAGAT**<br>**CTCCCACACCCAAAAGGCC**<br>**ACACTGGTGTGCCTGGCCA**<br>**CAGGCTTCTACCCCGACCA**<br>**CGTGGAGCTGAGCTGGTG**<br>**GGTGAATGGGAAGGAGGT**<br>**GCCGTGGGGTCAGCACA**<br>**GACCCAGCCCCTCAAGG**<br>**AGCCCGCCCTCAATGA**<br>**CTCCAGATACTGCCTGAGC**<br>**AGCCCTGAGGGTCTCGG**<br>**CCACCTTCTGGCAGAACCC**<br>**CCGCACCACTTCCGCTGT**<br>**CAAGTCCAGTTCTACGGGC**<br>**TCTCGGAGAATGACGAGTG** | MGTSLLCWMA<br>LCLLGADHADT<br>GVSQDPRHKIT<br>KRGQNVTFRCD<br>PISEHNRLYWY<br>RQTLGQGPEFL<br>TYFQNEAQLEK<br>SRLLSDRESAER<br>PKGSFSTLEIQR<br>TEQGDSAMYLC<br>ASSPDRNLGQY<br>FGPGTRLTVT**E**<br>**DLKNVFPPEVA**<br>**VFEPSEAEISH**<br>**TQKATLVCLA**<br>**TGFYPDHVELS**<br>**WWVNGKEVH**<br>**SGVSTDPQPLK**<br>**EQPALNDSRY**<br>**CLSSRLRVSAT**<br>**FWQNPRNHFR**<br>**CQVQFYGLSE**<br>**NDEWTQDRAK**<br>**PVTQIVSAEAW**<br>**GRADCGFTSES**<br>**YQQGVLSATIL**<br>**YEILLGKATLY**<br>**AVLVSALVLM**<br>**AMVKRKDSRG**<br>(SEQ ID NO: 630) | GATACTGGAGT<br>CTCCCAGGACC<br>CCAGACACAA<br>GATCACAAAG<br>AGGGGACAGA<br>ATGTAACTTTC<br>AGGTGTGATCC<br>AATTTCTGAAC<br>ACAACCGCCTT<br>TATTGGTACCG<br>ACAGACCCTG<br>GGGCAGGGCC<br>CAGAGTTTCTG<br>ACTTACTTCCA<br>GAATGAAGCT<br>CAACTAGAAA<br>AATCAAGGCT<br>GCTCAGTGATC<br>GGTTCTCTGCA<br>GAGAGGCCTA<br>AGGGATCTTTC<br>TCCACCTTGGA<br>GATCCAGCGC<br>ACAGAGCAGG<br>GGGACTCGGC<br>CATGTATCTCT<br>GTGCCAGCAG<br>CCCCGATCGGA<br>ATCTCGGGCAG<br>TACTTCGGGCC<br>GGGCACCAGG<br>CTCACGGTCAC<br>AG<br>(SEQ ID NO: 631) | DTGVSQDPRHK<br>ITKRGQNVTFR<br>CDPISEHNRLY<br>WYRQTLGQGP<br>EFLTYFQNEAQ<br>LEKSRLLSDRFS<br>AERPKGSFSTLE<br>IQRTEQGDSAM<br>YLCASSPDRNL<br>GQYFGPGTRLT<br>VT<br>(SEQ ID NO: 632) | TCTG<br>AACA<br>CAAC<br>CGC<br>(SEQ ID NO: 359) |

TABLE 5-continued

| | | | | | |
|---|---|---|---|---|---|
| | GACCCGGATAGGGCCAAA<br>CCTGTCACCCAGATCGTCA<br>GCGCCGAGGCCTGGGGTA<br>GAGCAGACTGTGGCTTCAC<br>CTCCGAGTCTTACCAGCAA<br>GGGGTCCTGTCTGCCACCA<br>TCCTCTATGAGATCTTGCT<br>AGGGAAGGCCACCTTGTAT<br>GCCGTGCTGGTCAGTGCCC<br>TCGTGCTGATGGCCATGGT<br>CAAGAGAAAGGATTCCAGA<br>GGCTAG (SEQ ID NO: 358) | | | | |
| 19 | GGGACATTGGCTAATATGCT<br>GATGTCACTGGAGGCCACAT<br>CTTACAGGGCCAAGAGACAG<br>ATTTGCTTTCCTTTTTCTCAT<br>GCTTGTAAGCTCCTTCATCTG<br>GAAATGTGATTTACCTGGGT<br>CCTGCCATGGTTTCCAGGCTT<br>CTCAGTTTAGTGTCCCTTTGT<br>CTCCTGGGAGCAAAGCACAT<br>AGAAGCTGGAGTTACTCAGT<br>TCCCCAGCCACAGCGTAATA<br>GAGAAGGGCCAGACTGTGAC<br>TCTGAGATGTGACCCAATTT<br>CTGGACATGATAATCTTTATT<br>GGTATCGACGTGTTATGGGA<br>AAAGAAATAAAATTTCTGTT<br>ACATTTTGTGAAAGAGTCTA<br>AACAGGATGAATCCGGTATG<br>CCCAACAATCGATTCTTAGC<br>TGAAAGGACTGGAGGGACGT<br>ATTCTACTCTGAAGGTGCAG<br>CCTGCAGAACTGGAGGATTC<br>TGGAGTTTATTTCTGTGCCAG<br>CAGCCAAGTCCAGGCTTTTA<br>ATGAGCAGTTCTTCGGGCCA<br>GGGACACGGCTCACCGTGCT<br>AGAGGACCTGAAAAACGTG<br>TTCCCACCCGAGGTCGCTG<br>TGTTTGAGCCATCAGAAGC<br>AGAGATCTCCCACACCCAA<br>AAGGCCACACTGGTGTGCC<br>TGGCCACAGGCTTCTACCC<br>CGACCACGTGGAGCTGAGC<br>TGGTGGGTGAATGGGAAG<br>GAGGTGCACAGTGGGGTC<br>AGCACAGACCCGCAGCCCC<br>TCAAGGAGCAGCCCGCCCT<br>CAATGACTCCAGATACTGC<br>CTGAGCAGCCGCCTGAGG<br>GTCTCGGCCACCTTCTGGC<br>AGAACCCCCGCAACCACTT<br>CCGCTGTCAAGTCCAGTTC<br>TACGGGCTCTCGGAGAATG<br>ACGAGTGGACCCAGGATAG<br>GGCCAAACCTGTCACCCAG<br>ATCGTCAGCGCCGAGGCCT<br>GGGGTAGAGCAGACTGTG<br>GCTTCACCTCCGAGTCTTA<br>CCAGCAAGGGGTCCTGTCT<br>GCCACCATCCTCTATGAGA<br>TCTTGCTAGGGAAGGCCAC<br>CTTGTATGCCGTGCTGGTC<br>AGTGCCCTCGTGCTGATGG<br>CCATGGTCAAGAGAAAGGA<br>TTCCAGAGGCTAG (SEQ ID NO: 365) | MVSRLLSLVSL<br>CLLGAKHIEAG<br>VTQFPSHSVIEK<br>GQTVTLRCDPIS<br>GHDNLYWYRR<br>VMGKEIKFLLH<br>FVKESKQDESG<br>MPNNRFLAERT<br>GGTYSTLKVQP<br>AELEDSGVYFC<br>ASSQVQAFNEQ<br>FFGPGTRLTVL<br>EDLKNVFPPEV<br>AVFEPSEAEIS<br>HTQKATLVCL<br>ATGFYPDHVE<br>LSWWVNGKE<br>VHSGVSTDPQP<br>LKEQPALNDS<br>RYCLSSRLRVS<br>ATFWQNPRNH<br>FRCQVQFYGL<br>SENDEWTQDR<br>AKPVTQIVSAE<br>AWGRADCGFT<br>SESYQQGVLSA<br>TILYEILLGKA<br>TLYAVLVSALV<br>LMAMVKRKDS<br>RG<br>(SEQ ID NO: 633) | GAAGCTGGAG<br>TTACTCAGTTC<br>CCCAGCCACA<br>GCGTAATAGA<br>GAAGGGCCAG<br>ACTGTGACTCT<br>GAGATGTGAC<br>CCAATTTCTGG<br>ACATGATAATC<br>TTTATTGGTAT<br>CGACGTGTTAT<br>GGGAAAAGAA<br>ATAAAATTTCT<br>GTTACATTTTG<br>TGAAAGAGTCT<br>AAACAGGATG<br>AATCCGGTATG<br>CCCAACAATCG<br>ATTCTTAGCTG<br>AAAGGACTGG<br>AGGGACGTATT<br>CTACTCTGAAG<br>GTGCAGCCTGC<br>AGAACTGGAG<br>GATTCTGGAGT<br>TTATTTCTGTG<br>CCAGCAGCCA<br>AGTCCAGGCTT<br>TTAATGAGCAG<br>TTCTTCGGGCC<br>AGGGACACGG<br>CTCACCGTGCT<br>AG<br>(SEQ ID NO: 634) | EAGVTQFPSHS<br>VIEKGQTVTLR<br>CDPISGHDNLY<br>WYRRVMGKEI<br>KFLLHFVKESK<br>QDESGMPNNRF<br>LAERTGGTYST<br>LKVQPAELEDS<br>GVYFCASSQVQ<br>AFNEQFFGPGT<br>RLTVL<br>(SEQ ID NO: 635) | TCTG<br>GACA<br>TGAT<br>AAT<br><br>(SEQ ID NO: 366) |
| 20 | TCTCTTTTATGTTGCCATCCA<br>AGTAAGACATGACTTGCCCC<br>TCCTTGCCTTCTGCCATGATT<br>GTGAGGCCTCCCCAGCCATG<br>TGGAACTAGGAAAAGTGAAT<br>CAAAACCAAGGGACATGCTG<br>AGACAACTGGAGAAATTTGA<br>ATGTGAAGCATTTGTGGAGG<br>CAATGATGTCACTGTGGGAA<br>CTGCCATGAGAGGACAGGGA | MRGQGRPSSSA<br>FAHSDPDWAKL<br>PSFPDPAMGTR<br>LLCWAALCLLG<br>AELTEAGVAQS<br>PRYKIIEKRQSV<br>AFWCNPISGHA<br>TLYWYQQILGQ<br>GPKLLIQFQNN<br>GVVDDSQLPKD | GAAGCTGGAG<br>TTGCCCAGTCT<br>CCCAGATATAA<br>GATTATAGAG<br>AAAAGGCAGA<br>GTGTGGCTTTT<br>TGGTGCAATCC<br>TATATCTGGCC<br>ATGCTACCCTT<br>TACTGGTACCA | EAGVAQSPRYK<br>IIEKRQSVAFWC<br>NPISGHATLYW<br>YQQILGQGPKL<br>LIQFQNNGVVD<br>DSQLPKDRFSA<br>ERLKGVDSTLK<br>IQPAKLEDSAV<br>YLCASSRGEPG<br>SGANVLTFGAG | TCTG<br>GCCA<br>TGCT<br>ACC<br>(SEQ ID NO: 373) |

TABLE 5-continued

| | | | | | |
|---|---|---|---|---|---|
| | CGTCCCTCCTCCTCTGCTTTT | RFSAERLKGVD | GCAGATCCTGG | SRLTVL | |
| | GCTCACAGTGACCCTGATTG | STLKIQPAKLED | GACAGGGCCC | (SEQ ID NO: | |
| | GGCAAAGCTCCCATCCTTCC | SAVYLCASSRG | AAAGCTTCTGA | 638) | |
| | CTGACCCTGCCATGGGCACC | EPGSGANVLTF | TTCAGTTTCAG | | |
| | AGGCTCCTCTGCTGGGCGGC | GAGSRLTVLED | AATAACGGTGT | | |
| | CCTCTGTCTCCTGGGAGCAG | LKNVFPPEVAV | AGTGGATGATT | | |
| | AACTCACAGAAGCTGGAGTT | FEPSEAEISHT | CACAGTTGCCT | | |
| | GCCCAGTCTCCCAGATATAA | QKATLVCLAT | AAGGATCGATT | | |
| | GATTATAGAGAAAAGGCAG | GFYPDHVELS | TTCTGCAGAGA | | |
| | AGTGTGGCTTTTTGGTGCAA | WWVNGKEVH | GGCTCAAAGG | | |
| | TCCTATATCTGGCCATGCTAC | SGVSTDPQPLK | AGTAGACTCCA | | |
| | CCTTTACTGGTACCAGCAGA | EQPALNDSRY | CTCTCAAGATC | | |
| | TCCTGGGACAGGGCCCAAAG | CLSSRLRVSAT | CAGCCTGCAA | | |
| | CTTCTGATTCAGTTTCAGAAT | FWQNPRNHFR | AGCTTGAGGA | | |
| | AACGGTGTAGTGGATGATTC | CQVQFYGLSE | CTCGGCCGTGT | | |
| | ACAGTTGCCTAAGGATCGAT | NDEWTQDRAK | ATCTCTGTGCC | | |
| | TTTCTGCAGAGAGGCTCAAA | PVTQIVSAEAW | AGCAGTCGAG | | |
| | GGAGTAGACTCCACTCTCAA | GRADCGFTSES | GGGAGCCAGG | | |
| | GATCCAGCCTGCAAAGCTTG | YQQGVLSATIL | CTCTGGGGCCA | | |
| | AGGACTCGGCCGTGTATCTC | YEILLGKATLY | ACGTCCTGACT | | |
| | TGTGCCAGCAGTCGAGGGGA | AVLVSALVLM | TTCGGGGCCGG | | |
| | GCCAGGCTCTGGGGCCAACG | AMVKRKDSRG | CAGCAGGCTG | | |
| | TCCTGACTTTCGGGGCCGGC | (SEQ ID NO: | ACCGTGCTGG | | |
| | AGCAGGCTGACCGTGCTGGA | 636) | (SEQ ID NO: | | |
| | GGACCTGAAAAACGTGTTC | | 637) | | |
| | CCACCCGAGGTCGCTGTGT | | | | |
| | TTGAGCCATCAGAAGCAGA | | | | |
| | GATCTCCCACACCCAAAAG | | | | |
| | GCCACACTGGTGTGCCTGG | | | | |
| | CCACAGGCTTCTACCCCGA | | | | |
| | CCACGTGGAGCTGAGCTGG | | | | |
| | TGGGTGAATGGGAAGGAG | | | | |
| | GTGCACAGTGGGGTCAGCA | | | | |
| | CAGACCCGCAGCCCCTCAA | | | | |
| | GGAGCAGCCCGCCCTCAAT | | | | |
| | GACTCCAGATACTGCCTGA | | | | |
| | GCAGCCGCCTGAGGGTCTC | | | | |
| | GGCCACCTTCTGGCAGAAC | | | | |
| | CCCCGCAACCACTTCCGCT | | | | |
| | GTCAAGTCCAGTTCTACGG | | | | |
| | GCTCTCGGAGAATGACGAG | | | | |
| | TGGACCCAGGATAGGGCCA | | | | |
| | AACCTGTCACCCAGATCGT | | | | |
| | CAGCGCCGAGGCCTGGGG | | | | |
| | TAGAGCAGACTGTGGCTTC | | | | |
| | ACCTCCGAGTCTTACCAGC | | | | |
| | AAGGGGTCCTGTCTGCCAC | | | | |
| | CATCCTCTATGAGATCTTG | | | | |
| | CTAGGGAAGGCCACCTTGT | | | | |
| | ATGCCGTGCTGGTCAGTGC | | | | |
| | CCTCGTGCTGATGGCCATG | | | | |
| | GTCAAGAGAAAGGATTCCA | | | | |
| | GAGGCTAG (SEQ ID NO: 372) | | | | |
| 21 | GGGGCAGTGTAGGCAGAGG | MQCFLSLCAM | GACGCTGGAG | DAGVTQSPTHL | TCTG |
| | AGGAACTGTATCACCACAGA | GPGLLCWALLC | TCACCCAAAGT | IKTRGQQVTLR | GGCA |
| | AACTTCTGCCTTCACACATCC | LLGAGLVDAG | CCCACACACCT | CSPKSGHDTVS | TGAC |
| | CTCCAGCTAGGCAGGACAGG | VTQSPTHLIKTR | GATCAAAACG | WYQQALGQGP | ACT |
| | TAGAGAGTCCAGTGTCCTGG | GQQVTLRCSPK | AGAGGACAGC | QFIFQYYEEEER | (SEQ |
| | AGCACTAGACCTAAGGAAGG | SGHDTVSWYQ | AAGTGACTCTG | QRGNFPDRFSG | ID NO: |
| | CTGCATGGGGAGGACAAAG | QALGQGPQFIF | AGATGCTCTCC | HQFPNYSSELN | 380) |
| | GACAGTGACATCACAGGATA | QYYEEEERQRG | TAAGTCTGGGC | VNALLLGDSAL | |
| | CCCCTCCCATCAGGAAAATC | NFPDRFSGHQF | ATGACACTGTG | YLCASSSGTDPS | |
| | AAGGCCCAGAACTCACTCGG | PNYSSELNVNA | TCCTGGTACCA | GANVLTFGAGS | |
| | CTCTTCCCCAGGAGAACCAA | LLLGDSALYLC | ACAGGCCCTG | RLTVL | |
| | GCCCTGAATCAGATGCAGTG | ASSSGTDPSGA | GGTCAGGGGC | (SEQ ID NO: | |
| | CTTCCTGTCCCTCTGTGCCAT | NVLTFGAGSRL | CCCAGTTTATC | 641) | |
| | GGGCCCCGGGCTCCTCTGCT | TVLEDLKNVFP | TTTCAGTATTA | | |
| | GGGCACTGCTTTGTCTCCTG | PEVAVFEPSEA | TGAGGAGGAA | | |
| | GGAGCAGGCTTAGTGGACGC | EISHTQKATLV | GAGAGACAGA | | |
| | TGGAGTCACCCAAAGTCCCA | CLATGFFPDH | GAGGCAACTTC | | |
| | CACACCTGATCAAAACGAGA | VELSWWVNG | CCTGATCGATT | | |
| | GGACAGCAAGTGACTCTGAG | KEVHSGVSTDP | CTCAGGTCACC | | |
| | ATGCTCTCCTAAGTCTGGGC | QPLKEQPALN | AGTTCCCTAAC | | |
| | ATGACACTGTGTCCTGGTAC | DSRYCLSSRLR | TATAGCTCTGA | | |
| | CAACAGGCCCTGGGTCAGGG | VSATFWQNPR | GCTGAATGTGA | | |
| | GCCCCAGTTTATCTTTCAGTA | NHFRCQVQFY | ACGCCTTGTTG | | |
| | TTATGAGGAGGAAGAGAGA | GLSENDEWTQ | CTGGGGGACTC | | |
| | CAGAGAGGCAACTTCCCTGA | DRAKPVTQIVS | GGCCCTCTATC | | |
| | TCGATTCTCAGGTCACCAGT | AEAWGRADCG | TCTGTGCCAGC | | |

TABLE 5-continued

| | | | | | |
|---|---|---|---|---|---|
| | TCCCTAACTATAGCTCTGAG<br>CTGAATGTGAACGCCTTGTT<br>GCTGGGGGACTCGGCCCTCT<br>ATCTCTGTGCCAGCAGCTCC<br>GGGACAGACCCCTCTGGGGC<br>CAACGTCCTGACTTTCGGGG<br>CCGGCAGCAGGCTGACCGTG<br>CTGGAGGACCTGAAAAACG<br>TGTTCCCACCCGAGGTCGC<br>TGTGTTTGAGCCATCAGAA<br>GCAGAGATCTCCCACACCC<br>AAAAGGCCACACTGGTGTG<br>CCTGGCCACAGGCTTCTTC<br>CCTGACCACGTGGAGCTGA<br>GCTGGTGGGTGAATGGGA<br>AGGAGGTGCACAGTGGGG<br>TCAGCACAGACCCGCAGCC<br>CCTCAAGGAGCAGCCCGCC<br>CTCAATGACTCCAGATACT<br>GCCTGAGCAGCCGCCTGAG<br>GGTCTCGGCCACCTTCTGG<br>CAGAACCCCCGCAACCACT<br>TCCGCTGTCAAGTCCAGTT<br>CTACGGGCTCTCGGAGAAT<br>GACGAGTGGACCCAGGATA<br>GGGCCAAACCTGTCACCCA<br>GATCGTCAGCGCCGAGGCC<br>TGGGGTAGAGCAGACTGTG<br>GCTTCACCTCCGAGTCTTA<br>CCAGCAAGGGGTCCTGTCT<br>GCCACCATCCTCTATGAGA<br>TCTTGCTAGGGAAGGCCAC<br>CTTGTATGCCGTGCTGGTC<br>AGTGCCCTCGTGCTGATGG<br>CCATGGTCAAGAGAAAGGA<br>TTCCAGAGGCTAG (SEQ ID NO: 379) | FTSESYQQGVL<br>SATILYEILLG<br>KATLYAVLVS<br>ALVLMAMVK<br>RKDSRG<br>(SEQ ID NO: 639) | AGCTCCGGGA<br>CAGACCCCTCT<br>GGGGCCAACG<br>TCCTGACTTTC<br>GGGGCCGGCA<br>GCAGGCTGAC<br>CGTGCTGG<br>(SEQ ID NO: 640) | | |
| 22 | GGGGTTTGTACACTTCAGCC<br>CTCTGAGCTGAAGTGGGAGT<br>GGTTTCTCTCCTGAAAATGTT<br>TCTGAGGCCCAAATAGCTGA<br>AGAGGTGGAGACGTTACAGA<br>AACCACCTGGAGCCCCCAGA<br>ACTGGCAGACACCTGCCTGA<br>TGCTGCCATGGGCCCCCAGC<br>TCCTTGGCTATGTGGTCCTTT<br>GCCTTCTAGGAGCAGGCCCC<br>CTGGAAGCCCAAGTGACCCA<br>GAACCCAAGATACCTCATCA<br>CAGTGACTGGAAAGAAGTTA<br>ACAGTGACTTGTTCTCAGAA<br>TATGAACCATGAGTATATGT<br>CCTGGTATCGACAAGACCCA<br>GGGCTGGGCTTAAGGCAGAT<br>CTACTATTCAATGAATGTTG<br>AGGTGACTGATAAGGGAGAT<br>GTTCCTGAAGGGTACAAAGT<br>CTCTCGAAAAGAGAAGAGG<br>AATTTCCCCCTGATCCTGGA<br>GTCGCCCAGCCCCAACCAGA<br>CCTCTCTGTACTTCTGTGCCA<br>GCAGTACCGGACAGAATATA<br>GGCGGGGAGCTGTTTTTTGG<br>AGAAGGCTCTAGGCTGACCG<br>TACTGGAGGACCTGAAAAA<br>CGTGTTCCCACCCGAGGTC<br>GCTGTGTTTGAGCCATCAG<br>AAGCAGAGATCTCCCACAC<br>CCAAAAGGCCACACTGGTG<br>TGCCTGGCCACAGGCTTCT<br>ACCCCGACCACGTGGAGCT<br>GAGCTGGTGGGTGAATGG<br>GAAGGAGGTGCACAGTGG<br>GGTCAGCACAGACCCGCAG<br>CCCCTCAAGGAGCAGCCCG<br>CCCTCAATGACTCCAGATA<br>CTGCCTGAGCAGCCGCCTG<br>AGGGTCTCGGCCACCTTCT<br>GGCAGAACCCCCGCAACCA | MGPQLLGYVV<br>LCLLGAGPLEA<br>QVTQNPRYLIT<br>VTGKKLTVTCS<br>QNMNHEYMSW<br>YRQDPGLGLRQ<br>IYYSMNVEVTD<br>KGDVPEGYKVS<br>RKEKRNFPLILE<br>SPSPNQTSLYFC<br>ASSTGQNIGGE<br>LFFGEGSRLTVL<br>EDLKNVFPPEV<br>AVFEPSEAEIS<br>HTQKATLVCL<br>ATGFYPDHVE<br>LSWWVNGKE<br>VHSGVSTDPQP<br>LKEQPALNDS<br>RYCLSSRLRVS<br>ATFWQNPRNH<br>FRCQVQFYGL<br>SENDEWTQDR<br>AKPVTQIVSAE<br>AWGRADCGFT<br>SESYQQGVLSA<br>TILYEILLGKA<br>TLYAVLVSALV<br>LMAMVKRKDS<br>RG<br>(SEQ ID NO: 642) | GAAGCCCAAG<br>TGACCCAGAA<br>CCCAAGATACC<br>TCATCACAGTG<br>ACTGGAAAGA<br>AGTTAACAGTG<br>ACTTGTTCTCA<br>GAATATGAAC<br>CATGAGTATAT<br>GTCCTGGTATC<br>GACAAGACCC<br>AGGGCTGGGC<br>TTAAGGCAGAT<br>CTACTATTCAA<br>TGAATGTTGAG<br>GTGACTGATAA<br>GGGAGATGTTC<br>CTGAAGGGTA<br>CAAAGTCTCTC<br>GAAAAGAGAA<br>GAGGAATTTCC<br>CCCTGATCCTG<br>GAGTCGCCCA<br>GCCCCAACCA<br>GACCTCTCTGT<br>ACTTCTGTGCC<br>AGCAGTACCG<br>GACAGAATAT<br>AGGCGGGGAG<br>CTGTTTTTTGG<br>AGAAGGCTCT<br>AGGCTGACCGT<br>ACTGG<br>(SEQ ID NO: 643) | EAQVTQNPRYL<br>ITVTGKKLTVT<br>CSQNMNHEYM<br>SWYRQDPGLGL<br>RQIYYSMNVEV<br>TDKGDVPEGYK<br>VSRKEKRNFPLI<br>LESPSPNQTSLY<br>FCASSTGQNIG<br>GELFFGEGSRLT<br>VL<br>(SEQ ID NO: 644) | ATGA<br>ACCA<br>TGAG<br>TAT<br>(SEQ ID NO: 387) |

TABLE 5-continued

| | | | | | |
|---|---|---|---|---|---|
| | **CTTCCGCTGTCAAGTCCAGTTCTACGGGCTCTCGGAGAATGACGAGTGGACCCAGGATAGGGCCAAACCTGTCACCCAGATCGTCAGCGCCGAGGCCTGGGGTAGAGCAGACTGTGGCTTCACCTCCGAGTCTTACCAGCAAGGGGTCCTGTCTGCCACCATCCTCTATGAGATCTTGCTAGGGAAGGCCACCTTGTATGCCGTGCTGGTCAGTGCCCTCGTGCTGATGGCCATGGTCAAGAGAAAGGATTCCAGAGGCTAG** (SEQ ID NO: 386) | | | | |
| 23 | TGGGAGAAACAGGAGATCTCCAAGGAAGGTTGACAGTCAGCACTGGGATCGTCTGTGTAAAGTGCTGCTGAAGCAGCCAGGTGGCATGTCCAGCCGACAATGCGAAAGGAAAAATGGTGCACATCAGAGTTGCTGCCATCTTAGACTTAACTCATCAGTATCAGGTGATCCTGAGGCTCAGTGATGTCACTGTGGGAACTGCTCTGTGGCGACAAGGACGTCCCTCATCCTCTGCTCCTGCTCACAGTGACCCTGATCTGGTAAAGCTCCCATCCTGCCCTGACCCTGCCATGGGCACCAGCCTCCTCTGCTGGATGGCCCTGTGTCTCCTGGGGGCAGATCACGCAGATACTGGAGTCTCCCAGGACCCCAGACACAAGATCACAAAGAGGGGACAGAATGTAACTTTCAGGTGTGATCCAATTTCTGAACACAACCGCCTTTATTGGTACCGACAGACCCTGGGGCAGGGCCCAGAGTTTCTGACTTACTTCCAGAATGAAGCTCAACTAGAAAAATCAAGGCTGCTCAGTGATCGGTTCTCTGCAGAGAGGCCTAAGGGATCTTTCTCCACCTTGGAGATCCAGCGCACAGAGCAGGGGGACTCGGCCATGTATCTCTGTGCCAGCAGCACACATGAAAAGACAGGGTGGAAATCACCCCTCCACTTTGGGAATGGGACCAGGCTCACTGTGACAGAG**GACCTGAACAAGGTGTTCCCACCCGAGGTCGCTGTGTTTGAGCCATCAGAAGCAGAGATCTCCCACACCCAAAAGGCCACACTGGTGTGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCCGTCACCCAGATCGTCAGCGCCGAGGCCTGGGGTAGAGCAGACTGTGGCTTTACCTCGGTGTCCTACCAGCAAGGGGTCCTGTCTGCCACCATCCTCTATGAGATCCTGCTAGGGAAGGCCACCCTGTATGCTGTGCTGGTCAGCGCCCTTGTGTTGATGGCCATGGTCAAGAGAAAGGATTTCTGA** (SEQ ID NO: 393) | MVHIRVAAILDLTHQYQVILRLSDVTVGTALWRQGRPSSSAPAHSDPDLVKLPSCPDPAMGTSLLCWMALCLLGADHADTGVSQDPRHKITKRGQNVTFRCDPISEHNRLYWYRQTLGQGPEFLTYFQNEAQLEKSRLLSDRFSAERPKGSFSTLEIQRTEQGDSAMYLCASSTHEKTGWKSPLHFGNGTRLTVT**EDLNKVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF** (SEQ ID NO: 645) | GATACTGGAGTCTCCCAGGACCCCAGACACAAGATCACAAAGAGGGGACAGAATGTAACTTTCAGGTGTGATCCAATTTCTGAACACAACCGCCTTTATTGGTACCGACAGACCCTGGGGCAGGGCCCAGAGTTTCTGACTTACTTCCAGAATGAAGCTCAACTAGAAAAATCAAGGCTGCTCAGTGATCGGTTCTCTGCAGAGAGGCCTAAGGGATCTTTCTCCACCTTGGAGATCCAGCGCACAGAGCAGGGGGACTCGGCCATGTATCTCTGTGCCAGCAGCACACATGAAAAGACAGGGTGGAAATCACCCCTCCACTTTGGGAATGGGACCAGGCTCACTGTGACAG (SEQ ID NO: 646) | DTGVSQDPRHKITKRGQNVTFRCDPISEHNRLYWYRQTLGQGPEFLTYFQNEAQLEKSRLLSDRFSAERPKGSFSTLEIQRTEQGDSAMYLCASSTHEKTGWKSPLHFGNGTRLTVT (SEQ ID NO: 647) | TCTGAACACAACCGC (SEQ ID NO: 394) |

TABLE 5-continued

| | | | | | |
|---|---|---|---|---|---|
| 24 | GGGGCCAGACCTTGCCTGTGGGGCCATGGGAGCTCAAAATGCCCCTCCTTTCCTCCACAGGACCAGATGCCTGAGCTAGGAAAGGCCTCATTCCTGCTGTGATCCTGCCATGGATACCTGGCTCGTATGCTGGGCAATTTTTAGTCTCTTGAAAGCAGGACTCACAGAACCTGAAGTCACCCAGACTCCCAGCCATCAGGTCACACAGATGGGACAGGAAGTGATCTTGCGCTGTGTCCCCATCTCTAATCACTTATACTTCTATTGGTACAGACAAATCTTGGGGCAGAAAGTCGAGTTTCTGGTTTCCTTTTATAATAATGAAATCTCAGAGAAGTCTGAAATATTCGATGATCAATTCTCAGTTGAAAGGCCTGATGGATCAAATTTCACTCTGAAGATCCGGTCCACAAAGCTGGAGGACTCAGCCATGTACTTCTGTGCCAGCAGTACGCACTCTGACAGGAACTTGAACACTGAAGCTTTCTTTGGACAAGGCACCAGACTCACAGTTGTAGAGGACCTGAACAAGGTGTTCCCACCCGAGGTCGCTGTGTTTGAGCCATCAGAAGCAGAGATCTCCCACACCCAAAAGGCCACACTGGTGTGCCTGGCCACAGGCTTCTTCCCTGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCCGTCACCCAGATCGTCAGCGCCGAGGCCTGGGGTAGAGCAGACTGTGGCTTTACCTCGGTGTCCTACCAGCAAGGGGTCCTGTCTGCCACCATCCTCTATGAGATCCTGCTAGGGAAGGCCACCCTGTATGCTGTGCTGGTCAGCGCCCTTGTGTTGATGGCCATGGTCAAGAGAAAGGATTTCTGA (SEQ ID NO: 400) | MDTWLVCWAIFSLLKAGLTEPEVTQTPSHQVTQMGQEVILRCVPISNHLYFYWYRQILGQKVEFLVSFYNNEISEKSEIFDDQFSVERPDGSNFTLKIRSTKLEDSAMYFCASSTHSDRNLNTEAFFGQGTRLTVVEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF (SEQ ID NO: 648) | GAACCTGAAGTCACCCAGACTCCCAGCCATCAGGTCACACAGATGGGACAGGAAGTGATCTTGCGCTGTGTCCCCATCTCTAATCACTTATACTTCTATTGGTACAGACAAATCTTGGGGCAGAAAGTCGAGTTTCTGGTTTCCTTTTATAATAATGAAATCTCAGAGAAGTCTGAAATATTCGATGATCAATTCTCAGTTGAAAGGCCTGATGGATCAAATTTCACTCTGAAGATCCGGTCCACAAAGCTGGAGGACTCAGCCATGTACTTCTGTGCCAGCAGTACGCACTCTGACAGGAACTTGAACACTGAAGCTTTCTTTGGACAAGGCACCAGACTCACAGTTGTAG (SEQ ID NO: 649) | EPEVTQTPSHQVTQMGQEVILRCVPISNHLYFYWYRQILGQKVEFLVSFYNNEISEKSEIFDDQFSVERPDGSNFTLKIRSTKLEDSAMYFCASSTHSDRNLNTEAFFGQGTRLTVV (SEQ ID NO: 650) | TCTAATCACTTATAC (SEQ ID NO: 401) |
| 25 | TGGGAGACCTTGCCTGTGGGGCCATGGGAGCTCAAAATGCCCCTCCTTTCCTCCACAGGACCAGATGCCTGAGCTAGGAAAGGCCTCATTCCTGCTGTGATCCTGCCATGGATACCTGGCTCGTATGCTGGGCAATTTTTAGTCTCTTGAAAGCAGGACTCACAGAACCTGAAGTCACCCAGACTCCCAGCCATCAGGTCACACAGATGGGACAGGAAGTGATCTTGCGCTGTGTCCCCATCTCTAATCACTTATACTTCTATTGGTACAGACAAATCTTGGGGCAGAAAGTCGAGTTTCTGGTTTCCTTTTATAATAATGAAATCTCAGAGAAGTCTGAAATATTCGATGATCAATTCTCAGTTGAAAGGCCTGATGGATCAAATTTCACTCTGAAGATCCGGTCCACAAAGCTGGAGGACTCAGCCATGTACTTCTGTGCCAGCAGCGTACAGGCTACGGGCC | MDTWLVCWAIFSLLKAGLTEPEVTQTPSHQVTQMGQEVILRCVPISNHLYFYWYRQILGQKVEFLVSFYNNEISEKSEIFDDQFSVERPDGSNFTLKIRSTKLEDSAMYFCASSVQATGHGYTFGSGTRLTVVEDLNKVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAK | GAACCTGAAGTCACCCAGACTCCCAGCCATCAGGTCACACAGATGGGACAGGAAGTGATCTTGCGCTGTGTCCCCATCTCTAATCACTTATACTTCTATTGGTACAGACAAATCTTGGGGCAGAAAGTCGAGTTTCTGGTTTCCTTTTATAATAATGAAATCTCAGAGAAGTCTGAAATATTCGATGATCAATTCTCAGTTGAAAGGCCTGATGGATCAAATTTCACTCTGAAGATCCGGTCCACA | EPEVTQTPSHQVTQMGQEVILRCVPISNHLYFYWYRQILGQKVEFLVSFYNNEISEKSEIFDDQFSVERPDGSNFTLKIRSTKLEDSAMYFCASSVQATGHGYTFGSGTRLTVV (SEQ ID NO: 653) | TCTAATCACTTATAC (SEQ ID NO: 08) |

TABLE 5-continued

| | | | | | |
|---|---|---|---|---|---|
| | ATGGCTACACCTTCGGTTCGGGGACCAGGTTAACCGTTGTAGAGGACCTGAACAAGGTGTTCCCACCCGAGGTCGCTGTGTTTGAGCCATCAGAAGCAGAGATCTCCCACACCCAAAAGGCCACACTGGTATGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTGGCCACCTTCTGGCAGAACCCCCGCAACCACTTCCGCTGTCAAGTCCAGTTCTACGGGCTCTCGGAGAATGACGAGTGGACCCAGGATAGGGCCAAACCCGTCACCCAGATCGTCAGCGCCGAGGCCTGGGGTAGAGCAGACTGTGGCTTTACCTCGGTGTCCTACCAGCAAGGGGTCCTGTCTGCCACCATCCTCTATGAGATCCTGCTAGGGAAGGCCACCCTGTATGCTGTGCTGGTCAGCGCCCTTGTGTTGATGGCCATGGTCAAGAGAAAGGATTTCTGA (SEQ ID NO: 407) | PVTQIVSAEAWGRADCGFTSVSYQQGVLSATILYEILLGKATLYAVLVSALVLMAMVKRKDF (SEQ ID NO: 651) | AAGCTGGAGGACTCCAGCCATGTACTTCTGTGCCAGCAGCGTACAGGCTACGGGCCATGGCTACACCTTCGGTTCGGGGACCAGGTTAACCGTTGTAG (SEQ ID NO: 652) | | |
| 26 | TGGGGTCACTGTGGGAACTGCCCTGTGGAGACAAGGACGGCCCTTATCCTCTGCTTCTGTTCACAGTGACACTGATCTGGTAAAGCCCCCATCCTGGCCTGACCCTGCCATGGGCACCAGGCTCCTCTGCTGGGTGGTCCTGGGTTTCCTAGGGACAGATCACACAGGTGCTGGAGTCTCCCAGTCCCCTAGGTACAAAGTCGCAAAGAGAGGACAGGATGTAGCTCTCAGGTGTGATCCAATTTCGGGTCATGTATCCCTTTTTTGGTACCAACAGGCCCTGGGGGCAGGGGCCAGAGTTTCTGACTTATTTCCAGAATGAAGCTCAACTAGACAAATCGGGGCTGCCCAGTGATCGCTTCTTTGCAGAAAGGCCTGAGGGATCCGTCTCCACTCTGAAGATCCAGCGCACACAGCAGGAGGACTCCGCCGTGTATCTCTGTGCCAGCACCCCCTCTGGCTATAACTCTTGGGAGCAGTTCTTCGGGCCAGGGACACGGCTCACCGTGCTAGAGGACCTGAAAAACGTGTTCCCACCCGAGGTCGCTGTGTTTGAGCCATCAGAAGCAGAGATCTCCCACACCCAAAAGGCCACACTGGTGTGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCCGTCACCCAGATCGTCAGCGCCGAGGCCTGGGGTAGAGCAGACTGTGGCTTTACCTCGGTGTCCTACCAGCAAGGGGTC | MGTRLLCWVVLGFLGTDHTGAGVSQSPRYKVAKRGQDVALRCDPISGHVSLFWYQQALGQGPEFLTYFQNEAQLDKSGLPSDRFFAERPEGSVSTLKIQRTQQEDSAVYLCASTPSGYNSWEQFFGPGTRLTVLEDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF (SEQ ID NO: 654) | GGTGCTGGAGTCTCCCAGTCCCCTAGGTACAAAGTCGCAAAGAGAGGACAGGATGTAGCTCTCAGGTGTGATCCAATTTCGGGTCATGTATCCCTTTTTTGGTACCAACAGGCCCTGGGGCAGGGGCCAGAGTTTCTGACTTATTTCCAGAATGAAGCTCAACTAGACAAATCGGGGCTGCCCAGTGATCGCTTCTTTGCAGAAAGGCCTGAGGGATCCGTCTCCACTCTGAAGATCCAGCGCACACAGCAGGAGGACTCCGCCGTGTATCTCTGTGCCAGCACCCCCTCTGGCTATAACTCTTGGGAGCAGTTCTTCGGGCCAGGGACACGGCTCACCGTGCTAG (SEQ ID NO: 655) | GAGVSQSPRYKVAKRGQDVALRCDPISGHVSLFWYQQALGQGPEFLTYFQNEAQLDKSGLPSDRFFAERPEGSVSTLKIQRTQQEDSAVYLCASTPSGYNSWEQFFGPGTRLTVL (SEQ ID NO: 656) | TCGGGTCATGTATCC (SEQ ID NO: 415) |

TABLE 5-continued

| | | | | | |
|---|---|---|---|---|---|
| | **CTGTCTGCCACCATCCTCT**<br>**ATGAGATCCTGCTAGGGAA**<br>**GGCCACCCTGTATGCTGTG**<br>**CTGGTCAGCGCCCTTGTGT**<br>**TGATGGCCATGGTCAAGAG**<br>**AAAGGATTTCTGA** (SEQ ID NO: 414) | | | | |
| 27 | GTGTTGCGTTTGTACACTTCA<br>GCCCTCTGAGCTGAAGTGGG<br>AGTGGTTTCTCTCCTGAAAA<br>TGTTTCTGAGGCCCAAATAG<br>CTGAAGAGGTGGAGACGTTA<br>CAGAAACCACCTGGAGCCCC<br>CAGAACTGGCAGACACCTGC<br>CTGATGCTGCCATGGGCCCC<br>CAGCTCCTTGGCTATGTGGT<br>CCTTTGCCTTCTAGGAGCAG<br>GCCCCCTGGAAGCCCAAGTG<br>ACCCAGAACCCAAGATACCT<br>CATCACAGTGACTGGAAAGA<br>AGTTAACAGTGACTTGTTCT<br>CAGAATATGAACCATGAGTA<br>TATGTCCTGGTATCGACAAG<br>ACCCAGGGCTGGGCTTAAGG<br>CAGATCTACTATTCAATGAA<br>TGTTGAGGTGACTGATAAGG<br>GAGATGTTCCTGAAGGGTAC<br>AAAGTCTCTCGAAAAGAGAA<br>GAGGAATTTCCCCCTGATCC<br>TGGAGTCGCCCAGCCCCAAC<br>CAGACCTCTCTGTACTTCTGT<br>GCCACCGCCCCCAGGGGTAG<br>CAATCAGCCCCAGCATTTTG<br>GTGATGGGACTCGACTCTCC<br>ATCCTAGAG**GACCTGAACA**<br>**AGGTGTTCCCACCCGAGGT**<br>**CGCTGTGTTTGAGCCATCA**<br>**GAAGCAGAGATCTCCCACA**<br>**CCCAAAAGGCCACACTGGT**<br>**GTGCCTGGCCACAGGCTTC**<br>**TACCCCGACCACGTGGAGC**<br>**TGAGCTGGTGGGTGAATGG**<br>**GAAGGAGGTGCACAGTGG**<br>**GGTCAGCACAGACCCGCAG**<br>**CCCCTCAAGGAGCAGCCCG**<br>**CCCTCAATGACTCCAGATA**<br>**CTGCCTGAGCAGCCGCCTG**<br>**AGGGTCTCGGCCACCTTCT**<br>**GGCAGAACCCCCGCAACCA**<br>**CTTCCGCTGTCAAGTCCAG**<br>**TTCTACGGGCTCTCGGAGA**<br>**ATGACGAGTGGACCCAGGA**<br>**TAGGGCCAAACCCGTCACC**<br>**CAGATCGTCAGCGCCGAGG**<br>**CCTGGGGTAGAGCAGACTG**<br>**TGGCTTTACCTCGGTGTCC**<br>**TACCAGCAAGGGGTCCTGT**<br>**CTGCCACCATCCTCTATGA**<br>**GATCCTGCTAGGGAAGGCC**<br>**ACCCTGTATGCTGTGCTGG**<br>**TCAGCGCCCTTGTGTTGAT**<br>**GGCCATGGTCAAGAGAAAG**<br>**GATTTCTGA** (SEQ ID NO: 421) | MGPQLLGYVV<br>LCLLGAGPLEA<br>QVTQNPRYLIT<br>VTGKKLTVTCS<br>QNMNHEYMSW<br>YRQDPGLGLRQ<br>IYYSMNVEVTD<br>KGDVPEGYKVS<br>RKEKRNFPLILE<br>SPSPNQTSLYFC<br>ATAPRGSNQPQ<br>HFGDGTRLSIL**E**<br>**DLNKVFPPEVA**<br>**VFEPSEAEISH**<br>**TQKATLVCLA**<br>**TGFYPDHVELS**<br>**WWVNGKEVH**<br>**SGVSTDPQPLK**<br>**EQPALNDSRY**<br>**CLSSRLRVSAT**<br>**FWQNPRNHFR**<br>**CQVQFYGLSE**<br>**NDEWTQDRAK**<br>**PVTQIVSAEAW**<br>**GRADCGFTSVS**<br>**YQQGVLSATIL**<br>**YEILLGKATLY**<br>**AVLVSALVLM**<br>**AMVKRKDF**<br>(SEQ ID NO: 657) | GAAGCCCAAG<br>TGACCCAGAA<br>CCCAAGATACC<br>TCATCACAGTG<br>ACTGGAAAGA<br>AGTTAACAGTG<br>ACTTGTTCTCA<br>GAATATGAAC<br>CATGAGTATAT<br>GTCCTGGTATC<br>GACAAGACCC<br>AGGGCTGGGC<br>TTAAGGCAGAT<br>CTACTATTCAA<br>TGAATGTTGAG<br>GTGACTGATAA<br>GGGAGATGTTC<br>CTGAAGGGTA<br>CAAAGTCTCTC<br>GAAAAGAGAA<br>GAGGAATTTCC<br>CCCTGATCCTG<br>GAGTCGCCCA<br>GCCCCAACCA<br>GACCTCTCTGT<br>ACTTCTGTGCC<br>ACCGCCCCCAG<br>GGGTAGCAAT<br>CAGCCCCAGC<br>ATTTTGGTGAT<br>GGGACTCGACT<br>CTCCATCCTAG<br>(SEQ ID NO: 658) | EAQVTQNPRYL<br>ITVTGKKLTVT<br>CSQNMNHEYM<br>SWYRQDPGLGL<br>RQIYYSMNVEV<br>TDKGDVPEGYK<br>VSRKEKRNFPLI<br>LESPSPNQTSLY<br>FCATAPRGSNQ<br>PQHFGDGTRLSI<br>L<br>(SEQ ID NO: 659) | ATGA<br>ACCA<br>TGAG<br>TAT<br>(SEQ ID NO: 422) |
| 28 | GGGGGGGATTCTGTGATCAG<br>TCATCCCTCCTCGCTGGTGA<br>ATGGAGGCAGTGGTCACAAC<br>TCTCCCCAGAGAAGGTGGTG<br>TGAGGCCATCACGGAAGATG<br>CTGCTGCTTCTGCTGCTTCTG<br>GGGCCAGGCTCCGGGCTTGG<br>TGCTGTCGTCTCTCAACATCC<br>GAGCTGGGTTATCTGTAAGA<br>GTGGAACCTCTGTGAAGATC<br>GAGTGCCGTTCCCTGGACTT<br>TCAGGCCACAACTATGTTTT<br>GGTATCGTCAGTTCCCGAAA<br>CAGAGTCTCATGCTGATGGC | MEAVVTTLPRE<br>GGVRPSRKMLL<br>LLLLGPGSGL<br>GAVVSQHPSW<br>VICKSGTSVKIE<br>CRSLDFQATTM<br>FWYRQFPKQSL<br>MLMATSNEGS<br>KATYEQGVEK<br>DKFLINHASLTL<br>STLTVTSAHPE<br>DSSFYICRAWG<br>GSSYNEQFFGP<br>GTRLTVL**EDLK** | GGTGCTGTCGT<br>CTCTCAACATC<br>CGAGCTGGGTT<br>ATCTGTAAGAG<br>TGGAACCTCTG<br>TGAAGATCGA<br>GTGCCGTTCCC<br>TGGACTTTCAG<br>GCCACAACTAT<br>GTTTTGGTATC<br>GTCAGTTCCCG<br>AAACAGAGTC<br>TCATGCTGATG<br>GCAACTTCCAA | GAVVSQHPSW<br>VICKSGTSVKIE<br>CRSLDFQATTM<br>FWYRQFPKQSL<br>MLMATSNEGS<br>KATYEQGVEK<br>DKFLINHASLTL<br>STLTVTSAHPE<br>DSSFYICRAWG<br>GSSYNEQFFGP<br>GTRLTVL<br>(SEQ ID NO: 662) | GACT<br>TTCA<br>GGCC<br>ACAA<br>CT<br>(SEQ ID NO: 429) |

TABLE 5-continued

| | | | | | |
|---|---|---|---|---|---|
| | AACTTCCAATGAGGGCTCCAAGGCCACATACGAGCAAGGCGTCGAGAAGGACAAGTTTCTCATCAACCATGCAAGCCTGACCTTGTCCACTCTGACAGTGACCAGTGCCCATCCTGAAGACAGCAGCTTCTACATCTGCAGGGCCTGGGGCGGGAGCTCCTACAATGAGCAGTTCTTCGGGCCAGGGACACGGCTCACCGTGCTAGAGGACCTGAAAAACGTGTTCCCACCCGAGGTCGCTGTGTTTGAGCCATCAGAAGCAGAGATCTCCCACACCCAAAAGGCCACACTGGTATGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCCGTCACCCAGATCGTCAGCGCCGAGGCCTGGGGTAGAGCAGACTGTGGCTTTACCTCGGTGTCCTACCAGCAAGGGGTCCTGTCTGCCACCATCCTCTATGAGATCCTGCTAGGGAAGGCCACCCTGTATGCTGTGCTGGTCAGCGCCCTTGTGTTGATGGCCATGGTCAAGAGAAAGGATTTCTGA (SEQ ID NO: 428) | NVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF (SEQ ID NO: 660) | TGAGGGCTCCAAGGCCACATACGAGCAAGGCGTCGAGAAGGACAAGTTTCTCATCAACCATGCAAGCCTGACCTTGTCCACTCTGACAGTGACCAGTGCCCATCCTGAAGACAGCAGCTTCTACATCTGCAGGGCCTGGGGCGGGAGCTCCTACAATGAGCAGTTCTTCGGGCCAGGGACACGGCTCACCGTGCTAG (SEQ ID NO: 661) | | |
| 29 | TGGGGAGTCATCCCTCCTCGCTGGTGAATGGAGGCAGTGGTCACAACTCTCCCCAGAGAAGGTGGTGTGAGGCCATCACGGAAGATGCTGCTGCTTCTGCTGCTTCTGGGGCCAGGCTCCGGGCTTGGTGCTGTCGTCTCTCAACATCCGAGCAGGGTTATCTGTAAGAGTGGAACCTCTGTGAAGATCGAGTGCCGTTCCCTGGACTTTCAGGCCACAACTATGTTTTGGTATCGTCAGTTCCCGAAACAGAGTCTCATGCTGATGGCAACTTCCAATGAGGGCTCCAAGGCCACATACGAGCAAGGCGTCGAGAAGGACAAGTTTCTCATCAACCATGCAAGCCTGACCTTGTCCACTCTGACAGTGACCAGTGCCCATCCTGAAGACAGCAGCTTCTACATCTGCAGTGCTAGAATTGGACAGGGTTTTATGAATGAGCAGTTCTTCGGGCCAGGGACACGGCTCACCGTGCTAGAGGACCTGAAAAACGTGTTCCCACCCGAGGTCGCTGTGTTTGAGCCATCAGAAGCAGAGATCTCCCACACCCAAAAGGCCACACTGGTGTGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGT | MEAVVTTLPREGGVRPSRKMLLLLLLLGPGSGLGAVVSQHPSRVICKSGTSVKIECRSLDFQATTMFWYRQFPKQSLMLMATSNEGSKATYEQGVEKDKFLINHASLTLSTLTVTSAHPEDSSFYICSARIGQGFMNEQFFGPGTRLTVLEDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG (SEQ ID NO: 663) | GGTGCTGTCGTCTCTCAACATCCGAGCAGGGTTATCTGTAAGAGTGGAACCTCTGTGAAGATCGAGTGCCGTTCCCTGGACTTTCAGGCCACAACTATGTTTTGGTATCGTCAGTTCCCGAAACAGAGTCTCATGCTGATGGCAACTTCCAATGAGGGCTCCAAGGCCACATACGAGCAAGGCGTCGAGAAGGACAAGTTTCTCATCAACCATGCAAGCCTGACCTTGTCCACTCTGACAGTGACCAGTGCCCATCCTGAAGACAGCAGCTTCTACATCTGCAGTGCTAGAATTGGACAGGGTTTTATGAATGAGCAGTTCTTCGGGCCAGGGACACGGCTCACCGTGCTAG (SEQ ID NO: 664) | GAVVSQHPSRVICKSGTSVKIECRSLDFQATTMFWYRQFPKQSLMLMATSNEGSKATYEQGVEKDKFLINHASLTLSTLTVTSAHPEDSSFYICSARIGQGFMNEQFFGPGTRLTVL (SEQ ID NO: 665) | GACTTTCAGGCCACAACT (SEQ ID NO: 436) |

TABLE 5-continued

| | | | | | |
|---|---|---|---|---|---|
| | **CAAGTCCAGTTCTACGGGC**<br>**TCTCGGAGAATGACGAGTG**<br>**GACCCAGGATAGGGCCAAA**<br>**CCTGTCACCCAGATCGTCA**<br>**GCGCCGAGGCCTGGGGTA**<br>**GAGCAGACTGTGGCTTCAC**<br>**CTCCGAGTCTTACCAGCAA**<br>**GGGGTCCTGTCTGCCACCA**<br>**TCCTCTATGAGATCTTGCT**<br>**AGGGAAGGCCACCTTGTAT**<br>**GCCGTGCTGGTCAGTGCCC**<br>**TCGTGCTGATGGCCATGGT**<br>**CAAGAGAAAGGATTCCAGA**<br>**GGCTAG** (SEQ ID NO: 435) | | | | |
| 30 | AGTCATGGGCAAAGATTACC<br>ACCAGGGGGCAGACTAGGG<br>CATCCTTGGGATTCTGTGATC<br>AGTCATCCCTCCTCGCTGGT<br>GAATGGAGGCAGTGGTCACA<br>ACTCTCCCCAGAGAAGGTGG<br>TGTGAGGCCATCACGGAAGA<br>TGCTGCTGCTTCTGCTGCTTC<br>TGGGGCCAGGCTCCGGGCTT<br>GGTGCTGTCGTCTCTCAACA<br>TCCGAGCAGGGTTATCTGTA<br>AGAGTGGAACCTCTGTGAAG<br>ATCGAGTGCCGTTCCCTGGA<br>CTTTCAGGCCACAACTATGT<br>TTTGGTATCGTCAGTTCCCGA<br>AAAAGAGTCTCATGCTGATG<br>GCAACTTCCAATGAGGGCTC<br>CAAGGCCACATACGAGCAAG<br>GCGTCGAGAAGGACAAGTTT<br>CTCATCAACCATGCAAGCCT<br>GACCTTGTCCACTCTGACAG<br>TGACCAGTGCCCATCCTGAA<br>GACAGCAGCTTCTACATCTG<br>CAGTGCTCCTGGGTGGCGTG<br>GCACTGAAGCTTTCTTTGGA<br>CAAGGCACCAGACTCACAGT<br>TGTAGAG**GACCTGAACAAG**<br>**GTGTTCCCACCCGAGGTCG**<br>**CTGTGTTTGAGCCATCAGA**<br>**AGCAGAGATCTCCCACACC**<br>**CAAAAGGCCACACTGGTGT**<br>**GCCTGGCCACAGGCTTCTT**<br>**CCCTGACCACGTGGAGCTG**<br>**AGCTGGTGGGTGAATGGG**<br>**AAGGAGGTGCACAGTGGG**<br>**GTCAGCACAGACCCGCAGC**<br>**CCCTCAAGGAGCAGCCCGC**<br>**CCTCAATGACTCCAGATAC**<br>**TGCCTGAGCAGCCGCCTGA**<br>**GGGTCTCGGCCACCTTCTG**<br>**GCAGAACCCCCGCAACCAC**<br>**TTCCGCTGTCAAGTCCAGT**<br>**TCTACGGGCTCTCGGAGAA**<br>**TGACGAGTGGACCCAGGAT**<br>**AGGGCCAAACCCGTCACCC**<br>**AGATCGTCAGCGCCGAGGC**<br>**CTGGGGTAGAGCAGACTGT**<br>**GGCTTTACCTCGGTGTCCT**<br>**ACCAGCAAGGGGTCCTGTC**<br>**TGCCACCATCCTCTATGAG**<br>**ATCCTGCTAGGGAAGGCCA**<br>**CCCTGTATGCTGTGCTGGT**<br>**CAGCGCCCTTGTGTTGATG**<br>**GCCATGGTCAAGAGAAAGG**<br>**ATTTCTGA** (SEQ ID NO: 442) | MEAVVTTLPRE<br>GGVRPSRKMLL<br>LLLLGPGSGL<br>GAVVSQHPSRV<br>ICKSGTSVKIEC<br>RSLDFQATTMF<br>WYRQFPKKSL<br>MLMATSNEGS<br>KATYEQGVEK<br>DKFLINHASLTL<br>STLTVTSAHPE<br>DSSFYICSAPG<br>WRGTEAFFGQG<br>TRLTVV**EDLNK**<br>**VFPPEVAVFEP**<br>**SEAEISHTQKA**<br>**TLVCLATGFFP**<br>**DHVELSWWVN**<br>**GKEVHSGVST**<br>**DPQPLKEQPA**<br>**LNDSRYCLSSR**<br>**LRVSATFWQN**<br>**PRNHFRCQVQ**<br>**FYGLSENDEW**<br>**TQDRAKPVTQI**<br>**VSAEAWGRAD**<br>**CGFTSVSYQQ**<br>**GVLSATILYEI**<br>**LLGKATLYAV**<br>**LVSALVLMAM**<br>**VKRKDF**<br>(SEQ ID NO: 666) | GGTGCTGTCGT<br>CTCTCAACATC<br>CGAGCAGGGT<br>TATCTGTAAGA<br>GTGGAACCTCT<br>GTGAAGATCG<br>AGTGCCGTTCC<br>CTGGACTTTCA<br>GGCCACAACT<br>ATGTTTTGGTA<br>TCGTCAGTTCC<br>CGAAAAAGAG<br>TCTCATGCTGA<br>TGGCAACTTCC<br>AATGAGGGCT<br>CCAAGGCCAC<br>ATACGAGCAA<br>GGCGTCGAGA<br>AGGACAAGTTT<br>CTCATCAACCA<br>TGCAAGCCTGA<br>CCTTGTCCACT<br>CTGACAGTGAC<br>CAGTGCCCATC<br>CTGAAGACAG<br>CAGCTTCTACA<br>TCTGCAGTGCT<br>CCTGGGTGGCG<br>TGGCACTGAA<br>GCTTTCTTTGG<br>ACAAGGCACC<br>AGACTCACAGT<br>TGTAG<br>(SEQ ID NO: 667) | GAVVSQHPSRV<br>ICKSGTSVKIEC<br>RSLDFQATTMF<br>WYRQFPKKSL<br>MLMATSNEGS<br>KATYEQGVEK<br>DKFLINHASLTL<br>STLTVTSAHPE<br>DSSFYICSAPG<br>WRGTEAFFGQG<br>TRLTVV<br>(SEQ ID NO: 668) | GACT<br>TTCA<br>GGCC<br>ACAA<br>CT<br>(SEQ ID NO: 443) |
| 31 | GGGACTGGCGCAGCACCTCT<br>CAGCGGCAGTGGAAACCACA<br>GCCTAGTCCTCTCACCACTG<br>CAGACCAGAATCCTGCCCTG<br>GGCCTTGCCTGGTCTGCCTC<br>ACTCTGCCATGGGCTGCAGG<br>CTCCTCTGCTGTGTGGTCTTC<br>TGCCTCCTCCAAGCAGGTCC<br>CTTGGACACAGCTGTTTCCC | MGCRLLCCVVF<br>CLLQAGPLDTA<br>VSQTPKYLVTQ<br>MGNDKSIKCEQ<br>NLGHDTMYWY<br>KQDSKKFLKIM<br>FSYNNKELIINE<br>TVPNRFSPKSPD<br>KAHLNLHINSL | GACACAGCTGT<br>TTCCCAGACTC<br>CAAAATACCTG<br>GTCACACAGAT<br>GGGAAACGAC<br>AAGTCCATTAA<br>ATGTGAACAA<br>AATCTGGGCCA<br>TGATACTATGT | DTAVSQTPKYL<br>VTQMGNDKSIK<br>CEQNLGHDTM<br>YWYKQDSKKF<br>LKIMFSYNNKE<br>LIINETVPNRFSP<br>KSPDKAHLNLH<br>INSLELGDSAV<br>YFCASSQDGLE | CTGG<br>GCCA<br>TGAT<br>ACT<br>(SEQ ID NO: 450) |

TABLE 5-continued

| | | | | | |
|---|---|---|---|---|---|
| | AGACTCCAAAATACCTGGTCACACAGATGGGAAACGACAAGTCCATTAAATGTGAACAAAATCTGGGCCATGATACTATGTATTGGTATAAACAGGACTCTAAGAAATTTCTGAAGATAATGTTTAGCTACAATAATAAGGAGCTCATTATAAATGAAACAGTTCCAAATCGCTTCTCACCTAAATCTCCAGACAAAGCTCACTTAAATCTTCACATCAATTCCCTGGAGCTTGGTGACTCTGCTGTGTATTTCTGTGCCAGCAGCCAAGATGGACTTGAGCAGTACTTCGGGCCGGGCACCAGGCTCACGGTCACAGAGGACCTGAAAAACGTGTTCCCACCCGAGGTCGCTGTGTTTGAGCCATCAGAAGCAGAGATCTCCCACACCCAAAAGGCCACACTGGTATGCCTGGCCACAGGCTTCTACCCCGACCACGTGGAGCTGAGCTGGTGGGTGAATGGGAAGGAGGTGCACAGTGGGGTCAGCACAGACCCGCAGCCCCTCAAGGAGCAGCCCGCCCTCAATGACTCCAGATACTGCCTGAGCAGCCGCCTGAGGGTCTCGGCCACCTTCTGGCAGAACCCCCGCAACCACTTCCGCTGTCAAGTCCAGTTCTACGGGCTCTCGGAGAATGACGAGTGGACCCAGGATAGGGCCAAACCTGTCACCCAGATCGTCAGCGCCGAGGCCTGGGGTAGAGCAGACTGTGGCTTCACCTCCGAGTCTTACCAGCAAGGGGTCCTGTCTGCCACCATCCTCTATGAGATCTTGCTAGGGAAGGCCACCTTGTATGCCGTGCTGGTCAGTGCCCTCGTGCTGATGGCCATGGTCAAGAGAAAGGATTCCAGAGGCTAG (SEQ ID NO: 449) | ELGDSAVYFCASSQDGLEQYFGPGTRLTVTEDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG (SEQ ID NO: 669) | ATTGGTATAAACAGGACTCTAAGAAATTTCTGAAGATAATGTTTAGCTACAATAATAAGGAGCTCATTATAAATGAAACAGTTCCAAATCGCTTCTCACCTAAATCTCCAGACAAAGCTCACTTAAATCTTCACATCAATTCCCTGGAGCTTGGTGACTCTGCTGTGTATTTCTGTGCCAGCAGCCAAGATGGACTTGAGCAGTACTTCGGGCCGGGCACCAGGCTCACGGTCACAG (SEQ ID NO: 670) | QYFGPGTRLTVT (SEQ ID NO: 671) | |
| 32 | GACCTCACTGGCGCAGCACCTCTCAGCGGCAGTGGAAACCACAGCCTAGTCCTCTCACCACTGCAGACCAGAATCCTGCCCTGGGCCTTGCCTGGTCTGCCTCACTCTGCCATGGGCTGCAGGCTCCTCTGCTGTGTGGTCTTCTGCCTCCTCCAAGCAGGTCCCTTGGACACAGCTGTTTCCCAGACTCCAAAATACCTGGTCACACAGATGGGAAACGACAAGTCCATTAAATGTGAACAAAATCTGGGCCATGATACTATGTATTGGTATAAACAGGACTCTAAGAAATTTCTGAAGATAATGTTTAGCTACAATAATAAGGAGCTCATTATAAATGAAACAGTTCCAAATCGCTTCTCACCTAAATCTCCAGACAAAGCTCACTTAAATCTTCACATCAATTCCCTGGAGCTTGGTGACTCTGCTGTGTATTTCTGTGCCAGCAGCCAAGAAGGATCTCAGGACCACACTAGCGGGAGGGCCACCGAGCAGTACTTCGGGCCGGGCACCAGGCTCACGGTCACAGAGGACCTGAAAAACGTGTTCCCACCCGAGGTCGCTGTGTTTGAGCCATCAGAAGCAGAGATCTCCCACACCCAAAAGGCCACACTGGTGTGCCTGGCCACAGGCTTCTACCCCGACCACGTGGAGCTGAGCTGGTGGGTGAATG | MGCRLLCCVVFCLLQAGPLDTAVSQTPKYLVTQMGNDKSIKCEQNLGHDTMYWYKQDSKKFLKIMFSYNNKELIINETVPNRFSPKSPDKAHLNLHINSLELGDSAVYFCASSQEGSQDHTSGRATEQYFGPGTRLTVTEDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG (SEQ ID NO: 672) | GACACAGCTGTTTCCCAGACTCCAAAATACCTGGTCACACAGATGGGAAACGACAAGTCCATTAAATGTGAACAAAATCTGGGCCATGATACTATGTATTGGTATAAACAGGACTCTAAGAAATTTCTGAAGATAATGTTTAGCTACAATAATAAGGAGCTCATTATAAATGAAACAGTTCCAAATCGCTTCTCACCTAAATCTCCAGACAAAGCTCACTTAAATCTTCACATCAATTCCCTGGAGCTTGGTGACTCTGCTGTGTATTTCTGTGCCAGCAGCCAAGAAGGATCTCAGGACCACACTAGCGGGAGGGCCACCGAGCAGTACTTCGGGCCGGGCACCAGGCTCACGGTCACAG | DTAVSQTPKYLVTQMGNDKSIKCEQNLGHDTMYWYKQDSKKFLKIMFSYNNKELIINETVPNRFSPKSPDKAHLNLHINSLELGDSAVYFCASSQEGSQDHTSGRATEQYFGPGTRLTVT (SEQ ID NO: 674) | CTGGGCCATGATACT (SEQ ID NO: 457) |

TABLE 5-continued

| | | | | | |
|---|---|---|---|---|---|
| | GGAAGGAGGTGCACAGTG<br>GGGTCAGCACAGACCCGCA<br>GCCCCTCAAGGAGCAGCCC<br>GCCCTCAATGACTCCAGAT<br>ACTGCCTGAGCAGCCGCCT<br>GAGGGTCTCGGCCACCTTC<br>TGGCAGAACCCCCGCAACC<br>ACTTCCGCTGTCAAGTCCA<br>GTTCTACGGGCTCTCGGAG<br>AATGACGAGTGGACCCAGG<br>ATAGGGCCAAACCTGTCAC<br>CCAGATCGTCAGCGCCGAG<br>GCCTGGGGTAGAGCAGACT<br>GTGGCTTCACCTCCGAGTC<br>TTACCAGCAAGGGGTCCTG<br>TCTGCCACCATCCTCTATG<br>AGATCTTGCTAGGGAAGGC<br>CACCTTGTATGCCGTGCTG<br>GTCAGTGCCCTCGTGCTGA<br>TGGCCATGGTCAAGAGAAA<br>GGATTCCAGAGGCTAG<br>(SEQ ID NO: 456) | | (SEQ ID NO: 673) | | |
| 33 | GGGGCTCTCCCTCCCTGGGG<br>CCCAGGCAGGGAGAATGTCT<br>CAGAATGACTTCCTTGAGAG<br>TCCTGCTCCCCTTTCATCAAT<br>GCACAGATACAGAAGACCCC<br>TCCGTCATGCAGCATCTGCC<br>ATGAGCATCGGCCTCCTGTG<br>CTGTGCAGCCTTGTCTCTCCT<br>GTGGGCAGGTCCAGTGAATG<br>CTGGTGTCACTCAGACCCCA<br>AAATTCCAGGTCCTGAAGAC<br>AGGACAGAGCATGACACTGC<br>AGTGTGCCCAGGATATGAAC<br>CATGAATACATGTCCTGGTA<br>TCGACAAGACCCAGGCATGG<br>GGCTGAGGCTGATTCATTAC<br>TCAGTTGGTGCTGGTATCAC<br>TGACCAAGGAGAAGTCCCCA<br>ATGGCTACAATGTCTCCAGA<br>TCAACCACAGAGGATTTCCC<br>GCTCAGGCTGCTGTCGGCTG<br>CTCCCTCCCAGACATCTGTGT<br>ACTTCTGTGCCAGCAGCCTG<br>ACAGAAGGAAGAAGCGAGC<br>AGTACTTCGGGCCGGGCACC<br>AGGCTCACGGTCACAGAGGA<br>CCTGAAAAACGTGTTCCCA<br>CCCGAGGTCGCTGTGTTTG<br>AGCCATCAGAAGCAGAGAT<br>CTCCCACACCCAAAAGGCC<br>ACACTGGTGTGCCTGGCCA<br>CAGGCTTCTACCCCGACCA<br>CGTGGAGCTGAGCTGGTG<br>GGTGAATGGGAAGGAGGT<br>GCACAGTGGGGTCAGCAC<br>GGACCCGCAGCCCCTCAAG<br>GAGCAGCCCGCCCTCAATG<br>ACTCCAGATACTGCCTGAG<br>CAGCCGCCTGAGGGTCTCG<br>GCCACCTTCTGGCAGAACC<br>CCCGCAACCACTTCCGCTG<br>TCAAGTCCAGTTCTACGGG<br>CTCTCGGAGAATGACGAGT<br>GGACCCAGGATAGGGCCA<br>AACCTGTCACCCAGATCGT<br>CAGCGCCGAGGCCTGGGG<br>TAGAGCAGACTGTGGCTTC<br>ACCTCCGAGTCTTACCAGC<br>AAGGGGTCCTGTCTGCCAC<br>CATCCTCTATGAGATCTTG<br>CTAGGGAAGGCCACCTTGT<br>ATGCCGTGCTGGTCAGTGC<br>CCTCGTGCTGATGGCCATG<br>GTCAAGAGAAAGGATTCCA<br>GAGGCTAG (SEQ ID NO: 463) | MSQNDFLESPA<br>PLSSMHRYRRP<br>LRHAASAMSIG<br>LLCCAALSLLW<br>AGPVNAGVTQT<br>PKFQVLKTGQS<br>MTLQCAQDMN<br>HEYMSWYRQD<br>PGMGLRLIHYS<br>VGAGITDQGEV<br>PNGYNVSRSTT<br>EDFPLRLLSAAP<br>SQTSVYFCASSL<br>TEGRSEQYFGP<br>GTRLTVTEDLK<br>NVFPPEVAVFE<br>PSEAEISHTQK<br>ATLVCLATGF<br>YPDHVELSWW<br>VNGKEVHSGV<br>STDPQPLKEQP<br>ALNDSRYCLSS<br>RLRVSATFWQ<br>NPRNHFRCQV<br>QFYGLSENDE<br>WTQDRAKPVT<br>QIVSAEAWGR<br>ADCGFTSESYQ<br>QGVLSATILYE<br>ILLGKATLYAV<br>LVSALVLMAM<br>VKRKDSRG<br>(SEQ ID NO: 675) | AATGCTGGTGT<br>CACTCAGACCC<br>CAAAATTCCAG<br>GTCCTGAAGAC<br>AGGACAGAGC<br>ATGACACTGCA<br>GTGTGCCCAGG<br>ATATGAACCAT<br>GAATACATGTC<br>CTGGTATCGAC<br>AAGACCCAGG<br>CATGGGGCTG<br>AGGCTGATTCA<br>TTACTCAGTTG<br>GTGCTGGTATC<br>ACTGACCAAG<br>GAGAAGTCCC<br>CAATGGCTACA<br>ATGTCTCCAGA<br>TCAACCACAG<br>AGGATTTCCCG<br>CTCAGGCTGCT<br>GTCGGCTGCTC<br>CCTCCCAGACA<br>TCTGTGTACTT<br>CTGTGCCAGCA<br>GCCTGACAGA<br>AGGAAGAAGC<br>GAGCAGTACTT<br>CGGGCCGGGC<br>ACCAGGCTCAC<br>GGTCACAG<br>(SEQ ID NO: 676) | NAGVTQTPKFQ<br>VLKTGQSMTLQ<br>CAQDMNHEYM<br>SWYRQDPGMG<br>LRLIHYSVGAGI<br>TDQGEVPNGYN<br>VSRSTTEDFPLR<br>LLSAAPSQTSV<br>YFCASSLTEGRS<br>EQYFGPGTRLT<br>VT<br>(SEQ ID NO: 677) | ATGA<br>ACCA<br>TGAA<br>TAC<br>(SEQ ID NO: 464) |
| 34 | GGGGAGTCATCCCTCCTCGC | MEAVVTTLPRE | GGTGCTGTCGT | GAVVSQHPSRV | GACT |

TABLE 5-continued

| | | | | |
|---|---|---|---|---|
| TGGTGAATGGAGGCAGTGGT | GGVRPSRKMLL | CTCTCAACATC | ICKSGTSVKIEC | TTCA |
| CACAACTCTCCCCAGAGAAG | LLLLLGPGSGL | CGAGCAGGGT | RSLDFQATTMF | GGCC |
| GTGGTGTGAGGCCATCACGG | GAVVSQHPSRV | TATCTGTAAGA | WYRQFPKKSL | ACAA |
| AAGATGCTGCTGCTTCTGCT | ICKSGTSVKIEC | GTGGAACCTCT | MLMATSNEGS | CT |
| GCTTCTGGGGCCAGGCTCCG | RSLDFQATTMF | GTGAAGATCG | KATYEQGVEK | (SEQ |
| GGCTTGGTGCTGTCGTCTCTC | WYRQFPKKSL | AGTGCCGTTCC | DKFLINHASLTL | ID NO: |
| AACATCCGAGCAGGGTTATC | MLMATSNEGS | CTGGACTTTCA | STLTVTSAHPE | 471) |
| TGTAAGAGTGGAACCTCTGT | KATYEQGVEK | GGCCACAACT | DSSFYICSAGGF | |
| GAAGATCGAGTGCCGTTCCC | DKFLINHASLTL | ATGTTTTGGTA | SGNTIYFGEGS | |
| TGGACTTTCAGGCCACAACT | STLTVTSAHPE | TCGTCAGTTCC | WLTVV | |
| ATGTTTTGGTATCGTCAGTTC | DSSFYICSAGGF | CGAAAAAGAG | (SEQ ID NO: | |
| CCGAAAAAGAGTCTCATGCT | SGNTIYFGEGS | TCTCATGCTGA | 680) | |
| GATGGCAACTTCCAATGAGG | WLTVV**EDLNK** | TGGCAACTTCC | | |
| GCTCCAAGGCCACATACGAG | **VFPPEVAVFEP** | AATGAGGGCT | | |
| CAAGGCGTCGAGAAGGACA | **SEAEISHTQKA** | CCAAGGCCAC | | |
| AGTTTCTCATCAACCATGCA | **TLVCLATGFYP** | ATACGAGCAA | | |
| AGCCTGACCTTGTCCACTCT | **DHVELSWWVN** | GGCGTCGAGA | | |
| GACAGTGACCAGTGCCCATC | **GKEVHSGVST** | AGGACAAGTTT | | |
| CTGAAGACAGCAGCTTCTAC | **DPQPLKEQPA** | CTCATCAACCA | | |
| ATCTGCAGTGCTGGGGGTTT | **LNDSRYCLSSR** | TGCAAGCCTGA | | |
| CTCTGGAAACACCATATATT | **LRVSATFWQN** | CCTTGTCCACT | | |
| TTGGAGAGGGAAGTTGGCTC | **PRNHERCQVQ** | CTGACAGTGAC | | |
| ACTGTTGTAGAG**GACCTGAA** | **FYGLSENDEW** | CAGTGCCCATC | | |
| **CAAGGTGTTCCCACCCGAG** | **TQDRAKPVTQI** | CTGAAGACAG | | |
| **GTCGCTGTGTTTGAGCCAT** | **VSAEAWGRAD** | CAGCTTCTACA | | |
| **CAGAAGCAGAGATCTCCCA** | **CGFTSVSYQQ** | TCTGCAGTGCT | | |
| **CACCCAAAAGGCCACACTG** | **GVLSATILYEI** | GGGGGTTTCTC | | |
| **GTGTGCCTGGCCACAGGCT** | **LLGKATLYAV** | TGGAAACACC | | |
| **TCTACCCCGACCACGTGGA** | **LVSALVLMAM** | ATATATTTTGG | | |
| **GCTGAGCTGGTGGGTGAAT** | **VKRKDF** | AGAGGGAAGT | | |
| **GGGAAGGAGGTGCACAGT** | (SEQ ID NO: | TGGCTCACTGT | | |
| **GGGGTCAGCACAGACCCG** | 678) | TGTAG | | |
| **CAGCCCCTCAAGGAGCAGC** | | (SEQ ID NO: | | |
| **CCGCCCTCAATGACTCCAG** | | 679) | | |
| **ATACTGCCTGAGCAGCCGC** | | | | |
| **CTGAGGGTCTCGGCCACCT** | | | | |
| **TCTGGCAGAACCCCCGCAA** | | | | |
| **CCACTTCCGCTGTCAAGTC** | | | | |
| **CAGTTCTACGGGCTCTCGG** | | | | |
| **AGAATGACGAGTGGACCCA** | | | | |
| **GGATAGGGCCAAACCCGTC** | | | | |
| **ACCCAGATCGTCAGCGCCG** | | | | |
| **AGGCCTGGGGTAGAGCAG** | | | | |
| **ACTGTGGCTTTACCTCGGT** | | | | |
| **GTCCTACCAGCAAGGGGTC** | | | | |
| **CTGTCTGCCACCATCCTCT** | | | | |
| **ATGAGATCCTGCTAGGGAA** | | | | |
| **GGCCACCCTGTATGCTGTG** | | | | |
| **CTGGTCAGCGCCCTTGTGT** | | | | |
| **TGATGGCCATGGTCAAGAG** | | | | |
| **AAAGGATTTCTGA** (SEQ ID | | | | |
| NO: 470) | | | | |

| ID | CDR1 (AA) | CDR2 (NT) | CDR2 (AA) | CDR3 (NT) | CDR3 (AA) |
|---|---|---|---|---|---|
| 1 | LGHN T (SEQ ID NO: 241) | TTCC GCAA CCGG GCTC CT (SEQ ID NO: 242) | FRNR AP (SEQ ID NO: 243) | GCTA GTGG TTTG GCCC TCAC TGAG GGGG GCTG GTAC GAGC AGTA C (SEQ ID NO: 244) | ASGL ALTE GGWY EQY (SEQ ID NO: 245) |
| 2 | SNHL Y (SEQ ID NO: 248) | TTTTA TAAT AATG AAAT C (SEQ ID NO: 249) | FYNN EI (SEQ ID NO: 250) | GCCA GCCT CCGA TGGG ACGG GGAC AATG AGCA | ASLR WDGD NEQF (SEQ ID NO: 252) |

TABLE 5-continued

| | | | | | |
|---|---|---|---|---|---|
| | | | | GTTC (SEQ ID NO: 251) | |
| 3 | MNHNS (SEQ ID NO: 255) | TCAGCTTCTGAGGGTACC (SEQ ID NO: 256) | SASEGT (SEQ ID NO: 257) | GCCAGCAGGGACAGGGCCCTGAACACTGAAGCTTTC SEQ ID NO: 258) | ASRDRALNTEAF (SEQ ID NO: 259) |
| 4 | MNHEY (SEQ ID NO: 262) | TCAGTTGGTGCTGGTATC (SEQ ID NO: 263) | SVGAGI (SEQ ID NO: 264) | GCCAGCAGAAACGGCGGGACACTAATCTACGAGCAGTAC (SEQ ID NO: 265) | ASRNGGTLIYEQY (SEQ ID NO: 266) |
| 5 | SGHRS (SEQ ID NO: 269) | TACTTCAGTGAGACACAG (SEQ ID NO: 270) | YFSETQ (SEQ ID NO: 271) | GCCAGCAGGCAGCGGACAGAACTTGAAGCTTTC (SEQ ID NO: 272) | ASRQRTELEAF SEQ ID NO: 273) |
| 6 | SNHLY (SEQ ID NO: 276) | TTTTATAATAATGAAATC (SEQ ID NO: 277) | FYNNEI (SEQ ID NO: 278) | GCCAGCAGTGAAGCCCCTGACAGGGGTACCTACGAGCAGTAC (SEQ ID NO: 279) | ASSEAPDRGTYEQY (SEQ ID NO: 280) |
| 7 | WSHSY (SEQ ID NO: 283) | TCAGCAGCTGCTGATATT (SEQ ID NO: 284) | SAAADI (SEQ ID NO: 285) | GCCAGCAGTGAGTTGGGCAGGGGTTTCTACGAGCAGTAC (SEQ ID NO: 286) | ASSELGRGFYEQY (SEQ ID NO: 287) |
| 8 | MNHEY (SEQ ID NO: 290) | TCAGTTGGTGCTGGTATC (SEQ ID NO: | SVGAGI (SEQ ID NO: 292) | GCCAGCAGCCATCTGGGGGCGGGAGGGC | ASSHLGAGGPHEQY (SEQ ID NO: 294) |

TABLE 5-continued

| | | | | | |
|---|---|---|---|---|---|
| | | 291) | | CGCACGAGCAGTAC (SEQ ID NO: 293) | |
| 9 | SGHVS (SEQ ID NO: 297) | TTCAATTATGAAGCCCAA (SEQ ID NO: 298) | FNYEAQ (SEQ ID NO: 299) | GCCAGCAGCCATACTGACGGCTCCTACGAGCAGTAC (SEQ ID NO: 300) | ASSHTDGSYEQY (SEQ ID NO: 301) |
| 10 | LNHDA (SEQ ID NO: 304) | TCACAGATAGTAAATGAC (SEQ ID NO: 305) | SQIVND (SEQ ID NO: 306) | GCCAGTAGCATAGGGGCATTTGCTGGTCAGCCCCAGCAT (SEQ ID NO: 307) | ASSIGAFAGQPQH (SEQ ID NO: 308) |
| 11 | SEHNR (SEQ ID NO: 311) | TTCCAGAATGAAGCTCAA (SEQ ID NO: 312) | FQNEAQ (SEQ ID NO: 313) | GCCAGCAGCTTAGCGCCTACCCCCGGGCCGGACACCGGGGAGCTGTTT (SEQ ID NO: 314) | ASSLAPTPGPDTGELF (SEQ ID NO: 315) |
| 12 | MNHEY (SEQ ID NO: 318) | TCAATGAATGTTGAGGTG (SEQ ID NO: 319) | SMNVEV (SEQ ID NO: 320) | GCCAGCAGTTTAGGGAATATCTACGAGCAGTAC (SEQ ID NO: 321) | ASSLGNIYEQY SEQ ID NO: 322) |
| 13 | SGHTA (SEQ ID NO: 325) | TTCCAAGGCACGGGTGCG (SEQ ID NO: 326) | FQGTGA (SEQ ID NO: 327) | GCCAGCAGCTTAGGGAGCGGTGAGCAGTTC (SEQ ID NO: 328) | ASSLGSGEQF (SEQ ID NO: 329) |
| 14 | SGHTS (SEQ ID NO: 332) | TATGACGAGGGTGAAG | YDEGEE (SEQ ID NO: | GCCAGCAGCTTACAGA | ASSLQTSYEQY (SEQ |

TABLE 5-continued

| | | | | | |
|---|---|---|---|---|---|
| | | AG (SEQ ID NO: 333) | 334) | CATC CTAC GAGC AGTA C (SEQ ID NO: 335) | ID NO: 336) |
| 15 | MNHE Y (SEQ ID NO: 339) | TCAA TGAA TGTT GAGG TG (SEQ ID NO: 340) | SMNV EV (SEQ ID NO: 341) | GCCA GCAG TTTAT CGTG GGGG ACCG GCAA AAGA GCAG ATAC GCAG TAT (SEQ ID NO: 342) | ASSLS WGTG KRAD TQY SEQ ID NO: 343) |
| 16 | SEHN R (SEQ ID NO: 346) | TTCC AGAA TGAA GCTC AA (SEQ ID NO: 347) | FQNE AQ (SEQ ID NO: 348) | GCCA GCAG CTTA GTTG GCGG CGGG AGCA ATGA GCAG TTC (SEQ ID NO: 349) | ASSLV GGGS NEQF (SEQ ID NO: 350) |
| 17 | SEHN R (SEQ ID NO: 353) | TTCC AGAA TGAA GCTC AA (SEQ ID NO: 354) | FQNE AQ (SEQ ID NO: 355) | GCCA GCAG CTTA GTCG GAGG CACT GAAG CTTTC (SEQ ID NO: 356) | ASSLV GGTE AF (SEQ ID NO: 357) |
| 18 | SEHN R (SEQ ID NO: 360) | TTCC AGAA TGAA GCTC AA (SEQ ID NO: 361) | FQNE AQ (SEQ ID NO: 362) | GCCA GCAG CCCC GATC GGAA TCTC GGGC AGTA C (SEQ ID NO: 363) | ASSPD RNLG QY (SEQ ID NO: 364) |
| 19 | SGHD N (SEQ ID NO: 367) | TTTGT GAAA GAGT CTAA A (SEQ ID NO: 368) | FVKES K (SEQ ID NO: 369) | GCCA GCAG CCAA GTCC AGGC TTTTA ATGA GCAG TTC (SEQ ID NO: 370) | ASSQ VQAF NEQF (SEQ ID NO: 371) |
| 20 | SGHA T (SEQ | TTTCA GAAT AACG | FQNN GV (SEQ | GCCA GCAG TCGA | ASSRG EPGSG ANVL |

TABLE 5-continued

| | | | | | |
|---|---|---|---|---|---|
| | ID NO: 374) | GTGTA (SEQ ID NO: 375) | ID NO: 376) | GGGGAGCCAGGCTCTGGGGCCAACGTCCTGACT (SEQ ID NO: 377) | T (SEQ ID NO: 378) |
| 21 | SGHDT (SEQ ID NO: 381) | TATTATGAGGAGGAAGAG (SEQ ID NO: 382) | YYEEEE (SEQ ID NO: 383) | GCCAGCAGCTCCGGGACAGACCCCTCTGGGGCCAACGTCCTGACT (SEQ ID NO: 384) | ASSSGTDPSGANVLT (SEQ ID NO: 385) |
| 22 | MNHEY (SEQ ID NO: 388) | TCAATGAATGTTGAGGTG (SEQ ID NO: 389) | SMNVEV (SEQ ID NO: 390) | GCCAGCAGTACCGGACAGAATATAGGCGGGGAGCTGTTT (SEQ ID NO: 391) | ASSTGQNIGGELF (SEQ ID NO: 392) |
| 23 | SEHNR (SEQ ID NO: 395) | TTCCAGAATGAAGCTCAA (SEQ ID NO: 396) | FQNEAQ (SEQ ID NO: 397) | GCCAGCAGCACACATGAAAAGACAGGGTGGAAATCACCCCTCCAC (SEQ ID NO: 398) | ASSTHEKTGWKSPLH (SEQ ID NO: 399) |
| 24 | SNHLY (SEQ ID NO: 402) | TTTTATAATAATGAAATC (SEQ ID NO: 403) | FYNNEI (SEQ ID NO: 404) | GCCAGCAGTACGCACTCTGACAGGAACTTGAACACTGAAGCTTTC (SEQ ID NO: 405) | ASSTHSDRNLNTEAF (SEQ ID NO: 406) |
| 25 | SNHLY (SEQ ID NO: 409) | TTTTATAATAATGAAATC (SEQ | FYNNEI (SEQ ID NO: 411) | GCCAGCAGCGTACAGGCTACGGGC | ASSVQATGHGYT (SEQ ID NO: 413) |

TABLE 5-continued

| | | | | | |
|---|---|---|---|---|---|
| | ID NO: 410) | | | CATG GCTA CACC (SEQ ID NO: 412) | |
| 26 | SGHV S (SEQ ID NO: 416) | TTCC AGAA TGAA GCTC AA (SEQ ID NO: 417) | FQNE AQ (SEQ ID NO: 418) | GCCA GCAC CCCC TCTG GCTA TAAC TCTTG GGAG CAGT TC (SEQ ID NO: 419) | ASTPS GYNS WEQF (SEQ ID NO: 420) |
| 27 | MNHE Y (SEQ ID NO: 423) | TCAA TGAA TGTT GAGG TG (SEQ ID NO: 424) | SMNV EV (SEQ ID NO: 425) | GCCA CCGC CCCC AGGG GTAG CAAT CAGC CCCA GCAT (SEQ ID NO: 426) | ATAP RGSN QPQH (SEQ ID NO: 427) |
| 28 | DFQA TT (SEQ ID NO: 430) | TCCA ATGA GGGC TCCA AGGC C (SEQ ID NO: 431) | SNEGS KA (SEQ ID NO: 432) | AGGG CCTG GGGC GGGA GCTC CTAC AATG AGCA GTTC (SEQ ID NO: 433) | RAWG GSSY NEQF (SEQ ID NO: 434) |
| 29 | DFQA TT (SEQ ID NO: 437) | TCCA ATGA GGGC TCCA AGGC C (SEQ ID NO: 438) | SNEGS KA (SEQ ID NO: 439) | AGTG CTAG AATT GGAC AGGG TTTTA TGAA TGAG CAGT TC (SEQ ID NO: 440) | SARIG QGFM NEQF (SEQ ID NO: 441) |
| 30 | DFQA TT (SEQ ID NO: 444) | TCCA ATGA GGGC TCCA AGGC C (SEQ ID NO: 445) | SNEGS KA (SEQ ID NO: 446) | AGTG CTCCT GGGT GGCG TGGC ACTG AAGC TTTC (SEQ ID NO: 447) | SAPG WRGT EAF (SEQ ID NO: 448) |
| 31 | LGHD T (SEQ ID NO: 451) | TACA ATAA TAAG GAGC TC (SEQ ID NO: | YNNK EL (SEQ ID NO: 453) | GCCA GCAG CCAA GATG GACT TGAG CAGT | ASSQ DGLE QY (SEQ ID NO: 455) |

TABLE 5-continued

| | | | | | |
|---|---|---|---|---|---|
| | | 452) | | AC (SEQ ID NO: 454) | |
| 32 | LGHDT (SEQ ID NO: 458) | TACAATAATAAGGAGCTC (SEQ ID NO 459) | YNNKEL (SEQ ID NO: 460) | GCCAGCAGCCAAGAAGGATCTCAGGACCACACTAGCGGGAGGGCCACCGAGCAGTAC (SEQ ID NO: 461) | ASSQEGSQDHTSGRATEQY (SEQ ID NO: 462) |
| 33 | MNHEY (SEQ ID NO: 465) | TCAGTTGGTGCTGGTATC (SEQ ID NO: 466) | SVGAGI (SEQ ID NO: 467) | GCCAGCAGCCTGACAGAAGGAAGAAGCGAGCAGTAC (SEQ ID NO: 468) | ASSLTEGRSEQY (SEQ ID NO: 469) |
| 34 | DFQATT (SEQ ID NO: 472) | TCCAATGAGGGCTCCAAGGCC (SEQ ID NO: 473) | SNEGSKA (SEQ ID NO: 474) | AGTGCTGGGGGTTTCTCTGGAAACACCATATAT (SEQ ID NO: 475) | SAGGFSGNTIY (SEQ ID NO: 476) |

Example 3. Lentivirus Design and Transduction

Vector Design

Unique complementary determining regions (CDR) from selected TCR α/β pairs will be combined with the associated constant regions to form a full length TCR DNA sequence. Sequences will have TCRα with the stop codon removed followed by a furin F2A cleavage site and then a TCRβ containing a stop codon. Native leader sequences will be used for each TCR sequence. The DNA will be synthesized and cloned into an EF1α promotor vector with puromycin resistance to produce lenti-virus constructs (VectorBuilder™).

Lentiviral Transduction of TCR KO Jurkat Cell Lines

Day 1: TCR KO Jurkat cells will be removed from flasks and counted. The cells will be washed by centrifuging at 1500 rpm for five minutes and resuspended in R10 (R10 Media: Gibco™, 61870 supplemented with 10% FBS Gibco™, 16140 and 1× Sodium Pyruvate Gibco™, 11360) at a density of 1.5e6 cells/mL. 500 μL of cells will be seeded (for a density of 7.5e5 cells/well) to appropriate wells of a 12 well plate(s) according to plate layout. In a BSL2+ environment, lentiviral constructs will be diluted in R10 media with 2× (final concentration: 4 μg/mL) Polybrene (Millipore™, Cat #: TR-1003-G) to concentrations of 20 Multiplicity of Infection (MOI) per 500 μL. 500 μL of each construct will be added to appropriate wells according to plate layout. Plate(s) will be centrifuged at 2000 rpm for two hours at 30° C. After centrifuging 1 mL R10 will be added to each well. Plates will be incubated at 37° C./5% CO2 overnight.

Day 2: Cells will be transferred to individual 15 mL tubes and washed by centrifuging at 300× g for five minutes. Pellets will be resuspended in DPBS (Gibco™, 14140). Washes will be repeated for a total of three washes. After the final wash, cells will be resuspended in 1 mL R10. Cells will be transferred to a 6 well plate and add 1 mL of prepared R10 media containing 2× (final concentration 1.25 μg/mL) puromycin (Gibco™, A11138-03). Cells will be returned to the incubator at 37° C./5% CO2.

Day 5: Cells will be counted, and density will be scaled to be 2e5 cells/mL in an appropriately sized plate/flask for the volume. For healthy cells, puromycin concentration may be increased from 1.25 μg/mL to 2.5 μg/mL. Cells will be returned to the incubator at 37° C./5% CO2.

Day 8 (and every 3-4 days after): Cells will be counted and scaled to maintain a density of 2e5 cells/mL. Puromycin will be gradually increased up to a final concentration of 5 μg/mL.

Example 4. TCR Engagement Assay

A TCR engagement assay will be performed to determine if the TCRα/β pair is able to bind to a defined peptide-MHC (pMHC) complex and induce a T-cell response. Antigen presenting cells (APC) will be harvested and plated into white clear bottom 96 well plates at 3e5 cells/well in 40 μL in RPMI 1640+10% FBS). Peptides will be prepared by adding Dimethylsulfoxide (DMSO) or water to lyophilized powder to achieve a 10 mg/mL concentration. Peptides will be exogenously loaded onto APCs by diluting to a 10× final concentration in media and adding 10 μL to the wells. DMSO or water and/or wild type (wt) peptide at the same concentrations will be used as controls. The cells will be placed in a 37° C., 5% CO2 incubator for 2 hours. Meanwhile, reporter T-cells expressing a single TCR α/β pair from Table 3 will be harvested and diluted to 3e6 cells/mL. After the 2 hour incubation, 50 μL of T-cells will be added to each well, resulting in a 2:1 APC:T-cell ratio. Cells will be returned to the incubator for 5-6 hours. After the incubation, 100 μL of BioGlo™ luciferase reagent (Promega™, cat #G7940) will be added to each well. Plates will be placed on a rotary plate shaker at medium speed for 2 minutes. Plates will be read on an Envision™ (Perkin Elmer™) plate reader using a 0.5 sec luminescence detection. Cross-talk corrected values will be analyzed using GraphPad™ Prism™ graphing software.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The following list of embodiments is intended to complement, rather than displace or supersede, the previous descriptions:

Embodiment 1. A T-cell receptor (TCR) comprising an alpha chain and a beta chain, wherein:

- (a) the alpha chain comprises a complementarity determining region 3 (CDR3) comprising the amino acid sequence of SEQ ID NO: 7, and the beta chain comprises a CDR3 comprising the amino acid sequence of SEQ ID NO: 245;
- (b) the alpha chain comprises a CDR3 comprising the amino acid sequence of SEQ ID NO: 14, and the beta chain comprises a CDR3 comprising the amino acid sequence of SEQ ID NO: 252;
- (c) the alpha chain comprises a CDR3 comprising the amino acid sequence of SEQ ID NO: 21, and the beta chain comprises a CDR3 comprising the amino acid sequence of SEQ ID NO: 259;
- (d) the alpha chain comprises a CDR3 comprising the amino acid sequence of SEQ ID NO: 28, and the beta chain comprises a CDR3 comprising the amino acid sequence of SEQ ID NO: 266;
- (e) the alpha chain comprises a CDR3 comprising the amino acid sequence of SEQ ID NO: 35, and the beta chain comprises a CDR3 comprising the amino acid sequence of SEQ ID NO: 273;
- (f) the alpha chain comprises a CDR3 comprising the amino acid sequence of SEQ ID NO: 42, and the beta chain comprises a CDR3 comprising the amino acid sequence of SEQ ID NO: 280;
- (g) the alpha chain comprises a CDR3 comprising the amino acid sequence of SEQ ID NO: 49, and the beta chain comprises a CDR3 comprising the amino acid sequence of SEQ ID NO: 287;
- (h) the alpha chain comprises a CDR3 comprising the amino acid sequence of SEQ ID NO: 56, and the beta chain comprises a CDR3 comprising the amino acid sequence of SEQ ID NO: 294;
- (i) the alpha chain comprises a CDR3 comprising the amino acid sequence of SEQ ID NO: 63, and the beta chain comprises a CDR3 comprising the amino acid sequence of SEQ ID NO: 301;
- (j) the alpha chain comprises a CDR3 comprising the amino acid sequence of SEQ ID NO: 70, and the beta chain comprises a CDR3 comprising the amino acid sequence of SEQ ID NO: 308;
- (k) the alpha chain comprises a CDR3 comprising the amino acid sequence of SEQ ID NO: 77, and the beta chain comprises a CDR3 comprising the amino acid sequence of SEQ ID NO: 315;
- (l) the alpha chain comprises a CDR3 comprising the amino acid sequence of SEQ ID NO: 84, and the beta chain comprises a CDR3 comprising the amino acid sequence of SEQ ID NO: 322;
- (m) the alpha chain comprises a CDR3 comprising the amino acid sequence of SEQ ID NO: 91, and the beta chain comprises a CDR3 comprising the amino acid sequence of SEQ ID NO: 329;
- (n) the alpha chain comprises a CDR3 comprising the amino acid sequence of SEQ ID NO: 98, and the beta chain comprises a CDR3 comprising the amino acid sequence of SEQ ID NO: 336;
- (o) the alpha chain comprises a CDR3 comprising the amino acid sequence of SEQ ID NO: 105, and the beta chain comprises a CDR3 comprising the amino acid sequence of SEQ ID NO: 343;
- (p) the alpha chain comprises a CDR3 comprising the amino acid sequence of SEQ ID NO: 112, and the beta chain comprises a CDR3 comprising the amino acid sequence of SEQ ID NO: 350;
- (q) the alpha chain comprises a CDR3 comprising the amino acid sequence of SEQ ID NO: 119, and the beta chain comprises a CDR3 comprising the amino acid sequence of SEQ ID NO: 357;
- (r) the alpha chain comprises a CDR3 comprising the amino acid sequence of SEQ ID NO: 126, and the beta chain comprises a CDR3 comprising the amino acid sequence of SEQ ID NO: 364;
- (s) the alpha chain comprises a CDR3 comprising the amino acid sequence of SEQ ID NO: 133, and the beta chain comprises a CDR3 comprising the amino acid sequence of SEQ ID NO: 371;
- (t) the alpha chain comprises a CDR3 comprising the amino acid sequence of SEQ ID NO: 140, and the beta chain comprises a CDR3 comprising the amino acid sequence of SEQ ID NO: 378;
- (u) the alpha chain comprises a CDR3 comprising the amino acid sequence of SEQ ID NO: 147, and the beta chain comprises a CDR3 comprising the amino acid sequence of SEQ ID NO: 385;
- (v) the alpha chain comprises a CDR3 comprising the amino acid sequence of SEQ ID NO: 154, and the beta chain comprises a CDR3 comprising the amino acid sequence of SEQ ID NO: 392;

(w) the alpha chain comprises a CDR3 comprising the amino acid sequence of SEQ ID NO: 161, and the beta chain comprises a CDR3 comprising the amino acid sequence of SEQ ID NO: 399;

(x) the alpha chain comprises a CDR3 comprising the amino acid sequence of SEQ ID NO: 168, and the beta chain comprises a CDR3 comprising the amino acid sequence of SEQ ID NO: 406;

(y) the alpha chain comprises a CDR3 comprising the amino acid sequence of SEQ ID NO: 175, and the beta chain comprises a CDR3 comprising the amino acid sequence of SEQ ID NO: 413;

(z) the alpha chain comprises a CDR3 comprising the amino acid sequence of SEQ ID NO: 182, and the beta chain comprises a CDR3 comprising the amino acid sequence of SEQ ID NO: 420;

(aa) the alpha chain comprises a CDR3 comprising the amino acid sequence of SEQ ID NO: 189, and the beta chain comprises a CDR3 comprising the amino acid sequence of SEQ ID NO: 427;

(bb) the alpha chain comprises a CDR3 comprising the amino acid sequence of SEQ ID NO: 196, and the beta chain comprises a CDR3 comprising the amino acid sequence of SEQ ID NO: 434;

(cc) the alpha chain comprises a CDR3 comprising the amino acid sequence of SEQ ID NO: 203, and the beta chain comprises a CDR3 comprising the amino acid sequence of SEQ ID NO: 441;

(dd) the alpha chain comprises a CDR3 comprising the amino acid sequence of SEQ ID NO: 210, and the beta chain comprises a CDR3 comprising the amino acid sequence of SEQ ID NO: 448;

(ee) the alpha chain comprises a CDR3 comprising the amino acid sequence of SEQ ID NO: 217, and the beta chain comprises a CDR3 comprising the amino acid sequence of SEQ ID NO: 455;

(ff) the alpha chain comprises a CDR3 comprising the amino acid sequence of SEQ ID NO: 224, and the beta chain comprises a CDR3 comprising the amino acid sequence of SEQ ID NO: 462;

(gg) the alpha chain comprises a CDR3 comprising the amino acid sequence of SEQ ID NO: 231, and the beta chain comprises a CDR3 comprising the amino acid sequence of SEQ ID NO: 469; or (hh) the alpha chain comprises a CDR3 comprising the amino acid sequence of SEQ ID NO: 238, and the beta chain comprises a CDR3 comprising the amino acid sequence of SEQ ID NO: 476.

Embodiment 2. A T-cell receptor (TCR) comprising an alpha chain and a beta chain, wherein:

(a) the alpha chain comprises a complementarity determining region 1 (CDR1) comprising the amino acid sequence of SEQ ID NO: 3, a complementarity determining region 2 (CDR2) comprising the amino acid sequence of SEQ ID NO: 5, and a complementarity determining region 3 (CDR3) comprising the amino acid sequence of SEQ ID NO: 7, and the beta chain comprises a CDR1 comprising the amino acid sequence of SEQ ID NO: 241, a CDR2 comprising the amino acid sequence of SEQ ID NO: 243, and a CDR3 comprising the amino acid sequence of SEQ ID NO: 245;

(b) the alpha chain comprises a CDR1 comprising the amino acid sequence of SEQ ID NO: 10, a CDR2 comprising the amino acid sequence of SEQ ID NO: 12, and a CDR3 comprising the amino acid sequence of SEQ ID NO: 14, and the beta chain comprises a CDR1 comprising the amino acid sequence of SEQ ID NO: 248, a CDR2 comprising the amino acid sequence of SEQ ID NO: 250, and a CDR3 comprising the amino acid sequence of SEQ ID NO: 252;

(c) the alpha chain comprises a CDR1 comprising the amino acid sequence of SEQ ID NO: 17, a CDR2 comprising the amino acid sequence of SEQ ID NO: 19, and a CDR3 comprising the amino acid sequence of SEQ ID NO: 21, and the beta chain comprises a CDR1 comprising the amino acid sequence of SEQ ID NO: 255, a CDR2 comprising the amino acid sequence of SEQ ID NO: 257, and a CDR3 comprising the amino acid sequence of SEQ ID NO: 259;

(d) the alpha chain comprises a CDR1 comprising the amino acid sequence of SEQ ID NO: 24, a CDR2 comprising the amino acid sequence of SEQ ID NO: 26, and a CDR3 comprising the amino acid sequence of SEQ ID NO: 28, and the beta chain comprises a CDR1 comprising the amino acid sequence of SEQ ID NO: 262, a CDR2 comprising the amino acid sequence of SEQ ID NO: 264, and a CDR3 comprising the amino acid sequence of SEQ ID NO: 266;

(e) the alpha chain comprises a CDR1 comprising the amino acid sequence of SEQ ID NO: 31, a CDR2 comprising the amino acid sequence of SEQ ID NO: 33, and a CDR3 comprising the amino acid sequence of SEQ ID NO: 35, and the beta chain comprises a CDR1 comprising the amino acid sequence of SEQ ID NO: 269, a CDR2 comprising the amino acid sequence of SEQ ID NO: 271, and a CDR3 comprising the amino acid sequence of SEQ ID NO: 273;

(f) the alpha chain comprises a CDR1 comprising the amino acid sequence of SEQ ID NO: 38, a CDR2 comprising the amino acid sequence of SEQ ID NO: 40, and a CDR3 comprising the amino acid sequence of SEQ ID NO: 42, and the beta chain comprises a CDR1 comprising the amino acid sequence of SEQ ID NO: 276, a CDR2 comprising the amino acid sequence of SEQ ID NO: 278, and a CDR3 comprising the amino acid sequence of SEQ ID NO: 280;

(g) the alpha chain comprises a CDR1 comprising the amino acid sequence of SEQ ID NO: 45, a CDR2 comprising the amino acid sequence of SEQ ID NO: 47, and a CDR3 comprising the amino acid sequence of SEQ ID NO: 49, and the beta chain comprises a CDR1 comprising the amino acid sequence of SEQ ID NO: 283, a CDR2 comprising the amino acid sequence of SEQ ID NO: 285, and a CDR3 comprising the amino acid sequence of SEQ ID NO: 287;

(h) the alpha chain comprises a CDR1 comprising the amino acid sequence of SEQ ID NO: 52, a CDR2 comprising the amino acid sequence of SEQ ID NO: 54, and a CDR3 comprising the amino acid sequence of SEQ ID NO: 56, and the beta chain comprises a CDR1 comprising the amino acid sequence of SEQ ID NO: 290, a CDR2 comprising the amino acid sequence of SEQ ID NO: 292, and a CDR3 comprising the amino acid sequence of SEQ ID NO: 294;

(i) the alpha chain comprises a CDR1 comprising the amino acid sequence of SEQ ID NO: 59, a CDR2 comprising the amino acid sequence of SEQ ID NO: 61, and a CDR3 comprising the amino acid sequence of SEQ ID NO: 63, and the beta chain comprises a CDR1 comprising the amino acid sequence of SEQ ID NO: 297, a CDR2 comprising the amino acid sequence of SEQ ID NO: 299, and a CDR3 comprising the amino acid sequence of SEQ ID NO: 301;

(j) the alpha chain comprises a CDR1 comprising the amino acid sequence of SEQ ID NO: 66, a CDR2 comprising the amino acid sequence of SEQ ID NO: 68, and a CDR3 comprising the amino acid sequence of SEQ ID NO: 70, and the beta chain comprises a CDR1 comprising the amino acid sequence of SEQ ID NO: 304, a CDR2 comprising the amino acid sequence of SEQ ID NO: 306, and a CDR3 comprising the amino acid sequence of SEQ ID NO: 308;

(k) the alpha chain comprises a CDR1 comprising the amino acid sequence of SEQ ID NO: 73, a CDR2 comprising the amino acid sequence of SEQ ID NO: 75, and a CDR3 comprising the amino acid sequence of SEQ ID NO: 77, and the beta chain comprises a CDR1 comprising the amino acid sequence of SEQ ID NO: 311, a CDR2 comprising the amino acid sequence of SEQ ID NO: 313, and a CDR3 comprising the amino acid sequence of SEQ ID NO: 315;

(l) the alpha chain comprises a CDR1 comprising the amino acid sequence of SEQ ID NO: 80, a CDR2 comprising the amino acid sequence of SEQ ID NO: 82, and a CDR3 comprising the amino acid sequence of SEQ ID NO: 84, and the beta chain comprises a CDR1 comprising the amino acid sequence of SEQ ID NO: 318, a CDR2 comprising the amino acid sequence of SEQ ID NO: 320, and a CDR3 comprising the amino acid sequence of SEQ ID NO: 322;

(m) the alpha chain comprises a CDR1 comprising the amino acid sequence of SEQ ID NO: 87, a CDR2 comprising the amino acid sequence of SEQ ID NO: 89, and a CDR3 comprising the amino acid sequence of SEQ ID NO: 91, and the beta chain comprises a CDR1 comprising the amino acid sequence of SEQ ID NO: 325, a CDR2 comprising the amino acid sequence of SEQ ID NO: 327, and a CDR3 comprising the amino acid sequence of SEQ ID NO: 329;

(n) the alpha chain comprises a CDR1 comprising the amino acid sequence of SEQ ID NO: 94, a CDR2 comprising the amino acid sequence of SEQ ID NO: 96, and a CDR3 comprising the amino acid sequence of SEQ ID NO: 98, and the beta chain comprises a CDR1 comprising the amino acid sequence of SEQ ID NO: 332, a CDR2 comprising the amino acid sequence of SEQ ID NO: 334, and a CDR3 comprising the amino acid sequence of SEQ ID NO: 336;

(o) the alpha chain comprises a CDR1 comprising the amino acid sequence of SEQ ID NO: 101, a CDR2 comprising the amino acid sequence of SEQ ID NO: 103, and a CDR3 comprising the amino acid sequence of SEQ ID NO: 105, and the beta chain comprises a CDR1 comprising the amino acid sequence of SEQ ID NO: 339, a CDR2 comprising the amino acid sequence of SEQ ID NO: 341, and a CDR3 comprising the amino acid sequence of SEQ ID NO: 343;

(p) the alpha chain comprises a CDR1 comprising the amino acid sequence of SEQ ID NO: 108, a CDR2 comprising the amino acid sequence of SEQ ID NO: 110, and a CDR3 comprising the amino acid sequence of SEQ ID NO: 112, and the beta chain comprises a CDR1 comprising the amino acid sequence of SEQ ID NO: 346, a CDR2 comprising the amino acid sequence of SEQ ID NO: 348, and a CDR3 comprising the amino acid sequence of SEQ ID NO: 350;

(q) the alpha chain comprises a CDR1 comprising the amino acid sequence of SEQ ID NO: 115, a CDR2 comprising the amino acid sequence of SEQ ID NO: 117, and a CDR3 comprising the amino acid sequence of SEQ ID NO: 119, and the beta chain comprises a CDR1 comprising the amino acid sequence of SEQ ID NO: 353, a CDR2 comprising the amino acid sequence of SEQ ID NO: 355, and a CDR3 comprising the amino acid sequence of SEQ ID NO: 357;

(r) the alpha chain comprises a CDR1 comprising the amino acid sequence of SEQ ID NO: 122, a CDR2 comprising the amino acid sequence of SEQ ID NO: 124, and a CDR3 comprising the amino acid sequence of SEQ ID NO: 126, and the beta chain comprises a CDR1 comprising the amino acid sequence of SEQ ID NO: 360, a CDR2 comprising the amino acid sequence of SEQ ID NO: 362, and a CDR3 comprising the amino acid sequence of SEQ ID NO: 364;

(s) the alpha chain comprises a CDR1 comprising the amino acid sequence of SEQ ID NO: 129, a CDR2 comprising the amino acid sequence of SEQ ID NO: 131, and a CDR3 comprising the amino acid sequence of SEQ ID NO: 133, and the beta chain comprises a CDR1 comprising the amino acid sequence of SEQ ID NO: 367, a CDR2 comprising the amino acid sequence of SEQ ID NO: 369, and a CDR3 comprising the amino acid sequence of SEQ ID NO: 371;

(t) the alpha chain comprises a CDR1 comprising the amino acid sequence of SEQ ID NO: 136, a CDR2 comprising the amino acid sequence of SEQ ID NO: 138, and a CDR3 comprising the amino acid sequence of SEQ ID NO: 140, and the beta chain comprises a CDR1 comprising the amino acid sequence of SEQ ID NO: 374, a CDR2 comprising the amino acid sequence of SEQ ID NO: 376, and a CDR3 comprising the amino acid sequence of SEQ ID NO: 378;

(u) the alpha chain comprises a CDR1 comprising the amino acid sequence of SEQ ID NO: 143, a CDR2 comprising the amino acid sequence of SEQ ID NO: 145, and a CDR3 comprising the amino acid sequence of SEQ ID NO: 147, and the beta chain comprises a CDR1 comprising the amino acid sequence of SEQ ID NO: 381, a CDR2 comprising the amino acid sequence of SEQ ID NO: 383, and a CDR3 comprising the amino acid sequence of SEQ ID NO: 385;

(v) the alpha chain comprises a CDR1 comprising the amino acid sequence of SEQ ID NO: 150, a CDR2 comprising the amino acid sequence of SEQ ID NO: 152, and a CDR3 comprising the amino acid sequence of SEQ ID NO: 154, and the beta chain comprises a CDR1 comprising the amino acid sequence of SEQ ID NO: 388, a CDR2 comprising the amino acid sequence of SEQ ID NO: 390, and a CDR3 comprising the amino acid sequence of SEQ ID NO: 392;

(w) the alpha chain comprises a CDR1 comprising the amino acid sequence of SEQ ID NO: 157, a CDR2 comprising the amino acid sequence of SEQ ID NO: 159, and a CDR3 comprising the amino acid sequence of SEQ ID NO: 161, and the beta chain comprises a CDR1 comprising the amino acid sequence of SEQ ID NO: 395, a CDR2 comprising the amino acid sequence of SEQ ID NO: 397, and a CDR3 comprising the amino acid sequence of SEQ ID NO: 399;

(x) the alpha chain comprises a CDR1 comprising the amino acid sequence of SEQ ID NO: 164, a CDR2 comprising the amino acid sequence of SEQ ID NO: 166, and a CDR3 comprising the amino acid sequence of SEQ ID NO: 168, and the beta chain comprises a CDR1 comprising the amino acid sequence of SEQ ID NO: 402, a CDR2 comprising the amino acid sequence of SEQ ID NO: 404, and a CDR3 comprising the amino acid sequence of SEQ ID NO: 406;

(y) the alpha chain comprises a CDR1 comprising the amino acid sequence of SEQ ID NO: 171, a CDR2 comprising the amino acid sequence of SEQ ID NO: 173, and a CDR3 comprising the amino acid sequence of SEQ ID NO: 175, and the beta chain comprises a CDR1 comprising the amino acid sequence of SEQ ID NO: 409, a CDR2 comprising the amino acid sequence of SEQ ID NO: 411, and a CDR3 comprising the amino acid sequence of SEQ ID NO: 413;

(z) the alpha chain comprises a CDR1 comprising the amino acid sequence of SEQ ID NO: 178, a CDR2 comprising the amino acid sequence of SEQ ID NO: 180, and a CDR3 comprising the amino acid sequence of SEQ ID NO: 182, and the beta chain comprises a CDR1 comprising the amino acid sequence of SEQ ID NO: 416, a CDR2 comprising the amino acid sequence of SEQ ID NO: 418, and a CDR3 comprising the amino acid sequence of SEQ ID NO: 420;

(aa) the alpha chain comprises a CDR1 comprising the amino acid sequence of SEQ ID NO: 185, a CDR2 comprising the amino acid sequence of SEQ ID NO: 187, and a CDR3 comprising the amino acid sequence of SEQ ID NO: 189, and the beta chain comprises a CDR1 comprising the amino acid sequence of SEQ ID NO: 423, a CDR2 comprising the amino acid sequence of SEQ ID NO: 425, and a CDR3 comprising the amino acid sequence of SEQ ID NO: 427;

(bb) the alpha chain comprises a CDR1 comprising the amino acid sequence of SEQ ID NO: 192, a CDR2 comprising the amino acid sequence of SEQ ID NO: 194, and a CDR3 comprising the amino acid sequence of SEQ ID NO: 196, and the beta chain comprises a CDR1 comprising the amino acid sequence of SEQ ID NO: 430, a CDR2 comprising the amino acid sequence of SEQ ID NO: 432, and a CDR3 comprising the amino acid sequence of SEQ ID NO: 434;

(cc) the alpha chain comprises a CDR1 comprising the amino acid sequence of SEQ ID NO: 199, a CDR2 comprising the amino acid sequence of SEQ ID NO: 201, and a CDR3 comprising the amino acid sequence of SEQ ID NO: 203, and the beta chain comprises a CDR1 comprising the amino acid sequence of SEQ ID NO: 437, a CDR2 comprising the amino acid sequence of SEQ ID NO: 439, and a CDR3 comprising the amino acid sequence of SEQ ID NO: 441;

(dd) the alpha chain comprises a CDR1 comprising the amino acid sequence of SEQ ID NO: 206, a CDR2 comprising the amino acid sequence of SEQ ID NO: 208, and a CDR3 comprising the amino acid sequence of SEQ ID NO: 210, and the beta chain comprises a CDR1 comprising the amino acid sequence of SEQ ID NO: 444, a CDR2 comprising the amino acid sequence of SEQ ID NO: 446, and a CDR3 comprising the amino acid sequence of SEQ ID NO: 448;

(ee) the alpha chain comprises a CDR1 comprising the amino acid sequence of SEQ ID NO: 213, a CDR2 comprising the amino acid sequence of SEQ ID NO: 215, and a CDR3 comprising the amino acid sequence of SEQ ID NO: 217, and the beta chain comprises a CDR1 comprising the amino acid sequence of SEQ ID NO: 451, a CDR2 comprising the amino acid sequence of SEQ ID NO: 453, and a CDR3 comprising the amino acid sequence of SEQ ID NO: 455;

(ff) the alpha chain comprises a CDR1 comprising the amino acid sequence of SEQ ID NO: 220, a CDR2 comprising the amino acid sequence of SEQ ID NO: 222, and a CDR3 comprising the amino acid sequence of SEQ ID NO: 224, and the beta chain comprises a CDR1 comprising the amino acid sequence of SEQ ID NO: 458, a CDR2 comprising the amino acid sequence of SEQ ID NO: 460, and a CDR3 comprising the amino acid sequence of SEQ ID NO: 462;

(gg) the alpha chain comprises a CDR1 comprising the amino acid sequence of SEQ ID NO: 227, a CDR2 comprising the amino acid sequence of SEQ ID NO: 229, and a CDR3 comprising the amino acid sequence of SEQ ID NO: 231, and the beta chain comprises a CDR1 comprising the amino acid sequence of SEQ ID NO: 465, a CDR2 comprising the amino acid sequence of SEQ ID NO: 467, and a CDR3 comprising the amino acid sequence of SEQ ID NO: 469; or (hh) the alpha chain comprises a CDR1 comprising the amino acid sequence of SEQ ID NO: 234, a CDR2 comprising the amino acid sequence of SEQ ID NO: 236, and a CDR3 comprising the amino acid sequence of SEQ ID NO: 238, and the beta chain comprises a CDR1 comprising the amino acid sequence of SEQ ID NO: 472, a CDR2 comprising the amino acid sequence of SEQ ID NO: 474, and a CDR3 comprising the amino acid sequence of SEQ ID NO: 476.

Embodiment 3. The TCR of embodiment 1 or 2, wherein:

(a) the alpha chain of embodiment 2(a) comprises a variable and joining (VJ) region comprising an amino acid sequence that is at least 90%, 95%, 96%, 97%, 98%, 99% or 100% identical to the amino acid sequence of SEQ ID NO: 479, and the beta chain of embodiment 2(a) comprises a variable, diversity and joining (VDJ) region comprising an amino acid sequence that is at least 90%, 95%, 96%, 97%, 98%, 99% or 100% identical to amino acid sequence of SEQ ID NO: 581;

(b) the alpha chain of embodiment 2(b) comprises a VJ region comprising an amino acid sequence that is at least 90%, 95%, 96%, 97%, 98%, 99% or 100% identical to amino acid sequence of SEQ ID NO: 482, and the beta chain of embodiment 2(b) comprises a VJD region comprising an amino acid sequence that is at least 90%, 95%, 96%, 97%, 98%, 99% or 100% identical to amino acid sequence of SEQ ID NO: 584;

(c) the alpha chain of embodiment 2(c) comprises a VJ region comprising an amino acid sequence that is at least 90%, 95%, 96%, 97%, 98%, 99% or 100% identical to amino acid sequence of SEQ ID NO: 485, and the beta chain of embodiment 2(c) comprises a VJD region comprising an amino acid sequence that is at least 90%, 95%, 96%, 97%, 98%, 99% or 100% identical to amino acid sequence of SEQ ID NO: 587;

(d) the alpha chain of embodiment 2(d) comprises a VJ region comprising an amino acid sequence that is at least 90%, 95%, 96%, 97%, 98%, 99% or 100% identical to amino acid sequence of SEQ ID NO: 488, and the beta chain of embodiment 2(d) comprises a VJD region comprising an amino acid sequence that is at least 90%, 95%, 96%, 97%, 98%, 99% or 100% identical to amino acid sequence of SEQ ID NO: 590;

(e) the alpha chain of embodiment 2(e) comprises a VJ region comprising an amino acid sequence that is at least 90%, 95%, 96%, 97%, 98%, 99% or 100% identical to amino acid sequence of SEQ ID NO: 491, and the beta chain of embodiment 2(e) comprises a VJD region comprising an amino acid sequence that is at least 90%, 95%, 96%, 97%, 98%, 99% or 100% identical to amino acid sequence of SEQ ID NO: 593;

(f) the alpha chain of embodiment 2(f) comprises a VJ region comprising an amino acid sequence that is at least 90%, 95%, 96%, 97%, 98%, 99% or 100% identical to amino acid sequence of SEQ ID NO: 494, and the beta chain of embodiment 2(f) comprises a VJD region comprising an amino acid sequence that is at least 90%, 95%, 96%, 97%, 98%, 99% or 100% identical to amino acid sequence of SEQ ID NO: 596;

(g) the alpha chain of embodiment 2(g) comprises a VJ region comprising an amino acid sequence that is at least 90%, 95%, 96%, 97%, 98%, 99% or 100% identical to amino acid sequence of SEQ ID NO: 497, and the beta chain of embodiment 2(g) comprises a VJD region comprising an amino acid sequence that is at least 90%, 95%, 96%, 97%, 98%, 99% or 100% identical to amino acid sequence of SEQ ID NO: 599;

(h) the alpha chain of embodiment 2(h) comprises a VJ region comprising an amino acid sequence that is at least 90%, 95%, 96%, 97%, 98%, 99% or 100% identical to amino acid sequence of SEQ ID NO: 500, and the beta chain of embodiment 2(h) comprises a VJD region comprising an amino acid sequence that is at least 90%, 95%, 96%, 97%, 98%, 99% or 100% identical to amino acid sequence of SEQ ID NO: 602;

(i) the alpha chain of embodiment 2(i) comprises a VJ region comprising an amino acid sequence that is at least 90%, 95%, 96%, 97%, 98%, 99% or 100% identical to amino acid sequence of SEQ ID NO: 503, and the beta chain of embodiment 2(i) comprises a VJD region comprising an amino acid sequence that is at least 90%, 95%, 96%, 97%, 98%, 99% or 100% identical to amino acid sequence of SEQ ID NO: 605;

(j) the alpha chain of embodiment 2(j) comprises a VJ region comprising an amino acid sequence that is at least 90%, 95%, 96%, 97%, 98%, 99% or 100% identical to amino acid sequence of SEQ ID NO: 506, and the beta chain of embodiment 2(j) comprises a VJD region comprising an amino acid sequence that is at least 90%, 95%, 96%, 97%, 98%, 99% or 100% identical to amino acid sequence of SEQ ID NO: 608;

(k) the alpha chain of embodiment 2(k) comprises a VJ region comprising an amino acid sequence that is at least 90%, 95%, 96%, 97%, 98%, 99% or 100% identical to amino acid sequence of SEQ ID NO: 509, and the beta chain of embodiment 2(k) comprises a VJD region comprising an amino acid sequence that is at least 90%, 95%, 96%, 97%, 98%, 99% or 100% identical to amino acid sequence of SEQ ID NO: 611;

(l) the alpha chain of embodiment 2(1) comprises a VJ region comprising an amino acid sequence that is at least 90%, 95%, 96%, 97%, 98%, 99% or 100% identical to amino acid sequence of SEQ ID NO: 512, and the beta chain of embodiment 2(1) comprises a VJD region comprising an amino acid sequence that is at least 90%, 95%, 96%, 97%, 98%, 99% or 100% identical to amino acid sequence of SEQ ID NO: 614;

(m) the alpha chain of embodiment 2(m) comprises a VJ region comprising an amino acid sequence that is at least 90%, 95%, 96%, 97%, 98%, 99% or 100% identical to amino acid sequence of SEQ ID NO: 515, and the beta chain of embodiment 2(m) comprises a VJD region comprising an amino acid sequence that is at least 90%, 95%, 96%, 97%, 98%, 99% or 100% identical to amino acid sequence of SEQ ID NO: 617;

(n) the alpha chain of embodiment 2(n) comprises a VJ region comprising an amino acid sequence that is at least 90%, 95%, 96%, 97%, 98%, 99% or 100% identical to amino acid sequence of SEQ ID NO: 518, and the beta chain of embodiment 2(n) comprises a VJD region comprising an amino acid sequence that is at least 90%, 95%, 96%, 97%, 98%, 99% or 100% identical to amino acid sequence of SEQ ID NO: 620;

(o) the alpha chain of embodiment 2(o) comprises a VJ region comprising an amino acid sequence that is at least 90%, 95%, 96%, 97%, 98%, 99% or 100% identical to amino acid sequence of SEQ ID NO: 521, and the beta chain of embodiment 2(o) comprises a VJD region comprising an amino acid sequence that is at least 90%, 95%, 96%, 97%, 98%, 99% or 100% identical to amino acid sequence of SEQ ID NO: 623;

(p) the alpha chain of embodiment 2(p) comprises a VJ region comprising an amino acid sequence that is at least 90%, 95%, 96%, 97%, 98%, 99% or 100% identical to amino acid sequence of SEQ ID NO: 524, and the beta chain of embodiment 2(p) comprises a VJD region comprising an amino acid sequence that is at least 90%, 95%, 96%, 97%, 98%, 99% or 100% identical to amino acid sequence of SEQ ID NO: 626;

(q) the alpha chain of embodiment 2(q) comprises a VJ region comprising an amino acid sequence that is at least 90%, 95%, 96%, 97%, 98%, 99% or 100% identical to amino acid sequence of SEQ ID NO: 527, and the beta chain of embodiment 2(q) comprises a VJD region comprising an amino acid sequence that is at least 90%, 95%, 96%, 97%, 98%, 99% or 100% identical to amino acid sequence of SEQ ID NO: 629;

(r) the alpha chain of embodiment 2(r) comprises a VJ region comprising an amino acid sequence that is at least 90%, 95%, 96%, 97%, 98%, 99% or 100% identical to amino acid sequence of SEQ ID NO: 530, and the beta chain of embodiment 2(r) comprises a VJD region comprising an amino acid sequence that is at least 90%, 95%, 96%, 97%, 98%, 99% or 100% identical to amino acid sequence of SEQ ID NO: 632;

(s) the alpha chain of embodiment 2(s) comprises a VJ region comprising an amino acid sequence that is at least 90%, 95%, 96%, 97%, 98%, 99% or 100% identical to amino acid sequence of SEQ ID NO: 533, and the beta chain of embodiment 2(s) comprises a VJD region comprising an amino acid sequence that is at least 90%, 95%, 96%, 97%, 98%, 99% or 100% identical to amino acid sequence of SEQ ID NO: 635;

(t) the alpha chain of embodiment 2(t) comprises a VJ region comprising an amino acid sequence that is at least 90%, 95%, 96%, 97%, 98%, 99% or 100% identical to amino acid sequence of SEQ ID NO: 536, and the beta chain of embodiment 2(t) comprises a VJD region comprising an amino acid sequence that is at least 90%, 95%, 96%, 97%, 98%, 99% or 100% identical to amino acid sequence of SEQ ID NO: 638;

(u) the alpha chain of embodiment 2(u) comprises a VJ region comprising an amino acid sequence that is at least 90%, 95%, 96%, 97%, 98%, 99% or 100% identical to amino acid sequence of SEQ ID NO: 539, and the beta chain of embodiment 2(u) comprises a VJD region comprising an amino acid sequence that is at least 90%, 95%, 96%, 97%, 98%, 99% or 100% identical to amino acid sequence of SEQ ID NO: 641;

(v) the alpha chain of embodiment 2(v) comprises a VJ region comprising an amino acid sequence that is at least 90%, 95%, 96%, 97%, 98%, 99% or 100% identical to amino acid sequence of SEQ ID NO: 542, and the beta chain of embodiment 2(v) comprises a VJD region comprising an amino acid sequence that is at least 90%, 95%, 96%, 97%, 98%, 99% or 100% identical to amino acid sequence of SEQ ID NO: 644;

(w) the alpha chain of embodiment 2(w) comprises a VJ region comprising an amino acid sequence that is at least 90%, 95%, 96%, 97%, 98%, 99% or 100% identical to amino acid sequence of SEQ ID NO: 545, and the beta chain of embodiment 2(w) comprises a VJD region comprising an amino acid sequence that is at least 90%, 95%, 96%, 97%, 98%, 99% or 100% identical to amino acid sequence of SEQ ID NO: 647;

(x) the alpha chain of embodiment 2(x) comprises a VJ region comprising an amino acid sequence that is at least 90%, 95%, 96%, 97%, 98%, 99% or 100% identical to amino acid sequence of SEQ ID NO: 548, and the beta chain of embodiment 2(x) comprises a VJD region comprising an amino acid sequence that is at least 90%, 95%, 96%, 97%, 98%, 99% or 100% identical to amino acid sequence of SEQ ID NO: 650;

(y) the alpha chain of embodiment 2(y) comprises a VJ region comprising an amino acid sequence that is at least 90%, 95%, 96%, 97%, 98%, 99% or 100% identical to amino acid sequence of SEQ ID NO: 551, and the beta chain of embodiment 2(y) comprises a VJD region comprising an amino acid sequence that is at least 90%, 95%, 96%, 97%, 98%, 99% or 100% identical to amino acid sequence of SEQ ID NO: 653;

(z) the alpha chain of embodiment 2(z) comprises a VJ region comprising an amino acid sequence that is at least 90%, 95%, 96%, 97%, 98%, 99% or 100% identical to amino acid sequence of SEQ ID NO: 554, and the beta chain of embodiment 2(z) comprises a VJD region comprising an amino acid sequence that is at least 90%, 95%, 96%, 97%, 98%, 99% or 100% identical to amino acid sequence of SEQ ID NO: 656;

(aa) the alpha chain of embodiment 2(aa) comprises a VJ region comprising an amino acid sequence that is at least 90%, 95%, 96%, 97%, 98%, 99% or 100% identical to amino acid sequence of SEQ ID NO: 557, and the beta chain of embodiment 2(aa) comprises a VJD region comprising an amino acid sequence that is at least 90%, 95%, 96%, 97%, 98%, 99% or 100% identical to amino acid sequence of SEQ ID NO: 659;

(bb) the alpha chain of embodiment 2(bb) comprises a VJ region comprising an amino acid sequence that is at least 90%, 95%, 96%, 97%, 98%, 99% or 100% identical to amino acid sequence of SEQ ID NO: 560, and the beta chain of embodiment 2(bb) comprises a VJD region comprising an amino acid sequence that is at least 90%, 95%, 96%, 97%, 98%, 99% or 100% identical to amino acid sequence of SEQ ID NO: 662;

(cc) the alpha chain of embodiment 2(cc) comprises a VJ region comprising an amino acid sequence that is at least 90%, 95%, 96%, 97%, 98%, 99% or 100% identical to amino acid sequence of SEQ ID NO: 563, and the beta chain of embodiment 2(cc) comprises a VJD region comprising an amino acid sequence that is at least 90%, 95%, 96%, 97%, 98%, 99% or 100% identical to amino acid sequence of SEQ ID NO: 665;

(dd) the alpha chain of embodiment 2(dd) comprises a VJ region comprising an amino acid sequence that is at least 90%, 95%, 96%, 97%, 98%, 99% or 100% identical to amino acid sequence of SEQ ID NO: 566, and the beta chain of embodiment 2(dd) comprises a VJD region comprising an amino acid sequence that is at least 90%, 95%, 96%, 97%, 98%, 99% or 100% identical to amino acid sequence of SEQ ID NO: 668;

(ee) the alpha chain of embodiment 2(ee) comprises a VJ region comprising an amino acid sequence that is at least 90%, 95%, 96%, 97%, 98%, 99% or 100% identical to amino acid sequence of SEQ ID NO: 569, and the beta chain of embodiment 2(ee) comprises a VJD region comprising an amino acid sequence that is at least 90%, 95%, 96%, 97%, 98%, 99% or 100% identical to amino acid sequence of SEQ ID NO: 671;

(ff) the alpha chain of embodiment 2(ff) comprises a VJ region comprising an amino acid sequence that is at least 90%, 95%, 96%, 97%, 98%, 99% or 100% identical to amino acid sequence of SEQ ID NO: 572, and the beta chain of embodiment 2(ff) comprises a VJD region comprising an amino acid sequence that is at least 90%, 95%, 96%, 97%, 98%, 99% or 100% identical to amino acid sequence of SEQ ID NO: 674;

(gg) the alpha chain of embodiment 2(gg) comprises a VJ region comprising an amino acid sequence that is at least 90%, 95%, 96%, 97%, 98%, 99% or 100% identical to amino acid sequence of SEQ ID NO: 575, and the beta chain of embodiment 2(gg) comprises a VJD region comprising an amino acid sequence that is at least 90%, 95%, 96%, 97%, 98%, 99% or 100% identical to amino acid sequence of SEQ ID NO: 677; or (hh) the alpha chain of embodiment 2(hh) comprises a VJ region comprising an amino acid sequence that is at least 90%, 95%, 96%, 97%, 98%, 99% or 100% identical to amino acid sequence of SEQ ID NO: 578, and the beta chain of embodiment 2(hh) comprises a VJD region comprising an amino acid sequence that is at least 90%, 95%, 96%, 97%, 98%, 99% or 100% identical to amino acid sequence of SEQ ID NO: 680.

Embodiment 4. The TCR of embodiment 1 or 2, wherein:

(a) the alpha chain of embodiment 2(a) comprises an amino acid sequence that is at least 90%, 95%, 96%, 97%, 98%, 99% or 100% identical to the amino acid sequence of SEQ ID NO: 477, and the beta chain of embodiment 2(a) comprises an amino acid sequence that is at least 90%, 95%, 96%, 97%, 98%, 99% or 100% identical to amino acid sequence of SEQ ID NO: 579;

(b) the alpha chain of embodiment 2(b) comprises an amino acid sequence that is at least 90%, 95%, 96%, 97%, 98%, 99% or 100% identical to amino acid sequence of SEQ ID NO: 480, and the beta chain of embodiment 2(b) comprises an amino acid sequence that is at least 90%, 95%, 96%, 97%, 98%, 99% or 100% identical to amino acid sequence of SEQ ID NO: 582;

(c) the alpha chain of embodiment 2(c) comprises an amino acid sequence that is at least 90%, 95%, 96%, 97%, 98%, 99% or 100% identical to amino acid sequence of SEQ ID NO: 483, and the beta chain of embodiment 2(c) comprises an amino acid sequence that is at least 90%, 95%, 96%, 97%, 98%, 99% or 100% identical to amino acid sequence of SEQ ID NO: 585;

(d) the alpha chain of embodiment 2(d) comprises an amino acid sequence that is at least 90%, 95%, 96%, 97%, 98%, 99% or 100% identical to amino acid sequence of SEQ ID NO: 486, and the beta chain of embodiment 2(d) comprises an amino acid sequence that is at least 90%, 95%, 96%, 97%, 98%, 99% or 100% identical to amino acid sequence of SEQ ID NO: 588;

(e) the alpha chain of embodiment 2(e) comprises an amino acid sequence that is at least 90%, 95%, 96%, 97%, 98%, 99% or 100% identical to amino acid sequence of SEQ ID NO: 489, and the beta chain of embodiment 2(e) comprises an amino acid sequence that is at least 90%, 95%, 96%, 97%, 98%, 99% or 100% identical to amino acid sequence of SEQ ID NO: 591;

(f) the alpha chain of embodiment 2(f) comprises an amino acid sequence that is at least 90%, 95%, 96%, 97%, 98%, 99% or 100% identical to amino acid sequence of SEQ ID NO: 492, and the beta chain of embodiment 2(f) comprises an amino acid sequence that is at least 90%, 95%, 96%, 97%, 98%, 99% or 100% identical to amino acid sequence of SEQ ID NO: 594;

(g) the alpha chain of embodiment 2(g) comprises an amino acid sequence that is at least 90%, 95%, 96%, 97%, 98%, 99% or 100% identical to amino acid sequence of SEQ ID NO: 495, and the beta chain of embodiment 2(g) comprises an amino acid sequence that is at least 90%, 95%, 96%, 97%, 98%, 99% or 100% identical to amino acid sequence of SEQ ID NO: 597;

(h) the alpha chain of embodiment 2(h) comprises an amino acid sequence that is at least 90%, 95%, 96%, 97%, 98%, 99% or 100% identical to amino acid sequence of SEQ ID NO: 498, and the beta chain of embodiment 2(h) comprises an amino acid sequence that is at least 90%, 95%, 96%, 97%, 98%, 99% or 100% identical to amino acid sequence of SEQ ID NO: 600;

(i) the alpha chain of embodiment 2(i) comprises an amino acid sequence that is at least 90%, 95%, 96%, 97%, 98%, 99% or 100% identical to amino acid sequence of SEQ ID NO: 501, and the beta chain of embodiment 2(i) comprises an amino acid sequence that is at least 90%, 95%, 96%, 97%, 98%, 99% or 100% identical to amino acid sequence of SEQ ID NO: 603;

(j) the alpha chain of embodiment 2(j) comprises an amino acid sequence that is at least 90%, 95%, 96%, 97%, 98%, 99% or 100% identical to amino acid sequence of SEQ ID NO: 504, and the beta chain of embodiment 2(j) comprises an amino acid sequence that is at least 90%, 95%, 96%, 97%, 98%, 99% or 100% identical to amino acid sequence of SEQ ID NO: 606;

(k) the alpha chain of embodiment 2(k) comprises an amino acid sequence that is at least 90%, 95%, 96%, 97%, 98%, 99% or 100% identical to amino acid sequence of SEQ ID NO: 507, and the beta chain of embodiment 2(k) comprises an amino acid sequence that is at least 90%, 95%, 96%, 97%, 98%, 99% or 100% identical to amino acid sequence of SEQ ID NO: 609;

(l) the alpha chain of embodiment 2(1) comprises an amino acid sequence that is at least 90%, 95%, 96%, 97%, 98%, 99% or 100% identical to amino acid sequence of SEQ ID NO: 510, and the beta chain of embodiment 2(1) comprises an amino acid sequence that is at least 90%, 95%, 96%, 97%, 98%, 99% or 100% identical to amino acid sequence of SEQ ID NO: 612;

(m) the alpha chain of embodiment 2(m) comprises an amino acid sequence that is at least 90%, 95%, 96%, 97%, 98%, 99% or 100% identical to amino acid sequence of SEQ ID NO: 513, and the beta chain of embodiment 2(m) comprises an amino acid sequence that is at least 90%, 95%, 96%, 97%, 98%, 99% or 100% identical to amino acid sequence of SEQ ID NO: 615;

(n) the alpha chain of embodiment 2(n) comprises an amino acid sequence that is at least 90%, 95%, 96%, 97%, 98%, 99% or 100% identical to amino acid sequence of SEQ ID NO: 516, and the beta chain of embodiment 2(n) comprises an amino acid sequence that is at least 90%, 95%, 96%, 97%, 98%, 99% or 100% identical to amino acid sequence of SEQ ID NO: 618;

(o) the alpha chain of embodiment 2(o) comprises an amino acid sequence that is at least 90%, 95%, 96%, 97%, 98%, 99% or 100% identical to amino acid sequence of SEQ ID NO: 519, and the beta chain of embodiment 2(o) comprises an amino acid sequence that is at least 90%, 95%, 96%, 97%, 98%, 99% or 100% identical to amino acid sequence of SEQ ID NO: 621;

(p) the alpha chain of embodiment 2(p) comprises an amino acid sequence that is at least 90%, 95%, 96%, 97%, 98%, 99% or 100% identical to amino acid sequence of SEQ ID NO: 522, and the beta chain of embodiment 2(p) comprises an amino acid sequence that is at least 90%, 95%, 96%, 97%, 98%, 99% or 100% identical to amino acid sequence of SEQ ID NO: 624;

(q) the alpha chain of embodiment 2(q) comprises an amino acid sequence that is at least 90%, 95%, 96%, 97%, 98%, 99% or 100% identical to amino acid sequence of SEQ ID NO: 525, and the beta chain of embodiment 2(q) comprises an amino acid sequence that is at least 90%, 95%, 96%, 97%, 98%, 99% or 100% identical to amino acid sequence of SEQ ID NO: 627;

(r) the alpha chain of embodiment 2(r) comprises an amino acid sequence that is at least 90%, 95%, 96%, 97%, 98%, 99% or 100% identical to amino acid sequence of SEQ ID NO: 528, and the beta chain of embodiment 2(r) comprises an amino acid sequence that is at least 90%, 95%, 96%, 97%, 98%, 99% or 100% identical to amino acid sequence of SEQ ID NO: 630;

(s) the alpha chain of embodiment 2(s) comprises an amino acid sequence that is at least 90%, 95%, 96%, 97%, 98%, 99% or 100% identical to amino acid sequence of SEQ ID NO: 531, and the beta chain of embodiment 2(s) comprises an amino acid sequence that is at least 90%, 95%, 96%, 97%, 98%, 99% or 100% identical to amino acid sequence of SEQ ID NO: 633;

(t) the alpha chain of embodiment 2(t) comprises an amino acid sequence that is at least 90%, 95%, 96%, 97%, 98%, 99% or 100% identical to amino acid sequence of SEQ ID NO: 534, and the beta chain of embodiment 2(t) comprises an amino acid sequence that is at least 90%, 95%, 96%, 97%, 98%, 99% or 100% identical to amino acid sequence of SEQ ID NO: 636;

(u) the alpha chain of embodiment 2(u) comprises an amino acid sequence that is at least 90%, 95%, 96%, 97%, 98%, 99% or 100% identical to amino acid sequence of SEQ ID NO: 537, and the beta chain of embodiment 2(u) comprises an amino acid sequence that is at least 90%, 95%, 96%, 97%, 98%, 99% or 100% identical to amino acid sequence of SEQ ID NO: 639;

(v) the alpha chain of embodiment 2(v) comprises an amino acid sequence that is at least 90%, 95%, 96%, 97%, 98%, 99% or 100% identical to amino acid sequence of SEQ ID NO: 540, and the beta chain of embodiment 2(v) comprises an amino acid sequence that is at least 90%, 95%, 96%, 97%, 98%, 99% or 100% identical to amino acid sequence of SEQ ID NO: 642;

(w) the alpha chain of embodiment 2(w) comprises an amino acid sequence that is at least 90%, 95%, 96%, 97%, 98%, 99% or 100% identical to amino acid sequence of SEQ ID NO: 543, and the beta chain of embodiment 2(w) comprises an amino acid sequence that is at least 90%, 95%, 96%, 97%, 98%, 99% or 100% identical to amino acid sequence of SEQ ID NO: 645;

(x) the alpha chain of embodiment 2(x) comprises an amino acid sequence that is at least 90%, 95%, 96%, 97%, 98%, 99% or 100% identical to amino acid sequence of SEQ ID NO: 546, and the beta chain of embodiment 2(x) comprises an amino acid sequence that is at least 90%, 95%, 96%, 97%, 98%, 99% or 100% identical to amino acid sequence of SEQ ID NO: 648;

(y) the alpha chain of embodiment 2(y) comprises an amino acid sequence that is at least 90%, 95%, 96%, 97%, 98%, 99% or 100% identical to amino acid sequence of SEQ ID NO: 549, and the beta chain of embodiment 2(y) comprises an amino acid sequence that is at least 90%, 95%, 96%, 97%, 98%, 99% or 100% identical to amino acid sequence of SEQ ID NO: 651;

(z) the alpha chain of embodiment 2(z) comprises an amino acid sequence that is at least 90%, 95%, 96%, 97%, 98%, 99% or 100% identical to amino acid sequence of SEQ ID NO: 552, and the beta chain of embodiment 2(z) comprises an amino acid sequence that is at least 90%, 95%, 96%, 97%, 98%, 99% or 100% identical to amino acid sequence of SEQ ID NO: 654;

(aa) the alpha chain of embodiment 2(aa) comprises an amino acid sequence that is at least 90%, 95%, 96%, 97%, 98%, 99% or 100% identical to amino acid sequence of SEQ ID NO: 555, and the beta chain of embodiment 2(aa) comprises an amino acid sequence that is at least 90%, 95%, 96%, 97%, 98%, 99% or 100% identical to amino acid sequence of SEQ ID NO: 657;

(bb) the alpha chain of embodiment 2(bb) comprises an amino acid sequence that is at least 90%, 95%, 96%, 97%, 98%, 99% or 100% identical to amino acid sequence of SEQ ID NO: 558, and the beta chain of embodiment 2(bb) comprises an amino acid sequence that is at least 90%, 95%, 96%, 97%, 98%, 99% or 100% identical to amino acid sequence of SEQ ID NO: 660;

(cc) the alpha chain of embodiment 2(cc) comprises an amino acid sequence that is at least 90%, 95%, 96%, 97%, 98%, 99% or 100% identical to amino acid sequence of SEQ ID NO: 561, and the beta chain of embodiment 2(cc) comprises an amino acid sequence that is at least 90%, 95%, 96%, 97%, 98%, 99% or 100% identical to amino acid sequence of SEQ ID NO: 663;

(dd) the alpha chain of embodiment 2(dd) comprises an amino acid sequence that is at least 90%, 95%, 96%, 97%, 98%, 99% or 100% identical to amino acid sequence of SEQ ID NO: 564, and the beta chain of embodiment 2(dd) comprises an amino acid sequence that is at least 90%, 95%, 96%, 97%, 98%, 99% or 100% identical to amino acid sequence of SEQ ID NO: 666;

(ee) the alpha chain of embodiment 2(ee) comprises an amino acid sequence that is at least 90%, 95%, 96%, 97%, 98%, 99% or 100% identical to amino acid sequence of SEQ ID NO: 567, and the beta chain of embodiment 2(ee) comprises an amino acid sequence that is at least 90%, 95%, 96%, 97%, 98%, 99% or 100% identical to amino acid sequence of SEQ ID NO: 669;

(ff) the alpha chain of embodiment 2(ff) comprises an amino acid sequence that is at least 90%, 95%, 96%, 97%, 98%, 99% or 100% identical to amino acid sequence of SEQ ID NO: 570, and the beta chain of embodiment 2(ff) comprises an amino acid sequence that is at least 90%, 95%, 96%, 97%, 98%, 99% or 100% identical to amino acid sequence of SEQ ID NO: 672;

(gg) the alpha chain of embodiment 2(gg) comprises an amino acid sequence that is at least 90%, 95%, 96%, 97%, 98%, 99% or 100% identical to amino acid sequence of SEQ ID NO: 573, and the beta chain of embodiment 2(gg) comprises an amino acid sequence that is at least 90%, 95%, 96%, 97%, 98%, 99% or 100% identical to amino acid sequence of SEQ ID NO: 675; or (hh) the alpha chain of embodiment 2(hh) comprises an amino acid sequence that is at least 90%, 95%, 96%, 97%, 98%, 99% or 100% identical to amino acid sequence of SEQ ID NO: 576, and the beta chain of embodiment 2(hh) comprises an amino acid sequence that is at least 90%, 95%, 96%, 97%, 98%, 99% or 100% identical to amino acid sequence of SEQ ID NO: 678.

Embodiment 5. A nucleic acid molecule encoding the TCR of any one of embodiments 1-4.

Embodiment 6. A vector comprising the nucleic acid molecule of embodiment 5.

Embodiment 7. A cell transformed to express the nucleic acid molecule of embodiment 5.

Embodiment 8. A cell comprising the vector of embodiment 6.

Embodiment 9. The cell of embodiment 7 or 8, wherein the cell is a CD8+ T cell.

Embodiment 10. A pharmaceutical composition comprising the TCR of any one of embodiment 1-4, the nucleic acid molecule of embodiment 5, the vector of embodiment 6, or the cell of any one of embodiments 7-9.

What is claimed:

1. A T-cell receptor (TCR) comprising an alpha chain and a beta chain, wherein:

(a) Lathe alpha chain comprises a CDR1 comprising the amino acid sequence of SEQ ID NO: 10, a CDR2 comprising the amino acid sequence of SEQ ID NO: 126, and a CDR3 comprising the amino acid sequence of SEQ ID NO: 14, and the beta chain comprises a CDR1 comprising the amino acid sequence of SEQ ID NO: 218, a CDR2 comprising the amino acid sequence of SEQ ID NO: 264, and a CDR3 comprising the amino acid sequence of SEQ ID NO: 266;

(b) the alpha chain comprises a CDR1 comprising the amino acid sequence of SEQ ID NO: 31, a CDR2 comprising the amino acid sequence of SEQ ID NO: 33, and a CDR3 comprising the amino acid sequence of SEQ ID NO: 35, and the beta chain comprises a CDR1 comprising the amino acid sequence of SEQ ID NO: 269, a CDR2 comprising the amino acid sequence of SEQ ID NO: 271, and a CDR3 comprising the amino acid sequence of SEQ ID NO: 273;

(c) the alpha chain comprises a CDR1 comprising the amino acid sequence of SEQ ID NO: 38, a CDR2 comprising the amino acid sequence of SEQ ID NO: 40, and a CDR3 comprising the amino acid sequence of SEQ ID NO: 42, and the beta chain comprises a CDR1 comprising the amino acid sequence of SEQ ID NO: 276, a CDR2 comprising the amino acid sequence of SEQ ID NO: 278, and a CDR3 comprising the amino acid sequence of SEQ ID NO: 280;

(d) the alpha chain comprises a CDR1 comprising the amino acid sequence of SEQ ID NO: 45, a CDR2 comprising the amino acid sequence of SEQ ID NO: 47, and a CDR3 comprising the amino acid sequence of SEQ ID NO: 49, and the beta chain comprises a CDR1 comprising the amino acid sequence of SEQ ID NO: 283, a CDR2 comprising the amino acid sequence of SEQ ID NO: 285, and a CDR3 comprising the amino acid sequence of SEQ ID NO: 287;

(e) the alpha chain comprises a CDR1 comprising the amino acid sequence of SEQ ID NO: 59, a CDR2 comprising the amino acid sequence of SEQ ID NO: 61, and a CDR3 comprising the amino acid sequence of SEQ ID NO: 63, and the beta chain comprises a CDR1 comprising the amino acid sequence of SEQ ID NO: 297, a CDR2 comprising the amino acid sequence of SEQ ID NO: 299, and a CDR3 comprising the amino acid sequence of SEQ ID NO: 301;

(f) the alpha chain comprises a CDR1 comprising the amino acid sequence of SEQ ID NO: 66, a CDR2 comprising the amino acid sequence of SEQ ID NO: 68, and a CDR3 comprising the amino acid sequence of SEQ ID NO: 70, and the beta chain comprises a CDR1 comprising the amino acid sequence of SEQ ID NO:

304, a CDR2 comprising the amino acid sequence of SEQ ID NO: 306, and a CDR3 comprising the amino acid sequence of SEQ ID NO: 308;

(g) the alpha chain comprises a CDR1 comprising the amino acid sequence of SEQ ID NO: 73, a CDR2 comprising the amino acid sequence of SEQ ID NO: 75, and a CDR3 comprising the amino acid sequence of SEQ ID NO: 77, and the beta chain comprises a CDR1 comprising the amino acid sequence of SEQ ID NO: 311, a CDR2 comprising the amino acid sequence of SEQ ID NO: 313, and a CDR3 comprising the amino acid sequence of SEQ ID NO: 315;

(h) the alpha chain comprises a CDR1 comprising the amino acid sequence of SEQ ID NO: 80, a CDR2 comprising the amino acid sequence of SEQ ID NO: 82, and a CDR3 comprising the amino acid sequence of SEQ ID NO: 84, and the beta chain comprises a CDR1 comprising the amino acid sequence of SEQ ID NO: 318, a CDR2 comprising the amino acid sequence of SEQ ID NO: 320, and a CDR3 comprising the amino acid sequence of SEQ ID NO: 322;

(i) the alpha chain comprises a CDR1 comprising the amino acid sequence of SEQ ID NO: 101, a CDR2 comprising the amino acid sequence of SEQ ID NO: 103, and a CDR3 comprising the amino acid sequence of SEQ ID NO: 105, and the beta chain comprises a CDR1 comprising the amino acid sequence of SEQ ID NO: 339, a CDR2 comprising the amino acid sequence of SEQ ID NO: 341, and a CDR3 comprising the amino acid sequence of SEQ ID NO: 343;

(j) the alpha chain comprises a CDR1 comprising the amino acid sequence of SEQ ID NO: 108, a CDR2 comprising the amino acid sequence of SEQ ID NO: 110, and a CDR3 comprising the amino acid sequence of SEQ ID NO: 112, and the beta chain comprises a CDR1 comprising the amino acid sequence of SEQ ID NO: 346, a CDR2 comprising the amino acid sequence of SEQ ID NO: 348, and a CDR3 comprising the amino acid sequence of SEQ ID NO: 350;

(k) the alpha chain comprises a CDR1 comprising the amino acid sequence of SEQ ID NO: 115, a CDR2 comprising the amino acid sequence of SEQ ID NO: 117, and a CDR3 comprising the amino acid sequence of SEQ ID NO: 119, and the beta chain comprises a CDR1 comprising the amino acid sequence of SEQ ID NO: 353, a CDR2 comprising the amino acid sequence of SEQ ID NO: 355, and a CDR3 comprising the amino acid sequence of SEQ ID NO: 357;

(l) the alpha chain comprises a CDR1 comprising the amino acid sequence of SEQ ID NO: 122, a CDR2 comprising the amino acid sequence of SEQ ID NO: 124, and a CDR3 comprising the amino acid sequence of SEQ ID NO: 126, and the beta chain comprises a CDR1 comprising the amino acid sequence of SEQ ID NO: 360, a CDR2 comprising the amino acid sequence of SEQ ID NO: 362, and a CDR3 comprising the amino acid sequence of SEQ ID NO: 364;

(m) the alpha chain comprises a CDR1 comprising the amino acid sequence of SEQ ID NO: 129, a CDR2 comprising the amino acid sequence of SEQ ID NO: 131, and a CDR3 comprising the amino acid sequence of SEQ ID NO: 133, and the beta chain comprises a CDR1 comprising the amino acid sequence of SEQ ID NO: 367, a CDR2 comprising the amino acid sequence of SEQ ID NO: 369, and a CDR3 comprising the amino acid sequence of SEQ ID NO: 371;

(n) the alpha chain comprises a CDR1 comprising the amino acid sequence of SEQ ID NO: 136, a CDR2 comprising the amino acid sequence of SEQ ID NO: 138, and a CDR3 comprising the amino acid sequence of SEQ ID NO: 140, and the beta chain comprises a CDR1 comprising the amino acid sequence of SEQ ID NO: 374, a CDR2 comprising the amino acid sequence of SEQ ID NO: 376, and a CDR3 comprising the amino acid sequence of SEQ ID NO: 378;

(o) the alpha chain comprises a CDR1 comprising the amino acid sequence of SEQ ID NO: 143, a CDR2 comprising the amino acid sequence of SEQ ID NO: 145, and a CDR3 comprising the amino acid sequence of SEQ ID NO: 147, and the beta chain comprises a CDR1 comprising the amino acid sequence of SEQ ID NO: 381, a CDR2 comprising the amino acid sequence of SEQ ID NO: 383, and a CDR3 comprising the amino acid sequence of SEQ ID NO: 385;

(p) the alpha chain comprises a CDR1 comprising the amino acid sequence of SEQ ID NO: 157, a CDR2 comprising the amino acid sequence of SEQ ID NO: 159, and a CDR3 comprising the amino acid sequence of SEQ ID NO: 161, and the beta chain comprises a CDR1 comprising the amino acid sequence of SEQ ID NO: 395, a CDR2 comprising the amino acid sequence of SEQ ID NO: 397, and a CDR3 comprising the amino acid sequence of SEQ ID NO: 399;

(q) the alpha chain comprises a CDR1 comprising the amino acid sequence of SEQ ID NO: 164, a CDR2 comprising the amino acid sequence of SEQ ID NO: 166, and a CDR3 comprising the amino acid sequence of SEQ ID NO: 168, and the beta chain comprises a CDR1 comprising the amino acid sequence of SEQ ID NO: 402, a CDR2 comprising the amino acid sequence of SEQ ID NO: 404, and a CDR3 comprising the amino acid sequence of SEQ ID NO: 406;

(r) the alpha chain comprises a CDR1 comprising the amino acid sequence of SEQ ID NO: 178, a CDR2 comprising the amino acid sequence of SEQ ID NO: 180, and a CDR3 comprising the amino acid sequence of SEQ ID NO: 182, and the beta chain comprises a CDR1 comprising the amino acid sequence of SEQ ID NO: 416, a CDR2 comprising the amino acid sequence of SEQ ID NO: 418, and a CDR3 comprising the amino acid sequence of SEQ ID NO: 420;

(s) the alpha chain comprises a CDR1 comprising the amino acid sequence of SEQ ID NO: 119, a CDR comprising the amino acid sequence of SEQ ID NO: 1, and a CDR3 comprising the amino acid sequence of SEQ ID NO: 203, and the beta chain comprises a CDR1 comprising the amino acid sequence of SEQ ID NO: 437, a CDR2 comprising the amino acid sequence of SEQ ID NO: 439, and a CDR3 comprising the amino acid sequence of SEQ ID NO: 441;

(t) the alpha chain comprises a CDR1 comprising the amino acid sequence of SEQ ID NO: 220, a CDR2 comprising the amino acid sequence of SEQ ID NO: 222, and a CDR3 comprising the amino acid sequence of SEQ ID NO: 224, and the beta chain comprises a CDR1 comprising the amino acid sequence of SEQ ID NO: 458, a CDR2 comprising the amino acid sequence of SEQ ID NO: 460, and a CDR3 comprising the amino acid sequence of SEQ ID NO: 462;

(u) the alpha chain comprises a CDR1 comprising the amino acid sequence of SEQ ID NO: 227, a CDR2 comprising the amino acid sequence of SEQ ID NO: 229, and a CDR3 comprising the amino acid sequence of SEQ ID NO: 231, and the beta chain comprises a CDR1 comprising the amino acid sequence of SEQ ID NO: 451, a CDR2 comprising the amino acid sequence of SEQ ID NO: 467, and a CDR3 comprising the amino acid sequence of SEQ ID NO: 469;

(v) the alpha chain comprises a CDR1 comprising the amino acid sequence of SEQ ID NO: 22, a CDR2 comprising the amino acid sequence of SEQ ID NO: 22, and a CDR3 comprising the amino acid sequence of SEQ ID NO: 238, and the beta chain comprises a CDR1 comprising the amino acid sequence of SEQ ID NO: 475, a CDR2 comprising the amino acid sequence of SEQ ID NO: 474, and a CDR3 comprising the amino acid sequence of SEQ ID NO: 476.

2. The TCR of claim 1, wherein:

(a) the alpha chain of claim 1(a) comprises a VJ region comprising an amino acid sequence that is at least 90%, 95%, 96%, 97%, 98%, 99%, or 100% identical to the amino acid sequence of SEQ ID NO: 488, and the beta chain of claim 1(a) comprises a VJD region comprising an amino acid sequence that is at least 90%, 95%, 96%, 97%, 98%, 99%, or 100% identical to the amino acid sequence of SEQ ID NO: 590;

(b) the alpha chain of claim 1(b) comprises a VJ region comprising an amino acid sequence that is at least 90%, 95%, 96%, 97%, 98%, 99%, or 100% identical to the amino acid sequence of SEQ ID NO: 488, and the beta chain of claim 1(b) comprises a VJD region comprising an amino acid sequence that is at least 90%, 95%, 96%, 97%, 98%, 99% or 100% identical to the amino acid sequence of SEQ ID NO: 593;

(c) the alpha chain of claim 1(c) comprises a VJ region comprising an amino acid sequence that is at least 90%, 95%, 96%, 97%, 98%, 99%, or 100% identical to the amino acid sequence of SEQ ID NO: 494, and the beta chain of claim 1(c) comprises a VJD region comprising an amino acid sequence that is at least 90%, 95%, 96%, 97%, 98%, 99%, or 100% identical to the amino acid sequence of SEQ ID NO: 596;

(d) the alpha chain of claim 1(d) comprises a VJ region comprising an amino acid sequence that is at least 90%, 95%, 96%, 97%, 98%, 99%, or 100% identical to the amino acid sequence of SEQ ID NO: 497, and the beta chain of claim 1(d) 2(comprises a VJD region comprising an amino acid sequence that is at least 90%, 95%, 96%, 97%, 98%, 99%, or 100% identical to the amino acid sequence of SEQ ID NO: 599;

(e) the alpha chain of claim 1(e) comprises a VJ region comprising an amino acid sequence that is at least 90%, 95%, 96%, 97%, 98%, 99%, or 100% identical to the amino acid sequence of SEQ ID NO: 503, and the beta chain of claim 1(e) comprises a VJD region comprising an amino acid sequence that is at least 90%, 95%, 96%, 97%, 98%, 99%, or 100% identical to the amino acid sequence of SEQ ID NO: 605;

(f) the alpha chain of claim 1(f) comprises a VJ region comprising an amino acid sequence that is at least 90%, 95%, 96%, 97%, 98%, 99%, or 100% identical to the amino acid sequence of SEQ ID NO: 506, and the beta chain of claim 1(f) comprises a VJD region comprising an amino acid sequence that is at least 90%, 95%, 96%, 97%, 98%, 99%, or 100% identical to the amino acid sequence of SEQ ID NO: 608;

(g) the alpha chain of claim 1(g) comprises a VJ region comprising an amino acid sequence that is at least 90%, 95%, 96%, 97%, 98%, 99%, or 100% identical to the amino acid sequence of SEQ ID NO: 509, and the beta chain of claim 1(g) comprises a VJD region comprising an amino acid sequence that is at least 90%, 95%, 96%, 97%, 98%, 99%, or 100% identical to the amino acid sequence of SEQ ID NO: 611;

(h) the alpha chain of claim 1(h) comprises a VJ region comprising an amino acid sequence that is at least 90%, 95%, 96%, 97%, 98%, 99%, or 100% identical to the amino acid sequence of SEQ ID NO: 512, and the beta chain of claim 1(h) comprises a VJD region comprising an amino acid sequence that is at least 90%, 95%, 96%, 97%, 98%, 99%, or 100% identical to the amino acid sequence of SEQ ID NO: 614;

(i) the alpha chain of claim 1(i) comprises a VJ region comprising an amino acid sequence that is at least 90%, 95%, 96%, 97%, 98%, 99%, or 100% identical to the amino acid sequence of SEQ ID NO: 521, and the beta chain of claim 1(i) comprises a VJD region comprising an amino acid sequence that is at least 90%, 95%, 96%, 97%, 98%, 99%, or 100% identical to the amino acid sequence of SEQ ID NO: 623;

(j) the alpha chain of claim 1(i) comprises a VJ region comprising an amino acid sequence that is at least 90%, 95%, 96%, 97%, 98%, 99%, or 100% identical to the amino acid sequence of SEQ ID NO: 524, and the beta chain of claim 1(j) comprises a VJD region comprising an amino acid sequence that is at least 90%, 95%, 96%, 97%, 98%, 99%, or 100% identical to the amino acid sequence of SEQ ID NO: 626;

(k) the alpha chain of claim 1(k) comprises a VJ region comprising an amino acid sequence that is at least 90%, 95%, 96%, 97%, 98%, 99%, or 100% identical to the amino acid sequence of SEQ ID NO: 527, and the beta chain of claim 1(k) comprises a VJD region comprising an amino acid sequence that is at least 90%, 95%, 96%, 97%, 98%, 99%, or 100% identical to the amino acid sequence of SEQ ID NO: 629;

(l) the alpha chain of claim 1(l) comprises a VJ region comprising an amino acid sequence that is at least 90%, 95%, 96%, 97%, 98%, 99%, or 100% identical to the amino acid sequence of SEQ ID NO: 530, and the beta chain of claim 1(l) comprises a VJD region comprising an amino acid sequence that is at least 90%, 95%, 96%, 97%, 98%, 99%, or 100% identical to the amino acid sequence of SEQ ID NO: 632;

(m) the alpha chain of claim 1(m) comprises a VJ region comprising an amino acid sequence that is at least 90%, 95%, 96%, 97%, 98%, 99%, or 100% identical to the amino acid sequence of SEQ ID NO: 533, and the beta chain of claim 1(m) comprises a VJD region comprising an amino acid sequence that is at least 90%, 95%, 96%, 97%, 98%, 99%, or 100% identical to the amino acid sequence of SEQ ID NO: 635;

(n) the alpha chain of claim 1(n) comprises a VJ region comprising an amino acid sequence that is at least 90%, 95%, 96%, 97%, 98%, 99%, or 100% identical to the amino acid sequence of SEQ ID NO: 536, and the beta chain of claim 1(n) comprises a VJD region comprising an amino acid sequence that is at least 90%, 95%, 96%, 97%, 98%, 99%, or 100% identical to the amino acid sequence of SEQ ID NO: 638;

(o) the alpha chain of claim 1(o) comprises a VJ region comprising an amino acid sequence that is at least 90%, 95%, 96%, 97%, 98%, 99%, or 100% identical to the amino acid sequence of SEQ ID NO: 539, and the beta chain of claim 1(o) comprises a VJD region comprising an amino acid sequence that is at least 90%, 95%, 96%, 97%, 98%, 99%, or 100% identical to the amino acid sequence of SEQ ID NO: 641;

(p) the alpha chain of claim 1(p) comprises a VJ region comprising an amino acid sequence that is at least 90%, 95%, 96%, 97%, 98%, 99%, or 100% identical to the amino acid sequence of SEQ ID NO: 545, and the beta chain of claim 1(p) comprises a VJD region comprising an amino acid sequence that is at least 90%, 95%, 96%, 97%, 98%, 99%, or 100% identical to the amino acid sequence of SEQ ID NO: 647;

(q) the alpha chain of claim 1(q) comprises a VJ region comprising an amino acid sequence that is at least 90%, 95%, 96%, 97%, 98%, 99%, or 100% identical to the amino acid sequence of SEQ ID NO: 548, and the beta chain of claim 1(q) comprises a VJD region comprising an amino acid sequence that is at least 90%, 95%, 96%, 97%, 98%, 99%, or 100% identical to the amino acid sequence of SEQ ID NO: 650;

(r) the alpha chain of claim 1(r) comprises a VJ region comprising an amino acid sequence that is at least 90%, 95%, 96%, 97%, 98%, 99%, or 100% identical to the amino acid sequence of SEQ ID NO: 554, and the beta chain of claim 1(r) comprises a VJD region comprising an amino acid sequence that is at least 90%, 95%, 96%, 97%, 98%, 99%, or 100% identical to the amino acid sequence of SEQ ID NO: 656;

(s) the alpha chain of claim 1(s) comprises a VJ region comprising an amino acid sequence that is at least 90%, 95%, 97%, 98%, 99%, or 100% identical to the amino acid sequence of SEQ ID NO: 563, and the beta chain of claim 1(s) comprises a VJD region region comprising an amino acid sequence that is at least 90%, 96%, 97%, 98%, 99%, or 100% identical to the amino acid sequence of SEQ ID NO: 665;

(t) the alpha chain of claim 1(t) comprises a VJ region comprising an amino acid sequence that is at least 90%, 95%, 96%, 97%, 98%, 99%, or 100% identical to the amino acid sequence of SEQ ID NO: 572, and the beta chain of claim 1(t) comprises a VJD region comprising an amino acid sequence that is at least 90%, 95%, 96%, 97%, 98%, 99%, or 100% identical to the amino acid sequence of SEQ ID NO: 674;

(u) the alpha chain of claim 1(u) comprises a VJ region comprising an amino acid sequence that is at least 90%, 95%, 96%, 97%, 98%, 99%, or 100% identical to the amino acid sequence of SEQ ID NO: 575, and the beta chain of claim 1(u) comprises a VJD region comprising an amino acid sequence that is at least 90%, 95%, 96%, 97%, 98%, 99%, or 100% identical to the amino acid sequence of SEQ ID NO: 677; or (v) the alpha chain of claim 1(v) comprises a VJ region comprising an amino acid sequence that is at least 90%, 95%, 96%, 97%, 98%, 99% or 100% identical to the amino acid sequence of SEQ ID NO: 575, and the beta chain of claim 1(v) comprises a VJD region comprising an amino acid sequence that is at least 90%, 95%, 96%, 97%, 98%, 99%, or 100% identical to the amino acid sequence of SEQ ID NO: 680.

3. The TCR of claim 1, wherein:

(a) the alpha chain of claim 2(a) comprises an amino acid sequence that is at least 90%, 95%, 96%, 97%, 98%, 99%, or 100% identical to the amino acid sequence of SEQ ID NO: 486, and the beta chain of claim 2(c) comprises an amino acid sequence that is at least 90%, 95%, 96%, 97%, 98%, 99%, or 100% identical to the amino acid sequence of SEQ ID NO: 588;

(b) the alpha chain of claim 2(b) comprises an amino acid sequence that is at least 900%, 95%, 96%, 97%, 98%, 99%, or 100% identical to the amino acid sequence of SEQ ID NO: 489, and the beta chain of claim 2(b) comprises an amino acid sequence that is at least 90%, 95%, 96%, 97%, 98%, 99%, or 100% identical to the amino acid sequence of SEQ ID NO: 591;

(c) the alpha chain of claim 2(c) comprises an amino acid sequence that is at least 90%, 95%, 96%, 97%, 98%, 99%, or 100% identical to the amino acid sequence of SEQ ID NO: 492, and the beta chain of claim 2(c) comprises an amino acid sequence that is at least 90%, 95%, 96%, 97%, 98%, 99%, or 100% identical to the amino acid sequence of SEQ ID NO: 594;

(g) the alpha chain of claim 2(d) comprises an amino acid sequence that is at least 90%, 95%, 96%, 97%, 98%, 99%, or 100% identical to the amino acid sequence of SEQ ID NO: 495, and the beta chain of claim 2(d) comprises an amino acid sequence that is at least 90%, 95%, 96%, 97%, 98%, 99%, or 100% identical to the amino acid sequence of SEQ ID NO: 597;

(e) the alpha chain of claim 2(e) comprises an amino acid sequence that is at least 90%, 95%, 96%, 97%, 98%, 99%, or 100% identical to the amino acid sequence of SEQ ID NO: 501, and the beta chain of claim 2(e) comprises an amino acid sequence that is at least 90%, 95%, 96%, 97%, 98%, 99%, or 100% identical to the amino acid sequence of SEQ ID NO: 603;

(f) the alpha chain of claim 2(f) comprises an amino acid sequence that is at least 90%, 95%, 96%, 97%, 98%, 99%, or 100% identical to the amino acid sequence of SEQ ID NO: 504, and the beta chain of claim 2(f) comprises an amino acid sequence that is at least 90%, 95%, 96%, 97%, 98%, 99%, or 100% identical to the amino acid sequence of SEQ ID NO: 606;

(g) the alpha chain of claim 2(g) comprises an amino acid sequence that is at least 90%, 95%, 96%, 97%, 98%, 99%, or 100% identical to the amino acid sequence of SEQ ID NO: 507, and the beta chain of claim 2(g) comprises an amino acid sequence that is at least 90%, 95%, 96%, 97%, 98%, 99%, or 100% identical to the amino acid sequence of SEQ ID NO: 609;

(h) the alpha chain of claim 2(h) comprises an amino acid sequence that is at least 90%, 95%, 96%, 97%, 98%, 99%, or 100% identical to the amino acid sequence of SEQ ID NO: 510, and the beta chain of claim 2(h) comprises an amino acid sequence that is at least 90%, 95%, 96%, 97%, 98%, 99%, or 100% identical to the amino acid sequence of SEQ ID NO: 612;

(i) the alpha chain of claim 2(i) comprises an amino acid sequence that is at least 90%, 95%, 96%, 97%, 98%, 99%, or 100% identical to the amino acid sequence of SEQ ID NO: 519, and the beta chain of claim 2(i) comprises an amino acid sequence that is at least 90%, 95%, 96%, 97%, 98%, 99%, or 100% identical to the amino acid sequence of SEQ ID NO: 621;

(j) the alpha chain of claim 2(j) comprises an amino acid sequence that is at least 90%, 95%, 96%, 97%, 98%, 99%, or 100% identical to the amino acid sequence of SEQ ID NO: 522, and the beta chain of claim 2(j) comprises an amino acid sequence that is at least 90%, 95%, 96%, 97%, 98%, 99%, or 100% identical to the amino acid sequence of SEQ ID NO: 624;

(k) the alpha chain of claim 2(k) comprises an amino acid sequence that is at least 90%, 95%, 96%, 97%, 98%, 99%, or 100% identical to the amino acid sequence of SEQ ID NO: 525, and the beta chain of claim 2(k)

comprises an amino acid sequence that is at least 90%, 95%, 96%, 97%, 98%, 99%, or 100% identical to the amino acid sequence of SEQ ID NO: 627;

(l) the alpha chain of claim 2(l) comprises an amino acid sequence that is at least 90%, 95%, 96%, 97%, 98%, 99%, or 100% identical to the amino acid sequence of SEQ ID NO: 528, and the beta chain of claim 2(l) comprises an amino acid sequence that is at least 90%, 95%, 96%, 97%, 98%, 99%, or 100% identical to the amino acid sequence of SEQ ID NO: 630;

(m) the alpha chain of claim 2(m) comprises an amino acid sequence that is at least 90%, 95%, 96%, 97%, 98%, 99%, or 100% identical to the amino acid sequence of SEQ ID NO: 531, and the beta chain of claim 2(m) comprises an amino acid sequence that is at least 90%, 95%, 96%, 97%, 98%, 99%, or 100% identical to the amino acid sequence of SEQ ID NO: 633;

(n) the alpha chain of claim 2(n) comprises an amino acid sequence that is at least 90%, 95%, 96%, 97%, 98%, 99%, or 100% identical to the amino acid sequence of SEQ ID NO: 534, and the beta chain of claim 2(n) comprises an amino acid sequence that is at least 90%, 95%, 96%, 97%, 98%, 99%, or 100% identical to the amino acid sequence of SEQ ID NO: 636;

(o) the alpha chain of claim 2(o) comprises an amino acid sequence that is at least 90%, 95%, 96%, 97%, 98%, 99%, or 100% identical to the amino acid sequence of SEQ ID NO: 537, and the beta chain of claim 2(o) comprises an amino acid sequence that is at least 90%, 95%, 96%, 97%, 98%, 99%, or 100% identical to the amino acid sequence of SEQ ID NO: 639;

(p) the alpha chain of claim 2(p) comprises an amino acid sequence that is at least 90%, 95%, 96%, 97%, 98%, 99%, or 100% identical to the amino acid sequence of SEQ ID NO: 543, and the eta chain of claim 2(p) comprises an amino acid sequence that is at leas 90%, 95%, 96%, 97%, 98%, 99%, or 100% identical to the amino acid sequence of SEQ ID NO: 645;

(q) the alpha chain of claim 2(q) comprises an amino acid sequence that is at least 90%, 95%, 96%, 97%, 98%, 99%, or 100% identical to the amino acid sequence of SEQ ID NO: 546, and the beta chain of claim 2(q) comprises an amino acid sequence that is at least 90%, 95%, 96%, 97%, 98%, 99%, or 100% identical to the amino acid sequence of SEQ ID NO: 648;

(r) the alpha chain of claim 2(r) comprises an amino acid sequence that is at least 90%, 95%, 96%, 97%, 98%, 99%, or 100% identical to the amino acid sequence of SEQ ID NO: 552, and the beta chain of claim 2(r) comprises an amino acid sequence that is at least 90%, 95%, 96%, 97%, 98%, 99%, or 100% identical to the amino acid sequence of SEQ ID NO: 654;

(s) the alpha chain of claim 2(s) comprises an amino acid sequence that is at least 90%, 95%, 96%, 97%, 98%, 99%, or 100% identical to the amino acid sequence of SEQ ID NO: 561, and the beta chain of claim 2(s) comprises an amino acid sequence that is at least 90%, 95%, 96%, 97%, 98%, 99%, or 100% identical to the amino acid sequence of SEQ ID NO: 663;

(t) the alpha chain of claim 2(f) comprises an amino acid sequence that is at least 90%, 95%, 96%, 97%, 98%, 99%, or 100% identical to the amino acid sequence of SEQ ID NO: 570, and the beta chain of claim 2(t) comprises an amino acid sequence that is at least 90%, 95%, 96%, 97%, 98%, 99%, or 100% identical to the amino acid sequence of SEQ ID NO: 672;

(u) the alpha chain of claim 2(u) comprises an amino acid sequence that is at least 90%, 95%, 96%, 97%, 98%, 99%, or 100% identical to the amino acid sequence of SEQ ID NO: 573, and the beta chain of claim 2(u) comprises an amino acid sequence that is at least 90%, 95%, 96%, 97%, 98%, 99%, or 100% identical to the amino acid sequence of SEQ ID NO: 675; or (v) the alpha chain of claim 2(v) comprises an amino acid sequence that is at least 90%, 95%, 96%, 97%, 98%, 99%, or 100% identical to the amino acid sequence of SEQ ID NO: 576, and the beta chain of claim 2(v) comprises an amino acid sequence that is at least 90%, 95%, 96%, 97%, 98%, 99%, or 100% identical to the amino acid sequence of SEQ ID NO: 678.

4. A nucleic acid molecule encoding the TCR of claim 1.

5. A vector comprising the nucleic acid molecule of claim 4.

6. A cell comprising the vector of claim 5.

7. A cell transformed to express the nucleic acid molecule of claim 4.

8. The cell of claim 7, wherein the cell is a CD8+ T cell.

9. A pharmaceutical composition comprising the TCR of claim 1.

10. A nucleic acid molecule encoding the TCR of claim 2.

11. A vector comprising the nucleic acid molecule of claim 10.

12. A cell comprising the vector of claim 11.

13. A cell transformed to express the nucleic acid molecule of claim 10.

14. The cell of claim 13, wherein the cell is a CD8+ T cell.

15. A pharmaceutical composition comprising the TCR of claim 2.

16. A nucleic acid molecule encoding the TCR of claim 3.

17. A vector comprising the nucleic acid molecule of claim 16.

18. A cell comprising the vector of claim 17.

19. A cell transformed to express the nucleic acid molecule of claim 16.

20. A pharmaceutical composition comprising the TCR of claim 3.

* * * * *

SEQUENCE LISTING

<160> NUMBER OF SEQ ID NOS: 706

<210> SEQ ID NO 1
<211> LENGTH: 955
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
ggggcaggat gtgattctaa ttggttggaa catcttttga aatcgtgttt ctgtagagaa     60

agaaaaacta ccatatttgg atagccctgg ccaactttca aggctcctaa atctgagttt    120

tcagtgaact ggacagaaaa aaaaaatgaa gaagctacta gcaatgattc tgtggcttca    180

actagaccgg ttaagtggag agctgaaagt ggaacaaaac cctctgttcc tgagcatgca    240

ggagggaaaa aactatacca tctactgcaa ttattcaacc acttcagaca gactgtattg    300

gtacaggcag gatcctggga aaagtctgga atctctgttt gtgttgctat caaatggagc    360

agtgaagcag gagggacgat taatggcctc acttgatacc aaagcccgtc tcagcaccct    420

ccacatcaca gctgccgtgc atgacctctc tgccacctac ttctgtgccg cccgatctta    480

taacaccgac aagctcatct ttgggactgg gaccagatta caagtctttc caaatatcca    540

gaaccctgac cctgccgtgt accagctgag agactctaaa tccagtgaca agtctgtctg    600

cctattcacc gattttgatt ctcaaacaaa tgtgtcacaa agtaaggatt ctgatgtgta    660

tatcacagac aaaactgtgc tagacatgag gtctatggac ttcaagagca acagtgctgt    720

ggcctggagc aacaaatctg actttgcatg tgcaaacgcc ttcaacaaca gcattattcc    780

agaagacacc ttcttcccca gcccagaaag ttcctgtgat gtcaagctgg tcgagaaaag    840

ctttgaaaca gatacgaacc taaactttca aaacctgtca gtgattgggt tccgaatcct    900

cctcctgaaa gtggccgggt ttaatctgct catgacgctg cggctgtggt ccagc         955
```

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2

```
accacttcag acaga                                                      15
```

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

```
Thr Thr Ser Asp Arg
1               5
```

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
accacttcag acaga 15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Leu Leu Ser Asn Gly Ala Val
1 5

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
gccgcccgat cttataacac cgacaagctc atc 33

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Cys Ala Ala Arg Ser Tyr Asn Thr Asp Lys Leu Ile Phe
1 5 10

<210> SEQ ID NO 8
<211> LENGTH: 1069
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
tggggagtct tgctcctcac agagctttga ggagctggat caaaattgtg ctccacagag 60
agaagatacc ggtgtcggga agcaccagtg ccctgaggaa gggccatttc caaaagccct 120
gtgctgacac agggttgctg gttcctcttc aagagcccac tctctggggt ggggccatat 180
ctccagcaga ggtgggctgg aaaggacccc cccaatcccg cccgccgtga gcttagctgg 240
agccatggcc tctgcaccca tctcgatgct tgcgatgctc ttcacattga gtgggctgag 300
agctcagtca gtggctcagc cggaagatca ggtcaacgtt gctgaaggga atcctctgac 360
tgtgaaatgc acctattcag tctctggaaa ccccttatct tttggtatg ttcaataccc 420 caaccgaggc ctccagttcc ttctgaaata catcacaggg gataacctgg ttaaaggcag 480
ctatggcttt gaagctgaat ttaacaagag ccaaacctcc ttccacctga agaaaccatc 540
tgcccttgtg agcgactccg ctttgtactt ctgtgctgtg agagacatgg ggggttctgc 600
aaggcaactg acctttggat ctgggacaca attgactgtt ttacctgata tccagaaccc 660
tgaccctgcc gtgtaccagc tgagagactc taaatccagt gacaagtctg tctgcctatt 720
caccgatttt gattctcaaa caaatgtgtc acaaagtaag gattctgatg tgtatatcac 780
agacaaaact gtgctagaca tgaggtctat ggacttcaag agcaacagtg ctgtggcctg 840
gagcaacaaa tctgactttg catgtgcaaa cgccttcaac aacagcatta ttccagaaga 900
caccttcttc cccagcccag aaagttcctg tgatgtcaag ctggtcgaga aaagctttga 960
aacagatacg aacctaaact ttcaaaacct gtcagtgatt gggttccgaa tcctcctcct 1020
gaaagtggcc gggtttaatc tgctcatgac gctgcggctg tggtccagc 1069

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
gtctctggaa acccttat 18

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Val Ser Gly Asn Pro Tyr
1 5

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
tacatcacag gggataacct ggtt 24

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Tyr Ile Thr Gly Asp Asn Leu Val
1 5

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
gctgtgagag acatgggggg ttctgcaagg caactgacc 39

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Cys Ala Val Arg Asp Met Gly Gly Ser Ala Arg Gln Leu Thr Phe
1 5 10 15

<210> SEQ ID NO 15
<211> LENGTH: 920
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
gagcctgagt gacagctgct ggtgtgggcc ctggcagttg ctgctgggct cattgcagct 60
cagacacagc aaaagagcct agaacctggg tcctagtttg cacctagaat atgaggcaag 120
tggcgagagt gatcgtgttc ctgaccctga gtactttgag ccttgctaag accacccagc 180
ccatctccat ggactcatat gaaggacaag aagtgaacat aacctgtagc cacaacaaca 240
ttgctacaaa tgattatatc acgtggtacc aacagtttcc cagccaagga ccacgattta 300
ttattcaagg atacaagaca aaagttacaa acgaagtggc ctccctgttt atccctgccg 360
acagaaagtc cagcactctg agcctgcccc gggtttccct gagcgacact gctgtgtact 420
actgcctcgt ggggacgttt tctggttctg caaggcaact gacctttgga tctgggacac 480
aattgactgt tttacctgat atccagaacc ctgaccctgc cgtgtaccag ctgagagact 540
ctaaatccag tgacaagtct gtctgcctat tcaccgattt tgattctcaa acaaatgtgt 600
cacaaagtaa ggattctgat gtgtatatca cagacaaaac tgtgctagac atgaggtcta 660
tggacttcaa gagcaacagt gctgtggcct ggagcaacaa atctgacttt gcatgtgcaa 720
acgccttcaa caacagcatt attccagaag acaccttctt ccccagccca gaaagttcct 780
gtgatgtcaa gctggtcgag aaaagctttg aaacagatac gaacctaaac tttcaaaacc 840
tgtcagtgat tgggttccga atcctcctcc tgaaagtggc cgggtttaat ctgctcatga 900
cgctgcggct gtggtccagc 920

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
aacattgcta caaatgatta t 21

<210> SEQ ID NO 17
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 17

Asn Ile Ala Thr Asn Asp Tyr
1               5


<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

ggatacaaga caaaa                                                     15


<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Tyr Lys Thr Lys
1               5


<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

ctcgtgggga cgttttctgg ttctgcaagg caactgacc                           39


<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Leu Val Gly Thr Phe Ser Gly Ser Ala Arg Gln Leu Thr Phe
1               5                   10                  15


<210> SEQ ID NO 22
<211> LENGTH: 1088
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

ggcataataa atgtctacgc ctcatgccac taggtggcaa tgtgggtgtt atactgaaaa     60

gatcacagat ggttcacttt gcaagtaaaa ctgtaaatgt tcttaagtgt gcatttctgc    120

tgcttctgat gggctgaaaa tcccctttga tttctaaagt aaatgtagag acgttttaaa    180
```

aataaaggac tcctttgtcc aagatatatt ccgaaatcct ccaacagaga cctgtgtgag 240
cttctgctgc agtaataatg gtgaagatcc ggcaattttt gttggctatt ttgtggcttc 300
agctaagctg tgtaagtgcc gccaaaaatg aagtggagca gagtcctcag aacctgactg 360
cccaggaagg agaatttatc acaatcaact gcagttactc ggtaggaata agtgccttac 420
actggctgca acagcatcca ggaggaggca ttgtttcctt gtttatgctg agctcaggga 480
agaagaagca tggaagatta attgccacaa taaacataca ggaaaagcac agctccctgc 540
acatcacagc ctcccatccc agagactctg ccgtctacat ctgtgctgtc agcacctcta 600
tgtattcagg aggaggtgct gacggactca cctttggcaa agggactcat ctaatcatcc 660
agccctatat ccagaaccct gaccctgccg tgtaccagct gagagactct aaatccagtg 720
acaagtctgt ctgcctattc accgattttg attctcaaac aaatgtgtca caaagtaagg 780
attctgatgt gtatatcaca gacaaaactg tgctagacat gaggtctatg gacttcaaga 840
gcaacagtgc tgtggcctgg agcaacaaat ctgactttgc atgtgcaaac gccttcaaca 900
acagcattat tccagaagac accttcttcc ccagcccaga aagttcctgt gatgtcaagc 960
tggtcgagaa aagctttgaa acagatacga acctaaactt tcaaaacctg tcagtgattg 1020
ggttccgaat cctcctcctg aaagtggccg ggtttaatct gctcatgacg ctgcggctgt 1080
ggtccagc 1088

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
gtaggaataa gtgcc 15

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Val Gly Ile Ser Ala
1 5

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
ctgagctcag ggaag 15

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Leu Ser Ser Gly Lys
1 5

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gctgtcagca cctctatgta ttcaggagga ggtgctgacg gactcacc 48

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Cys Ala Val Ser Thr Ser Met Tyr Ser Gly Gly Gly Ala Asp Gly Leu
1 5 10 15

Thr Phe

<210> SEQ ID NO 29
<211> LENGTH: 971
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
ggcttagtgg tgaattaggg gtgttaaaaa gagcatcatt tttttgaact ggtaaagcag 60
attcttttta tgatttttaa agtagaaata tccattccag gtgcattttt taagggttta 120
aaatttgaat cctcagtgaa ccagggcaga gaagaatgat gaaatccttg agagttttac 180
tagtgatcct gtggcttcag ttgagctggg tttggagcca acagaaggag gtggagcaga 240
attctggacc cctcagtgtt ccagagggag ccattgcctc tctcaactgc acttacagtg 300
accgaggttc ccagtccttc ttctggtaca gacaatattc tgggaaaagc cctgagttga 360
taatgtccat atactccaat ggtgacaaag aagatggaag gtttacagca cagctcaata 420
aagccagcca gtatgtttct ctgctcatca gagactccca gcccagtgat tcagccacct 480
acctctgtgc cgtgaaggga gggtatgcac tcaacttcgg caaaggcacc tcgctgttgg 540
tcacacccca tatccagaac cctgaccctg ccgtgtacca gctgagagac tctaaatcca 600
gtgacaagtc tgtctgccta ttcaccgatt ttgattctca aacaaatgtg tcacaaagta 660
aggattctga tgtgtatatc acagacaaaa ctgtgctaga catgaggtct atggacttca 720
agagcaacag tgctgtggcc tggagcaaca aatctgactt tgcatgtgca aacgccttca 780
acaacagcat tattccagaa gacaccttct tccccagccc agaaagttcc tgtgatgtca 840
agctggtcga gaaaagcttt gaaacagata cgaacctaaa ctttcaaaac ctgtcagtga 900
ttgggttccg aatcctcctc ctgaaagtgg ccgggtttaa tctgctcatg acgctgcggc 960
tgtggtccag c 971

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
gaccgaggtt cccagtcc 18

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Asp Arg Gly Ser Gln Ser
1 5

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
atatactcca atggtgac 18

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Ile Tyr Ser Asn Gly Asp
1 5

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
gccgtgaagg gagggtatgc actcaac 27

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Cys Ala Val Lys Gly Gly Tyr Ala Leu Asn Phe
1 5 10

<210> SEQ ID NO 36
<211> LENGTH: 931
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36
ggcccatttc ctgttctgaa gcagctacgg caccagtgca gctgatactc aaggttcaga 60
tcagaagagg aggcttctca ccctgcagca gggacctgtg agcatggcat gccctggctt 120
cctgtgggca cttgtgatct ccacctgtct tgaatttagc atggctcaga cagtcactca 180
gtctcaacca gagatgtctg tgcaggaggc agagaccgtg accctgagct gcacatatga 240
caccagtgag agtgattatt atttattctg gtacaagcag cctcccagca ggcagatgat 300
tctcgttatt cgccaagaag cttataagca acagaatgca acagagaatc gtttctctgt 360
gaacttccag aaagcagcca aatccttcag tctcaagatc tcagactcac agctggggga 420
tgccgcgatg tatttctgtg cttatagtcc cccccctcccc ggtaaccagt tctattttgg 480
gacagggaca agtttgacgg tcattccaaa tatccagaac cctgaccctg ccgtgtacca 540
gctgagagac tctaaatcca gtgacaagtc tgtctgccta ttcaccgatt ttgattctca 600
aacaaatgtg tcacaaagta aggattctga tgtgtatatc acagacaaaa ctgtgctaga 660
catgaggtct atggacttca agagcaacag tgctgtggcc tggagcaaca aatctgactt 720
tgcatgtgca aacgccttca acaacagcat tattccagaa gacaccttct tccccagccc 780
agaaagttcc tgtgatgtca agctggtcga gaaaagcttt gaaacagata cgaacctaaa 840
ctttcaaaac ctgtcagtga ttgggttccg aatcctcctc ctgaaagtgg ccgggtttaa 900
tctgctcatg acgctgcggc tgtggtccag c 931

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
accagtgaga gtgattatta t 21

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Thr Ser Glu Ser Asp Tyr Tyr
1 5

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
caagaagctt ataagcaaca gaat 24

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Gln Glu Ala Tyr Lys Gln Gln Asn
1 5

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
gcttatagtc cccccctccc cggtaaccag ttctat 36

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Cys Ala Tyr Ser Pro Pro Leu Pro Gly Asn Gln Phe Tyr Phe
1 5 10

<210> SEQ ID NO 43
<211> LENGTH: 925
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43 gctttttga aatcgtgttt ctgtagagaa agaaaaacta ccatatttgg atagccctgg 60
ccaactttca aggctcctaa atctgagttt tcagtgaact ggacagaaaa aaaaaatgaa 120
gaagctacta gcaatgattc tgtggcttca actagaccgg ttaagtggag agctgaaagt 180
ggaacaaaac cctctgttcc tgagcatgca ggagggaaaa aactatacca tctactgcaa 240
ttattcaacc acttcagaca gactgtattg gtacaggcag gatcctggga aaagtctgga 300
atctctgttt gtgttgctat caaatggagc agtgaagcag gagggacgat taatggcctc 360
acttgatacc aaagcccgtc tcagcaccct ccacatcaca gctgccgtgc atgacctctc 420
tgccacctac ttctgtgccg gtgaacctga tagcaactat cagttaatct ggggcgctgg 480
gaccaagcta attataaagc cagatatcca gaaccctgac cctgccgtgt accagctgag 540
agactctaaa tccagtgaca agtctgtctg cctattcacc gattttgatt ctcaaacaaa 600
tgtgtcacaa agtaaggatt ctgatgtgta tatcacagac aaaactgtgc tagacatgag 660
gtctatggac ttcaagagca acagtgctgt ggcctggagc aacaaatctg actttgcatg 720
tgcaaacgcc ttcaacaaca gcattattcc agaagacacc ttcttcccca gcccagaaag 780
ttcctgtgat gtcaagctgg tcgagaaaag ctttgaaaca gatacgaacc taaactttca 840
aaacctgtca gtgattgggt tccgaatcct cctcctgaaa gtggccgggt ttaatctgct 900
catgacgctg cggctgtggt ccagc 925

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
accacttcag acaga 15

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Thr Thr Ser Asp Arg
1 5

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
ttgctatcaa atggagcagt g 21

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Leu Leu Ser Asn Gly Ala Val
1 5

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
gccggtgaac ctgatagcaa ctatcagtta atc 33

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Cys Ala Gly Glu Pro Asp Ser Asn Tyr Gln Leu Ile Trp
1 5 10

<210> SEQ ID NO 50
<211> LENGTH: 1034
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50
agagagagag agagagagag gaggaggagg aggaggagga aggatgaggg gaggggctta 60
gtggtgaatt aggggtgtta aaaagagcat cattttttg aactggtaaa gcagattctt 120
tttatgattt ttaaagtaga aatatccatt ccaggtgcat tttttaaggg tttaaaattt 180
gaatcctcag tgaaccaggg cagagaagaa tgatgaaatc cttgagagtt ttactagtga 240
tcctgtggct tcagttgagc tgggtttgga gccaacagaa ggaggtggag cagaattctg 300
gacccctcag tgttccagag ggagccattg cctctctcaa ctgcacttac agtgaccgag 360
gttcccagtc cttcttctgg tacagacaat attctgggaa aagccctgag ttgataatgt 420
ccatatactc caatggtgac aaagaagatg gaaggtttac agcacagctc aataaagcca 480
gccagtatgt ttctctgctc atcagagact cccagcccag tgattcagcc acctacctct 540
gtgccgtggg gggggccggg ggttaccaga aagttacctt tggaactgga acaaagctcc 600
aagtcatccc aaatatccag aaccctgacc ctgccgtgta ccagctgaga gactctaaat 660
ccagtgacaa gtctgtctgc ctattcaccg attttgattc tcaaacaaat gtgtcacaaa 720
gtaaggattc tgatgtgtat atcacagaca aaactgtgct agacatgagg tctatggact 780
tcaagagcaa cagtgctgtg gcctggagca acaaatctga ctttgcatgt gcaaacgcct 840
tcaacaacag cattattcca gaagacacct tcttccccag cccagaaagt tcctgtgatg 900
tcaagctggt cgagaaaagc tttgaaacag atacgaacct aaactttcaa aacctgtcag 960
tgattgggtt ccgaatcctc ctcctgaaag tggccgggtt taatctgctc atgacgctgc 1020
ggctgtggtc cagc 1034

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
gaccgaggtt cccagtcc 18

<210> SEQ ID NO 52
<211> LENGTH: 6
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 52

Asp Arg Gly Ser Gln Ser
1 5

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
atatactcca atggtgac 18

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Ile Tyr Ser Asn Gly Asp
1 5

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
gccgtggggg gggccggggg ttaccagaaa gttacc 36

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Cys Ala Val Gly Gly Ala Gly Gly Tyr Gln Lys Val Thr Phe
1 5 10

<210> SEQ ID NO 57
<211> LENGTH: 953
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 57
gtcctccctt tgtatttcta ctgggttttg catccggact gatcttcctt ccctcaccca 60
catgaagtgt ctaccttctg cagactacag tggctcagga accggggatg cagtgccagg 120

```
ctcatggtat cctgcagcag atgtggggag ctttccttct ctatgtttcc atgaagatgg    180

gaggcactgc aggacaaagc cttgagcagc cctctgaagt gacagctgtg gaaggagcca    240

ttgtccagat aaactgcacg taccagacat ctgggtttta tgggctgtcc tggtaccagc    300

aacatgatgg cggagcaccc acatttcttt cttacaatgc tctggatggt ttggaggaga    360

caggtcgttt ttcttcattc cttagtcgct ctgatagtta tggttacctc cttctacagg    420

agctccagat gaaagactct gcctcttact tctgcgctgt gagagatcct ctttctggtg    480

gctacaataa gctgattttt ggagcaggga ccaggctggc tgtacaccca tatatccaga    540

accctgaccc tgccgtgtac cagctgagag actctaaatc cagtgacaag tctgtctgcc    600

tattcaccga ttttgattct caaacaaatg tgtcacaaag taaggattct gatgtgtata    660

tcacagacaa aactgtgcta gacatgaggt ctatggactt caagagcaac agtgctgtgg    720

cctggagcaa caaatctgac tttgcatgtg caaacgcctt caacaacagc attattccag    780

aagacacctt cttccccagc ccagaaagtt cctgtgatgt caagctggtc gagaaaagct    840

ttgaaacaga tacgaaccta aactttcaaa acctgtcagt gattgggttc cgaatcctcc    900

tcctgaaagt ggccgggttt aatctgctca tgacgctgcg gctgtggtcc agc           953
```

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58

```
acatctgggt tttatggg                                                   18
```

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

```
Thr Ser Gly Phe Tyr Gly
1               5
```

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60

```
aatgctctgg atggtttg                                                   18
```

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Asn Ala Leu Asp Gly Leu
1 5

<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
gctgtgagag atcctctttc tggtggctac aataagctga tt 42

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Cys Ala Val Arg Asp Pro Leu Ser Gly Gly Tyr Asn Lys Leu Ile Phe
1 5 10 15

<210> SEQ ID NO 64
<211> LENGTH: 941
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
gagcactcaa attgaaacct gcctgatgtg ggatgtgctg tggctgctgc tttgttgctt 60
gggacctcct ctgacctagg atcagacaca gagtctgagt tctggggcct ggaacctcaa 120
tgtgcacttg aacaatgaag ttggtgacaa gcattactgt actcctatct ttgggtatta 180
tgggtgatgc taagaccaca cagccaaatt caatggagag taacgaagaa gagcctgttc 240
acttgccttg taaccactcc acaatcagtg gaactgatta catacattgg tatcgacagc 300
ttccctccca gggtccagag tacgtgattc atggtcttac aagcaatgtg aacaacagaa 360
tggcctctct ggcaatcgct gaagacagaa agtccagtac cttgatcctg caccgtgcta 420
ccttgagaga tgctgctgtg tactactgca tcctgtattc aggaggaggt gctgacggac 480
tcacctttgg caaagggact catctaatca tccagcccta tatccagaac cctgaccctg 540
ccgtgtacca gctgagagac tctaaatcca gtgacaagtc tgtctgccta ttcaccgatt 600
ttgattctca aacaaatgtg tcacaaagta aggattctga tgtgtatatc acagacaaaa 660
ctgtgctaga catgaggtct atggacttca agagcaacag tgctgtggcc tggagcaaca 720
aatctgactt tgcatgtgca aacgccttca acaacagcat tattccagaa gacaccttct 780
tccccagccc agaaagttcc tgtgatgtca agctggtcga gaaaagcttt gaaacagata 840
cgaacctaaa ctttcaaaac ctgtcagtga ttgggttccg aatcctcctc ctgaaagtgg 900
ccgggtttaa tctgctcatg acgctgcggc tgtggtccag c 941

<210> SEQ ID NO 65
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 65
acaatcagtg gaactgatta c                                              21

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ile Ser Gly Thr Asp Tyr
1               5

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggtcttacaa gcaat                                                     15

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Leu Thr Ser Asn
1               5

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
atcctgtatt caggaggagg tgctgacgga ctcacc                              36

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Ile Leu Tyr Ser Gly Gly Gly Ala Asp Gly Leu Thr Phe
1               5                   10

<210> SEQ ID NO 71
<211> LENGTH: 1487
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 71
ttcctgtctt gagaagagaa acacttatgg ggaaattgaa tactttgtct ttttttttt 60 tttttttgag acggagtctc actttgtcgc ccaggctgga gtgcagtggc gcgatctctg 120
ctcactgcaa actccgcctc ccgggttccc gccattctcc tgcctcagcc tctcgagtag 180
ctgggactac aggcgcccgc cacagcgccc agctaatttt tttgtatttt ttggtagaga 240
cggggtttca ccgtgttagc caggatggtc tcgatctcct gacctcgtga tccgcccacc 300
tcggcctccc aaagcgctgg gattaaaggc gtgagccacc gcgcccggcc tactttgtct 360
tatgttattc ccatttgccg tctctgttcc ttatacatta tgctttttca actttaccag 420
aatcacttgg attaaaaccc gtggatttct cagtaggaaa tgttcatgtg aagacacttc 480
tgtagtaaca gaacctacag ctgctcctgt agaaggaagt tgaaagtcat cccttcaaga 540
aaggggctcc tccccttgta attctactgg gttttgcatc cagactgagt ttccttccct 600
cacccacatg aagtgtctac cttctgcaga ctccaatggc tcaggaactg ggaatgcagt 660
gccaggctcg tggtatcctg cagcagatgt ggggagtttt ccttctttat gtttccatga 720
agatgggagg cactacagga caaaacattg accagcccac tgagatgaca gctacggaag 780
gtgccattgt ccagatcaac tgcacgtacc agacatctgg gttcaacggg ctgttctggt 840
accagcaaca tgctggcgaa gcacccacat ttctgtctta caatgttctg gatggtttgg 900
aggagaaagg tcgtttttct tcattcctta gtcggtctaa agggtacagt tacctccttt 960
tgaaggagct ccagatgaaa gactctgcct cttacctctg tgctggcctc ttcggaaaca 1020
cacctcttgt ctttggaaag ggcacaagac tttctgtgat tgcaaatatc cagaaccctg 1080
accctgccgt gtaccagctg agagactcta aatccagtga caagtctgtc tgcctattca 1140
ccgattttga ttctcaaaca aatgtgtcac aaagtaagga ttctgatgtg tatatcacag 1200
acaaaactgt gctagacatg aggtctatgg acttcaagag caacagtgct gtggcctgga 1260
gcaacaaatc tgactttgca tgtgcaaacg ccttcaacaa cagcattatt ccagaagaca 1320
ccttcttccc cagcccagaa agttcctgtg atgtcaagct ggtcgagaaa agctttgaaa 1380
cagatacgaa cctaaacttt caaaacctgt cagtgattgg gttccgaatc ctcctcctga 1440
aagtggccgg gtttaatctg ctcatgacgc tgcggctgtg gtccagc 1487

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
acatctgggt tcaacggg 18

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Thr Ser Gly Phe Asn Gly
1 5

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
aatgttctgg atggtttg 18

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Asn Val Leu Asp Gly Leu
1 5

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
gctggcctct tcggaaacac acctcttgtc 30

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Cys Ala Gly Leu Phe Gly Asn Thr Pro Leu Val Phe
1 5 10

<210> SEQ ID NO 78
<211> LENGTH: 917
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78
tggggctgtt ctgaagcagc tacggcacca gtgcagctga tactcaaggt tcagatcaga 60
agaggaggct tctcaccctg cagcagggac ctgtgagcat ggcatgccct ggcttcctgt 120
gggcacttgt gatctccacc tgtcttgaat ttagcatggc tcagacagtc actcagtctc 180
aaccagagat gtctgtgcag gaggcagaga ccgtgaccct gagctgcaca tatgacacca 240
gtgagagtga ttattattta ttctggtaca agcagcctcc cagcaggcag atgattctcg 300
ttattcgcca agaagcttat aagcaacaga atgcaacaga gaatcgtttc tctgtgaact 360
tccagaaagc agccaaatcc ttcagtctca agatctcaga ctcacagctg ggggatgccg 420
cgatgtattt ctgtgcttat tttaacaccg acaagctcat ctttgggact gggaccagat 480
tacaagtctt tccaaatatc cagaaccctg accctgccgt gtaccagctg agagactcta 540
aatccagtga caagtctgtc tgcctattca ccgattttga ttctcaaaca aatgtgtcac 600
aaagtaagga ttctgatgtg tatatcacag acaaaactgt gctagacatg aggtctatgg 660
acttcaagag caacagtgct gtggcctgga gcaacaaatc tgactttgca tgtgcaaacg 720
ccttcaacaa cagcattatt ccagaagaca ccttcttccc cagcccagaa agttcctgtg 780
atgtcaagct ggtcgagaaa agctttgaaa cagatacgaa cctaaacttt caaaacctgt 840
cagtgattgg gttccgaatc ctcctcctga aagtggccgg gtttaatctg ctcatgacgc 900
tgcggctgtg gtccagc 917

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
accagtgaga gtgattatta t 21

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Thr Ser Glu Ser Asp Tyr Tyr
1 5

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
caagaagctt ataagcaaca gaat 24

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Gln Glu Ala Tyr Lys Gln Gln Asn
1 5

<210> SEQ ID NO 83

<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
gcttatttta acaccgacaa gctcatc 27

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Cys Ala Tyr Phe Asn Thr Asp Lys Leu Ile Phe
1 5 10

<210> SEQ ID NO 85
<211> LENGTH: 1035
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85
ggcacacaca cacatgaata agagcaagac agagggagag atgagggagg agcttaatga 60
tggagcagag gtgttaaaaa gaacatcctt tttctaattg gtaggacaga tttcttttat 120
gattcctaca gcagaaaaat gagaaacgtt tgttattatt tttttttcgt gtttaaggtt 180
tgaatcctca gtgaaccagg gcagaaaaga atgatgaaat ccttgagagt tttactggtg 240
atcctgtggc ttcagttaag ctgggtttgg agccaacaga aggaggtgga gcaggatcct 300
ggaccactca gtgttccaga gggagccatt gtttctctca actgcactta cagcaacagt 360
gcttttcaat acttcatgtg gtacagacag tattccagaa aaggccctga gttgctgatg 420
tacacatact ccagtggtaa caaagaagat ggaaggttta cagcacaggt cgataaatcc 480
agcaagtata tctccttgtt catcagagac tcacagccca gtgattcagc cacctacctc 540
tgtgcaatgg ggggccaagg aggtgctgac ggactcacct ttggcaaagg gactcatcta 600
atcatccagc cctatatcca gaaccctgac cctgccgtgt accagctgag agactctaaa 660
tccagtgaca agtctgtctg cctattcacc gattttgatt ctcaaacaaa tgtgtcacaa 720
agtaaggatt ctgatgtgta tatcacagac aaaactgtgc tagacatgag gtctatggac 780
ttcaagagca acagtgctgt ggcctggagc aacaaatctg actttgcatg tgcaaacgcc 840
ttcaacaaca gcattattcc agaagacacc ttcttcccca gcccagaaag ttcctgtgat 900
gtcaagctgg tcgagaaaag ctttgaaaca gatacgaacc taaactttca aaacctgtca 960
gtgattgggt tccgaatcct cctcctgaaa gtggccgggt ttaatctgct catgacgctg 1020
cggctgtggt ccagc 1035

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
aacagtgctt ttcaatac 18

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Asn Ser Ala Phe Gln Tyr
1 5

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
acatactcca gtggtaac 18

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Thr Tyr Ser Ser Gly Asn
1 5

<210> SEQ ID NO 90
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
gcaatggggg gccaaggagg tgctgacgga ctcacc 36

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Cys Ala Met Gly Gly Gln Gly Gly Ala Asp Gly Leu Thr Phe
1 5 10

<210> SEQ ID NO 92
<211> LENGTH: 898
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
gggagtgtca ctctaagccc aagagagttt cttgaagcaa aaaaaaaaaa aaacccattc 60
aggaaataat tctttgctga taaggatgct ccttgaacat ttattaataa tcttgtggat 120
gcagctgaca tgggtcagtg gtcaacagct gaatcagagt cctcaatcta tgtttatcca 180
ggaaggagaa gatgtctcca tgaactgcac ttcttcaagc atatttaaca cctggctatg 240
gtacaagcag gaccctgggg aaggtcctgt cctcttgata gccttatata aggctggtga 300
attgacctca aatggaagac tgactgctca gtttggtata accagaaagg acagcttcct 360
gaatatctca gcatccatac ctagtgatgt aggcatctac ttctgtgctg gccccaagag 420
ggaatatgga aacaagctgg tctttggcgc aggaaccatt ctgagagtca agtcctatat 480
ccagaaccct gaccctgccg tgtaccagct gagagactct aaatccagtg acaagtctgt 540
ctgcctattc accgattttg attctcaaac aaatgtgtca caaagtaagg attctgatgt 600
gtatatcaca gacaaaactg tgctagacat gaggtctatg gacttcaaga gcaacagtgc 660
tgtggcctgg agcaacaaat ctgactttgc atgtgcaaac gccttcaaca acagcattat 720
tccagaagac accttcttcc ccagcccaga aagttcctgt gatgtcaagc tggtcgagaa 780
aagctttgaa acagatacga acctaaactt tcaaaacctg tcagtgattg ggttccgaat 840
cctcctcctg aaagtggccg ggtttaatct gctcatgacg ctgcggctgt ggtccagc 898

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
agcatattta acacc 15

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Ser Ile Phe Asn Thr
1 5

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
ttatataagg ctggtgaatt g 21

<210> SEQ ID NO 96
<211> LENGTH: 7

<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Leu Tyr Lys Ala Gly Glu Leu
1 5

<210> SEQ ID NO 97
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
gctggcccca agagggaata tggaaacaag ctggtc 36

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Cys Ala Gly Pro Lys Arg Glu Tyr Gly Asn Lys Leu Val Phe
1 5 10

<210> SEQ ID NO 99
<211> LENGTH: 943
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99
ggggacaact gtagcaaccc ttctaaaggt tgtagattct ggctgatgat gtcactgaca 60
caaaggaaaa aatgcaaaac aggtagtctt aaataagcat tctggtgaga ccaactgcat 120
tttggccatg gctttgcaga gcactctggg ggcggtgtgg ctagggcttc tcctcaactc 180
tctctggaag gttgcagaaa gcaaggacca agtgtttcag ccttccacag tggcatcttc 240
agagggagct gtggtggaaa tcttctgtaa tcactctgtg tccaatgctt acaacttctt 300
ctggtacctt cacttcccgg gatgtgcacc aagactcctt gttaaaggct caaagccttc 360
tcagcaggga cgatacaaca tgacctatga acggttctct tcatcgctgc tcatcctcca 420
ggtgcgggag gcagatgctg ctgtttacta ctgtgctgtg gaggataaca ataacaatga 480
catgcgcttt ggagcaggga ccagactgac agtaaaacca aatatccaga accctgaccc 540
tgccgtgtac cagctgagag actctaaatc cagtgacaag tctgtctgcc tattcaccga 600
ttttgattct caaacaaatg tgtcacaaag taaggattct gatgtgtata tcacagacaa 660
aactgtgcta gacatgaggt ctatggactt caagagcaac agtgctgtgg cctggagcaa 720
caaatctgac tttgcatgtg caaacgcctt caacaacagc attattccag aagacacctt 780
cttccccagc ccagaaagtt cctgtgatgt caagctggtc gagaaaagct ttgaaacaga 840
tacgaaccta aactttcaaa acctgtcagt gattgggttc cgaatcctcc tcctgaaagt 900

-continued ggccgggttt aatctgctca tgacgctgcg gctgtggtcc agc 943

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
gtgtccaatg cttacaac 18

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Val Ser Asn Ala Tyr Asn
1 5

<210> SEQ ID NO 102
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
ggctcaaagc ct 12

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Gly Ser Lys Pro
1

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
gctgtggagg ataacaataa caatgacatg cgc 33

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Cys Ala Val Glu Asp Asn Asn Asn Asn Asp Met Arg Phe
1 5 10

<210> SEQ ID NO 106
<211> LENGTH: 1277
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106
tcaaattgac tagttttgac tttgccttat gttcccattt gttttctctg ttctttacat 60
gttcgatgtt caccataatc acttggatta aaatgtgtgg attagttttt ggagataggg 120
acctcaccat gttgcttagg ctggtctcca gttcctggcc tcaagggatt cttctacctc 180
agcgtcttga gtagctggga ttacaggcat aagccactgt gcccagctta aaacctgtgg 240
atttatcagt agaaaatgtt catgtaaaga tactcctgta agagaaacca tagctgctcc 300
agtggaagga agcttaaact catcccttca agaaagaagc tcctcccttt gtatttctac 360
tgggttttgc atccggactg atcttccttc cctcacccac atgaagtgtc taccttctgc 420
agactacagt ggctcaggaa ccggggatgc agtgccaggc tcatggtatc ctgcagcaga 480
tgtggggagc tttccttctc tatgtttcca tgaagatggg aggcactgca ggacaaagcc 540
ttgagcagcc ctctgaagtg acagctgtgg aaggagccat tgtccagata aactgcacgt 600
accagacatc tgggttttat gggctgtcct ggtaccagca acatgatggc ggagcaccca 660
catttctttc ttacaatgct ctggatggtt tggaggagac aggtcgtttt tcttcattcc 720
ttagtcgctc tgatagttat ggttacctcc ttctacagga gctccagatg aaagactctg 780
cctcttactt ctgcgctgtg aataacaatg ccagactcat gtttggagat ggaactcagc 840
tggtggtgaa gcccaatatc cagaaccctg accctgccgt gtaccagctg agagactcta 900
aatccagtga caagtctgtc tgcctattca ccgattttga ttctcaaaca aatgtgtcac 960
aaagtaagga ttctgatgtg tatatcacag acaaaactgt gctagacatg aggtctatgg 1020
acttcaagag caacagtgct gtggcctgga gcaacaaatc tgactttgca tgtgcaaacg 1080
ccttcaacaa cagcattatt ccagaagaca ccttcttccc cagcccagaa agttcctgtg 1140
atgtcaagct ggtcgagaaa agctttgaaa cagatacgaa cctaaacttt caaaacctgt 1200
cagtgattgg gttccgaatc ctcctcctga aagtggccgg gtttaatctg ctcatgacgc 1260
tgcggctgtg gtccagc 1277

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
acatctgggt tttatggg 18

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Thr Ser Gly Phe Tyr Gly
1 5

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
aatgctctgg atggtttg 18

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Asn Ala Leu Asp Gly Leu
1 5

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 111
gctgtgaata acaatgccag actcatg 27

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Cys Ala Val Asn Asn Asn Ala Arg Leu Met Phe
1 5 10

<210> SEQ ID NO 113
<211> LENGTH: 1479
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113
tgtcttgaga agagaaacac ttatggggaa attgaatact tttttttttt tttttttttg 60
agacggagtc tcactttgtc gcccaggctg gagtgcagtg gcgcgatctc tgctcactgc 120
aaactccgcc tcccgggttc ccgccattct cctgcctcag cctctcgagt agctgggact 180
acaggcgccc gccacagcgc ccagctaatt tttttgtatt ttttggtaga gacggggttt 240
caccgtgtta gccaggatgg tctcgatctc ctgacctcgt gatccgccca cctcggcctc 300
ccaaagcgct gggattaaag gcgtgagcca ccgcgcccgg cctactttgt cttatgttat 360
tcccatttgc cgtctctgtt ccttatacat tatgcttttt caactttacc agaatcactt 420
ggattaaaac ccgtggattt ctcagtagga aatgttcatg tgaagacact tctgtagtaa 480
cagaacctac agctgctcct gtagaaggaa gttgaaagtc atcccttcaa gaaaggggct 540 cctcccccttg taattctact gggttttgca tccagactga gtttccttcc ctcacccaca 600
tgaagtgtct accttctgca gactccaatg gctcaggaac tgggaatgca gtgccaggct 660
cgtggtatcc tgcagcagat gtggggagtt ttccttcttt atgtttccat gaagatggga 720
ggcactacag gacaaaacat tgaccagccc actgagatga cagctacgga aggtgccatt 780
gtccagatca actgcacgta ccagacatct gggttcaacg ggctgttctg gtaccagcaa 840
catgctggcg aagcacccac atttctgtct tacaatgttc tggatggttt ggaggagaaa 900
ggtcgttttt cttcattcct tagtcggtct aaagggtaca gttacctcct tttgaaggag 960
ctccagatga aagactctgc ctcttacctc tgtgctgtga gagatccggg caatgacatg 1020
cgctttggag cagggaccag actgacagta aaaccaaata tccagaaccc tgaccctgcc 1080
gtgtaccagc tgagagactc taaatccagt gacaagtctg tctgcctatt caccgatttt 1140
gattctcaaa caaatgtgtc acaaagtaag gattctgatg tgtatatcac agacaaaact 1200
gtgctagaca tgaggtctat ggacttcaag agcaacagtg ctgtggcctg gagcaacaaa 1260
tctgactttg catgtgcaaa cgccttcaac aacagcatta ttccagaaga caccttcttc 1320
cccagcccag aaagttcctg tgatgtcaag ctggtcgaga aaagctttga aacagatacg 1380
aacctaaact ttcaaaacct gtcagtgatt gggttccgaa tcctcctcct gaaagtggcc 1440
gggtttaatc tgctcatgac gctgcggctg tggtccagc 1479

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
acatctgggt tcaacggg 18

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Thr Ser Gly Phe Asn Gly
1 5

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
aatgttctgg atggtttg 18

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Asn Val Leu Asp Gly Leu
1 5

<210> SEQ ID NO 118
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
gctgtgagag atccgggcaa tgacatgcgc 30

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Cys Ala Val Arg Asp Pro Gly Asn Asp Met Arg Phe
1 5 10

<210> SEQ ID NO 120
<211> LENGTH: 938
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120
gggacccacc tatcatagca tttcctgccc tgaaggagaa ttctcaccaa gcacagagga 60
gaacccatca gagcaggaga cttttcactc tgcaggggag cgctgtcagc atgacacgag 120
ttagcttgct gtgggcagtc gtggtctcca cctgtcttga atccggcatg gcccagacag 180
tcactcagtc tcaaccagag atgtctgtgc aggaggcaga gactgtgacc ctgagttgca 240
catatgacac cagtgagaat aattattatt tgttctggta caagcagcct cccagcaggc 300
agatgattct cgttattcgc caagaagctt ataagcaaca gaatgcaacg gagaatcgtt 360
tctctgtgaa cttccagaaa gcagccaaat ccttcagtct caagatctca gactcacagc 420
tgggggacac tgcgatgtat ttctgtgctt tcgggggaga aaccagtggc tctaggttga 480
cctttgggga aggaacacag ctcacagtga atcctgatat ccagaaccct gaccctgccg 540
tgtaccagct gagagactct aaatccagtg acaagtctgt ctgcctattc accgattttg 600
attctcaaac aaatgtgtca caaagtaagg attctgatgt gtatatcaca gacaaaactg 660
tgctagacat gaggtctatg gacttcaaga gcaacagtgc tgtggcctgg agcaacaaat 720
ctgactttgc atgtgcaaac gccttcaaca acagcattat tccagaagac accttcttcc 780
ccagcccaga aagttcctgt gatgtcaagc tggtcgagaa aagctttgaa acagatacga 840
acctaaactt tcaaaacctg tcagtgattg ggttccgaat cctcctcctg aaagtggccg 900
ggtttaatct gctcatgacg ctgcggctgt ggtccagc 938

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
accagtgaga ataattatta t 21

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Thr Ser Glu Asn Asn Tyr Tyr
1 5

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
caagaagctt ataagcaaca gaat 24

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Gln Glu Ala Tyr Lys Gln Gln Asn
1 5

<210> SEQ ID NO 125
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
gctttcgggg gagaaaccag tggctctagg ttgacc 36

<210> SEQ ID NO 126
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Cys Ala Phe Gly Gly Glu Thr Ser Gly Ser Arg Leu Thr Phe
1               5                   10

<210> SEQ ID NO 127
<211> LENGTH: 905
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127
agggatgttt ttcttatatg gggagttgct gctgggctca ttgcagctca gacacagcaa     60
aagagcctag aacctgggtc ctagtttgca cctagaatat gaggcaagtg gcgagagtga    120
tcgtgttcct gaccctgagt actttgagcc ttgctaagac cacccagccc atctccatgg    180
actcatatga aggacaagaa gtgaacataa cctgtagcca caacaacatt gctacaaatg    240
attatatcac gtggtaccaa cagtttccca gccaaggacc acgatttatt attcaaggat    300
acaagacaaa agttacaaac gaagtggcct ccctgtttat ccctgccgac agaaagtcca    360
gcactctgag cctgccccgg gtttccctga gcgacactgc tgtgtactac tgcctcgtgg    420
gtgacaaagg aagcaactat cagttaatct ggggcgctgg gaccaagcta attataaagc    480
cagatatcca gaaccctgac cctgccgtgt accagctgag agactctaaa tccagtgaca    540
agtctgtctg cctattcacc gattttgatt ctcaaacaaa tgtgtcacaa agtaaggatt    600
ctgatgtgta tatcacagac aaaactgtgc tagacatgag gtctatggac ttcaagagca    660
acagtgctgt ggcctggagc aacaaatctg actttgcatg tgcaaacgcc ttcaacaaca    720
gcattattcc agaagacacc ttcttcccca gcccagaaag ttcctgtgat gtcaagctgg    780
tcgagaaaag ctttgaaaca gatacgaacc taaactttca aaacctgtca gtgattgggt    840
tccgaatcct cctcctgaaa gtggccgggt ttaatctgct catgacgctg cggctgtggt    900
ccagc                                                                905

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128
aacattgcta caaatgatta t                                               21

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Asn Ile Ala Thr Asn Asp Tyr 1 5

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130
ggatacaaga caaaa 15

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Gly Tyr Lys Thr Lys
1 5

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 132
ctcgtgggtg acaaaggaag caactatcag ttaatc 36

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Cys Leu Val Gly Asp Lys Gly Ser Asn Tyr Gln Leu Ile Trp
1 5 10

<210> SEQ ID NO 134
<211> LENGTH: 1063
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134
gaagttcagt agttagggat gtggccacaa gatggcagtg ctcctctgct gaggcagaat 60
acagggttca ctttagtgtg tcctgaatga ataggtttat ggtagcagca gagccttttt 120
cttattggtt ggctacacag tgtgagaaac ccctatggct gccagaggag agaagagaca 180
acctgatgat agaagtaact cttataactg gaggttgcag gtcaatgact gatcttaatt 240
gggaagaaca aggatgacat ccattcgagc tgtatttata ttcctgtggc tgcagctgga 300
cttggtgaat ggagagaatg tggagcagca tccttcaacc ctgagtgtcc aggagggaga 360

```
cagcgctgtt atcaagtgta cttattcaga cagtgcctca aactacttcc cttggtataa    420

gcaagaactt ggaaaaagac ctcagcttat tatagacatt cgttcaaatg tgggcgaaaa    480

gaaagaccaa cgaattgctg ttacattgaa caagacagcc aaacatttct ccctgcacat    540

cacagagacc caacctgaag actcggctgt ctacttctgt gcagcaagtt atctccctga    600

catgcgcttt ggagcaggga ccagactgac agtaaaacca aatatccaga accctgaccc    660

tgccgtgtac cagctgagag actctaaatc cagtgacaag tctgtctgcc tattcaccga    720

ttttgattct caaacaaatg tgtcacaaag taaggattct gatgtgtata tcacagacaa    780

aactgtgcta gacatgaggt ctatggactt caagagcaac agtgctgtgg cctggagcaa    840

caaatctgac tttgcatgtg caaacgcctt caacaacagc attattccag aagacacctt    900

cttccccagc ccagaaagtt cctgtgatgt caagctggtc gagaaaagct ttgaaacaga    960

tacgaaccta aactttcaaa acctgtcagt gattgggttc cgaatcctcc tcctgaaagt   1020

ggccgggttt aatctgctca tgacgctgcg gctgtggtcc agc                     1063


<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135

gacagtgcct caaactac                                                   18


<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Ser Ala Ser Asn Tyr
1               5


<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137

attcgttcaa atgtgggcga a                                               21


<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ile Arg Ser Asn Val Gly Glu
1               5
```

<210> SEQ ID NO 139
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
gcagcaagtt atctccctga catgcgc 27

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Cys Ala Ala Ser Tyr Leu Pro Asp Met Arg Phe
1 5 10

<210> SEQ ID NO 141
<211> LENGTH: 1036
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141
gtctagcatc ttccatctct acaggaagta tgtgacatga cacagtcaaa ctcatcatat 60
atctgttaac tatacttcct gtaaaaggca gaagcctcac acagcccagt aactttgcta 120
gtacctcttg agtgcaaggt ggagaattaa gatctggatt tgagacggag cacggaacat 180
ttcactcagg ggaagagcta tgaacatgct gactgccagc ctgttgaggg cagtcatagc 240
ctccatctgt gttgtatcca gcatggctca gaaggtaact caagcgcaga ctgaaatttc 300
tgtggtggag aaggaggatg tgaccttgga ctgtgtgtat gaaacccgtg atactactta 360
ttacttattc tggtacaagc aaccaccaag tggagaattg gttttcctta ttcgtcggaa 420
ctcttttgat gagcaaaatg aaataagtgg tcggtattct tggaacttcc agaaatccac 480
cagttccttc aacttcacca tcacagcctc acaagtcgtg gactcagcag tatacttctg 540
tgctctgagt gagctcaaag ctgcaggcaa caagctaact tttggaggag gaaccagggt 600
gctagttaaa ccaaatatcc agaaccctga ccctgccgtg taccagctga gagactctaa 660
atccagtgac aagtctgtct gcctattcac cgattttgat tctcaaacaa atgtgtcaca 720
aagtaaggat tctgatgtgt atatcacaga caaaactgtg ctagacatga ggtctatgga 780
cttcaagagc aacagtgctg tggcctggag caacaaatct gactttgcat gtgcaaacgc 840
cttcaacaac agcattattc cagaagacac cttcttcccc agcccagaaa gttcctgtga 900
tgtcaagctg gtcgagaaaa gctttgaaac agatacgaac ctaaactttc aaaacctgtc 960
agtgattggg ttccgaatcc tcctcctgaa agtggccggg tttaatctgc tcatgacgct 1020
gcggctgtgg tccagc 1036

<210> SEQ ID NO 142
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 142
acccgtgata ctacttatta c 21

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Thr Arg Asp Thr Thr Tyr Tyr
1 5

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
cggaactctt ttgatgagca aaat 24

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Arg Asn Ser Phe Asp Glu Gln Asn
1 5

<210> SEQ ID NO 146
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
gctctgagtg agctcaaagc tgcaggcaac aagctaact 39

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Cys Ala Leu Ser Glu Leu Lys Ala Ala Gly Asn Lys Leu Thr Phe
1 5 10 15

<210> SEQ ID NO 148
<211> LENGTH: 939
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 148

ggctgtactg gggcagcctg agtgacagct gctggtgtgg gccctggcag ttgctgctgg     60

gctcattgca gctcagacac agcaaaagag cctagaacct gggtcctagt ttgcacctag    120

aatatgaggc aagtggcgag agtgatcgtg ttcctgaccc tgagtacttt gagccttgct    180

aagaccaccc agcccatctc catggactca tatgaaggac aagaagtgaa cataacctgt    240

agccacaaca acattgctac aaatgattat atcacgtggt accaacagtt tcccagccaa    300

ggaccacgat ttattattca aggatacaag acaaaagtta caaacgaagt ggcctccctg    360

tttatccctg ccgacagaaa gtccagcact ctgagcctgc cccgggtttc cctgagcgac    420

actgctgtgt actactgcct cgtgggtgac aaggtttatg gaggaagcca aggaaatctc    480

atctttggaa aaggcactaa actctctgtt aaaccaaata tccagaaccc tgaccctgcc    540

gtgtaccagc tgagagactc taaatccagt gacaagtctg tctgcctatt caccgatttt    600

gattctcaaa caaatgtgtc acaaagtaag gattctgatg tgtatatcac agacaaaact    660

gtgctagaca tgaggtctat ggacttcaag agcaacagtg ctgtggcctg gagcaacaaa    720

tctgactttg catgtgcaaa cgccttcaac aacagcatta ttccagaaga caccttcttc    780

cccagcccag aaagttcctg tgatgtcaag ctggtcgaga aaagctttga aacagatacg    840

aacctaaact ttcaaaacct gtcagtgatt gggttccgaa tcctcctcct gaaagtggcc    900

gggtttaatc tgctcatgac gctgcggctg tggtccagc                           939


<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149

aacattgcta caaatgatta t                                               21


<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Ile Ala Thr Asn Asp Tyr
1               5


<210> SEQ ID NO 151
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151

ggatacaaga caaaa                                                      15
```

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Gly Tyr Lys Thr Lys
1 5

<210> SEQ ID NO 153
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
ctcgtgggtg acaaggttta tggaggaagc caaggaaatc tcatc 45

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Cys Leu Val Gly Asp Lys Val Tyr Gly Gly Ser Gln Gly Asn Leu Ile
1 5 10 15

Phe

<210> SEQ ID NO 155
<211> LENGTH: 1074
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 155
ggggagttgg ttgatccaaa agaaagtctg cattgggtga gcttctcagc cagtacatag 60
agaagtgtga gatgacacac actagtttgc tataccagga aacctctgtt tcctgttcta 120
gggcagcagt agcagcagca catggcccag taattcttct ctcaccatgc caggttcact 180
tcacagtaca gagtcctgaa aataaagaag aaaatttttt tttatctaga aaaagaacca 240
aacatgtcac tttctagcct gctgaaggtg gtcacagctt cactgtggct aggacctggc 300
attgcccaga agataactca aacccaacca ggaatgttcg tgcaggaaaa ggaggctgtg 360
actctggact gcacatatga caccagtgat ccaagttatg gtctattctg gtacaagcag 420
cccagcagtg gggaaatgat tttcttatt tatcaggggt cttatgacca gcaaaatgca 480
acagaaggtc gctactcatt gaatttccag aaggcaagaa aatccgccaa ccttgtcatc 540
tccgcttcac aactggggga ctcagcaatg tatttctgtg caatgagaga gggccaggat 600
agcagctata aattgatctt cgggagtggg accagactgc tggtcaggcc tgatatccag 660
aaccctgacc ctgccgtgta ccagctgaga gactctaaat ccagtgacaa gtctgtctgc 720
ctattcaccg attttgattc tcaaacaaat gtgtcacaaa gtaaggattc tgatgtgtat 780
atcacagaca aaactgtgct agacatgagg tctatggact tcaagagcaa cagtgctgtg 840
gcctggagca acaaatctga ctttgcatgt gcaaacgcct tcaacaacag cattattcca 900
gaagacacct tcttccccag cccagaaagt tcctgtgatg tcaagctggt cgagaaaagc 960
tttgaaacag atacgaacct aaactttcaa aacctgtcag tgattgggtt ccgaatcctc 1020
ctcctgaaag tggccgggtt taatctgctc atgacgctgc ggctgtggtc cagc 1074

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
accagtgatc caagttatgg t 21

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Thr Ser Asp Pro Ser Tyr Gly
1 5

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
caggggtctt atgaccagca aaat 24

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Gln Gly Ser Tyr Asp Gln Gln Asn
1 5

<210> SEQ ID NO 160
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 160
gcaatgagag agggccagga tagcagctat aaattgatc 39

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Cys Ala Met Arg Glu Gly Gln Asp Ser Ser Tyr Lys Leu Ile Phe
1 5 10 15

<210> SEQ ID NO 162
<211> LENGTH: 964
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162
tctggggttc atatgtaaaa tgaagggtct gtggaaggac atgaataaag cacaggaggt 60
tgaagtcaga tttgcagctt tctaggcagg agacaagaca atctgcatct tcacaggagg 120
gatggccatg ctcctggggg catcagtgct gattctgtgg cttcagccag actgggtaaa 180
cagtcaacag aagaatgatg accagcaagt taagcaaaat tcaccatccc tgagcgtcca 240
ggaaggaaga atttctattc tgaactgtga ctatactaac agcatgtttg attatttcct 300
atggtacaaa aaataccctg ctgaaggtcc tacattcctg atatctataa gttccattaa 360
ggataaaaat gaagatggaa gattcactgt cttcttaaac aaaagtgcca agcacctctc 420
tctgcacatt gtgccctccc agcctggaga ctctgcagtg tacttctgtg cagcaaggat 480
ttatggagga agccaaggaa atctcatctt tggaaaaggc actaaactct ctgttaaacc 540
aaatatccag aaccctgacc ctgccgtgta ccagctgaga gactctaaat ccagtgacaa 600
gtctgtctgc ctattcaccg attttgattc tcaaacaaat gtgtcacaaa gtaaggattc 660
tgatgtgtat atcacagaca aaactgtgct agacatgagg tctatggact tcaagagcaa 720
cagtgctgtg gcctggagca acaaatctga ctttgcatgt gcaaacgcct tcaacaacag 780
cattattcca gaagacacct tcttccccag cccagaaagt tcctgtgatg tcaagctggt 840
cgagaaaagc tttgaaacag atacgaacct aaactttcaa aacctgtcag tgattgggtt 900
ccgaatcctc ctcctgaaag tggccgggtt taatctgctc atgacgctgc ggctgtggtc 960
cagc 964

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
aacagcatgt ttgattat 18

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Asn Ser Met Phe Asp Tyr
1 5

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
ataagttcca ttaaggataa a 21

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Ile Ser Ser Ile Lys Asp Lys
1 5

<210> SEQ ID NO 167
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
gcagcaagga tttatggagg aagccaagga aatctcatc 39

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Cys Ala Ala Arg Ile Tyr Gly Gly Ser Gln Gly Asn Leu Ile Phe
1 5 10 15

<210> SEQ ID NO 169
<211> LENGTH: 1059
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 169
gaaagtctgc attgggtgag cttctcagcc agtacataga gaagtgtgag atgacacaca 60
ctagtttgct ataccaggaa acctctgttt cctgttctag ggcagcagta gcagcagcac 120
atggcccagt aattcttctc tcaccatgcc aggttcactt cacagtacag agtcctgaaa 180
ataaagaaga aaattttttt ttatctagaa aaagaaccaa acatgtcact ttctagcctg 240

-continued

```
ctgaaggtgg tcacagcttc actgtggcta ggacctggca ttgcccagaa gataactcaa    300

acccaaccag gaatgttcgt gcaggaaaag gaggctgtga ctctggactg cacatatgac    360

accagtgatc caagttatgg tctattctgg tacaagcagc ccagcagtgg ggaaatgatt    420

tttcttattt atcaggggtc ttatgaccag caaaatgcaa cagaaggtcg ctactcattg    480

aatttccaga aggcaagaaa atccgccaac cttgtcatct ccgcttcaca actgggggac    540

tcagcaatgt acttctgtgc aatgagagag ggcgaacctt ctggttctgc aaggcaactg    600

acctttggat ctgggacaca attgactgtt ttacctgata tccagaaccc tgaccctgcc    660

gtgtaccagc tgagagactc taaatccagt gacaagtctg tctgcctatt caccgatttt    720

gattctcaaa caaatgtgtc acaaagtaag gattctgatg tgtatatcac agacaaaact    780

gtgctagaca tgaggtctat ggacttcaag agcaacagtg ctgtggcctg gagcaacaaa    840

tctgactttg catgtgcaaa cgccttcaac aacagcatta ttccagaaga caccttcttc    900

cccagcccag aaagttcctg tgatgtcaag ctggtcgaga aaagctttga aacagatacg    960

aacctaaact ttcaaaacct gtcagtgatt gggttccgaa tcctcctcct gaaagtggcc   1020

gggtttaatc tgctcatgac gctgcggctg tggtccagc                          1059


<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170

accagtgatc caagttatgg t                                               21


<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Thr Ser Asp Pro Ser Tyr Gly
1               5


<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172

caggggtctt atgaccagca aaat                                            24


<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173
```

Gln Gly Ser Tyr Asp Gln Gln Asn
1 5

<210> SEQ ID NO 174
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
gcaatgagag agggcgaacc ttctggttct gcaaggcaac tgacc 45

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Cys Ala Met Arg Glu Gly Glu Pro Ser Gly Ser Ala Arg Gln Leu Thr
1 5 10 15

Phe

<210> SEQ ID NO 176
<211> LENGTH: 962
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176
tggggttcat atgtaaaatg aagggtctgt ggaaggacat gaataaagca caggaggttg 60
aagtcagatt tgcagctttc taggcaggag acaagacaat ctgcatcttc acaggaggga 120
tggccatgct cctgggggca tcagtgctga ttctgtggct tcagccagac tgggtaaaca 180
gtcaacagaa gaatgatgac cagcaagtta agcaaaattc accatccctg agcgtccagg 240
aaggaagaat ttctattctg aactgtgact atactaacag catgtttgat tatttcctat 300
ggtacaaaaa ataccctgct gaaggtccta cattcctgat atctataagt tccattaagg 360
ataaaaatga agatggaaga ttcactgtct tcttaaacaa aagtgccaag cacctctctc 420
tgcacattgt gccctcccag cctggagact ctgcagtgta cttctgtgca gttaatgctg 480
gtggtactag ctatggaaag ctgacatttg gacaagggac catcttgact gtccatccaa 540
atatccagaa ccctgaccct gccgtgtacc agctgagaga ctctaaatcc agtgacaagt 600
ctgtctgcct attcaccgat tttgattctc aaacaaatgt gtcacaaagt aaggattctg 660
atgtgtatat cacagacaaa actgtgctag acatgaggtc tatggacttc aagagcaaca 720
gtgctgtggc ctggagcaac aaatctgact ttgcatgtgc aaacgccttc aacaacagca 780
ttattccaga agacaccttc ttccccagcc cagaaagttc ctgtgatgtc aagctggtcg 840
agaaaagctt tgaaacagat acgaacctaa actttcaaaa cctgtcagtg attgggttcc 900
gaatcctcct cctgaaagtg gccgggttta atctgctcat gacgctgcgg ctgtggtcca 960
gc 962

<210> SEQ ID NO 177

<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
aacagcatgt ttgattat 18

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asn Ser Met Phe Asp Tyr
1               5

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ataagttcca ttaaggataa a 21

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ile Ser Ser Ile Lys Asp Lys
1               5

<210> SEQ ID NO 181
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gcagttaatg ctggtggtac tagctatgga aagctgaca 39

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Ala Val Asn Ala Gly Gly Thr Ser Tyr Gly Lys Leu Thr Phe
1               5                   10                  15

<210> SEQ ID NO 183
<211> LENGTH: 1202
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 183
gacatttctc aaatgagaag caaacagttc acttccttgg atccgtggtt tcgcctgtgg 60
ccttcagggg gcgacgttgc actaaggagg catctgtgtt cattgccgac catcctcatc 120
cactgagcct cctccctgca gctggctgat gtagctcact ggtgtctgtg tagataggga 180
gctgtgatga gaacaagagg tcagaacaca tccaggctcc ttaagagaaa gcctttcttt 240
aaccattttt gaaacccttc aaaggcagag acttgtccag cctaacctgc ctgctgctcc 300
tagctcctga ggctcagggc ccttggcttc tgtccgctct gctcagggcc ctccagcgtg 360
gccactgctc agccatgctc ctgctgctcg tcccagtgct cgaggtgatt tttaccctgg 420
gaggaaccag agcccagtcg gtgacccagc ttggcagcca cgtctctgtc tctgagggag 480
ccctggttct gctgaggtgc aactactcat cgtctgttcc accatatctc ttctggtatg 540
tgcaataccc caaccaagga ctccagcttc tcctgaagta cacaacaggg gccaccctgg 600
ttaaaggcat caacggtttt gaggctgaat ttaagaagag tgaaacctcc ttccacctga 660
cgaaaccctc agcccatatg agcgacgcgg ctgagtactt ctgtgctgtg agtgagaagt 720
tttctggtgg ctacaataag ctgatttttg gagcagggac caggctggct gtacacccat 780
atatccagaa ccctgaccct gccgtgtacc agctgagaga ctctaaatcc agtgacaagt 840
ctgtctgcct attcaccgat tttgattctc aaacaaatgt gtcacaaagt aaggattctg 900
atgtgtatat cacagacaaa actgtgctag acatgaggtc tatggacttc aagagcaaca 960
gtgctgtggc ctggagcaac aaatctgact ttgcatgtgc aaacgccttc aacaacagca 1020
ttattccaga agacaccttc ttccccagcc cagaaagttc ctgtgatgtc aagctggtcg 1080
agaaaagctt tgaaacagat acgaacctaa actttcaaaa cctgtcagtg attgggttcc 1140
gaatcctcct cctgaaagtg gccgggttta atctgctcat gacgctgcgg ctgtggtcca 1200
gc 1202

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
tcgtctgttc caccatat 18

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Ser Ser Val Pro Pro Tyr
1 5

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 186
tacacaacag gggccaccct ggtt 24

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Tyr Thr Thr Gly Ala Thr Leu Val
1 5

<210> SEQ ID NO 188
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 188
gctgtgagtg agaagttttc tggtggctac aataagctga tt 42

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Cys Ala Val Ser Glu Lys Phe Ser Gly Gly Tyr Asn Lys Leu Ile Phe
1 5 10 15

<210> SEQ ID NO 190
<211> LENGTH: 971
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190
tgggggttaa ctatacttcc tgtaaaaggc agaagcctca cacagcccag taactttgct 60
agtacctctt gagtgcaagg tggagaatta agatctggat ttgagacgga gcacggaaca 120
tttcactcag gggaagagct atgaacatgc tgactgccag cctgttgagg gcagtcatag 180
cctccatctg tgttgtatcc agcatggctc agaaggtaac tcaagcgcag actgaaattt 240
ctgtggtgga gaaggaggat gtgaccttgg actgtgtgta tgaaacccgt gatactactt 300
attacttatt ctggtacaag caaccaccaa gtggagaatt ggttttcctt attcgtcgga 360
actcttttga tgagcaaaat gaaataagtg gtcggtattc ttggaacttc cagaaatcca 420
ccagttcctt caacttcacc atcacagcct cacaagtcgt ggactcagca gtatacttct 480
gtgctctgag tgaggcaaaa gatgacaaga tcatctttgg aaaagggaca cgacttcata 540
ttctccccaa tatccagaac cctgaccctg ccgtgtacca gctgagagac tctaaatcca 600
gtgacaagtc tgtctgccta ttcaccgatt ttgattctca aacaaatgtg tcacaaagta 660
aggattctga tgtgtatatc acagacaaaa ctgtgctaga catgaggtct atggacttca 720
agagcaacag tgctgtggcc tggagcaaca aatctgactt tgcatgtgca aacgccttca 780
acaacagcat tattccagaa gacaccttct tccccagccc agaaagttcc tgtgatgtca 840
agctggtcga gaaaagcttt gaaacagata cgaacctaaa ctttcaaaac ctgtcagtga 900
ttgggttccg aatcctcctc ctgaaagtgg ccgggtttaa tctgctcatg acgctgcggc 960
tgtggtccag c 971

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
acccgtgata ctacttatta c 21

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Thr Arg Asp Thr Thr Tyr Tyr
1 5

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 193
cggaactctt ttgatgagca aaat 24

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 194

Arg Asn Ser Phe Asp Glu Gln Asn
1 5

<210> SEQ ID NO 195
<211> LENGTH: 33
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 195
gctctgagtg aggcaaaaga tgacaagatc atc 33

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 196

Cys Ala Leu Ser Glu Ala Lys Asp Asp Lys Ile Ile Phe
1 5 10

<210> SEQ ID NO 197
<211> LENGTH: 1008
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 197
ctcctatatc ggtttttctt atatgggaga atctccatgg cagcgttttc ttatatgggg 60
ttcatatgta aaatgaaggg tctgtggaag gacatgaata aagcacagga ggttgaagtc 120
agatttgcag ctttctaggc aggagacaag acaatctgca tcttcacagg agggatggcc 180
atgctcctgg gggcatcagt gctgattctg tggcttcagc cagactgggt aaacagtcaa 240
cagaagaatg atgaccagca agttaagcaa aattcaccat ccctgagcgt ccaggaagga 300
agaatttcta ttctgaactg tgactatact aacagcatgt ttgattattt cctatggtac 360
aaaaaatacc ctgctgaagg tcctacattc ctgatatcta taagttccat taaggataaa 420
aatgaagatg gaagattcac tgtcttctta aacaaaagtg ccaagcacct ctctctgcac 480
attgtgccct cccagcctgg agactctgca gtgtacttct gtgccattta taaccaggga 540
ggaaagctta tcttcggaca gggaacggag ttatctgtga aacccaatat ccagaaccct 600
gaccctgccg tgtaccagct gagagactct aaatccagtg acaagtctgt ctgcctattc 660
accgattttg attctcaaac aaatgtgtca caaagtaagg attctgatgt gtatatcaca 720
gacaaaactg tgctagacat gaggtctatg gacttcaaga gcaacagtgc tgtggcctgg 780
agcaacaaat ctgactttgc atgtgcaaac gccttcaaca acagcattat tccagaagac 840
accttcttcc ccagcccaga aagttcctgt gatgtcaagc tggtcgagaa aagctttgaa 900
acagatacga acctaaactt tcaaaacctg tcagtgattg ggttccgaat cctcctcctg 960
aaagtggccg ggtttaatct gctcatgacg ctgcggctgt ggtccagc 1008

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
aacagcatgt ttgattat 18

<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Asn Ser Met Phe Asp Tyr
1 5

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 200
ataagttcca ttaaggataa a 21

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Ile Ser Ser Ile Lys Asp Lys
1 5

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
gccatttata accagggagg aaagcttatc 30

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Cys Ala Ile Tyr Asn Gln Gly Gly Lys Leu Ile Phe
1 5 10

<210> SEQ ID NO 204
<211> LENGTH: 890
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 204
tacattctca atttcttata tggggactgt gatttcttca tgttaaggat caagaccatt 60
atttgggtaa cacactaaag atgaactatt ctccaggctt agtatctctg atactcttac 120
tgcttggaag aacccgtgga aattcagtga cccagatgga agggccagtg actctctcag 180
aagaggcctt cctgactata aactgcacgt acacagccac aggataccct tcccttttct 240
ggtatgtcca atatcctgga gaaggtctac agctcctcct gaaagccacg aaggctgatg 300
acaagggaag caacaaaggt tttgaagcca cataccgtaa agaaaccact tctttccact 360
tggagaaagg ctcagttcaa gtgtcagact cagcggtgta cttctgtgct ctgatgaccg 420
actacaagct cagctttgga gccggaacca cagtaactgt aagagcaaat atccagaacc 480
ctgaccctgc cgtgtaccag ctgagagact ctaaatccag tgacaagtct gtctgcctat 540
tcaccgattt tgattctcaa acaaatgtgt cacaaagtaa ggattctgat gtgtatatca 600
cagacaaaac tgtgctagac atgaggtcta tggacttcaa gagcaacagt gctgtggcct 660
ggagcaacaa atctgacttt gcatgtgcaa acgccttcaa caacagcatt attccagaag 720
acaccttctt ccccagccca gaaagttcct gtgatgtcaa gctggtcgag aaaagctttg 780
aaacagatac gaacctaaac tttcaaaacc tgtcagtgat tgggttccga atcctcctcc 840
tgaaagtggc cgggtttaat ctgctcatga cgctgcggct gtggtccagc 890

<210> SEQ ID NO 205
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 205
gccacaggat acccttcc 18

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 206

Ala Thr Gly Tyr Pro Ser
1 5

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 207
gccacgaagg ctgatgacaa g 21

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Ala Thr Lys Ala Asp Asp Lys
1 5

<210> SEQ ID NO 209
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 209
gctctgatga ccgactacaa gctcagc 27

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Cys Ala Leu Met Thr Asp Tyr Lys Leu Ser Phe
1 5 10

<210> SEQ ID NO 211
<211> LENGTH: 987
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 211
gggagtggtg aattaggggt gttaaaaaga gcatcatttt tttgaactgg taaagcagat 60
tctttttatg atttttaaag tagaaatatc cattccaggt gcattttta agggtttaaa 120 atttgaatcc tcagtgaacc agggcagaga agaatgatga aatccttgag agttttacta 180
gtgatcctgt ggcttcagtt gagctgggtt tggagccaac agaaggaggt ggagcagaat 240
tctggacccc tcagtgttcc agagggagcc attgcctctc tcaactgcac ttacagtgac 300
cgaggttccc agtccttctt ctggtacaga caatattctg ggaaaagccc tgagttgata 360
atgtccatat actccaatgg tgacaaagaa gatggaaggt ttacagcaca gctcaataaa 420
gccagccagt atgtttctct gctcatcaga gactcccagc ccagtgattc agccacctac 480
ctctgtgccg tgaggagtgt aggggtttct ggtggctaca ataagctgat ttttggagca 540
gggaccaggc tggctgtaca cccatatatc cagaaccctg accctgccgt gtaccagctg 600
agagactcta aatccagtga caagtctgtc tgcctattca ccgattttga ttctcaaaca 660
aatgtgtcac aaagtaagga ttctgatgtg tatatcacag acaaaactgt gctagacatg 720
aggtctatgg acttcaagag caacagtgct gtggcctgga gcaacaaatc tgactttgca 780
tgtgcaaacg ccttcaacaa cagcattatt ccagaagaca ccttcttccc cagcccagaa 840
agttcctgtg atgtcaagct ggtcgagaaa agctttgaaa cagatacgaa cctaaacttt 900
caaaacctgt cagtgattgg gttccgaatc ctcctcctga aagtggccgg gtttaatctg 960
ctcatgacgc tgcggctgtg gtccagc 987

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 212
gaccgaggtt cccagtcc 18

<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Asp Arg Gly Ser Gln Ser
1 5

<210> SEQ ID NO 214
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
atatactcca atggtgac 18

<210> SEQ ID NO 215
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Ile Tyr Ser Asn Gly Asp
1 5

<210> SEQ ID NO 216
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
gccgtgagga gtgtaggggt ttctggtggc tacaataagc tgatt 45

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Cys Ala Val Arg Ser Val Gly Val Ser Gly Gly Tyr Asn Lys Leu Ile 1 5 10 15

Phe

<210> SEQ ID NO 218
<211> LENGTH: 911
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218
gggtgacagc tgctggtgtg ggccctggca gttgctgctg ggctcattgc agctcagaca 60
cagcaaaaga gcctagaacc tgggtcctag tttgcaccta gaatatgagg caagtggcga 120
gagtgatcgt gttcctgacc ctgagtactt tgagccttgc taagaccacc cagcccatct 180
ccatggactc atatgaagga caagaagtga acataacctg tagccacaac aacattgcta 240
caaatgatta tatcacgtgg taccaacagt ttcccagcca aggaccacga tttattattc 300
aaggatacaa gacaaaagtt acaaacgaag tggcctccct gtttatccct gccgacagaa 360
agtccagcac tctgagcctg ccccgggttt ccctgagcga cactgctgtg tactactgcc 420
tcgttctact ctctagcaac acaggcaaac taatctttgg gcaagggaca actttacaag 480
taaaaccaga tatccagaac cctgaccctg ccgtgtacca gctgagagac tctaaatcca 540
gtgacaagtc tgtctgccta ttcaccgatt ttgattctca aacaaatgtg tcacaaagta 600
aggattctga tgtgtatatc acagacaaaa ctgtgctaga catgaggtct atggacttca 660
agagcaacag tgctgtggcc tggagcaaca aatctgactt tgcatgtgca aacgccttca 720
acaacagcat tattccagaa gacaccttct tccccagccc agaaagttcc tgtgatgtca 780
agctggtcga gaaaagcttt gaaacagata cgaacctaaa ctttcaaaac ctgtcagtga 840
ttgggttccg aatcctcctc ctgaaagtgg ccgggtttaa tctgctcatg acgctgcggc 900
tgtggtccag c 911

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
aacattgcta caaatgatta t 21

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asn Ile Ala Thr Asn Asp Tyr
1 5

<210> SEQ ID NO 221
<211> LENGTH: 15
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 221

ggatacaaga caaaa                                                              15

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Tyr Lys Thr Lys
1               5

<210> SEQ ID NO 223
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223

ctcgttctac tctctagcaa cacaggcaaa ctaatc                                       36

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Cys Leu Val Leu Leu Ser Ser Asn Thr Gly Lys Leu Ile Phe
1               5                   10

<210> SEQ ID NO 225
<211> LENGTH: 923
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225

tggggctgtt ctgaagcagc tacggcacca gtgcagctga tactcaaggt tcagatcaga      60

agaggaggct tctcaccctg cagcagggac ctgtgagcat ggcatgccct ggcttcctgt     120

gggcacttgt gatctccacc tgtcttgaat ttagcatggc tcagacagtc actcagtctc     180

aaccagagat gtctgtgcag gaggcagaga ccgtgaccct gagctgcaca tatgacacca     240

gtgagagtga ttattattta ttctggtaca agcagcctcc cagcaggcag atgattctcg     300

ttattcgcca agaagcttat aagcaacaga atgcaacaga gaatcgtttc tctgtgaact     360

tccagaaagc agccaaatcc ttcagtctca agatctcaga ctcacagctg ggggatgccg     420

cgatgtattt ctgtgcttat aggagcgcga ataacaatga catgcgcttt ggagcaggga     480

ccagactgac agtaaaacca aatatccaga accctgaccc tgccgtgtac cagctgagag     540

actctaaatc cagtgacaag tctgtctgcc tattcaccga ttttgattct caaacaaatg     600
```

tgtcacaaag taaggattct gatgtgtata tcacagacaa aactgtgcta gacatgaggt 660
ctatggactt caagagcaac agtgctgtgg cctggagcaa caaatctgac tttgcatgtg 720
caaacgcctt caacaacagc attattccag aagacacctt cttccccagc ccagaaagtt 780
cctgtgatgt caagctggtc gagaaaagct ttgaaacaga tacgaaccta aactttcaaa 840
acctgtcagt gattgggttc cgaatcctcc tcctgaaagt ggccgggttt aatctgctca 900
tgacgctgcg gctgtggtcc agc 923

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 226
accagtgaga gtgattatta t 21

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Thr Ser Glu Ser Asp Tyr Tyr
1 5

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
caagaagctt ataagcaaca gaat 24

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Gln Glu Ala Tyr Lys Gln Gln Asn
1 5

<210> SEQ ID NO 230
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 230
gcttatagga gcgcgaataa caatgacatg cgc 33

<210> SEQ ID NO 231
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Cys Ala Tyr Arg Ser Ala Asn Asn Asn Asp Met Arg Phe
1 5 10

<210> SEQ ID NO 232
<211> LENGTH: 1054
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 232
gggggtgtgt gtgtgtgctt gagagagaga gaaggagaga aagagagaga atgggaaggg 60
cgataagagg aggggttagt gatataccag gggttgtgaa aataacctct tttttctaat 120
tggtaggaca gattcttttt atgattccta aagtggaaga aataaagtat ctctgctatg 180
ttcatttctt tttggattga aaattttaat cctcagtgaa ccagggcaga aaagaatgat 240
gatatccttg agagttttac tggtgatcct gtggcttcag ttaagctggg tttggagcca 300
acggaaggag gtggagcagg atcctggacc cttcaatgtt ccagagggag ccactgtcgc 360
tttcaactgt acttacagca acagtgcttc tcagtctttc ttctggtaca gacaggattg 420
caggaaagaa cctaagttgc tgatgtccgt atactccagt ggtaatgaag atggaaggtt 480
tacagcacag ctcaatagag ccagccagta tatttccctg ctcatcagag actccaagct 540
cagtgattca gccacctacc tctgtgtggt tttcccagga ggaagctaca tacctacatt 600
tggaagagga accagcctta ttgttcatcc gtatatccag aagcctgacc ctgccgtgta 660
ccagctgaga gactctaaat ccagtgacaa gtctgtctgc ctattcaccg attttgattc 720
tcaaacaaat gtgtcacaaa gtaaggattc tgatgtgtat atcacagaca aaactgtgct 780
agacatgagg tctatggact tcaagagcaa cagtgctgtg gcctggagca acaaatctga 840
ctttgcatgt gcaaacgcct tcaacaacag cattattcca gaagacacct tcttccccag 900
cccagaaagt tcctgtgatg tcaagctggt cgagaaaagc tttgaaacag atacgaacct 960
aaactttcaa aacctgtcag tgattgggtt ccgaatcctc ctcctgaaag tggccgggtt 1020
taatctgctc atgacgctgc ggctgtggtc cagc 1054

<210> SEQ ID NO 233
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 233
aacagtgctt ctcagtct 18

<210> SEQ ID NO 234
<211> LENGTH: 6
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 234

Asn Ser Ala Ser Gln Ser
1               5

<210> SEQ ID NO 235
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gtatactcca gtggtaat 18

<210> SEQ ID NO 236
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Val Tyr Ser Ser Gly Asn
1               5

<210> SEQ ID NO 237
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gtggttttcc caggaggaag ctacatacct aca 33

<210> SEQ ID NO 238
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Cys Val Val Phe Pro Gly Gly Ser Tyr Ile Pro Thr Phe
1               5                   10

<210> SEQ ID NO 239
<211> LENGTH: 1262
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
agaaagcaga atgggtgatg tgatgtgcaa tgccacagaa gcactgcagc caggagaggt 60
gacagctaat ggggatgttt ggagtctttg agtgaaccaa acacatccca gagtaattgt 120

-continued aatttatttc agtcaatctt ctgtacagac ttagcattca cctttggagg aaggtccttt 180
gagcagggac agagatggtg atgtcactga cagtccccct tttactctgg gtgagaggtc 240
tagaatcctc agctcctgta ttcgtgccca caagggcctc atctaggtga aggctccacc 300
tgccccaccc tgccatggcc accaggctcc tctgctgtgt ggttctttgt ctcctgggag 360
aagagcttat agatgctaga gtcacccaga caccaaggca caaggtgaca gagatgggac 420
aagaagtaac aatgagatgt cagccaattt taggccacaa tactgttttc tggtacagac 480
agaccatgat gcaaggactg gagttgctgg cttacttccg caaccgggct cctctagatg 540
attcggggat gccgaaggat cgattctcag cagagatgcc tgatgcaact ttagccactc 600
tgaagatcca gccctcagaa cccagggact cagctgtgta tttttgtgct agtggtttgg 660
ccctcactga ggggggctgg tacgagcagt acttcgggcc gggcaccagg ctcacggtca 720
cagaggacct gaaaaacgtg ttcccacccg aggtcgctgt gtttgagcca tcagaagcag 780
agatctccca cacccaaaag gccacactgg tatgcctggc cacaggcttc taccccgacc 840
acgtggagct gagctggtgg gtgaatggga aggaggtgca cagtggggtc agcacagacc 900
cgcagcccct caaggagcag cccgccctca atgactccag atactgcctg agcagccgcc 960
tgagggtctc ggccaccttc tggcagaacc cccgcaacca cttccgctgt caagtccagt 1020
tctacgggct ctcggagaat gacgagtgga cccaggatag ggccaaacct gtcacccaga 1080
tcgtcagcgc cgaggcctgg ggtagagcag actgtggctt cacctccgag tcttaccagc 1140
aaggggtcct gtctgccacc atcctctatg agatcttgct agggaaggcc accttgtatg 1200
ccgtgctggt cagtgccctc gtgctgatgg ccatggtcaa gagaaaggat tccagaggct 1260
ag 1262

<210> SEQ ID NO 240
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 240
ttaggccaca atact 15

<210> SEQ ID NO 241
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Leu Gly His Asn Thr
1 5

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
ttccgcaacc gggctcct 18

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Phe Arg Asn Arg Ala Pro
1               5

<210> SEQ ID NO 244
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 244
gctagtggtt tggccctcac tgagggggc tggtacgagc agtac 45

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

Ala Ser Gly Leu Ala Leu Thr Glu Gly Gly Trp Tyr Glu Gln Tyr
1               5                   10                  15

<210> SEQ ID NO 246
<211> LENGTH: 1068
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 246
gggccagaga caccagtaat tctgccagac cttgcctgtg gggccatggg agctcaaaat 60
gcccctcctt tcctccacag gaccagatgc ctgagctagg aaaggcctca ttcctgctgt 120
gatcctgcca tggatacctg gctcgtatgc tgggcaattt ttagtctctt gaaagcagga 180
ctcacagaac ctgaagtcac ccagactccc agccatcagg tcacacagat gggacaggaa 240
gtgatcttgc gctgtgtccc catctctaat cacttatact tctattggta cagacaaatc 300
ttggggcaga aagtcgagtt tctggtttcc ttttataata atgaaatctc agagaagtct 360
gaaatattcg atgatcaatt ctcagttgaa aggcctgatg gatcaaattt cactctgaag 420
atccggtcca caaagctgga ggactcagcc atgtacttct gtgccagcct ccgatgggac 480
ggggacaatg agcagttctt cgggccaggg acacggctca ccgtgctaga ggacctgaaa 540
aacgtgttcc cacccgaggt cgctgtgttt gagccatcag aagcagagat ctcccacacc 600
caaaaggcca cactggtatg cctggccaca ggcttctacc ccgaccacgt ggagctgagc 660
tggtgggtga atgggaagga ggtgcacagt ggggtcagca cagacccgca gcccctcaag 720
gagcagcccg ccctcaatga ctccagatac tgcctgagca gccgcctgag ggtctcggcc 780

-continued accttctggc agaacccccg caaccacttc cgctgtcaag tccagttcta cgggctctcg 840
gagaatgacg agtggaccca ggatagggcc aaacctgtca cccagatcgt cagcgccgag 900
gcctggggta gagcagactg tggcttcacc tccgagtctt accagcaagg ggtcctgtct 960
gccaccatcc tctatgagat cttgctaggg aaggccacct tgtatgccgt gctggtcagt 1020
gccctcgtgc tgatggccat ggtcaagaga aaggattcca gaggctag 1068

<210> SEQ ID NO 247
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 247
tctaatcact tatac 15

<210> SEQ ID NO 248
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

Ser Asn His Leu Tyr
1 5

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 249
ttttataata atgaaatc 18

<210> SEQ ID NO 250
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 250

Phe Tyr Asn Asn Glu Ile
1 5

<210> SEQ ID NO 251
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 251
gccagcctcc gatgggacgg ggacaatgag cagttc 36

<210> SEQ ID NO 252

<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Ala Ser Leu Arg Trp Asp Gly Asp Asn Glu Gln Phe
1 5 10

<210> SEQ ID NO 253
<211> LENGTH: 1089
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 253
gaatttgacc atctggggaa ggggcgtggc ctctcctgac aggaaggctc tggggcccag 60
gcagggagaa tgaagtctca gaatgacccc cttgagagta ctgttcccct atcaccgatg 120
cacagaccca gaagacccct ccatcctgta gcacctgcca tgagcatcgg gctcctgtgc 180
tgtgtggcct tttctctcct gtgggcaagt ccagtgaatg ctggtgtcac tcagacccca 240
aaattccagg tcctgaagac aggacagagc atgacactgc agtgtgccca ggatatgaac 300
cataactcca tgtactggta tcgacaagac ccaggcatgg gactgaggct gatttattac 360
tcagcttctg agggtaccac tgacaaagga gaagtcccca atggctacaa tgtctccaga 420
ttaaacaaac gggagttctc gctcaggctg gagtcggctg ctccctccca gacatctgtg 480
tacttctgtg ccagcaggga cagggccctg aacactgaag ctttctttgg acaaggcacc 540
agactcacag ttgtagagga cctgaacaag gtgttcccac ccgaggtcgc tgtgtttgag 600
ccatcagaag cagagatctc ccacacccaa aaggccacac tggtgtgcct ggccacaggc 660
ttctaccccg accacgtgga gctgagctgg tgggtgaatg ggaaggaggt gcacagtggg 720
gtcagcacag acccgcagcc cctcaaggag cagcccgccc tcaatgactc cagatactgc 780
ctgagcagcc gcctgagggt ctcggccacc ttctggcaga acccccgcaa ccacttccgc 840
tgtcaagtcc agttctacgg gctctcggag aatgacgagt ggacccagga tagggccaaa 900
cccgtcaccc agatcgtcag cgccgaggcc tggggtagag cagactgtgg ctttacctcg 960
gtgtcctacc agcaaggggt cctgtctgcc accatcctct atgagatcct gctagggaag 1020
gccaccctgt atgctgtgct ggtcagcgcc cttgtgttga tggccatggt caagagaaag 1080
gatttctga 1089

<210> SEQ ID NO 254
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
atgaaccata actcc 15

<210> SEQ ID NO 255
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Met Asn His Asn Ser
1 5

<210> SEQ ID NO 256
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 256
tcagcttctg agggtacc 18

<210> SEQ ID NO 257
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Ser Ala Ser Glu Gly Thr
1 5

<210> SEQ ID NO 258
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 258
gccagcaggg acagggccct gaacactgaa gctttc 36

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Ala Ser Arg Asp Arg Ala Leu Asn Thr Glu Ala Phe
1 5 10

<210> SEQ ID NO 260
<211> LENGTH: 1258
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 260
gaagaagtct catctgtcag tgagttgaca agaaacagag caaaacgact cctccaatgt 60
tgacgagcct gcccctggga tttggaaact tcataacaga aaaaaccaat atagacaaag 120
gattttaaac aggattaagc tgttcactgg tgcatttatt ttggatttga ccatctgggg 180
aatgggtgtg gcctctcctg gcctctccct ccctggggcc caggcaggga gaatgtctca 240
gaatgacttc cttgagagtc ctgctcccct ttcatcaatg cacagataca gaagacccct 300
ccgtcatgca gcatctgcca tgagcatcgg cctcctgtgc tgtgcagcct tgtctctcct 360
gtgggcaggt ccagtgaatg ctggtgtcac tcagacccca aaattccagg tcctgaagac 420
aggacagagc atgacactgc agtgtgccca ggatatgaac catgaataca tgtcctggta 480
tcgacaagac ccaggcatgg ggctgaggct gattcattac tcagttggtg ctggtatcac 540
tgaccaagga gaagtcccca atggctacaa tgtctccaga tcaaccacag aggatttccc 600
gctcaggctg ctgtcggctg ctccctccca gacatctgtg tacttctgtg ccagcagaaa 660
cggcgggaca ctaatctacg agcagtactt cgggccgggc accaggctca cggtcacaga 720
ggacctgaaa aacgtgttcc cacccgaggt cgctgtgttt gagccatcag aagcagagat 780
ctcccacacc caaaaggcca cactggtatg cctggccaca ggcttctacc ccgaccacgt 840
ggagctgagc tggtgggtga atgggaagga ggtgcacagt ggggtcagca cagacccgca 900
gcccctcaag gagcagcccg ccctcaatga ctccagatac tgcctgagca gccgcctgag 960
ggtctcggcc accttctggc agaacccccg caaccacttc cgctgtcaag tccagttcta 1020
cgggctctcg gagaatgacg agtggaccca ggatagggcc aaacctgtca cccagatcgt 1080
cagcgccgag gcctggggta gagcagactg tggcttcacc tccgagtctt accagcaagg 1140
ggtcctgtct gccaccatcc tctatgagat cttgctaggg aaggccacct tgtatgccgt 1200
gctggtcagt gccctcgtgc tgatggccat ggtcaagaga aaggattcca gaggctag 1258

<210> SEQ ID NO 261
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 261
atgaaccatg aatac 15

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

Met Asn His Glu Tyr
1 5

<210> SEQ ID NO 263
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 263
tcagttggtg ctggtatc 18

<210> SEQ ID NO 264

<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 264

Ser Val Gly Ala Gly Ile
1 5

<210> SEQ ID NO 265
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 265
gccagcagaa acggcgggac actaatctac gagcagtac 39

<210> SEQ ID NO 266
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 266

Ala Ser Arg Asn Gly Gly Thr Leu Ile Tyr Glu Gln Tyr
1 5 10

<210> SEQ ID NO 267
<211> LENGTH: 1262
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 267
tgggggcaat gcccaaaacc ccagctctca gaggaccagt atccctcaca gggtgacacc 60
tgaccagctc tgtcccacct ggccatgggc tccaggtacc tctgatggga agacctttgt 120
ctcttgggaa caagtgaatc cttggcacag gcccagtgga ttctgctgtg cagaacagag 180
agcagtggac ctcaggaggc ctgcaagggg aggacatagg acagtgacat cacagtatgc 240
ccctcccacc aggaaaagca aggctgagaa tttagctctt tcccaggagg accaagccct 300
gagcacagac acagtgctgc ctgccccttt gtgccatggg ctccaggctg ctctgttggg 360
tgctgctttg tctcctggga gcaggcccag taaaggctgg agtcactcaa actccaagat 420
atctgatcaa aacgagagga cagcaagtga cactgagctg ctcccctatc tctgggcata 480
ggagtgtatc ctggtaccaa cagaccccag gacagggcct tcagttcctc tttgaatact 540
tcagtgagac acagagaaac aaaggaaact tccctggtcg attctcaggg cgccagttct 600
ctaactctcg ctctgagatg aatgtgagca ccttggagct gggggactcg gccctttatc 660
tttgcgccag caggcagcgg acagaacttg aagctttctt tggacaaggc accagactca 720
cagttgtaga ggacctgaac aaggtgttcc cacccgaggt cgctgtgttt gagccatcag 780
aagcagagat ctcccacacc caaaaggcca cactggtgtg cctggccaca ggcttctacc 840
ccgaccacgt ggagctgagc tggtgggtga atgggaagga ggtgcacagt ggggtcagca 900
cagacccgca gcccctcaag gagcagcccg ccctcaatga ctccagatac tgcctgagca 960
gccgcctgag ggtctcggcc accttctggc agaacccccg caaccacttc cgctgtcaag 1020
tccagttcta cgggctctcg gagaatgacg agtggaccca ggatagggcc aaacccgtca 1080
cccagatcgt cagcgccgag gcctggggta gagcagactg tggctttacc tcggtgtcct 1140
accagcaagg ggtcctgtct gccaccatcc tctatgagat cctgctaggg aaggccaccc 1200
tgtatgctgt gctggtcagc gcccttgtgt tgatggccat ggtcaagaga aaggatttct 1260
ga 1262

<210> SEQ ID NO 268
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 268
tctgggcata ggagt 15

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Ser Gly His Arg Ser
1 5

<210> SEQ ID NO 270
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 270
tacttcagtg agacacag 18

<210> SEQ ID NO 271
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 271

Tyr Phe Ser Glu Thr Gln
1 5

<210> SEQ ID NO 272
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 272

-continued

```
gccagcaggc agcggacaga acttgaagct ttc                                33
```

```
<210> SEQ ID NO 273
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ala Ser Arg Gln Arg Thr Glu Leu Glu Ala Phe
1               5                   10

<210> SEQ ID NO 274
<211> LENGTH: 1073
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274

ggccagagac accagtaatt ctgccagacc ttgcctgtgg ggccatggga gctcaaaatg      60

cccctccttt cctccacagg accagatgcc tgagctagga aaggcctcat tcctgctgtg     120

atcctgccat ggatacctgg ctcgtatgct gggcaatttt tagtctcttg aaagcaggac     180

tcacagaacc tgaagtcacc cagactccca gccatcaggt cacacagatg ggacaggaag     240

tgatcttgcg ctgtgtcccc atctctaatc acttatactt ctattggtac agacaaatct     300

tggggcagaa agtcgagttt ctggtttcct tttataataa tgaaatctca gagaagtctg     360

aaatattcga tgatcaattc tcagttgaaa ggcctgatgg atcaaatttc actctgaaga     420

tccggtccac aaagctggag gactcagcca tgtacttctg tgccagcagt gaagcccctg     480

acaggggtac ctacgagcag tacttcgggc cgggcaccag gctcacggtc acagaggacc     540

tgaaaaacgt gttcccaccc gaggtcgctg tgtttgagcc atcagaagca gagatctccc     600

acacccaaaa ggccacactg gtgtgcctgg ccacaggctt ctaccccgac cacgtggagc     660

tgagctggtg ggtgaatggg aaggaggtgc acagtggggt cagcacagac ccgcagcccc     720

tcaaggagca gcccgccctc aatgactcca gatactgcct gagcagccgc ctgagggtct     780

cggccacctt ctggcagaac ccccgcaacc acttccgctg tcaagtccag ttctacgggc     840

tctcggagaa tgacgagtgg acccaggata gggccaaacc tgtcacccag atcgtcagcg     900

ccgaggcctg gggtagagca gactgtggct tcacctccga gtcttaccag caaggggtcc     960

tgtctgccac catcctctat gagatcttgc tagggaaggc caccttgtat gccgtgctgg    1020

tcagtgccct cgtgctgatg gccatggtca agagaaagga ttccagaggc tag           1073

<210> SEQ ID NO 275
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275

tctaatcact tatac                                                      15

<210> SEQ ID NO 276
```

<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ser Asn His Leu Tyr
1               5

<210> SEQ ID NO 277
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ttttataata atgaaatc                                                    18

<210> SEQ ID NO 278
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Phe Tyr Asn Asn Glu Ile
1               5

<210> SEQ ID NO 279
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gccagcagtg aagcccctga caggggtacc tacgagcagt ac                         42

<210> SEQ ID NO 280
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Ser Ser Glu Ala Pro Asp Arg Gly Thr Tyr Glu Gln Tyr
1               5                   10

<210> SEQ ID NO 281
<211> LENGTH: 1011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
ggggactgag agctcaactt caatttgccc acagcagggc tgggagacac aagatcctgc      60
cctggagctg aaatgggcac caggctcttc ttctatgtgg ccctttgtct gctgtgggca 120
ggacacaggg atgctggaat cacccagagc ccaagataca agatcacaga gacaggaagg 180
caggtgacct tgatgtgtca ccagacttgg agccacagct atatgttctg gtatcgacaa 240
gacctgggac atgggctgag gctgatctat tactcagcag ctgctgatat tacagataaa 300
ggagaagtcc ccgatggcta cgttgtctcc agatccaaga cagagaattt ccccctcact 360
ctggagtcag ctacccgctc ccagacatct gtgtatttct gcgccagcag tgagttgggc 420
aggggtttct acgagcagta cttcgggccg ggcaccaggc tcacggtcac agaggacctg 480
aaaaacgtgt tcccacccga ggtcgctgtg tttgagccat cagaagcaga gatctcccac 540
acccaaaagg ccacactggt gtgcctggcc acaggcttct accccgacca cgtggagctg 600
agctggtggg tgaatgggaa ggaggtgcac agtggggtca gcacagaccc gcagcccctc 660
aaggagcagc ccgccctcaa tgactccaga tactgcctga gcagccgcct gagggtctcg 720
gccaccttct ggcagaaccc ccgcaaccac ttccgctgtc aagtccagtt ctacgggctc 780
tcggagaatg acgagtggac ccaggatagg gccaaacctg tcacccagat cgtcagcgcc 840
gaggcctggg gtagagcaga ctgtggcttc acctccgagt cttaccagca aggggtcctg 900
tctgccacca tcctctatga gatcttgcta gggaaggcca ccttgtatgc cgtgctggtc 960
agtgccctcg tgctgatggc catggtcaag agaaaggatt ccagaggcta g 1011

<210> SEQ ID NO 282
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 282
tggagccaca gctat 15

<210> SEQ ID NO 283
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Trp Ser His Ser Tyr
1               5

<210> SEQ ID NO 284
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 284
tcagcagctg ctgatatt 18

<210> SEQ ID NO 285
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Ser Ala Ala Ala Asp Ile
1 5

<210> SEQ ID NO 286
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 286
gccagcagtg agttgggcag gggtttctac gagcagtac 39

<210> SEQ ID NO 287
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

Ala Ser Ser Glu Leu Gly Arg Gly Phe Tyr Glu Gln Tyr
1 5 10

<210> SEQ ID NO 288
<211> LENGTH: 1191
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 288
gatggaaagc aagagccctg ggtggagctg aaggtgctca gctgggtttg tcagaagtct 60
catctgtcac tgttcactgg tgcatttatt ttggatttga ccatctgggg aatgggtgtg 120
gcctctcctg gcctctccct ccctggggcc caggcaggga gaatgtctca gaatgacttc 180
cttgagagtc ctgctcccct ttcatcaatg cacagataca gaagacccct ccgtcatgca 240
gcatctgcca tgagcatcgg cctcctgtgc tgtgcagcct tgtctctcct gtgggcaggt 300
ccagtgaatg ctggtgtcac tcagacccca aaattccagg tcctgaagac aggacagagc 360
atgacactgc agtgtgccca ggatatgaac catgaataca tgtcctggta tcgacaagac 420
ccaggcatgg ggctgaggct gattcattac tcagttggtg ctggtatcac tgaccaagga 480
gaagtcccca atggctacaa tgtctccaga tcaaccacag aggatttccc gctcaggctg 540
ctgtcggctg ctccctccca gacatctgtg tacttctgtg ccagcagcca tctgggggcg 600
ggagggccgc acgagcagta cttcgggccg ggcaccaggc tcacggtcac agaggacctg 660
aaaaacgtgt tcccacccga ggtcgctgtg tttgagccat cagaagcaga gatctcccac 720
acccaaaagg ccacactggt gtgcctggcc acaggcttct accccgacca cgtggagctg 780
agctggtggg tgaatgggaa ggaggtgcac agtggggtca gcacagaccc gcagcccctc 840
aaggagcagc ccgccctcaa tgactccaga tactgcctga gcagccgcct gagggtctcg 900
gccaccttct ggcagaaccc ccgcaaccac ttccgctgtc aagtccagtt ctacgggctc 960
tcggagaatg acgagtggac ccaggatagg gccaaacctg tcacccagat cgtcagcgcc 1020
gaggcctggg gtagagcaga ctgtggcttc acctccgagt cttaccagca aggggtcctg 1080
tctgccacca tcctctatga gatcttgcta gggaaggcca ccttgtatgc cgtgctggtc 1140
agtgccctcg tgctgatggc catggtcaag agaaaggatt ccagaggcta g 1191

<210> SEQ ID NO 289
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 289
atgaaccatg aatac 15

<210> SEQ ID NO 290
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 290

Met Asn His Glu Tyr
1 5

<210> SEQ ID NO 291
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 291
tcagttggtg ctggtatc 18

<210> SEQ ID NO 292
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 292

Ser Val Gly Ala Gly Ile
1 5

<210> SEQ ID NO 293
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 293
gccagcagcc atctgggggc gggagggccg cacgagcagt ac 42

<210> SEQ ID NO 294
<211> LENGTH: 14
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 294

Ala Ser Ser His Leu Gly Ala Gly Gly Pro His Glu Gln Tyr
1               5                   10

<210> SEQ ID NO 295
<211> LENGTH: 1397
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 295
ggtgactggg ggaatggagg aggctggagc atgaatgggg atggcactgg ggaccctgac     60
ttgcaggaaa tgcaatgagc tcaccacttt gtgccctatg ttaggggcgg tgttggtgca    120
tcctagagta aatgtccagc agacaaagga gcaagaagcg gctgtgggat gacaagataa    180
actcagagat acagcatgag acctccgggt ccagacagct ctggagccca aggcgatgag    240
ccatgcattg atgttgttaa aaaggagctg ataaatattt aaagcagcac ccaactgtgt    300
tctaatagaa atgctgtgat cctgaggtcc tggggattga gagaggaagt gatgtcactg    360
tgggaactgc cctgtggaga caaggacatc cctcatcctc tgctgctgct cacagtgaca    420
ctgatctggt aaagccctca tcctgtcctg accctgccat gggcaccagt ctcctatgct    480
gggtggtcct gggtttccta gggacagatc acacaggtgc tggagtctcc cagtctccca    540
ggtacaaagt cacaaagagg ggacaggatg tagctctcag gtgtgatcca atttcgggtc    600
atgtatccct ttattggtac cgacaggccc tggggcaggg cccagagttt ctgacttact    660
tcaattatga agcccaacaa gacaaatcag ggctgcccaa tgatcggttc tctgcagaga    720
ggcctgaggg atccatctcc actctgacga tccagcgcac agagcagcgg gactcggcca    780
tgtatcgctg tgccagcagc catactgacg gctcctacga gcagtacttc gggccgggca    840
ccaggctcac ggtcacagag gacctgaaaa acgtgttccc acccgaggtc gctgtgtttg    900
agccatcaga agcagagatc tcccacaccc aaaaggccac actggtatgc ctggccacag    960
gcttctaccc cgaccacgtg gagctgagct ggtgggtgaa tgggaaggag gtgcacagtg   1020
gggtcagcac agacccgcag cccctcaagg agcagcccgc cctcaatgac tccagatact   1080
gcctgagcag ccgcctgagg gtctcggcca ccttctggca gaacccccgc aaccacttcc   1140
gctgtcaagt ccagttctac gggctctcgg agaatgacga gtggacccag gatagggcca   1200
aacctgtcac ccagatcgtc agcgccgagg cctggggtag agcagactgt ggcttcacct   1260
ccgagtctta ccagcaaggg gtcctgtctg ccaccatcct ctatgagatc ttgctaggga   1320
aggccacctt gtatgccgtg ctggtcagtg ccctcgtgct gatggccatg gtcaagagaa   1380
aggattccag aggctag                                                   1397

<210> SEQ ID NO 296
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
tcgggtcatg tatcc                                                       15

<210> SEQ ID NO 297
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 297

Ser Gly His Val Ser
1 5

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 298
ttcaattatg aagcccaa 18

<210> SEQ ID NO 299
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 299

Phe Asn Tyr Glu Ala Gln
1 5

<210> SEQ ID NO 300
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 300
gccagcagcc atactgacgg ctcctacgag cagtac 36

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 301

Ala Ser Ser His Thr Asp Gly Ser Tyr Glu Gln Tyr
1 5 10

<210> SEQ ID NO 302
<211> LENGTH: 1168
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 302

```
tggggacaga tgcaatgcag agttatggga ggtgcgaatg actctgctct ctgtcctgtc     60

tcctcatctg caaaattagg aagcctgtct tgattatctc caggaacctc ccacctcttc    120

attccagcct ctgacaaact ctgcacatta ggccaggaga agcccccgag ccaagtctct    180

tttctcattc tcttccaaca agtgcttgga gctccaagaa ggcccccttt gcactatgag    240

caaccaggtg ctctgctgtg tggtcctttg tctcctggga gcaaacaccg tggatggtgg    300

aatcactcag tccccaaagt acctgttcag aaaggaagga cagaatgtga ccctgagttg    360

tgaacagaat ttgaaccacg atgccatgta ctggtaccga caggacccag ggcaagggct    420

gagattgatc tactactcac agatagtaaa tgactttcag aaaggagata tagctgaagg    480

gtacagcgtc tctcgggaga agaaggaatc ctttcctctc actgtgacat cggcccaaaa    540

gaacccgaca gctttctatc tctgtgccag tagcataggg gcatttgctg gtcagcccca    600

gcattttggt gatgggactc gactctccat cctagaggac ctgaacaagg tgttcccacc    660

cgaggtcgct gtgtttgagc catcagaagc agagatctcc cacacccaaa aggccacact    720

ggtgtgcctg gccacaggct tctaccccga ccacgtggag ctgagctggt gggtgaatgg    780

gaaggaggtg cacagtgggg tcagcacaga cccgcagccc ctcaaggagc agcccgccct    840

caatgactcc agatactgcc tgagcagccg cctgagggtc tcggccacct tctggcagaa    900

cccccgcaac cacttccgct gtcaagtcca gttctacggg ctctcggaga atgacgagtg    960

gacccaggat agggccaaac ccgtcaccca gatcgtcagc gccgaggcct ggggtagagc   1020

agactgtggc tttacctcgg tgtcctacca gcaaggggtc ctgtctgcca ccatcctcta   1080

tgagatcctg ctagggaagg ccaccctgta tgctgtgctg gtcagcgccc ttgtgttgat   1140

ggccatggtc aagagaaagg atttctga                                      1168
```

<210> SEQ ID NO 303
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303

```
ttgaaccacg atgcc                                                      15
```

<210> SEQ ID NO 304
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

```
Leu Asn His Asp Ala
1               5
```

<210> SEQ ID NO 305
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 305
tcacagatag taaatgac 18

<210> SEQ ID NO 306
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Ser Gln Ile Val Asn Asp
1 5

<210> SEQ ID NO 307
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 307
gccagtagca taggggcatt tgctggtcag ccccagcat 39

<210> SEQ ID NO 308
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Ala Ser Ser Ile Gly Ala Phe Ala Gly Gln Pro Gln His
1 5 10

<210> SEQ ID NO 309
<211> LENGTH: 1061
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 309
tgggggtcac tgtgggaact gctctgtggc gacaaggacg tccctcatcc tctgctcctg 60
ctcacagtga ccctgatctg gtaaagctcc catcctgccc tgaccctgcc atgggcacca 120
gcctcctctg ctggatggcc ctgtgtctcc tgggggcaga tcacgcagat actggagtct 180
cccagaaccc cagacacaag atcacaaaga ggggacagaa tgtaactttc aggtgtgatc 240
caatttctga acacaaccgc ctttattggt accgacagac cctggggcag ggcccagagt 300
ttctgactta cttccagaat gaagctcaac tagaaaaatc aaggctgctc agtgatcggt 360
tctctgcaga gaggcctaag ggatctttct ccaccttgga gatccagcgc acagagcagg 420
gggactcggc catgtatctc tgtgccagca gcttagcgcc tacccccggg ccggacaccg 480
gggagctgtt ttttggagaa ggctctaggc tgaccgtact ggaggacctg aaaaacgtgt 540
tcccacccga ggtcgctgtg tttgagccat cagaagcaga gatctcccac acccaaaagg 600
ccacactggt gtgcctggcc acaggcttct accccgacca cgtggagctg agctggtggg 660
tgaatgggaa ggaggtgcac agtggggtca gcacagaccc gcagcccctc aaggagcagc 720
ccgccctcaa tgactccaga tactgcctga gcagccgcct gagggtctcg gccaccttct 780
ggcagaaccc ccgcaaccac ttccgctgtc aagtccagtt ctacgggctc tcggagaatg 840
acgagtggac ccaggatagg gccaaacctg tcacccagat cgtcagcgcc gaggcctggg 900
gtagagcaga ctgtggcttc acctccgagt cttaccagca aggggtcctg tctgccacca 960
tcctctatga gatcttgcta gggaaggcca ccttgtatgc cgtgctggtc agtgccctcg 1020
tgctgatggc catggtcaag agaaaggatt ccagaggcta g 1061

<210> SEQ ID NO 310
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 310
tctgaacaca accgc 15

<210> SEQ ID NO 311
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

Ser Glu His Asn Arg
1 5

<210> SEQ ID NO 312
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 312
ttccagaatg aagctcaa 18

<210> SEQ ID NO 313
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 313

Phe Gln Asn Glu Ala Gln
1 5

<210> SEQ ID NO 314
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 314
gccagcagct tagcgcctac ccccgggccg gacaccgggg agctgttt 48

<210> SEQ ID NO 315
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 315

Ala Ser Ser Leu Ala Pro Thr Pro Gly Pro Asp Thr Gly Glu Leu Phe
1 5 10 15

<210> SEQ ID NO 316
<211> LENGTH: 1081
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 316
ggcgtttgta cacttcagcc ctctgagctg aagtgggagt ggtttctctc ctgaaaatgt 60
ttctgaggcc caaatagctg aagaggtgga gacgttacag aaaccacctg gagcccccag 120
aactggcaga cacctgcctg atgctgccat gggcccccag ctccttggct atgtggtcct 180
ttgccttcta ggagcaggcc ccctggaagc ccaagtgacc cagaacccaa gatacctcat 240
cacagtgact ggaaagaagt taacagtgac ttgttctcag aatatgaacc atgagtatat 300
gtcctggtat cgacaagacc cagggctggg cttaaggcag atctactatt caatgaatgt 360
tgaggtgact gataagggag atgttcctga agggtacaaa gtctctcgaa aagagaagag 420
gaatttcccc ctgatcctgg agtcgcccag ccccaaccag acctctctgt acttctgtgc 480
cagcagttta gggaatatct acgagcagta cttcgggccg ggcaccaggc tcacggtcac 540
agaggacctg aaaaacgtgt tcccacccga ggtcgctgtg tttgagccat cagaagcaga 600
gatctcccac acccaaaagg ccacactggt gtgcctggcc acaggcttct accccgacca 660
cgtggagctg agctggtggg tgaatgggaa ggaggtgcac agtggggtca gcacagaccc 720
gcagcccctc aaggagcagc ccgccctcaa tgactccaga tactgcctga gcagccgcct 780
gagggtctcg gccaccttct ggcagaaccc ccgcaaccac ttccgctgtc aagtccagtt 840
ctacgggctc tcggagaatg acgagtggac ccaggatagg gccaaacctg tcacccagat 900
cgtcagcgcc gaggcctggg gtagagcaga ctgtggcttc acctccgagt cttaccagca 960
aggggtcctg tctgccacca tcctctatga gatcttgcta gggaaggcca ccttgtatgc 1020
cgtgctggtc agtgccctcg tgctgatggc catggtcaag agaaaggatt ccagaggcta 1080
g 1081

<210> SEQ ID NO 317
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 317
atgaaccatg agtat 15

<210> SEQ ID NO 318
<211> LENGTH: 5
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 318

Met Asn His Glu Tyr
1 5

<210> SEQ ID NO 319
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 319
tcaatgaatg ttgaggtg 18

<210> SEQ ID NO 320
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 320

Ser Met Asn Val Glu Val
1 5

<210> SEQ ID NO 321
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 321
gccagcagtt tagggaatat ctacgagcag tac 33

<210> SEQ ID NO 322
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 322

Ala Ser Ser Leu Gly Asn Ile Tyr Glu Gln Tyr
1 5 10

<210> SEQ ID NO 323
<211> LENGTH: 1055
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 323
gagagaggaa gtgatgtcac tgtgggtact gttctgtgtc aggacaagga cgtccctcct 60
cctctgctcc tgctcacagt gaccctgatc tggtaaagct cccatcctgc cctgactctg 120

-continued tcatgggcac caggctcctc tgctgggcag ccctgtgcct cctgggggca gatcacacag 180
gtgctggagt ctcccagacc cccagtaaca aggtcacaga gaagggaaaa tatgtagagc 240
tcaggtgtga tccaatttca ggtcatactg ccctttactg gtaccgacaa agcctggggc 300
agggcccaga gtttctaatt tacttccaag gcacgggtgc ggcagatgac tcagggctgc 360
ccaacgatcg gttctttgca gtcaggcctg agggatccgt ctctactctg aagatccagc 420
gcacagagcg gggggactca gccgtgtatc tctgtgccag cagcttaggg agcggtgagc 480
agttcttcgg gccagggaca cggctcaccg tgctagagga cctgaaaaac gtgttcccac 540
ccgaggtcgc tgtgtttgag ccatcagaag cagagatctc ccacacccaa aaggccacac 600
tggtgtgcct ggccacaggc ttctaccccg accacgtgga gctgagctgg tgggtgaatg 660
ggaaggaggt gcacagtggg gtcagcacag acccgcagcc cctcaaggag cagcccgccc 720
tcaatgactc cagatactgc ctgagcagcc gcctgagggt ctcggccacc ttctggcaga 780
acccccgcaa ccacttccgc tgtcaagtcc agttctacgg gctctcggag aatgacgagt 840
ggacccagga tagggccaaa cctgtcaccc agatcgtcag cgccgaggcc tggggtagag 900
cagactgtgg cttcacctcc gagtcttacc agcaaggggt cctgtctgcc accatcctct 960
atgagatctt gctagggaag gccaccttgt atgccgtgct ggtcagtgcc ctcgtgctga 1020
tggccatggt caagagaaag gattccagag gctag 1055

<210> SEQ ID NO 324
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 324
tcaggtcata ctgcc 15

<210> SEQ ID NO 325
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Ser Gly His Thr Ala
1 5

<210> SEQ ID NO 326
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 326
ttccaaggca cgggtgcg 18

<210> SEQ ID NO 327
<211> LENGTH: 6
<212> TYPE: PRT
<213> ORGANISM: Artificial Sequence
<220> FEATURE:
<223> OTHER INFORMATION: Description of Artificial Sequence: Synthetic

```
          peptide

<400> SEQUENCE: 327

Phe Gln Gly Thr Gly Ala
1               5

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328

gccagcagct tagggagcgg tgagcagttc                                       30

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Ala Ser Ser Leu Gly Ser Gly Glu Gln Phe
1               5                   10

<210> SEQ ID NO 330
<211> LENGTH: 1233
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 330

tgggggtctt gggtgcttgc ttccccttcc ttctgccttg gataacagca ggaggccctc     60

atcagttatg gacccttgat cttggacttc ccagtctcca gatctacaac ccagctctgc    120

tttggatctg atcagatgga ctaaatcttg gggactctgc accactggcc actgaggaaa    180

gggaagagaa tgttgcctgg gacaggaaaa tatagaaaat gaaggcccag aactcactcg    240

gctcttcccc aggaagacca agccctgaat caggtgcagt gccgcctggc ccactgtgcc    300

atgggaccca ggctcctctt ctgggcactg ctttgtctcc tcggaacagg cccagtggag    360

gctggagtca cacaaagtcc cacacacctg atcaaaacga gaggacagca agcgactctg    420

agatgctctc ctatctctgg gcacaccagt gtgtactggt accaacaggc cctgggtctg     480

ggcctccagt tcctcctttg gtatgacgag ggtgaagaga gaaacagagg aaacttccct    540

cctagatttt caggtcgcca gttccctaat tatagctctg agctgaatgt gaacgccttg    600

gagctggagg actcggccct gtatctctgt gccagcagct tacagacatc ctacgagcag    660

tacttcgggc cgggcaccag gctcacggtc acagaggacc tgaaaaacgt gttcccaccc    720

gaggtcgctg tgtttgagcc atcagaagca gagatctccc acacccaaaa ggccacactg    780

gtatgcctgg ccacaggctt ctaccccgac cacgtggagc tgagctggtg ggtgaatggg    840

aaggaggtgc acagtggggt cagcacagac ccgcagcccc tcaaggagca gcccgccctc    900

aatgactcca gatactgcct gagcagccgc ctgagggtct cggccacctt ctggcagaac    960

ccccgcaacc acttccgctg tcaagtccag ttctacgggc tctcggagaa tgacgagtgg   1020
```

acccaggata gggccaaacc tgtcacccag atcgtcagcg ccgaggcctg gggtagagca 1080
gactgtggct tcacctccga gtcttaccag caaggggtcc tgtctgccac catcctctat 1140
gagatcttgc tagggaaggc caccttgtat gccgtgctgg tcagtgccct cgtgctgatg 1200
gccatggtca agagaaagga ttccagaggc tag 1233

<210> SEQ ID NO 331
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 331
tctgggcaca ccagt 15

<210> SEQ ID NO 332
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 332

Ser Gly His Thr Ser
1 5

<210> SEQ ID NO 333
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 333
tatgacgagg gtgaagag 18

<210> SEQ ID NO 334
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 334

Tyr Asp Glu Gly Glu Glu
1 5

<210> SEQ ID NO 335
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 335
gccagcagct tacagacatc ctacgagcag tac 33

<210> SEQ ID NO 336
<211> LENGTH: 11
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 336

Ala Ser Ser Leu Gln Thr Ser Tyr Glu Gln Tyr
1 5 10

<210> SEQ ID NO 337
<211> LENGTH: 1120
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 337
gggctcagcc tgagttggct gtgttgcgtt tgtacacttc agccctctga gctgaagtgg 60
gagtggtttc tctcctgaaa atgtttctga ggcccaaata gctgaagagg tggagacgtt 120
acagaaacca cctggagccc ccagaactgg cagacacctg cctgatgctg ccatgggccc 180
ccagctcctt ggctatgtgg tcctttgcct tctaggagca ggcccccctgg aagcccaagt 240 gacccagaac ccaagatacc tcatcacagt gactggaaag aagttaacag tgacttgttc 300
tcagaatatg aaccatgagt atatgtcctg gtatcgacaa gacccagggc tgggcttaag 360
gcagatctac tattcaatga atgttgaggt gactgataag ggagatgttc ctgaagggta 420
caaagtctct cgaaaagaga agaggaattt ccccctgatc ctggagtcgc ccagccccaa 480
ccagacctct ctgtacttct gtgccagcag tttatcgtgg gggaccggca aaagagcaga 540
tacgcagtat tttggcccag gcacccggct gacagtgctc gaggacctga aaaacgtgtt 600
cccacccgag gtcgctgtgt ttgagccatc agaagcagag atctcccaca cccaaaaggc 660
cacactggtg tgcctggcca caggcttcta ccccgaccac gtggagctga gctggtgggt 720
gaatgggaag gaggtgcaca gtggggtcag cacagacccg cagcccctca aggagcagcc 780
cgccctcaat gactccagat actgcctgag cagccgcctg agggtctcgg ccaccttctg 840
gcagaacccc cgcaaccact tccgctgtca agtccagttc tacgggctct cggagaatga 900
cgagtggacc caggataggg ccaaacctgt cacccagatc gtcagcgccg aggcctgggg 960
tagagcagac tgtggcttca cctccgagtc ttaccagcaa ggggtcctgt ctgccaccat 1020
cctctatgag atcttgctag ggaaggccac cttgtatgcc gtgctggtca gtgccctcgt 1080
gctgatggcc atggtcaaga gaaaggattc cagaggctag 1120

<210> SEQ ID NO 338
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 338
atgaaccatg agtat 15

<210> SEQ ID NO 339
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 339

Met Asn His Glu Tyr
1 5

<210> SEQ ID NO 340
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 340
tcaatgaatg ttgaggtg 18

<210> SEQ ID NO 341
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Ser Met Asn Val Glu Val
1 5

<210> SEQ ID NO 342
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 342
gccagcagtt tatcgtgggg gaccggcaaa agagcagata cgcagtat 48

<210> SEQ ID NO 343
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Ala Ser Ser Leu Ser Trp Gly Thr Gly Lys Arg Ala Asp Thr Gln Tyr
1 5 10 15

<210> SEQ ID NO 344
<211> LENGTH: 1321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 344
cgaaggcgga gggtggaatg cgggcagcag ccccctggag ggctgagtgg ggaaaacaaa 60
atggacctca cagaagctgt gtgtgtggaa acccacttct gacttatcac ttgtcatgaa 120
ttctatgctt catggtgtta caccgtttat tgtttctgat gagtgacagt aattattttc 180
tttcttgctg gtacataata aagtggtgca catcagagtt gctgccatct tagacttaac 240
tcatcagtat caggtgatcc tgaggctcag tgatgtcact gtgggaactg ctctgtggcg 300
acaaggacgt ccctcatcct ctgctcctgc tcacagtgac cctgatctgg taaagctccc 360
atcctgccct gaccctgcca tgggcaccag cctcctctgc tggatggccc tgtgtctcct 420
gggggcagat cacgcagata ctggagtctc ccaggacccc agacacaaga tcacaaagag 480
gggacagaat gtaactttca ggtgtgatcc aatttctgaa cacaaccgcc tttattggta 540
ccgacagacc ctggggcagg gcccagagtt tctgacttac ttccagaatg aagctcaact 600
agaaaaatca aggctgctca gtgatcggtt ctctgcagag aggcctaagg gatctttctc 660
caccttggag atccagcgca cagagcaggg ggactcggcc atgtatctct gtgccagcag 720
cttagttggc ggcgggagca atgagcagtt cttcgggcca gggacacggc tcaccgtgct 780
agaggacctg aaaaacgtgt tcccacccga ggtcgctgtg tttgagccat cagaagcaga 840
gatctcccac acccaaaagg ccacactggt gtgcctggcc acaggcttct accccgacca 900
cgtggagctg agctggtggg tgaatgggaa ggaggtgcac agtggggtca gcacagaccc 960
gcagcccctc aaggagcagc ccgccctcaa tgactccaga tactgcctga gcagccgcct 1020
gagggtctcg gccaccttct ggcagaaccc ccgcaaccac ttccgctgtc aagtccagtt 1080
ctacgggctc tcggagaatg acgagtggac ccaggatagg gccaaacctg tcacccagat 1140
cgtcagcgcc gaggcctggg gtagagcaga ctgtggcttc acctccgagt cttaccagca 1200
aggggtcctg tctgccacca tcctctatga gatcttgcta gggaaggcca ccttgtatgc 1260
cgtgctggtc agtgccctcg tgctgatggc catggtcaag agaaaggatt ccagaggcta 1320
g 1321

<210> SEQ ID NO 345
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 345
tctgaacaca accgc 15

<210> SEQ ID NO 346
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Ser Glu His Asn Arg
1 5

<210> SEQ ID NO 347
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 347
ttccagaatg aagctcaa 18

<210> SEQ ID NO 348
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

Phe Gln Asn Glu Ala Gln
1 5

<210> SEQ ID NO 349
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 349
gccagcagct tagttggcgg cgggagcaat gagcagttc 39

<210> SEQ ID NO 350
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Ala Ser Ser Leu Val Gly Gly Gly Ser Asn Glu Gln Phe
1 5 10

<210> SEQ ID NO 351
<211> LENGTH: 1487
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 351
gacctcccac tcctacccag accgtggatg ggcaggaaat gcaggaacag agccagaaac 60
aggagatctc caaggaaggt tgacagtcag cactgggatc gtctgtgtaa agtgctgctg 120
aagcagccag gtggcatgtc cagccgacaa tgcgaaagga aaaagtgaga agacttcccg 180
aaggcggagg gtggaatgcg ggcagcagcc ccctggaggg ctgagtgggg aaaacaaaat 240
ggacctcaca gaagctgtgt gtgtggaaac ccacttctga cttatcactt gtcatgaatt 300
ctatgcttca tggtgttaca ccgtttattg tttctgatga gtgacagtaa ttattttctt 360
tcttgctggt acataataaa gtggtgcaca tcagagttgc tgccatctta gacttaactc 420
atcagtatca ggtgatcctg aggctcagtg atgtcactgt gggaactgct ctgtggcgac 480
aaggacgtcc ctcatcctct gctcctgctc acagtgaccc tgatctggta aagctcccat 540
cctgccctga ccctgccatg ggcaccagcc tcctctgctg gatggccctg tgtctcctgg 600
gggcagatca cgcagatact ggagtctccc aggaccccag acacaagatc acaaagaggg 660
gacagaatgt aactttcagg tgtgatccaa tttctgaaca caaccgcctt tattggtacc 720
gacagaccct ggggcagggc ccagagtttc tgacttactt ccagaatgaa gctcaactag 780
aaaaatcaag gctgctcagt gatcggttct ctgcagagag gcctaaggga tctttctcca 840

```
ccttggagat ccagcgcaca gagcaggggg actcggccat gtatctctgt gccagcagct    900

tagtcggagg cactgaagct ttctttggac aaggcaccag actcacagtt gtagaggacc    960

tgaacaaggt gttcccaccc gaggtcgctg tgtttgagcc atcagaagca gagatctccc   1020

acacccaaaa ggccacactg gtgtgcctgg ccacaggctt ctaccccgac cacgtggagc   1080

tgagctggtg ggtgaatggg aaggaggtgc acagtggggt cagcacagac ccgcagcccc   1140

tcaaggagca gcccgccctc aatgactcca gatactgcct gagcagccgc ctgagggtct   1200

cggccacctt ctggcagaac ccccgcaacc acttccgctg tcaagtccag ttctacgggc   1260

tctcggagaa tgacgagtgg acccaggata gggccaaacc cgtcacccag atcgtcagcg   1320

ccgaggcctg ggtagagca gactgtggct ttacctcggt gtcctaccag caaggggtcc   1380

tgtctgccac catcctctat gagatcctgc tagggaaggc caccctgtat gctgtgctgg   1440

tcagcgccct tgtgttgatg gccatggtca agagaaagga tttctga                 1487
```

<210> SEQ ID NO 352
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352

```
tctgaacaca accgc                                                      15
```

<210> SEQ ID NO 353
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

```
Ser Glu His Asn Arg
1               5
```

<210> SEQ ID NO 354
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 354

```
ttccagaatg aagctcaa                                                   18
```

<210> SEQ ID NO 355
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 355

```
Phe Gln Asn Glu Ala Gln
1               5
```

<210> SEQ ID NO 356

<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 356
gccagcagct tagtcggagg cactgaagct ttc 33

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 357

Ala Ser Ser Leu Val Gly Gly Thr Glu Ala Phe
1 5 10

<210> SEQ ID NO 358
<211> LENGTH: 1094
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 358
gggccatctt agacttaact catcagtatc aggtgatcct gaggctcagt gatgtcactg 60
tgggaactgc tctgtggcga caaggacgtc cctcatcctc tgctcctgct cacagtgacc 120
ctgatctggt aaagctccca tcctgccctg accctgccat gggcaccagc ctcctctgct 180
ggatggccct gtgtctcctg gggcagatc acgcagatac tggagtctcc caggacccca 240
gacacaagat cacaaagagg ggacagaatg taactttcag gtgtgatcca atttctgaac 300
acaaccgcct ttattggtac cgacagaccc tggggcaggg cccagagttt ctgacttact 360
tccagaatga agctcaacta gaaaaatcaa ggctgctcag tgatcggttc tctgcagaga 420
ggcctaaggg atctttctcc accttggaga tccagcgcac agagcagggg gactcggcca 480
tgtatctctg tgccagcagc cccgatcgga atctcgggca gtacttcggg ccgggcacca 540
ggctcacggt cacagaggac ctgaaaaacg tgttcccacc cgaggtcgct gtgtttgagc 600
catcagaagc agagatctcc cacacccaaa aggccacact ggtgtgcctg gccacaggct 660
tctaccccga ccacgtggag ctgagctggt gggtgaatgg gaaggaggtg cacagtgggg 720
tcagcacaga cccgcagccc ctcaaggagc agcccgccct caatgactcc agatactgcc 780
tgagcagccg cctgagggtc tcggccacct tctggcagaa cccccgcaac cacttccgct 840
gtcaagtcca gttctacggg ctctcggaga atgacgagtg gacccaggat agggccaaac 900
ctgtcaccca gatcgtcagc gccgaggcct ggggtagagc agactgtggc ttcacctccg 960
agtcttacca gcaaggggtc ctgtctgcca ccatcctcta tgagatcttg ctagggaagg 1020
ccaccttgta tgccgtgctg gtcagtgccc tcgtgctgat ggccatggtc aagagaaagg 1080
attccagagg ctag 1094

<210> SEQ ID NO 359
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 359
tctgaacaca accgc 15

<210> SEQ ID NO 360
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 360

Ser Glu His Asn Arg
1 5

<210> SEQ ID NO 361
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 361
ttccagaatg aagctcaa 18

<210> SEQ ID NO 362
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Phe Gln Asn Glu Ala Gln
1 5

<210> SEQ ID NO 363
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 363
gccagcagcc ccgatcggaa tctcgggcag tac 33

<210> SEQ ID NO 364
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Ala Ser Ser Pro Asp Arg Asn Leu Gly Gln Tyr
1 5 10

<210> SEQ ID NO 365
<211> LENGTH: 1067

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 365
gggacattgg ctaatatgct gatgtcactg gaggccacat cttacagggc caagagacag 60
atttgctttc ctttttctca tgcttgtaag ctccttcatc tggaaatgtg atttacctgg 120
gtcctgccat ggtttccagg cttctcagtt tagtgtccct ttgtctcctg ggagcaaagc 180
acatagaagc tggagttact cagttcccca gccacagcgt aatagagaag ggccagactg 240
tgactctgag atgtgaccca atttctggac atgataatct ttattggtat cgacgtgtta 300
tgggaaaaga aataaaattt ctgttacatt ttgtgaaaga gtctaaacag gatgaatccg 360
gtatgcccaa caatcgattc ttagctgaaa ggactggagg gacgtattct actctgaagg 420
tgcagcctgc agaactggag gattctggag tttatttctg tgccagcagc caagtccagg 480
cttttaatga gcagttcttc gggccaggga cacggctcac cgtgctagag gacctgaaaa 540
acgtgttccc acccgaggtc gctgtgtttg agccatcaga agcagagatc tcccacaccc 600
aaaaggccac actggtgtgc ctggccacag gcttctaccc cgaccacgtg gagctgagct 660
ggtgggtgaa tgggaaggag gtgcacagtg ggtcagcac agacccgcag cccctcaagg 720
agcagcccgc cctcaatgac tccagatact gcctgagcag ccgcctgagg gtctcggcca 780
ccttctggca gaacccccgc aaccacttcc gctgtcaagt ccagttctac gggctctcgg 840
agaatgacga gtggacccag gatagggcca aacctgtcac ccagatcgtc agcgccgagg 900
cctggggtag agcagactgt ggcttcacct ccgagtctta ccagcaaggg gtcctgtctg 960
ccaccatcct ctatgagatc ttgctaggga aggccacctt gtatgccgtg ctggtcagtg 1020
ccctcgtgct gatggccatg gtcaagagaa aggattccag aggctag 1067

<210> SEQ ID NO 366
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 366
tctggacatg ataat 15

<210> SEQ ID NO 367
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 367

Ser Gly His Asp Asn
1 5

<210> SEQ ID NO 368
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 368
tttgtgaaag agtctaaa 18

<210> SEQ ID NO 369
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 369

Phe Val Lys Glu Ser Lys
1 5

<210> SEQ ID NO 370
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 370
gccagcagcc aagtccaggc ttttaatgag cagttc 36

<210> SEQ ID NO 371
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 371

Ala Ser Ser Gln Val Gln Ala Phe Asn Glu Gln Phe
1 5 10

<210> SEQ ID NO 372
<211> LENGTH: 1222
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 372
tctcttttat gttgccatcc aagtaagaca tgacttgccc ctccttgcct tctgccatga 60
ttgtgaggcc tccccagcca tgtggaacta ggaaaagtga atcaaaacca agggacatgc 120
tgagacaact ggagaaattt gaatgtgaag catttgtgga ggcaatgatg tcactgtggg 180
aactgccatg agaggacagg gacgtccctc ctcctctgct tttgctcaca gtgaccctga 240
ttgggcaaag ctcccatcct tccctgaccc tgccatgggc accaggctcc tctgctgggc 300
ggccctctgt ctcctgggag cagaactcac agaagctgga gttgcccagt ctcccagata 360
taagattata gagaaaaggc agagtgtggc tttttggtgc aatcctatat ctggccatgc 420
taccctttac tggtaccagc agatcctggg acagggccca aagcttctga ttcagtttca 480
gaataacggt gtagtggatg attcacagtt gcctaaggat cgattttctg cagagaggct 540
caaaggagta gactccactc tcaagatcca gcctgcaaag cttgaggact cggccgtgta 600
tctctgtgcc agcagtcgag gggagccagg ctctggggcc aacgtcctga ctttcggggc 660

-continued

```
cggcagcagg ctgaccgtgc tggaggacct gaaaaacgtg ttcccacccg aggtcgctgt    720

gtttgagcca tcagaagcag agatctccca cacccaaaag gccacactgg tgtgcctggc    780

cacaggcttc taccccgacc acgtggagct gagctggtgg gtgaatggga aggaggtgca    840

cagtggggtc agcacagacc cgcagcccct caaggagcag cccgccctca atgactccag    900

atactgcctg agcagccgcc tgagggtctc ggccaccttc tggcagaacc cccgcaacca    960

cttccgctgt caagtccagt tctacgggct ctcggagaat gacgagtgga cccaggatag   1020

ggccaaacct gtcacccaga tcgtcagcgc cgaggcctgg ggtagagcag actgtggctt   1080

cacctccgag tcttaccagc aaggggtcct gtctgccacc atcctctatg agatcttgct   1140

agggaaggcc accttgtatg ccgtgctggt cagtgccctc gtgctgatgg ccatggtcaa   1200

gagaaaggat tccagaggct ag                                            1222
```

<210> SEQ ID NO 373
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 373
tctggccatg ctacc 15

<210> SEQ ID NO 374
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 374

Ser Gly His Ala Thr
1               5

<210> SEQ ID NO 375
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375
tttcagaata acggtgta 18

<210> SEQ ID NO 376
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 376

Phe Gln Asn Asn Gly Val
1               5

<210> SEQ ID NO 377
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 377
gccagcagtc gaggggagcc aggctctggg gccaacgtcc tgact 45

<210> SEQ ID NO 378
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 378

Ala Ser Ser Arg Gly Glu Pro Gly Ser Gly Ala Asn Val Leu Thr
1 5 10 15

<210> SEQ ID NO 379
<211> LENGTH: 1203
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 379
ggggcagtgt aggcagagga ggaactgtat caccacagaa acttctgcct tcacacatcc 60
ctccagctag gcaggacagg tagagagtcc agtgtcctgg agcactagac ctaaggaagg 120
ctgcatgggg aggacaaagg acagtgacat cacaggatac ccctcccatc aggaaaatca 180
aggcccagaa ctcactcggc tcttccccag gagaaccaag ccctgaatca gatgcagtgc 240
ttcctgtccc tctgtgccat gggccccggg ctcctctgct gggcactgct ttgtctcctg 300
ggagcaggct tagtggacgc tggagtcacc caaagtccca cacacctgat caaaacgaga 360
ggacagcaag tgactctgag atgctctcct aagtctgggc atgacactgt gtcctggtac 420
caacaggccc tgggtcaggg gccccagttt atctttcagt attatgagga ggaagagaga 480
cagagaggca acttccctga tcgattctca ggtcaccagt tccctaacta tagctctgag 540
ctgaatgtga acgccttgtt gctgggggac tcggccctct atctctgtgc cagcagctcc 600
gggacagacc cctctggggc caacgtcctg actttcgggg ccggcagcag gctgaccgtg 660
ctggaggacc tgaaaaacgt gttcccaccc gaggtcgctg tgtttgagcc atcagaagca 720
gagatctccc acacccaaaa ggccacactg gtgtgcctgg ccacaggctt cttccctgac 780
cacgtggagc tgagctggtg ggtgaatggg aaggaggtgc acagtggggt cagcacagac 840
ccgcagcccc tcaaggagca gcccgccctc aatgactcca gatactgcct gagcagccgc 900
ctgagggtct cggccacctt ctggcagaac ccccgcaacc acttccgctg tcaagtccag 960
ttctacgggc tctcggagaa tgacgagtgg acccaggata gggccaaacc tgtcacccag 1020
atcgtcagcg ccgaggcctg ggtagagca gactgtggct tcacctccga gtcttaccag 1080
caaggggtcc tgtctgccac catcctctat gagatcttgc tagggaaggc caccttgtat 1140
gccgtgctgg tcagtgccct cgtgctgatg gccatggtca agagaaagga ttccagaggc 1200
tag 1203

<210> SEQ ID NO 380
<211> LENGTH: 15
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 380

tctgggcatg acact                                                     15


<210> SEQ ID NO 381
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ser Gly His Asp Thr
1               5


<210> SEQ ID NO 382
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382

tattatgagg aggaagag                                                  18


<210> SEQ ID NO 383
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Tyr Tyr Glu Glu Glu Glu
1               5


<210> SEQ ID NO 384
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384

gccagcagct ccgggacaga cccctctggg gccaacgtcc tgact                    45


<210> SEQ ID NO 385
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ala Ser Ser Ser Gly Thr Asp Pro Ser Gly Ala Asn Val Leu Thr
1               5                   10                  15


<210> SEQ ID NO 386
```

<211> LENGTH: 1087
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 386
ggggtttgta cacttcagcc ctctgagctg aagtgggagt ggtttctctc ctgaaaatgt 60
ttctgaggcc caaatagctg aagaggtgga gacgttacag aaaccacctg gagcccccag 120
aactggcaga cacctgcctg atgctgccat gggcccccag ctccttggct atgtggtcct 180
ttgccttcta ggagcaggcc ccctggaagc ccaagtgacc cagaacccaa gatacctcat 240
cacagtgact ggaaagaagt taacagtgac ttgttctcag aatatgaacc atgagtatat 300
gtcctggtat cgacaagacc cagggctggg cttaaggcag atctactatt caatgaatgt 360
tgaggtgact gataagggag atgttcctga agggtacaaa gtctctcgaa aagagaagag 420
gaatttcccc ctgatcctgg agtcgcccag ccccaaccag acctctctgt acttctgtgc 480
cagcagtacc ggacagaata taggcgggga gctgtttttt ggagaaggct ctaggctgac 540
cgtactggag gacctgaaaa acgtgttccc acccgaggtc gctgtgtttg agccatcaga 600
agcagagatc tcccacaccc aaaaggccac actggtgtgc ctggccacag gcttctaccc 660
cgaccacgtg gagctgagct ggtgggtgaa tgggaaggag gtgcacagtg gggtcagcac 720
agacccgcag cccctcaagg agcagcccgc cctcaatgac tccagatact gcctgagcag 780
ccgcctgagg gtctcggcca ccttctggca gaacccccgc aaccacttcc gctgtcaagt 840
ccagttctac gggctctcgg agaatgacga gtggacccag gatagggcca aacctgtcac 900
ccagatcgtc agcgccgagg cctggggtag agcagactgt ggcttcacct ccgagtctta 960
ccagcaaggg gtcctgtctg ccaccatcct ctatgagatc ttgctaggga aggccacctt 1020
gtatgccgtg ctggtcagtg ccctcgtgct gatggccatg gtcaagagaa aggattccag 1080
aggctag 1087

<210> SEQ ID NO 387
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 387
atgaaccatg agtat 15

<210> SEQ ID NO 388
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 388

Met Asn His Glu Tyr
1 5

<210> SEQ ID NO 389
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
tcaatgaatg ttgaggtg 18

<210> SEQ ID NO 390
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ser Met Asn Val Glu Val
1               5

<210> SEQ ID NO 391
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
gccagcagta ccggacagaa tataggcggg gagctgttt 39

<210> SEQ ID NO 392
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ala Ser Ser Thr Gly Gln Asn Ile Gly Gly Glu Leu Phe
1               5                   10

<210> SEQ ID NO 393
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 393
tgggagaaac aggagatctc caaggaaggt tgacagtcag cactgggatc gtctgtgtaa 60
agtgctgctg aagcagccag gtggcatgtc cagccgacaa tgcgaaagga aaaatggtgc 120
acatcagagt tgctgccatc ttagacttaa ctcatcagta tcaggtgatc ctgaggctca 180
gtgatgtcac tgtgggaact gctctgtggc gacaaggacg tccctcatcc tctgctcctg 240
ctcacagtga ccctgatctg gtaaagctcc catcctgccc tgaccctgcc atgggcacca 300
gcctcctctg ctggatggcc ctgtgtctcc tgggggcaga tcacgcagat actggagtct 360
cccaggaccc cagacacaag atcacaaaga ggggacagaa tgtaactttc aggtgtgatc 420
caatttctga acacaaccgc ctttattggt accgacagac cctggggcag ggcccagagt 480
ttctgactta cttccagaat gaagctcaac tagaaaaatc aaggctgctc agtgatcggt 540
tctctgcaga gaggcctaag ggatctttct ccaccttgga gatccagcgc acagagcagg 600

```
gggactcggc catgtatctc tgtgccagca gcacacatga aaagacaggg tggaaatcac    660

ccctccactt tgggaatggg accaggctca ctgtgacaga ggacctgaac aaggtgttcc    720

cacccgaggt cgctgtgttt gagccatcag aagcagagat ctcccacacc caaaaggcca    780

cactggtgtg cctggccaca ggcttctacc ccgaccacgt ggagctgagc tggtgggtga    840

atgggaagga ggtgcacagt ggggtcagca cagacccgca gcccctcaag gagcagcccg    900

ccctcaatga ctccagatac tgcctgagca gccgcctgag ggtctcggcc accttctggc    960

agaacccccg caaccacttc cgctgtcaag tccagttcta cgggctctcg gagaatgacg   1020

agtggaccca ggatagggcc aaacccgtca cccagatcgt cagcgccgag gcctggggta   1080

gagcagactg tggctttacc tcggtgtcct accagcaagg ggtcctgtct gccaccatcc   1140

tctatgagat cctgctaggg aaggccaccc tgtatgctgt gctggtcagc gcccttgtgt   1200

tgatggccat ggtcaagaga aaggatttct ga                                 1232
```

<210> SEQ ID NO 394
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 394

```
tctgaacaca accgc                                                      15
```

<210> SEQ ID NO 395
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 395

```
Ser Glu His Asn Arg
1               5
```

<210> SEQ ID NO 396
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 396

```
ttccagaatg aagctcaa                                                   18
```

<210> SEQ ID NO 397
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 397

```
Phe Gln Asn Glu Ala Gln
1               5
```

<210> SEQ ID NO 398

<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 398
gccagcagca cacatgaaaa gacagggtgg aaatcacccc tccac 45

<210> SEQ ID NO 399
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 399

Ala Ser Ser Thr His Glu Lys Thr Gly Trp Lys Ser Pro Leu His
1 5 10 15

<210> SEQ ID NO 400
<211> LENGTH: 1051
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 400
ggggccagac cttgcctgtg gggccatggg agctcaaaat gcccctcctt tcctccacag 60
gaccagatgc ctgagctagg aaaggcctca ttcctgctgt gatcctgcca tggatacctg 120
gctcgtatgc tgggcaattt ttagtctctt gaaagcagga ctcacagaac ctgaagtcac 180
ccagactccc agccatcagg tcacacagat gggacaggaa gtgatcttgc gctgtgtccc 240
catctctaat cacttatact tctattggta cagacaaatc ttggggcaga aagtcgagtt 300
tctggtttcc ttttataata atgaaatctc agagaagtct gaaatattcg atgatcaatt 360
ctcagttgaa aggcctgatg gatcaaattt cactctgaag atccggtcca caaagctgga 420
ggactcagcc atgtacttct gtgccagcag tacgcactct gacaggaact tgaacactga 480
agctttcttt ggacaaggca ccagactcac agttgtagag gacctgaaca aggtgttccc 540
acccgaggtc gctgtgtttg agccatcaga agcagagatc tcccacaccc aaaaggccac 600
actggtgtgc ctggccacag gcttcttccc tgaccacgtg gagctgagct ggtgggtgaa 660
tgggaaggag gtgcacagtg gggtcagcac agacccgcag cccctcaagg agcagcccgc 720
cctcaatgac tccagatact gcctgagcag ccgcctgagg gtctcggcca ccttctggca 780
gaacccccgc aaccacttcc gctgtcaagt ccagttctac gggctctcgg agaatgacga 840
gtggacccag gatagggcca aacccgtcac ccagatcgtc agcgccgagg cctggggtag 900
agcagactgt ggctttacct cggtgtccta ccagcaaggg gtcctgtctg ccaccatcct 960
ctatgagatc ctgctaggga aggccaccct gtatgctgtg ctggtcagcg cccttgtgtt 1020
gatggccatg gtcaagagaa aggatttctg a 1051

<210> SEQ ID NO 401
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 401
tctaatcact tatac 15

<210> SEQ ID NO 402
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 402

Ser Asn His Leu Tyr
1 5

<210> SEQ ID NO 403
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 403
ttttataata atgaaatc 18

<210> SEQ ID NO 404
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

Phe Tyr Asn Asn Glu Ile
1 5

<210> SEQ ID NO 405
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 405
gccagcagta cgcactctga caggaacttg aacactgaag ctttc 45

<210> SEQ ID NO 406
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 406

Ala Ser Ser Thr His Ser Asp Arg Asn Leu Asn Thr Glu Ala Phe
1 5 10 15

<210> SEQ ID NO 407
<211> LENGTH: 1040
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 407
tgggagacct tgcctgtggg gccatgggag ctcaaaatgc ccctcctttc ctccacagga 60
ccagatgcct gagctaggaa aggcctcatt cctgctgtga tcctgccatg gatacctggc 120
tcgtatgctg ggcaattttt agtctcttga aagcaggact cacagaacct gaagtcaccc 180
agactcccag ccatcaggtc acacagatgg gacaggaagt gatcttgcgc tgtgtcccca 240
tctctaatca cttatacttc tattggtaca gacaaatctt ggggcagaaa gtcgagtttc 300
tggtttcctt ttataataat gaaatctcag agaagtctga aatattcgat gatcaattct 360
cagttgaaag gcctgatgga tcaaatttca ctctgaagat ccggtccaca aagctggagg 420
actcagccat gtacttctgt gccagcagcg tacaggctac gggccatggc tacaccttcg 480
gttcggggac caggttaacc gttgtagagg acctgaacaa ggtgttccca cccgaggtcg 540
ctgtgtttga gccatcagaa gcagagatct cccacaccca aaaggccaca ctggtatgcc 600
tggccacagg cttctacccc gaccacgtgg agctgagctg gtgggtgaat gggaaggagg 660
tgcacagtgg ggtcagcaca gacccgcagc ccctcaagga gcagcccgcc ctcaatgact 720
ccagatactg cctgagcagc cgcctgaggg tctcggccac cttctggcag aaccccccgca 780 accacttccg ctgtcaagtc cagttctacg ggctctcgga gaatgacgag tggacccagg 840
atagggccaa acccgtcacc cagatcgtca gcgccgaggc ctggggtaga gcagactgtg 900
gctttacctc ggtgtcctac cagcaagggg tcctgtctgc caccatcctc tatgagatcc 960
tgctagggaa ggccaccctg tatgctgtgc tggtcagcgc ccttgtgttg atggccatgg 1020
tcaagagaaa ggatttctga 1040

<210> SEQ ID NO 408
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 408
tctaatcact tatac 15

<210> SEQ ID NO 409
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 409

Ser Asn His Leu Tyr
1 5

<210> SEQ ID NO 410
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 410
ttttataata atgaaatc 18

<210> SEQ ID NO 411
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 411

Phe Tyr Asn Asn Glu Ile
1 5

<210> SEQ ID NO 412
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 412
gccagcagcg tacaggctac gggccatggc tacacc 36

<210> SEQ ID NO 413
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 413

Ala Ser Ser Val Gln Ala Thr Gly His Gly Tyr Thr
1 5 10

<210> SEQ ID NO 414
<211> LENGTH: 1045
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 414
tggggtcact gtgggaactg ccctgtggag acaaggacgg cccttatcct ctgcttctgt 60
tcacagtgac actgatctgg taaagccccc atcctggcct gaccctgcca tgggcaccag 120
gctcctctgc tgggtggtcc tgggtttcct agggacagat cacacaggtg ctggagtctc 180
ccagtcccct aggtacaaag tcgcaaagag aggacaggat gtagctctca ggtgtgatcc 240
aatttcgggt catgtatccc ttttttggta ccaacaggcc ctggggcagg ggccagagtt 300
tctgacttat ttccagaatg aagctcaact agacaaatcg gggctgccca gtgatcgctt 360
ctttgcagaa aggcctgagg gatccgtctc cactctgaag atccagcgca cacagcagga 420
ggactccgcc gtgtatctct gtgccagcac cccctctggc tataactctt gggagcagtt 480
cttcgggcca gggacacggc tcaccgtgct agaggacctg aaaaacgtgt tcccacccga 540
ggtcgctgtg tttgagccat cagaagcaga gatctcccac acccaaaagg ccacactggt 600
gtgcctggcc acaggcttct accccgacca cgtggagctg agctggtggg tgaatgggaa 660
ggaggtgcac agtggggtca gcacagaccc gcagcccctc aaggagcagc ccgccctcaa 720
tgactccaga tactgcctga gcagccgcct gagggtctcg gccaccttct ggcagaaccc 780
ccgcaaccac ttccgctgtc aagtccagtt ctacgggctc tcggagaatg acgagtggac 840
ccaggatagg gccaaacccg tcacccagat cgtcagcgcc gaggcctggg gtagagcaga 900
ctgtggcttt acctcggtgt cctaccagca aggggtcctg tctgccacca tcctctatga 960
gatcctgcta gggaaggcca ccctgtatgc tgtgctggtc agcgcccttg tgttgatggc 1020
catggtcaag agaaaggatt tctga 1045

<210> SEQ ID NO 415
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 415
tcgggtcatg tatcc 15

<210> SEQ ID NO 416
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 416

Ser Gly His Val Ser
1 5

<210> SEQ ID NO 417
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 417
ttccagaatg aagctcaa 18

<210> SEQ ID NO 418
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 418

Phe Gln Asn Glu Ala Gln
1 5

<210> SEQ ID NO 419
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 419
gccagcaccc cctctggcta taactcttgg gagcagttc 39

<210> SEQ ID NO 420
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 420

Ala Ser Thr Pro Ser Gly Tyr Asn Ser Trp Glu Gln Phe
1 5 10

<210> SEQ ID NO 421
<211> LENGTH: 1082
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 421
gtgttgcgtt tgtacacttc agccctctga gctgaagtgg gagtggtttc tctcctgaaa 60
atgtttctga ggcccaaata gctgaagagg tggagacgtt acagaaacca cctggagccc 120
ccagaactgg cagacacctg cctgatgctg ccatgggccc ccagctcctt ggctatgtgg 180
tcctttgcct tctaggagca ggcccccctgg aagcccaagt gacccagaac ccaagatacc 240
tcatcacagt gactggaaag aagttaacag tgacttgttc tcagaatatg aaccatgagt 300
atatgtcctg gtatcgacaa gacccagggc tgggcttaag gcagatctac tattcaatga 360
atgttgaggt gactgataag ggagatgttc ctgaagggta caaagtctct cgaaaagaga 420
agaggaattt ccccctgatc ctggagtcgc ccagccccaa ccagacctct ctgtacttct 480
gtgccaccgc ccccaggggt agcaatcagc cccagcattt tggtgatggg actcgactct 540
ccatcctaga ggacctgaac aaggtgttcc cacccgaggt cgctgtgttt gagccatcag 600
aagcagagat ctcccacacc caaaaggcca cactggtgtg cctggccaca ggcttctacc 660
ccgaccacgt ggagctgagc tggtgggtga atgggaagga ggtgcacagt ggggtcagca 720
cagacccgca gcccctcaag gagcagcccg ccctcaatga ctccagatac tgcctgagca 780
gccgcctgag ggtctcggcc accttctggc agaacccccg caaccacttc cgctgtcaag 840
tccagttcta cgggctctcg gagaatgacg agtggaccca ggatagggcc aaacccgtca 900
cccagatcgt cagcgccgag gcctggggta gagcagactg tggctttacc tcggtgtcct 960
accagcaagg ggtcctgtct gccaccatcc tctatgagat cctgctaggg aaggccaccc 1020
tgtatgctgt gctggtcagc gcccttgtgt tgatggccat ggtcaagaga aaggatttct 1080
ga 1082

<210> SEQ ID NO 422
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 422
atgaaccatg agtat 15

<210> SEQ ID NO 423
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Met Asn His Glu Tyr
1               5

<210> SEQ ID NO 424
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424

tcaatgaatg ttgaggtg                                                    18

<210> SEQ ID NO 425
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Ser Met Asn Val Glu Val
1               5

<210> SEQ ID NO 426
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426

gccaccgccc ccaggggtag caatcagccc cagcat                                36

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ala Thr Ala Pro Arg Gly Ser Asn Gln Pro Gln His
1               5                   10

<210> SEQ ID NO 428
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 428

gggggggatt ctgtgatcag tcatccctcc tcgctggtga atggaggcag tggtcacaac    60

tctccccaga gaaggtggtg tgaggccatc acggaagatg ctgctgcttc tgctgcttct   120
```

gggggccaggc tccgggcttg gtgctgtcgt ctctcaacat ccgagctggg ttatctgtaa 180
gagtggaacc tctgtgaaga tcgagtgccg ttccctggac tttcaggcca caactatgtt 240
ttggtatcgt cagttcccga aacagagtct catgctgatg gcaacttcca atgagggctc 300
caaggccaca tacgagcaag gcgtcgagaa ggacaagttt ctcatcaacc atgcaagcct 360
gaccttgtcc actctgacag tgaccagtgc ccatcctgaa gacagcagct tctacatctg 420
cagggcctgg ggcgggagct cctacaatga gcagttcttc gggccaggga cacggctcac 480
cgtgctagag gacctgaaaa acgtgttccc acccgaggtc gctgtgtttg agccatcaga 540
agcagagatc tcccacaccc aaaaggccac actggtatgc ctggccacag gcttctaccc 600
cgaccacgtg gagctgagct ggtgggtgaa tgggaaggag gtgcacagtg ggtcagcac 660 agacccgcag cccctcaagg agcagcccgc cctcaatgac tccagatact gcctgagcag 720
ccgcctgagg gtctcggcca ccttctggca gaacccccgc aaccacttcc gctgtcaagt 780
ccagttctac gggctctcgg agaatgacga gtggacccag gatagggcca aacccgtcac 840
ccagatcgtc agcgccgagg cctggggtag agcagactgt ggctttacct cggtgtccta 900
ccagcaaggg gtcctgtctg ccaccatcct ctatgagatc ctgctaggga aggccaccct 960
gtatgctgtg ctggtcagcg cccttgtgtt gatggccatg gtcaagagaa aggatttctg 1020
a 1021

<210> SEQ ID NO 429
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
gactttcagg ccacaact 18

<210> SEQ ID NO 430
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Asp Phe Gln Ala Thr Thr
1               5

<210> SEQ ID NO 431
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
tccaatgagg gctccaaggc c 21

<210> SEQ ID NO 432
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 432

Ser Asn Glu Gly Ser Lys Ala
1               5

<210> SEQ ID NO 433
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
agggcctggg gcgggagctc ctacaatgag cagttc 36

<210> SEQ ID NO 434
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Arg Ala Trp Gly Gly Ser Ser Tyr Asn Glu Gln Phe
1               5                   10

<210> SEQ ID NO 435
<211> LENGTH: 1017
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 435
tggggagtca tccctcctcg ctggtgaatg gaggcagtgg tcacaactct ccccagagaa 60
ggtggtgtga ggccatcacg gaagatgctg ctgcttctgc tgcttctggg gccaggctcc 120
gggcttggtg ctgtcgtctc tcaacatccg agcagggtta tctgtaagag tggaacctct 180
gtgaagatcg agtgccgttc cctggacttt caggccacaa ctatgttttg gtatcgtcag 240
ttcccgaaac agagtctcat gctgatggca acttccaatg agggctccaa ggccacatac 300
gagcaaggcg tcgagaagga caagtttctc atcaaccatg caagcctgac cttgtccact 360
ctgacagtga ccagtgccca tcctgaagac agcagcttct acatctgcag tgctagaatt 420
ggacagggtt ttatgaatga gcagttcttc gggccaggga cacggctcac cgtgctagag 480
gacctgaaaa acgtgttccc acccgaggtc gctgtgtttg agccatcaga agcagagatc 540
tcccacaccc aaaaggccac actggtgtgc ctggccacag gcttctaccc cgaccacgtg 600
gagctgagct ggtgggtgaa tgggaaggag gtgcacagtg ggtcagcac agacccgcag 660 cccctcaagg agcagcccgc cctcaatgac tccagatact gcctgagcag ccgcctgagg 720
gtctcggcca ccttctggca gaacccccgc aaccacttcc gctgtcaagt ccagttctac 780
gggctctcgg agaatgacga gtggacccag gatagggcca aacctgtcac ccagatcgtc 840
agcgccgagg cctggggtag agcagactgt ggcttcacct ccgagtctta ccagcaaggg 900
gtcctgtctg ccaccatcct ctatgagatc ttgctaggga aggccacctt gtatgccgtg 960
ctggtcagtg ccctcgtgct gatggccatg gtcaagagaa aggattccag aggctag 1017

<210> SEQ ID NO 436
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 436
gactttcagg ccacaact 18

<210> SEQ ID NO 437
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 437

Asp Phe Gln Ala Thr Thr
1 5

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 438
tccaatgagg gctccaaggc c 21

<210> SEQ ID NO 439
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 439

Ser Asn Glu Gly Ser Lys Ala
1 5

<210> SEQ ID NO 440
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 440
agtgctagaa ttggacaggg ttttatgaat gagcagttc 39

<210> SEQ ID NO 441
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 441

Ser Ala Arg Ile Gly Gln Gly Phe Met Asn Glu Gln Phe
1 5 10

<210> SEQ ID NO 442
<211> LENGTH: 1060
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 442
agtcatgggc aaagattacc accagggggc agactagggc atccttggga ttctgtgatc 60
agtcatccct cctcgctggt gaatggaggc agtggtcaca actctcccca gagaaggtgg 120
tgtgaggcca tcacggaaga tgctgctgct tctgctgctt ctggggccag gctccgggct 180
tggtgctgtc gtctctcaac atccgagcag ggttatctgt aagagtggaa cctctgtgaa 240
gatcgagtgc cgttccctgg actttcaggc cacaactatg ttttggtatc gtcagttccc 300
gaaaaagagt ctcatgctga tggcaacttc caatgagggc tccaaggcca catacgagca 360
aggcgtcgag aaggacaagt ttctcatcaa ccatgcaagc ctgaccttgt ccactctgac 420
agtgaccagt gcccatcctg aagacagcag cttctacatc tgcagtgctc ctgggtggcg 480
tggcactgaa gctttctttg gacaaggcac cagactcaca gttgtagagg acctgaacaa 540
ggtgttccca cccgaggtcg ctgtgtttga gccatcagaa gcagagatct cccacaccca 600
aaaggccaca ctggtgtgcc tggccacagg cttcttccct gaccacgtgg agctgagctg 660
gtgggtgaat gggaaggagg tgcacagtgg ggtcagcaca gacccgcagc ccctcaagga 720
gcagcccgcc ctcaatgact ccagatactg cctgagcagc cgcctgaggg tctcggccac 780
cttctggcag aacccccgca accacttccg ctgtcaagtc cagttctacg ggctctcgga 840
gaatgacgag tggacccagg atagggccaa acccgtcacc cagatcgtca gcgccgaggc 900
ctggggtaga gcagactgtg gctttacctc ggtgtcctac cagcaagggg tcctgtctgc 960
caccatcctc tatgagatcc tgctagggaa ggccaccctg tatgctgtgc tggtcagcgc 1020
ccttgtgttg atggccatgg tcaagagaaa ggatttctga 1060

<210> SEQ ID NO 443
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 443
gactttcagg ccacaact 18

<210> SEQ ID NO 444
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 444

Asp Phe Gln Ala Thr Thr
1 5

<210> SEQ ID NO 445

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 445
tccaatgagg gctccaaggc c 21

<210> SEQ ID NO 446
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 446

Ser Asn Glu Gly Ser Lys Ala
1 5

<210> SEQ ID NO 447
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 447
agtgctcctg ggtggcgtgg cactgaagct ttc 33

<210> SEQ ID NO 448
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 448

Ser Ala Pro Gly Trp Arg Gly Thr Glu Ala Phe
1 5 10

<210> SEQ ID NO 449
<211> LENGTH: 1038
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 449
gggactggcg cagcacctct cagcggcagt ggaaaccaca gcctagtcct ctcaccactg 60
cagaccagaa tcctgccctg ggccttgcct ggtctgcctc actctgccat gggctgcagg 120
ctcctctgct gtgtggtctt ctgcctcctc caagcaggtc ccttggacac agctgtttcc 180
cagactccaa aatacctggt cacacagatg ggaaacgaca agtccattaa atgtgaacaa 240
aatctgggcc atgatactat gtattggtat aaacaggact ctaagaaatt tctgaagata 300
atgtttagct acaataataa ggagctcatt ataaatgaaa cagttccaaa tcgcttctca 360
cctaaatctc cagacaaagc tcacttaaat cttcacatca attccctgga gcttggtgac 420
tctgctgtgt atttctgtgc cagcagccaa gatggacttg agcagtactt cgggccgggc 480

-continued

```
accaggctca cggtcacaga ggacctgaaa aacgtgttcc cacccgaggt cgctgtgttt    540

gagccatcag aagcagagat ctcccacacc caaaaggcca cactggtatg cctggccaca    600

ggcttctacc ccgaccacgt ggagctgagc tggtgggtga atgggaagga ggtgcacagt    660

ggggtcagca cagacccgca gcccctcaag gagcagcccg ccctcaatga ctccagatac    720

tgcctgagca gccgcctgag ggtctcggcc accttctggc agaacccccg caaccacttc    780

cgctgtcaag tccagttcta cgggctctcg gagaatgacg agtggaccca ggatagggcc    840

aaacctgtca cccagatcgt cagcgccgag gcctggggta gagcagactg tggcttcacc    900

tccgagtctt accagcaagg ggtcctgtct gccaccatcc tctatgagat cttgctaggg    960

aaggccacct tgtatgccgt gctggtcagt gccctcgtgc tgatggccat ggtcaagaga   1020

aaggattcca gaggctag                                                 1038
```

<210> SEQ ID NO 450
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 450
ctgggccatg atact 15

<210> SEQ ID NO 451
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 451

```
Leu Gly His Asp Thr
1               5
```

<210> SEQ ID NO 452
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 452
tacaataata aggagctc 18

<210> SEQ ID NO 453
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 453

```
Tyr Asn Asn Lys Glu Leu
1               5
```

<210> SEQ ID NO 454
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
gccagcagcc aagatggact tgagcagtac 30

<210> SEQ ID NO 455
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Ala Ser Ser Gln Asp Gly Leu Glu Gln Tyr
1               5                   10

<210> SEQ ID NO 456
<211> LENGTH: 1068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456
gacctcactg gcgcagcacc tctcagcggc agtggaaacc acagcctagt cctctcacca 60
ctgcagacca gaatcctgcc ctgggccttg cctggtctgc ctcactctgc catgggctgc 120
aggctcctct gctgtgtggt cttctgcctc ctccaagcag gtcccttgga cacagctgtt 180
tcccagactc caaaatacct ggtcacacag atgggaaacg acaagtccat taaatgtgaa 240
caaaatctgg gccatgatac tatgtattgg tataaacagg actctaagaa atttctgaag 300
ataatgttta gctacaataa taaggagctc attataaatg aaacagttcc aaatcgcttc 360
tcacctaaat ctccagacaa agctcactta aatcttcaca tcaattccct ggagcttggt 420
gactctgctg tgtatttctg tgccagcagc caagaaggat ctcaggacca cactagcggg 480
agggccaccg agcagtactt cgggccgggc accaggctca cggtcacaga ggacctgaaa 540
aacgtgttcc cacccgaggt cgctgtgttt gagccatcag aagcagagat ctcccacacc 600
caaaaggcca cactggtgtg cctggccaca ggcttctacc ccgaccacgt ggagctgagc 660
tggtgggtga atgggaagga ggtgcacagt ggggtcagca cagacccgca gcccctcaag 720
gagcagcccg ccctcaatga ctccagatac tgcctgagca gccgcctgag ggtctcggcc 780
accttctggc agaacccccg caaccacttc cgctgtcaag tccagttcta cgggctctcg 840
gagaatgacg agtggaccca ggatagggcc aaacctgtca cccagatcgt cagcgccgag 900
gcctggggta gagcagactg tggcttcacc tccgagtctt accagcaagg ggtcctgtct 960
gccaccatcc tctatgagat cttgctaggg aaggccacct tgtatgccgt gctggtcagt 1020
gccctcgtgc tgatggccat ggtcaagaga aaggattcca gaggctag 1068

<210> SEQ ID NO 457
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
ctgggccatg atact 15

<210> SEQ ID NO 458
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 458

Leu Gly His Asp Thr
1 5

<210> SEQ ID NO 459
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 459
tacaataata aggagctc 18

<210> SEQ ID NO 460
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 460

Tyr Asn Asn Lys Glu Leu
1 5

<210> SEQ ID NO 461
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 461
gccagcagcc aagaaggatc tcaggaccac actagcggga gggccaccga gcagtac 57

<210> SEQ ID NO 462
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 462

Ala Ser Ser Gln Glu Gly Ser Gln Asp His Thr Ser Gly Arg Ala Thr
1 5 10 15

Glu Gln Tyr

<210> SEQ ID NO 463
<211> LENGTH: 1057
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 463
ggggctctcc ctccctgggg cccaggcagg gagaatgtct cagaatgact tccttgagag 60
tcctgctccc ctttcatcaa tgcacagata cagaagaccc ctccgtcatg cagcatctgc 120
catgagcatc ggcctcctgt gctgtgcagc cttgtctctc ctgtgggcag gtccagtgaa 180
tgctggtgtc actcagaccc caaaattcca ggtcctgaag acaggacaga gcatgacact 240
gcagtgtgcc caggatatga accatgaata catgtcctgg tatcgacaag acccaggcat 300
ggggctgagg ctgattcatt actcagttgg tgctggtatc actgaccaag gagaagtccc 360
caatggctac aatgtctcca gatcaaccac agaggatttc ccgctcaggc tgctgtcggc 420
tgctccctcc cagacatctg tgtacttctg tgccagcagc ctgacagaag gaagaagcga 480
gcagtacttc gggccgggca ccaggctcac ggtcacagag gacctgaaaa acgtgttccc 540
acccgaggtc gctgtgtttg agccatcaga agcagagatc tcccacaccc aaaaggccac 600
actggtgtgc ctggccacag gcttctaccc cgaccacgtg gagctgagct ggtgggtgaa 660
tgggaaggag gtgcacagtg gggtcagcac ggacccgcag cccctcaagg agcagcccgc 720
cctcaatgac tccagatact gcctgagcag ccgcctgagg gtctcggcca ccttctggca 780
gaacccccgc aaccacttcc gctgtcaagt ccagttctac gggctctcgg agaatgacga 840
gtggacccag gatagggcca aacctgtcac ccagatcgtc agcgccgagg cctggggtag 900
agcagactgt ggcttcacct ccgagtctta ccagcaaggg gtcctgtctg ccaccatcct 960
ctatgagatc ttgctaggga aggccacctt gtatgccgtg ctggtcagtg ccctcgtgct 1020
gatggccatg gtcaagagaa aggattccag aggctag 1057

<210> SEQ ID NO 464
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
atgaaccatg aatac 15

<210> SEQ ID NO 465
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Met Asn His Glu Tyr
1               5

<210> SEQ ID NO 466
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
tcagttggtg ctggtatc 18

<210> SEQ ID NO 467
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 467

Ser Val Gly Ala Gly Ile
1 5

<210> SEQ ID NO 468
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 468
gccagcagcc tgacagaagg aagaagcgag cagtac 36

<210> SEQ ID NO 469
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 469

Ala Ser Ser Leu Thr Glu Gly Arg Ser Glu Gln Tyr
1 5 10

<210> SEQ ID NO 470
<211> LENGTH: 1004
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 470
ggggagtcat ccctcctcgc tggtgaatgg aggcagtggt cacaactctc cccagagaag 60
gtggtgtgag gccatcacgg aagatgctgc tgcttctgct gcttctgggg ccaggctccg 120
ggcttggtgc tgtcgtctct caacatccga gcagggttat ctgtaagagt ggaacctctg 180
tgaagatcga gtgccgttcc ctggactttc aggccacaac tatgttttgg tatcgtcagt 240
tcccgaaaaa gagtctcatg ctgatggcaa cttccaatga gggctccaag gccacatacg 300
agcaaggcgt cgagaaggac aagtttctca tcaaccatgc aagcctgacc ttgtccactc 360
tgacagtgac cagtgcccat cctgaagaca gcagcttcta catctgcagt gctgggggtt 420
tctctggaaa caccatatat tttggagagg gaagttggct cactgttgta gaggacctga 480
acaaggtgtt cccacccgag gtcgctgtgt ttgagccatc agaagcagag atctcccaca 540
cccaaaaggc cacactggtg tgcctggcca caggcttcta ccccgaccac gtggagctga 600
gctggtgggt gaatgggaag gaggtgcaca gtggggtcag cacagacccg cagcccctca 660
aggagcagcc cgccctcaat gactccagat actgcctgag cagccgcctg agggtctcgg 720
ccaccttctg gcagaacccc cgcaaccact tccgctgtca agtccagttc tacgggctct 780
cggagaatga cgagtggacc caggataggg ccaaacccgt cacccagatc gtcagcgccg 840
aggcctgggg tagagcagac tgtggcttta cctcggtgtc ctaccagcaa ggggtcctgt 900
ctgccaccat cctctatgag atcctgctag ggaaggccac cctgtatgct gtgctggtca 960
gcgcccttgt gttgatggcc atggtcaaga gaaaggattt ctga 1004

<210> SEQ ID NO 471
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 471
gactttcagg ccacaact 18

<210> SEQ ID NO 472
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 472

Asp Phe Gln Ala Thr Thr
1 5

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 473
tccaatgagg gctccaaggc c 21

<210> SEQ ID NO 474
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 474

Ser Asn Glu Gly Ser Lys Ala
1 5

<210> SEQ ID NO 475
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 475
agtgctgggg gtttctctgg aaacaccata tat 33

<210> SEQ ID NO 476
<211> LENGTH: 11

<212> TYPE: PRT
<213> ORGANISM: Artificial Sequence
<220> FEATURE:
<223> OTHER INFORMATION: Description of Artificial Sequence: Synthetic peptide

<400> SEQUENCE: 476

```
Ser Ala Gly Gly Phe Ser Gly Asn Thr Ile Tyr
1               5                   10
```

<210> SEQ ID NO 477
<211> LENGTH: 270
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 477

```
Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Ala Arg Ser Tyr
            100                 105                 110

Asn Thr Asp Lys Leu Ile Phe Gly Thr Gly Thr Arg Leu Gln Val Phe
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 478
<211> LENGTH: 334
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 478
gagctgaaag tggaacaaaa ccctctgttc ctgagcatgc aggagggaaa aaactatacc 60
atctactgca attattcaac cacttcagac agactgtatt ggtacaggca ggatcctggg 120
aaaagtctgg aatctctgtt tgtgttgcta tcaaatggag cagtgaagca ggagggacga 180
ttaatggcct cacttgatac caaagcccgt ctcagcaccc tccacatcac agctgccgtg 240
catgacctct ctgccaccta cttctgtgcc gcccgatctt ataacaccga caagctcatc 300
tttgggactg ggaccagatt acaagtcttt ccaa 334

<210> SEQ ID NO 479
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 479

Glu Leu Lys Val Glu Gln Asn Pro Leu Phe Leu Ser Met Gln Glu Gly
1 5 10 15

Lys Asn Tyr Thr Ile Tyr Cys Asn Tyr Ser Thr Thr Ser Asp Arg Leu
20 25 30

Tyr Trp Tyr Arg Gln Asp Pro Gly Lys Ser Leu Glu Ser Leu Phe Val
35 40 45

Leu Leu Ser Asn Gly Ala Val Lys Gln Glu Gly Arg Leu Met Ala Ser
50 55 60

Leu Asp Thr Lys Ala Arg Leu Ser Thr Leu His Ile Thr Ala Ala Val
65 70 75 80

His Asp Leu Ser Ala Thr Tyr Phe Cys Ala Ala Arg Ser Tyr Asn Thr
85 90 95

Asp Lys Leu Ile Phe Gly Thr Gly Thr Arg Leu Gln Val Phe Pro
100 105 110

<210> SEQ ID NO 480
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 480

Met Ala Ser Ala Pro Ile Ser Met Leu Ala Met Leu Phe Thr Leu Ser
1 5 10 15

Gly Leu Arg Ala Gln Ser Val Ala Gln Pro Glu Asp Gln Val Asn Val
20 25 30

Ala Glu Gly Asn Pro Leu Thr Val Lys Cys Thr Tyr Ser Val Ser Gly
35 40 45

Asn Pro Tyr Leu Phe Trp Tyr Val Gln Tyr Pro Asn Arg Gly Leu Gln
50 55 60

Phe Leu Leu Lys Tyr Ile Thr Gly Asp Asn Leu Val Lys Gly Ser Tyr
65 70 75 80

Gly Phe Glu Ala Glu Phe Asn Lys Ser Gln Thr Ser Phe His Leu Lys
85 90 95

Lys Pro Ser Ala Leu Val Ser Asp Ser Ala Leu Tyr Phe Cys Ala Val

```
            100                 105                 110

Arg Asp Met Gly Gly Ser Ala Arg Gln Leu Thr Phe Gly Ser Gly Thr
        115                 120                 125

Gln Leu Thr Val Leu Pro Asp Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275


<210> SEQ ID NO 481
<211> LENGTH: 346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 481

gctcagtcag tggctcagcc ggaagatcag gtcaacgttg ctgaagggaa tcctctgact      60

gtgaaatgca cctattcagt ctctggaaac ccttatcttt tttggtatgt tcaatacccc     120

aaccgaggcc tccagttcct tctgaaatac atcacagggg ataacctggt taaaggcagc     180

tatggctttg aagctgaatt taacaagagc caaacctcct tccacctgaa gaaaccatct     240

gcccttgtga gcgactccgc tttgtacttc tgtgctgtga gagacatggg gggttctgca     300

aggcaactga cctttggatc tgggacacaa ttgactgttt tacctg                   346


<210> SEQ ID NO 482
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Ile Thr Gly Asp Asn Leu Val Lys Gly Ser Tyr Gly Phe Glu
```

```
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Met
                85                  90                  95

Gly Gly Ser Ala Arg Gln Leu Thr Phe Gly Ser Gly Thr Gln Leu Thr
            100                 105                 110

Val Leu Pro
        115


<210> SEQ ID NO 483
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Asn Met Arg Gln Val Ala Arg Val Ile Val Phe Leu Thr Leu Ser Thr
1               5                   10                  15

Leu Ser Leu Ala Lys Thr Thr Gln Pro Ile Ser Met Asp Ser Tyr Glu
            20                  25                  30

Gly Gln Glu Val Asn Ile Thr Cys Ser His Asn Asn Ile Ala Thr Asn
        35                  40                  45

Asp Tyr Ile Thr Trp Tyr Gln Gln Phe Pro Ser Gln Gly Pro Arg Phe
    50                  55                  60

Ile Ile Gln Gly Tyr Lys Thr Lys Val Thr Asn Glu Val Ala Ser Leu
65                  70                  75                  80

Phe Ile Pro Ala Asp Arg Lys Ser Ser Thr Leu Ser Leu Pro Arg Val
                85                  90                  95

Ser Leu Ser Asp Thr Ala Val Tyr Tyr Cys Leu Val Gly Thr Phe Ser
            100                 105                 110

Gly Ser Ala Arg Gln Leu Thr Phe Gly Ser Gly Thr Gln Leu Thr Val
        115                 120                 125

Leu Pro Asp Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270


<210> SEQ ID NO 484
<211> LENGTH: 337
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 484
cttgctaaga ccacccagcc catctccatg gactcatatg aaggacaaga agtgaacata 60
acctgtagcc acaacaacat tgctacaaat gattatatca cgtggtacca acagtttccc 120
agccaaggac cacgatttat tattcaagga tacaagacaa aagttacaaa cgaagtggcc 180
tccctgttta tccctgccga cagaaagtcc agcactctga gcctgccccg ggtttccctg 240
agcgacactg ctgtgtacta ctgcctcgtg gggacgtttt ctggttctgc aaggcaactg 300
acctttggat ctgggacaca attgactgtt ttacctg 337

<210> SEQ ID NO 485
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 485

Leu Ala Lys Thr Thr Gln Pro Ile Ser Met Asp Ser Tyr Glu Gly Gln
1 5 10 15

Glu Val Asn Ile Thr Cys Ser His Asn Asn Ile Ala Thr Asn Asp Tyr
20 25 30

Ile Thr Trp Tyr Gln Gln Phe Pro Ser Gln Gly Pro Arg Phe Ile Ile
35 40 45

Gln Gly Tyr Lys Thr Lys Val Thr Asn Glu Val Ala Ser Leu Phe Ile
50 55 60

Pro Ala Asp Arg Lys Ser Ser Thr Leu Ser Leu Pro Arg Val Ser Leu
65 70 75 80

Ser Asp Thr Ala Val Tyr Tyr Cys Leu Val Gly Thr Phe Ser Gly Ser
85 90 95

Ala Arg Gln Leu Thr Phe Gly Ser Gly Thr Gln Leu Thr Val Leu Pro
100 105 110

<210> SEQ ID NO 486
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 486

Met Val Lys Ile Arg Gln Phe Leu Leu Ala Ile Leu Trp Leu Gln Leu
1 5 10 15

Ser Cys Val Ser Ala Ala Lys Asn Glu Val Glu Gln Ser Pro Gln Asn
20 25 30

Leu Thr Ala Gln Glu Gly Glu Phe Ile Thr Ile Asn Cys Ser Tyr Ser
35 40 45

Val Gly Ile Ser Ala Leu His Trp Leu Gln Gln His Pro Gly Gly Gly
50 55 60

Ile Val Ser Leu Phe Met Leu Ser Ser Gly Lys Lys Lys His Gly Arg
65 70 75 80

Leu Ile Ala Thr Ile Asn Ile Gln Glu Lys His Ser Ser Leu His Ile

```
                85                  90                  95

Thr Ala Ser His Pro Arg Asp Ser Ala Val Tyr Ile Cys Ala Val Ser
            100                 105                 110

Thr Ser Met Tyr Ser Gly Gly Gly Ala Asp Gly Leu Thr Phe Gly Lys
        115                 120                 125

Gly Thr His Leu Ile Ile Gln Pro Tyr Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275
```

<210> SEQ ID NO 487
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 487

```
aaaaatgaag tggagcagag tcctcagaac ctgactgccc aggaaggaga atttatcaca      60

atcaactgca gttactcggt aggaataagt gccttacact ggctgcaaca gcatccagga     120

ggaggcattg tttccttgtt tatgctgagc tcagggaaga agaagcatgg aagattaatt     180

gccacaataa acatacagga aaagcacagc tccctgcaca tcacagcctc ccatcccaga     240

gactctgccg tctacatctg tgctgtcagc acctctatgt attcaggagg aggtgctgac     300

ggactcacct ttggcaaagg gactcatcta atcatccagc cct                       343
```

<210> SEQ ID NO 488
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 488

```
Lys Asn Glu Val Glu Gln Ser Pro Gln Asn Leu Thr Ala Gln Glu Gly
1               5                   10                  15

Glu Phe Ile Thr Ile Asn Cys Ser Tyr Ser Val Gly Ile Ser Ala Leu
            20                  25                  30

His Trp Leu Gln Gln His Pro Gly Gly Gly Ile Val Ser Leu Phe Met
```

```
        35                  40                  45

Leu Ser Ser Gly Lys Lys Lys His Gly Arg Leu Ile Ala Thr Ile Asn
    50                  55                  60

Ile Gln Glu Lys His Ser Ser Leu His Ile Thr Ala Ser His Pro Arg
65                  70                  75                  80

Asp Ser Ala Val Tyr Ile Cys Ala Val Ser Thr Ser Met Tyr Ser Gly
                85                  90                  95

Gly Gly Ala Asp Gly Leu Thr Phe Gly Lys Gly Thr His Leu Ile Ile
            100                 105                 110

Gln Pro


<210> SEQ ID NO 489
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 489

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Lys Gly Gly Tyr Ala Leu Asn Phe Gly Lys Gly Thr Ser Leu Leu
        115                 120                 125

Val Thr Pro His Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270
```

<210> SEQ ID NO 490
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 490

```
cagaaggagg tggagcagaa ttctggaccc ctcagtgttc cagagggagc cattgcctct     60

ctcaactgca cttacagtga ccgaggttcc cagtccttct tctggtacag acaatattct    120

gggaaaagcc ctgagttgat aatgtccata tactccaatg gtgacaaaga agatggaagg    180

tttacagcac agctcaataa agccagccag tatgtttctc tgctcatcag agactcccag    240

cccagtgatt cagccaccta cctctgtgcc gtgaagggag ggtatgcact caacttcggc    300

aaaggcacct cgctgttggt cacacccc                                       328
```

<210> SEQ ID NO 491
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 491

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Lys Gly Gly Tyr Ala
                85                  90                  95

Leu Asn Phe Gly Lys Gly Thr Ser Leu Leu Val Thr Pro
            100                 105
```

<210> SEQ ID NO 492
<211> LENGTH: 276
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 492

```
Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80
```

```
Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Ser Pro Pro Leu Pro Gly Asn Gln Phe Tyr Phe Gly Thr Gly
        115                 120                 125

Thr Ser Leu Thr Val Ile Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275


<210> SEQ ID NO 493
<211> LENGTH: 346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 493

gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt atagtccccc cctccccggt    300

aaccagttct attttgggac agggacaagt ttgacggtca ttccaa                   346


<210> SEQ ID NO 494
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30
```

```
Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Ser Pro
                85                  90                  95

Pro Leu Pro Gly Asn Gln Phe Tyr Phe Gly Thr Gly Thr Ser Leu Thr
            100                 105                 110

Val Ile Pro
        115


<210> SEQ ID NO 495
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495

Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Gly Glu Pro Asp
            100                 105                 110

Ser Asn Tyr Gln Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
```

260 265 270

<210> SEQ ID NO 496
<211> LENGTH: 334
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 496
gagctgaaag tggaacaaaa ccctctgttc ctgagcatgc aggagggaaa aaactatacc 60
atctactgca attattcaac cacttcagac agactgtatt ggtacaggca ggatcctggg 120
aaaagtctgg aatctctgtt tgtgttgcta tcaaatggag cagtgaagca ggagggacga 180
ttaatggcct cacttgatac caaagcccgt ctcagcaccc tccacatcac agctgccgtg 240
catgacctct ctgccaccta cttctgtgcc ggtgaacctg atagcaacta tcagttaatc 300
tggggcgctg ggaccaagct aattataaag ccag 334

<210> SEQ ID NO 497
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 497

Glu Leu Lys Val Glu Gln Asn Pro Leu Phe Leu Ser Met Gln Glu Gly
1 5 10 15

Lys Asn Tyr Thr Ile Tyr Cys Asn Tyr Ser Thr Thr Ser Asp Arg Leu
20 25 30

Tyr Trp Tyr Arg Gln Asp Pro Gly Lys Ser Leu Glu Ser Leu Phe Val
35 40 45

Leu Leu Ser Asn Gly Ala Val Lys Gln Glu Gly Arg Leu Met Ala Ser
50 55 60

Leu Asp Thr Lys Ala Arg Leu Ser Thr Leu His Ile Thr Ala Ala Val
65 70 75 80

His Asp Leu Ser Ala Thr Tyr Phe Cys Ala Gly Glu Pro Asp Ser Asn
85 90 95

Tyr Gln Leu Ile Trp Gly Ala Gly Thr Lys Leu Ile Ile Lys Pro
100 105 110

<210> SEQ ID NO 498
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 498

Met Met Lys Ser Leu Arg Val Leu Leu Val Ile Leu Trp Leu Gln Leu
1 5 10 15

Ser Trp Val Trp Ser Gln Gln Lys Glu Val Glu Gln Asn Ser Gly Pro
20 25 30

Leu Ser Val Pro Glu Gly Ala Ile Ala Ser Leu Asn Cys Thr Tyr Ser
35 40 45

Asp Arg Gly Ser Gln Ser Phe Phe Trp Tyr Arg Gln Tyr Ser Gly Lys
50 55 60

Ser Pro Glu Leu Ile Met Ser Ile Tyr Ser Asn Gly Asp Lys Glu Asp
65 70 75 80

Gly Arg Phe Thr Ala Gln Leu Asn Lys Ala Ser Gln Tyr Val Ser Leu
85 90 95

Leu Ile Arg Asp Ser Gln Pro Ser Asp Ser Ala Thr Tyr Leu Cys Ala
100 105 110

Val Gly Gly Ala Gly Gly Tyr Gln Lys Val Thr Phe Gly Thr Gly Thr
115 120 125

Lys Leu Gln Val Ile Pro Asn Ile Gln Asn Pro Asp Pro Ala Val Tyr
130 135 140

Gln Leu Arg Asp Ser Lys Ser Ser Asp Lys Ser Val Cys Leu Phe Thr
145 150 155 160

Asp Phe Asp Ser Gln Thr Asn Val Ser Gln Ser Lys Asp Ser Asp Val
165 170 175

Tyr Ile Thr Asp Lys Thr Val Leu Asp Met Arg Ser Met Asp Phe Lys
180 185 190

Ser Asn Ser Ala Val Ala Trp Ser Asn Lys Ser Asp Phe Ala Cys Ala
195 200 205

Asn Ala Phe Asn Asn Ser Ile Ile Pro Glu Asp Thr Phe Phe Pro Ser
210 215 220

Pro Glu Ser Ser Cys Asp Val Lys Leu Val Glu Lys Ser Phe Glu Thr
225 230 235 240

Asp Thr Asn Leu Asn Phe Gln Asn Leu Ser Val Ile Gly Phe Arg Ile
245 250 255

Leu Leu Leu Lys Val Ala Gly Phe Asn Leu Leu Met Thr Leu Arg Leu
260 265 270

Trp Ser Ser
275

<210> SEQ ID NO 499
<211> LENGTH: 337
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 499
cagaaggagg tggagcagaa ttctggaccc ctcagtgttc cagagggagc cattgcctct 60
ctcaactgca cttacagtga ccgaggttcc cagtccttct tctggtacag acaatattct 120
gggaaaagcc ctgagttgat aatgtccata tactccaatg gtgacaaaga agatggaagg 180
tttacagcac agctcaataa agccagccag tatgtttctc tgctcatcag agactcccag 240
cccagtgatt cagccaccta cctctgtgcc gtgggggggg ccgggggtta ccagaaagtt 300
acctttggaa ctggaacaaa gctccaagtc atcccaa 337

<210> SEQ ID NO 500
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 500

Gln Lys Glu Val Glu Gln Asn Ser Gly Pro Leu Ser Val Pro Glu Gly
1 5 10 15

```
Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Gly Gly Ala Gly Gly
                85                  90                  95

Tyr Gln Lys Val Thr Phe Gly Thr Gly Thr Lys Leu Gln Val Ile Pro
            100                 105                 110


<210> SEQ ID NO 501
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Met Gln Cys Gln Ala His Gly Ile Leu Gln Gln Met Trp Gly Ala Phe
1               5                   10                  15

Leu Leu Tyr Val Ser Met Lys Met Gly Gly Thr Ala Gly Gln Ser Leu
            20                  25                  30

Glu Gln Pro Ser Glu Val Thr Ala Val Glu Gly Ala Ile Val Gln Ile
        35                  40                  45

Asn Cys Thr Tyr Gln Thr Ser Gly Phe Tyr Gly Leu Ser Trp Tyr Gln
    50                  55                  60

Gln His Asp Gly Gly Ala Pro Thr Phe Leu Ser Tyr Asn Ala Leu Asp
65                  70                  75                  80

Gly Leu Glu Glu Thr Gly Arg Phe Ser Ser Phe Leu Ser Arg Ser Asp
                85                  90                  95

Ser Tyr Gly Tyr Leu Leu Leu Gln Glu Leu Gln Met Lys Asp Ser Ala
            100                 105                 110

Ser Tyr Phe Cys Ala Val Arg Asp Pro Leu Ser Gly Gly Tyr Asn Lys
        115                 120                 125

Leu Ile Phe Gly Ala Gly Thr Arg Leu Ala Val His Pro Tyr Ile Gln
    130                 135                 140

Asn Pro Asp Pro Ala Val Tyr Gln Leu Arg Asp Ser Lys Ser Ser Asp
145                 150                 155                 160

Lys Ser Val Cys Leu Phe Thr Asp Phe Asp Ser Gln Thr Asn Val Ser
                165                 170                 175

Gln Ser Lys Asp Ser Asp Val Tyr Ile Thr Asp Lys Thr Val Leu Asp
            180                 185                 190

Met Arg Ser Met Asp Phe Lys Ser Asn Ser Ala Val Ala Trp Ser Asn
        195                 200                 205

Lys Ser Asp Phe Ala Cys Ala Asn Ala Phe Asn Asn Ser Ile Ile Pro
    210                 215                 220

Glu Asp Thr Phe Phe Pro Ser Pro Glu Ser Ser Cys Asp Val Lys Leu
225                 230                 235                 240

Val Glu Lys Ser Phe Glu Thr Asp Thr Asn Leu Asn Phe Gln Asn Leu
                245                 250                 255

Ser Val Ile Gly Phe Arg Ile Leu Leu Leu Lys Val Ala Gly Phe Asn
```

```
            260                 265                 270

Leu Leu Met Thr Leu Arg Leu Trp Ser Ser
        275                 280


<210> SEQ ID NO 502
<211> LENGTH: 340
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 502

ggacaaagcc ttgagcagcc ctctgaagtg acagctgtgg aaggagccat tgtccagata     60

aactgcacgt accagacatc tgggttttat gggctgtcct ggtaccagca acatgatggc    120

ggagcaccca catttctttc ttacaatgct ctggatggtt tggaggagac aggtcgtttt    180

tcttcattcc ttagtcgctc tgatagttat ggttacctcc ttctacagga gctccagatg    240

aaagactctg cctcttactt ctgcgctgtg agagatcctc tttctggtgg ctacaataag    300

ctgatttttg gagcagggac caggctggct gtacacccat                          340


<210> SEQ ID NO 503
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Gly Gln Ser Leu Glu Gln Pro Ser Glu Val Thr Ala Val Glu Gly Ala
1               5                   10                  15

Ile Val Gln Ile Asn Cys Thr Tyr Gln Thr Ser Gly Phe Tyr Gly Leu
            20                  25                  30

Ser Trp Tyr Gln Gln His Asp Gly Gly Ala Pro Thr Phe Leu Ser Tyr
        35                  40                  45

Asn Ala Leu Asp Gly Leu Glu Glu Thr Gly Arg Phe Ser Ser Phe Leu
    50                  55                  60

Ser Arg Ser Asp Ser Tyr Gly Tyr Leu Leu Leu Gln Glu Leu Gln Met
65                  70                  75                  80

Lys Asp Ser Ala Ser Tyr Phe Cys Ala Val Arg Asp Pro Leu Ser Gly
                85                  90                  95

Gly Tyr Asn Lys Leu Ile Phe Gly Ala Gly Thr Arg Leu Ala Val His
            100                 105                 110

Pro


<210> SEQ ID NO 504
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30
```

```
Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Tyr Ser Gly Gly Gly
            100                 105                 110

Ala Asp Gly Leu Thr Phe Gly Lys Gly Thr His Leu Ile Ile Gln Pro
        115                 120                 125

Tyr Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 505
<211> LENGTH: 334
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 505

```
gatgctaaga ccacacagcc aaattcaatg gagagtaacg aagaagagcc tgttcacttg     60

ccttgtaacc actccacaat cagtggaact gattacatac attggtatcg acagcttccc    120

tcccagggtc cagagtacgt gattcatggt cttacaagca atgtgaacaa cagaatggcc    180

tctctggcaa tcgctgaaga cagaaagtcc agtaccttga tcctgcaccg tgctaccttg    240

agagatgctg ctgtgtacta ctgcatcctg tattcaggag gaggtgctga cggactcacc    300

tttggcaaag ggactcatct aatcatccag ccct                                334
```

<210> SEQ ID NO 506
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 506

```
Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Tyr Ser Gly Gly Gly Ala
                85                  90                  95

Asp Gly Leu Thr Phe Gly Lys Gly Thr His Leu Ile Ile Gln Pro
            100                 105                 110


<210> SEQ ID NO 507
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Met Ala Gln Glu Leu Gly Met Gln Cys Gln Ala Arg Gly Ile Leu Gln
1               5                   10                  15

Gln Met Trp Gly Val Phe Leu Leu Tyr Val Ser Met Lys Met Gly Gly
            20                  25                  30

Thr Thr Gly Gln Asn Ile Asp Gln Pro Thr Glu Met Thr Ala Thr Glu
        35                  40                  45

Gly Ala Ile Val Gln Ile Asn Cys Thr Tyr Gln Thr Ser Gly Phe Asn
    50                  55                  60

Gly Leu Phe Trp Tyr Gln Gln His Ala Gly Glu Ala Pro Thr Phe Leu
65                  70                  75                  80

Ser Tyr Asn Val Leu Asp Gly Leu Glu Glu Lys Gly Arg Phe Ser Ser
                85                  90                  95

Phe Leu Ser Arg Ser Lys Gly Tyr Ser Tyr Leu Leu Leu Lys Glu Leu
            100                 105                 110

Gln Met Lys Asp Ser Ala Ser Tyr Leu Cys Ala Gly Leu Phe Gly Asn
        115                 120                 125

Thr Pro Leu Val Phe Gly Lys Gly Thr Arg Leu Ser Val Ile Ala Asn
    130                 135                 140

Ile Gln Asn Pro Asp Pro Ala Val Tyr Gln Leu Arg Asp Ser Lys Ser
145                 150                 155                 160

Ser Asp Lys Ser Val Cys Leu Phe Thr Asp Phe Asp Ser Gln Thr Asn
                165                 170                 175

Val Ser Gln Ser Lys Asp Ser Asp Val Tyr Ile Thr Asp Lys Thr Val
            180                 185                 190

Leu Asp Met Arg Ser Met Asp Phe Lys Ser Asn Ser Ala Val Ala Trp
        195                 200                 205

Ser Asn Lys Ser Asp Phe Ala Cys Ala Asn Ala Phe Asn Asn Ser Ile
    210                 215                 220

Ile Pro Glu Asp Thr Phe Phe Pro Ser Pro Glu Ser Ser Cys Asp Val
225                 230                 235                 240

Lys Leu Val Glu Lys Ser Phe Glu Thr Asp Thr Asn Leu Asn Phe Gln
                245                 250                 255
```

Asn Leu Ser Val Ile Gly Phe Arg Ile Leu Leu Leu Lys Val Ala Gly
            260                 265                 270

Phe Asn Leu Leu Met Thr Leu Arg Leu Trp Ser Ser
        275                 280

<210> SEQ ID NO 508
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 508
ggacaaaaca ttgaccagcc cactgagatg acagctacgg aaggtgccat tgtccagatc 60
aactgcacgt accagacatc tgggttcaac gggctgttct ggtaccagca acatgctggc 120
gaagcaccca catttctgtc ttacaatgtt ctggatggtt tggaggagaa aggtcgtttt 180
tcttcattcc ttagtcggtc taaagggtac agttacctcc ttttgaagga gctccagatg 240
aaagactctg cctcttacct ctgtgctggc ctcttcggaa acacacctct tgtctttgga 300
aagggcacaa gactttctgt gattgcaa 328

<210> SEQ ID NO 509
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Gly Gln Asn Ile Asp Gln Pro Thr Glu Met Thr Ala Thr Glu Gly Ala
1               5                   10                  15

Ile Val Gln Ile Asn Cys Thr Tyr Gln Thr Ser Gly Phe Asn Gly Leu
            20                  25                  30

Phe Trp Tyr Gln Gln His Ala Gly Glu Ala Pro Thr Phe Leu Ser Tyr
        35                  40                  45

Asn Val Leu Asp Gly Leu Glu Glu Lys Gly Arg Phe Ser Ser Phe Leu
    50                  55                  60

Ser Arg Ser Lys Gly Tyr Ser Tyr Leu Leu Leu Lys Glu Leu Gln Met
65                  70                  75                  80

Lys Asp Ser Ala Ser Tyr Leu Cys Ala Gly Leu Phe Gly Asn Thr Pro
                85                  90                  95

Leu Val Phe Gly Lys Gly Thr Arg Leu Ser Val Ile Ala
            100                 105

<210> SEQ ID NO 510
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

-continued

```
Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Phe Asn Thr Asp Lys Leu Ile Phe Gly Thr Gly Thr Arg Leu
        115                 120                 125

Gln Val Phe Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

<210> SEQ ID NO 511
<211> LENGTH: 337
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 511

```
gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt attttaacac cgacaagctc    300

atctttggga ctgggaccag attacaagtc tttccaa                             337
```

<210> SEQ ID NO 512
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 512

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Phe Asn
85 90 95

Thr Asp Lys Leu Ile Phe Gly Thr Gly Thr Arg Leu Gln Val Phe Pro
100 105 110

<210> SEQ ID NO 513
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 513

Met Met Lys Ser Leu Arg Val Leu Leu Val Ile Leu Trp Leu Gln Leu
1 5 10 15

Ser Trp Val Trp Ser Gln Gln Lys Glu Val Glu Gln Asp Pro Gly Pro
20 25 30

Leu Ser Val Pro Glu Gly Ala Ile Val Ser Leu Asn Cys Thr Tyr Ser
35 40 45

Asn Ser Ala Phe Gln Tyr Phe Met Trp Tyr Arg Gln Tyr Ser Arg Lys
50 55 60

Gly Pro Glu Leu Leu Met Tyr Thr Tyr Ser Ser Gly Asn Lys Glu Asp
65 70 75 80

Gly Arg Phe Thr Ala Gln Val Asp Lys Ser Ser Lys Tyr Ile Ser Leu
85 90 95

Phe Ile Arg Asp Ser Gln Pro Ser Asp Ser Ala Thr Tyr Leu Cys Ala
100 105 110

Met Gly Gly Gln Gly Gly Ala Asp Gly Leu Thr Phe Gly Lys Gly Thr
115 120 125

His Leu Ile Ile Gln Pro Tyr Ile Gln Asn Pro Asp Pro Ala Val Tyr
130 135 140

Gln Leu Arg Asp Ser Lys Ser Ser Asp Lys Ser Val Cys Leu Phe Thr
145 150 155 160

Asp Phe Asp Ser Gln Thr Asn Val Ser Gln Ser Lys Asp Ser Asp Val
165 170 175

Tyr Ile Thr Asp Lys Thr Val Leu Asp Met Arg Ser Met Asp Phe Lys
180 185 190

Ser Asn Ser Ala Val Ala Trp Ser Asn Lys Ser Asp Phe Ala Cys Ala
195 200 205

Asn Ala Phe Asn Asn Ser Ile Ile Pro Glu Asp Thr Phe Phe Pro Ser
210 215 220

Pro Glu Ser Ser Cys Asp Val Lys Leu Val Glu Lys Ser Phe Glu Thr
225 230 235 240

```
Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275
```

<210> SEQ ID NO 514
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 514

```
cagaaggagg tggagcagga tcctggacca ctcagtgttc cagagggagc cattgtttct      60

ctcaactgca cttacagcaa cagtgctttt caatacttca tgtggtacag acagtattcc     120

agaaaaggcc ctgagttgct gatgtacaca tactccagtg gtaacaaaga agatggaagg     180

tttacagcac aggtcgataa atccagcaag tatatctcct tgttcatcag agactcacag     240

cccagtgatt cagccaccta cctctgtgca atggggggcc aaggaggtgc tgacggactc     300

acctttggca aagggactca tctaatcatc cagccct                               337
```

<210> SEQ ID NO 515
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

```
Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Gly Gly Gln Gly Gly
                85                  90                  95

Ala Asp Gly Leu Thr Phe Gly Lys Gly Thr His Leu Ile Ile Gln Pro
            100                 105                 110
```

<210> SEQ ID NO 516
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

```
Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
```

```
            20                  25                  30

Glu Gly Glu Asp Val Ser Met Asn Cys Thr Ser Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly Pro Lys Arg
            100                 105                 110

Glu Tyr Gly Asn Lys Leu Val Phe Gly Ala Gly Thr Ile Leu Arg Val
        115                 120                 125

Lys Ser Tyr Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270
```

<210> SEQ ID NO 517
<211> LENGTH: 337
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 517

```
ggtcaacagc tgaatcagag tcctcaatct atgtttatcc aggaaggaga agatgtctcc     60

atgaactgca cttcttcaag catatttaac acctggctat ggtacaagca ggaccctggg    120

gaaggtcctg tcctcttgat agccttatat aaggctggtg aattgacctc aaatggaaga    180

ctgactgctc agtttggtat aaccagaaag gacagcttcc tgaatatctc agcatccata    240

cctagtgatg taggcatcta cttctgtgct ggccccaaga gggaatatgg aaacaagctg    300

gtctttggcg caggaaccat tctgagagtc aagtcct                             337
```

<210> SEQ ID NO 518
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 518

Gly Gln Gln Leu Asn Gln Ser Pro Gln Ser Met Phe Ile Gln Glu Gly
1 5 10 15

Glu Asp Val Ser Met Asn Cys Thr Ser Ser Ser Ile Phe Asn Thr Trp
20 25 30

Leu Trp Tyr Lys Gln Asp Pro Gly Glu Gly Pro Val Leu Leu Ile Ala
35 40 45

Leu Tyr Lys Ala Gly Glu Leu Thr Ser Asn Gly Arg Leu Thr Ala Gln
50 55 60

Phe Gly Ile Thr Arg Lys Asp Ser Phe Leu Asn Ile Ser Ala Ser Ile
65 70 75 80

Pro Ser Asp Val Gly Ile Tyr Phe Cys Ala Gly Pro Lys Arg Glu Tyr
85 90 95

Gly Asn Lys Leu Val Phe Gly Ala Gly Thr Ile Leu Arg Val Lys Ser
100 105 110

<210> SEQ ID NO 519
<211> LENGTH: 272
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 519

Met Ala Leu Gln Ser Thr Leu Gly Ala Val Trp Leu Gly Leu Leu Leu
1 5 10 15

Asn Ser Leu Trp Lys Val Ala Glu Ser Lys Asp Gln Val Phe Gln Pro
20 25 30

Ser Thr Val Ala Ser Ser Glu Gly Ala Val Val Glu Ile Phe Cys Asn
35 40 45

His Ser Val Ser Asn Ala Tyr Asn Phe Phe Trp Tyr Leu His Phe Pro
50 55 60

Gly Cys Ala Pro Arg Leu Leu Val Lys Gly Ser Lys Pro Ser Gln Gln
65 70 75 80

Gly Arg Tyr Asn Met Thr Tyr Glu Arg Phe Ser Ser Ser Leu Leu Ile
85 90 95

Leu Gln Val Arg Glu Ala Asp Ala Ala Val Tyr Tyr Cys Ala Val Glu
100 105 110

Asp Asn Asn Asn Asn Asp Met Arg Phe Gly Ala Gly Thr Arg Leu Thr
115 120 125

Val Lys Pro Asn Ile Gln Asn Pro Asp Pro Ala Val Tyr Gln Leu Arg
130 135 140

Asp Ser Lys Ser Ser Asp Lys Ser Val Cys Leu Phe Thr Asp Phe Asp
145 150 155 160

Ser Gln Thr Asn Val Ser Gln Ser Lys Asp Ser Asp Val Tyr Ile Thr
165 170 175

Asp Lys Thr Val Leu Asp Met Arg Ser Met Asp Phe Lys Ser Asn Ser
180 185 190

Ala Val Ala Trp Ser Asn Lys Ser Asp Phe Ala Cys Ala Asn Ala Phe
195 200 205

Asn Asn Ser Ile Ile Pro Glu Asp Thr Phe Phe Pro Ser Pro Glu Ser
210 215 220

Ser Cys Asp Val Lys Leu Val Glu Lys Ser Phe Glu Thr Asp Thr Asn
225 230 235 240

```
Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270


<210> SEQ ID NO 520
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 520

aaggaccaag tgtttcagcc ttccacagtg gcatcttcag agggagctgt ggtggaaatc      60

ttctgtaatc actctgtgtc caatgcttac aacttcttct ggtaccttca cttcccggga     120

tgtgcaccaa gactccttgt taaaggctca aagccttctc agcagggacg atacaacatg     180

acctatgaac ggttctcttc atcgctgctc atcctccagg tgcgggaggc agatgctgct     240

gtttactact gtgctgtgga ggataacaat aacaatgaca tgcgctttgg agcagggacc     300

agactgacag taaaaccaa                                                  319


<210> SEQ ID NO 521
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

Lys Asp Gln Val Phe Gln Pro Ser Thr Val Ala Ser Ser Glu Gly Ala
1               5                   10                  15

Val Val Glu Ile Phe Cys Asn His Ser Val Ser Asn Ala Tyr Asn Phe
            20                  25                  30

Phe Trp Tyr Leu His Phe Pro Gly Cys Ala Pro Arg Leu Leu Val Lys
        35                  40                  45

Gly Ser Lys Pro Ser Gln Gln Gly Arg Tyr Asn Met Thr Tyr Glu Arg
    50                  55                  60

Phe Ser Ser Ser Leu Leu Ile Leu Gln Val Arg Glu Ala Asp Ala Ala
65                  70                  75                  80

Val Tyr Tyr Cys Ala Val Glu Asp Asn Asn Asn Asn Asp Met Arg Phe
                85                  90                  95

Gly Ala Gly Thr Arg Leu Thr Val Lys Pro
            100                 105


<210> SEQ ID NO 522
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 522

Met Gln Cys Gln Ala His Gly Ile Leu Gln Gln Met Trp Gly Ala Phe
1               5                   10                  15

Leu Leu Tyr Val Ser Met Lys Met Gly Gly Thr Ala Gly Gln Ser Leu
            20                  25                  30

Glu Gln Pro Ser Glu Val Thr Ala Val Glu Gly Ala Ile Val Gln Ile
```

```
        35                  40                  45

Asn Cys Thr Tyr Gln Thr Ser Gly Phe Tyr Gly Leu Ser Trp Tyr Gln
    50                  55                  60

Gln His Asp Gly Gly Ala Pro Thr Phe Leu Ser Tyr Asn Ala Leu Asp
65                  70                  75                  80

Gly Leu Glu Glu Thr Gly Arg Phe Ser Ser Phe Leu Ser Arg Ser Asp
                85                  90                  95

Ser Tyr Gly Tyr Leu Leu Leu Gln Glu Leu Gln Met Lys Asp Ser Ala
            100                 105                 110

Ser Tyr Phe Cys Ala Val Asn Asn Asn Ala Arg Leu Met Phe Gly Asp
        115                 120                 125

Gly Thr Gln Leu Val Val Lys Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275
```

<210> SEQ ID NO 523
<211> LENGTH: 325
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 523

```
ggacaaagcc ttgagcagcc ctctgaagtg acagctgtgg aaggagccat tgtccagata     60

aactgcacgt accagacatc tgggttttat gggctgtcct ggtaccagca acatgatggc    120

ggagcaccca catttctttc ttacaatgct ctggatggtt tggaggagac aggtcgtttt    180

tcttcattcc ttagtcgctc tgatagttat ggttacctcc ttctacagga gctccagatg    240

aaagactctg cctcttactt ctgcgctgtg aataacaatg ccagactcat gtttggagat    300

ggaactcagc tggtggtgaa gccca                                          325
```

<210> SEQ ID NO 524
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 524

Gly Gln Ser Leu Glu Gln Pro Ser Glu Val Thr Ala Val Glu Gly Ala
1 5 10 15

Ile Val Gln Ile Asn Cys Thr Tyr Gln Thr Ser Gly Phe Tyr Gly Leu
20 25 30

Ser Trp Tyr Gln Gln His Asp Gly Gly Ala Pro Thr Phe Leu Ser Tyr
35 40 45

Asn Ala Leu Asp Gly Leu Glu Glu Thr Gly Arg Phe Ser Ser Phe Leu
50 55 60

Ser Arg Ser Asp Ser Tyr Gly Tyr Leu Leu Leu Gln Glu Leu Gln Met
65 70 75 80

Lys Asp Ser Ala Ser Tyr Phe Cys Ala Val Asn Asn Asn Ala Arg Leu
85 90 95

Met Phe Gly Asp Gly Thr Gln Leu Val Val Lys Pro
100 105

<210> SEQ ID NO 525
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 525

Met Ala Gln Glu Leu Gly Met Gln Cys Gln Ala Arg Gly Ile Leu Gln
1 5 10 15

Gln Met Trp Gly Val Phe Leu Leu Tyr Val Ser Met Lys Met Gly Gly
20 25 30

Thr Thr Gly Gln Asn Ile Asp Gln Pro Thr Glu Met Thr Ala Thr Glu
35 40 45

Gly Ala Ile Val Gln Ile Asn Cys Thr Tyr Gln Thr Ser Gly Phe Asn
50 55 60

Gly Leu Phe Trp Tyr Gln Gln His Ala Gly Glu Ala Pro Thr Phe Leu
65 70 75 80

Ser Tyr Asn Val Leu Asp Gly Leu Glu Glu Lys Gly Arg Phe Ser Ser
85 90 95

Phe Leu Ser Arg Ser Lys Gly Tyr Ser Tyr Leu Leu Leu Lys Glu Leu
100 105 110

Gln Met Lys Asp Ser Ala Ser Tyr Leu Cys Ala Val Arg Asp Pro Gly
115 120 125

Asn Asp Met Arg Phe Gly Ala Gly Thr Arg Leu Thr Val Lys Pro Asn
130 135 140

Ile Gln Asn Pro Asp Pro Ala Val Tyr Gln Leu Arg Asp Ser Lys Ser
145 150 155 160

Ser Asp Lys Ser Val Cys Leu Phe Thr Asp Phe Asp Ser Gln Thr Asn
165 170 175

Val Ser Gln Ser Lys Asp Ser Asp Val Tyr Ile Thr Asp Lys Thr Val
180 185 190

Leu Asp Met Arg Ser Met Asp Phe Lys Ser Asn Ser Ala Val Ala Trp
195 200 205

Ser Asn Lys Ser Asp Phe Ala Cys Ala Asn Ala Phe Asn Asn Ser Ile
210 215 220

Ile Pro Glu Asp Thr Phe Phe Pro Ser Pro Glu Ser Ser Cys Asp Val
225 230 235 240

Lys Leu Val Glu Lys Ser Phe Glu Thr Asp Thr Asn Leu Asn Phe Gln
245 250 255

Asn Leu Ser Val Ile Gly Phe Arg Ile Leu Leu Leu Lys Val Ala Gly
260 265 270

Phe Asn Leu Leu Met Thr Leu Arg Leu Trp Ser Ser
275 280

<210> SEQ ID NO 526
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 526
ggacaaaaca ttgaccagcc cactgagatg acagctacgg aaggtgccat tgtccagatc 60
aactgcacgt accagacatc tgggttcaac gggctgttct ggtaccagca acatgctggc 120
gaagcaccca catttctgtc ttacaatgtt ctggatggtt tggaggagaa aggtcgtttt 180
tcttcattcc ttagtcggtc taaagggtac agttacctcc ttttgaagga gctccagatg 240
aaagactctg cctcttacct ctgtgctgtg agagatccgg gcaatgacat gcgctttgga 300
gcagggacca gactgacagt aaaaccaa 328

<210> SEQ ID NO 527
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 527

Gly Gln Asn Ile Asp Gln Pro Thr Glu Met Thr Ala Thr Glu Gly Ala
1 5 10 15

Ile Val Gln Ile Asn Cys Thr Tyr Gln Thr Ser Gly Phe Asn Gly Leu
20 25 30

Phe Trp Tyr Gln Gln His Ala Gly Glu Ala Pro Thr Phe Leu Ser Tyr
35 40 45

Asn Val Leu Asp Gly Leu Glu Glu Lys Gly Arg Phe Ser Ser Phe Leu
50 55 60

Ser Arg Ser Lys Gly Tyr Ser Tyr Leu Leu Leu Lys Glu Leu Gln Met
65 70 75 80

Lys Asp Ser Ala Ser Tyr Leu Cys Ala Val Arg Asp Pro Gly Asn Asp
85 90 95

Met Arg Phe Gly Ala Gly Thr Arg Leu Thr Val Lys Pro
100 105

<210> SEQ ID NO 528
<211> LENGTH: 276
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 528

Met Thr Arg Val Ser Leu Leu Trp Ala Val Val Val Ser Thr Cys Leu
1 5 10 15

Glu Ser Gly Met Ala Gln Thr Val Thr Gln Ser Gln Pro Glu Met Ser

```
            20                  25                  30

Val Gln Glu Ala Glu Thr Val Thr Leu Ser Cys Thr Tyr Asp Thr Ser
        35                  40                  45

Glu Asn Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Gly Gly Glu Thr Ser Gly Ser Arg Leu Thr Phe Gly Glu Gly
        115                 120                 125

Thr Gln Leu Thr Val Asn Pro Asp Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275
```

<210> SEQ ID NO 529
<211> LENGTH: 346
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 529

```
gcccagacag tcactcagtc tcaaccagag atgtctgtgc aggaggcaga gactgtgacc     60

ctgagttgca catatgacac cagtgagaat aattattatt tgttctggta caagcagcct    120

cccagcaggc agatgattct cgttattcgc caagaagctt ataagcaaca gaatgcaacg    180

gagaatcgtt tctctgtgaa cttccagaaa gcagccaaat ccttcagtct caagatctca    240

gactcacagc tgggggacac tgcgatgtat ttctgtgctt tcgggggaga aaccagtggc    300

tctaggttga cctttgggga aggaacacag ctcacagtga atcctg                   346
```

<210> SEQ ID NO 530
<211> LENGTH: 115
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 530

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Asn Asn Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Thr Ala Met Tyr Phe Cys Ala Phe Gly Gly
85 90 95

Glu Thr Ser Gly Ser Arg Leu Thr Phe Gly Glu Gly Thr Gln Leu Thr
100 105 110

Val Asn Pro
115

<210> SEQ ID NO 531
<211> LENGTH: 269
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 531

Met Arg Gln Val Ala Arg Val Ile Val Phe Leu Thr Leu Ser Thr Leu
1 5 10 15

Ser Leu Ala Lys Thr Thr Gln Pro Ile Ser Met Asp Ser Tyr Glu Gly
20 25 30

Gln Glu Val Asn Ile Thr Cys Ser His Asn Asn Ile Ala Thr Asn Asp
35 40 45

Tyr Ile Thr Trp Tyr Gln Gln Phe Pro Ser Gln Gly Pro Arg Phe Ile
50 55 60

Ile Gln Gly Tyr Lys Thr Lys Val Thr Asn Glu Val Ala Ser Leu Phe
65 70 75 80

Ile Pro Ala Asp Arg Lys Ser Ser Thr Leu Ser Leu Pro Arg Val Ser
85 90 95

Leu Ser Asp Thr Ala Val Tyr Tyr Cys Leu Val Gly Asp Lys Gly Ser
100 105 110

Asn Tyr Gln Leu Ile Trp Gly Ala Gly Thr Lys Leu Ile Ile Lys Pro
115 120 125

Asp Ile Gln Asn Pro Asp Pro Ala Val Tyr Gln Leu Arg Asp Ser Lys
130 135 140

Ser Ser Asp Lys Ser Val Cys Leu Phe Thr Asp Phe Asp Ser Gln Thr
145 150 155 160

Asn Val Ser Gln Ser Lys Asp Ser Asp Val Tyr Ile Thr Asp Lys Thr
165 170 175

Val Leu Asp Met Arg Ser Met Asp Phe Lys Ser Asn Ser Ala Val Ala
180 185 190

Trp Ser Asn Lys Ser Asp Phe Ala Cys Ala Asn Ala Phe Asn Asn Ser
195 200 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 532
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 532
cttgctaaga ccacccagcc catctccatg gactcatatg aaggacaaga agtgaacata     60
acctgtagcc acaacaacat tgctacaaat gattatatca cgtggtacca acagtttccc    120
agccaaggac cacgatttat tattcaagga tacaagacaa aagttacaaa cgaagtggcc    180
tccctgttta tccctgccga cagaaagtcc agcactctga gcctgccccg ggtttccctg    240
agcgacactg ctgtgtacta ctgcctcgtg ggtgacaaag gaagcaacta tcagttaatc    300
tggggcgctg ggaccaagct aattataaag ccag                                334

<210> SEQ ID NO 533
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 533

Leu Ala Lys Thr Thr Gln Pro Ile Ser Met Asp Ser Tyr Glu Gly Gln
1               5                   10                  15

Glu Val Asn Ile Thr Cys Ser His Asn Asn Ile Ala Thr Asn Asp Tyr
            20                  25                  30

Ile Thr Trp Tyr Gln Gln Phe Pro Ser Gln Gly Pro Arg Phe Ile Ile
        35                  40                  45

Gln Gly Tyr Lys Thr Lys Val Thr Asn Glu Val Ala Ser Leu Phe Ile
    50                  55                  60

Pro Ala Asp Arg Lys Ser Ser Thr Leu Ser Leu Pro Arg Val Ser Leu
65                  70                  75                  80

Ser Asp Thr Ala Val Tyr Tyr Cys Leu Val Gly Asp Lys Gly Ser Asn
                85                  90                  95

Tyr Gln Leu Ile Trp Gly Ala Gly Thr Lys Leu Ile Ile Lys Pro
            100                 105                 110

<210> SEQ ID NO 534
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

Met Thr Ser Ile Arg Ala Val Phe Ile Phe Leu Trp Leu Gln Leu Asp

-continued

```
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Tyr Leu Pro Asp Met Arg Phe Gly Ala Gly Thr Arg Leu Thr Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 535
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 535

```
ggagagaatg tggagcagca tccttcaacc ctgagtgtcc aggagggaga cagcgctgtt      60

atcaagtgta cttattcaga cagtgcctca aactacttcc cttggtataa gcaagaactt     120

ggaaaaagac ctcagcttat tatagacatt cgttcaaatg tgggcgaaaa gaaagaccaa     180

cgaattgctg ttacattgaa caagacagcc aaacatttct ccctgcacat cacagagacc     240

caacctgaag actcggctgt ctacttctgt gcagcaagtt atctccctga catgcgcttt     300

ggagcaggga ccagactgac agtaaaacca a                                    331
```

<210> SEQ ID NO 536
<211> LENGTH: 110
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 536

Gly Glu Asn Val Glu Gln His Pro Ser Thr Leu Ser Val Gln Glu Gly
1 5 10 15

Asp Ser Ala Val Ile Lys Cys Thr Tyr Ser Asp Ser Ala Ser Asn Tyr
20 25 30

Phe Pro Trp Tyr Lys Gln Glu Leu Gly Lys Arg Pro Gln Leu Ile Ile
35 40 45

Asp Ile Arg Ser Asn Val Gly Glu Lys Lys Asp Gln Arg Ile Ala Val
50 55 60

Thr Leu Asn Lys Thr Ala Lys His Phe Ser Leu His Ile Thr Glu Thr
65 70 75 80

Gln Pro Glu Asp Ser Ala Val Tyr Phe Cys Ala Ala Ser Tyr Leu Pro
85 90 95

Asp Met Arg Phe Gly Ala Gly Thr Arg Leu Thr Val Lys Pro
100 105 110

<210> SEQ ID NO 537
<211> LENGTH: 279
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 537

Met Asn Met Leu Thr Ala Ser Leu Leu Arg Ala Val Ile Ala Ser Ile
1 5 10 15

Cys Val Val Ser Ser Met Ala Gln Lys Val Thr Gln Ala Gln Thr Glu
20 25 30

Ile Ser Val Val Glu Lys Glu Asp Val Thr Leu Asp Cys Val Tyr Glu
35 40 45

Thr Arg Asp Thr Thr Tyr Tyr Leu Phe Trp Tyr Lys Gln Pro Pro Ser
50 55 60

Gly Glu Leu Val Phe Leu Ile Arg Arg Asn Ser Phe Asp Glu Gln Asn
65 70 75 80

Glu Ile Ser Gly Arg Tyr Ser Trp Asn Phe Gln Lys Ser Thr Ser Ser
85 90 95

Phe Asn Phe Thr Ile Thr Ala Ser Gln Val Val Asp Ser Ala Val Tyr
100 105 110

Phe Cys Ala Leu Ser Glu Leu Lys Ala Ala Gly Asn Lys Leu Thr Phe
115 120 125

Gly Gly Gly Thr Arg Val Leu Val Lys Pro Asn Ile Gln Asn Pro Asp
130 135 140

Pro Ala Val Tyr Gln Leu Arg Asp Ser Lys Ser Ser Asp Lys Ser Val
145 150 155 160

Cys Leu Phe Thr Asp Phe Asp Ser Gln Thr Asn Val Ser Gln Ser Lys
165 170 175

Asp Ser Asp Val Tyr Ile Thr Asp Lys Thr Val Leu Asp Met Arg Ser
180 185 190

Met Asp Phe Lys Ser Asn Ser Ala Val Ala Trp Ser Asn Lys Ser Asp
195 200 205

Phe Ala Cys Ala Asn Ala Phe Asn Asn Ser Ile Ile Pro Glu Asp Thr
210 215 220

```
Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
        275
```

<210> SEQ ID NO 538
<211> LENGTH: 349
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 538

```
gctcagaagg taactcaagc gcagactgaa atttctgtgg tggagaagga ggatgtgacc      60

ttggactgtg tgtatgaaac ccgtgatact acttattact tattctggta caagcaacca     120

ccaagtggag aattggtttt ccttattcgt cggaactctt ttgatgagca aaatgaaata     180

agtggtcggt attcttggaa cttccagaaa tccaccagtt ccttcaactt caccatcaca     240

gcctcacaag tcgtggactc agcagtatac ttctgtgctc tgagtgagct caaagctgca     300

ggcaacaagc taacttttgg aggaggaacc agggtgctag ttaaaccaa                 349
```

<210> SEQ ID NO 539
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 539

```
Ala Gln Lys Val Thr Gln Ala Gln Thr Glu Ile Ser Val Val Glu Lys
1               5                   10                  15

Glu Asp Val Thr Leu Asp Cys Val Tyr Glu Thr Arg Asp Thr Thr Tyr
            20                  25                  30

Tyr Leu Phe Trp Tyr Lys Gln Pro Pro Ser Gly Glu Leu Val Phe Leu
        35                  40                  45

Ile Arg Arg Asn Ser Phe Asp Glu Gln Asn Glu Ile Ser Gly Arg Tyr
    50                  55                  60

Ser Trp Asn Phe Gln Lys Ser Thr Ser Ser Phe Asn Phe Thr Ile Thr
65                  70                  75                  80

Ala Ser Gln Val Val Asp Ser Ala Val Tyr Phe Cys Ala Leu Ser Glu
                85                  90                  95

Leu Lys Ala Ala Gly Asn Lys Leu Thr Phe Gly Gly Gly Thr Arg Val
            100                 105                 110

Leu Val Lys Pro
        115
```

<210> SEQ ID NO 540
<211> LENGTH: 272
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 540

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Lys Val Tyr
            100                 105                 110

Gly Gly Ser Gln Gly Asn Leu Ile Phe Gly Lys Gly Thr Lys Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 541
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 541
cttgctaaga ccacccagcc catctccatg gactcatatg aaggacaaga agtgaacata 60
acctgtagcc acaacaacat tgctacaaat gattatatca cgtggtacca acagtttccc 120
agccaaggac cacgatttat tattcaagga tacaagacaa aagttacaaa cgaagtggcc 180
tccctgttta tccctgccga cagaaagtcc agcactctga gcctgccccg ggtttccctg 240
agcgacactg ctgtgtacta ctgcctcgtg ggtgacaagg tttatggagg aagccaagga 300
aatctcatct ttggaaaagg cactaaactc tctgttaaac caa 343

<210> SEQ ID NO 542
<211> LENGTH: 114

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 542

Leu Ala Lys Thr Thr Gln Pro Ile Ser Met Asp Ser Tyr Glu Gly Gln
1 5 10 15

Glu Val Asn Ile Thr Cys Ser His Asn Asn Ile Ala Thr Asn Asp Tyr
20 25 30

Ile Thr Trp Tyr Gln Gln Phe Pro Ser Gln Gly Pro Arg Phe Ile Ile
35 40 45

Gln Gly Tyr Lys Thr Lys Val Thr Asn Glu Val Ala Ser Leu Phe Ile
50 55 60

Pro Ala Asp Arg Lys Ser Ser Thr Leu Ser Leu Pro Arg Val Ser Leu
65 70 75 80

Ser Asp Thr Ala Val Tyr Tyr Cys Leu Val Gly Asp Lys Val Tyr Gly
85 90 95

Gly Ser Gln Gly Asn Leu Ile Phe Gly Lys Gly Thr Lys Leu Ser Val
100 105 110

Lys Pro

<210> SEQ ID NO 543
<211> LENGTH: 277
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 543

Met Ser Leu Ser Ser Leu Leu Lys Val Val Thr Ala Ser Leu Trp Leu
1 5 10 15

Gly Pro Gly Ile Ala Gln Lys Ile Thr Gln Thr Gln Pro Gly Met Phe
20 25 30

Val Gln Glu Lys Glu Ala Val Thr Leu Asp Cys Thr Tyr Asp Thr Ser
35 40 45

Asp Pro Ser Tyr Gly Leu Phe Trp Tyr Lys Gln Pro Ser Ser Gly Glu
50 55 60

Met Ile Phe Leu Ile Tyr Gln Gly Ser Tyr Asp Gln Gln Asn Ala Thr
65 70 75 80

Glu Gly Arg Tyr Ser Leu Asn Phe Gln Lys Ala Arg Lys Ser Ala Asn
85 90 95

Leu Val Ile Ser Ala Ser Gln Leu Gly Asp Ser Ala Met Tyr Phe Cys
100 105 110

Ala Met Arg Glu Gly Gln Asp Ser Ser Tyr Lys Leu Ile Phe Gly Ser
115 120 125

Gly Thr Arg Leu Leu Val Arg Pro Asp Ile Gln Asn Pro Asp Pro Ala
130 135 140

Val Tyr Gln Leu Arg Asp Ser Lys Ser Ser Asp Lys Ser Val Cys Leu
145 150 155 160

Phe Thr Asp Phe Asp Ser Gln Thr Asn Val Ser Gln Ser Lys Asp Ser
165 170 175

Asp Val Tyr Ile Thr Asp Lys Thr Val Leu Asp Met Arg Ser Met Asp
180 185 190

Phe Lys Ser Asn Ser Ala Val Ala Trp Ser Asn Lys Ser Asp Phe Ala

```
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275
```

<210> SEQ ID NO 544
<211> LENGTH: 349
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 544

```
gcccagaaga taactcaaac ccaaccagga atgttcgtgc aggaaaagga ggctgtgact     60

ctggactgca catatgacac cagtgatcca agttatggtc tattctggta caagcagccc    120

agcagtgggg aaatgatttt tcttatttat caggggtctt atgaccagca aaatgcaaca    180

gaaggtcgct actcattgaa tttccagaag gcaagaaaat ccgccaacct tgtcatctcc    240

gcttcacaac tgggggactc agcaatgtat ttctgtgcaa tgagagaggg ccaggatagc    300

agctataaat tgatcttcgg gagtgggacc agactgctgg tcaggcctg                349
```

<210> SEQ ID NO 545
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 545

```
Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Gln Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Gln Asp Ser Ser Tyr Lys Leu Ile Phe Gly Ser Gly Thr Arg Leu
            100                 105                 110

Leu Val Arg Pro
        115
```

<210> SEQ ID NO 546
<211> LENGTH: 281
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 546

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
            85                  90                  95

Lys His Leu Ser Leu His Ile Val Pro Ser Gln Pro Gly Asp Ser Ala
            100                 105                 110

Val Tyr Phe Cys Ala Ala Arg Ile Tyr Gly Gly Ser Gln Gly Asn Leu
        115                 120                 125

Ile Phe Gly Lys Gly Thr Lys Leu Ser Val Lys Pro Asn Ile Gln Asn
    130                 135                 140

Pro Asp Pro Ala Val Tyr Gln Leu Arg Asp Ser Lys Ser Ser Asp Lys
145                 150                 155                 160

Ser Val Cys Leu Phe Thr Asp Phe Asp Ser Gln Thr Asn Val Ser Gln
            165                 170                 175

Ser Lys Asp Ser Asp Val Tyr Ile Thr Asp Lys Thr Val Leu Asp Met
            180                 185                 190

Arg Ser Met Asp Phe Lys Ser Asn Ser Ala Val Ala Trp Ser Asn Lys
        195                 200                 205

Ser Asp Phe Ala Cys Ala Asn Ala Phe Asn Asn Ser Ile Ile Pro Glu
    210                 215                 220

Asp Thr Phe Phe Pro Ser Pro Glu Ser Ser Cys Asp Val Lys Leu Val
225                 230                 235                 240

Glu Lys Ser Phe Glu Thr Asp Thr Asn Leu Asn Phe Gln Asn Leu Ser
            245                 250                 255

Val Ile Gly Phe Arg Ile Leu Leu Leu Lys Val Ala Gly Phe Asn Leu
            260                 265                 270

Leu Met Thr Leu Arg Leu Trp Ser Ser
        275                 280

<210> SEQ ID NO 547
<211> LENGTH: 343
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 547

gaccagcaag ttaagcaaaa ttcaccatcc ctgagcgtcc aggaaggaag aatttctatt      60

ctgaactgtg actatactaa cagcatgttt gattatttcc tatggtacaa aaaataccct     120

gctgaaggtc ctacattcct gatatctata agttccatta aggataaaaa tgaagatgga     180

agattcactg tcttcttaaa caaaagtgcc aagcacctct ctctgcacat tgtgccctcc     240
```

```
cagcctggag actctgcagt gtacttctgt gcagcaagga tttatggagg aagccaagga    300

aatctcatct ttggaaaagg cactaaactc tctgttaaac caa                      343


<210> SEQ ID NO 548
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Arg Ile Tyr Gly
                85                  90                  95

Gly Ser Gln Gly Asn Leu Ile Phe Gly Lys Gly Thr Lys Leu Ser Val
            100                 105                 110

Lys Pro


<210> SEQ ID NO 549
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 549

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Gly Glu Pro Ser Gly Ser Ala Arg Gln Leu Thr Phe
        115                 120                 125

Gly Ser Gly Thr Gln Leu Thr Val Leu Pro Asp Ile Gln Asn Pro Asp
    130                 135                 140

Pro Ala Val Tyr Gln Leu Arg Asp Ser Lys Ser Ser Asp Lys Ser Val
145                 150                 155                 160
```

```
Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
        195                 200                 205

Phe Ala Cys Ala Asn Ala Phe Asn Asn Ser Ile Ile Pro Glu Asp Thr
    210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
        275
```

<210> SEQ ID NO 550
<211> LENGTH: 355
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 550

```
gcccagaaga taactcaaac ccaaccagga atgttcgtgc aggaaaagga ggctgtgact     60

ctggactgca catatgacac cagtgatcca agttatggtc tattctggta caagcagccc    120

agcagtgggg aaatgatttt tcttatttat caggggtctt atgaccagca aaatgcaaca    180

gaaggtcgct actcattgaa tttccagaag gcaagaaaat ccgccaacct tgtcatctcc    240

gcttcacaac tgggggactc agcaatgtac ttctgtgcaa tgagagaggg cgaaccttct    300

ggttctgcaa ggcaactgac ctttggatct gggacacaat tgactgtttt acctg         355
```

<210> SEQ ID NO 551
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 551

```
Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Gln Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Glu Pro Ser Gly Ser Ala Arg Gln Leu Thr Phe Gly Ser Gly Thr
            100                 105                 110
```

Gln Leu Thr Val Leu Pro
        115

<210> SEQ ID NO 552
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 552

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Val Asn Ala Gly Gly Thr Ser Tyr Gly Lys Leu
        115                 120                 125

Thr Phe Gly Gln Gly Thr Ile Leu Thr Val His Pro Asn Ile Gln Asn
    130                 135                 140

Pro Asp Pro Ala Val Tyr Gln Leu Arg Asp Ser Lys Ser Ser Asp Lys
145                 150                 155                 160

Ser Val Cys Leu Phe Thr Asp Phe Asp Ser Gln Thr Asn Val Ser Gln
                165                 170                 175

Ser Lys Asp Ser Asp Val Tyr Ile Thr Asp Lys Thr Val Leu Asp Met
            180                 185                 190

Arg Ser Met Asp Phe Lys Ser Asn Ser Ala Val Ala Trp Ser Asn Lys
        195                 200                 205

Ser Asp Phe Ala Cys Ala Asn Ala Phe Asn Asn Ser Ile Ile Pro Glu
    210                 215                 220

Asp Thr Phe Phe Pro Ser Pro Glu Ser Ser Cys Asp Val Lys Leu Val
225                 230                 235                 240

Glu Lys Ser Phe Glu Thr Asp Thr Asn Leu Asn Phe Gln Asn Leu Ser
                245                 250                 255

Val Ile Gly Phe Arg Ile Leu Leu Leu Lys Val Ala Gly Phe Asn Leu
            260                 265                 270

Leu Met Thr Leu Arg Leu Trp Ser Ser
        275                 280

<210> SEQ ID NO 553
<211> LENGTH: 343
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 553
gaccagcaag ttaagcaaaa ttcaccatcc ctgagcgtcc aggaaggaag aatttctatt 60
ctgaactgtg actatactaa cagcatgttt gattatttcc tatggtacaa aaaataccct 120
gctgaaggtc ctacattcct gatatctata agttccatta aggataaaaa tgaagatgga 180
agattcactg tcttcttaaa caaaagtgcc aagcacctct ctctgcacat tgtgccctcc 240
cagcctggag actctgcagt gtacttctgt gcagttaatg ctggtggtac tagctatgga 300
aagctgacat ttggacaagg gaccatcttg actgtccatc caa 343

<210> SEQ ID NO 554
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 554

Asp Gln Gln Val Lys Gln Asn Ser Pro Ser Leu Ser Val Gln Glu Gly
1 5 10 15

Arg Ile Ser Ile Leu Asn Cys Asp Tyr Thr Asn Ser Met Phe Asp Tyr
20 25 30

Phe Leu Trp Tyr Lys Lys Tyr Pro Ala Glu Gly Pro Thr Phe Leu Ile
35 40 45

Ser Ile Ser Ser Ile Lys Asp Lys Asn Glu Asp Gly Arg Phe Thr Val
50 55 60

Phe Leu Asn Lys Ser Ala Lys His Leu Ser Leu His Ile Val Pro Ser
65 70 75 80

Gln Pro Gly Asp Ser Ala Val Tyr Phe Cys Ala Val Asn Ala Gly Gly
85 90 95

Thr Ser Tyr Gly Lys Leu Thr Phe Gly Gln Gly Thr Ile Leu Thr Val
100 105 110

His Pro

<210> SEQ ID NO 555
<211> LENGTH: 276
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 555

Met Leu Leu Leu Leu Val Pro Val Leu Glu Val Ile Phe Thr Leu Gly
1 5 10 15

Gly Thr Arg Ala Gln Ser Val Thr Gln Leu Gly Ser His Val Ser Val
20 25 30

Ser Glu Gly Ala Leu Val Leu Leu Arg Cys Asn Tyr Ser Ser Ser Val
35 40 45

Pro Pro Tyr Leu Phe Trp Tyr Val Gln Tyr Pro Asn Gln Gly Leu Gln
50 55 60

Leu Leu Leu Lys Tyr Thr Thr Gly Ala Thr Leu Val Lys Gly Ile Asn
65 70 75 80

Gly Phe Glu Ala Glu Phe Lys Lys Ser Glu Thr Ser Phe His Leu Thr
85 90 95

Lys Pro Ser Ala His Met Ser Asp Ala Ala Glu Tyr Phe Cys Ala Val
100 105 110

```
Ser Glu Lys Phe Ser Gly Gly Tyr Asn Lys Leu Ile Phe Gly Ala Gly
        115                 120                 125

Thr Arg Leu Ala Val His Pro Tyr Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275
```

<210> SEQ ID NO 556
<211> LENGTH: 349
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 556

```
gcccagtcgg tgacccagct tggcagccac gtctctgtct ctgagggagc cctggttctg      60

ctgaggtgca actactcatc gtctgttcca ccatatctct tctggtatgt gcaatacccc     120

aaccaaggac tccagcttct cctgaagtac acaacagggg ccaccctggt taaaggcatc     180

aacggttttg aggctgaatt taagaagagt gaaacctcct tccacctgac gaaaccctca     240

gcccatatga gcgacgcggc tgagtacttc tgtgctgtga gtgagaagtt ttctggtggc     300

tacaataagc tgatttttgg agcagggacc aggctggctg tacacccat                 349
```

<210> SEQ ID NO 557
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 557

```
Ala Gln Ser Val Thr Gln Leu Gly Ser His Val Ser Val Ser Glu Gly
1               5                   10                  15

Ala Leu Val Leu Leu Arg Cys Asn Tyr Ser Ser Ser Val Pro Pro Tyr
            20                  25                  30

Leu Phe Trp Tyr Val Gln Tyr Pro Asn Gln Gly Leu Gln Leu Leu Leu
        35                  40                  45

Lys Tyr Thr Thr Gly Ala Thr Leu Val Lys Gly Ile Asn Gly Phe Glu
    50                  55                  60
```

-continued

```
Ala Glu Phe Lys Lys Ser Glu Thr Ser Phe His Leu Thr Lys Pro Ser
65                  70                  75                  80

Ala His Met Ser Asp Ala Ala Glu Tyr Phe Cys Ala Val Ser Glu Lys
                85                  90                  95

Phe Ser Gly Gly Tyr Asn Lys Leu Ile Phe Gly Ala Gly Thr Arg Leu
            100                 105                 110

Ala Val His Pro
        115


<210> SEQ ID NO 558
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 558

Met Asn Met Leu Thr Ala Ser Leu Leu Arg Ala Val Ile Ala Ser Ile
1               5                   10                  15

Cys Val Val Ser Ser Met Ala Gln Lys Val Thr Gln Ala Gln Thr Glu
            20                  25                  30

Ile Ser Val Val Glu Lys Glu Asp Val Thr Leu Asp Cys Val Tyr Glu
        35                  40                  45

Thr Arg Asp Thr Thr Tyr Tyr Leu Phe Trp Tyr Lys Gln Pro Pro Ser
    50                  55                  60

Gly Glu Leu Val Phe Leu Ile Arg Arg Asn Ser Phe Asp Glu Gln Asn
65                  70                  75                  80

Glu Ile Ser Gly Arg Tyr Ser Trp Asn Phe Gln Lys Ser Thr Ser Ser
                85                  90                  95

Phe Asn Phe Thr Ile Thr Ala Ser Gln Val Val Asp Ser Ala Val Tyr
            100                 105                 110

Phe Cys Ala Leu Ser Glu Ala Lys Asp Asp Lys Ile Ile Phe Gly Lys
        115                 120                 125

Gly Thr Arg Leu His Ile Leu Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275


<210> SEQ ID NO 559
```

<211> LENGTH: 343
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 559
gctcagaagg taactcaagc gcagactgaa atttctgtgg tggagaagga ggatgtgacc 60
ttggactgtg tgtatgaaac ccgtgatact acttattact tattctggta caagcaacca 120
ccaagtggag aattggtttt ccttattcgt cggaactctt ttgatgagca aaatgaaata 180
agtggtcggt attcttggaa cttccagaaa tccaccagtt ccttcaactt caccatcaca 240
gcctcacaag tcgtggactc agcagtatac ttctgtgctc tgagtgaggc aaaagatgac 300
aagatcatct ttggaaaagg gacacgactt catattctcc cca 343

<210> SEQ ID NO 560
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 560

Ala Gln Lys Val Thr Gln Ala Gln Thr Glu Ile Ser Val Val Glu Lys
1 5 10 15

Glu Asp Val Thr Leu Asp Cys Val Tyr Glu Thr Arg Asp Thr Thr Tyr
20 25 30

Tyr Leu Phe Trp Tyr Lys Gln Pro Pro Ser Gly Glu Leu Val Phe Leu
35 40 45

Ile Arg Arg Asn Ser Phe Asp Glu Gln Asn Glu Ile Ser Gly Arg Tyr
50 55 60

Ser Trp Asn Phe Gln Lys Ser Thr Ser Ser Phe Asn Phe Thr Ile Thr
65 70 75 80

Ala Ser Gln Val Val Asp Ser Ala Val Tyr Phe Cys Ala Leu Ser Glu
85 90 95

Ala Lys Asp Asp Lys Ile Ile Phe Gly Lys Gly Thr Arg Leu His Ile
100 105 110

Leu Pro

<210> SEQ ID NO 561
<211> LENGTH: 278
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 561

Met Ala Met Leu Leu Gly Ala Ser Val Leu Ile Leu Trp Leu Gln Pro
1 5 10 15

Asp Trp Val Asn Ser Gln Gln Lys Asn Asp Asp Gln Gln Val Lys Gln
20 25 30

Asn Ser Pro Ser Leu Ser Val Gln Glu Gly Arg Ile Ser Ile Leu Asn
35 40 45

Cys Asp Tyr Thr Asn Ser Met Phe Asp Tyr Phe Leu Trp Tyr Lys Lys
50 55 60

Tyr Pro Ala Glu Gly Pro Thr Phe Leu Ile Ser Ile Ser Ser Ile Lys

-continued

```
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ile Tyr Asn Gln Gly Gly Lys Leu Ile Phe Gly
        115                 120                 125

Gln Gly Thr Glu Leu Ser Val Lys Pro Asn Ile Gln Asn Pro Asp Pro
    130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
        275
```

<210> SEQ ID NO 562
<211> LENGTH: 334
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 562

```
gaccagcaag ttaagcaaaa ttcaccatcc ctgagcgtcc aggaaggaag aatttctatt      60

ctgaactgtg actatactaa cagcatgttt gattatttcc tatggtacaa aaaataccct     120

gctgaaggtc ctacattcct gatatctata agttccatta aggataaaaa tgaagatgga     180

agattcactg tcttcttaaa caaaagtgcc aagcacctct ctctgcacat tgtgccctcc     240

cagcctggag actctgcagt gtacttctgt gccatttata accagggagg aaagcttatc     300

ttcggacagg gaacggagtt atctgtgaaa ccca                                 334
```

<210> SEQ ID NO 563
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 563

```
Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
```

```
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ile Tyr Asn Gln Gly
                85                  90                  95

Gly Lys Leu Ile Phe Gly Gln Gly Thr Glu Leu Ser Val Lys Pro
            100                 105                 110


<210> SEQ ID NO 564
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 564

Met Asn Tyr Ser Pro Gly Leu Val Ser Leu Ile Leu Leu Leu Leu Gly
1               5                   10                  15

Arg Thr Arg Gly Asn Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
        35                  40                  45

Tyr Pro Ser Leu Phe Trp Tyr Val Gln Tyr Pro Gly Glu Gly Leu Gln
    50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Met
            100                 105                 110

Thr Asp Tyr Lys Leu Ser Phe Gly Ala Gly Thr Thr Val Thr Val Arg
        115                 120                 125

Ala Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 565
<211> LENGTH: 331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 565
ggaaattcag tgacccagat ggaagggcca gtgactctct cagaagaggc cttcctgact 60
ataaactgca cgtacacagc cacaggatac ccttcccttt tctggtatgt ccaatatcct 120
ggagaaggtc tacagctcct cctgaaagcc acgaaggctg atgacaaggg aagcaacaaa 180
ggttttgaag ccacataccg taaagaaacc acttctttcc acttggagaa aggctcagtt 240
caagtgtcag actcagcggt gtacttctgt gctctgatga ccgactacaa gctcagcttt 300
ggagccggaa ccacagtaac tgtaagagca a 331

<210> SEQ ID NO 566
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 566

Gly Asn Ser Val Thr Gln Met Glu Gly Pro Val Thr Leu Ser Glu Glu
1 5 10 15

Ala Phe Leu Thr Ile Asn Cys Thr Tyr Thr Ala Thr Gly Tyr Pro Ser
20 25 30

Leu Phe Trp Tyr Val Gln Tyr Pro Gly Glu Gly Leu Gln Leu Leu Leu
35 40 45

Lys Ala Thr Lys Ala Asp Asp Lys Gly Ser Asn Lys Gly Phe Glu Ala
50 55 60

Thr Tyr Arg Lys Glu Thr Thr Ser Phe His Leu Glu Lys Gly Ser Val
65 70 75 80

Gln Val Ser Asp Ser Ala Val Tyr Phe Cys Ala Leu Met Thr Asp Tyr
85 90 95

Lys Leu Ser Phe Gly Ala Gly Thr Thr Val Thr Val Arg Ala
100 105 110

<210> SEQ ID NO 567
<211> LENGTH: 278
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 567

Met Met Lys Ser Leu Arg Val Leu Leu Val Ile Leu Trp Leu Gln Leu
1 5 10 15

Ser Trp Val Trp Ser Gln Gln Lys Glu Val Glu Gln Asn Ser Gly Pro
20 25 30

Leu Ser Val Pro Glu Gly Ala Ile Ala Ser Leu Asn Cys Thr Tyr Ser
35 40 45

Asp Arg Gly Ser Gln Ser Phe Phe Trp Tyr Arg Gln Tyr Ser Gly Lys
50 55 60

Ser Pro Glu Leu Ile Met Ser Ile Tyr Ser Asn Gly Asp Lys Glu Asp

```
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Arg Ser Val Gly Val Ser Gly Gly Tyr Asn Lys Leu Ile Phe Gly
        115                 120                 125

Ala Gly Thr Arg Leu Ala Val His Pro Tyr Ile Gln Asn Pro Asp Pro
    130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
        275
```

<210> SEQ ID NO 568
<211> LENGTH: 346
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 568

```
cagaaggagg tggagcagaa ttctggaccc ctcagtgttc cagagggagc cattgcctct     60

ctcaactgca cttacagtga ccgaggttcc cagtccttct tctggtacag acaatattct    120

gggaaaagcc ctgagttgat aatgtccata tactccaatg gtgacaaaga agatggaagg    180

tttacagcac agctcaataa agccagccag tatgtttctc tgctcatcag agactcccag    240

cccagtgatt cagccaccta cctctgtgcc gtgaggagtg taggggtttc tggtggctac    300

aataagctga tttttggagc agggaccagg ctggctgtac acccat                   346
```

<210> SEQ ID NO 569
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 569

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
```

```
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Arg Ser Val Gly Val
                85                  90                  95

Ser Gly Gly Tyr Asn Lys Leu Ile Phe Gly Ala Gly Thr Arg Leu Ala
            100                 105                 110

Val His Pro
        115


<210> SEQ ID NO 570
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 570

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Leu Leu Ser Ser Asn
            100                 105                 110

Thr Gly Lys Leu Ile Phe Gly Gln Gly Thr Thr Leu Gln Val Lys Pro
        115                 120                 125

Asp Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255
```

```
Gly Phe Asn Leu Leu Met Thr Leu Arg Leu Trp Ser Ser
            260                 265


<210> SEQ ID NO 571
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 571

cttgctaaga ccacccagcc catctccatg gactcatatg aaggacaaga agtgaacata      60

acctgtagcc acaacaacat tgctacaaat gattatatca cgtggtacca acagtttccc     120

agccaaggac cacgatttat tattcaagga tacaagacaa aagttacaaa cgaagtggcc     180

tccctgttta tccctgccga cagaaagtcc agcactctga gcctgccccg ggtttccctg     240

agcgacactg ctgtgtacta ctgcctcgtt ctactctcta gcaacacagg caaactaatc     300

tttgggcaag ggacaacttt acaagtaaaa ccag                                 334


<210> SEQ ID NO 572
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 572

Leu Ala Lys Thr Thr Gln Pro Ile Ser Met Asp Ser Tyr Glu Gly Gln
1               5                   10                  15

Glu Val Asn Ile Thr Cys Ser His Asn Asn Ile Ala Thr Asn Asp Tyr
            20                  25                  30

Ile Thr Trp Tyr Gln Gln Phe Pro Ser Gln Gly Pro Arg Phe Ile Ile
        35                  40                  45

Gln Gly Tyr Lys Thr Lys Val Thr Asn Glu Val Ala Ser Leu Phe Ile
    50                  55                  60

Pro Ala Asp Arg Lys Ser Ser Thr Leu Ser Leu Pro Arg Val Ser Leu
65                  70                  75                  80

Ser Asp Thr Ala Val Tyr Tyr Cys Leu Val Leu Leu Ser Ser Asn Thr
                85                  90                  95

Gly Lys Leu Ile Phe Gly Gln Gly Thr Thr Leu Gln Val Lys Pro
            100                 105                 110


<210> SEQ ID NO 573
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 573

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
```

```
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Ser Ala Asn Asn Asn Asp Met Arg Phe Gly Ala Gly Thr
        115                 120                 125

Arg Leu Thr Val Lys Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275
```

<210> SEQ ID NO 574
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 574

```
gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt ataggagcgc gaataacaat    300

gacatgcgct ttggagcagg gaccagactg acagtaaaac caa                      343
```

<210> SEQ ID NO 575
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 575

```
Ala Gln Thr Val Thr Gln Ser Gln Pro Glu Met Ser Val Gln Glu Ala
```

-continued

```
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Asn Asn Asn Asp Met Arg Phe Gly Ala Gly Thr Arg Leu Thr Val
            100                 105                 110

Lys Pro


<210> SEQ ID NO 576
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 576

Met Met Ile Ser Leu Arg Val Leu Leu Val Ile Leu Trp Leu Gln Leu
1               5                   10                  15

Ser Trp Val Trp Ser Gln Arg Lys Glu Val Glu Gln Asp Pro Gly Pro
            20                  25                  30

Phe Asn Val Pro Glu Gly Ala Thr Val Ala Phe Asn Cys Thr Tyr Ser
        35                  40                  45

Asn Ser Ala Ser Gln Ser Phe Phe Trp Tyr Arg Gln Asp Cys Arg Lys
    50                  55                  60

Glu Pro Lys Leu Leu Met Ser Val Tyr Ser Ser Gly Asn Glu Asp Gly
65                  70                  75                  80

Arg Phe Thr Ala Gln Leu Asn Arg Ala Ser Gln Tyr Ile Ser Leu Leu
                85                  90                  95

Ile Arg Asp Ser Lys Leu Ser Asp Ser Ala Thr Tyr Leu Cys Val Val
            100                 105                 110

Phe Pro Gly Gly Ser Tyr Ile Pro Thr Phe Gly Arg Gly Thr Ser Leu
        115                 120                 125

Ile Val His Pro Tyr Ile Gln Lys Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
```

```
                245                 250                 255

Leu Lys Val Ala Gly Phe Asn Leu Leu Met Thr Leu Arg Leu Trp Ser
            260                 265                 270

Ser


<210> SEQ ID NO 577
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 577

cggaaggagg tggagcagga tcctggaccc ttcaatgttc cagagggagc cactgtcgct      60

ttcaactgta cttacagcaa cagtgcttct cagtctttct tctggtacag acaggattgc     120

aggaaagaac ctaagttgct gatgtccgta tactccagtg gtaatgaaga tggaaggttt     180

acagcacagc tcaatagagc cagccagtat atttccctgc tcatcagaga ctccaagctc     240

agtgattcag ccacctacct ctgtgtggtt ttcccaggag gaagctacat acctacattt     300

ggaagaggaa ccagccttat tgttcatccg t                                     331


<210> SEQ ID NO 578
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 578

Arg Lys Glu Val Glu Gln Asp Pro Gly Pro Phe Asn Val Pro Glu Gly
1               5                   10                  15

Ala Thr Val Ala Phe Asn Cys Thr Tyr Ser Asn Ser Ala Ser Gln Ser
            20                  25                  30

Phe Phe Trp Tyr Arg Gln Asp Cys Arg Lys Glu Pro Lys Leu Leu Met
        35                  40                  45

Ser Val Tyr Ser Ser Gly Asn Glu Asp Gly Arg Phe Thr Ala Gln Leu
    50                  55                  60

Asn Arg Ala Ser Gln Tyr Ile Ser Leu Leu Ile Arg Asp Ser Lys Leu
65                  70                  75                  80

Ser Asp Ser Ala Thr Tyr Leu Cys Val Val Phe Pro Gly Gly Ser Tyr
                85                  90                  95

Ile Pro Thr Phe Gly Arg Gly Thr Ser Leu Ile Val His Pro
            100                 105                 110


<210> SEQ ID NO 579
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

Met Ala Thr Arg Leu Leu Cys Cys Val Val Leu Cys Leu Leu Gly Glu
1               5                   10                  15

Glu Leu Ile Asp Ala Arg Val Thr Gln Thr Pro Arg His Lys Val Thr
            20                  25                  30
```

```
Glu Met Gly Gln Glu Val Thr Met Arg Cys Gln Pro Ile Leu Gly His
        35                  40                  45

Asn Thr Val Phe Trp Tyr Arg Gln Thr Met Met Gln Gly Leu Glu Leu
    50                  55                  60

Leu Ala Tyr Phe Arg Asn Arg Ala Pro Leu Asp Asp Ser Gly Met Pro
65                  70                  75                  80

Lys Asp Arg Phe Ser Ala Glu Met Pro Asp Ala Thr Leu Ala Thr Leu
                85                  90                  95

Lys Ile Gln Pro Ser Glu Pro Arg Asp Ser Ala Val Tyr Phe Cys Ala
            100                 105                 110

Ser Gly Leu Ala Leu Thr Glu Gly Gly Trp Tyr Glu Gln Tyr Phe Gly
        115                 120                 125

Pro Gly Thr Arg Leu Thr Val Thr Glu Asp Leu Lys Asn Val Phe Pro
    130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Tyr Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Glu
            260                 265                 270

Ser Tyr Gln Gln Gly Val Leu Ser Ala Thr Ile Leu Tyr Glu Ile Leu
        275                 280                 285

Leu Gly Lys Ala Thr Leu Tyr Ala Val Leu Val Ser Ala Leu Val Leu
    290                 295                 300

Met Ala Met Val Lys Arg Lys Asp Ser Arg Gly
305                 310                 315
```

<210> SEQ ID NO 580
<211> LENGTH: 352
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 580

```
gatgctagag tcacccagac accaaggcac aaggtgacag agatgggaca agaagtaaca      60

atgagatgtc agccaatttt aggccacaat actgttttct ggtacagaca gaccatgatg     120

caaggactgg agttgctggc ttacttccgc aaccgggctc ctctagatga ttcggggatg     180

ccgaaggatc gattctcagc agagatgcct gatgcaactt tagccactct gaagatccag     240

ccctcagaac ccagggactc agctgtgtat ttttgtgcta gtggtttggc cctcactgag     300

gggggctggt acgagcagta cttcgggccg ggcaccaggc tcacggtcac ag             352
```

<210> SEQ ID NO 581

<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 581

Asp Ala Arg Val Thr Gln Thr Pro Arg His Lys Val Thr Glu Met Gly
1 5 10 15

Gln Glu Val Thr Met Arg Cys Gln Pro Ile Leu Gly His Asn Thr Val
20 25 30

Phe Trp Tyr Arg Gln Thr Met Met Gln Gly Leu Glu Leu Leu Ala Tyr
35 40 45

Phe Arg Asn Arg Ala Pro Leu Asp Asp Ser Gly Met Pro Lys Asp Arg
50 55 60

Phe Ser Ala Glu Met Pro Asp Ala Thr Leu Ala Thr Leu Lys Ile Gln
65 70 75 80

Pro Ser Glu Pro Arg Asp Ser Ala Val Tyr Phe Cys Ala Ser Gly Leu
85 90 95

Ala Leu Thr Glu Gly Gly Trp Tyr Glu Gln Tyr Phe Gly Pro Gly Thr
100 105 110

Arg Leu Thr Val Thr
115

<210> SEQ ID NO 582
<211> LENGTH: 312
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 582

Met Asp Thr Trp Leu Val Cys Trp Ala Ile Phe Ser Leu Leu Lys Ala
1 5 10 15

Gly Leu Thr Glu Pro Glu Val Thr Gln Thr Pro Ser His Gln Val Thr
20 25 30

Gln Met Gly Gln Glu Val Ile Leu Arg Cys Val Pro Ile Ser Asn His
35 40 45

Leu Tyr Phe Tyr Trp Tyr Arg Gln Ile Leu Gly Gln Lys Val Glu Phe
50 55 60

Leu Val Ser Phe Tyr Asn Asn Glu Ile Ser Glu Lys Ser Glu Ile Phe
65 70 75 80

Asp Asp Gln Phe Ser Val Glu Arg Pro Asp Gly Ser Asn Phe Thr Leu
85 90 95

Lys Ile Arg Ser Thr Lys Leu Glu Asp Ser Ala Met Tyr Phe Cys Ala
100 105 110

Ser Leu Arg Trp Asp Gly Asp Asn Glu Gln Phe Phe Gly Pro Gly Thr
115 120 125

Arg Leu Thr Val Leu Glu Asp Leu Lys Asn Val Phe Pro Pro Glu Val
130 135 140

Ala Val Phe Glu Pro Ser Glu Ala Glu Ile Ser His Thr Gln Lys Ala
145 150 155 160

Thr Leu Val Cys Leu Ala Thr Gly Phe Tyr Pro Asp His Val Glu Leu
165 170 175

Ser Trp Trp Val Asn Gly Lys Glu Val His Ser Gly Val Ser Thr Asp
180 185 190

Pro Gln Pro Leu Lys Glu Gln Pro Ala Leu Asn Asp Ser Arg Tyr Cys
195 200 205

Leu Ser Ser Arg Leu Arg Val Ser Ala Thr Phe Trp Gln Asn Pro Arg
210 215 220

Asn His Phe Arg Cys Gln Val Gln Phe Tyr Gly Leu Ser Glu Asn Asp
225 230 235 240

Glu Trp Thr Gln Asp Arg Ala Lys Pro Val Thr Gln Ile Val Ser Ala
245 250 255

Glu Ala Trp Gly Arg Ala Asp Cys Gly Phe Thr Ser Glu Ser Tyr Gln
260 265 270

Gln Gly Val Leu Ser Ala Thr Ile Leu Tyr Glu Ile Leu Leu Gly Lys
275 280 285

Ala Thr Leu Tyr Ala Val Leu Val Ser Ala Leu Val Leu Met Ala Met
290 295 300

Val Lys Arg Lys Asp Ser Arg Gly
305 310

<210> SEQ ID NO 583
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 583
gaacctgaag tcacccagac tcccagccat caggtcacac agatgggaca ggaagtgatc 60
ttgcgctgtg tccccatctc taatcactta tacttctatt ggtacagaca aatcttgggg 120
cagaaagtcg agtttctggt ttccttttat aataatgaaa tctcagagaa gtctgaaata 180
ttcgatgatc aattctcagt tgaaaggcct gatggatcaa atttcactct gaagatccgg 240
tccacaaagc tggaggactc agccatgtac ttctgtgcca gcctccgatg ggacggggac 300
aatgagcagt tcttcgggcc agggacacgg ctcaccgtgc tag 343

<210> SEQ ID NO 584
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 584

Glu Pro Glu Val Thr Gln Thr Pro Ser His Gln Val Thr Gln Met Gly
1 5 10 15

Gln Glu Val Ile Leu Arg Cys Val Pro Ile Ser Asn His Leu Tyr Phe
20 25 30

Tyr Trp Tyr Arg Gln Ile Leu Gly Gln Lys Val Glu Phe Leu Val Ser
35 40 45

Phe Tyr Asn Asn Glu Ile Ser Glu Lys Ser Glu Ile Phe Asp Asp Gln
50 55 60

Phe Ser Val Glu Arg Pro Asp Gly Ser Asn Phe Thr Leu Lys Ile Arg
65 70 75 80

Ser Thr Lys Leu Glu Asp Ser Ala Met Tyr Phe Cys Ala Ser Leu Arg
85 90 95

Trp Asp Gly Asp Asn Glu Gln Phe Phe Gly Pro Gly Thr Arg Leu Thr
100 105 110

Val Leu

<210> SEQ ID NO 585
<211> LENGTH: 339
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 585

Met Lys Ser Gln Asn Asp Pro Leu Glu Ser Thr Val Pro Leu Ser Pro
1 5 10 15

Met His Arg Pro Arg Arg Pro Leu His Pro Val Ala Pro Ala Met Ser
20 25 30

Ile Gly Leu Leu Cys Cys Val Ala Phe Ser Leu Leu Trp Ala Ser Pro
35 40 45

Val Asn Ala Gly Val Thr Gln Thr Pro Lys Phe Gln Val Leu Lys Thr
50 55 60

Gly Gln Ser Met Thr Leu Gln Cys Ala Gln Asp Met Asn His Asn Ser
65 70 75 80

Met Tyr Trp Tyr Arg Gln Asp Pro Gly Met Gly Leu Arg Leu Ile Tyr
85 90 95

Tyr Ser Ala Ser Glu Gly Thr Thr Asp Lys Gly Glu Val Pro Asn Gly
100 105 110

Tyr Asn Val Ser Arg Leu Asn Lys Arg Glu Phe Ser Leu Arg Leu Glu
115 120 125

Ser Ala Ala Pro Ser Gln Thr Ser Val Tyr Phe Cys Ala Ser Arg Asp
130 135 140

Arg Ala Leu Asn Thr Glu Ala Phe Phe Gly Gln Gly Thr Arg Leu Thr
145 150 155 160

Val Val Glu Asp Leu Asn Lys Val Phe Pro Pro Glu Val Ala Val Phe
165 170 175

Glu Pro Ser Glu Ala Glu Ile Ser His Thr Gln Lys Ala Thr Leu Val
180 185 190

Cys Leu Ala Thr Gly Phe Tyr Pro Asp His Val Glu Leu Ser Trp Trp
195 200 205

Val Asn Gly Lys Glu Val His Ser Gly Val Ser Thr Asp Pro Gln Pro
210 215 220

Leu Lys Glu Gln Pro Ala Leu Asn Asp Ser Arg Tyr Cys Leu Ser Ser
225 230 235 240

Arg Leu Arg Val Ser Ala Thr Phe Trp Gln Asn Pro Arg Asn His Phe
245 250 255

Arg Cys Gln Val Gln Phe Tyr Gly Leu Ser Glu Asn Asp Glu Trp Thr
260 265 270

Gln Asp Arg Ala Lys Pro Val Thr Gln Ile Val Ser Ala Glu Ala Trp
275 280 285

Gly Arg Ala Asp Cys Gly Phe Thr Ser Val Ser Tyr Gln Gln Gly Val
290 295 300

Leu Ser Ala Thr Ile Leu Tyr Glu Ile Leu Leu Gly Lys Ala Thr Leu
305 310 315 320

Tyr Ala Val Leu Val Ser Ala Leu Val Leu Met Ala Met Val Lys Arg
325 330 335

Lys Asp Phe

<210> SEQ ID NO 586
<211> LENGTH: 340
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 586
aatgctggtg tcactcagac cccaaaattc caggtcctga agacaggaca gagcatgaca 60
ctgcagtgtg cccaggatat gaaccataac tccatgtact ggtatcgaca agacccaggc 120
atgggactga ggctgattta ttactcagct tctgagggta ccactgacaa aggagaagtc 180
cccaatggct acaatgtctc cagattaaac aaacgggagt tctcgctcag gctggagtcg 240
gctgctccct cccagacatc tgtgtacttc tgtgccagca gggacagggc cctgaacact 300
gaagctttct ttggacaagg caccagactc acagttgtag 340

<210> SEQ ID NO 587
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 587

Asn Ala Gly Val Thr Gln Thr Pro Lys Phe Gln Val Leu Lys Thr Gly
1 5 10 15

Gln Ser Met Thr Leu Gln Cys Ala Gln Asp Met Asn His Asn Ser Met
20 25 30

Tyr Trp Tyr Arg Gln Asp Pro Gly Met Gly Leu Arg Leu Ile Tyr Tyr
35 40 45

Ser Ala Ser Glu Gly Thr Thr Asp Lys Gly Glu Val Pro Asn Gly Tyr
50 55 60

Asn Val Ser Arg Leu Asn Lys Arg Glu Phe Ser Leu Arg Leu Glu Ser
65 70 75 80

Ala Ala Pro Ser Gln Thr Ser Val Tyr Phe Cys Ala Ser Arg Asp Arg
85 90 95

Ala Leu Asn Thr Glu Ala Phe Phe Gly Gln Gly Thr Arg Leu Thr Val
100 105 110

Val

<210> SEQ ID NO 588
<211> LENGTH: 358
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 588

Met Gly Val Ala Ser Pro Gly Leu Ser Leu Pro Gly Ala Gln Ala Gly
1 5 10 15

Arg Met Ser Gln Asn Asp Phe Leu Glu Ser Pro Ala Pro Leu Ser Ser
20 25 30

Met His Arg Tyr Arg Arg Pro Leu Arg His Ala Ala Ser Ala Met Ser
35 40 45

Ile Gly Leu Leu Cys Cys Ala Ala Leu Ser Leu Leu Trp Ala Gly Pro
50 55 60

Val Asn Ala Gly Val Thr Gln Thr Pro Lys Phe Gln Val Leu Lys Thr
65 70 75 80

Gly Gln Ser Met Thr Leu Gln Cys Ala Gln Asp Met Asn His Glu Tyr
85 90 95

Met Ser Trp Tyr Arg Gln Asp Pro Gly Met Gly Leu Arg Leu Ile His
100 105 110

Tyr Ser Val Gly Ala Gly Ile Thr Asp Gln Gly Glu Val Pro Asn Gly
115 120 125

Tyr Asn Val Ser Arg Ser Thr Thr Glu Asp Phe Pro Leu Arg Leu Leu
130 135 140

Ser Ala Ala Pro Ser Gln Thr Ser Val Tyr Phe Cys Ala Ser Arg Asn
145 150 155 160

Gly Gly Thr Leu Ile Tyr Glu Gln Tyr Phe Gly Pro Gly Thr Arg Leu
165 170 175

Thr Val Thr Glu Asp Leu Lys Asn Val Phe Pro Pro Glu Val Ala Val
180 185 190

Phe Glu Pro Ser Glu Ala Glu Ile Ser His Thr Gln Lys Ala Thr Leu
195 200 205

Val Cys Leu Ala Thr Gly Phe Tyr Pro Asp His Val Glu Leu Ser Trp
210 215 220

Trp Val Asn Gly Lys Glu Val His Ser Gly Val Ser Thr Asp Pro Gln
225 230 235 240

Pro Leu Lys Glu Gln Pro Ala Leu Asn Asp Ser Arg Tyr Cys Leu Ser
245 250 255

Ser Arg Leu Arg Val Ser Ala Thr Phe Trp Gln Asn Pro Arg Asn His
260 265 270

Phe Arg Cys Gln Val Gln Phe Tyr Gly Leu Ser Glu Asn Asp Glu Trp
275 280 285

Thr Gln Asp Arg Ala Lys Pro Val Thr Gln Ile Val Ser Ala Glu Ala
290 295 300

Trp Gly Arg Ala Asp Cys Gly Phe Thr Ser Glu Ser Tyr Gln Gln Gly
305 310 315 320

Val Leu Ser Ala Thr Ile Leu Tyr Glu Ile Leu Leu Gly Lys Ala Thr
325 330 335

Leu Tyr Ala Val Leu Val Ser Ala Leu Val Leu Met Ala Met Val Lys
340 345 350

Arg Lys Asp Ser Arg Gly
355

<210> SEQ ID NO 589
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 589
aatgctggtg tcactcagac cccaaaattc caggtcctga agacaggaca gagcatgaca 60
ctgcagtgtg cccaggatat gaaccatgaa tacatgtcct ggtatcgaca agacccaggc 120
atggggctga ggctgattca ttactcagtt ggtgctggta tcactgacca aggagaagtc 180
cccaatggct acaatgtctc cagatcaacc acagaggatt tcccgctcag gctgctgtcg 240
gctgctccct cccagacatc tgtgtacttc tgtgccagca gaaacggcgg gacactaatc 300

-continued tacgagcagt acttcgggcc gggcaccagg ctcacggtca cag 343

<210> SEQ ID NO 590
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 590

Asn Ala Gly Val Thr Gln Thr Pro Lys Phe Gln Val Leu Lys Thr Gly
1 5 10 15

Gln Ser Met Thr Leu Gln Cys Ala Gln Asp Met Asn His Glu Tyr Met
20 25 30

Ser Trp Tyr Arg Gln Asp Pro Gly Met Gly Leu Arg Leu Ile His Tyr
35 40 45

Ser Val Gly Ala Gly Ile Thr Asp Gln Gly Glu Val Pro Asn Gly Tyr
50 55 60

Asn Val Ser Arg Ser Thr Thr Glu Asp Phe Pro Leu Arg Leu Leu Ser
65 70 75 80

Ala Ala Pro Ser Gln Thr Ser Val Tyr Phe Cys Ala Ser Arg Asn Gly
85 90 95

Gly Thr Leu Ile Tyr Glu Gln Tyr Phe Gly Pro Gly Thr Arg Leu Thr
100 105 110

Val Thr

<210> SEQ ID NO 591
<211> LENGTH: 308
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 591

Met Gly Ser Arg Leu Leu Cys Trp Val Leu Leu Cys Leu Leu Gly Ala
1 5 10 15

Gly Pro Val Lys Ala Gly Val Thr Gln Thr Pro Arg Tyr Leu Ile Lys
20 25 30

Thr Arg Gly Gln Gln Val Thr Leu Ser Cys Ser Pro Ile Ser Gly His
35 40 45

Arg Ser Val Ser Trp Tyr Gln Gln Thr Pro Gly Gln Gly Leu Gln Phe
50 55 60

Leu Phe Glu Tyr Phe Ser Glu Thr Gln Arg Asn Lys Gly Asn Phe Pro
65 70 75 80

Gly Arg Phe Ser Gly Arg Gln Phe Ser Asn Ser Arg Ser Glu Met Asn
85 90 95

Val Ser Thr Leu Glu Leu Gly Asp Ser Ala Leu Tyr Leu Cys Ala Ser
100 105 110

Arg Gln Arg Thr Glu Leu Glu Ala Phe Phe Gly Gln Gly Thr Arg Leu
115 120 125

Thr Val Val Glu Asp Leu Asn Lys Val Phe Pro Pro Glu Val Ala Val
130 135 140

Phe Glu Pro Ser Glu Ala Glu Ile Ser His Thr Gln Lys Ala Thr Leu
145 150 155 160

Val Cys Leu Ala Thr Gly Phe Tyr Pro Asp His Val Glu Leu Ser Trp
165 170 175

Trp Val Asn Gly Lys Glu Val His Ser Gly Val Ser Thr Asp Pro Gln
180 185 190

Pro Leu Lys Glu Gln Pro Ala Leu Asn Asp Ser Arg Tyr Cys Leu Ser
195 200 205

Ser Arg Leu Arg Val Ser Ala Thr Phe Trp Gln Asn Pro Arg Asn His
210 215 220

Phe Arg Cys Gln Val Gln Phe Tyr Gly Leu Ser Glu Asn Asp Glu Trp
225 230 235 240

Thr Gln Asp Arg Ala Lys Pro Val Thr Gln Ile Val Ser Ala Glu Ala
245 250 255

Trp Gly Arg Ala Asp Cys Gly Phe Thr Ser Val Ser Tyr Gln Gln Gly
260 265 270

Val Leu Ser Ala Thr Ile Leu Tyr Glu Ile Leu Leu Gly Lys Ala Thr
275 280 285

Leu Tyr Ala Val Leu Val Ser Ala Leu Val Leu Met Ala Met Val Lys
290 295 300

Arg Lys Asp Phe
305

<210> SEQ ID NO 592
<211> LENGTH: 337
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 592
aaggctggag tcactcaaac tccaagatat ctgatcaaaa cgagaggaca gcaagtgaca 60
ctgagctgct cccctatctc tggcatagg agtgtatcct ggtaccaaca gaccccagga 120
cagggccttc agttcctctt tgaatacttc agtgagacac agagaaacaa aggaaacttc 180
cctggtcgat tctcagggcg ccagttctct aactctcgct ctgagatgaa tgtgagcacc 240
ttggagctgg gggactcggc cctttatctt tgcgccagca ggcagcggac agaacttgaa 300
gctttctttg gacaaggcac cagactcaca gttgtag 337

<210> SEQ ID NO 593
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 593

Lys Ala Gly Val Thr Gln Thr Pro Arg Tyr Leu Ile Lys Thr Arg Gly
1 5 10 15

Gln Gln Val Thr Leu Ser Cys Ser Pro Ile Ser Gly His Arg Ser Val
20 25 30

Ser Trp Tyr Gln Gln Thr Pro Gly Gln Gly Leu Gln Phe Leu Phe Glu
35 40 45

Tyr Phe Ser Glu Thr Gln Arg Asn Lys Gly Asn Phe Pro Gly Arg Phe
50 55 60

Ser Gly Arg Gln Phe Ser Asn Ser Arg Ser Glu Met Asn Val Ser Thr
65 70 75 80

Leu Glu Leu Gly Asp Ser Ala Leu Tyr Leu Cys Ala Ser Arg Gln Arg
85 90 95

Thr Glu Leu Glu Ala Phe Phe Gly Gln Gly Thr Arg Leu Thr Val Val
            100                 105                 110

<210> SEQ ID NO 594
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 594

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Ala Pro Asp Arg Gly Thr Tyr Glu Gln Tyr Phe Gly Pro
        115                 120                 125

Gly Thr Arg Leu Thr Val Thr Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 595
<211> LENGTH: 349
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 595
gaacctgaag tcacccagac tcccagccat caggtcacac agatgggaca ggaagtgatc 60
ttgcgctgtg tccccatctc taatcactta tacttctatt ggtacagaca aatcttgggg 120
cagaaagtcg agtttctggt ttccttttat aataatgaaa tctcagagaa gtctgaaata 180
ttcgatgatc aattctcagt tgaaaggcct gatggatcaa atttcactct gaagatccgg 240
tccacaaagc tggaggactc agccatgtac ttctgtgcca gcagtgaagc ccctgacagg 300
ggtacctacg agcagtactt cgggccgggc accaggctca cggtcacag 349

<210> SEQ ID NO 596
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 596

Glu Pro Glu Val Thr Gln Thr Pro Ser His Gln Val Thr Gln Met Gly
1 5 10 15

Gln Glu Val Ile Leu Arg Cys Val Pro Ile Ser Asn His Leu Tyr Phe
20 25 30

Tyr Trp Tyr Arg Gln Ile Leu Gly Gln Lys Val Glu Phe Leu Val Ser
35 40 45

Phe Tyr Asn Asn Glu Ile Ser Glu Lys Ser Glu Ile Phe Asp Asp Gln
50 55 60

Phe Ser Val Glu Arg Pro Asp Gly Ser Asn Phe Thr Leu Lys Ile Arg
65 70 75 80

Ser Thr Lys Leu Glu Asp Ser Ala Met Tyr Phe Cys Ala Ser Ser Glu
85 90 95

Ala Pro Asp Arg Gly Thr Tyr Glu Gln Tyr Phe Gly Pro Gly Thr Arg
100 105 110

Leu Thr Val Thr
115

<210> SEQ ID NO 597
<211> LENGTH: 312
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 597

Met Gly Thr Arg Leu Phe Phe Tyr Val Ala Leu Cys Leu Leu Trp Ala
1 5 10 15

Gly His Arg Asp Ala Gly Ile Thr Gln Ser Pro Arg Tyr Lys Ile Thr
20 25 30

Glu Thr Gly Arg Gln Val Thr Leu Met Cys His Gln Thr Trp Ser His
35 40 45

Ser Tyr Met Phe Trp Tyr Arg Gln Asp Leu Gly His Gly Leu Arg Leu
50 55 60

Ile Tyr Tyr Ser Ala Ala Ala Asp Ile Thr Asp Lys Gly Glu Val Pro
65 70 75 80

```
Asp Gly Tyr Val Val Ser Arg Ser Lys Thr Glu Asn Phe Pro Leu Thr
                85                  90                  95

Leu Glu Ser Ala Thr Arg Ser Gln Thr Ser Val Tyr Phe Cys Ala Ser
            100                 105                 110

Ser Glu Leu Gly Arg Gly Phe Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310
```

<210> SEQ ID NO 598
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 598

```
gatgctggaa tcacccagag cccaagatac aagatcacag agacaggaag gcaggtgacc     60

ttgatgtgtc accagacttg gagccacagc tatatgttct ggtatcgaca agacctggga    120

catgggctga ggctgatcta ttactcagca gctgctgata ttacagataa aggagaagtc    180

cccgatggct acgttgtctc cagatccaag acagagaatt tccccctcac tctggagtca    240

gctacccgct cccagacatc tgtgtatttc tgcgccagca gtgagttggg caggggtttc    300

tacgagcagt acttcgggcc gggcaccagg ctcacggtca cag                      343
```

<210> SEQ ID NO 599
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 599

```
Asp Ala Gly Ile Thr Gln Ser Pro Arg Tyr Lys Ile Thr Glu Thr Gly
1               5                   10                  15

Arg Gln Val Thr Leu Met Cys His Gln Thr Trp Ser His Ser Tyr Met
            20                  25                  30

Phe Trp Tyr Arg Gln Asp Leu Gly His Gly Leu Arg Leu Ile Tyr Tyr
        35                  40                  45

Ser Ala Ala Ala Asp Ile Thr Asp Lys Gly Glu Val Pro Asp Gly Tyr
    50                  55                  60

Val Val Ser Arg Ser Lys Thr Glu Asn Phe Pro Leu Thr Leu Glu Ser
65                  70                  75                  80

Ala Thr Arg Ser Gln Thr Ser Val Tyr Phe Cys Ala Ser Ser Glu Leu
                85                  90                  95

Gly Arg Gly Phe Tyr Glu Gln Tyr Phe Gly Pro Gly Thr Arg Leu Thr
            100                 105                 110

Val Thr


<210> SEQ ID NO 600
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 600

Met Gly Val Ala Ser Pro Gly Leu Ser Leu Pro Gly Ala Gln Ala Gly
1               5                   10                  15

Arg Met Ser Gln Asn Asp Phe Leu Glu Ser Pro Ala Pro Leu Ser Ser
            20                  25                  30

Met His Arg Tyr Arg Arg Pro Leu Arg His Ala Ala Ser Ala Met Ser
        35                  40                  45

Ile Gly Leu Leu Cys Cys Ala Ala Leu Ser Leu Leu Trp Ala Gly Pro
    50                  55                  60

Val Asn Ala Gly Val Thr Gln Thr Pro Lys Phe Gln Val Leu Lys Thr
65                  70                  75                  80

Gly Gln Ser Met Thr Leu Gln Cys Ala Gln Asp Met Asn His Glu Tyr
                85                  90                  95

Met Ser Trp Tyr Arg Gln Asp Pro Gly Met Gly Leu Arg Leu Ile His
            100                 105                 110

Tyr Ser Val Gly Ala Gly Ile Thr Asp Gln Gly Glu Val Pro Asn Gly
        115                 120                 125

Tyr Asn Val Ser Arg Ser Thr Thr Glu Asp Phe Pro Leu Arg Leu Leu
    130                 135                 140

Ser Ala Ala Pro Ser Gln Thr Ser Val Tyr Phe Cys Ala Ser Ser His
145                 150                 155                 160

Leu Gly Ala Gly Gly Pro His Glu Gln Tyr Phe Gly Pro Gly Thr Arg
                165                 170                 175

Leu Thr Val Thr Glu Asp Leu Lys Asn Val Phe Pro Pro Glu Val Ala
            180                 185                 190

Val Phe Glu Pro Ser Glu Ala Glu Ile Ser His Thr Gln Lys Ala Thr
        195                 200                 205

Leu Val Cys Leu Ala Thr Gly Phe Tyr Pro Asp His Val Glu Leu Ser
    210                 215                 220

Trp Trp Val Asn Gly Lys Glu Val His Ser Gly Val Ser Thr Asp Pro
225                 230                 235                 240
```

Gln Pro Leu Lys Glu Gln Pro Ala Leu Asn Asp Ser Arg Tyr Cys Leu
                245                 250                 255

Ser Ser Arg Leu Arg Val Ser Ala Thr Phe Trp Gln Asn Pro Arg Asn
            260                 265                 270

His Phe Arg Cys Gln Val Gln Phe Tyr Gly Leu Ser Glu Asn Asp Glu
        275                 280                 285

Trp Thr Gln Asp Arg Ala Lys Pro Val Thr Gln Ile Val Ser Ala Glu
    290                 295                 300

Ala Trp Gly Arg Ala Asp Cys Gly Phe Thr Ser Glu Ser Tyr Gln Gln
305                 310                 315                 320

Gly Val Leu Ser Ala Thr Ile Leu Tyr Glu Ile Leu Leu Gly Lys Ala
                325                 330                 335

Thr Leu Tyr Ala Val Leu Val Ser Ala Leu Val Leu Met Ala Met Val
            340                 345                 350

Lys Arg Lys Asp Ser Arg Gly
        355

<210> SEQ ID NO 601
<211> LENGTH: 346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 601
aatgctggtg tcactcagac cccaaaattc caggtcctga agacaggaca gagcatgaca      60
ctgcagtgtg cccaggatat gaaccatgaa tacatgtcct ggtatcgaca agacccaggc     120
atggggctga ggctgattca ttactcagtt ggtgctggta tcactgacca aggagaagtc     180
cccaatggct acaatgtctc cagatcaacc acagaggatt tcccgctcag gctgctgtcg     240
gctgctccct cccagacatc tgtgtacttc tgtgccagca gccatctggg ggcgggaggg     300
ccgcacgagc agtacttcgg gccgggcacc aggctcacgg tcacag                    346

<210> SEQ ID NO 602
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 602

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser His Leu
                85                  90                  95

Gly Ala Gly Gly Pro His Glu Gln Tyr Phe Gly Pro Gly Thr Arg Leu
            100                 105                 110

Thr Val Thr
        115

<210> SEQ ID NO 603
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 603

```
Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
        35                  40                  45

Val Ser Leu Tyr Trp Tyr Arg Gln Ala Leu Gly Gln Gly Pro Glu Phe
    50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser His Thr Asp Gly Ser Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310
```

<210> SEQ ID NO 604
<211> LENGTH: 343
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 604
ggtgctggag tctcccagtc tcccaggtac aaagtcacaa agaggggaca ggatgtagct 60
ctcaggtgtg atccaatttc gggtcatgta tccctttatt ggtaccgaca ggccctgggg 120
cagggcccag agtttctgac ttacttcaat tatgaagccc aacaagacaa atcagggctg 180
cccaatgatc ggttctctgc agagaggcct gagggatcca tctccactct gacgatccag 240
cgcacagagc agcgggactc ggccatgtat cgctgtgcca gcagccatac tgacggctcc 300
tacgagcagt acttcgggcc gggcaccagg ctcacggtca cag 343

<210> SEQ ID NO 605
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 605

Gly Ala Gly Val Ser Gln Ser Pro Arg Tyr Lys Val Thr Lys Arg Gly
1 5 10 15

Gln Asp Val Ala Leu Arg Cys Asp Pro Ile Ser Gly His Val Ser Leu
20 25 30

Tyr Trp Tyr Arg Gln Ala Leu Gly Gln Gly Pro Glu Phe Leu Thr Tyr
35 40 45

Phe Asn Tyr Glu Ala Gln Gln Asp Lys Ser Gly Leu Pro Asn Asp Arg
50 55 60

Phe Ser Ala Glu Arg Pro Glu Gly Ser Ile Ser Thr Leu Thr Ile Gln
65 70 75 80

Arg Thr Glu Gln Arg Asp Ser Ala Met Tyr Arg Cys Ala Ser Ser His
85 90 95

Thr Asp Gly Ser Tyr Glu Gln Tyr Phe Gly Pro Gly Thr Arg Leu Thr
100 105 110

Val Thr

<210> SEQ ID NO 606
<211> LENGTH: 209
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 606

Met Ser Asn Gln Val Leu Cys Cys Val Val Leu Cys Leu Leu Gly Ala
1 5 10 15

Asn Thr Val Asp Gly Gly Ile Thr Gln Ser Pro Lys Tyr Leu Phe Arg
20 25 30

Lys Glu Gly Gln Asn Val Thr Leu Ser Cys Glu Gln Asn Leu Asn His
35 40 45

Asp Ala Met Tyr Trp Tyr Arg Gln Asp Pro Gly Gln Gly Leu Arg Leu
50 55 60

Ile Tyr Tyr Ser Gln Ile Val Asn Asp Phe Gln Lys Gly Asp Ile Ala
65 70 75 80

```
Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Gly Ala Phe Ala Gly Gln Pro Gln His Phe Gly Asp Gly Thr
        115                 120                 125

Arg Leu Ser Ile Leu Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu


<210> SEQ ID NO 607
<211> LENGTH: 343
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 607

gatggtggaa tcactcagtc cccaaagtac ctgttcagaa aggaaggaca gaatgtgacc      60

ctgagttgtg aacagaattt gaaccacgat gccatgtact ggtaccgaca ggacccaggg     120

caagggctga gattgatcta ctactcacag atagtaaatg actttcagaa aggagatata     180

gctgaagggt acagcgtctc tcgggagaag aaggaatcct ttcctctcac tgtgacatcg     240

gcccaaaaga acccgacagc tttctatctc tgtgccagta gcataggggc atttgctggt     300

cagccccagc attttggtga tgggactcga ctctccatcc tag                       343


<210> SEQ ID NO 608
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 608

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Ala Phe Ala Gly Gln Pro Gln His Phe Gly Asp Gly Thr Arg Leu Ser
```

100 105 110

Ile Leu

<210> SEQ ID NO 609
<211> LENGTH: 316
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 609

Met Gly Thr Ser Leu Leu Cys Trp Met Ala Leu Cys Leu Leu Gly Ala
1 5 10 15

Asp His Ala Asp Thr Gly Val Ser Gln Asn Pro Arg His Lys Ile Thr
20 25 30

Lys Arg Gly Gln Asn Val Thr Phe Arg Cys Asp Pro Ile Ser Glu His
35 40 45

Asn Arg Leu Tyr Trp Tyr Arg Gln Thr Leu Gly Gln Gly Pro Glu Phe
50 55 60

Leu Thr Tyr Phe Gln Asn Glu Ala Gln Leu Glu Lys Ser Arg Leu Leu
65 70 75 80

Ser Asp Arg Phe Ser Ala Glu Arg Pro Lys Gly Ser Phe Ser Thr Leu
85 90 95

Glu Ile Gln Arg Thr Glu Gln Gly Asp Ser Ala Met Tyr Leu Cys Ala
100 105 110

Ser Ser Leu Ala Pro Thr Pro Gly Pro Asp Thr Gly Glu Leu Phe Phe
115 120 125

Gly Glu Gly Ser Arg Leu Thr Val Leu Glu Asp Leu Lys Asn Val Phe
130 135 140

Pro Pro Glu Val Ala Val Phe Glu Pro Ser Glu Ala Glu Ile Ser His
145 150 155 160

Thr Gln Lys Ala Thr Leu Val Cys Leu Ala Thr Gly Phe Tyr Pro Asp
165 170 175

His Val Glu Leu Ser Trp Trp Val Asn Gly Lys Glu Val His Ser Gly
180 185 190

Val Ser Thr Asp Pro Gln Pro Leu Lys Glu Gln Pro Ala Leu Asn Asp
195 200 205

Ser Arg Tyr Cys Leu Ser Ser Arg Leu Arg Val Ser Ala Thr Phe Trp
210 215 220

Gln Asn Pro Arg Asn His Phe Arg Cys Gln Val Gln Phe Tyr Gly Leu
225 230 235 240

Ser Glu Asn Asp Glu Trp Thr Gln Asp Arg Ala Lys Pro Val Thr Gln
245 250 255

Ile Val Ser Ala Glu Ala Trp Gly Arg Ala Asp Cys Gly Phe Thr Ser
260 265 270

Glu Ser Tyr Gln Gln Gly Val Leu Ser Ala Thr Ile Leu Tyr Glu Ile
275 280 285

Leu Leu Gly Lys Ala Thr Leu Tyr Ala Val Leu Val Ser Ala Leu Val
290 295 300

Leu Met Ala Met Val Lys Arg Lys Asp Ser Arg Gly
305 310 315

<210> SEQ ID NO 610
<211> LENGTH: 355
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 610

```
gatactggag tctcccagaa ccccagacac aagatcacaa agaggggaca gaatgtaact     60

ttcaggtgtg atccaatttc tgaacacaac cgcctttatt ggtaccgaca gaccctgggg    120

cagggcccag agtttctgac ttacttccag aatgaagctc aactagaaaa atcaaggctg    180

ctcagtgatc ggttctctgc agagaggcct aagggatctt tctccacctt ggagatccag    240

cgcacagagc agggggactc ggccatgtat ctctgtgcca gcagcttagc gcctaccccc    300

gggccggaca ccggggagct gtttttttgga gaaggctcta ggctgaccgt actgg        355
```

<210> SEQ ID NO 611
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 611

```
Asp Thr Gly Val Ser Gln Asn Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Leu
                85                  90                  95

Ala Pro Thr Pro Gly Pro Asp Thr Gly Glu Leu Phe Phe Gly Glu Gly
            100                 105                 110

Ser Arg Leu Thr Val Leu
        115
```

<210> SEQ ID NO 612
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 612

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80
```

```
Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Leu Gly Asn Ile Tyr Glu Gln Tyr Phe Gly Pro Gly Thr Arg Leu
            115                 120                 125

Thr Val Thr Glu Asp Leu Lys Asn Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Ser Arg Gly
305                 310
```

```
<210> SEQ ID NO 613
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 613

gaagcccaag tgacccagaa cccaagatac ctcatcacag tgactggaaa gaagttaaca      60

gtgacttgtt ctcagaatat gaaccatgag tatatgtcct ggtatcgaca agacccaggg     120

ctgggcttaa ggcagatcta ctattcaatg aatgttgagg tgactgataa gggagatgtt     180

cctgaagggt acaaagtctc tcgaaaagag aagaggaatt tccccctgat cctggagtcg     240

cccagcccca accagacctc tctgtacttc tgtgccagca gtttagggaa tatctacgag     300

cagtacttcg ggccgggcac caggctcacg gtcacag                             337
```

```
<210> SEQ ID NO 614
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 614
```

```
Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Gly
                85                  90                  95

Asn Ile Tyr Glu Gln Tyr Phe Gly Pro Gly Thr Arg Leu Thr Val Thr
            100                 105                 110


<210> SEQ ID NO 615
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 615

Met Gly Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Leu Gly Ser Gly Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
```

```
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310
```

<210> SEQ ID NO 616
<211> LENGTH: 337
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 616

```
ggtgctggag tctcccagac ccccagtaac aaggtcacag agaagggaaa atatgtagag     60

ctcaggtgtg atccaatttc aggtcatact gccctttact ggtaccgaca aagcctgggg    120

cagggcccag agtttctaat ttacttccaa ggcacgggtg cggcagatga ctcagggctg    180

cccaacgatc ggttctttgc agtcaggcct gagggatccg tctctactct gaagatccag    240

cgcacagagc gggggactc agccgtgtat ctctgtgcca gcagcttagg gagcggtgag    300

cagttcttcg ggccagggac acggctcacc gtgctag                             337
```

<210> SEQ ID NO 617
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 617

```
Gly Ala Gly Val Ser Gln Thr Pro Ser Asn Lys Val Thr Glu Lys Gly
1               5                   10                  15

Lys Tyr Val Glu Leu Arg Cys Asp Pro Ile Ser Gly His Thr Ala Leu
            20                  25                  30

Tyr Trp Tyr Arg Gln Ser Leu Gly Gln Gly Pro Glu Phe Leu Ile Tyr
        35                  40                  45

Phe Gln Gly Thr Gly Ala Ala Asp Asp Ser Gly Leu Pro Asn Asp Arg
    50                  55                  60

Phe Phe Ala Val Arg Pro Glu Gly Ser Val Ser Thr Leu Lys Ile Gln
65                  70                  75                  80

Arg Thr Glu Arg Gly Asp Ser Ala Val Tyr Leu Cys Ala Ser Ser Leu
                85                  90                  95

Gly Ser Gly Glu Gln Phe Phe Gly Pro Gly Thr Arg Leu Thr Val Leu
            100                 105                 110
```

<210> SEQ ID NO 618
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 618

Met Gly Pro Arg Leu Leu Phe Trp Ala Leu Leu Cys Leu Leu Gly Thr
1 5 10 15

Gly Pro Val Glu Ala Gly Val Thr Gln Ser Pro Thr His Leu Ile Lys
20 25 30

Thr Arg Gly Gln Gln Ala Thr Leu Arg Cys Ser Pro Ile Ser Gly His
35 40 45

Thr Ser Val Tyr Trp Tyr Gln Gln Ala Leu Gly Leu Gly Leu Gln Phe
50 55 60

Leu Leu Trp Tyr Asp Glu Gly Glu Glu Arg Asn Arg Gly Asn Phe Pro
65 70 75 80

Pro Arg Phe Ser Gly Arg Gln Phe Pro Asn Tyr Ser Ser Glu Leu Asn
85 90 95

Val Asn Ala Leu Glu Leu Glu Asp Ser Ala Leu Tyr Leu Cys Ala Ser
100 105 110

Ser Leu Gln Thr Ser Tyr Glu Gln Tyr Phe Gly Pro Gly Thr Arg Leu
115 120 125

Thr Val Thr Glu Asp Leu Lys Asn Val Phe Pro Pro Glu Val Ala Val
130 135 140

Phe Glu Pro Ser Glu Ala Glu Ile Ser His Thr Gln Lys Ala Thr Leu
145 150 155 160

Val Cys Leu Ala Thr Gly Phe Tyr Pro Asp His Val Glu Leu Ser Trp
165 170 175

Trp Val Asn Gly Lys Glu Val His Ser Gly Val Ser Thr Asp Pro Gln
180 185 190

Pro Leu Lys Glu Gln Pro Ala Leu Asn Asp Ser Arg Tyr Cys Leu Ser
195 200 205

Ser Arg Leu Arg Val Ser Ala Thr Phe Trp Gln Asn Pro Arg Asn His
210 215 220

Phe Arg Cys Gln Val Gln Phe Tyr Gly Leu Ser Glu Asn Asp Glu Trp
225 230 235 240

Thr Gln Asp Arg Ala Lys Pro Val Thr Gln Ile Val Ser Ala Glu Ala
245 250 255

Trp Gly Arg Ala Asp Cys Gly Phe Thr Ser Glu Ser Tyr Gln Gln Gly
260 265 270

Val Leu Ser Ala Thr Ile Leu Tyr Glu Ile Leu Leu Gly Lys Ala Thr
275 280 285

Leu Tyr Ala Val Leu Val Ser Ala Leu Val Leu Met Ala Met Val Lys
290 295 300

Arg Lys Asp Ser Arg Gly
305 310

<210> SEQ ID NO 619
<211> LENGTH: 337
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 619
gaggctggag tcacacaaag tcccacacac ctgatcaaaa cgagaggaca gcaagcgact 60
ctgagatgct ctcctatctc tgggcacacc agtgtgtact ggtaccaaca ggccctgggt 120
ctgggcctcc agttcctcct ttggtatgac gagggtgaag agagaaacag aggaaacttc 180
cctcctagat tttcaggtcg ccagttccct aattatagct ctgagctgaa tgtgaacgcc 240
ttggagctgg aggactcggc cctgtatctc tgtgccagca gcttacagac atcctacgag 300
cagtacttcg ggccgggcac caggctcacg gtcacag 337

<210> SEQ ID NO 620
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 620

Glu Ala Gly Val Thr Gln Ser Pro Thr His Leu Ile Lys Thr Arg Gly
1 5 10 15

Gln Gln Ala Thr Leu Arg Cys Ser Pro Ile Ser Gly His Thr Ser Val
20 25 30

Tyr Trp Tyr Gln Gln Ala Leu Gly Leu Gly Leu Gln Phe Leu Leu Trp
35 40 45

Tyr Asp Glu Gly Glu Glu Arg Asn Arg Gly Asn Phe Pro Pro Arg Phe
50 55 60

Ser Gly Arg Gln Phe Pro Asn Tyr Ser Ser Glu Leu Asn Val Asn Ala
65 70 75 80

Leu Glu Leu Glu Asp Ser Ala Leu Tyr Leu Cys Ala Ser Ser Leu Gln
85 90 95

Thr Ser Tyr Glu Gln Tyr Phe Gly Pro Gly Thr Arg Leu Thr Val Thr
100 105 110

<210> SEQ ID NO 621
<211> LENGTH: 315
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 621

Met Gly Pro Gln Leu Leu Gly Tyr Val Val Leu Cys Leu Leu Gly Ala
1 5 10 15

Gly Pro Leu Glu Ala Gln Val Thr Gln Asn Pro Arg Tyr Leu Ile Thr
20 25 30

Val Thr Gly Lys Lys Leu Thr Val Thr Cys Ser Gln Asn Met Asn His
35 40 45

Glu Tyr Met Ser Trp Tyr Arg Gln Asp Pro Gly Leu Gly Leu Arg Gln
50 55 60

Ile Tyr Tyr Ser Met Asn Val Glu Val Thr Asp Lys Gly Asp Val Pro
65 70 75 80

Glu Gly Tyr Lys Val Ser Arg Lys Glu Lys Arg Asn Phe Pro Leu Ile
85 90 95

Leu Glu Ser Pro Ser Pro Asn Gln Thr Ser Leu Tyr Phe Cys Ala Ser
100 105 110

Ser Leu Ser Trp Gly Thr Gly Lys Arg Ala Asp Thr Gln Tyr Phe Gly
115 120 125

Pro Gly Thr Arg Leu Thr Val Leu Glu Asp Leu Lys Asn Val Phe Pro
130 135 140

Pro Glu Val Ala Val Phe Glu Pro Ser Glu Ala Glu Ile Ser His Thr
145 150 155 160

Gln Lys Ala Thr Leu Val Cys Leu Ala Thr Gly Phe Tyr Pro Asp His

```
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Glu
            260                 265                 270

Ser Tyr Gln Gln Gly Val Leu Ser Ala Thr Ile Leu Tyr Glu Ile Leu
        275                 280                 285

Leu Gly Lys Ala Thr Leu Tyr Ala Val Leu Val Ser Ala Leu Val Leu
    290                 295                 300

Met Ala Met Val Lys Arg Lys Asp Ser Arg Gly
305                 310                 315


<210> SEQ ID NO 622
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 622

gaagcccaag tgacccagaa cccaagatac ctcatcacag tgactggaaa gaagttaaca     60

gtgacttgtt ctcagaatat gaaccatgag tatatgtcct ggtatcgaca agacccaggg    120

ctgggcttaa ggcagatcta ctattcaatg aatgttgagg tgactgataa gggagatgtt    180

cctgaagggt acaaagtctc tcgaaaagag aagaggaatt tccccctgat cctggagtcg    240

cccagcccca accagacctc tctgtacttc tgtgccagca gtttatcgtg ggggaccggc    300

aaaagagcag atacgcagta ttttggccca ggcacccggc tgacagtgct cg            352


<210> SEQ ID NO 623
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 623

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Ser
```

```
                85                  90                  95

Trp Gly Thr Gly Lys Arg Ala Asp Thr Gln Tyr Phe Gly Pro Gly Thr
            100                 105                 110

Arg Leu Thr Val Leu
        115
```

<210> SEQ ID NO 624
<211> LENGTH: 313
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 624

```
Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Gly Gly Gly Ser Asn Glu Gln Phe Phe Gly Pro Gly
        115                 120                 125

Thr Arg Leu Thr Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser Arg Gly
305                 310
```

<210> SEQ ID NO 625
<211> LENGTH: 346
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 625
gatactggag tctcccagga ccccagacac aagatcacaa agaggggaca gaatgtaact 60
ttcaggtgtg atccaatttc tgaacacaac cgcctttatt ggtaccgaca gaccctgggg 120
cagggcccag agtttctgac ttacttccag aatgaagctc aactagaaaa atcaaggctg 180
ctcagtgatc ggttctctgc agagaggcct aagggatctt tctccacctt ggagatccag 240
cgcacagagc agggggactc ggccatgtat ctctgtgcca gcagcttagt tggcggcggg 300
agcaatgagc agttcttcgg gccagggaca cggctcaccg tgctag 346

<210> SEQ ID NO 626
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 626

Asp Thr Gly Val Ser Gln Asp Pro Arg His Lys Ile Thr Lys Arg Gly
1 5 10 15

Gln Asn Val Thr Phe Arg Cys Asp Pro Ile Ser Glu His Asn Arg Leu
20 25 30

Tyr Trp Tyr Arg Gln Thr Leu Gly Gln Gly Pro Glu Phe Leu Thr Tyr
35 40 45

Phe Gln Asn Glu Ala Gln Leu Glu Lys Ser Arg Leu Leu Ser Asp Arg
50 55 60

Phe Ser Ala Glu Arg Pro Lys Gly Ser Phe Ser Thr Leu Glu Ile Gln
65 70 75 80

Arg Thr Glu Gln Gly Asp Ser Ala Met Tyr Leu Cys Ala Ser Ser Leu
85 90 95

Val Gly Gly Gly Ser Asn Glu Gln Phe Phe Gly Pro Gly Thr Arg Leu
100 105 110

Thr Val Leu
115

<210> SEQ ID NO 627
<211> LENGTH: 309
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 627

Met Gly Thr Ser Leu Leu Cys Trp Met Ala Leu Cys Leu Leu Gly Ala
1 5 10 15

Asp His Ala Asp Thr Gly Val Ser Gln Asp Pro Arg His Lys Ile Thr
20 25 30

Lys Arg Gly Gln Asn Val Thr Phe Arg Cys Asp Pro Ile Ser Glu His
35 40 45

Asn Arg Leu Tyr Trp Tyr Arg Gln Thr Leu Gly Gln Gly Pro Glu Phe

```
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Gly Gly Thr Glu Ala Phe Phe Gly Gln Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305
```

<210> SEQ ID NO 628
<211> LENGTH: 340
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 628

```
gatactggag tctcccagga ccccagacac aagatcacaa agaggggaca gaatgtaact     60

ttcaggtgtg atccaatttc tgaacacaac cgcctttatt ggtaccgaca gaccctgggg    120

cagggcccag agtttctgac ttacttccag aatgaagctc aactagaaaa atcaaggctg    180

ctcagtgatc ggttctctgc agagaggcct aagggatctt tctccacctt ggagatccag    240

cgcacagagc agggggactc ggccatgtat ctctgtgcca gcagcttagt cggaggcact    300

gaagctttct ttggacaagg caccagactc acagttgtag                          340
```

<210> SEQ ID NO 629
<211> LENGTH: 113
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 629

```
Asp Thr Gly Val Ser Gln Asp Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Leu
                85                  90                  95

Val Gly Gly Thr Glu Ala Phe Phe Gly Gln Gly Thr Arg Leu Thr Val
            100                 105                 110

Val
```

<210> SEQ ID NO 630
<211> LENGTH: 311
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 630

```
Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Pro Asp Arg Asn Leu Gly Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
```

```
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310
```

```
<210> SEQ ID NO 631
<211> LENGTH: 340
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 631

gatactggag tctcccagga ccccagacac aagatcacaa agaggggaca gaatgtaact     60

ttcaggtgtg atccaatttc tgaacacaac cgcctttatt ggtaccgaca gaccctgggg    120

cagggcccag agtttctgac ttacttccag aatgaagctc aactagaaaa atcaaggctg    180

ctcagtgatc ggttctctgc agagaggcct aagggatctt tctccacctt ggagatccag    240

cgcacagagc agggggactc ggccatgtat ctctgtgcca gcagccccga tcggaatctc    300

gggcagtact tcgggccggg caccaggctc acggtcacag                          340
```

```
<210> SEQ ID NO 632
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 632

Asp Thr Gly Val Ser Gln Asp Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Pro
                85                  90                  95

Asp Arg Asn Leu Gly Gln Tyr Phe Gly Pro Gly Thr Arg Leu Thr Val
            100                 105                 110

Thr
```

```
<210> SEQ ID NO 633
```

<211> LENGTH: 312
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 633

```
Met Val Ser Arg Leu Leu Ser Leu Val Ser Leu Cys Leu Leu Gly Ala
1               5                   10                  15

Lys His Ile Glu Ala Gly Val Thr Gln Phe Pro Ser His Ser Val Ile
            20                  25                  30

Glu Lys Gly Gln Thr Val Thr Leu Arg Cys Asp Pro Ile Ser Gly His
        35                  40                  45

Asp Asn Leu Tyr Trp Tyr Arg Arg Val Met Gly Lys Glu Ile Lys Phe
    50                  55                  60

Leu Leu His Phe Val Lys Glu Ser Lys Gln Asp Glu Ser Gly Met Pro
65                  70                  75                  80

Asn Asn Arg Phe Leu Ala Glu Arg Thr Gly Gly Thr Tyr Ser Thr Leu
                85                  90                  95

Lys Val Gln Pro Ala Glu Leu Glu Asp Ser Gly Val Tyr Phe Cys Ala
            100                 105                 110

Ser Ser Gln Val Gln Ala Phe Asn Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310
```

<210> SEQ ID NO 634
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 634

```
gaagctggag ttactcagtt ccccagccac agcgtaatag agaagggcca gactgtgact      60

ctgagatgtg acccaatttc tggacatgat aatctttatt ggtatcgacg tgttatggga     120

aaagaaataa aatttctgtt acattttgtg aaagagtcta aacaggatga atccggtatg     180

cccaacaatc gattcttagc tgaaaggact ggagggacgt attctactct gaaggtgcag     240

cctgcagaac tggaggattc tggagtttat ttctgtgcca gcagccaagt ccaggctttt     300

aatgagcagt tcttcgggcc agggacacgg ctcaccgtgc tag                       343
```

```
<210> SEQ ID NO 635
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 635

Glu Ala Gly Val Thr Gln Phe Pro Ser His Ser Val Ile Glu Lys Gly
1               5                   10                  15

Gln Thr Val Thr Leu Arg Cys Asp Pro Ile Ser Gly His Asp Asn Leu
            20                  25                  30

Tyr Trp Tyr Arg Arg Val Met Gly Lys Glu Ile Lys Phe Leu Leu His
        35                  40                  45

Phe Val Lys Glu Ser Lys Gln Asp Glu Ser Gly Met Pro Asn Asn Arg
    50                  55                  60

Phe Leu Ala Glu Arg Thr Gly Gly Thr Tyr Ser Thr Leu Lys Val Gln
65                  70                  75                  80

Pro Ala Glu Leu Glu Asp Ser Gly Val Tyr Phe Cys Ala Ser Ser Gln
                85                  90                  95

Val Gln Ala Phe Asn Glu Gln Phe Phe Gly Pro Gly Thr Arg Leu Thr
            100                 105                 110

Val Leu


<210> SEQ ID NO 636
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 636

Met Arg Gly Gln Gly Arg Pro Ser Ser Ser Ala Phe Ala His Ser Asp
1               5                   10                  15

Pro Asp Trp Ala Lys Leu Pro Ser Phe Pro Asp Pro Ala Met Gly Thr
            20                  25                  30

Arg Leu Leu Cys Trp Ala Ala Leu Cys Leu Leu Gly Ala Glu Leu Thr
        35                  40                  45

Glu Ala Gly Val Ala Gln Ser Pro Arg Tyr Lys Ile Ile Glu Lys Arg
    50                  55                  60

Gln Ser Val Ala Phe Trp Cys Asn Pro Ile Ser Gly His Ala Thr Leu
65                  70                  75                  80

Tyr Trp Tyr Gln Gln Ile Leu Gly Gln Gly Pro Lys Leu Leu Ile Gln
                85                  90                  95

Phe Gln Asn Asn Gly Val Val Asp Asp Ser Gln Leu Pro Lys Asp Arg
            100                 105                 110
```

```
Phe Ser Ala Glu Arg Leu Lys Gly Val Asp Ser Thr Leu Lys Ile Gln
        115                 120                 125

Pro Ala Lys Leu Glu Asp Ser Ala Val Tyr Leu Cys Ala Ser Ser Arg
    130                 135                 140

Gly Glu Pro Gly Ser Gly Ala Asn Val Leu Thr Phe Gly Ala Gly Ser
145                 150                 155                 160

Arg Leu Thr Val Leu Glu Asp Leu Lys Asn Val Phe Pro Pro Glu Val
                165                 170                 175

Ala Val Phe Glu Pro Ser Glu Ala Glu Ile Ser His Thr Gln Lys Ala
            180                 185                 190

Thr Leu Val Cys Leu Ala Thr Gly Phe Tyr Pro Asp His Val Glu Leu
        195                 200                 205

Ser Trp Trp Val Asn Gly Lys Glu Val His Ser Gly Val Ser Thr Asp
    210                 215                 220

Pro Gln Pro Leu Lys Glu Gln Pro Ala Leu Asn Asp Ser Arg Tyr Cys
225                 230                 235                 240

Leu Ser Ser Arg Leu Arg Val Ser Ala Thr Phe Trp Gln Asn Pro Arg
                245                 250                 255

Asn His Phe Arg Cys Gln Val Gln Phe Tyr Gly Leu Ser Glu Asn Asp
            260                 265                 270

Glu Trp Thr Gln Asp Arg Ala Lys Pro Val Thr Gln Ile Val Ser Ala
        275                 280                 285

Glu Ala Trp Gly Arg Ala Asp Cys Gly Phe Thr Ser Glu Ser Tyr Gln
    290                 295                 300

Gln Gly Val Leu Ser Ala Thr Ile Leu Tyr Glu Ile Leu Leu Gly Lys
305                 310                 315                 320

Ala Thr Leu Tyr Ala Val Leu Val Ser Ala Leu Val Leu Met Ala Met
                325                 330                 335

Val Lys Arg Lys Asp Ser Arg Gly
            340
```

<210> SEQ ID NO 637
<211> LENGTH: 352
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 637

```
gaagctggag ttgcccagtc tcccagatat aagattatag agaaaaggca gagtgtggct      60

ttttggtgca atcctatatc tggccatgct accctttact ggtaccagca gatcctggga     120

cagggcccaa agcttctgat tcagtttcag aataacggtg tagtggatga ttcacagttg     180

cctaaggatc gattttctgc agagaggctc aaaggagtag actccactct caagatccag     240

cctgcaaagc ttgaggactc ggccgtgtat ctctgtgcca gcagtcgagg ggagccaggc     300

tctggggcca acgtcctgac tttcggggcc ggcagcaggc tgaccgtgct gg             352
```

<210> SEQ ID NO 638
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 638

```
Glu Ala Gly Val Ala Gln Ser Pro Arg Tyr Lys Ile Ile Glu Lys Arg
1               5                   10                  15

Gln Ser Val Ala Phe Trp Cys Asn Pro Ile Ser Gly His Ala Thr Leu
            20                  25                  30

Tyr Trp Tyr Gln Gln Ile Leu Gly Gln Gly Pro Lys Leu Leu Ile Gln
        35                  40                  45

Phe Gln Asn Asn Gly Val Val Asp Asp Ser Gln Leu Pro Lys Asp Arg
    50                  55                  60

Phe Ser Ala Glu Arg Leu Lys Gly Val Asp Ser Thr Leu Lys Ile Gln
65                  70                  75                  80

Pro Ala Lys Leu Glu Asp Ser Ala Val Tyr Leu Cys Ala Ser Ser Arg
                85                  90                  95

Gly Glu Pro Gly Ser Gly Ala Asn Val Leu Thr Phe Gly Ala Gly Ser
            100                 105                 110

Arg Leu Thr Val Leu
        115


<210> SEQ ID NO 639
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 639

Met Gln Cys Phe Leu Ser Leu Cys Ala Met Gly Pro Gly Leu Leu Cys
1               5                   10                  15

Trp Ala Leu Leu Cys Leu Leu Gly Ala Gly Leu Val Asp Ala Gly Val
            20                  25                  30

Thr Gln Ser Pro Thr His Leu Ile Lys Thr Arg Gly Gln Gln Val Thr
        35                  40                  45

Leu Arg Cys Ser Pro Lys Ser Gly His Asp Thr Val Ser Trp Tyr Gln
    50                  55                  60

Gln Ala Leu Gly Gln Gly Pro Gln Phe Ile Phe Gln Tyr Tyr Glu Glu
65                  70                  75                  80

Glu Glu Arg Gln Arg Gly Asn Phe Pro Asp Arg Phe Ser Gly His Gln
                85                  90                  95

Phe Pro Asn Tyr Ser Ser Glu Leu Asn Val Asn Ala Leu Leu Leu Gly
            100                 105                 110

Asp Ser Ala Leu Tyr Leu Cys Ala Ser Ser Ser Gly Thr Asp Pro Ser
        115                 120                 125

Gly Ala Asn Val Leu Thr Phe Gly Ala Gly Ser Arg Leu Thr Val Leu
    130                 135                 140

Glu Asp Leu Lys Asn Val Phe Pro Pro Glu Val Ala Val Phe Glu Pro
145                 150                 155                 160

Ser Glu Ala Glu Ile Ser His Thr Gln Lys Ala Thr Leu Val Cys Leu
                165                 170                 175

Ala Thr Gly Phe Phe Pro Asp His Val Glu Leu Ser Trp Trp Val Asn
            180                 185                 190

Gly Lys Glu Val His Ser Gly Val Ser Thr Asp Pro Gln Pro Leu Lys
        195                 200                 205

Glu Gln Pro Ala Leu Asn Asp Ser Arg Tyr Cys Leu Ser Ser Arg Leu
    210                 215                 220

Arg Val Ser Ala Thr Phe Trp Gln Asn Pro Arg Asn His Phe Arg Cys
225                 230                 235                 240
```

```
Gln Val Gln Phe Tyr Gly Leu Ser Glu Asn Asp Glu Trp Thr Gln Asp
                245                 250                 255

Arg Ala Lys Pro Val Thr Gln Ile Val Ser Ala Glu Ala Trp Gly Arg
            260                 265                 270

Ala Asp Cys Gly Phe Thr Ser Glu Ser Tyr Gln Gln Gly Val Leu Ser
        275                 280                 285

Ala Thr Ile Leu Tyr Glu Ile Leu Leu Gly Lys Ala Thr Leu Tyr Ala
    290                 295                 300

Val Leu Val Ser Ala Leu Val Leu Met Ala Met Val Lys Arg Lys Asp
305                 310                 315                 320

Ser Arg Gly


<210> SEQ ID NO 640
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 640

gacgctggag tcacccaaag tcccacacac ctgatcaaaa cgagaggaca gcaagtgact      60

ctgagatgct ctcctaagtc tgggcatgac actgtgtcct ggtaccaaca ggccctgggt     120

caggggcccc agtttatctt tcagtattat gaggaggaag agagacagag aggcaacttc     180

cctgatcgat tctcaggtca ccagttccct aactatagct ctgagctgaa tgtgaacgcc     240

ttgttgctgg gggactcggc cctctatctc tgtgccagca gctccgggac agacccctct     300

ggggccaacg tcctgacttt cggggccggc agcaggctga ccgtgctgg                 349


<210> SEQ ID NO 641
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 641

Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Ser Gly
                85                  90                  95

Thr Asp Pro Ser Gly Ala Asn Val Leu Thr Phe Gly Ala Gly Ser Arg
            100                 105                 110

Leu Thr Val Leu
        115


<210> SEQ ID NO 642
<211> LENGTH: 312
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 642

Met Gly Pro Gln Leu Leu Gly Tyr Val Val Leu Cys Leu Leu Gly Ala
1 5 10 15

Gly Pro Leu Glu Ala Gln Val Thr Gln Asn Pro Arg Tyr Leu Ile Thr
20 25 30

Val Thr Gly Lys Lys Leu Thr Val Thr Cys Ser Gln Asn Met Asn His
35 40 45

Glu Tyr Met Ser Trp Tyr Arg Gln Asp Pro Gly Leu Gly Leu Arg Gln
50 55 60

Ile Tyr Tyr Ser Met Asn Val Glu Val Thr Asp Lys Gly Asp Val Pro
65 70 75 80

Glu Gly Tyr Lys Val Ser Arg Lys Glu Lys Arg Asn Phe Pro Leu Ile
85 90 95

Leu Glu Ser Pro Ser Pro Asn Gln Thr Ser Leu Tyr Phe Cys Ala Ser
100 105 110

Ser Thr Gly Gln Asn Ile Gly Gly Glu Leu Phe Phe Gly Glu Gly Ser
115 120 125

Arg Leu Thr Val Leu Glu Asp Leu Lys Asn Val Phe Pro Pro Glu Val
130 135 140

Ala Val Phe Glu Pro Ser Glu Ala Glu Ile Ser His Thr Gln Lys Ala
145 150 155 160

Thr Leu Val Cys Leu Ala Thr Gly Phe Tyr Pro Asp His Val Glu Leu
165 170 175

Ser Trp Trp Val Asn Gly Lys Glu Val His Ser Gly Val Ser Thr Asp
180 185 190

Pro Gln Pro Leu Lys Glu Gln Pro Ala Leu Asn Asp Ser Arg Tyr Cys
195 200 205

Leu Ser Ser Arg Leu Arg Val Ser Ala Thr Phe Trp Gln Asn Pro Arg
210 215 220

Asn His Phe Arg Cys Gln Val Gln Phe Tyr Gly Leu Ser Glu Asn Asp
225 230 235 240

Glu Trp Thr Gln Asp Arg Ala Lys Pro Val Thr Gln Ile Val Ser Ala
245 250 255

Glu Ala Trp Gly Arg Ala Asp Cys Gly Phe Thr Ser Glu Ser Tyr Gln
260 265 270

Gln Gly Val Leu Ser Ala Thr Ile Leu Tyr Glu Ile Leu Leu Gly Lys
275 280 285

Ala Thr Leu Tyr Ala Val Leu Val Ser Ala Leu Val Leu Met Ala Met
290 295 300

Val Lys Arg Lys Asp Ser Arg Gly
305 310

<210> SEQ ID NO 643
<211> LENGTH: 343
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 643

```
gaagcccaag tgacccagaa cccaagatac ctcatcacag tgactggaaa gaagttaaca      60

gtgacttgtt ctcagaatat gaaccatgag tatatgtcct ggtatcgaca agacccaggg     120

ctgggcttaa ggcagatcta ctattcaatg aatgttgagg tgactgataa gggagatgtt     180

cctgaagggt acaaagtctc tcgaaaagag aagaggaatt tccccctgat cctggagtcg     240

cccagcccca accagacctc tctgtacttc tgtgccagca gtaccggaca gaatataggc     300

ggggagctgt tttttggaga aggctctagg ctgaccgtac tgg                       343


<210> SEQ ID NO 644
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 644

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Thr Gly
                85                  90                  95

Gln Asn Ile Gly Gly Glu Leu Phe Phe Gly Glu Gly Ser Arg Leu Thr
            100                 105                 110

Val Leu


<210> SEQ ID NO 645
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 645

Met Val His Ile Arg Val Ala Ala Ile Leu Asp Leu Thr His Gln Tyr
1               5                   10                  15

Gln Val Ile Leu Arg Leu Ser Asp Val Thr Val Gly Thr Ala Leu Trp
            20                  25                  30

Arg Gln Gly Arg Pro Ser Ser Ser Ala Pro Ala His Ser Asp Pro Asp
        35                  40                  45

Leu Val Lys Leu Pro Ser Cys Pro Asp Pro Ala Met Gly Thr Ser Leu
    50                  55                  60

Leu Cys Trp Met Ala Leu Cys Leu Leu Gly Ala Asp His Ala Asp Thr
65                  70                  75                  80

Gly Val Ser Gln Asp Pro Arg His Lys Ile Thr Lys Arg Gly Gln Asn
                85                  90                  95

Val Thr Phe Arg Cys Asp Pro Ile Ser Glu His Asn Arg Leu Tyr Trp
            100                 105                 110

Tyr Arg Gln Thr Leu Gly Gln Gly Pro Glu Phe Leu Thr Tyr Phe Gln
```

```
        115                 120                 125

Asn Glu Ala Gln Leu Glu Lys Ser Arg Leu Leu Ser Asp Arg Phe Ser
    130                 135                 140

Ala Glu Arg Pro Lys Gly Ser Phe Ser Thr Leu Glu Ile Gln Arg Thr
145                 150                 155                 160

Glu Gln Gly Asp Ser Ala Met Tyr Leu Cys Ala Ser Ser Thr His Glu
                165                 170                 175

Lys Thr Gly Trp Lys Ser Pro Leu His Phe Gly Asn Gly Thr Arg Leu
            180                 185                 190

Thr Val Thr Glu Asp Leu Asn Lys Val Phe Pro Pro Glu Val Ala Val
        195                 200                 205

Phe Glu Pro Ser Glu Ala Glu Ile Ser His Thr Gln Lys Ala Thr Leu
    210                 215                 220

Val Cys Leu Ala Thr Gly Phe Tyr Pro Asp His Val Glu Leu Ser Trp
225                 230                 235                 240

Trp Val Asn Gly Lys Glu Val His Ser Gly Val Ser Thr Asp Pro Gln
                245                 250                 255

Pro Leu Lys Glu Gln Pro Ala Leu Asn Asp Ser Arg Tyr Cys Leu Ser
            260                 265                 270

Ser Arg Leu Arg Val Ser Ala Thr Phe Trp Gln Asn Pro Arg Asn His
        275                 280                 285

Phe Arg Cys Gln Val Gln Phe Tyr Gly Leu Ser Glu Asn Asp Glu Trp
    290                 295                 300

Thr Gln Asp Arg Ala Lys Pro Val Thr Gln Ile Val Ser Ala Glu Ala
305                 310                 315                 320

Trp Gly Arg Ala Asp Cys Gly Phe Thr Ser Val Ser Tyr Gln Gln Gly
                325                 330                 335

Val Leu Ser Ala Thr Ile Leu Tyr Glu Ile Leu Leu Gly Lys Ala Thr
            340                 345                 350

Leu Tyr Ala Val Leu Val Ser Ala Leu Val Leu Met Ala Met Val Lys
        355                 360                 365

Arg Lys Asp Phe
    370
```

<210> SEQ ID NO 646
<211> LENGTH: 352
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 646

```
gatactggag tctcccagga ccccagacac aagatcacaa agaggggaca gaatgtaact      60

ttcaggtgtg atccaatttc tgaacacaac cgcctttatt ggtaccgaca gaccctgggg     120

cagggcccag agtttctgac ttacttccag aatgaagctc aactagaaaa atcaaggctg     180

ctcagtgatc ggttctctgc agagaggcct aagggatctt tctccacctt ggagatccag     240

cgcacagagc agggggactc ggccatgtat ctctgtgcca gcagcacaca tgaaaagaca     300

gggtggaaat cacccctcca ctttgggaat gggaccaggc tcactgtgac ag             352
```

<210> SEQ ID NO 647
<211> LENGTH: 117
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 647

Asp Thr Gly Val Ser Gln Asp Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Thr
                85                  90                  95

His Glu Lys Thr Gly Trp Lys Ser Pro Leu His Phe Gly Asn Gly Thr
            100                 105                 110

Arg Leu Thr Val Thr
        115

<210> SEQ ID NO 648
<211> LENGTH: 313
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 648

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Thr His Ser Asp Arg Asn Leu Asn Thr Glu Ala Phe Phe Gly
        115                 120                 125

Gln Gly Thr Arg Leu Thr Val Val Glu Asp Leu Asn Lys Val Phe Pro
    130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
210 215 220

Asn Pro Arg Asn His Phe Arg Cys Gln Val Gln Phe Tyr Gly Leu Ser
225 230 235 240

Glu Asn Asp Glu Trp Thr Gln Asp Arg Ala Lys Pro Val Thr Gln Ile
245 250 255

Val Ser Ala Glu Ala Trp Gly Arg Ala Asp Cys Gly Phe Thr Ser Val
260 265 270

Ser Tyr Gln Gln Gly Val Leu Ser Ala Thr Ile Leu Tyr Glu Ile Leu
275 280 285

Leu Gly Lys Ala Thr Leu Tyr Ala Val Leu Val Ser Ala Leu Val Leu
290 295 300

Met Ala Met Val Lys Arg Lys Asp Phe
305 310

<210> SEQ ID NO 649
<211> LENGTH: 352
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 649
gaacctgaag tcacccagac tcccagccat caggtcacac agatgggaca ggaagtgatc 60
ttgcgctgtg tccccatctc taatcactta tacttctatt ggtacagaca aatcttgggg 120
cagaaagtcg agtttctggt ttccttttat aataatgaaa tctcagagaa gtctgaaata 180
ttcgatgatc aattctcagt tgaaaggcct gatggatcaa atttcactct gaagatccgg 240
tccacaaagc tggaggactc agccatgtac ttctgtgcca gcagtacgca ctctgacagg 300
aacttgaaca ctgaagcttt ctttggacaa ggcaccagac tcacagttgt ag 352

<210> SEQ ID NO 650
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 650

Glu Pro Glu Val Thr Gln Thr Pro Ser His Gln Val Thr Gln Met Gly
1 5 10 15

Gln Glu Val Ile Leu Arg Cys Val Pro Ile Ser Asn His Leu Tyr Phe
20 25 30

Tyr Trp Tyr Arg Gln Ile Leu Gly Gln Lys Val Glu Phe Leu Val Ser
35 40 45

Phe Tyr Asn Asn Glu Ile Ser Glu Lys Ser Glu Ile Phe Asp Asp Gln
50 55 60

Phe Ser Val Glu Arg Pro Asp Gly Ser Asn Phe Thr Leu Lys Ile Arg
65 70 75 80

Ser Thr Lys Leu Glu Asp Ser Ala Met Tyr Phe Cys Ala Ser Ser Thr
85 90 95

His Ser Asp Arg Asn Leu Asn Thr Glu Ala Phe Phe Gly Gln Gly Thr
100 105 110

Arg Leu Thr Val Val
115

<210> SEQ ID NO 651
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 651

Met Asp Thr Trp Leu Val Cys Trp Ala Ile Phe Ser Leu Leu Lys Ala
1 5 10 15

Gly Leu Thr Glu Pro Glu Val Thr Gln Thr Pro Ser His Gln Val Thr
20 25 30

Gln Met Gly Gln Glu Val Ile Leu Arg Cys Val Pro Ile Ser Asn His
35 40 45

Leu Tyr Phe Tyr Trp Tyr Arg Gln Ile Leu Gly Gln Lys Val Glu Phe
50 55 60

Leu Val Ser Phe Tyr Asn Asn Glu Ile Ser Glu Lys Ser Glu Ile Phe
65 70 75 80

Asp Asp Gln Phe Ser Val Glu Arg Pro Asp Gly Ser Asn Phe Thr Leu
85 90 95

Lys Ile Arg Ser Thr Lys Leu Glu Asp Ser Ala Met Tyr Phe Cys Ala
100 105 110

Ser Ser Val Gln Ala Thr Gly His Gly Tyr Thr Phe Gly Ser Gly Thr
115 120 125

Arg Leu Thr Val Val Glu Asp Leu Asn Lys Val Phe Pro Pro Glu Val
130 135 140

Ala Val Phe Glu Pro Ser Glu Ala Glu Ile Ser His Thr Gln Lys Ala
145 150 155 160

Thr Leu Val Cys Leu Ala Thr Gly Phe Tyr Pro Asp His Val Glu Leu
165 170 175

Ser Trp Trp Val Asn Gly Lys Glu Val His Ser Gly Val Ser Thr Asp
180 185 190

Pro Gln Pro Leu Lys Glu Gln Pro Ala Leu Asn Asp Ser Arg Tyr Cys
195 200 205

Leu Ser Ser Arg Leu Arg Val Ser Ala Thr Phe Trp Gln Asn Pro Arg
210 215 220

Asn His Phe Arg Cys Gln Val Gln Phe Tyr Gly Leu Ser Glu Asn Asp
225 230 235 240

Glu Trp Thr Gln Asp Arg Ala Lys Pro Val Thr Gln Ile Val Ser Ala
245 250 255

Glu Ala Trp Gly Arg Ala Asp Cys Gly Phe Thr Ser Val Ser Tyr Gln
260 265 270

Gln Gly Val Leu Ser Ala Thr Ile Leu Tyr Glu Ile Leu Leu Gly Lys
275 280 285

Ala Thr Leu Tyr Ala Val Leu Val Ser Ala Leu Val Leu Met Ala Met
290 295 300

Val Lys Arg Lys Asp Phe
305 310

<210> SEQ ID NO 652
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 652
gaacctgaag tcacccagac tcccagccat caggtcacac agatgggaca ggaagtgatc 60
ttgcgctgtg tccccatctc taatcactta tacttctatt ggtacagaca aatcttgggg 120
cagaaagtcg agtttctggt ttccttttat aataatgaaa tctcagagaa gtctgaaata 180
ttcgatgatc aattctcagt tgaaaggcct gatggatcaa atttcactct gaagatccgg 240
tccacaaagc tggaggactc agccatgtac ttctgtgcca gcagcgtaca ggctacgggc 300
catggctaca ccttcggttc ggggaccagg ttaaccgttg tag 343

<210> SEQ ID NO 653
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 653

Glu Pro Glu Val Thr Gln Thr Pro Ser His Gln Val Thr Gln Met Gly
1 5 10 15

Gln Glu Val Ile Leu Arg Cys Val Pro Ile Ser Asn His Leu Tyr Phe
20 25 30

Tyr Trp Tyr Arg Gln Ile Leu Gly Gln Lys Val Glu Phe Leu Val Ser
35 40 45

Phe Tyr Asn Asn Glu Ile Ser Glu Lys Ser Glu Ile Phe Asp Asp Gln
50 55 60

Phe Ser Val Glu Arg Pro Asp Gly Ser Asn Phe Thr Leu Lys Ile Arg
65 70 75 80

Ser Thr Lys Leu Glu Asp Ser Ala Met Tyr Phe Cys Ala Ser Ser Val
85 90 95

Gln Ala Thr Gly His Gly Tyr Thr Phe Gly Ser Gly Thr Arg Leu Thr
100 105 110

Val Val

<210> SEQ ID NO 654
<211> LENGTH: 311
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 654

Met Gly Thr Arg Leu Leu Cys Trp Val Val Leu Gly Phe Leu Gly Thr
1 5 10 15

Asp His Thr Gly Ala Gly Val Ser Gln Ser Pro Arg Tyr Lys Val Ala
20 25 30

Lys Arg Gly Gln Asp Val Ala Leu Arg Cys Asp Pro Ile Ser Gly His
35 40 45

Val Ser Leu Phe Trp Tyr Gln Gln Ala Leu Gly Gln Gly Pro Glu Phe
50 55 60

Leu Thr Tyr Phe Gln Asn Glu Ala Gln Leu Asp Lys Ser Gly Leu Pro
65 70 75 80

Ser Asp Arg Phe Phe Ala Glu Arg Pro Glu Gly Ser Val Ser Thr Leu
85 90 95

Lys Ile Gln Arg Thr Gln Gln Glu Asp Ser Ala Val Tyr Leu Cys Ala

```
            100                 105                 110

Ser Thr Pro Ser Gly Tyr Asn Ser Trp Glu Gln Phe Phe Gly Pro Gly
        115                 120                 125

Thr Arg Leu Thr Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310


<210> SEQ ID NO 655
<211> LENGTH: 346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 655

ggtgctggag tctcccagtc ccctaggtac aaagtcgcaa agagaggaca ggatgtagct     60

ctcaggtgtg atccaatttc gggtcatgta tcccttttttt ggtaccaaca ggccctgggg    120

caggggccag agtttctgac ttatttccag aatgaagctc aactagacaa atcggggctg    180

cccagtgatc gcttctttgc agaaaggcct gagggatccg tctccactct gaagatccag    240

cgcacacagc aggaggactc cgccgtgtat ctctgtgcca gcaccccctc tggctataac    300

tcttgggagc agttcttcgg gccagggaca cggctcaccg tgctag                   346


<210> SEQ ID NO 656
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 656

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
```

20 25 30

Phe Trp Tyr Gln Gln Ala Leu Gly Gln Gly Pro Glu Phe Leu Thr Tyr
35 40 45

Phe Gln Asn Glu Ala Gln Leu Asp Lys Ser Gly Leu Pro Ser Asp Arg
50 55 60

Phe Phe Ala Glu Arg Pro Glu Gly Ser Val Ser Thr Leu Lys Ile Gln
65 70 75 80

Arg Thr Gln Gln Glu Asp Ser Ala Val Tyr Leu Cys Ala Ser Thr Pro
85 90 95

Ser Gly Tyr Asn Ser Trp Glu Gln Phe Phe Gly Pro Gly Thr Arg Leu
100 105 110

Thr Val Leu
115

<210> SEQ ID NO 657
<211> LENGTH: 309
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 657

Met Gly Pro Gln Leu Leu Gly Tyr Val Val Leu Cys Leu Leu Gly Ala
1 5 10 15

Gly Pro Leu Glu Ala Gln Val Thr Gln Asn Pro Arg Tyr Leu Ile Thr
20 25 30

Val Thr Gly Lys Lys Leu Thr Val Thr Cys Ser Gln Asn Met Asn His
35 40 45

Glu Tyr Met Ser Trp Tyr Arg Gln Asp Pro Gly Leu Gly Leu Arg Gln
50 55 60

Ile Tyr Tyr Ser Met Asn Val Glu Val Thr Asp Lys Gly Asp Val Pro
65 70 75 80

Glu Gly Tyr Lys Val Ser Arg Lys Glu Lys Arg Asn Phe Pro Leu Ile
85 90 95

Leu Glu Ser Pro Ser Pro Asn Gln Thr Ser Leu Tyr Phe Cys Ala Thr
100 105 110

Ala Pro Arg Gly Ser Asn Gln Pro Gln His Phe Gly Asp Gly Thr Arg
115 120 125

Leu Ser Ile Leu Glu Asp Leu Asn Lys Val Phe Pro Pro Glu Val Ala
130 135 140

Val Phe Glu Pro Ser Glu Ala Glu Ile Ser His Thr Gln Lys Ala Thr
145 150 155 160

Leu Val Cys Leu Ala Thr Gly Phe Tyr Pro Asp His Val Glu Leu Ser
165 170 175

Trp Trp Val Asn Gly Lys Glu Val His Ser Gly Val Ser Thr Asp Pro
180 185 190

Gln Pro Leu Lys Glu Gln Pro Ala Leu Asn Asp Ser Arg Tyr Cys Leu
195 200 205

Ser Ser Arg Leu Arg Val Ser Ala Thr Phe Trp Gln Asn Pro Arg Asn
210 215 220

His Phe Arg Cys Gln Val Gln Phe Tyr Gly Leu Ser Glu Asn Asp Glu
225 230 235 240

Trp Thr Gln Asp Arg Ala Lys Pro Val Thr Gln Ile Val Ser Ala Glu
245 250 255

-continued

Ala Trp Gly Arg Ala Asp Cys Gly Phe Thr Ser Val Ser Tyr Gln Gln
260 265 270

Gly Val Leu Ser Ala Thr Ile Leu Tyr Glu Ile Leu Leu Gly Lys Ala
275 280 285

Thr Leu Tyr Ala Val Leu Val Ser Ala Leu Val Leu Met Ala Met Val
290 295 300

Lys Arg Lys Asp Phe
305

<210> SEQ ID NO 658
<211> LENGTH: 340
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 658
gaagcccaag tgacccagaa cccaagatac ctcatcacag tgactggaaa gaagttaaca 60
gtgacttgtt ctcagaatat gaaccatgag tatatgtcct ggtatcgaca agacccaggg 120
ctgggcttaa ggcagatcta ctattcaatg aatgttgagg tgactgataa gggagatgtt 180
cctgaagggt acaaagtctc tcgaaaagag aagaggaatt tccccctgat cctggagtcg 240
cccagcccca accagacctc tctgtacttc tgtgccaccg cccccagggg tagcaatcag 300
ccccagcatt ttggtgatgg gactcgactc tccatcctag 340

<210> SEQ ID NO 659
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 659

Glu Ala Gln Val Thr Gln Asn Pro Arg Tyr Leu Ile Thr Val Thr Gly
1 5 10 15

Lys Lys Leu Thr Val Thr Cys Ser Gln Asn Met Asn His Glu Tyr Met
20 25 30

Ser Trp Tyr Arg Gln Asp Pro Gly Leu Gly Leu Arg Gln Ile Tyr Tyr
35 40 45

Ser Met Asn Val Glu Val Thr Asp Lys Gly Asp Val Pro Glu Gly Tyr
50 55 60

Lys Val Ser Arg Lys Glu Lys Arg Asn Phe Pro Leu Ile Leu Glu Ser
65 70 75 80

Pro Ser Pro Asn Gln Thr Ser Leu Tyr Phe Cys Ala Thr Ala Pro Arg
85 90 95

Gly Ser Asn Gln Pro Gln His Phe Gly Asp Gly Thr Arg Leu Ser Ile
100 105 110

Leu

<210> SEQ ID NO 660
<211> LENGTH: 326
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 660

```
Met Glu Ala Val Val Thr Thr Leu Pro Arg Glu Gly Gly Val Arg Pro
1               5                   10                  15

Ser Arg Lys Met Leu Leu Leu Leu Leu Leu Leu Gly Pro Gly Ser Gly
            20                  25                  30

Leu Gly Ala Val Val Ser Gln His Pro Ser Trp Val Ile Cys Lys Ser
        35                  40                  45

Gly Thr Ser Val Lys Ile Glu Cys Arg Ser Leu Asp Phe Gln Ala Thr
    50                  55                  60

Thr Met Phe Trp Tyr Arg Gln Phe Pro Lys Gln Ser Leu Met Leu Met
65                  70                  75                  80

Ala Thr Ser Asn Glu Gly Ser Lys Ala Thr Tyr Glu Gln Gly Val Glu
                85                  90                  95

Lys Asp Lys Phe Leu Ile Asn His Ala Ser Leu Thr Leu Ser Thr Leu
            100                 105                 110

Thr Val Thr Ser Ala His Pro Glu Asp Ser Ser Phe Tyr Ile Cys Arg
        115                 120                 125

Ala Trp Gly Gly Ser Ser Tyr Asn Glu Gln Phe Phe Gly Pro Gly Thr
    130                 135                 140

Arg Leu Thr Val Leu Glu Asp Leu Lys Asn Val Phe Pro Pro Glu Val
145                 150                 155                 160

Ala Val Phe Glu Pro Ser Glu Ala Glu Ile Ser His Thr Gln Lys Ala
                165                 170                 175

Thr Leu Val Cys Leu Ala Thr Gly Phe Tyr Pro Asp His Val Glu Leu
            180                 185                 190

Ser Trp Trp Val Asn Gly Lys Glu Val His Ser Gly Val Ser Thr Asp
        195                 200                 205

Pro Gln Pro Leu Lys Glu Gln Pro Ala Leu Asn Asp Ser Arg Tyr Cys
    210                 215                 220

Leu Ser Ser Arg Leu Arg Val Ser Ala Thr Phe Trp Gln Asn Pro Arg
225                 230                 235                 240

Asn His Phe Arg Cys Gln Val Gln Phe Tyr Gly Leu Ser Glu Asn Asp
                245                 250                 255

Glu Trp Thr Gln Asp Arg Ala Lys Pro Val Thr Gln Ile Val Ser Ala
            260                 265                 270

Glu Ala Trp Gly Arg Ala Asp Cys Gly Phe Thr Ser Val Ser Tyr Gln
        275                 280                 285

Gln Gly Val Leu Ser Ala Thr Ile Leu Tyr Glu Ile Leu Leu Gly Lys
    290                 295                 300

Ala Thr Leu Tyr Ala Val Leu Val Ser Ala Leu Val Leu Met Ala Met
305                 310                 315                 320

Val Lys Arg Lys Asp Phe
                325
```

<210> SEQ ID NO 661
<211> LENGTH: 349
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 661

```
ggtgctgtcg tctctcaaca tccgagctgg gttatctgta agagtggaac ctctgtgaag      60

atcgagtgcc gttccctgga ctttcaggcc acaactatgt tttggtatcg tcagttcccg     120
```

aaacagagtc tcatgctgat ggcaacttcc aatgagggct ccaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagggcctg gggcgggagc 300
tcctacaatg agcagttctt cgggccaggg acacggctca ccgtgctag 349

<210> SEQ ID NO 662
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 662

Gly Ala Val Val Ser Gln His Pro Ser Trp Val Ile Cys Lys Ser Gly
1 5 10 15

Thr Ser Val Lys Ile Glu Cys Arg Ser Leu Asp Phe Gln Ala Thr Thr
20 25 30

Met Phe Trp Tyr Arg Gln Phe Pro Lys Gln Ser Leu Met Leu Met Ala
35 40 45

Thr Ser Asn Glu Gly Ser Lys Ala Thr Tyr Glu Gln Gly Val Glu Lys
50 55 60

Asp Lys Phe Leu Ile Asn His Ala Ser Leu Thr Leu Ser Thr Leu Thr
65 70 75 80

Val Thr Ser Ala His Pro Glu Asp Ser Ser Phe Tyr Ile Cys Arg Ala
85 90 95

Trp Gly Gly Ser Ser Tyr Asn Glu Gln Phe Phe Gly Pro Gly Thr Arg
100 105 110

Leu Thr Val Leu
115

<210> SEQ ID NO 663
<211> LENGTH: 329
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 663

Met Glu Ala Val Val Thr Thr Leu Pro Arg Glu Gly Gly Val Arg Pro
1 5 10 15

Ser Arg Lys Met Leu Leu Leu Leu Leu Leu Leu Gly Pro Gly Ser Gly
20 25 30

Leu Gly Ala Val Val Ser Gln His Pro Ser Arg Val Ile Cys Lys Ser
35 40 45

Gly Thr Ser Val Lys Ile Glu Cys Arg Ser Leu Asp Phe Gln Ala Thr
50 55 60

Thr Met Phe Trp Tyr Arg Gln Phe Pro Lys Gln Ser Leu Met Leu Met
65 70 75 80

Ala Thr Ser Asn Glu Gly Ser Lys Ala Thr Tyr Glu Gln Gly Val Glu
85 90 95

Lys Asp Lys Phe Leu Ile Asn His Ala Ser Leu Thr Leu Ser Thr Leu
100 105 110

Thr Val Thr Ser Ala His Pro Glu Asp Ser Ser Phe Tyr Ile Cys Ser
115 120 125

Ala Arg Ile Gly Gln Gly Phe Met Asn Glu Gln Phe Phe Gly Pro Gly 130 135 140

Thr Arg Leu Thr Val Leu Glu Asp Leu Lys Asn Val Phe Pro Pro Glu
145 150 155 160

Val Ala Val Phe Glu Pro Ser Glu Ala Glu Ile Ser His Thr Gln Lys
165 170 175

Ala Thr Leu Val Cys Leu Ala Thr Gly Phe Tyr Pro Asp His Val Glu
180 185 190

Leu Ser Trp Trp Val Asn Gly Lys Glu Val His Ser Gly Val Ser Thr
195 200 205

Asp Pro Gln Pro Leu Lys Glu Gln Pro Ala Leu Asn Asp Ser Arg Tyr
210 215 220

Cys Leu Ser Ser Arg Leu Arg Val Ser Ala Thr Phe Trp Gln Asn Pro
225 230 235 240

Arg Asn His Phe Arg Cys Gln Val Gln Phe Tyr Gly Leu Ser Glu Asn
245 250 255

Asp Glu Trp Thr Gln Asp Arg Ala Lys Pro Val Thr Gln Ile Val Ser
260 265 270

Ala Glu Ala Trp Gly Arg Ala Asp Cys Gly Phe Thr Ser Glu Ser Tyr
275 280 285

Gln Gln Gly Val Leu Ser Ala Thr Ile Leu Tyr Glu Ile Leu Leu Gly
290 295 300

Lys Ala Thr Leu Tyr Ala Val Leu Val Ser Ala Leu Val Leu Met Ala
305 310 315 320

Met Val Lys Arg Lys Asp Ser Arg Gly
325

<210> SEQ ID NO 664
<211> LENGTH: 352
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 664
ggtgctgtcg tctctcaaca tccgagcagg gttatctgta agagtggaac ctctgtgaag 60
atcgagtgcc gttccctgga ctttcaggcc acaactatgt tttggtatcg tcagttcccg 120
aaacagagtc tcatgctgat ggcaacttcc aatgagggct ccaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagtgctag aattggacag 300
ggttttatga atgagcagtt cttcgggcca gggacacggc tcaccgtgct ag 352

<210> SEQ ID NO 665
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 665

Gly Ala Val Val Ser Gln His Pro Ser Arg Val Ile Cys Lys Ser Gly
1 5 10 15

Thr Ser Val Lys Ile Glu Cys Arg Ser Leu Asp Phe Gln Ala Thr Thr
20 25 30

Met Phe Trp Tyr Arg Gln Phe Pro Lys Gln Ser Leu Met Leu Met Ala

```
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Ile Gly Gln Gly Phe Met Asn Glu Gln Phe Phe Gly Pro Gly Thr
            100                 105                 110

Arg Leu Thr Val Leu
        115


<210> SEQ ID NO 666
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 666

Met Glu Ala Val Val Thr Thr Leu Pro Arg Glu Gly Gly Val Arg Pro
1               5                   10                  15

Ser Arg Lys Met Leu Leu Leu Leu Leu Leu Leu Gly Pro Gly Ser Gly
            20                  25                  30

Leu Gly Ala Val Val Ser Gln His Pro Ser Arg Val Ile Cys Lys Ser
        35                  40                  45

Gly Thr Ser Val Lys Ile Glu Cys Arg Ser Leu Asp Phe Gln Ala Thr
    50                  55                  60

Thr Met Phe Trp Tyr Arg Gln Phe Pro Lys Lys Ser Leu Met Leu Met
65                  70                  75                  80

Ala Thr Ser Asn Glu Gly Ser Lys Ala Thr Tyr Glu Gln Gly Val Glu
                85                  90                  95

Lys Asp Lys Phe Leu Ile Asn His Ala Ser Leu Thr Leu Ser Thr Leu
            100                 105                 110

Thr Val Thr Ser Ala His Pro Glu Asp Ser Ser Phe Tyr Ile Cys Ser
        115                 120                 125

Ala Pro Gly Trp Arg Gly Thr Glu Ala Phe Phe Gly Gln Gly Thr Arg
    130                 135                 140

Leu Thr Val Val Glu Asp Leu Asn Lys Val Phe Pro Pro Glu Val Ala
145                 150                 155                 160

Val Phe Glu Pro Ser Glu Ala Glu Ile Ser His Thr Gln Lys Ala Thr
                165                 170                 175

Leu Val Cys Leu Ala Thr Gly Phe Phe Pro Asp His Val Glu Leu Ser
            180                 185                 190

Trp Trp Val Asn Gly Lys Glu Val His Ser Gly Val Ser Thr Asp Pro
        195                 200                 205

Gln Pro Leu Lys Glu Gln Pro Ala Leu Asn Asp Ser Arg Tyr Cys Leu
    210                 215                 220

Ser Ser Arg Leu Arg Val Ser Ala Thr Phe Trp Gln Asn Pro Arg Asn
225                 230                 235                 240

His Phe Arg Cys Gln Val Gln Phe Tyr Gly Leu Ser Glu Asn Asp Glu
                245                 250                 255

Trp Thr Gln Asp Arg Ala Lys Pro Val Thr Gln Ile Val Ser Ala Glu
            260                 265                 270
```

```
Ala Trp Gly Arg Ala Asp Cys Gly Phe Thr Ser Val Ser Tyr Gln Gln
        275                 280                 285

Gly Val Leu Ser Ala Thr Ile Leu Tyr Glu Ile Leu Leu Gly Lys Ala
    290                 295                 300

Thr Leu Tyr Ala Val Leu Val Ser Ala Leu Val Leu Met Ala Met Val
305                 310                 315                 320

Lys Arg Lys Asp Phe
                325


<210> SEQ ID NO 667
<211> LENGTH: 346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 667

ggtgctgtcg tctctcaaca tccgagcagg gttatctgta agagtggaac ctctgtgaag     60

atcgagtgcc gttccctgga ctttcaggcc acaactatgt tttggtatcg tcagttcccg    120

aaaaagagtc tcatgctgat ggcaacttcc aatgagggct ccaaggccac atacgagcaa    180

ggcgtcgaga aggacaagtt tctcatcaac catgcaagcc tgaccttgtc cactctgaca    240

gtgaccagtg cccatcctga agacagcagc ttctacatct gcagtgctcc tgggtggcgt    300

ggcactgaag ctttctttgg acaaggcacc agactcacag ttgtag                   346


<210> SEQ ID NO 668
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 668

Gly Ala Val Val Ser Gln His Pro Ser Arg Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Lys Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Pro Gly Trp Arg Gly Thr Glu Ala Phe Phe Gly Gln Gly Thr Arg Leu
            100                 105                 110

Thr Val Val
        115


<210> SEQ ID NO 669
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 669

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Gln Asp Gly Leu Glu Gln Tyr Phe Gly Pro Gly Thr Arg Leu Thr
        115                 120                 125

Val Thr Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305

<210> SEQ ID NO 670
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 670
gacacagctg tttcccagac tccaaaatac ctggtcacac agatgggaaa cgacaagtcc      60
attaaatgtg aacaaaatct gggccatgat actatgtatt ggtataaaca ggactctaag     120
aaatttctga agataatgtt tagctacaat aataaggagc tcattataaa tgaaacagtt     180
ccaaatcgct tctcacctaa atctccagac aaagctcact taaatcttca catcaattcc 240
ctggagcttg gtgactctgc tgtgtatttc tgtgccagca gccaagatgg acttgagcag 300
tacttcgggc cgggcaccag gctcacggtc acag 334

<210> SEQ ID NO 671
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 671

```
Asp Thr Ala Val Ser Gln Thr Pro Lys Tyr Leu Val Thr Gln Met Gly
1               5                   10                  15

Asn Asp Lys Ser Ile Lys Cys Glu Gln Asn Leu Gly His Asp Thr Met
            20                  25                  30

Tyr Trp Tyr Lys Gln Asp Ser Lys Lys Phe Leu Lys Ile Met Phe Ser
        35                  40                  45

Tyr Asn Asn Lys Glu Leu Ile Ile Asn Glu Thr Val Pro Asn Arg Phe
    50                  55                  60

Ser Pro Lys Ser Pro Asp Lys Ala His Leu Asn Leu His Ile Asn Ser
65                  70                  75                  80

Leu Glu Leu Gly Asp Ser Ala Val Tyr Phe Cys Ala Ser Ser Gln Asp
                85                  90                  95

Gly Leu Glu Gln Tyr Phe Gly Pro Gly Thr Arg Leu Thr Val Thr
            100                 105                 110
```

<210> SEQ ID NO 672
<211> LENGTH: 318
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 672

```
Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Gln Glu Gly Ser Gln Asp His Thr Ser Gly Arg Ala Thr Glu Gln
        115                 120                 125

Tyr Phe Gly Pro Gly Thr Arg Leu Thr Val Thr Glu Asp Leu Lys Asn
    130                 135                 140

Val Phe Pro Pro Glu Val Ala Val Phe Glu Pro Ser Glu Ala Glu Ile
145                 150                 155                 160
```

-continued

```
Ser His Thr Gln Lys Ala Thr Leu Val Cys Leu Ala Thr Gly Phe Tyr
                165                 170                 175

Pro Asp His Val Glu Leu Ser Trp Trp Val Asn Gly Lys Glu Val His
            180                 185                 190

Ser Gly Val Ser Thr Asp Pro Gln Pro Leu Lys Glu Gln Pro Ala Leu
        195                 200                 205

Asn Asp Ser Arg Tyr Cys Leu Ser Ser Arg Leu Arg Val Ser Ala Thr
    210                 215                 220

Phe Trp Gln Asn Pro Arg Asn His Phe Arg Cys Gln Val Gln Phe Tyr
225                 230                 235                 240

Gly Leu Ser Glu Asn Asp Glu Trp Thr Gln Asp Arg Ala Lys Pro Val
                245                 250                 255

Thr Gln Ile Val Ser Ala Glu Ala Trp Gly Arg Ala Asp Cys Gly Phe
            260                 265                 270

Thr Ser Glu Ser Tyr Gln Gln Gly Val Leu Ser Ala Thr Ile Leu Tyr
        275                 280                 285

Glu Ile Leu Leu Gly Lys Ala Thr Leu Tyr Ala Val Leu Val Ser Ala
    290                 295                 300

Leu Val Leu Met Ala Met Val Lys Arg Lys Asp Ser Arg Gly
305                 310                 315
```

<210> SEQ ID NO 673
<211> LENGTH: 361
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 673

```
gacacagctg tttcccagac tccaaaatac ctggtcacac agatgggaaa cgacaagtcc     60

attaaatgtg aacaaaatct gggccatgat actatgtatt ggtataaaca ggactctaag    120

aaatttctga agataatgtt tagctacaat aataaggagc tcattataaa tgaaacagtt    180

ccaaatcgct tctcacctaa atctccagac aaagctcact taaatcttca catcaattcc    240

ctggagcttg gtgactctgc tgtgtatttc tgtgccagca gccaagaagg atctcaggac    300

cacactagcg ggagggccac cgagcagtac ttcgggccgg gcaccaggct cacggtcaca    360

g                                                                    361
```

<210> SEQ ID NO 674
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 674

```
Asp Thr Ala Val Ser Gln Thr Pro Lys Tyr Leu Val Thr Gln Met Gly
1               5                   10                  15

Asn Asp Lys Ser Ile Lys Cys Glu Gln Asn Leu Gly His Asp Thr Met
            20                  25                  30

Tyr Trp Tyr Lys Gln Asp Ser Lys Lys Phe Leu Lys Ile Met Phe Ser
        35                  40                  45

Tyr Asn Asn Lys Glu Leu Ile Ile Asn Glu Thr Val Pro Asn Arg Phe
    50                  55                  60

Ser Pro Lys Ser Pro Asp Lys Ala His Leu Asn Leu His Ile Asn Ser
```

```
65                  70                  75                  80

Leu Glu Leu Gly Asp Ser Ala Val Tyr Phe Cys Ala Ser Ser Gln Glu
                85                  90                  95

Gly Ser Gln Asp His Thr Ser Gly Arg Ala Thr Glu Gln Tyr Phe Gly
            100                 105                 110

Pro Gly Thr Arg Leu Thr Val Thr
        115                 120


<210> SEQ ID NO 675
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

Met Ser Gln Asn Asp Phe Leu Glu Ser Pro Ala Pro Leu Ser Ser Met
1               5                   10                  15

His Arg Tyr Arg Arg Pro Leu Arg His Ala Ala Ser Ala Met Ser Ile
            20                  25                  30

Gly Leu Leu Cys Cys Ala Ala Leu Ser Leu Leu Trp Ala Gly Pro Val
        35                  40                  45

Asn Ala Gly Val Thr Gln Thr Pro Lys Phe Gln Val Leu Lys Thr Gly
    50                  55                  60

Gln Ser Met Thr Leu Gln Cys Ala Gln Asp Met Asn His Glu Tyr Met
65                  70                  75                  80

Ser Trp Tyr Arg Gln Asp Pro Gly Met Gly Leu Arg Leu Ile His Tyr
                85                  90                  95

Ser Val Gly Ala Gly Ile Thr Asp Gln Gly Glu Val Pro Asn Gly Tyr
            100                 105                 110

Asn Val Ser Arg Ser Thr Thr Glu Asp Phe Pro Leu Arg Leu Leu Ser
        115                 120                 125

Ala Ala Pro Ser Gln Thr Ser Val Tyr Phe Cys Ala Ser Ser Leu Thr
    130                 135                 140

Glu Gly Arg Ser Glu Gln Tyr Phe Gly Pro Gly Thr Arg Leu Thr Val
145                 150                 155                 160

Thr Glu Asp Leu Lys Asn Val Phe Pro Pro Glu Val Ala Val Phe Glu
                165                 170                 175

Pro Ser Glu Ala Glu Ile Ser His Thr Gln Lys Ala Thr Leu Val Cys
            180                 185                 190

Leu Ala Thr Gly Phe Tyr Pro Asp His Val Glu Leu Ser Trp Trp Val
        195                 200                 205

Asn Gly Lys Glu Val His Ser Gly Val Ser Thr Asp Pro Gln Pro Leu
    210                 215                 220

Lys Glu Gln Pro Ala Leu Asn Asp Ser Arg Tyr Cys Leu Ser Ser Arg
225                 230                 235                 240

Leu Arg Val Ser Ala Thr Phe Trp Gln Asn Pro Arg Asn His Phe Arg
                245                 250                 255

Cys Gln Val Gln Phe Tyr Gly Leu Ser Glu Asn Asp Glu Trp Thr Gln
            260                 265                 270

Asp Arg Ala Lys Pro Val Thr Gln Ile Val Ser Ala Glu Ala Trp Gly
        275                 280                 285

Arg Ala Asp Cys Gly Phe Thr Ser Glu Ser Tyr Gln Gln Gly Val Leu
    290                 295                 300
```

-continued

Ser Ala Thr Ile Leu Tyr Glu Ile Leu Leu Gly Lys Ala Thr Leu Tyr
305 310 315 320

Ala Val Leu Val Ser Ala Leu Val Leu Met Ala Met Val Lys Arg Lys
325 330 335

Asp Ser Arg Gly
340

<210> SEQ ID NO 676
<211> LENGTH: 340
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 676
aatgctggtg tcactcagac cccaaaattc caggtcctga agacaggaca gagcatgaca 60
ctgcagtgtg cccaggatat gaaccatgaa tacatgtcct ggtatcgaca agacccaggc 120
atggggctga ggctgattca ttactcagtt ggtgctggta tcactgacca aggagaagtc 180
cccaatggct acaatgtctc cagatcaacc acagaggatt tcccgctcag gctgctgtcg 240
gctgctccct cccagacatc tgtgtacttc tgtgccagca gcctgacaga aggaagaagc 300
gagcagtact tcgggccggg caccaggctc acggtcacag 340

<210> SEQ ID NO 677
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 677

Asn Ala Gly Val Thr Gln Thr Pro Lys Phe Gln Val Leu Lys Thr Gly
1 5 10 15

Gln Ser Met Thr Leu Gln Cys Ala Gln Asp Met Asn His Glu Tyr Met
20 25 30

Ser Trp Tyr Arg Gln Asp Pro Gly Met Gly Leu Arg Leu Ile His Tyr
35 40 45

Ser Val Gly Ala Gly Ile Thr Asp Gln Gly Glu Val Pro Asn Gly Tyr
50 55 60

Asn Val Ser Arg Ser Thr Thr Glu Asp Phe Pro Leu Arg Leu Leu Ser
65 70 75 80

Ala Ala Pro Ser Gln Thr Ser Val Tyr Phe Cys Ala Ser Ser Leu Thr
85 90 95

Glu Gly Arg Ser Glu Gln Tyr Phe Gly Pro Gly Thr Arg Leu Thr Val
100 105 110

Thr

<210> SEQ ID NO 678
<211> LENGTH: 325
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 678

Met Glu Ala Val Val Thr Thr Leu Pro Arg Glu Gly Gly Val Arg Pro
1 5 10 15

```
Ser Arg Lys Met Leu Leu Leu Leu Leu Leu Leu Gly Pro Gly Ser Gly
            20                  25                  30

Leu Gly Ala Val Val Ser Gln His Pro Ser Arg Val Ile Cys Lys Ser
        35                  40                  45

Gly Thr Ser Val Lys Ile Glu Cys Arg Ser Leu Asp Phe Gln Ala Thr
    50                  55                  60

Thr Met Phe Trp Tyr Arg Gln Phe Pro Lys Lys Ser Leu Met Leu Met
65                  70                  75                  80

Ala Thr Ser Asn Glu Gly Ser Lys Ala Thr Tyr Glu Gln Gly Val Glu
                85                  90                  95

Lys Asp Lys Phe Leu Ile Asn His Ala Ser Leu Thr Leu Ser Thr Leu
            100                 105                 110

Thr Val Thr Ser Ala His Pro Glu Asp Ser Ser Phe Tyr Ile Cys Ser
        115                 120                 125

Ala Gly Gly Phe Ser Gly Asn Thr Ile Tyr Phe Gly Glu Gly Ser Trp
    130                 135                 140

Leu Thr Val Val Glu Asp Leu Asn Lys Val Phe Pro Pro Glu Val Ala
145                 150                 155                 160

Val Phe Glu Pro Ser Glu Ala Glu Ile Ser His Thr Gln Lys Ala Thr
                165                 170                 175

Leu Val Cys Leu Ala Thr Gly Phe Tyr Pro Asp His Val Glu Leu Ser
            180                 185                 190

Trp Trp Val Asn Gly Lys Glu Val His Ser Gly Val Ser Thr Asp Pro
        195                 200                 205

Gln Pro Leu Lys Glu Gln Pro Ala Leu Asn Asp Ser Arg Tyr Cys Leu
    210                 215                 220

Ser Ser Arg Leu Arg Val Ser Ala Thr Phe Trp Gln Asn Pro Arg Asn
225                 230                 235                 240

His Phe Arg Cys Gln Val Gln Phe Tyr Gly Leu Ser Glu Asn Asp Glu
                245                 250                 255

Trp Thr Gln Asp Arg Ala Lys Pro Val Thr Gln Ile Val Ser Ala Glu
            260                 265                 270

Ala Trp Gly Arg Ala Asp Cys Gly Phe Thr Ser Val Ser Tyr Gln Gln
        275                 280                 285

Gly Val Leu Ser Ala Thr Ile Leu Tyr Glu Ile Leu Leu Gly Lys Ala
    290                 295                 300

Thr Leu Tyr Ala Val Leu Val Ser Ala Leu Val Leu Met Ala Met Val
305                 310                 315                 320

Lys Arg Lys Asp Phe
                325


<210> SEQ ID NO 679
<211> LENGTH: 346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 679

ggtgctgtcg tctctcaaca tccgagcagg gttatctgta agagtggaac ctctgtgaag     60

atcgagtgcc gttccctgga ctttcaggcc acaactatgt tttggtatcg tcagttcccg    120

aaaaagagtc tcatgctgat ggcaacttcc aatgagggct ccaaggccac atacgagcaa    180

ggcgtcgaga aggacaagtt tctcatcaac catgcaagcc tgaccttgtc cactctgaca    240
```

gtgaccagtg cccatcctga agacagcagc ttctacatct gcagtgctgg gggtttctct 300
ggaaacacca tatattttgg agagggaagt tggctcactg ttgtag 346

<210> SEQ ID NO 680
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 680

Gly Ala Val Val Ser Gln His Pro Ser Arg Val Ile Cys Lys Ser Gly
1 5 10 15

Thr Ser Val Lys Ile Glu Cys Arg Ser Leu Asp Phe Gln Ala Thr Thr
20 25 30

Met Phe Trp Tyr Arg Gln Phe Pro Lys Lys Ser Leu Met Leu Met Ala
35 40 45

Thr Ser Asn Glu Gly Ser Lys Ala Thr Tyr Glu Gln Gly Val Glu Lys
50 55 60

Asp Lys Phe Leu Ile Asn His Ala Ser Leu Thr Leu Ser Thr Leu Thr
65 70 75 80

Val Thr Ser Ala His Pro Glu Asp Ser Ser Phe Tyr Ile Cys Ser Ala
85 90 95

Gly Gly Phe Ser Gly Asn Thr Ile Tyr Phe Gly Glu Gly Ser Trp Leu
100 105 110

Thr Val Val
115

<210> SEQ ID NO 681
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 681

Val Leu Asn Tyr Gly Val Cys Phe Cys
1 5

<210> SEQ ID NO 682
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 682

Phe Cys Gly Asp Glu Asn Ile Leu Val
1 5

<210> SEQ ID NO 683
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 683

-continued

Met Lys Asp Lys Gln Asp Glu Glu Gln Arg Thr Arg Arg Met Met Arg
1               5                   10                  15

Thr Lys Met Arg Met Arg Arg Met Arg Arg Thr Arg Arg Lys Met Arg
            20                  25                  30

Arg Lys Met Ser Pro Ala Arg Pro Arg Thr Ser Cys Arg Glu Ala Cys
        35                  40                  45

Leu Gln Gly Trp Thr Glu Ala Ala Tyr Glu Glu Ala Glu Asp Asn Cys
    50                  55                  60

Arg Arg Met Met Arg Thr Lys Ala Ala Tyr Val Leu Asn Tyr Gly Val
65                  70                  75                  80

Cys Phe Cys Ala Ala Tyr Phe Cys Gly Asp Glu Asn Ile Leu Val
                85                  90                  95

<210> SEQ ID NO 684
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 684

Arg Pro Arg Thr Ser Cys Arg Glu Ala
1               5

<210> SEQ ID NO 685
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 685

Ser Pro Ala Arg Pro Arg Thr Ser Cys
1               5

<210> SEQ ID NO 686
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 686

Arg Lys Met Ser Pro Ala Arg Pro Arg
1               5

<210> SEQ ID NO 687
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 687

Met Arg Arg Lys Met Ser Pro Ala Arg
1               5

<210> SEQ ID NO 688
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 688

Lys Met Arg Arg Lys Met Ser Pro Ala
1 5

<210> SEQ ID NO 689
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 689

Thr Arg Arg Lys Met Arg Arg Lys Met
1 5

<210> SEQ ID NO 690
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 690

Arg Thr Arg Arg Lys Met Arg Arg Lys
1 5

<210> SEQ ID NO 691
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 691

Arg Arg Thr Arg Arg Lys Met Arg Arg
1 5

<210> SEQ ID NO 692
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 692

Arg Met Arg Arg Thr Arg Arg Lys Met
1 5

<210> SEQ ID NO 693
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 693

Arg Arg Met Arg Arg Thr Arg Arg Lys
1 5

<210> SEQ ID NO 694
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 694

Met Arg Arg Met Arg Arg Thr Arg Arg
1 5

<210> SEQ ID NO 695
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 695

Met Arg Met Arg Arg Met Arg Arg Thr
1 5

<210> SEQ ID NO 696
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 696

Lys Met Arg Met Arg Arg Met Arg Arg
1 5

<210> SEQ ID NO 697
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 697

Met Arg Thr Lys Met Arg Met Arg Arg
1 5

<210> SEQ ID NO 698
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 698

Met Met Arg Thr Lys Met Arg Met Arg
1 5

<210> SEQ ID NO 699
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 699

Arg Met Met Arg Thr Lys Met Arg Met
1 5

<210> SEQ ID NO 700
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 700

Arg Arg Met Met Arg Thr Lys Met Arg
1 5

<210> SEQ ID NO 701
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 701

Arg Thr Arg Arg Met Met Arg Thr Lys
1 5

<210> SEQ ID NO 702
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 702

Met Ala Cys Pro Gly Phe Leu Trp Ala Leu Val Ile Ser Thr Cys Leu
1 5 10 15

Glu Phe Ser Met Ala Met Lys Asp Lys Gln Asp Glu Glu Gln Arg Thr
20 25 30

Arg Arg Met Met Arg Thr Lys Met Arg Met Arg Arg Met Arg Arg Thr
35 40 45

Arg Arg Lys Met Arg Arg Lys Met Ser Pro Ala Arg Pro Arg Thr Ser
50 55 60

Cys Arg Glu Ala Cys Leu Gln Gly Trp Thr Glu Ala Ala Tyr Glu Glu
65 70 75 80

Ala Glu Asp Asn Cys Arg Arg Met Met Arg Thr Lys Ala Ala Tyr Val
85 90 95

Leu Asn Tyr Gly Val Cys Phe Cys Ala Ala Tyr Phe Cys Gly Asp Glu
100 105 110

Asn Ile Leu Val
115

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 703

-continued

```
aatgatacgg cgaccaccga                                              20


<210> SEQ ID NO 704
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704

caagcagaag acggcatacg agat                                         24


<210> SEQ ID NO 705
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 705

nnnnnnnn                                                            8


<210> SEQ ID NO 706
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706

agatcggaag agcacacgtc tgaactccag tcac                              34
```